US012746073B2

(12) United States Patent
Lang et al.

(10) Patent No.: US 12,746,073 B2
(45) Date of Patent: Sep. 29, 2026

(54) AUGMENTED REALITY GUIDANCE METHODS AND SYSTEMS FOR USE WITH MICROSCOPES OR ENDOSCOPES IN SURGICAL PROCEDURES

(71) Applicant: OnPoint Medical, Inc., Franconia, NH (US)

(72) Inventors: Philipp K Lang, Franconia, NH (US); Daniel Steines, Lexington, MA (US)

(73) Assignee: OnPoint Medical, Inc., Franconia, NH (US)

( * ) Notice: Subject to any disclaimer, the term of this patent is extended or adjusted under 35 U.S.C. 154(b) by 0 days.

(21) Appl. No.: 19/565,794

(22) Filed: Mar. 13, 2026

(65) Prior Publication Data

US 2026/0224299 A1 Aug. 6, 2026

Related U.S. Application Data

(63) Continuation of application No. PCT/US2024/046696, filed on Sep. 13, 2024.

(Continued)

(51) Int. Cl.
*A61B 34/20* (2016.01)
*A61B 90/00* (2016.01)

(Continued)

(52) U.S. Cl.
CPC .............. *A61B 34/20* (2016.02); *A61B 90/37* (2016.02); *G06T 7/13* (2017.01); *G06T 7/248* (2017.01);

(Continued)

(58) Field of Classification Search
CPC .............. A61B 34/20; A61B 2090/365; A61B 2090/372; G16H 20/40; G16H 40/67;

(Continued)

(56) References Cited

U.S. PATENT DOCUMENTS 10,154,239 B2 * 12/2018 Casas .................. H04N 13/111
11,553,969 B1 * 1/2023 Lang ...................... A61B 34/10

(Continued)

OTHER PUBLICATIONS

Lai et al. "Fusion of augmented reality imaging with the endoscopic view for endonasal skull base surgery; a novel application for surgical navigation based on intraoperative cone beam computed tomography and optical tracking", PLoS One. Jan. 16, 2020; 15(1):e0227312.

(Continued)

*Primary Examiner* — Timothy J Neal

(74) *Attorney, Agent, or Firm* — Greenberg Traurig, LLP; Natalie Salem

(57) ABSTRACT

Aspects of the present disclosure relate to systems, devices and methods for performing a surgical step or surgical procedure using a microscope or endoscope with virtual display(s) by an augmented reality display device (ARDD). A computer processor can be configured to adjust or select the focal plane and/or focal point of the display of the virtual data by the ARDD based on a focal plane of the microscope or endoscope. The depth of field of the virtual display can be adjusted to overlap with the depth of field of the microscope or endoscope. The field of view of the ARDD can be larger than that of the microscope or endoscope and the ARDD can be configured to display target tissues that extend outside the field of view projection of the microscope or endoscope.

20 Claims, 78 Drawing Sheets

Related U.S. Application Data

(60) Provisional application No. 63/582,591, filed on Sep. 14, 2023.

(51) Int. Cl.

| | |
|---|---|
| ***G06T 7/13*** | (2017.01) |
| ***G06T 7/246*** | (2017.01) |
| ***G06T 19/00*** | (2011.01) |
| ***G16H 20/40*** | (2018.01) |
| ***G16H 40/67*** | (2018.01) |

(52) U.S. Cl.
CPC ........... *G06T 19/006* (2013.01); *G16H 20/40* (2018.01); *G16H 40/67* (2018.01); *A61B 2090/365* (2016.02); *A61B 2090/372* (2016.02); *G06T 2207/10021* (2013.01); *G06T 2207/10081* (2013.01); *G06T 2207/10088* (2013.01); *G06T 2207/10104* (2013.01); *G06T 2207/10108* (2013.01); *G06T 2207/10128* (2013.01); *G06T 2207/10136* (2013.01); *G06T 2207/30004* (2013.01); *G06T 2207/30204* (2013.01); *G06T 2210/41* (2013.01)

(58) Field of Classification Search
CPC ....... G06T 2210/41; G06T 7/13; G06T 7/248; G06T 2207/10021; G06T 2207/100821; G06T 2207/10088; G06T 2207/10104; G06T 2207/10128; G06T 2207/10136; G06T 2207/30004; G06T 2207/30204
See application file for complete search history.

(56) References Cited

U.S. PATENT DOCUMENTS

| | | | | |
|---|---|---|---|---|
| 12,211,151 | B1 * | 1/2025 | Chiou | G06T 19/003 |
| 2021/0335483 | A1 | 10/2021 | Freeman et al. | |
| 2022/0287676 | A1 | 9/2022 | Steines et al. | |
| 2023/0149099 | A1 | 5/2023 | Murphy | |

OTHER PUBLICATIONS

Mikamo et al. "3D endoscope system with AR display superimposing dense and wide-angle-of-view 3D points obtained by using micro pattern projector", 2022 44th Annual International Conference of the IEEE Engineering in Medicine & Biology Society (EMBC) Scottish Event Campus, Glasgow, UK, Jul. 11-15, 2022.
International Search Report and Written Opinion in PCT International Application No. PCT/US2024/046696 mailed Jan. 8, 2025.

* cited by examiner

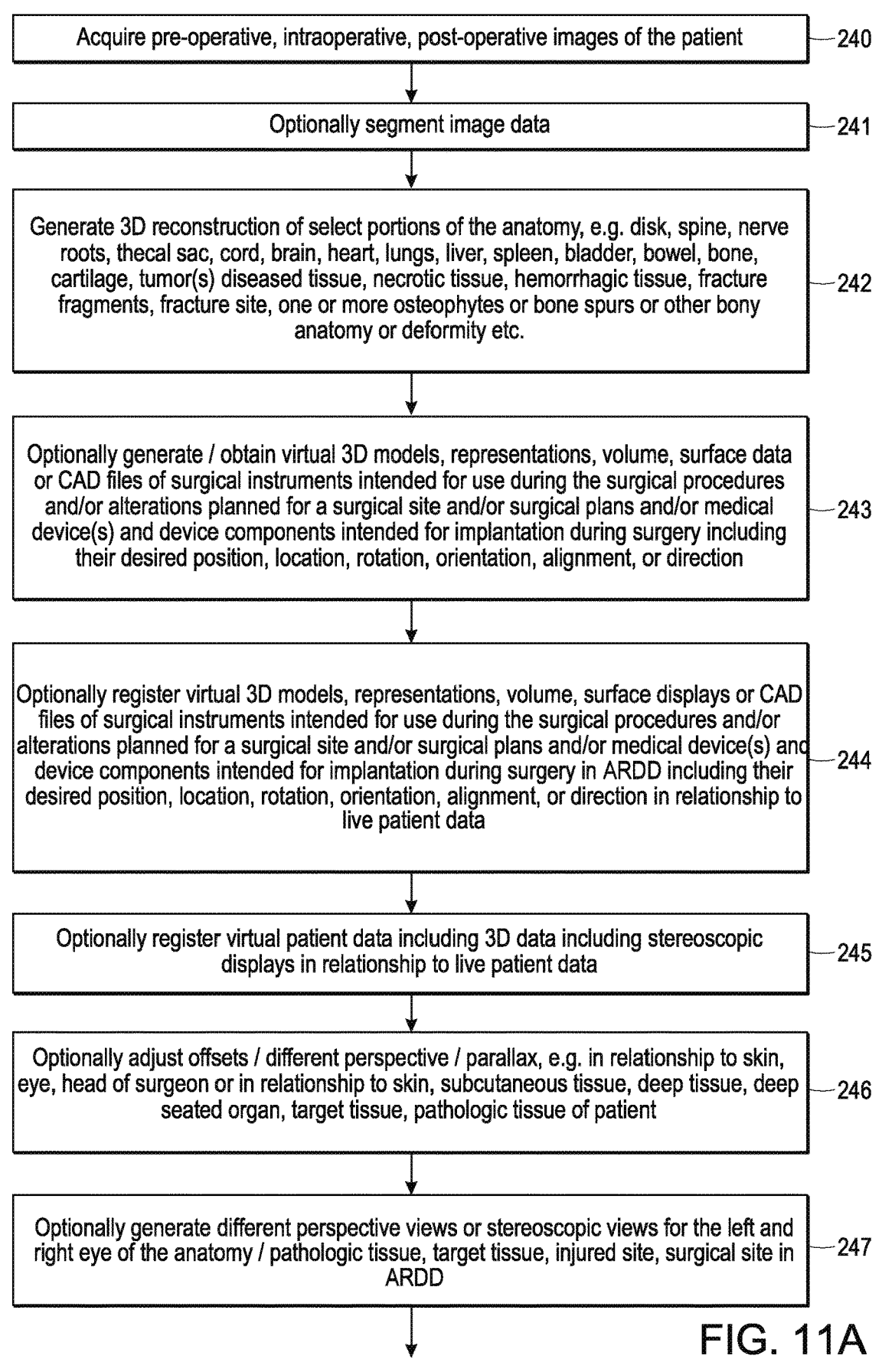

Acquire pre-operative, intraoperative, post-operative images of the patient — 240

↓

Optionally segment image data — 241

↓

Generate 3D reconstruction of select portions of the anatomy, e.g. disk, spine, nerve roots, thecal sac, cord, brain, heart, lungs, liver, spleen, bladder, bowel, bone, cartilage, tumor(s) diseased tissue, necrotic tissue, hemorrhagic tissue, fracture fragments, fracture site, one or more osteophytes or bone spurs or other bony anatomy or deformity etc. — 242

↓

Optionally generate / obtain virtual 3D models, representations, volume, surface data or CAD files of surgical instruments intended for use during the surgical procedures and/or alterations planned for a surgical site and/or surgical plans and/or medical device(s) and device components intended for implantation during surgery including their desired position, location, rotation, orientation, alignment, or direction — 243

↓

Optionally register virtual 3D models, representations, volume, surface displays or CAD files of surgical instruments intended for use during the surgical procedures and/or alterations planned for a surgical site and/or surgical plans and/or medical device(s) and device components intended for implantation during surgery in ARDD including their desired position, location, rotation, orientation, alignment, or direction in relationship to live patient data — 244

↓

Optionally register virtual patient data including 3D data including stereoscopic displays in relationship to live patient data — 245

↓

Optionally adjust offsets / different perspective / parallax, e.g. in relationship to skin, eye, head of surgeon or in relationship to skin, subcutaneous tissue, deep tissue, deep seated organ, target tissue, pathologic tissue of patient — 246

↓

Optionally generate different perspective views or stereoscopic views for the left and right eye of the anatomy / pathologic tissue, target tissue, injured site, surgical site in ARDD — 247

↓

FIG. 11A

FIG. 11B CONTINUED

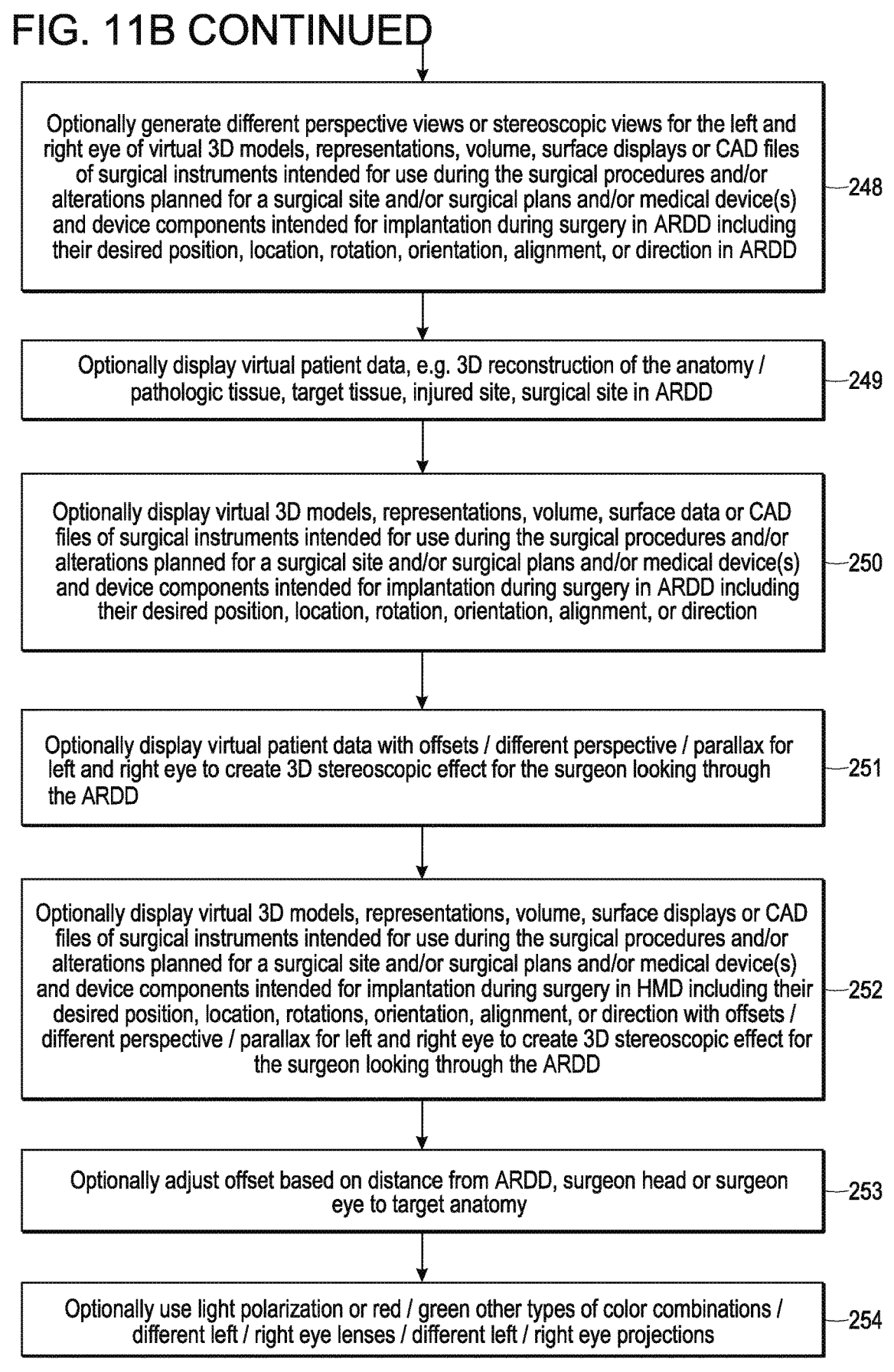

Optionally generate different perspective views or stereoscopic views for the left and right eye of virtual 3D models, representations, volume, surface displays or CAD files of surgical instruments intended for use during the surgical procedures and/or alterations planned for a surgical site and/or surgical plans and/or medical device(s) and device components intended for implantation during surgery in ARDD including their desired position, location, rotation, orientation, alignment, or direction in ARDD — 248

Optionally display virtual patient data, e.g. 3D reconstruction of the anatomy / pathologic tissue, target tissue, injured site, surgical site in ARDD — 249

Optionally display virtual 3D models, representations, volume, surface data or CAD files of surgical instruments intended for use during the surgical procedures and/or alterations planned for a surgical site and/or surgical plans and/or medical device(s) and device components intended for implantation during surgery in ARDD including their desired position, location, rotation, orientation, alignment, or direction — 250

Optionally display virtual patient data with offsets / different perspective / parallax for left and right eye to create 3D stereoscopic effect for the surgeon looking through the ARDD — 251

Optionally display virtual 3D models, representations, volume, surface displays or CAD files of surgical instruments intended for use during the surgical procedures and/or alterations planned for a surgical site and/or surgical plans and/or medical device(s) and device components intended for implantation during surgery in HMD including their desired position, location, rotations, orientation, alignment, or direction with offsets / different perspective / parallax for left and right eye to create 3D stereoscopic effect for the surgeon looking through the ARDD — 252

Optionally adjust offset based on distance from ARDD, surgeon head or surgeon eye to target anatomy — 253

Optionally use light polarization or red / green other types of color combinations / different left / right eye lenses / different left / right eye projections — 254

FIG. 22B

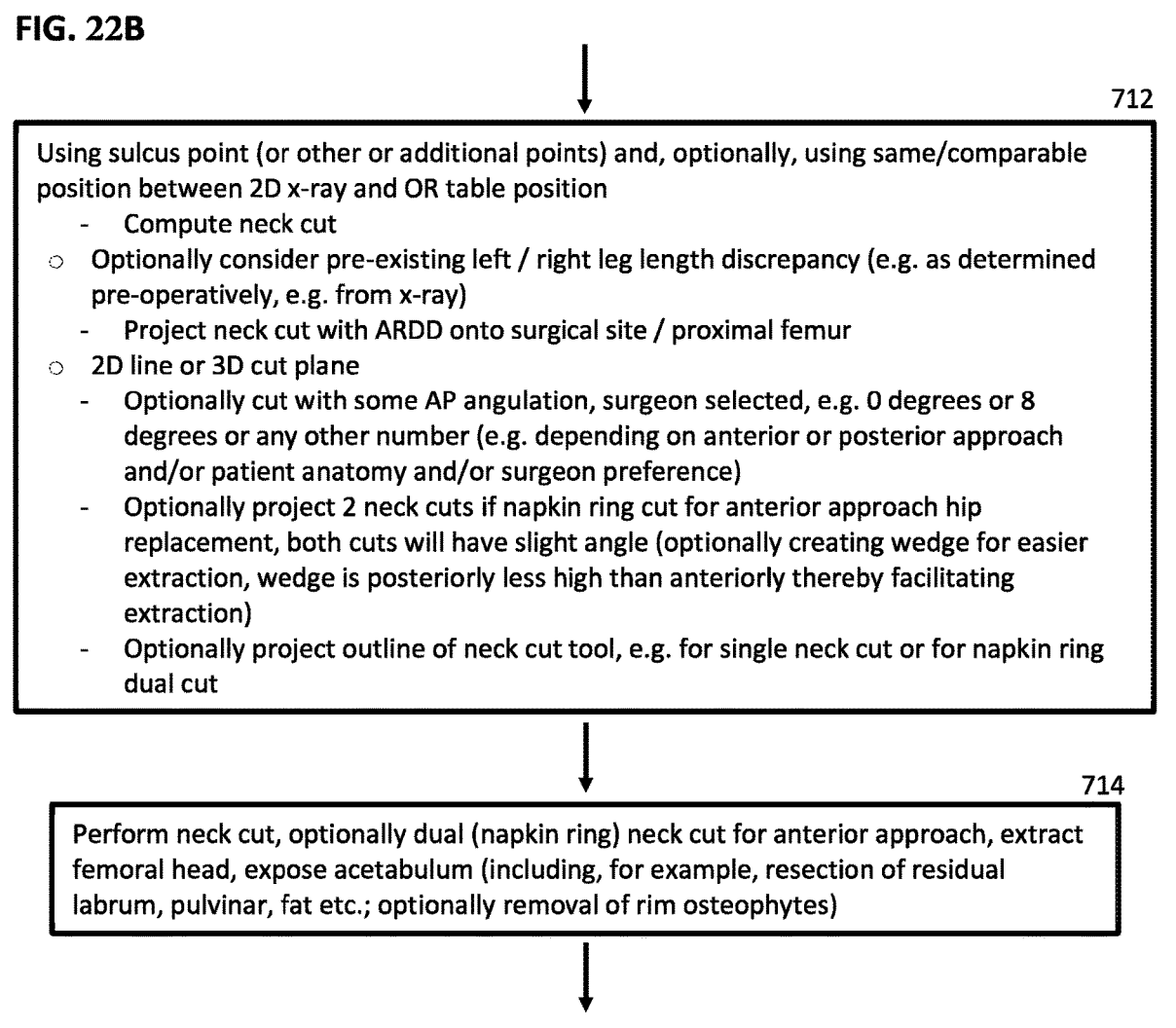

712

Using sulcus point (or other or additional points) and, optionally, using same/comparable position between 2D x-ray and OR table position

- Compute neck cut
  - Optionally consider pre-existing left / right leg length discrepancy (e.g. as determined pre-operatively, e.g. from x-ray)
- Project neck cut with ARDD onto surgical site / proximal femur
  - 2D line or 3D cut plane
- Optionally cut with some AP angulation, surgeon selected, e.g. 0 degrees or 8 degrees or any other number (e.g. depending on anterior or posterior approach and/or patient anatomy and/or surgeon preference)
- Optionally project 2 neck cuts if napkin ring cut for anterior approach hip replacement, both cuts will have slight angle (optionally creating wedge for easier extraction, wedge is posteriorly less high than anteriorly thereby facilitating extraction)
- Optionally project outline of neck cut tool, e.g. for single neck cut or for napkin ring dual cut

714

Perform neck cut, optionally dual (napkin ring) neck cut for anterior approach, extract femoral head, expose acetabulum (including, for example, resection of residual labrum, pulvinar, fat etc.; optionally removal of rim osteophytes)

FIG. 22C

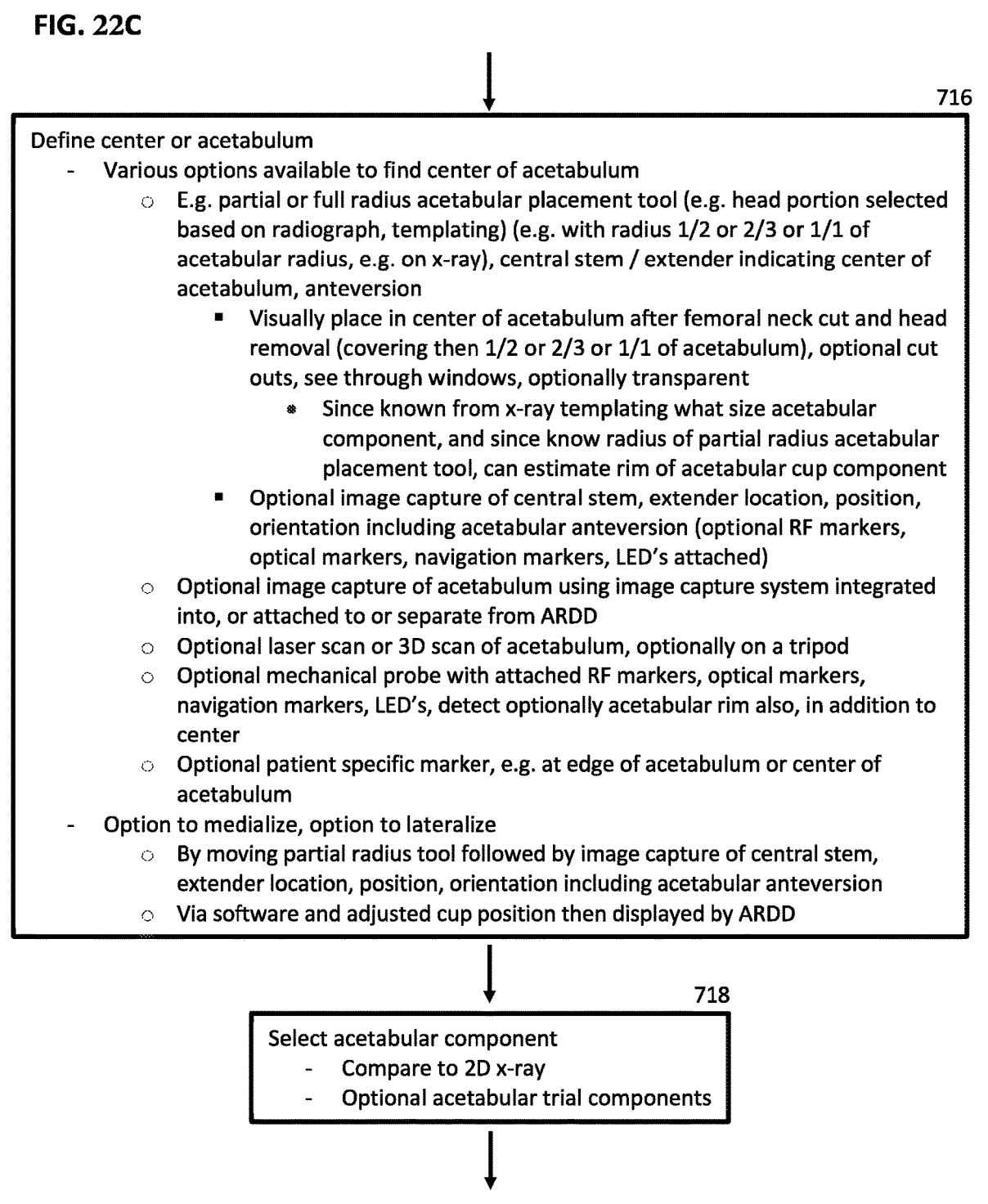

716

Define center or acetabulum
- Various options available to find center of acetabulum
  - E.g. partial or full radius acetabular placement tool (e.g. head portion selected based on radiograph, templating) (e.g. with radius 1/2 or 2/3 or 1/1 of acetabular radius, e.g. on x-ray), central stem / extender indicating center of acetabulum, anteversion
    - Visually place in center of acetabulum after femoral neck cut and head removal (covering then 1/2 or 2/3 or 1/1 of acetabulum), optional cut outs, see through windows, optionally transparent
      - Since known from x-ray templating what size acetabular component, and since know radius of partial radius acetabular placement tool, can estimate rim of acetabular cup component
    - Optional image capture of central stem, extender location, position, orientation including acetabular anteversion (optional RF markers, optical markers, navigation markers, LED's attached)
  - Optional image capture of acetabulum using image capture system integrated into, or attached to or separate from ARDD
  - Optional laser scan or 3D scan of acetabulum, optionally on a tripod
  - Optional mechanical probe with attached RF markers, optical markers, navigation markers, LED's, detect optionally acetabular rim also, in addition to center
  - Optional patient specific marker, e.g. at edge of acetabulum or center of acetabulum
- Option to medialize, option to lateralize
  - By moving partial radius tool followed by image capture of central stem, extender location, position, orientation including acetabular anteversion
  - Via software and adjusted cup position then displayed by ARDD

718

Select acetabular component
- Compare to 2D x-ray
- Optional acetabular trial components

FIG. 22D

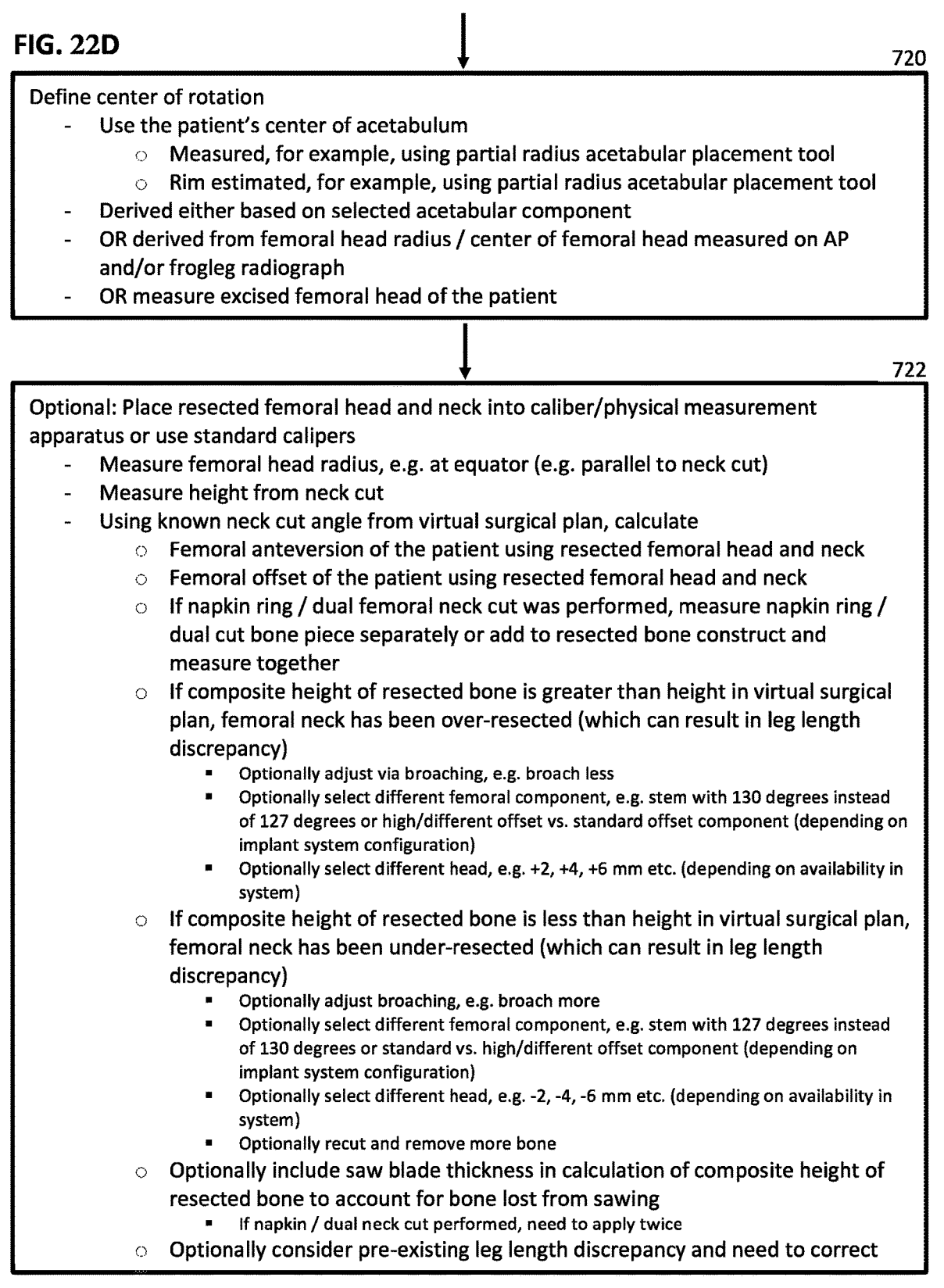

720

Define center of rotation
- Use the patient's center of acetabulum
  - Measured, for example, using partial radius acetabular placement tool
  - Rim estimated, for example, using partial radius acetabular placement tool
- Derived either based on selected acetabular component
- OR derived from femoral head radius / center of femoral head measured on AP and/or frogleg radiograph
- OR measure excised femoral head of the patient

722

Optional: Place resected femoral head and neck into caliber/physical measurement apparatus or use standard calipers
- Measure femoral head radius, e.g. at equator (e.g. parallel to neck cut)
- Measure height from neck cut
- Using known neck cut angle from virtual surgical plan, calculate
  - Femoral anteversion of the patient using resected femoral head and neck
  - Femoral offset of the patient using resected femoral head and neck
  - If napkin ring / dual femoral neck cut was performed, measure napkin ring / dual cut bone piece separately or add to resected bone construct and measure together
  - If composite height of resected bone is greater than height in virtual surgical plan, femoral neck has been over-resected (which can result in leg length discrepancy)
    - Optionally adjust via broaching, e.g. broach less
    - Optionally select different femoral component, e.g. stem with 130 degrees instead of 127 degrees or high/different offset vs. standard offset component (depending on implant system configuration)
    - Optionally select different head, e.g. +2, +4, +6 mm etc. (depending on availability in system)
  - If composite height of resected bone is less than height in virtual surgical plan, femoral neck has been under-resected (which can result in leg length discrepancy)
    - Optionally adjust broaching, e.g. broach more
    - Optionally select different femoral component, e.g. stem with 127 degrees instead of 130 degrees or standard vs. high/different offset component (depending on implant system configuration)
    - Optionally select different head, e.g. -2, -4, -6 mm etc. (depending on availability in system)
    - Optionally recut and remove more bone
  - Optionally include saw blade thickness in calculation of composite height of resected bone to account for bone lost from sawing
    - If napkin / dual neck cut performed, need to apply twice
  - Optionally consider pre-existing leg length discrepancy and need to correct

FIG. 22E

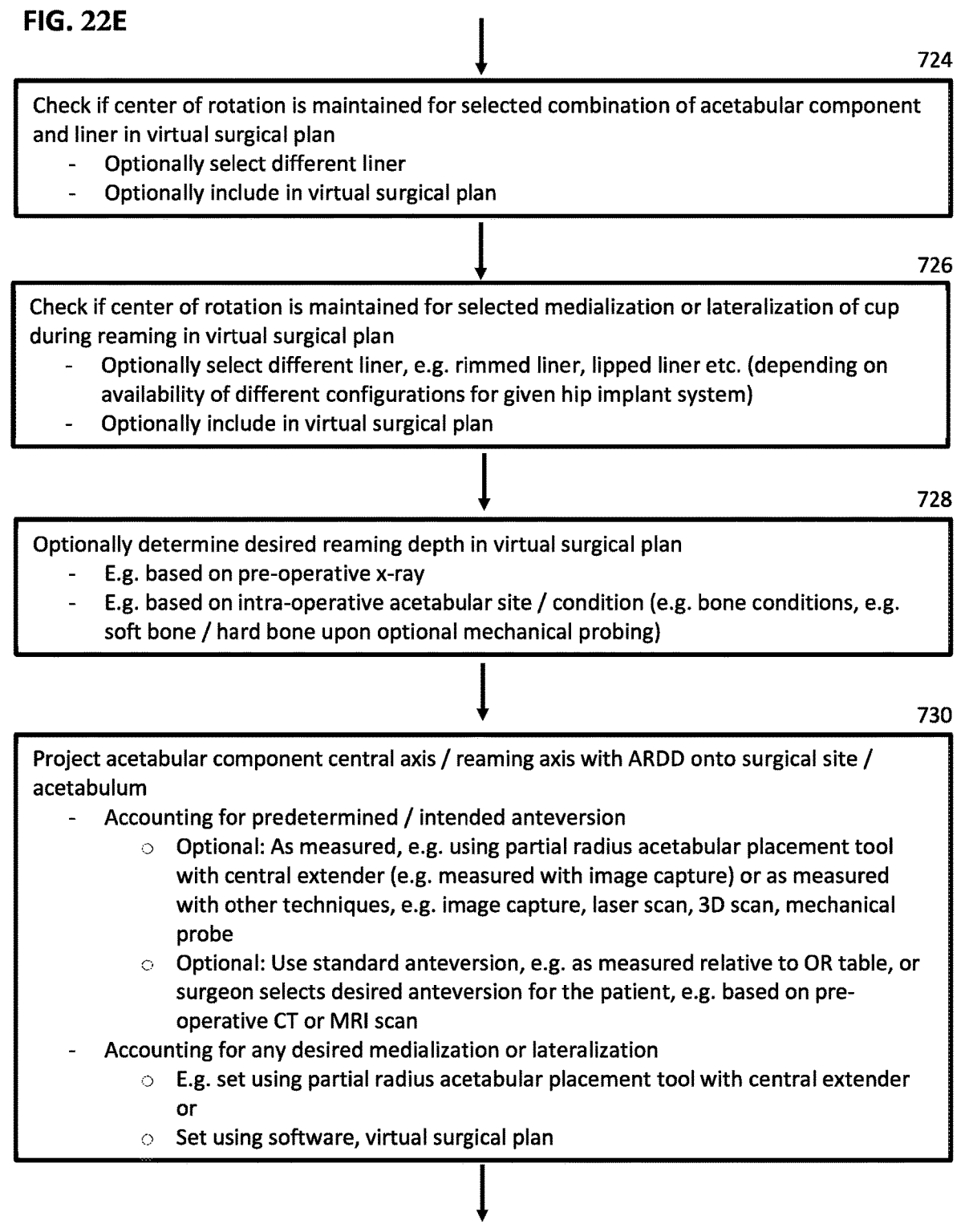

724

Check if center of rotation is maintained for selected combination of acetabular component and liner in virtual surgical plan
- Optionally select different liner
- Optionally include in virtual surgical plan

726

Check if center of rotation is maintained for selected medialization or lateralization of cup during reaming in virtual surgical plan
- Optionally select different liner, e.g. rimmed liner, lipped liner etc. (depending on availability of different configurations for given hip implant system)
- Optionally include in virtual surgical plan

728

Optionally determine desired reaming depth in virtual surgical plan
- E.g. based on pre-operative x-ray
- E.g. based on intra-operative acetabular site / condition (e.g. bone conditions, e.g. soft bone / hard bone upon optional mechanical probing)

730

Project acetabular component central axis / reaming axis with ARDD onto surgical site / acetabulum
- Accounting for predetermined / intended anteversion
    - Optional: As measured, e.g. using partial radius acetabular placement tool with central extender (e.g. measured with image capture) or as measured with other techniques, e.g. image capture, laser scan, 3D scan, mechanical probe
    - Optional: Use standard anteversion, e.g. as measured relative to OR table, or surgeon selects desired anteversion for the patient, e.g. based on pre-operative CT or MRI scan
- Accounting for any desired medialization or lateralization
    - E.g. set using partial radius acetabular placement tool with central extender or
    - Set using software, virtual surgical plan

FIG. 22F

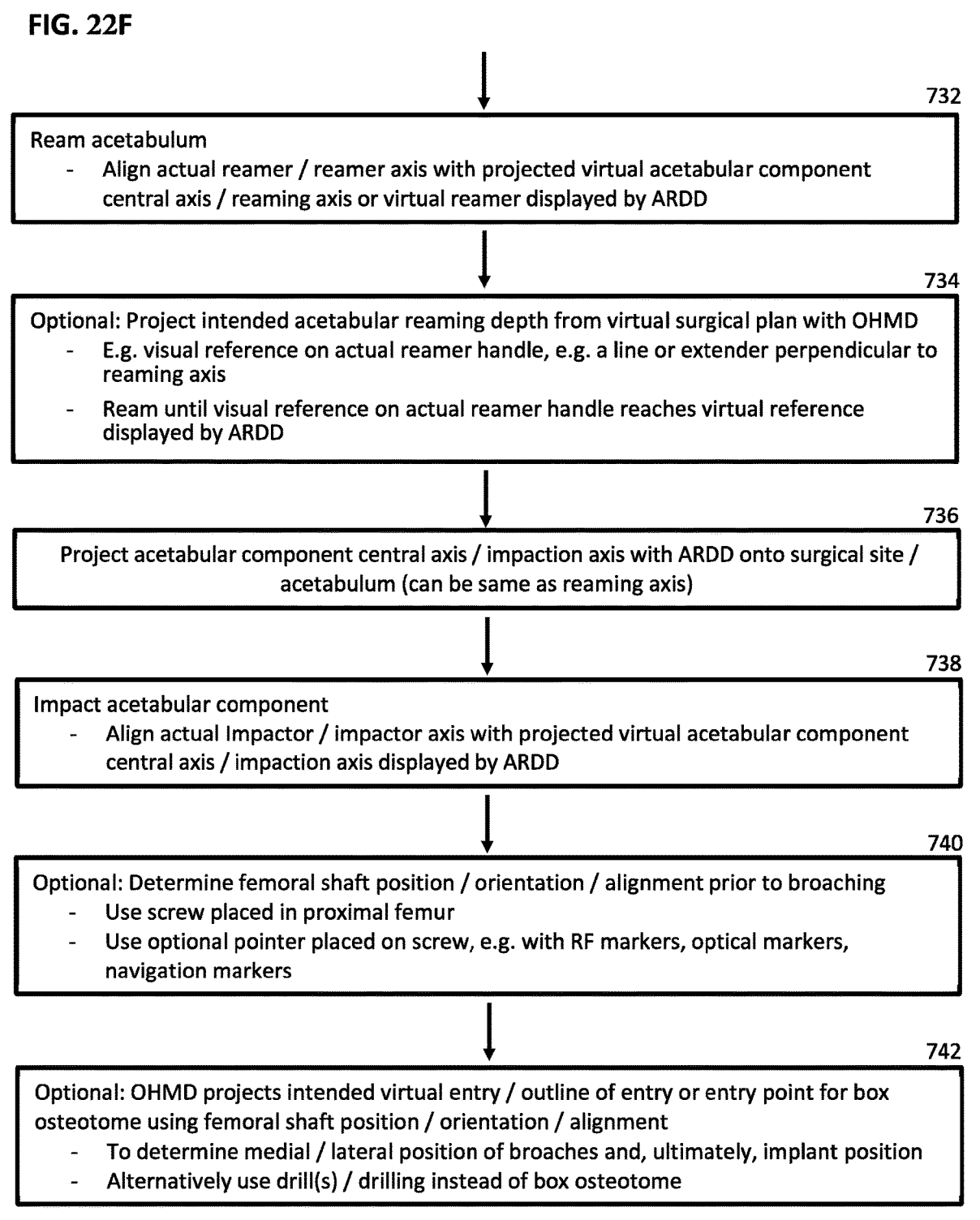

732

Ream acetabulum
- Align actual reamer / reamer axis with projected virtual acetabular component central axis / reaming axis or virtual reamer displayed by ARDD

734

Optional: Project intended acetabular reaming depth from virtual surgical plan with OHMD
- E.g. visual reference on actual reamer handle, e.g. a line or extender perpendicular to reaming axis
- Ream until visual reference on actual reamer handle reaches virtual reference displayed by ARDD

736

Project acetabular component central axis / impaction axis with ARDD onto surgical site / acetabulum (can be same as reaming axis)

738

Impact acetabular component
- Align actual Impactor / impactor axis with projected virtual acetabular component central axis / impaction axis displayed by ARDD

740

Optional: Determine femoral shaft position / orientation / alignment prior to broaching
- Use screw placed in proximal femur
- Use optional pointer placed on screw, e.g. with RF markers, optical markers, navigation markers

742

Optional: OHMD projects intended virtual entry / outline of entry or entry point for box osteotome using femoral shaft position / orientation / alignment
- To determine medial / lateral position of broaches and, ultimately, implant position
- Alternatively use drill(s) / drilling instead of box osteotome

AUGMENTED REALITY GUIDANCE METHODS AND SYSTEMS FOR USE WITH MICROSCOPES OR ENDOSCOPES IN SURGICAL PROCEDURES

RELATED APPLICATION(S)

This application is a continuation application of PCT International Application No. PCT/US2024/046696, filed Sep. 13, 2024, which claims the benefit of and the priority to U.S. Provisional Application No. 63/582,591, filed Sep. 14, 2023, the entire contents of each of which are incorporated by reference herein in its entirety.

TECHNICAL FIELD

Aspects of the present disclosure relate to devices and methods for performing a surgical step or surgical procedure with visual guidance by an augmented reality display device (ARDD) used in conjunction with microscopes or endoscopes.

BACKGROUND

With computer assisted surgery, e.g. surgical navigation or robotics, pre-operative and/or intra-operative imaging studies of the patient can be used, optionally in conjunction with microscopes or endoscopes during a procedure.

SUMMARY

Aspects of the disclosure relate to a system comprising a microscope or an endoscope, an augmented reality display device, a computer processor. In some embodiments, the computer processor is configured for tracking the microscope or endoscope in a coordinate system. In some embodiments, the computer processor is configured for receiving at least one image of a physical target tissue, wherein the at least one image comprises an x-ray image, ultrasound image, computed tomography (CT) image, magnetic resonance imaging (MRI) image, single photon emission computed tomography (SPECT) image, positron emission tomography (PET) image, cone beam CT image, nuclear scintigraphy image or a combination thereof, and wherein the at least one image is registered in the coordinate system. In some embodiments, the computer processor is configured for generating a virtual display of the physical target tissue, wherein the virtual display comprises a three-dimensional digital representation of the at least one image of the physical target tissue. In some embodiments, the computer processor is configured for tracking the patient, a physical tissue visible through the microscope or endoscope, the physical target tissue or a combination thereof in the coordinate system. In some embodiments, the computer processor is configured for generating an augmented view, the augmented view comprising the virtual display, wherein the augmented reality display device is configured to display the augmented view at the coordinates of the physical target tissue in the coordinate system. In some embodiments, the microscope or endoscope comprises a first field of view, the augmented reality display device comprises a second field of view. In some embodiments, the second field of view is larger than the first field of view and comprises a portion that extends outside the first field of view. In some embodiments, the augmented reality display device is configured for displaying in at least one dimension a portion of the virtual display of the physical target tissue that extends outside the first field of view, outside a boundary of physical tissue visible through the microscope or endoscope, or a combination thereof.

In some embodiments, the system comprises an access, a portal, an access portal, a tube, a retractor, or a combination thereof configured to insert the microscope, the endoscope, a surgical tool, a surgical instrument, a device, an implant, or a combination thereof. In some embodiments, the access, portal, access portal, tube, retractor, or combination thereof is configured for viewing the physical tissue or the plane of the physical tissue through the microscope or endoscope, wherein the boundary is determined by the inner dimension of the access, portal, access portal, tube, retractor, or combination thereof.

In some embodiments, the boundary comprises a wall, an edge, or a limit of one or more of an access, a portal, an access portal, a tube, a retractor, or a combination thereof, that limits area of the physical tissue visible through the microscope or endoscope.

In some embodiments, the field of view of the microscope or endoscope is an optical field of view.

In some embodiments, the field of view of the microscope or endoscope is a digital field of view.

In some embodiments, the augmented reality display device displays a digital image from the endoscope.

In some embodiments, the augmented reality display device is integrated into or attached to the microscope.

In some embodiments, the augmented view comprises a two dimensional (2D) stereoscopic view, a three-dimensional (3D) stereoscopic view or a combination thereof.

In some embodiments, the microscope is a digital microscope. In some embodiments, the microscope is configured for capturing video images of the physical tissue.

In some embodiments, the microscope is a stereoscopic microscope.

In some embodiments, the endoscope is a digital endoscope. In some embodiments, the endoscope is configured for capturing video images of the physical tissue.

In some embodiments, the endoscope is a stereoscopic endoscope.

In some embodiments, the at least one image of the physical target tissue is acquired by an imaging device intra-operatively, pre-operatively, or intra-operatively and pre-operatively. In some embodiments, the imaging device is an x-ray device, ultrasound device, computed tomography (CT) device, magnetic resonance imaging (MRI) device, single photon emission computed tomography (SPECT) device, positron emission tomography (PET) device, cone beam CT device, or a nuclear scintigraphy device. In some embodiments, the imaging device is different than the microscope or endoscope.

In some embodiments, the physical target tissue is, at least in part, hidden from the view through the microscope or endoscope by the physical tissue visible through the microscope or endoscope. In some embodiments, the physical target tissue is not visible through the microscope or endoscope.

In some embodiments, the augmented reality display device is a computer monitor, a tablet computer, a head mounted display, a stereoscopic optical see through head mounted display, or a stereoscopic video see through head mounted display. In some embodiments, the augmented reality display device is an augmented reality display unit integrated into or attached to a microscope or endoscope.

In some embodiments, the augmented reality display device comprises at least one augmented reality display unit. In some embodiments, the augmented reality display unit comprises at least one of a cathode ray tube, liquid crystal display, organic light emitting diodes (OLED), mirror, waveguide, optical fiber, light pipe, combiner, or a combination thereof. In some embodiments, the waveguide comprises at least one of a planar waveguide, slab waveguide, dielectric waveguide, strip waveguide, rib waveguide, segmented waveguide, rectangular waveguide, photonic crystal waveguide, laser inscribed waveguide, or a combination thereof.

In some embodiments, the field of view of the augmented reality display device is larger than the field of view of the microscope or endoscope.

In some embodiments, the at least one image of the physical target tissue comprises a volume of images. In some embodiments, the volume of images of the physical target tissue extends in at least one dimension outside a boundary of the physical tissue or the plane of the physical tissue visible through the microscope or endoscope. In some embodiments, the at least dimension comprises an x-dimension, y-dimension, z-dimension or a combination thereof.

In some embodiments, the virtual display comprises a 2D or a 3D representation of a virtual tool, virtual instrument, virtual implant, virtual device or a combination thereof, wherein the virtual tool, virtual instrument, virtual implant, virtual device or a combination thereof correspond to a physical tool, physical instrument, physical implant, physical device or a combination thereof.

In some embodiments, the system comprises a tracking device configured for tracking the physical tool, physical instrument, physical implant, physical device or a combination thereof in the coordinate system. In some embodiments, the physical tool, physical instrument, physical implant, physical device or a combination thereof comprises at least one infrared marker, retroreflective marker, radio frequency (RF) marker, active marker, passive marker, Inertial measurement unit (IMU), light emitting diode (LED), optical marker, geometric pattern, and the tracking device comprises a surgical navigation system, camera, video system, image capture system, depth sensor, laser scanner, 3D scanner, Lidar system, patient specific marker, patient specific template, x-ray system, imaging system, electromagnetic field, electromagnetic sensor, or combination thereof configured for tracking the physical tool, physical instrument, physical implant, physical device or combination thereof.

In some embodiments, the physical target tissue is a normal tissue, a diseased tissue, a neoplastic tissue, an inflamed tissue, an infected tissue, an edematous tissue, a tumor, a disc, a disc herniation, a free fragment, a bone, a bone spur, an organ tissue, a bowel, a bowel wall, a stomach, an esophagus, a stomach tissue, an esophageal wall, a bladder, a bladder all, a bladder tissue, a urethra, a urether, a renal pelvis, a renal tissue, a bronchus, a bronchial tissue, a trachea, a tracheal tissue, an intra-articular tissue, a ligament, a meniscus, a cartilage, a subchondral bone, a vessel, or a vascular tissue.

In some embodiments, the physical target tissue and the physical tissue are different.

In some embodiments, the computer processor is configured for real-time tracking of the microscope or endoscope, the patient, a physical tissue visible through the microscope or endoscope, the physical target tissue or a combination thereof in the coordinate system.

In some embodiments, the augmented reality display device is configured to display the augmented view at the coordinates of the physical target tissue in the coordinate system superimposed onto the physical tissue visible through the microscope or endoscope.

Aspects of the disclosure relates to a computer-implemented method comprising: tracking a microscope or an endoscope in a coordinate system; receiving at least one image of a physical target tissue from an imaging system different than the microscope or endoscope, wherein the physical target tissue is not visible through the microscope or endoscope; registering the at least one image in the coordinate system; generating a virtual display of the physical target tissue, wherein the virtual display comprises a three-dimensional digital representation of the at least one image of the physical target tissue; tracking a patient, a physical tissue visible through the microscope or endoscope, the physical target tissue or a combination thereof in the coordinate system, wherein the physical target tissue and the physical tissue are different; generating an augmented view, the augmented view comprising the virtual display; displaying the augmented view at the coordinates of the physical target tissue in the coordinate system; and displaying the physical target tissue outside a field of view of the microscope or endoscope, wherein a portion of the augmented view extends outside the field of view of view of the microscope or endoscope.

In some embodiments, the method comprises displaying the augmented view at the coordinates of the physical target tissue in the coordinate system superimposed onto the physical tissue visible through the microscope or endoscope.

In some embodiments, the method comprises acquiring the at least one image of the physical target tissue intra-operatively, pre-operatively, or intra-operatively and pre-operatively. In some embodiments, the at least one image comprises an x-ray, ultrasound scan, CT scan, MRI scan, SPECT scan, PET scan, cone beam CT scan, nuclear scintigraphy scan, or a combination thereof. In some embodiments, the at least one image of the physical target tissue comprises a volume of images. In some embodiments, the volume of images of the physical target tissue extends in at least one dimension outside a boundary of the physical tissue or the plane of the physical tissue visible through the microscope or endoscope. In some embodiments, the at least dimension comprises an x-dimension, y-dimension, z-dimension or a combination thereof.

Aspects of the disclosure relates to a surgical method comprising: placing an access, a portal, an access portal, a tube, a retractor, or a combination thereof in a patient; inserting a microscope, an endoscope, a surgical tool, a surgical instrument, a device, an implant, or a combination thereof through the access, a portal, an access portal, a tube, a retractor, or a combination thereof in a patient; tracking the microscope or endoscope in a coordinate system; receiving at least one image of a physical target tissue from an imaging system different than the microscope or endoscope, wherein the physical target tissue is not visible through the microscope or endoscope; registering the at least one image in the coordinate system; generating a virtual display of the physical target tissue, wherein the virtual display comprises a three-dimensional digital representation of the at least one image of the physical target tissue; tracking a patient, a physical tissue visible through the microscope or endoscope, the physical target tissue or a combination thereof in the coordinate system, wherein the physical target tissue and the physical tissue are different; generating an augmented view, the augmented view comprising the virtual display; displaying the augmented view at the coordinates of the physical target tissue in the coordinate system; displaying the physical target tissue outside a field of view of the microscope or endoscope, wherein a portion of the augmented view extends outside the field of view of view of the microscope or endoscope; generating a virtual display comprising a 2D or a 3D representation of a virtual tool, virtual instrument, virtual implant, virtual device or a combination thereof, wherein the virtual tool, virtual instrument, virtual implant, virtual device or a combination thereof correspond to a physical tool, physical instrument, physical implant, physical device or a combination thereof; tracking the surgical tool, surgical instrument, device, implant or combination thereof in the coordinate system outside the field of view of the microscope or endoscope.

Aspects of the disclosure relate to methods of performing a surgery in a patient using a microscope or endoscope intra-operatively comprising: tracking the microscope or endoscope in a coordinate system; adjusting a focal plane of the microscope or endoscope so that the focal plane extends, at least in part, through a physical tissue or a plane of a physical tissue exposed or accessed during the surgery; determining coordinates of the focal plane of the microscope or endoscope in the coordinate system; determining coordinates of a physical target tissue in the coordinate system or determining coordinates of an image of the physical target tissue in the coordinate system, wherein the physical target tissue has, at least in part, coordinates different from the physical tissue or the plane of the physical tissue; tracking the patient, the physical tissue or the plane or the physical tissue, the physical target tissue or a combination thereof in the coordinate system; displaying a computer-generated virtual display of the physical target tissue, a computer-generated virtual display of a three-dimensional (3D) representation of the image of the physical target tissue, or an image of the physical target tissue by an augmented reality display device at the coordinates of the physical target tissue in the coordinate system; and adjusting the focal plane of the virtual display or the focal plane of the image of the physical target tissue so that the focal plane of the virtual display or the image of the physical target tissue is the same as the focal plane of the microscope or endoscope, and/or so that a depth of field of the virtual display or of image of the physical target tissue overlaps, at least partially, with a depth of field of the microscope or endoscope.

In some embodiments, the focal plane of the microscope or endoscope is, at least in part, parallel to a portion of the physical tissue exposed or accessed during the surgery or to the plane of the physical tissue exposed or accessed during the surgery.

In some embodiments, the physical target tissue is, at least in part, hidden from the view through the microscope or endoscope by the physical tissue exposed or accessed during surgery or the plane of the physical tissue exposed or accessed during surgery.

In some embodiments, the method comprises digitally transferring the coordinates of the focal plane of the microscope or endoscope from a computer processor of the microscope or endoscope to a computer processor of the augmented reality display device.

In some embodiments, the method comprises adjusting the focal plane of the virtual display to be the same or similar as the focal plane of the microscope or endoscope using the computer processor of the augmented reality display device.

In some embodiments, the focal plane of the virtual display is parallel to the focal plane of the microscope or endoscope. In some embodiments, the focal plane of the virtual display differs from the focal plane of the microscope or endoscope by from about 0.001 mm to about 10 mm.

In some embodiments, the focal plane of the virtual display comprises one or more coordinates that are the same as the coordinates of the focal plane of the microscope or endoscope.

In some embodiments, the field of view of the augmented reality device is the same or smaller than the field of view of the microscope or endoscope.

In some embodiments, the field of view of the augmented reality device is larger than the field of view of the microscope or endoscope.

In some embodiments, the image of the physical target tissue comprises a volume of images.

In some embodiments, the volume of images of the physical target tissue extends in at least one dimension outside a boundary of the physical tissue or the plane of the physical tissue visible through the microscope or endoscope. In some embodiments, the at least dimension comprises an x-dimension, y-dimension, z-dimension or a combination thereof.

In some embodiments, the method comprises displaying by augmented reality display device a computer-generated virtual display comprising a portion of the physical target tissue, wherein the computer-generated virtual display extends outside the boundary, the field of view of the microscope or endoscope or a combination thereof, wherein the field of view of the augmented reality display device is wider than the boundary, the field of view of the microscope or endoscope or a combination thereof.

In some embodiments, the method comprises placing a tube for viewing the physical tissue or the plane of the physical tissue through the microscope or endoscope, wherein the boundary is determined by the inner dimension of the tube.

In some embodiments, the virtual display comprises the three-dimensional representation of the image of the physical target tissue.

In some embodiments, the method comprises setting shading of the three-dimensional representation for the coordinates of the physical target tissue in the coordinate system or for the coordinates of the at least one image of the physical target tissue in the coordinate system.

In some embodiments, the method comprises acquiring the image of the physical target tissue intra-operatively, pre-operatively, or intra-operatively and pre-operatively, wherein the image comprises an x-ray, ultrasound scan, CT scan, MRI scan, single photon emission computed tomography (SPECT) scan, positron emission tomography (PET) scan, cone beam CT scan, nuclear scintigraphy scan, or a combination thereof.

In some embodiments, the method comprises displaying, by the augmented reality display device, at least one two-dimensional (2D) image of the patient, 2D image of the target tissue, or combination thereof in a window adjacent to a window displaying the tissue or tissue plane visible through the microscope or endoscope.

In some embodiments, the computer-generated virtual display comprises a 2D or a 3D representation of a virtual tool, virtual instrument, virtual implant, virtual device or a combination thereof, wherein the virtual tool, virtual instrument, virtual implant, virtual device or a combination thereof correspond to a physical tool, physical instrument, physical implant, physical device or a combination thereof.

In some embodiments, the method comprises tracking the physical tool, physical instrument, physical implant, physical device or a combination thereof in the coordinate system. In some embodiments, the method comprises tracking the physical tool, physical instrument, physical implant, physical device or combination thereof with at least one infrared marker, retroreflective marker, RF marker, active marker, passive marker, IMU, LED, optical marker, geometric pattern, or a combination thereof using a surgical navigation system, camera, video system, image capture system, depth sensor, laser scanner, 3D scanner, Lidar system, patient specific marker, patient specific template, x-ray system, imaging system, electromagnetic field, electromagnetic sensor, or combination thereof.

In some embodiments, the depth of field of the virtual display by the augmented reality display device overlaps, at least in part, with the depth of field of the microscope or endoscope, wherein the overlap is from about 0.1 mm to about 40 mm.

In some embodiments, the method comprises adjusting magnification of the computer-generated virtual display to match magnification of the microscope or endoscope, wherein the magnification of the microscope or endoscope is about 0.5× to about 30.0×. In some embodiments, the magnified computer-generated virtual display comprises the image of the physical target tissue, a virtual 3D representation of the physical target tissue, a virtual surgical guide, a virtual axis, a virtual plane, a virtual tool, a virtual instrument, a virtual implant, a virtual device or a combination thereof.

In some embodiments, the target tissue is a normal tissue, a diseased tissue, a neoplastic tissue, an inflamed tissue, an infected tissue, an edematous tissue, a tumor, a disc, a disc herniation, a free fragment, a bone, a bone spur, an organ tissue, a bowel, a bowel wall, a stomach, an esophagus, a stomach tissue, an esophageal wall, a bladder, a bladder all, a bladder tissue, a urethra, a urether, a renal pelvis, a renal tissue, a bronchus, a bronchial tissue, a trachea, a tracheal tissue, an intra-articular tissue, a ligament, a meniscus, a cartilage, a subchondral bone, a vessel, or a vascular tissue.

In some embodiments, the method comprises tracking in real-time the microscope or endoscope, the patient, a physical tissue visible through the microscope or endoscope, the physical target tissue or a combination thereof in the coordinate system.

In some embodiments, the method comprises displaying the computer-generated virtual display by an augmented reality display device at the coordinates of the physical target tissue in the coordinate system overlaid onto the physical tissue or physical tissue plane visible through the microscope or endoscope.

In some embodiments, the physical target tissue is different than the physical tissue.

In some embodiments, the method comprises the augmented reality display device comprises a computer monitor, a tablet computer, a head mounted display, a stereoscopic optical see through head mounted display, or a stereoscopic video see through head mounted display, or wherein the augmented reality display device comprises an augmented reality display united integrated or attached into the microscope or endoscope.

Aspects of the disclosure relates to a method of performing a surgery in a patient using a microscope or endoscope intra-operatively comprising: tracking the microscope or endoscope in a coordinate system; adjusting a focal plane of the microscope or endoscope so that the focal plane extends, at least in part, through a physical tissue or a plane of a physical tissue exposed or accessed during the surgery; determining coordinates of the focal plane of the microscope or endoscope in the coordinate system; determining coordinates of a physical target tissue in the coordinate system or determining coordinates of an image of the physical target tissue in the coordinate system, wherein the physical target tissue and the image of the physical target tissue have, at least in part, coordinates different from the physical tissue or the plane of the physical tissue; tracking the patient, the physical tissue or the plane of the physical tissue, the physical target tissue or a combination thereof in the coordinate system; generating, by a computer processor, a virtual display of the physical target tissue, wherein the virtual display is a three-dimensional representation of at least one image of the physical target tissue; displaying a computer-generated virtual display of the physical target tissue, a computer-generated virtual display of a three-dimensional (3D) representation of the image of the physical target tissue, or an image of the physical target tissue at the coordinates of the physical target tissue in the coordinate system; adjusting the focal plane of the virtual display or the image of the physical target tissue so that the focal plane of the virtual display or the image of the physical target tissue is the same as the focal plane of the microscope or endoscope, and/or so that a depth of field of the virtual display or of the image of the physical target tissue overlaps, at least partially, with a depth of field of the microscope or endoscope. Aspects of the disclosure relates to a method of performing a surgery in a patient using a microscope or endoscope intra-operatively comprising: tracking the microscope or endoscope in a coordinate system; adjusting a focal plane of the microscope or endoscope so that the focal plane extends, at least in part, through a physical tissue or a plane of a physical tissue exposed or accessed during the surgery; determining coordinates of the focal plane of the microscope or endoscope in the coordinate system; determining coordinates of a physical target tissue in the coordinate system and/or determining coordinates of an image of the physical target tissue in the coordinate system, wherein the physical target tissue has, at least in part, coordinates different from the physical tissue or the plane of the physical tissue; tracking the patient, the physical tissue or the plane or the physical tissue, the physical target tissue or a combination thereof in the coordinate system; displaying a computer-generated virtual display of the physical target tissue, a computer-generated virtual display of a 3D representation of the image of the physical target tissue, or an image of the physical target tissue at the coordinates of the physical target tissue in the coordinate system; and adjusting the depth of field of the virtual display or of the image of the physical target tissue so that the depth of field overlaps, at least partially, with a depth of field of the microscope or endoscope. Aspects of the disclosure relates to a system comprising: a microscope or an endoscope, wherein the microscope or endoscope has an adjustable focal plane, an augmented reality device, a tracking device, and a computer processor. In some embodiments, the computer processor is configured to determine coordinates of the focal plane of the microscope or endoscope in the coordinate system. In some embodiments, the computer processor is configured to determine coordinates of a physical target tissue in the coordinate system and/or determining coordinates of an image of the physical target tissue in the coordinate system. In some embodiments, the physical target tissue has, at least in part, coordinates different from the physical tissue or the plane of the physical tissue. In some embodiments, the tracking device is configured to track the patient, the physical tissue or the plane or the physical tissue, the physical target tissue or a combination thereof in the coordinate system. In some embodiments, the augmented reality device is configured to display a virtual display of the physical target tissue, a virtual display of a 3D representation of the image of the physical target tissue, or an image of the physical target tissue at the coordinates of the physical target tissue in the coordinate system overlaid onto the physical tissue or physical tissue plane visible through the microscope or endoscope. In some embodiments, the computer processor is configured to adjust the depth of field of the virtual display or of the image of the physical target tissue so that the depth of field overlaps, at least partially, with a depth of field of the microscope or endoscope.

In some embodiments, the augmented reality display device is a computer monitor, a tablet computer, a head mounted display, a stereoscopic optical see through head mounted display, or a stereoscopic video see through head mounted display.

In some embodiments, the augmented reality display device is an augmented reality display unit integrated into or attached to a microscope or endoscope.

In some embodiments, a computer processor of the microscope or endoscope and a computer processor of the augmented reality display device are the same. In some embodiments, a computer processor of the microscope or endoscope and a computer processor of the augmented reality display device are different.

In some embodiments, the augmented reality display device comprises at least one augmented reality display unit. In some embodiments, the augmented reality display unit comprises at least one of a cathode ray tube, liquid crystal display, organic light emitting diodes (OLED), mirror, waveguide, optical fiber, light pipe, combiner, or a combination thereof. In some embodiments, the waveguide comprises at least one of a planar waveguide, slab waveguide, dielectric waveguide, strip waveguide, rib waveguide, segmented waveguide, rectangular waveguide, photonic crystal waveguide, laser inscribed waveguide, or a combination thereof.

Aspects of the disclosure relates to a method of performing a surgery in a patient using an endoscope intra-operatively comprising: tracking the endoscope in a coordinate system, wherein a focal plane of the endoscope extends, at least in part, through a physical tissue or a plane of a physical tissue exposed or accessed during the surgery; determining coordinates of the focal plane of the endoscope in the coordinate system; determining coordinates of a physical target tissue in the coordinate system or determining coordinates of at least one image of the physical target tissue in the coordinate system, wherein the physical target tissue has, at least in part, coordinates different from the physical tissue or the plane of the physical tissue; tracking the patient, the physical tissue or the plane of the physical tissue, the physical target tissue or a combination thereof in the coordinate system; generating, by a computer processor, a virtual display of the physical target tissue, wherein the virtual display is a three-dimensional digital representation of at least one image of the physical target tissue; displaying a computer-generated virtual display of the physical target tissue by an augmented reality display device at the coordinates of the physical target tissue in the coordinate system; and setting the focal plane of the virtual display so that the focal plane of the virtual display is the same as the focal plane of the endoscope, wherein a depth of field of the virtual display overlaps, at least partially, with a depth of field of the endoscope.

Aspects of the disclosure relates to a method of performing a surgery in a patient using an endoscope intra-operatively comprising: tracking the endoscope in a coordinate system, wherein a focal plane of the endoscope extends, at least in part, through a physical tissue or a plane of a physical tissue exposed or accessed during the surgery; determining coordinates of the focal plane of the endoscope in the coordinate system; determining coordinates of a physical target tissue in the coordinate system and/or determining coordinates of at least one image of the physical target tissue in the coordinate system, wherein the physical target tissue has, at least in part, coordinates different from the physical tissue or the plane of the physical tissue; tracking the patient, the physical tissue or the plane or the physical tissue, the physical target tissue or a combination thereof in the coordinate system; displaying a computer-generated virtual display of the physical target tissue by an augmented reality display device at the coordinates of the physical target tissue in the coordinate system; and setting the focal plane of the virtual display so that the focal plane of the virtual display is the same as the focal plane of the endoscope, wherein a depth of field of the virtual display overlaps, at least partially, with a depth of field of the endoscope.

Aspects of the disclosure relates to a method of performing a surgery in a patient using an endoscope intra-operatively comprising: tracking the endoscope in a coordinate system, wherein a focal plane of the endoscope extends, at least in part, through a physical tissue or a plane of a physical tissue exposed or accessed during the surgery; determining coordinates of the focal plane and a depth of field of the endoscope in the coordinate system; determining coordinates of a physical target tissue in the coordinate system and/or determining coordinates of at least one image of the physical target tissue in the coordinate system, wherein the physical target tissue has, at least in part, coordinates different from the physical tissue or the plane of the physical tissue; tracking the patient, the physical tissue or the plane or the physical tissue, the physical target tissue or a combination thereof in the coordinate system; displaying a computer-generated virtual display of the physical target tissue by an augmented reality display device at the coordinates of the physical target tissue in the coordinate system; and setting the depth of field of the virtual display so that the depth of field of the virtual display overlaps, at least partially, with a depth of field of the endoscope. In some embodiments, the method comprises displaying a computer-generated virtual display overlaid onto the physical tissue or physical tissue plane visible through the endoscope.

BRIEF DESCRIPTION OF THE DRAWINGS

Illustrative, non-limiting example embodiments will be more clearly understood from the following detailed description taken in conjunction with the accompanying drawings.

FIGS. 11A-11C are flow charts summarizing model generation, registration and view projection for one or more ARDD (e.g. HMD), e.g. by a primary surgeon, second surgeon, surgical assistant nurse, or others according to some embodiments of the present disclosure.

FIGS. 22A-22G are an illustrative, non-limiting example of a process flow for ARDD (e.g. HMD) guided surgery for hip replacement according to some embodiments of the present disclosure.

DETAILED DESCRIPTION

Figure 1:
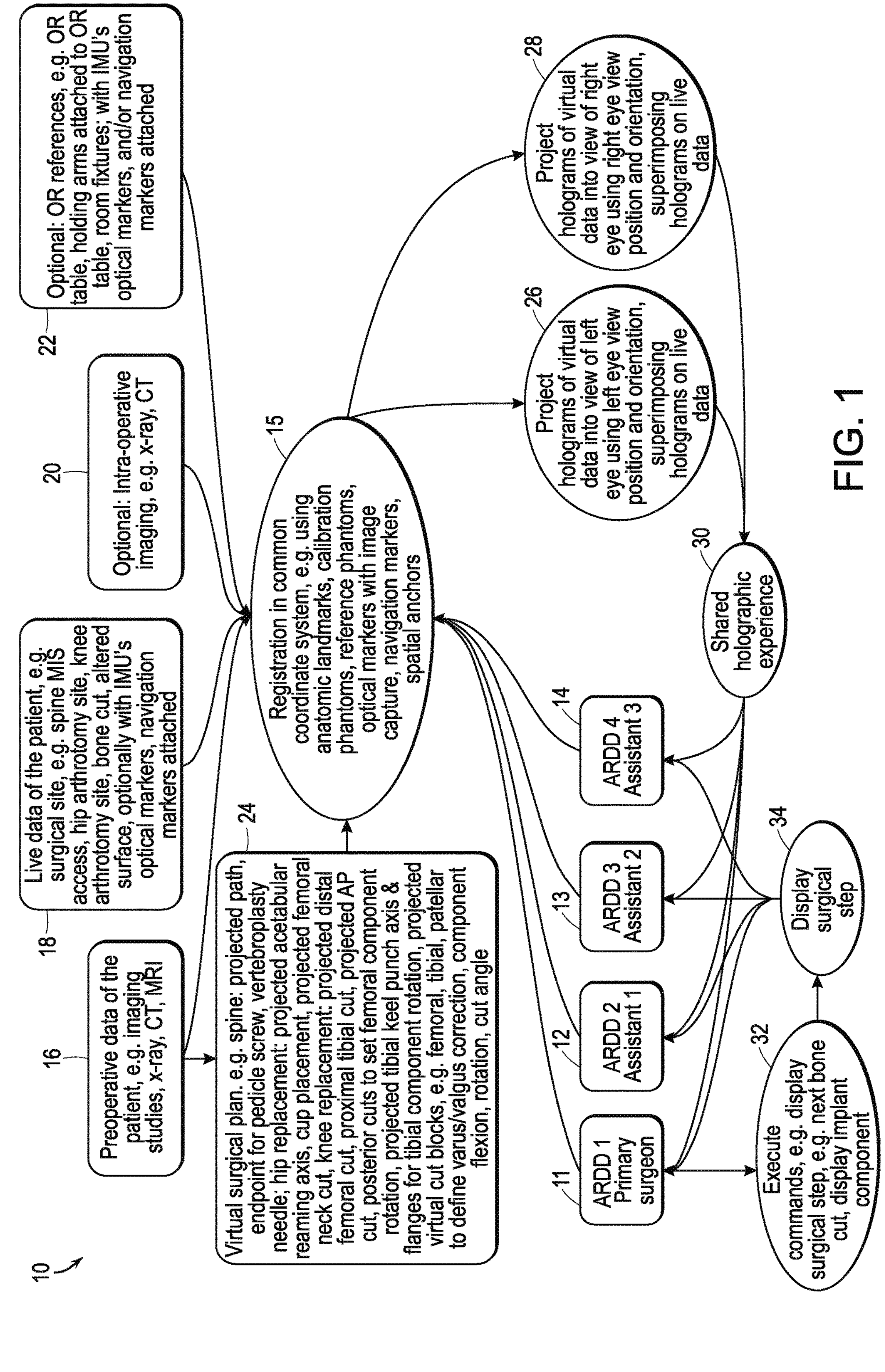
FIG. 1 shows the use of multiple ARDDs (e.g. HMD) for multiple viewer's, e.g. a primary surgeon, second surgeon, surgical assistant(s) and/or nurses(s) according to some embodiments of the present disclosure.

Aspects of the present disclosure provide, among other things, systems, devices and methods for a simultaneous visualization of live data of the patient and digital representations of virtual data such as virtual cuts and/or virtual surgical guides including cut blocks or drilling guides through an augmented reality display device (ARDD). The ARDDs can be a computer monitor, a tablet computer, a head mounted display, a stereoscopic optical see through head mounted display, or a stereoscopic video see through head mounted display. The ARDD can be an augmented reality display unit integrated into or attached to a microscope or endoscope. In some embodiments, the system can include one or more ARDD, one or more processor (e.g. one or more computer processors, including graphics processors or processors developed for artificial intelligence applications (for example, Nvidia [Santa Clara, CA] GEForce RTX 3060, GTX 1650, RTX 3060, Blackwell) and one or more user interfaces. The systems provided herein can include a processor, an electronic storage location operatively coupled with the processor, and processor executable code stored on the electronic storage location and embodied in a tangible non-transitory computer readable medium. The processor can be any suitable integrated circuits, such as computing platforms or microprocessors, logic devices and the like.

Any suitable computer readable medium may be utilized for storing the software for execution on one or more of the computers or ARDD or microscope or endoscope for realizing the methods described herein and for storing the disclosed data and information. The computer usable medium may include a propagated data signal with the computer-usable program code embodied therewith, either in baseband or as part of a carrier wave. The computer usable program code may be transmitted using any appropriate medium, including but not limited to the Internet, wireline, optical fiber cable, radio frequency (RF) or other means.

A software comprises specialized computer program instructions that are executed by being provided to an executing device, which can include a processor, or other programmable data processing apparatus or component, configured such that the instructions of the specialized computer program, when executed, create means for implementing the functions/acts described herein.

The ARDDs can be a computer monitor, a tablet computer, a head mounted display (HMD), a stereoscopic optical see through head mounted display, or a stereoscopic video see through head mounted display. The ARDD can be an augmented reality display unit integrated into or attached to a microscope or endoscope. In some embodiments, the surgical site including live data of the patient, the ARDD, and the virtual data are registered in a common coordinate system. In some embodiments, the virtual data are superimposed onto and aligned with the live data of the patient. In some embodiments, the head mounted display is a see-through ARDD. Unlike virtual reality head systems that blend out live data, the ARDD allows the surgeon to see the live data of the patient through the ARDD, e.g. the surgical field, while at the same time observing virtual data of the patient and/or virtual surgical instruments or implants with a predetermined position and/or orientation using the display of the ARDD unit. In some embodiments, an operator such as a surgeon can look through an ARDD observing physical data or information on a patient, e.g. a surgical site or changes induced on a surgical site, while pre-existing data of the patient are superimposed onto the physical visual representation of the live patient. Systems, methods and techniques to improve the accuracy of the display of the virtual data superimposed onto the live data of the patient are described in International Patent Application No. PCT/US2018/012459, which is incorporated herein by reference in its entirety.

Methods and systems of registration and cross-referencing including registration and cross-referencing surgical sites and one or more ARDDs (e.g. HMD or OHMD) such as the ones described in PCT International Application Serial Nos. PCT/US2017/021859, PCT/US2018/13774 and PCT/US2019/015522 and U.S. Pat. Nos. 11,727,581 B2, 9,861,446 and 10,154,239 can be used. Methods and systems of displaying virtual data in various surgical, medical or dental applications using one or more ARDDs such as the ones described in PCT International Application Serial Nos. PCT/US2017/021859, PCT/US2018/13774 and PCT/US2019/015522 and U.S. Pat. Nos. 11,727,581, 9,861,446 and 10,154,239. These applications are hereby incorporated by reference in their entireties.

Aspects of the present disclosure relate to systems, devices and methods for performing a surgical step or surgical procedure with visual guidance using a head mounted display (HMD). In some embodiments, the head mounted display can be a see-through head mounted display, e.g. an optical see through head mounted display (see through OHMD), for example for augmented reality applications. In some embodiments, the head mounted display can be a non-see-through head mounted display, e.g. video see through type, for virtual reality applications, optionally with video display including video streaming of live data from the patient, e.g. video feed from a camera integrated into, attached to, or separate from the head mounted display. The head mounted display can provide surgical guidance in a mixed reality environment. Various embodiments are described for adjusting the focal plane or focal point or selecting the focal plane or focal point for displaying virtual structures, objects, instruments, implants (e.g. implant components) or device using, for example, the distance between the head mounted display and the surgical site, e.g. an uncut or a cut bone in a joint replacement, a vertebral body or spinal element in a spinal procedure, a vessel or vascular structure in a cardiovascular, neurovascular, or general vascular procedure, or a tooth or gum in a dental procedure, or in any other surgical procedures, e.g. brain surgery, thoracic surgery, pelvic surgery, breast surgery etc.

Some aspects of the disclosure relate to a system for performing a surgical procedure, the system comprising: a processor; a see through head mounted display; and a marker attached to a patient, wherein, the system is configured to generate a 3D stereoscopic view of a virtual surgical guide, wherein the virtual surgical guide is a placement indicator at one or more predetermined coordinates indicating a predetermined position, predetermined orientation or combination thereof for aligning a physical surgical tool or a physical surgical instrument, wherein the system is configured to display the 3D stereoscopic view by the see through head mounted display onto the patient, wherein the processor is configured to determine a distance between the one or more predetermined coordinates of the virtual surgical guide and the see through head mounted display, wherein the one or more predetermined coordinates of the virtual surgical guide are referenced to or based on the marker, wherein the processor is configured to adjust at least one focal plane, focal point, or combination thereof of the display of the 3D stereoscopic view based on the determined distance.

In some embodiments, the system comprises one or more markers. In some embodiments, the marker is configured to reflect or emit light with a wavelength between 380 nm and 700 nm. In some embodiments, the marker is configured to reflect or emit light with a wavelength greater than 700 nm. In some embodiments, the marker is a radiofrequency marker (RF), or wherein the marker is an optical marker, wherein the optical marker includes a geometric pattern.

In some embodiments, the one or more markers comprise at least one marker attached to the patient, at least one marker attached to the see through head mounted display, at least one marker attached to a structure in the operating room or any combination thereof.

In some embodiments, the system is configured to determine one or more coordinates using one or more cameras.

In some embodiments, the one or more cameras detect light with a wavelength between 380 nm and 700 nm. In some embodiments, the one or more cameras detect light with a wavelength above 700 nm.

In some embodiments, the system comprises at least one camera integrated into or attached to the see through head mounted display. In some embodiments, at least one camera is separate from the head mounted display. In some embodiments, the one or more cameras are configured to determine the position, orientation, or position and orientation of the marker. In some embodiments, the one or more cameras are configured to determine one or more coordinates of the marker. In some embodiments, the one or more cameras are configured to track the one or more coordinates of the marker during movement of the marker. In some embodiments, the one or more cameras are configured to determine one or more coordinates of the see through head mounted display.

In some embodiments, the system is configured to track the one or more coordinates of the see through head mounted display during movement of the patient, the see through head mounted display, or the patient and the see through head mounted display.

In some embodiments, the system comprises one or more processors. In some embodiments, the one or more processors are configured to generate the 3D stereoscopic view of the virtual surgical guide. In some embodiments, the one or more processors are configured to determine the distance between the one or more predetermined coordinates of the virtual surgical guide and the see through head mounted display. In some embodiments, the one or more processors are configured to track one or more coordinates of at least one or more markers, one or more see through head mounted displays, or combinations thereof during movement of the patient, the see through head mounted display or the patient and the see through head mounted display. In some embodiments, the one or more processors are configured to determine the distance between the one or more predetermined coordinates of the virtual surgical guide and the see through head mounted display during movement of the marker, movement of the see through head mounted display, or movement of the marker and the see through head mounted display, and wherein the one or more processors are configured to adjust the at least one focal plane, focal point, or combination thereof based on the change in the determined distance.

In some embodiments, the one or more processors are configured to adjust the at least one focal plane, focal point or combination thereof intermittently. In some embodiments, the one or more processors are configured to adjust the at least one focal plane, focal point or combination thereof continuously.

In some embodiments, the physical surgical tool or physical surgical instrument is configured to effect a tissue removal in the patient. The tissue removal can be a removal of bone or a removal of cartilage or a removal of bone and cartilage.

In some embodiments, the system comprises one or more see through head mounted displays. The one or more see through head mounted displays can comprise one or more combiners and/or one or more waveguides. The one or more see through head mounted displays can comprise one or more mirrors.

In some embodiments, the one or more see through head mounted displays comprise a first display unit for the left eye and a second display unit for the right eye. In some embodiments, the one or more see through head mounted displays comprise a stack of one or more planar or non-planar display units. The one or more planar or non-planar display units comprise at least one of a combiner, a mirror, a waveguide, or combinations thereof. In some embodiments, the at least one focal plane, focal point or combination thereof matching the determined distance coincides with at least one of the planar or non-planar display units in the stack. In some embodiments, the stack of one or more planar or non-planar display units display a range of focal planes, focal points or combination thereof and wherein the range of focal planes, focal points or combination thereof includes a focal plane, focal point or combination thereof near the determined distance.

In some embodiments, the one or more see through head mounted displays comprise at least one active optical element for adjustment of the at least one focal plane, focal point or combination thereof. The system comprises one or more mechanical, electrical, electromagnetic, piezoelectric adjustment effectors, or combinations thereof, and wherein the mechanical, electrical, electromagnetic, piezoelectric adjustment effectors, or combination thereof are configured to move at least a portion of the at least one active optical element to adjust the at least one focal plane, focal point or combination thereof. In some embodiments, the movement of the at least portion of the at least one active optical element comprises at least one translation, rotation, pivoting, or combination thereof of the of the at least portion of the at least one active optical element. In some embodiments, the at least one active optical element comprises a deformable lens or a deformable mirror or combinations thereof.

In some embodiments, the virtual surgical guide is a virtual path, a virtual trajectory, a virtual surgical tool, a virtual surgical instrument, a virtual cut block, a virtual trial implant, a virtual implant component, a virtual implant, a virtual device, a predetermined start point, a predetermined start position, a predetermined start orientation or alignment, a predetermined intermediate point, a predetermined intermediate position, a predetermined intermediate orientation or alignment, a predetermined end point, a predetermined end position, a predetermined end orientation or alignment, a predetermined plane, a predetermined cut plane, a predetermined depth marker, a predetermined stop, a predetermined angle or orientation or rotation marker, a predetermined axis, or a predetermined tissue change or alteration.

Aspects of the disclosure relate to a system for performing a surgical procedure in a patient, the system comprising: a processor; a see through head mounted display; and a marker attached to a patient, wherein the see through head mounted display comprises a first display unit for the left eye and a second display unit for the right eye, wherein the system is configured to generate a first view of a virtual surgical guide for the first display unit and a second view of the virtual surgical guide for the second display unit, wherein the virtual surgical guide is a placement indicator at one or more predetermined coordinates indicating a predetermined position, predetermined orientation or combination thereof for aligning a physical surgical tool or a physical surgical instrument, wherein the system is configured to generate using the first view and using the second view a 3D stereoscopic view of the virtual surgical guide based on the one or more predetermined coordinates, wherein the system is configured to display the 3D stereoscopic view by the see through head mounted display onto the patient, wherein the system is configured to determine a distance between the one or more predetermined coordinates and the see through head mounted display, wherein the one or more predetermined coordinates are referenced to or based on the marker, wherein the system is configured to adjust the convergence between the first and second views displayed by the first display unit and the second display unit of the virtual surgical guide based on the determined distance.

In some embodiments, the system comprises one or more processors, one or more markers, one or more see through head mounted display or combinations thereof. In some embodiments, the one or more processors are configured to generate the 3D stereoscopic view of the virtual surgical guide. In some embodiments, the one or more processors are configured to determine the distance between the one or more predetermined coordinates of the virtual surgical guide and the see through head mounted display. In some embodiments, the one or more processors are configured to track one or more coordinates of one or more markers, one or more see through head mounted displays, or combinations thereof during movement of the patient, movement of the see through head mounted display or movement of the patient and the see through head mounted display. In some embodiments, the one or more processors are configured to determine the distance between the one or more predetermined coordinates of the virtual surgical guide and the see through head mounted display during movement of the marker, movement of the see through head mounted display, or movement of the marker and the see through head mounted display, and wherein the one or more processors are configured to adjust the convergence based on a change in the determined distance. In some embodiments, the one or more processors are configured to adjust the convergence intermittently. In some embodiments, the one or more processors are configured to adjust the convergence continuously.

In some embodiments, the system comprises one or more see through head mounted displays. The one or more see through head mounted displays can comprise one or more combiners and/or one or more waveguides. The one or more see through head mounted displays can comprise one or more mirrors.

In some embodiments, the one or more see through head mounted displays comprise a stack of planar or non-planar display units. The one or more planar or non-planar display units comprise at least one combiner, a mirror, a waveguide, or combinations thereof.

In some embodiments, the one or more see through head mounted displays comprise at least one active optical element to adjust the convergence. In some embodiments, the system comprises one or more mechanical, electrical, electromagnetic, piezoelectric adjustment effectors, or combination thereof and wherein the mechanical, electrical, electromagnetic, piezoelectric adjustment effectors, or combination thereof are configured to move at least a portion of the at least one active optical element to adjust the convergence. The movement can comprise a translation, rotation, pivoting, or combination thereof of the at least one active optical element. In some embodiments, the at least one active optical element comprises a deformable lens or a deformable mirror or combinations thereof.

In some embodiments, the convergence between the first and second views is adjusted by adjusting a size, dimension, position, orientation or combination thereof of the first and second views on the first and second display units based on the determined distance.

In some embodiments, the virtual surgical guide is a virtual path, a virtual trajectory, a virtual surgical tool, a virtual surgical instrument, a virtual cut block, a virtual trial implant, a virtual implant component, a virtual implant, a virtual device, a predetermined start point, a predetermined start position, a predetermined start orientation or alignment, a predetermined intermediate point, a predetermined intermediate position, a predetermined intermediate orientation or alignment, a predetermined end point, a predetermined end position, a predetermined end orientation or alignment, a predetermined plane, a predetermined cut plane, a predetermined depth marker, a predetermined stop, a predetermined angle or orientation or rotation marker, a predetermined axis, or a predetermined tissue change or alteration.

In some embodiments, the system is configured to determine one or more coordinates using one or more cameras. The one or more cameras can detect light with a wavelength between 380 nm and 700 nm or with a wavelength above 700 nm.

In some embodiments, at least one camera integrated into or attached to the see through head mounted display. In some embodiments, at least one camera is separate from the head mounted display.

In some embodiments, the one or more cameras are configured to determine the position, orientation, or position and orientation of the marker. In some embodiments, the one or more cameras are configured to determine one or more coordinates of the marker.

In some embodiments, the system is configured to track the one or more coordinates of the marker during movement of the marker.

In some embodiments, the one or more cameras are configured to determine one or more coordinates of the see through head mounted display.

In some embodiments, the system is configured to track the one or more coordinates of the see through head mounted display during movement of the patient, movement of the see through head mounted display, or movement of the patient and the see through head mounted display.

In some embodiments, the physical surgical tool or physical surgical instrument is configured to effect a tissue removal in the patient. In some embodiments, the tissue removal is a removal of bone or a removal of cartilage or a removal of bone and cartilage.

In some embodiments, the marker is configured to reflect or emit light with a wavelength between 380 nm and 700 nm. In some embodiments, the marker is configured to reflect or emit light with a wavelength greater than 700 nm. In some embodiments, the marker is a radiofrequency marker, or wherein the marker is an optical marker, wherein the optical marker includes a geometric pattern.

In some embodiments, the system comprises one or more markers. In some embodiments, the one or more markers comprise at least one marker attached to the patient, at least one marker attached to the see through head mounted display, at least one marker attached to a structure in the operating room or any combination thereof.

Aspects of the present disclosure describe novel systems, devices and methods for performing a surgical step or surgical procedure with visual guidance using a head mounted display, e.g. by displaying virtual representations of one or more of a virtual surgical tool, virtual surgical instrument including a virtual surgical guide or cut block, virtual trial implant, virtual implant component, virtual implant or virtual device, a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration, on a live patient. In some embodiments, the head mounted display (HMD) is a see-through head mounted display. In some embodiments, an optical see through HMD is used. In some embodiments, a video see through HMD can be used, for example with a camera integrated into, attached to, or separate from the HMD, generating video feed.

In some embodiments, one or more optical head mounted display can be used wirelessly.

Bluetooth

In some embodiments, the device can comprise a Bluetooth transmitter and/or receiver. Bluetooth can be a packet-based protocol with a master/slave architecture. One master can communicate with multiple slaves in a piconet. A master Bluetooth device can communicate with multiple devices in a piconet. The devices can switch roles, by agreement, and the slave can become the master (for example, a headset initiating a connection to a phone necessarily begins as master—as an initiator of the connection—but may subsequently operate as the slave).

Bluetooth can be a layer protocol architecture comprising core protocols, cable replacement protocols, telephony control protocols, and adopted protocols.

The device can, in some embodiments, employ high-speed Bluetooth protocols.

The device can comprise an interface between a server and the device using a Bluetooth device. The interface can be HCI (Host Controller Interface).

The Host Controller Interface can provide a command interface for the controller and for the link manager, which can allow access to the hardware status and control certain registers. This interface can provide an access layer for all Bluetooth devices. The HCI layer of the machine can exchange commands and data with the HCI firmware present in the Bluetooth device. The HCI can, in some embodiments, automatically discover other Bluetooth devices that are within the coverage radius.

The hardware that constitutes a Bluetooth device, including the Bluetooth device that can optionally be within the device, can include two parts: a radio device, responsible for modulating and transmitting the signal and a digital controller. These specific parts can, in some embodiments be physically separate and can in other embodiments be physically together.

The digital controller can, in some embodiments, be CPU. In some embodiments, the CPU can run a Link Controller; and interfaces with the host device, such as the Host Controller Interface. The Link Controller can be responsible for the processing of the baseband and the management of ARQ and physical layer FEC protocols. The CPU can, in some embodiments, handle the transfer functions (both asynchronous and synchronous), audio coding, and data encryption. The CPU of the device is, in some embodiments, responsible for performing the instructions related to the Bluetooth of the host device, in order to simplify its operation. For the performance of specific instructions related to the Bluetooth of the host device, the CPU can run software called Link Manager that has the function of communicating with other devices through the LMP protocol.

The Link Manager can, in some embodiments, establish the connection between devices. For example, the Link Manager can establish the connection between the device, either between the drill or saw handle and saw battery or integrated within the drill or saw and the server. The Link Manager can be responsible for the establishment, authentication and configuration of the link. The Link Manager can furthermore find other managers and communicates with them due to the management protocol of the LMP link.

The Link Manager Protocol can comprise a number of PDUs (Protocol Data Units) that can be sent from one device to another. The following is a list of supported services:

1) Transmission and reception of data.
2) Name request
3) Request of the link addresses.
4) Establishment of the connection.
5) Authentication.
6) Negotiation of link mode and connection establishment.

The system, when in discoverable mode, can transmit the following information on demand:

1) Device name
2) Device class
3) List of services
4) Technical information (for example: device features, manufacturer, Bluetooth specification used, clock offset)

The system can have a unique 48-bit address. The system can have a friendly Bluetooth name, which can be set by the user. This name can appear when another user scans for devices and in lists of paired devices.

During pairing between the server and the system attached to or integrated into the saw or drill, the two can establish a relationship by creating a shared secret or a link key. If both devices store the same link key, they are paired or bonded.

The following are pairing mechanisms that can be used in some embodiments:

1) Legacy pairing, wherein each device must enter a PIN code; pairing is only successful if both devices enter the same PIN code. Legacy has the following authentication mechanisms:
   a. Limited input devices, wherein the devices have a fixed PIN, for example "1111" or "2222", that are hard-coded into the device
   b. Numeric input devices, wherein the user can enter a numeric value up to 16 digits in length c. Alpha-numeric input devices wherein the user can enter full UTF-8 text as a PIN code 2) Secure Simple Pairing (SSP), using a public key cryptography, and certain modifications can help protect against man in the middle, or MITM attacks. SSP has the following authentication mechanisms:

a. Just works: This method functions with no user interaction. However, the device may prompt the user to confirm the pairing process.

b. Numeric comparison: The devices being paired display a 6-digit numeric code. The user can compare the numbers to ensure they are the exact same. If the comparison succeeds, the user(s) can confirm pairing on the device(s) that can accept an input. This method provides MITM protection, assuming the user confirms on both devices and actually performs the comparison properly.

c. Passkey Entry: This mechanism can be used between a device with a display and a device with numeric keypad entry (such as a keyboard), or two devices with numeric keypad entry. In the first case, the display presents a 6-digit numeric code to the user, who then enters the code on the keypad. In the second case, the user of each device enters the same 6-digit number.

d. Out of band (OOB): This method uses an external means of communication, such as near-field communication (NFC) to exchange information used in the pairing process. Pairing is completed using the Bluetooth radio, but requires information from the OOB mechanism.

In some embodiments, the device comprises a Bluetooth transmitter and/or receiver wherein the Bluetooth transmitter and/or receiver is configured to work in conjunction with an augmented reality surgical guidance system, a surgical navigation system, a robot, a robotic system, and/or a handheld robot.

In some embodiments, the Bluetooth transmitter and/or receiver and the established connection between the Bluetooth transmitter and/or receiver and the augmented reality surgical guidance system, surgical navigation system, robot, robotic system, and/or handheld robot can work in conjunction with one or more on/off switches and/or one or more potentiometers, e.g. digital potentiometers, and/or one or more rheostats and/or one or more actuators to regulate the speed of the movement of a saw blade or movement of a drill bit or to provide haptic feedback.

For example, in cases where the augmented reality surgical guidance system, surgical navigation system, robot, robotic system, and/or handheld robot detects a movement of the drill or saw deviating from the intended surgical axis, target, target area, target volume, tissue resection target, area, volume (e.g. bone or tissue removal or resection, e.g. with a bone drill or bone saw) by a specific distance in any direction in one or more dimensions the augmented reality surgical guidance system, surgical navigation system, robot, robotic system, and/or handheld robot can transmit information to the Bluetooth receiver which can regulate the Bluetooth switch, including both a transmitter and receiver, to activate an on/off switch and/or a potentiometer, e.g. digital, and/or a rheostat and/or a specific actuator for haptic feedback. In cases where the augmented reality surgical guidance system, surgical navigation system, robot, robotic system, and/or handheld robot detects a movement of the drill or saw that approaches, for example, a specific anatomical structure or safe zone, the augmented reality surgical guidance system, surgical navigation system, robot, robotic system, and/or handheld robot can similarly work in conjunction with the Bluetooth switch within the device attached to the drill or saw to adjust, control, and/or regulate an on/off switch and/or a potentiometer and/or a rheostat and/or a specific actuator for haptic feedback. The same concept can similarly work for turning on or increasing the speed of the movement of the saw blade or the drill bit or other power tool or instrument when approaching certain anatomic structures.

The Bluetooth switch, Bluetooth receiver, and/or Bluetooth transmitter can, in some embodiments, employ low latency Bluetooth in order to provide instant saw or drill speed regulation or instant haptic feedback.

WiFi

In some embodiments, the device comprises a WiFi transmitter and/or receiver. In some embodiments, the device can comprise WiFi capability. Different versions of WiFi can be used including but not limited to: 802.11a, 802.11b, 802.11g, 802.11n (Wi-Fi 4[40]), 802.11h, 802.11i, 802.11-2007, 802.11-2012, 802.11ac (Wi-Fi 5[40]), 802.11ad, 802.11af, 802.11-2016, 802.11ah, 802.11ai, 802.11aj, 802.11aq, 802.11ax (Wi-Fi 6[40]), and 802.11ay.

In some embodiments, the device comprises a WiFi transmitter and/or receiver wherein the WiFi transmitter and/or receiver is configured to work in conjunction with a surgical guidance system.

In some embodiments, the system can include routers that can be configured for intranet and internet connections.

In some embodiments, the system can utilize several distinct radio frequency ranges. For example, the system utilizes the 802.11 standard, it can include distinct radio frequencies ranges for use in Wi-FI communications such as: 900 MHz, 2.4 GHz, 5 GHz, 5.9 GHz, and 60 GHz bands. Each frequency or range can have a multitude of channels.

In some embodiments, the system and/or device's Wi-Fi can be part of the IEEE 802 protocol family. In some embodiments, the system and/or device can comprise one or more transmitters. WiFi transmitters are low power devices.

In some embodiments, the system and/or device can comprise one or more antennas. The system and/or device can comprise an access point compliant with 802.11b and/or 802.11g. Using the stock omnidirectional antenna can have a range of 100 m (0.062 mi). The identical radio with an external semi parabolic antenna (15 dB gain) with a similarly equipped receiver at the far end can have a range over 20 miles.

In some embodiments, the system and/or device can comprise multiple-input and multiple-output. The system and/or device including but not limited to standards such as IEEE 802.11n and IEEE 802.11ac, can comprise multiple antennas for extended range and higher speeds.

In some embodiments, the WiFi can comprise Local Area Networks (LAN).

In some embodiments, the device can include one or more access points. A wireless access point can connect a group of wireless devices to an adjacent wired LAN.

In some embodiments, the device can include one or more wireless adapters. Wireless adapters can allow devices to connect to a wireless network.

In some embodiments, the device can include one or more routers. Wireless routers can integrate a Wireless Access Point, Ethernet switch, and internal router firmware application that provides IProuting, NAT, and DNS forwarding through an integrated WAN-interface.

In some embodiments, the device can include one or more wireless network bridges. Wireless network bridges can act to connect two networks to form a single network at the data-link layer over Wi-Fi. The main standard is the wireless distribution system (WDS). Wireless bridging can connect a wired network to a wireless network.

In some embodiments, the device can include one or more security features. Security features can be any security standard known in the art.

In some embodiments, the WiFi transmitter and/or receiver and the established connection between the WiFi transmitter and/or receiver and the augmented reality surgical guidance system can work in conjunction with one or more on/off switches and/or one or more potentiometers and/or one or more rheostats and/or one or more actuators to regulate the oscillation of a saw blade or movement of a drill bit or to provide haptic feedback.

For example, in cases where the augmented reality surgical guidance system detects a movement of the drill or saw or other power tool or instrument deviating from the intended cut/drill surgical axis, the surgical guidance system can regulate the WiFi switch, including both a transmitter and receiver, to activate an on/off switch and/or a potentiometer, e.g. digital, and/or a rheostat and/or a specific actuator for haptic feedback. In cases where the surgical guidance system detects a movement of the drill or saw or other power tool or instrument that approaches, for example, a specific anatomical structure or safe zone, the surgical guidance system can similarly work in conjunction with the WiFi switch within the device attached to the drill or saw or other power tool or instrument to activate an on/off switch and/or a potentiometer and/or a rheostat and/or a specific actuator for haptic feedback. The same concept can similarly work for turning on or increasing the speed of the movement of the saw blade or the drill bit or other power tool or instrument when approaching certain anatomic structures.

LiFi

In some embodiments, the device comprises a LiFi transmitter and/or receiver. In some embodiments, the device can comprise LiFi capability. LiFi can use light from light-emitting diodes (LEDs) as a medium to deliver networked, mobile, high-speed communication.

In some embodiments, the system can comprise visible light communications (VLC). VLC works by switching the current to the LEDs off and on at very high speeds.

In some embodiments, the system can comprise Bg-Fi. Bg-Fi can be a Li-Fi system consisting of an application for a mobile device, and a simple consumer product device, with color sensor, microcontroller, and embedded software. Light from the mobile device display communicates to the color sensor on the consumer product, which converts the light into digital information. Light emitting diodes enable the consumer product to communicate synchronously with the mobile device.

In some embodiments, the Li-Fi system can be wireless and can use 802.11 protocols. In some embodiments, the LiFi system can use ultraviolet, infrared and visible light communication. One part of the visible light communication can be designed from communication protocols established by the IEEE 802 workgroup. The IEEE 802.15.7 standard can, in some embodiments, define the physical layer (PHY) and media access control (MAC) layer. The modulation formats recognized for PHY I and PHY II are on-off keying (OOK) and variable pulse position modulation (VPPM). The Manchester coding used for the PHY I and PHY II layers can include the clock inside the transmitted data by representing a logic 0 with an OOK symbol "01" and a logic 1 with an OOK symbol "10", all with a DC component. The DC component avoids light extinction in case of an extended run of logic 0's.

The use of LiFi provides additional benefits as the light waves are unlikely to affect or hinder the efficiency of a medical procedure or medical devices.

In some embodiments, the device can comprise a LiFi transmitter and/or receiver wherein the LiFi transmitter and/or receiver is configured to work in conjunction with a surgical guidance system. Aspects of the disclosure can be applied to knee replacement surgery, hip replacement surgery, shoulder replacement surgery, ankle replacement surgery, spinal surgery, e.g. spinal fusion, brain surgery, heart surgery, lung surgery, liver surgery, spleen surgery, kidney surgery vascular surgery or procedures, prostate, genitourinary, uterine or other abdominal or pelvic surgery, and trauma surgery. In some embodiments, one or more head mounted displays can display virtual data, e.g. virtual surgical guides, for knee replacement surgery, hip replacement surgery, shoulder replacement surgery, ankle replacement surgery, spinal surgery, e.g. spinal fusion, brain surgery, heart surgery, lung surgery, liver surgery, spleen surgery, kidney surgery vascular surgery or procedures, prostate, genitourinary, uterine or other abdominal or pelvic surgery, and trauma surgery.

In some embodiments, one or more ARDD can be used to display volume data or surface data, e.g. of a patient, of imaging studies, of graphical representation and/or CAD files.

Aspects of the disclosure relate to a system or device comprising at least one head mounted display, the device being configured to generate a virtual surgical guide. In some embodiments, the virtual surgical guide is a three-dimensional representation in digital format which corresponds to at least one of a portion of a physical surgical guide, a placement indicator of a physical surgical guide, or a combination thereof. In some embodiments, the at least one head mounted display is configured to display the virtual surgical guide superimposed onto a physical joint based at least in part on coordinates of a predetermined position of the virtual surgical guide, and the virtual surgical guide is configured to align the physical surgical guide or a physical saw blade with the virtual surgical guide to guide a bone cut of the joint.

In some embodiments, the at least one head mounted display is configured to display the virtual surgical guide superimposed onto a physical joint based at least in part on coordinates of a predetermined position of the virtual surgical guide, and the virtual surgical guide is configured to align the physical surgical guide or a physical saw drill, pin, burr, mill, reamer, broach, or impactor with the virtual surgical guide to guide a drilling, pinning, burring, milling, reaming, broach or impacting of the joint.

In some embodiments, the at least one head mounted display is configured to display the virtual surgical guide superimposed onto a physical spine based at least in part on coordinates of a predetermined position of the virtual surgical guide, and the virtual surgical guide is configured to align the physical surgical guide or a physical tool or physical instrument with the virtual surgical guide to guide an awl, a drill, a pin, a tap, a screw driver or other instrument or tool.

In some embodiments, the system or device comprises one, two, three or more head mounted displays.

In some embodiments, the virtual surgical guide is configured to guide a bone cut in a knee replacement, hip replacement, shoulder joint replacement or ankle joint replacement.

In some embodiments, the virtual surgical guide includes a virtual slot for a virtual or a physical saw blade. In some embodiments, the virtual surgical guide includes a planar area for aligning a virtual or a physical saw blade.

In some embodiments, the virtual surgical guide includes two or more virtual guide holes or paths for aligning two or more physical drills or pins.

In some embodiments, the predetermined position of the virtual surgical guide includes anatomical information, and/or alignment information of the joint. For example, the anatomic and/or alignment information of the joint can be based on at least one of coordinates of the joint, an anatomical axis of the joint, a biomechanical axis of the joint, a mechanical axis, or combinations thereof.

In some embodiments, the at least one head mounted display is configured to align the virtual surgical guide based on a predetermined limb alignment. For example, the predetermined limb alignment can be a normal mechanical axis alignment of a leg.

In some embodiments, the at least one head mounted display is configured to align the virtual surgical guide based on a predetermined femoral or tibial component rotation. In some embodiments, the at least one head mounted display is configured to align the virtual surgical guide based on a predetermined flexion of a femoral component or a predetermined slope of a tibial component.

In some embodiments, the virtual surgical guide is configured to guide a proximal femoral bone cut based on a predetermined leg length.

In some embodiments, the virtual surgical guide is configured to guide a bone cut of a distal tibia or a talus in an ankle joint replacement and the at least one head mounted display is configured to align the virtual surgical guide based on a predetermined ankle alignment, wherein the predetermined ankle alignment includes a coronal plane implant component alignment, a sagittal plane implant component alignment, an axial plane component alignment, an implant component rotation or combinations thereof.

In some embodiments, the virtual surgical guide is configured to guide a bone cut of a proximal humerus in a shoulder joint replacement and the at least one head mounted display is configured to align the virtual surgical guide based on a predetermined humeral implant component alignment, wherein the humeral implant component alignment includes a coronal plane implant component alignment, a sagittal plane implant component alignment, an axial plane component alignment, an implant component, or combinations thereof.

In some embodiments, the predetermined position of the surgical guide is based on a pre-operative or intra-operative imaging study, one or more intra-operative measurements, intra-operative data or combinations thereof.

Aspects of the disclosure relate to a system or device comprising two or more head mounted displays for two or more users, wherein the device is configured to generate a virtual surgical guide, wherein the virtual surgical guide is a three-dimensional representation in digital format which corresponds to at least one of a portion of a physical surgical guide, a placement indicator of a physical surgical guide, or a combination thereof, wherein the head mounted display is configured to display the virtual surgical guide superimposed onto a physical joint based at least in part on coordinates of a predetermined position of the virtual surgical guide, and wherein the virtual surgical guide is configured for aligning the physical surgical guide or a saw blade to guide a bone cut of the joint.

Aspects of the disclosure relate to a system or device comprising at least one head mounted display and a virtual bone cut plane, wherein the virtual bone cut plane is configured to guide a bone cut of a joint, wherein the virtual bone cut plane corresponds to at least one portion of a bone cut plane, and wherein the head mounted display is configured to display the virtual bone cut plane superimposed onto a physical joint based at least in part on coordinates of a predetermined position of the virtual bone cut plane. In some embodiments, the virtual bone cut plane is configured to guide a bone cut in a predetermined varus or valgus orientation or in a predetermined tibial slope or in a predetermined femoral flexion of an implant component or in a predetermined leg length.

Aspects of the disclosure relate to a method of preparing a joint for a prosthesis in a patient. In some embodiments, the method comprises registering one or more head mounted displays worn by a surgeon or surgical assistant in a coordinate system, obtaining one or more intra-operative measurements from the patient's physical joint to determine one or more intra-operative coordinates, registering the one or more intra-operative coordinates from the patient's physical joint in the coordinate system, generating a virtual surgical guide, determining a predetermined position and/or orientation of the virtual surgical guide based on the one or more intra-operative measurements, displaying and superimposing the virtual surgical guide, using the one or more head mounted displays, onto the physical joint based at least in part on coordinates of the predetermined position of the virtual surgical guide, and aligning the physical surgical guide or a physical saw blade with the virtual surgical guide to guide a bone cut of the joint.

In some embodiments, the one or more head mounted displays are registered in a common coordinate system. In some embodiments, the common coordinate system is a shared coordinate system.

In some embodiments, the virtual surgical guide is configured to guide a bone cut in a knee replacement, hip replacement, shoulder joint replacement or ankle joint replacement.

In some embodiments, the predetermined position of the virtual surgical guide determines a tibial slope for implantation of one or more tibial implant components in a knee replacement.

In some embodiments, the predetermined position of the virtual surgical guide determines an angle of varus or valgus correction for a femoral and/or a tibial component in a knee replacement.

In some embodiments, the virtual surgical guide corresponds to a physical distal femoral guide or cut block and the predetermined position of the virtual surgical guide determines a femoral component flexion.

In some embodiments, the virtual surgical guide corresponds to a physical anterior or posterior femoral surgical guide or cut block and the predetermined position of the virtual surgical guide determines a femoral component rotation.

In some embodiments, the virtual surgical guide corresponds to a physical chamfer femoral guide or cut block.

In some embodiments, the virtual surgical guide corresponds to a physical multi-cut femoral guide or cut block and the predetermined position of the virtual surgical guide determines one or more of an anterior cut, posterior cut, chamfer cuts and a femoral component rotation.

In some embodiments, the virtual surgical guide is used in a hip replacement and the predetermined position of the virtual surgical guide determines a leg length after implantation.

In some embodiments, the virtual surgical guide is a virtual plane for aligning the physical saw blade to guide the bone cut of the joint.

In some embodiments, the one or more intraoperative measurements include detecting one or more optical markers attached to the patient's joint, the operating room table, fixed structures in the operating room or combinations thereof. In some embodiments, one or more cameras or image capture or video capture systems and/or a 3D scanner included in the head mounted display can detect one or more optical markers including their coordinates (x, y, z) and at least one or more of a position, orientation, alignment, direction of movement or speed of movement of the one or more optical markers.

In some embodiments, registration of one or more of head mounted displays, surgical site, joint, spine, surgical instruments or implant components can be performed using spatial mapping techniques.

In some embodiments, registration of one or more of head mounted displays, surgical site, joint, spine, surgical instruments or implant components can be performed using depth sensors.

In some embodiments, the virtual surgical guide is configured to guide a bone cut of a distal tibia or a talus in an ankle joint replacement and the one or more head mounted display is configured to align the virtual surgical guide based on a predetermined tibial or talar implant component alignment, wherein the predetermined tibial or talar implant component alignment includes a coronal plane implant component alignment, a sagittal plane implant component alignment, an axial plane component alignment, an implant component rotation of an implant component or combinations thereof.

In some embodiments, the virtual surgical guide is configured to guide a bone cut of a proximal humerus in a shoulder joint replacement and wherein the one or more head mounted display is configured to align the virtual surgical guide based on a predetermined humeral implant component alignment, wherein the humeral implant component alignment includes a coronal plane implant component alignment, a sagittal plane implant component alignment, an axial plane component alignment, a humeral implant component rotation, or combinations thereof.

Aspects of the disclosure relate to a system comprising at least one head mounted display and a library of virtual implants, wherein the library of virtual implants comprises at least one virtual implant component, wherein the virtual implant component has at least one dimension that corresponds to a dimension of the implant component or has a dimension that is substantially identical to the dimension of the implant component, wherein the at least one head mounted display is configured to display the virtual implant component in substantial alignment with a tissue intended for placement of the implant component, wherein the placement of the virtual implant component is intended to achieve a predetermined implant component position and/or orientation. In some embodiments, the system further comprises at least one user interface.

Aspects of the disclosure relate to methods of selecting an implant or a prosthesis in three dimensions in a surgical site of a physical joint of a patient. In some embodiments, the method comprises registering, in a coordinate system, one or more head mounted displays worn by a user. In some embodiments, the head mounted display is a see-through head mounted display. In some embodiments, the method comprises obtaining one or more intra-operative measurements from the physical joint of the patient to determine one or more intra-operative coordinates. In some embodiments, the method comprises registering the one or more intra-operative coordinates from the physical joint of the patient in the coordinate system. In some embodiments, the method comprises displaying a three-dimensional graphical representation of a first implant or prosthesis projected over the physical joint using the one or more head mounted displays. In some embodiments, the three-dimensional graphical representation of the first implant or prosthesis is from a library of three-dimensional graphical representations of physical implants or prostheses. In some embodiments, the three-dimensional graphical representation corresponds to at least one portion of the physical implant or prosthesis. In some embodiments, the method comprises moving the three-dimensional graphical representation of the first implant or prosthesis to align with or to be near with or to intersect one or more of an internal or external margin, periphery, edge, perimeter, anteroposterior, mediolateral, oblique dimension, diameter, radius, curvature, geometry, shape or surface of one or more structures of the physical joint. In some embodiments, the method comprises visually evaluating the fit or alignment between the three-dimensional graphical representation of the first implant or prosthesis and the one or more of an internal or external margin, periphery, edge, perimeter, anteroposterior, mediolateral, oblique dimension, diameter, radius, curvature, geometry, shape or surface, of the one or more structures of the physical joint. In some embodiments, the method comprises repeating the steps of displaying, optionally moving and visually evaluating the fit or alignment with one or more three-dimensional graphical representations of one or more additional physical implants or prostheses, wherein the one or more additional physical implants or prostheses have one or more of a different dimension, size, diameter, radius, curvature, geometry shape or surface than the first and subsequently evaluated implant or prosthesis. In some embodiments, the method comprises selecting a three-dimensional graphical representation of an implant or prosthesis with a satisfactory fit relative to the one or more structures of the physical joint from the library of three-dimensional graphical representations of physical implants or prostheses.

In some embodiments, the method comprises obtaining one or more intra-operative measurements from the physical joint of the patient to determine one or more intra-operative coordinates and registering the one or more intra-operative coordinates from the physical joint of the patient in the coordinate system.

In some embodiments, the step of visually evaluating the fit includes comparing one or more of a radius, curvature, geometry, shape or surface of the graphical representation of the first or subsequent prosthesis with one or more of an articular radius, curvature, shape or geometry of the joint. In some embodiments, the graphical representation of the first or subsequent implant or prosthesis is moved to improve the fit between the one or more of a radius, curvature, geometry, shape or surface of the graphical representation of the first or subsequent prosthesis and the one or more of an articular radius, curvature, shape or geometry of the joint. In some embodiments, the one or more of the size, location, position, and orientation of the selected graphical representation of the implant or prosthesis with its final coordinates is used to develop or modify a surgical plan for implantation of the implant or prosthesis. In some embodiments, the one or more of the location, position or orientation of the selected graphical representation is used to determine one or more bone resections for implantation of the implant or prosthesis. In some embodiments, the one or more of an internal or external margin, periphery, edge, perimeter, anteroposterior, mediolateral, oblique dimension, diameter, radius, curvature, geometry, shape or surface of one or more structures of the physical joint have not been surgically altered. In other embodiments, the one or more of an internal or external margin, periphery, edge, perimeter, anteroposterior, mediolateral, oblique dimension, diameter, radius, curvature, geometry, shape or surface of one or more structures of the physical joint have been surgically altered. For example, the surgically altering can include removal of bone or cartilage. In some embodiments, the bone removal can be a bone cut.

In some embodiments, the head mounted display is a see-through head mounted display. In some embodiments, the head mounted display is a virtual reality (VR) type head mounted display and the joint of the patient is imaged using one or more cameras and the images are displayed by the head mounted display.

In some embodiments, the satisfactory fit includes a fit within 1, 2, 3, 4 or 5 mm distance between the selected graphical representation of the prosthesis and at least portions of the one or more of an internal or external margin, periphery, edge, perimeter anteroposterior, mediolateral, oblique dimension, radius, curvature, geometry, shape or surface, of the one or more structures of the physical joint.

In some embodiments, the one or more structures of the physical joint include one or more anatomic landmarks. In some embodiments, the one or more anatomic landmarks define one or more anatomical or biomechanical axes.

In some embodiments, the steps of moving and visually evaluating the fit of the graphical representation of the prosthesis include evaluating the alignment of the graphical representation of the prosthesis relative to the one or more anatomic or biomechanical axis.

In some embodiments, the step of moving the three-dimensional graphical representation of the prosthesis is performed with one, two, three, four, five or six degrees of freedom. In some embodiments, the step of moving the three-dimensional graphical representation of the prosthesis includes one or more of translation or rotation of the three-dimensional graphical representation of the prosthesis.

In some embodiments, the step of visually evaluating the fit or alignment between the three-dimensional graphical representation of the first or subsequent prosthesis includes comparing one or more of an anteroposterior or mediolateral dimension of one or more of the prosthesis components with one or more with one or more of an anteroposterior or mediolateral dimension of the distal femur or the proximal tibia of the joint. In some embodiments, the step of visually evaluating the fit or alignment between the three-dimensional graphical representation of the first or subsequent prosthesis includes comparing one or more of a dimension, size, radius, curvature, geometry shape or surface of at least portions of the prosthesis with one or more of a dimension, size, radius, curvature, geometry shape or surface of at least portions of a medial condyle or a lateral condyle of the joint.

In some embodiments, the joint is a knee joint and the prosthesis includes one or more components of a knee replacement device. In some embodiments, the joint is a hip joint and the prosthesis includes one or more components of a hip replacement device. In some embodiments, the joint is a shoulder joint and the prosthesis includes one or more components of a shoulder replacement device. In some embodiments, the joint is an ankle and the prosthesis includes one or more components of an ankle replacement device.

In some embodiments, the library of three-dimensional graphical representations of physical implants or prostheses includes symmetrical and asymmetrical implant's or prosthesis' components. In some embodiments, the symmetrical or asymmetrical implant's or prosthesis' components include at least one of symmetrical and asymmetrical femoral components and symmetrical and asymmetrical tibial components.

Aspects of the disclosure relate to methods of selecting a medical device in three dimensions in a physical site of a patient selected for implantation. In some embodiments, the method comprises registering, in a coordinate system, one or more head mounted displays worn by a user. In some embodiments, the method comprises obtaining one or more measurements from the physical site of the patient to determine one or more coordinates. In some embodiments, the method comprises registering the one or more coordinates from the physical site of the patient in the coordinate system. In some embodiments, the method comprises displaying a three-dimensional graphical representation of a first medical device projected over the physical site using the one or more head mounted displays. In some embodiments, the three-dimensional graphical representation of the first medical device is from a library of three-dimensional graphical representations of physical medical devices and the three-dimensional graphical representation corresponds to at least one portion of the physical first medical device.

In some embodiments, the method comprises moving the three-dimensional graphical representation of the first medical device to align with or to be near with or to intersect one or more of an internal or external margin, periphery, edge, perimeter, anteroposterior, mediolateral, oblique dimension, diameter, radius, curvature, geometry, shape or surface of one or more structures at the physical site. In some embodiments, the method comprises visually evaluating the fit or alignment between the three-dimensional graphical representation of the first medical device and the one or more of an internal or external margin, periphery, edge, perimeter, anteroposterior, mediolateral, oblique dimension, diameter, radius, curvature, geometry, shape or surface, of the one or more structures at the physical site. In some embodiments, the method comprises repeating the steps of displaying, optionally moving and visually evaluating the fit or alignment with one or more three-dimensional graphical representations of one or more additional physical medical devices, wherein the one or more additional physical medical devices have one or more of a different dimension, size, diameter, radius, curvature, geometry shape or surface than the first and subsequently evaluated medical device. In some embodiments, the method comprises selecting a three-dimensional graphical representation of a medical device with a satisfactory fit relative to the one or more structures at the physical site from the library of three-dimensional graphical representations of physical medical devices.

In some embodiments, the one or more structures at the physical site include an anatomic or pathologic tissue intended for implantation. In some embodiments, the one or more structures at the physical site include an anatomic or pathologic tissue surrounding or adjacent or subjacent to the intended implantation site. In some embodiments, the one or more structures at the physical site include a pre-existing medical device near the implantation site or adjacent or subjacent or opposing or articulating with or to be connected with the medical device planned for implantation. In some embodiments, the one or more structures at the physical site include a one or more of a tissue, organ or vascular surface, diameter, dimension, radius, curvature, geometry, shape or volume.

In some embodiments, the one or more ARDD are registered with the physical surgical site, using, for example, one or more markers, e.g. attached to the surgical site or attached near the surgical site (for example by attaching the one or more markers to an anatomic structure), one or more of a pre- or intra-operative imaging study. The one or more ARDDs can display live images of the physical surgical site, one or more of a pre- or intra-operative imaging study, 2D or 3D images of the patient, graphical representations of one or more medical devices, and/or CAD files of one or more medical devices. In some embodiments, the one or more ARDDs are registered in relationship to at least one marker, e.g. attached to the patient, for example a bony structure in a spine, knee, hip, shoulder or ankle joint, or attached to the OR table or another structure in the operating room.

In some embodiments, the information from the one or more structures at the physical site and from the one or more of a pre- or intra-operative imaging study, 2D or 3D images of the patient, graphical representations of one or more medical devices, CAD files of one or more medical devices are used to select one or more of an anchor or attachment mechanism or fixation member.

In some embodiments, the information from the one or more structures at the physical site and from the one or more of a pre- or intra-operative imaging study, 2D or 3D images of the patient, graphical representations of one or more medical devices, CAD files of one or more medical devices are used to direct one or more of an anchor or attachment mechanism or fixation member.

In some embodiments, the medical device is an implant and/or an instrument. In some embodiments, the implant is an implant component. In some embodiments, the medical device can be, but not limited to, a joint replacement implant, a stent, a wire, a catheter, a screw, an otoplasty prosthesis, a dental implant, a dental implant component, a prosthetic disk, a catheter, a guide wire, a coil, an aneurysm clip.

Aspects of the disclosure relate to methods of aligning an implant or a prosthesis in a joint of a patient. In some embodiments, the method comprises registering, in a coordinate system, one or more head mounted displays worn by a user. In some embodiments, the method comprises obtaining one or more intra-operative measurements from the physical joint of the patient to determine one or more coordinates of the physical joint. In some embodiments, the method comprises registering the one or more coordinates of the physical joint of the patient in the coordinate system. In some embodiments, the method comprises displaying a three-dimensional graphical representation of an implant or implant component or a prosthesis or prosthesis component projected over the physical joint using the one or more head mounted displays, wherein the three-dimensional graphical representation corresponds to at least one portion of the physical prosthesis. In some embodiments, the method comprises moving the three-dimensional graphical representation of the prosthesis to align with or to be near with or to intersect one or more of an internal or external margin, periphery, edge, perimeter, anteroposterior, mediolateral, oblique dimension, diameter, radius, curvature, geometry, shape or surface of one or more structures of the physical joint.

In some embodiments, the method comprises registering one or more coordinates from the graphical representation of the prosthesis in the coordinate system after the moving and aligning.

In some embodiments, the moving of the three-dimensional graphical representation of the implant or prosthesis is performed using one or more of a computer interface (also referred to user interface), an acoustic interface, optionally including voice recognition, a virtual interface, optionally including gesture recognition. In some embodiments, the one or more coordinates from the graphical representation of the prosthesis in the coordinate system after the moving and aligning are used to derive or modify a surgical plan. In some embodiments, the one or more coordinates from the graphical representation of the implant or prosthesis in the coordinate system after the moving and aligning are used to determine one or more of a location, orientation, or alignment or coordinates of a bone removal for placing the implant or prosthesis. In some embodiments, the bone removal is one or more of a bone cut, a burring, a drilling, a pinning, a reaming, or an impacting. In some embodiments, the surgical plan is used to derive one or more of a location, position, orientation, alignment, trajectory, plane, start point, or end point for one or more surgical instruments. In some embodiments, the one or more of a location, orientation, or alignment or coordinates of bone removal are used to derive one or more of a location, position, orientation, alignment, trajectory, plane, start point, or end point for one or more surgical instruments. In some embodiments, the one or more head mounted displays visualize the one or more of a location, position, orientation, alignment, trajectory, plane, start point, or end point for one or more surgical instruments projected onto and registered with the physical joint. In some embodiments, the prosthesis is an acetabular cup of a hip replacement and wherein a graphical representation of the acetabular up is aligned with at least a portion of the physical acetabular rim of the patient. In some embodiments, the implant or prosthesis is a femoral component of a hip replacement and wherein a graphical representation of the femoral component is aligned with at least a portion of the physical endosteal bone or cortical bone of the patient. In some embodiments, the aligning means positioning the femoral component in substantially equidistant location between at least a portion of one or more of an anterior and a posterior endosteal or cortical bone or a medial and a lateral endosteal bone or cortical bone. In some embodiments, the femoral component includes a femoral neck. In some embodiments, the one or more coordinates from the femoral component in the coordinate system after the moving and aligning is used to determine at least one of a femoral component stem position, a femoral component stem orientation, a femoral component neck angle, a femoral component offset, and a femoral component neck anteversion. In some embodiments, the implant or prosthesis is a glenoid component of a shoulder replacement and wherein a graphical representation of the glenoid component is aligned with at least a portion of the physical glenoid rim of the patient. In some embodiments, the implant or prosthesis is a humeral component of a shoulder replacement and wherein a graphical representation of the humeral component is aligned with at least a portion of the physical endosteal bone or cortical bone of the patient. In some embodiments, the aligning means positioning the humeral component in substantially equidistant location between at least a portion of one or more of an anterior and a posterior endosteal or cortical bone or a medial and a lateral endosteal bone or cortical bone. In some embodiments, the humeral component includes a humeral neck. In some embodiments, the one or more coordinates from the humeral component in the coordinate system after the moving and aligning is used to determine at least one of a humeral component stem position, a humeral component stem orientation, a humeral component neck angle, a humeral component offset, and a humeral component neck anteversion. In some embodiments, the one or more of a margin, periphery, edge, perimeter, anteroposterior, mediolateral, oblique dimension, diameter, radius, curvature, geometry, shape or surface of one or more structures of the physical joint includes one or more of a cartilage, normal cartilage, damaged or diseased cartilage, subchondral bone or osteophyte. In some embodiments, the one or more of a margin, periphery, edge, perimeter, anteroposterior, mediolateral, oblique dimension, diameter, radius, curvature, geometry, shape or surface of one or more structures of the physical joint excludes one or more of a cartilage, normal cartilage, damaged or diseased cartilage, subchondral bone or osteophyte. In some embodiments, the one or more head mounted displays display registered with and superimposed onto the physical joint one or more of a pre- or intra-operative imaging study, 2D or 3D images of the patient, graphical representations of one or more medical devices, CAD files of one or more medical devices, wherein the display assists with the moving and aligning of the three-dimensional graphical representation of the graphical representation of the prosthesis. In some embodiments, the implant or prosthesis is a femoral component or a tibial component of a knee replacement system, wherein the one or more coordinates from the graphical representation of the implant or prosthesis in the coordinate system after the moving and aligning include a center of the graphical representation of the femoral component or a center of the graphical representation of the tibial component. In some embodiments, the moving or aligning includes aligning the femoral component on the distal femur. In some embodiments, the aligning includes aligning the femoral component substantially equidistant to a medial edge of the medial femoral condyle and the lateral edge of a lateral femoral condyle. In some embodiments, the aligning includes aligning the femoral component tangent with the articular surface of at least one of the medial condyle and the lateral condyle in at least one of a distal weight-bearing zone or a weight-bearing zone at 5, 10, 15, 20, 25, 30, 40 or 45 degrees of knee flexion. In some embodiments, the moving or aligning includes aligning the tibial component on the proximal tibia. In some embodiments, the aligning includes aligning the tibial component substantially equidistant to a medial edge of the medial tibial plateau and the lateral edge of a lateral tibial plateau and/or the anterior edge of the anterior tibial plateau and the posterior edge of the posterior tibial plateau or centered over the tibial spines. In some embodiments, the aligning includes aligning the tibial component tangent with at least portions of the articular surface of at least one of the medial tibial plateau and the lateral tibial plateau.

In some embodiments, the center of the graphical representation of the femoral component after the aligning and the center of the hip joint are used to determine a femoral mechanical axis. In some embodiments, the center of the graphical representation of the tibial component after aligning and the center of the ankle joint are used to determine a tibial mechanical axis. In some embodiments, the femoral and tibial mechanical axes are used to determine a desired leg axis correction relative to the mechanical axis of the leg. In some embodiments, the leg axis correction is one of a full correction to normal mechanical axis, partial correction to normal mechanical axis or no correction to normal mechanical axis. In some embodiments, the leg axis correction is used to determine the coordinates and/or alignment for the bone removal or bone cuts. In some embodiments, the bone removal or bone cuts for a full correction to normal mechanical axis or a partial correction to normal mechanical axis or no correction to normal mechanical axis are used to adjust the femoral and/or tibial prosthesis coordinates. In some embodiments, the bone removal or bone cuts are executed using at least one of a robot guidance, a surgical navigation system and visual guidance using the one or more HMDs. In some embodiments, the one or more head mounted display project a graphical representation of one or more of a cut block, a cut plane or a drill path registered with and superimposed onto the physical joint for aligning one or more of a physical cut guide, a saw blade or a drill.

Various exemplary embodiments will be described more fully hereinafter with reference to the accompanying drawings, in which some example embodiments are shown. The present inventive concept may, however, be embodied in many different forms and should not be construed as limited to the example embodiments set forth herein. Rather, these example embodiments are provided so that this disclosure will be thorough and complete, and will fully convey the scope of the present inventive concept to those skilled in the art. In the drawings, the sizes and relative sizes of layers and regions may be exaggerated for clarity. The term live data of the patient, as used herein, includes the surgical site, anatomy, anatomic structures or tissues and/or pathology, pathologic structures or tissues of the patient as seen by the surgeon's or viewer's eyes without information from virtual data, stereoscopic views of virtual data, or imaging studies. The term live data of the patient does not include internal or subsurface tissues or structures or hidden tissues or structures that can only be seen with assistance of a computer monitor or HMD.

The terms real surgical instrument, actual surgical instrument, physical surgical instrument and surgical instrument are used interchangeably throughout the application; the terms real surgical instrument, actual surgical instrument, physical surgical instrument and surgical instrument do not include virtual surgical instruments. For example, the physical surgical instruments can be surgical instruments provided by manufacturers or vendors for spinal surgery, pedicle screw instrumentation, anterior spinal fusion, knee replacement, hip replacement, ankle replacement and/or shoulder replacement; physical surgical instruments can be, for example, cut blocks, pin guides, awls, reamers, impactors, broaches. Physical surgical instruments can be re-useable or disposable or combinations thereof. Physical surgical instruments can be patient specific. The term virtual surgical instrument does not include real surgical instrument, actual surgical instrument, physical surgical instrument and surgical instrument.

The terms real surgical tool, actual surgical tool, physical surgical tool and surgical tool are used interchangeably throughout the application; the terms real surgical tool, actual surgical tool, physical surgical tool and surgical tool do not include virtual surgical tools. The physical surgical tools can be surgical tools provided by manufacturers or vendors. For example, the physical surgical tools can be pins, drills, saw blades, retractors, frames for tissue distraction and other tools used for orthopedic, neurologic, urologic or cardiovascular surgery. The term virtual surgical tool does not include real surgical tool, actual surgical tool, physical surgical tool and surgical tool.

The terms real implant or implant component, actual implant or implant component, physical implant or implant component and implant or implant component are used interchangeably throughout the application; the terms real implant or implant component, actual implant or implant component, physical implant or implant component and implant or implant component do not include virtual implant or implant components. The physical implants or implant components can be implants or implant components provided by manufacturers or vendors. For example, the physical surgical implants can be a pedicle screw, a spinal rod, a spinal cage, a femoral or tibial component in a knee replacement, an acetabular cup or a femoral stem and head in hip replacement. The term virtual implant or implant component does not include real implant or implant component, actual implant or implant component, physical implant or implant component and implant or implant component.

The terms "image capture system", "video capture system", "image or video capture system", "image and/or video capture system, and/or optical imaging system" can be used interchangeably. In some embodiments, a single or more than one, e.g. two or three or more, image capture system, video capture system, image or video capture system, image and/or video capture system, and/or optical imaging system can be used in one or more locations (e.g. in one, two, three, or more locations), for example integrated into, attached to or separate from an HMD, attached to an OR table, attached to a fixed structure in the OR, integrated or attached to or separate from an instrument, integrated or attached to or separate from an arthroscope, integrated or attached to or separate from an endoscope, internal to the patient's skin, internal to a surgical site, internal to a target tissue, internal to an organ, internal to a cavity (e.g. an abdominal cavity or a bladder cavity or a cistern or a CSF space, or an internal to a vascular lumen), internal to a vascular bifurcation, internal to a bowel, internal to a small intestine, internal to a stomach, internal to a biliary structure, internal to a urethra and or urether, internal to a renal pelvis, external to the patient's skin, external to a surgical site, external to a target tissue, external to an organ, external to a cavity (e.g. an abdominal cavity or a bladder cavity or a cistern or a CSF space, or an external to a vascular lumen), external to a vascular bifurcation, external to a bowel, external to a small intestine, external to a stomach, external to a biliary structure, external to a urethra and or urether, and/or external to a renal pelvis. In some embodiments, the position and/or orientation and/or coordinates of the one or more image capture system, video capture system, image or video capture system, image and/or video capture system, and/or optical imaging system can be tracked using any of the registration and/or tracking methods described in the disclosure, e.g. direct tracking using optical imaging systems and/or a 3D scanner(s), in any of the foregoing locations and/or tissues and/or organs and any other location and/or tissue and/or organ described in the disclosure or known in the art. Tracking of the one or more image capture system, video capture system, image or video capture system, image and/or video capture system, and/or optical imaging system can, for example, be advantageous when the one or more 3D scanners are integrated into or attached to an instrument, an arthroscope, an endoscope, and/or when they are located internal to any structures, e.g. inside a joint or a cavity or a lumen.

In some embodiments, a single or more than one, e.g. two or three or more, 3D scanners can be present in one or more locations (e.g. in one, two, three, or more locations), for example integrated into, attached to or separate from an ARDD (e.g. HMD), attached to an OR table, attached to a fixed structure in the OR, integrated or attached to or separate from an instrument, integrated or attached to or separate from an arthroscope, integrated or attached to or separate from an endoscope, internal to the patient's skin, internal to a surgical site, internal to a target tissue, internal to an organ, internal to a cavity (e.g. an abdominal cavity or a bladder cavity or a cistern or a CSF space, and/or internal to a vascular lumen), internal to a vascular bifurcation, internal to a bowel, internal to a small intestine, internal to a stomach, internal to a biliary structure, internal to a urethra and or urether, internal to a renal pelvis, external to the patient's skin, external to a surgical site, external to a target tissue, external to an organ, external to a cavity (e.g. an abdominal cavity or a bladder cavity or a cistern or a CSF space, and/or external to a vascular lumen), external to a vascular bifurcation, external to a bowel, external to a small intestine, external to a stomach, external to a biliary structure, external to a urethra and or urether, and/or external to a renal pelvis. In some embodiments, the position and/or orientation and/or coordinates of the one or more 3D scanners can be tracked using any of the registration and/or tracking methods described in the disclosure, e.g. direct tracking using optical imaging systems and/or a 3D scanner(s), in any of the foregoing locations and/or tissues and/or organs and any other location and/or tissue and/or organ mentioned in the disclosure or known in the art. Tracking of the one or more 3D scanners can, for example, be advantageous when the one or more 3D scanners are integrated into or attached to an instrument, an arthroscope, an endoscope, and/or when they are located internal to any structures, e.g. inside a joint or a cavity or a lumen.

In some embodiments, one or more image capture system, video capture system, image or video capture system, image and/or video capture system, and/or optical imaging system can be used in conjunction with one or more 3D scanners, e.g. in any of the foregoing locations and/or tissues and/or organs and any other location and/or tissue and/or organ described in the disclosure or known in the art.

With surgical navigation, a first virtual instrument can be displayed on a computer monitor which is a representation of a physical instrument tracked with navigation markers, e.g. infrared or RF markers, and the position and/or orientation of the first virtual instrument can be compared with the position and/or orientation of a corresponding second virtual instrument generated in a virtual surgical plan. Thus, with surgical navigation the positions and/or orientations of the first and the second virtual instruments are compared.

Aspects of the disclosure relates to devices, systems and methods for positioning a virtual path, virtual plane, virtual tool, virtual surgical instrument or virtual implant component in a mixed reality environment using a head mounted display device, optionally coupled to one or more processing units.

With guidance in mixed reality environment, a virtual surgical guide, tool, instrument or implant can be superimposed onto the physical joint, spine or surgical site. Further, the physical guide, tool, instrument or implant can be aligned with the virtual surgical guide, tool, instrument or implant displayed or projected by the ARDD. Thus, guidance in mixed reality environment does not need to use a plurality of virtual representations of the guide, tool, instrument or implant and does not need to compare the positions and/or orientations of the plurality of virtual representations of the virtual guide, tool, instrument or implant.

In some embodiments, the ARDD can display one or more of a virtual surgical tool, virtual surgical instrument including a virtual surgical guide or virtual cut block, virtual trial implant, virtual implant component, virtual implant or virtual device, predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, estimated or predetermined non-visualized portions for one or more devices or implants or implant components or surgical instruments or surgical tools, and/or one or more of a predetermined tissue change or alteration.

In some embodiments, the one or more of a virtual surgical tool, virtual surgical instrument including a virtual surgical guide or virtual cut block, virtual trial implant, virtual implant component, virtual implant or virtual device, predetermined start point, predetermined start position, predetermined start orientation or alignment, predetermined intermediate point(s), predetermined intermediate position (s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, estimated or predetermined non-visualized portions for one or more devices or implants or implant components or surgical instruments or surgical tools, and/or one or more of a predetermined tissue change or alteration can be displayed by the ARDD at one or more predetermined coordinates, e.g. indicating a predetermined position predetermined orientation or combination thereof for superimposing and/or aligning a physical surgical tool, physical surgical instrument, physical implant, or a physical device.

In some embodiments, one or more of a virtual surgical tool, virtual surgical instrument including a virtual surgical guide or virtual cut block, virtual trial implant, virtual implant component, virtual implant or virtual device, predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, estimated or predetermined non-visualized portions for one or more devices or implants or implant components or surgical instruments or surgical tools, and/or one or more of a predetermined tissue change or alteration displayed by the ARDD can be a placement indicator for one or more of a physical surgical tool, physical surgical instrument, physical implant, or a physical device.

Any of a position, location, orientation, alignment, direction, speed of movement, force applied of a surgical instrument or tool, virtual and/or physical, can be predetermined using, for example, pre-operative imaging studies, pre-operative data, pre-operative measurements, intra-operative imaging studies, intra-operative data, and/or intra-operative measurements.

Any of a position, location, orientation, alignment, sagittal plane alignment, coronal plane alignment, axial plane alignment, rotation, slope of implantation, angle of implantation, flexion of implant component, offset, anteversion, retroversion, and position, location, orientation, alignment relative to one or more anatomic landmarks, position, location, orientation, alignment relative to one or more anatomic planes, position, location, orientation, alignment relative to one or more anatomic axes, position, location, orientation, alignment relative to one or more biomechanical axes, position, location, orientation, alignment relative to a mechanical axis of a trial implant, an implant component or implant, virtual and/or physical, can be predetermined using, for example, pre-operative imaging studies, pre-operative data, pre-operative measurements, intra-operative imaging studies, intra-operative data, and/or intra-operative measurements. Intra-operative measurements can include measurements for purposes of registration, e.g. of a joint, a spine, a surgical site, a bone, a cartilage, a HMD, a surgical tool or instrument, a trial implant, an implant component or an implant.

In some embodiments throughout the disclosure, measurements can include measurements of coordinate(s) or coordinate information. A coordinate can be a set of numbers used in specifying the location of a point on a line, on a surface, or in space, e.g. x, y, z. Coordinate can be predetermined, e.g. for a virtual surgical guide.

In some embodiments, multiple coordinate systems can be used instead of a common or shared coordinate system. In this case, coordinate transfers can be applied from one coordinate system to another coordinate system, for example for registering the HMD, live data of the patient including the surgical site, virtual instruments and/or virtual implants and physical instruments and physical implants.

Head Mounted Displays

In some embodiments, head mounted displays (HMDs) can be used. Head mounted displays can be of non-see-through type (such as the Oculus VR HMD (Facebook, San Mateo, CA)), optionally with a video camera to image the live data of the patient as a video-see through head mounted display, or they can be of optical see through type as an optical see-through head mounted display or see-through optical head mounted display.

A head mounted display can include a first display unit for the left eye and a second display unit for the right eye. The first and second display units can be transparent, semi-transparent or non-transparent. The system, comprising, for example, the head mounted display, one or more computer processors and/or an optional marker attached to the patient, can be configured to generate a first view of virtual data, e.g. a virtual surgical guide, for the first display unit and a second view of virtual data, e.g. a virtual surgical guide, for the second display unit. The virtual data can be a placement indicator for a physical surgical tool, physical surgical instrument, physical implant or physical device. The virtual data, e.g. a virtual surgical guide, can be a three-dimensional digital representation at one or more predetermined coordinates indicating, for example, a predetermined position, predetermined orientation or combination thereof for superimposing and/or aligning a physical surgical tool, physical surgical instrument, physical implant or physical device.

The system can be configured to generate a first view displayed by a first display unit (e.g. for the left eye) and a second view displayed by a second display unit (e.g. for the right eye), wherein the first view and the second view create a 3D stereoscopic view of the virtual data, e.g. a virtual surgical guide, which can optionally be based on one or more predetermined coordinates. The system can be configured to display the 3D stereoscopic view by the head mounted display onto the patient.

In some embodiments, a pair of glasses is utilized. The glasses can include an optical head-mounted display. An optical see through head-mounted display can be a wearable display that has the capability of reflecting projected images as well as allowing the user to see through it. Various types OHMD known in the art can be used in order to practice embodiments of the present disclosure. These include curved mirror or curved combiner OHMDs as well as wave-guide or light-guide OHMDs. The OHMDs can optionally utilize diffraction optics, holographic optics, polarized optics, and reflective optics.

Traditional input devices that can be used with the OHMDs include, but are not limited to touchpad or buttons, smartphone controllers, speech recognition, and gesture recognition. Advanced interfaces are possible, e.g. a brain-computer interface.

In some embodiments, a computer or server or a workstation can transmit data to the ARDD (e.g. OHMD). The data transmission can occur via cable, Bluetooth, WiFi, optical signals and any other method or mode of data transmission known in the art. The ARDD can display virtual data, e.g. virtual data of the patient, in uncompressed form or in compressed form. Virtual data of a patient can optionally be reduced in resolution when transmitted to the ARDD or when displayed by the ARDD.

When virtual data are transmitted to the ARDD (e.g. OHMD), they can be in compressed form during the transmission. The ARDD can then optionally decompress them so that uncompressed virtual data are being displayed by the ARDD.

Alternatively, when virtual data are transmitted to the ARDD (e.g. OHMD), they can be of reduced resolution during the transmission, for example by increasing the slice thickness of image data prior to the transmission. The ARDD can then optionally increase the resolution, for example by re-interpolating to the original slice thickness of the image data or even thinner slices so that virtual data with resolution equal to or greater than the original virtual data or at least greater in resolution than the transmitted data are being displayed by the ARDD.

In some embodiments, the ARDD can transmit data back to a computer, a server or a workstation. Such data can include, but are not limited to:

- Positional, orientational or directional information about the ARDD or the operator or surgeon wearing the ARDD (e.g. HMD)
- Changes in position, orientation or direction of the ARDD
- Data generated by one or more IMU's
- Data generated by markers (radiofrequency, optical, light, other) attached to, integrated with or coupled to the ARDD
- Data generated by a surgical navigation system attached to, integrated with or coupled to the ARDD
- Data generated by an image and/or video capture system attached to, integrated with or coupled to the ARDD
- Parallax data, e.g. using two or more image and/or video capture systems attached to, integrated with or coupled to the ARDD (e.g. HMD), for example one positioned over or under or near the left eye and a second positioned over or under or near the right eye
- Distance data, e.g. parallax data generated by two or more image and/or video capture systems evaluating changes in distance between the ARDD (e.g. HMD) and a surgical field or an object
- Motion parallax data
- Data related to calibration or registration phantoms (see other sections of this disclosure)
- Any type of live data of the patient captured by the ARDD including image and/or video capture systems attached to, integrated with or coupled to the ARDD
  - For example, alterations to a live surgical site
  - For example, use of certain surgical instruments detected by the image and/or video capture system
  - For example, use of certain medical devices or trial implants detected by the image and/or video capture system
- Any type of modification to a surgical plan
  - Portions or aspects of a live surgical plan
  - Portions or aspects of a virtual surgical plan Radiofrequency tags used throughout the embodiments can be of active or passive kind with or without a battery.

Exemplary optical see through head mounted displays include the ODG R-7, R-8 and R-8 smart glasses from ODG (Osterhout Group, San Francisco, CA), the NVIDIA 942 3-D vision wireless glasses (NVIDIA, Santa Clara, CA) the Microsoft Hololens and Hololens 2 (Microsoft, Redmond, WI), the Daqri Smart Glass (Daqri, Los Angeles, CA) the Meta2 (Meta Vision, San Mateo, CA), the Moverio BT-300 (Epson, Suwa, Japan), the Blade 3000 and the Blade M300 (Vuzix, West Henrietta, NY), and the Lenovo ThinkA6 (Lenovo, Beijing, China). The Microsoft Hololens is manufactured by Microsoft. It is a pair of augmented reality smart glasses. Hololens is a see-through optical head mounted display (or optical see through head mounted display) 1125 (see FIG. 7). Hololens can use the Windows 10 operating system. The front portion of the Hololens includes, among others, sensors, related hardware, several cameras and processors. The visor includes a pair of transparent combiner lenses, in which the projected images are displayed. The Hololens can be adjusted for the interpupillary distance (IPD) using an integrated program that recognizes gestures. A pair of speakers is also integrated. The speakers do not exclude external sounds and allow the user to hear virtual sounds. A USB 2.0 micro-B receptacle is integrated. A 3.5 mm audio jack is also present. The HoloLens has an inertial measurement unit (IMU) with an accelerometer, gyroscope, and a magnetometer, four environment mapping sensors/cameras (two on each side), a depth camera with a 120°×120° angle of view, a 2.4-megapixel photographic video camera, a four-microphone array, and an ambient light sensor. Hololens has an Intel Cherry Trail SoC containing the CPU and GPU. Hololens includes also a custom-made Microsoft Holographic Processing Unit (HPU). The SoC and the HPU each have 1 GB LPDDR3 and share 8 MB SRAM, with the SoC also controlling 64 GB eMMC and running the Windows 10 operating system. The HPU processes and integrates data from the sensors, as well as handling tasks such as spatial mapping, gesture recognition, and voice and speech recognition. Hololens includes IEEE 802.11ac Wi-Fi and Bluetooth 4.1 Low Energy (LE) wireless connectivity. The headset uses Bluetooth LE and can connect to a clicker, a finger-operating input device that can be used for selecting menus and functions.

A number of applications are available for Microsoft Hololens, for example a catalogue of holograms, HoloStudio, a 3D modelling application by Microsoft with 3D print capability, Autodesk Maya 3D creation application, FreeForm, integrating Hololens with the Autodesk Fusion 360 cloud-based 3D development application, and others. Hololens utilizing the HPU can employ sensual and natural interface commands—voice, gesture, and gesture. Gaze commands, e.g. head-tracking, allows the user to bring application focus to whatever the user is perceiving. Any virtual application or button can be selected using an air tap method, similar to clicking a virtual computer mouse. The tap can be held for a drag simulation to move a display. Voice commands can also be utilized. The Hololens shell utilizes many components or concepts from the Windows desktop environment. A bloom gesture for opening the main menu is performed by opening one's hand, with the palm facing up and the fingers spread. Windows can be dragged to a particular position, locked and/or resized. Virtual windows or menus can be fixed at locations or physical objects. Virtual windows or menus can move with the user or can be fixed in relationship to the user. Or they can follow the user as he or she moves around. The Microsoft Hololens App for Windows 10 PC's and Windows 10 Mobile devices can be used by developers to run apps and to view live stream from the Hololens user's point of view, and to capture augmented reality photos and videos. Almost all Universal Windows Platform apps can run on Hololens. These apps can be projected in 2D. Select Windows 10 APIs are currently supported by Hololens. Hololens apps can also be developed on Windows 10 PC's. Holographic applications can use Windows Holographic APIs. Unity (Unity Technologies, San Francisco, CA) and Vuforia (PTC, Inc., Needham, MA) are some apps that can be utilized. Applications can also be developed using DirectX and Windows API's.

Many of the embodiments throughout the disclosure can be implemented also using non see through head mounted displays, e.g. virtual reality head mounted displays. Non see through head mounted displays can be used, for example, with one or more image or video capture systems (e.g. cameras) or 3D scanners to image the live data of the patient, e.g. a skin, a subcutaneous tissue, a surgical site, an anatomic landmark, an organ, or an altered tissue, e.g. a surgically altered tissue, as well as any physical surgical tools, instruments, devices and/or implants, or portions of the surgeon's body, e.g. his or her fingers, hands or arms. Non see through HMDs can be used, for example, for displaying virtual data, e.g. pre- or intra-operative imaging data of the patient, virtual surgical guides, virtual tools, virtual instruments, virtual implants and/or virtual implants, for example together with live data of the patient, e.g. from the surgical site, imaged through the one or more cameras or video or image capture systems or 3D scanners, for knee replacement surgery, hip replacement surgery, shoulder replacement surgery, ankle replacement surgery, spinal surgery, e.g. spinal fusion, brain surgery, heart surgery, lung surgery, liver surgery, spleen surgery, kidney surgery vascular surgery or procedures, prostate, genitourinary, uterine or other abdominal or pelvic surgery, and trauma surgery. Exemplary non see through head mounted displays, e.g. virtual reality head mounted displays, are, for example, the Oculus Rift (Google, Mountain View, CA), the HTC Vive (HTC, Taipei, Taiwan) and the Totem (Vrvana, Apple, Cupertino, CA).

Computer Graphics Viewing Pipeline

In some embodiments, the head mounted display uses a computer graphics viewing pipeline that consists of the following steps to display 3D objects or 2D objects positioned in 3D space or other computer-generated objects and models FIG. 11B:

1. Registration
2. View projection

Registration:

In some embodiments, the different objects to be displayed by the HMD computer graphics system (for instance virtual anatomical models, virtual models of instruments, geometric and surgical references and guides) are initially all defined in their own independent model coordinate system. During the registration process, spatial relationships between the different objects are defined, and each object is transformed from its own model coordinate system into a common global coordinate system. Different techniques that are described below can be applied for the registration process.

For augmented reality ARDDs that superimpose computer-generated objects with live views of the physical environment, the global coordinate system is defined by the environment. A process called spatial mapping, described below, creates a computer representation of the environment that allows for merging and registration with the computer-generated objects, thus defining a spatial relationship between the computer-generated objects and the physical environment.

View Projection:

In some embodiments, once all objects to be displayed have been registered and transformed into the common global coordinate system, they are prepared for viewing on a display by transforming their coordinates from the global coordinate system into the view coordinate system and subsequently projecting them onto the display plane. This view projection step can use the viewpoint and view direction to define the transformations applied in this step. For stereoscopic displays, such as an HMD, two different view projections can be used, one for the left eye and the other one for the right eye. For see-through OHMD the position of the viewpoint and view direction relative to the physical environment can be known in order to correctly superimpose the computer-generated objects with the physical environment. As the viewpoint and view direction change, for example due to head movement, the view projections are updated so that the computer-generated display follows the new view.

Positional Tracking Systems

In some embodiments, the position and/or orientation of the HMDs can be tracked. For example, in order to calculate and update the view projection of the computer graphics view pipeline as described in the previous section and to display the computer-generated overlay images in the HMD, the view position and direction needs to be known.

Different methods to track the HMDs can be used. For example, the HMDs can be tracked using outside-in tracking. For outside-in tracking, one or more external sensors or cameras can be installed in a stationary location, e.g. on the ceiling, the wall or on a stand. The sensors or camera capture the movement of the HMDs, for example through shape detection or markers attached to the HMDs or the user's head. The sensor data or camera image is typically processed on a central computer to which the one or more sensors or cameras are connected. The tracking information obtained on the central computer can then be used to compute the view projection for the HMD (including multiple HMDs). The view projection can be computed on the central computer or on the HMD. Outside-in tracking can be performed with use of surgical navigation system using, for example, infrared (IR) and/or RF markers, active and/or passive markers. One or more external infrared or RF emitters and receivers or cameras can be installed in a stationary location, e.g. on the ceiling, the wall or a stand or attached to the OR table. One or more infrared and/or RF markers, active and/or passive markers can be applied to the HMD for tracking the coordinates and/or the position and/or orientation of the HMD. One or more infrared and/or RF markers, active and/or passive markers can be applied to the anatomic structure or near the anatomic structure tracking the coordinates and/or the position and/or orientation of the anatomic structure. One or more infrared and/or RF markers, active and/or passive markers can be applied to a physical tool, physical instrument, physical implant or physical device tracking the coordinates and/or the position and/or orientation of the physical tool, physical instrument, physical implant or physical device. One or more infrared and/or RF markers, active and/or passive markers can be applied to the surgeon.

In some embodiments, outside-in tracking can be performed with use of an image capture or video capture system using, for example, optical markers, e.g. with geometric patterns. One or more external cameras can be installed in a stationary location, e.g. on the ceiling, the wall or a stand or attached to the OR table. One or more optical markers can be applied to the HMD for tracking the coordinates and/or the position and/or orientation of the HMD. One or more optical markers can be applied to the anatomic structure or near the anatomic structure tracking the coordinates and/or the position and/or orientation of the anatomic structure. One or more optical markers can be applied to a physical tool, physical instrument, physical implant or physical device tracking the coordinates and/or the position and/or orientation of the physical tool, physical instrument, physical implant or physical device. One or more optical markers can be applied to the surgeon.

In some embodiments, including for outside-in and inside-out tracking, a camera, image capture or video capture system can detect light from the spectrum visible to the human eye, e.g. from about 380 to 750 nanometers wavelength, or from about 400 to 720 nanometers wavelength, or from about 420 to 680 nanometers wavelength, or similar combinations. In embodiments throughout the disclosure, including for outside-in and inside-out tracking, a camera, image capture or video capture system can detect light from the spectrum not visible to the human eye, e.g. from the infrared spectrum, e.g. from 700 nm or above to, for example, 1 mm wavelength, 720 nm or above to, for example, 1 mm wavelength, 740 nm or above to, for example, 1 mm wavelength, or similar combinations. In embodiments throughout the disclosure, including for outside-in and inside-out tracking, a camera, image capture or video capture system can detect light from the spectrum visible and from the spectrum not visible to the human eye.

In some embodiments, including for outside-in and inside-out tracking, a marker, e.g. a marker with a geometric pattern and/or a marker used with a navigation system, can be configured to reflect or emit light from the spectrum visible to the human eye, e.g. from about 380 to 750 nanometers wavelength, or from about 400 to 720 nanometers wavelength, or from about 420 to 680 nanometers wavelength, or similar combinations. In embodiments throughout the disclosure, including for outside-in and inside-out tracking, a marker, e.g. a marker with a geometric pattern and/or a marker used with a navigation system, can be configured to reflect or emit light from the spectrum not visible to the human eye, e.g. from the infrared spectrum, e.g. from 700 nm or above to, for example, 1 mm wavelength, 720 nm or above to, for example, 1 mm wavelength, 740 nm or above to, for example, 1 mm wavelength, or similar combinations. In embodiments throughout the disclosure, including for outside-in and inside-out tracking, a marker, e.g. a marker with a geometric pattern and/or a marker used with a navigation system, can be configured to reflect or emit light from the spectrum visible and from the spectrum not visible to the human eye.

In some embodiments, outside-in tracking can be performed with use of a 3D scanner or a laser scanner. One or more external 3D scanners or laser scanners can be installed in a stationary location, e.g. on the ceiling, the wall or a stand or attached to the OR table. The 3D scanner or laser scanner can be used to track objects directly, e.g. the HMD, the anatomic structure, the physical tool, physical instrument, physical implant or physical device or the surgeon. Optionally, markers can be applied to one or more of the HMD, the anatomic structure, the physical tool, physical instrument, physical implant or physical device or the surgeon for tracking any of the foregoing using the 3D scanner or laser scanner.

In some embodiments, the inside-out tracking method can be employed. One or more sensors or cameras can be attached to the HMD or the user's head or integrated with the HMD. The sensors or cameras can be dedicated to the tracking functionality. The cameras attached or integrated into the HMD can include infrared cameras. Infrared LED's or emitters can also be included in the HMD. The sensors or cameras attached or integrated into the HMD can include an image capture system, a video capture system, a 3D scanner, a laser scanner, a surgical navigation system or a depth camera. In some embodiments, the data collected by the sensors or cameras is used for positional tracking as well as for other purposes, e.g. image recording or spatial mapping. Information gathered by the sensors and/or cameras is used to determine the HMD's position and orientation in 3D space. This can be done, for example, by detecting optical, infrared, RF or electromagnetic markers attached to the external environment. Changes in the position of the markers relative to the sensors or cameras are used to continuously determine the position and orientation of the HMD. Data processing of the sensor and camera information can be performed by a mobile processing unit attached to or integrated with the HMD, which can allow for increased mobility of the HMD user as compared to outside-in tracking. Alternatively, the data can be transmitted to and processed on the central computer.

Inside-out tracking can also utilize markerless techniques. For example, spatial mapping data acquired by the HMD sensors can be aligned with a virtual model of the environment, thus determining the position and orientation of the HMD in the 3D environment. Alternatively, or additionally, information from inertial measurement units can be used. Potential advantages of inside-out tracking include greater mobility for the HMD user, a greater field of view not limited by the viewing angle of stationary cameras and reduced or eliminated problems with marker occlusion.

Referring to FIG. 1, a system 10 for using multiple HMDs (ARDDs 11, 12, 13, 14) for multiple viewer's, e.g. a primary surgeon, second surgeon, surgical assistant(s) and/or nurses(s) is shown. The multiple ARDDs can be registered in a common coordinate system 15 using anatomic structures, anatomic landmarks, calibration phantoms, reference phantoms, optical markers, navigation markers, and/or spatial anchors, for example like the spatial anchors used by the Microsoft Hololens. Pre-operative data 16 of the patient can also be registered in the common coordinate system 15. Live data 18 of the patient, for example from the surgical site, e.g. a spine, optionally with minimally invasive access, a hip arthrotomy site, a knee arthrotomy site, a bone cut, an altered surface can be measured, for example using one or more IMUs, optical markers, navigation markers, image or video capture systems and/or spatial anchors. The live data 18 of the patient can be registered in the common coordinate system 15. Intra-operative imaging studies 20 can be registered in the common coordinate system 15. OR references, e.g. an OR table or room fixtures can be registered in the common coordinate system 15 using, for example, optical markers IMUs, navigation markers or spatial mapping 22. The pre-operative data 16 or live data 18 including intra-operative measurements or combinations thereof can be used to develop, generate or modify a virtual surgical plan 24. The virtual surgical plan 24 can be registered in the common coordinate system 15. The ARDDs 11, 12, 13, 14 can project digital holograms of the virtual data or virtual data into the view of the left eye using the view position and orientation of the left eye 26 and can project digital holograms of the virtual data or virtual data into the view of the right eye using the view position and orientation of the right eye 28 of each user, resulting in a shared digital holographic experience 30. Using a virtual or other interface, the surgeon wearing ARDD 11 can execute commands 32, e.g. to display the next predetermined bone cut, e.g. from a virtual surgical plan or an imaging study or intra-operative measurements, which can trigger the ARDDs 11, 12, 13, 14 to project digital holograms of the next surgical step 34 superimposed onto and aligned with the surgical site in a predetermined position and/or orientation.

Virtual data of the patient can be projected superimposed onto live data of the patient for each individual viewer by each individual ARDD for their respective view angle or perspective by registering live data of the patient, e.g. the surgical field, and virtual data of the patient as well as each ARDD in a common, shared coordinate system. Thus, virtual data of the patient including aspects of a virtual surgical plan can remain superimposed and/or aligned with live data of the patient irrespective of the view angle or perspective of the viewer and alignment and/or superimposition can be maintained as the viewer moves his or her head or body.

User Interfaces

Aspects of the present disclosure provide a user interface where the human eye including eye movements and lid movements including movements induced by the orbital and peri-orbital and select skull muscles are detected by the eye tracking system and are processed to execute predefined, actionable computer commands.

Any combination of blinks, eye movements, sequences, and time intervals is possible for encoding various types of commands. These commands can be computer commands that can direct or steer, for example, a surgical instrument or a robot. Methods of executing commands by way of facial movements and movements of the head are also provided. In some embodiments, eye movements, lid movements, facial movement, head movements alone or in combination can be used to signal numerical codes or sequences of numbers or sequences of machine operations. Such sequences of numbers can, for example, be used to execute certain machine operating sequences.

Fusing Physical World with Imaging and Other Data of a Patient

In some embodiments, an operator such as a surgeon may look through an OHMD observing physical data or information on a patient, e.g. a surgical site or changes induced on a surgical site, while pre-existing data of the patient are superimposed onto the physical visual representation of the live patient. Systems, methods and techniques to improve the accuracy of the display of the virtual data superimposed onto the live data of the patient are described in International Patent Application No. PCT/US2018/012459, which is incorporated herein by reference in its entirety.

The pre-existing data of the patient can be an imaging test or imaging data or other types of data including metabolic information or functional information.

The pre-existing data of the patient including one or more imaging tests or other types of data including metabolic or functional information can be obtained at a time different from the time of the surgical procedure. For example, the pre-existing data of the patient can be obtained one, two, three or more days or weeks prior to the surgical procedure.

The pre-existing data of the patient including one or more imaging tests or other types of data including metabolic or functional information are typically obtained with the patient or the surgical site being located in a different location or a different object coordinate system in the pre-existing data when compared to the location or the object coordinate system of the live patient or the surgical site in the live patient. Thus, pre-existing data of the patient or the surgical site are typically located in a first object coordinate system and live data of the patient or the surgical site are typically located in a second object coordinate systems; the first and the second object coordinate system are typically different from each other. The first object coordinate system with the pre-existing data needs to be registered with the second object coordinate system with the live data of the patient including, for example, the live surgical site.

Scan Technology

The following is an exemplary list of scanning and imaging techniques that can be used or applied for various aspects of the present disclosure; this list is not exhaustive, but only exemplary. Anyone skilled in the art can identify other scanning or imaging techniques that can be used in practicing the present disclosure: X-ray imaging, 2D, 3D, supine, upright or in other body positions and poses, including analog and digital x-ray imaging; Digital tomosynthesis; Cone beam CT; Ultrasound; Doppler ultrasound; Elastography, e.g. using ultrasound or MRI; CT; MRI, including, for example, fMRI, diffusion imaging, stroke imaging, MRI with contrast media; Functional MRI (fMRI), e.g. for brain imaging and functional brain mapping; Magnetic resonance spectroscopy; PET; SPECT-CT; PET-CT; PET-MRI; Upright scanning, optionally in multiple planes or in 3D using any of the foregoing modalities, including x-ray imaging, ultrasound etc.; Contrast media (e.g. iodinated contrast agents for x-ray and CT scanning, or MRI contrast agents; contrast agents can include antigens or antibodies for cell or tissue specific targeting; other targeting techniques, e.g. using liposomes, can also be applied; molecular imaging, e.g. to highlight metabolic abnormalities in the brain and target surgical instruments towards area of metabolic abnormality; any contrast agent known in the art can be used in conjunction with the present disclosure); 3D optical imaging, including Laser scanning, Confocal imaging, e.g. including with use of fiberoptics, single bundle, multiple bundle, Confocal microscopy, e.g. including with use of fiberoptics, single bundle, multiple bundles, Optical coherence tomography, Photogrammetry, Stereovision (active or passive), Triangulation (active or passive), Interferometry, Phase shift imaging, Active wavefront sampling, Structured light imaging, Other optical techniques to acquire 3D surface information, Combination of imaging data, e.g. optical imaging, wavefront imaging, interferometry, optical coherence tomography and/or confocal laser imaging or scanning, Image fusion or co-display of different imaging modalities, e.g. in 2D or 3D, optionally registered, optionally more than two modalities combined, fused or co-displayed, e.g. optical imaging, e.g. direct visualization or through an arthroscope, and/or laser scan data, e.g. direct visualization or through an arthroscope, and/or virtual data, e.g. intra-articular, extra-articular, intra-osseous, hidden, not directly visible, and/or external to skin, and/or confocal imaging or microscopy images/data, e.g. direct visualization or through an arthroscope. For a detailed description of illustrative scanning and imaging techniques, see for example, Bushberg et al. The Essential Physics of Medical Imaging, 3rd edition, Wolters, Kluwer, Lippincott, 2012.

In embodiments, 3D scanning can be used for imaging of the patient and/or the surgical site and/or anatomic landmarks and/or pathologic structures and/or tissues (e.g. damaged or diseased cartilage or exposed subchondral bone) and/or the surgeon's hands and/or fingers and/or the OR table and/or reference areas or points and/or marker, e.g. optical markers, in the operating room and/or on the patient and/or on the surgical field. 3D scanning can be accomplished with multiple different modalities including combinations thereof, for example, optical imaging, e.g. using a video or image capture system integrated into, attached to, or separate from one or more HMDs, laser scanning, confocal imaging, optical coherence tomography, photogrammetry, active and passive stereovision and triangulation, interferometry and phase shift principles and/or imaging, wavefront sampling and/or imaging. One or more optical imaging systems or 3D scanners can, for example, be used to image and/or monitor, e.g. the coordinates, position, orientation, alignment, direction of movement, speed of movement of,

- Anatomic landmarks, patient surface(s), organ surface(s), tissue surface(s), pathologic tissues and/or surface(s), e.g. for purposes of registration, e.g. of the patient and/or the surgical site, e.g. one or more bones or cartilage, and/or one or more HMDs, e.g. in a common coordinate system
- The surgeon's hands and/or fingers, e.g. for
  - Monitoring steps in a surgical procedure. Select hand and/or finger movements can be associated with corresponding surgical steps. When the 3D scanner system detects a particular hand and/or finger movement, it can trigger the display of the corresponding surgical step or the next surgical step, e.g. by displaying a predetermined virtual axis, e.g. a reaming, broaching or drilling axis, a virtual cut plane, a virtual instrument, a virtual implant component etc.
  - Executing virtual commands, e.g. using gesture recognition or a virtual interface, e.g. a virtual touch pad
  - One or more HMDs, e.g. registered in a common coordinate system, e.g. with the surgical site and/or the surgeon's hands and/or fingers The use of optical imaging systems and/or 3D scanners for registration, e.g. of the surgical site and/or one or more HMDs can be helpful when markerless registration is desired, e.g. without use of optical markers, e.g. with geometric patterns, and/or IMUs, and/or LEDs, and/or navigation markers. The use of optical imaging systems and/or 3D scanners for registration can also be combined with the use of one or more of optical markers, e.g. with geometric patterns, and/or IMUs, and/or LEDs, and/or navigation markers.

In embodiments, one or more 3D models and/or 3D surfaces generated by an optical imaging system and/or a 3D scanner can be registered with, superimposed with and/or aligned with one or more 3D models and/or 3D surfaces generated by another imaging test, e.g. a CT scan, MRI scan, PET scan, other scan, or combinations thereof, and/or a 3D model and/or 3D surfaces generated from or derived from an x-ray or multiple x-rays, e.g. using bone morphing technologies, as described in the disclosure or known in the art.

With optical imaging systems or 3D scanners, a virtual 3D model can be reconstructed by postprocessing single images, e.g. acquired from a single perspective. In this case, the reconstruction cannot be performed in real time with continuous data capture. Optical imaging systems or 3D scanners can also operate in real time generating true 3D data.

For example, with confocal microscopy using, for example, an active triangulation technique, a projector can project a changing pattern of light, e.g. blue light, onto the surgical field, e.g. an articular surface exposed by arthroscopy or a bone or a soft-tissue, e.g. using projection grids that can have a transmittance random distribution and which can be formed by sub regions containing transparent and opaque structures. By using elements for varying the length of the optical path, it can possible, for each acquired profile, to state a specific relationship between the characteristic of the light and the optical distance of the image plane from the imaging optics. A light source can produce an illumination beam that can be focused onto the surface of the surgical field, e.g. the articular surface. An image sensor can receive the observation beam reflected by the surface of the target object. A focusing system can focus the observation beam onto the image sensor. The light source can split into a plurality of regions that can be independently regulated in terms of light intensity. Thus, the intensity of light detected by each sensor element can be a direct measure of the distance between the scan head and a corresponding point on the target object.

Parallel confocal imaging can be performed, e.g. by shining an array of incident laser light beams, e.g. passing through focusing optics and a probing face, on the surgical field, e.g. an articular surface, a bone or a soft-tissue. The focusing optics can define one or more focal planes forward to the probe face in one or more positions which can be changed, e.g. by a motor or other mechanism. The laser light beams can generate illuminated spots or patterns on the surgical field and the intensity of returning light rays can be measured at various positions of the focal plane determining spot-specific positions yielding a maximum intensity of the reflected light beams. Data can be generated which can represent the topology of the three-dimensional structure of the surgical field, e.g. an articular surface, e.g. exposed and/or visible and/or accessible during arthroscopy, a bone or a soft-tissue. By determining surface topologies of adjacent portions or tissues, e.g. an adjacent articular surface or bone or soft-tissue, from two or more different angular locations and then combining such surface topologies, a complete three-dimensional representation of the entire surgical field can be obtained. Optionally, a color wheel can be included in the acquisition unit itself. In this example, a two-dimensional (2D) color image of the 3D structure of the surgical field, e.g. an articular surface, a bone or a soft-tissue, can also be taken at the same angle and orientation with respect to the structure. Thus, each point with its unique coordinates on the 2D image can correspond to a similar point on the 3D scan having the same x and y coordinates. The imaging process can be based on illuminating the target surface with three differently-colored illumination beams (e.g. red, green or blue light) combinable to provide white light, thus, for example, capturing a monochromatic image of the target portion of the surgical field, e.g. an articular surface, a bone, a cartilage or a soft-tissue, corresponding to each illuminating radiation. The monochromatic images can optionally be combined to create a full color image. Three differently-colored illumination beams can be provided by means of one white light source optically coupled with color filters.

With optical coherence tomography (OCT), using, for example, a confocal sensor, a laser digitizer can include a laser source, e.g. coupled to a fiber optic cable, a coupler and a detector. The coupler can split the light from the light source into two paths. The first path can lead to the imaging optics, which can focus the beam onto a scanner mirror, which can steer the light to the surface of the surgical field, e.g. an articular surface, e.g. as seen or accessible during arthroscopy, a cartilage, a bone and/or a soft-tissue. A second path of light from the light source can be coupled via the coupler to the optical delay line and to the reflector. The second path of light, e.g. the reference path, can be of a controlled and known path length, as configured by the parameters of the optical delay line. Light can be reflected from the surface of the surgical field, e.g. an articular surface, a cartilage, a bone and/or a soft-tissue, returned via the scanner mirror and combined by the coupler with the reference path light from the optical delay line. The combined light can be coupled to an imaging system and imaging optics via a fiber optic cable. By utilizing a low coherence light source and varying the reference path by a known variation, the laser digitizer can provide an optical coherence tomography (OCT) sensor or a low coherence reflectometry sensor. The focusing optics can be placed on a positioning device in order to alter the focusing position of the laser beam and to operate as a confocal sensor. A series of imaged laser segments on the object from a single sample/tissue position can be interlaced between two or multiple 3D maps of the sample/tissue from essentially the same sample/tissue position. The motion of the operator between each subframe can be tracked mathematically through reference points. Operator motion can optionally be removed.

Active wavefront sampling and/or imaging can be performed using structured light projection. The scanning system can include an active three-dimensional imaging system that can include an off-axis rotating aperture element, e.g. placed in the illumination path or in the imaging path. Out-of-plane coordinates of object points can be measured by sampling the optical wavefront, e.g. with an off-axis rotating aperture element, and measuring the defocus blur diameter. The system can include a lens, a rotating aperture element and an image plane. The single aperture can help avoid overlapping of images from different object regions and can help increase spatial resolution. The rotating aperture can allow taking images at several aperture positions. The aperture movement can make it possible to record on a CCD element a single exposed image at different aperture locations. To process the image, localized cross correlation can be applied to reveal image disparity between image frames.

In another embodiment, a scanner can use a polarizing multiplexer. The scanner can project laser sheet onto the surgical cite, e.g. an articular surface, e.g. as exposed or accessible during arthroscopy, a cartilage, damaged, diseased or normal, a subchondral bone, a cortical bone etc., and can then utilize the polarizing multiplexer to optically combine multiple views of the profile illuminated by the sheet of laser light. The scanner head can use a laser diode to create a laser beam that can pass through a collimating lens which can be followed by a sheet generator lens that can convert the beam of laser light into a sheet of laser light. The sheet of laser light can be reflected by a folding mirror and can illuminate the surface of the surgical field. A system like this can optionally combine the light from two perspectives onto a single camera using passive or active triangulation. A system like this system can be configured to achieve the independence of lateral resolution and depth of field. In order to achieve this independence, the imaging system, can be physically oriented so as to satisfy the Scheimpflug principle. The Scheimpflug principle is a geometric rule that describes the orientation of the plane of focus of an optical system wherein the lens plane is not parallel to the image plane. This enables sheet of light based triangulation systems to maintain the high lateral resolution required for applications requiring high accuracy, e.g. accuracy of registration, while providing a large depth of focus.

A 3D scanner probe can sweep a sheet of light across one or more tissue surfaces, where the sheet of light projector and imaging aperture within the scanner probe can rapidly move back and forth along all or part of the full scan path, and can display, for example near real-time, a live 3D preview of the digital 3D model of the scanned tissue surface(s). A 3D preview display can provide feedback on how the probe is positioned and oriented with respect to the target tissue surface.

In other embodiments, the principle of active stereophotogrammetry with structured light projection can be employed. The surgical field can be illuminated by a 2D array of structured illumination points. 3D models can be obtained from the single image by triangulation with a stored image of the structured illumination onto a reference surface such as a plane. A single or multiple cameras can be used. To obtain information in z-direction, the surgical site can be illuminated by a 2D image of structured illumination projected from a first angle with respect to the surgical site. Then the camera can be positioned at a second angle with respect to the surgical site, to produce a normal image containing two-dimensional information in x and y direction as seen at that second angle. The structured illumination projected from a photographic slide can superimpose a 2D array of patterns over the surgical site and can appear in the captured image. The information in z-direction is then recovered from the camera image of the surgical site under the structured illumination by performing a triangulation of each of the patterns in the array on the image with reference to an image of the structured illumination projected on a reference plane, which can also be illuminated from the first angle. In order to unambiguously match corresponding points in the image of the surgical site and in the stored image, the points of the structured illumination can be spatially-modulated with two-dimensional random patterns which can be generated and saved in a projectable medium. Random patterns are reproducible, so that the patterns projected onto the surgical site to be imaged are the same as the corresponding patterns in the saved image.

Accordion fringe interferometry (AFI) can employ light from two-point sources to illuminate an object with an interference fringe pattern. A high precision digital camera can be used to record the curvature of the fringes. The degree of apparent fringe curvature coupled with the known geometry between the camera and laser source enable the AFI algorithms to digitize the surface of the object being scanned. AFI can offer advantages over other scanners as lower sensitivity to ambient light variations and noise, high accuracy, large projector depth of field, enhanced ability to scan shiny and translucent surfaces, e.g. cartilage, and the ability to scan without targets and photogrammetric systems. A grating and lens can be used. Alternatively, coherent point source of electromagnetic radiation can also be generated without a grating and lens. For example, electromagnetic radiation can be emitted from a pair or pairs of optical fibers which can be used to illuminate target objects with interferometric fringes. Consequently, movement of a macroscopic grating which requires several milliseconds or more to effect a phase shift can be avoided. A fiber-based phase shifter can be used to change the relative phase of the electromagnetic radiation emitted from the exit ends of two optical fibers in a few microseconds or less. Optical radiation scattered from surfaces and subsurface regions of illuminated objects can be received by a detector array. Electrical signals can be generated by a detector array in response to the received electromagnetic radiation. A processor receives the electrical signals and calculates three-dimensional position information of tissue surfaces based on changes in the relative phase of the emitted optical radiation and the received optical radiation scattered by the surfaces. Sources of optical radiation with a wavelength between about 350 nm and 500 nm can be used; other wavelengths are possible.

Other optical imaging systems and/or 3D scanners can use the principle of human stereoscopic vision and the principle of linear projection: if straight lines are projected onto an object the lines will be curved around the object. This distortion of the lines allows conclusions to be drawn about the surface contour.

When optical imaging and/or 3D scanning is performed in the context of an arthroscopy procedure, the optical imaging and/or 3D scanning apparatus can be integrated into the endoscope, including by sharing the same fiberoptic(s) or with use of separate fiberoptic(s), e.g. in the same housing or a separate housing. An arthroscopic optical imaging and/or 3D scanning probe can be inserted through the same portal as the one used for the arthroscope, including when integrated into the arthroscope or in a common housing with the arthroscope, or it can be inserted through a second, separate portal. An optical imaging and/or 3D scanning probe used with an arthroscopic procedure can optionally be tracked by tracking the position, location, orientation, alignment and/or direction of movement using optical markers, e.g. with one or more geometric patterns, e.g. in 2D or 3D, or LED's using one or more camera or video systems integrated into, attached to, or separate from one or more HMDs. The camera or video systems can be arranged at discrete, defined angles thereby utilizing angular information including parallax information for tracking distances, angles, orientation or alignment of optical markers attached to the probe, e.g. the arthroscope and/or optical imaging and/or 3D scanning probe. An optical imaging and/or 3D scanning probe and/or an arthroscope used with an arthroscopic procedure can optionally be tracked by tracking the position, location, orientation, alignment and/or direction of movement using navigation markers, e.g. infrared or RF markers, and a surgical navigation system. An optical imaging and/or 3D scanning probe and/or an arthroscope used with an arthroscopic procedure can optionally be tracked by tracking the position, location, orientation, alignment and/or direction of movement directly with one or more camera or video systems integrated into, attached to or separate from one or more HMDs, wherein a computer system and software processing the information can use image processing and pattern recognition to recognize the known geometry of the one or more probes and their location within a coordinate system, e.g. in relationship to the patient, the surgical site and/or the OR table.

With any of the optical imaging and/or 3D scanner techniques, if there are holes in the acquisition and/or scan and/or 3D surface, repeat scanning can be performed to fill the holes. The scanned surface can also be compared against a 3D surface or 3D model of the surgical site, e.g. an articular surface, a cartilage, damaged or diseased or normal, a subchondral bone, a bone and/or a soft-tissue, obtained from an imaging study, e.g. an ultrasound, a CT or MRI scan, or obtained via bone morphing from x-rays as described in other parts of the disclosure. Discrepancies in surface geometry between the 3D model or 3D surface generated with the optical imaging system and/or the 3D scanner and the 3D surface or 3D model obtained from an imaging study or bone morphing from x-rays, can be determined; similarly, it can be determined if the surfaces or 3D models display sufficient commonality to allow for registration of the intra-operative 3D surface or 3D model obtained with the optical imaging system and/or 3D scanner and the 3D surface or 3D model obtained from the pre-operative imaging study or bone morphing from x-rays. If there is not sufficient commonality, additional scanning can be performed using the optical imaging and/or 3D scanner technique, for example in order to increase the spatial resolution of the scanned data, the accuracy of the scanned data and/or to fill any holes in the model or surface. Any surface matching algorithm known in the art can be utilized to register overlapping surface areas and thereby transform all surface portions into the same coordinate space, for example the Iterative Closest Point method described in Besl et al., *A Method for Registration of* 3-*D Shapes;* 1992*; IEEE Trans PAMI* 14(2): 239-255.

Optionally, with any of the foregoing embodiments, the optical imaging system or 3D scanner can have a form of boot or stabilization advice attached to it, which can, for example, be rested against and moved over the target tissue, e.g. an articular surface, a bone or a soft-tissue. The boot or stabilization device can help maintain a constant distance between the scanner and the target tissue. The boot or stabilization device can also help maintain a constant angle between the scanner and the target tissue. For example, a boot or stabilization device can be used with an optical imaging system or scanner used during arthroscopy, maintaining, for example, a constant distance to the articular surface or intra-articular ligament, cartilage, bone or other structures, e.g. a femoral notch or a tibial spine or a tri-radiate cartilage region or fovea capitis in a hip.

Multi-Dimensional Imaging, Reconstruction and Visualization

Various embodiments can be practiced in one, two, three or more dimensions. The following is an exemplary list of potential dimensions, views, projections, angles, or reconstructions that can be applied; this list is not exhaustive, but only exemplary. Anyone skilled in the art can identify additional dimensions, views, projections, angles or reconstructions that can be used in practicing the present disclosure. Exemplary dimensions are listed in Table 1.

TABLE 1: Exemplary list of potential dimensions, views, projections, angles, or reconstructions that can be displayed using virtual representations with ARDD (e.g. HMD), optionally stereoscopic

- 1st dimension: superoinferior, e.g. patient physical data
- 2nd dimension: mediolateral, e.g. patient physical data
- 3rd dimension: anteroposterior, e.g. patient physical data
- 4th-6th dimension: head motion (and with it motion of glasses/HMD) in 1, 2 or 3 dimensions
- 7th-9th dimension: instrument motion in 1, 2 or 3 dimensions, e.g. in relationship to surgical field, organ or head including head motion
- 10th-13th dimension: arm or hand motion in 1, 2 or 3 dimensions, e.g. in relationship to surgical field, organ or head including head motion
- 14th-16th dimension: virtual 3D data of patient, obtained, for example from a scan or intraoperative measurements
- 17th-19th dimension: vascular flow; in 1, 2 or 3 dimensions, e.g. in relationship to surgical field, organ or head including head motion
- 20th-22nd dimension: temperature map (including changes induced by cryo- or hyperthermia), thermal imaging, in 1, 2 or 3 dimensions, e.g. in relationship to surgical field
- 25th-28th dimension: metabolic map (e.g. using MRS, PET-CT, SPECT-CT), in 1, 2 or 3 dimensions, e.g. in relationship to surgical field
- 29th-32nd dimension: functional map (e.g. using fMRI, PET-CT, SPECT-CT, PET, kinematic imaging), in 1, 2 or 3 dimensions, e.g. in relationship to surgical field or patient
- 33rd-35th dimension: confocal imaging data and/or microscopy data in 1, 2, or 3 dimensions, e.g. in relationship to surgical field or patient, e.g. obtained through an endoscope or arthroscope or dental scanner or direct visualization/imaging of an exposed surface
- 36th-38th dimension: optical imaging data in 1, 2 or 3 dimensions, e.g. in relationship to surgical field or patient, e.g. obtained through an endoscope or arthroscope or dental scanner or direct visualization/imaging of an exposed surface
- 39th-40th dimension: laser scan data in 1, 2 or 3 dimensions, e.g. in relationship to surgical field or patient, e.g. obtained through an endoscope or arthroscope or dental scanner or direct visualization/imaging of an exposed surface Any oblique planes are possible. Any perspective projections are possible. Any oblique angles are possible. Any curved planes are possible. Any curved perspective projections are possible.

Any combination of 1D, 2D, and 3D data between the different types of data is possible. Any of the virtual data or virtual representations for display by one or ARDD (e.g. HMD) in Table 1 or described in the disclosure can be adjusted with regard to the focal plane or focal point of the display using any of the embodiments described in the disclosure.

Registering Virtual Data with Live Data Seen Through Head Mounted Display

In some embodiments, virtual data of a patient can be superimposed onto live data seen through the head mounted display. The virtual data can be raw data in unprocessed form, e.g. preoperative images of a patient, or they can be processed data, e.g. filtered data or segmented data.

Data Segmentation

Figure 2:
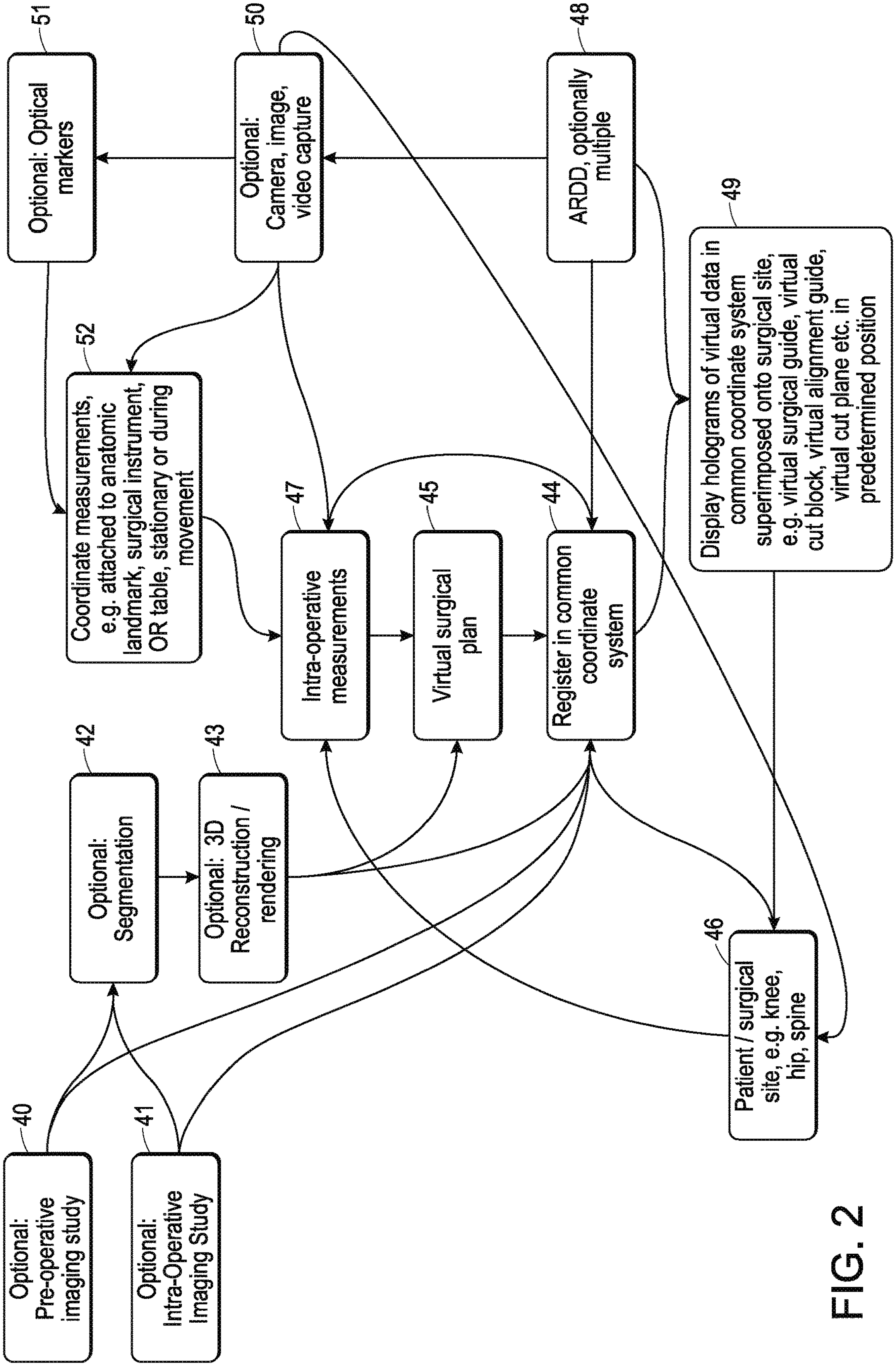
FIG. 2 shows a workflow for segmentation and select subsequent steps according to some embodiments of the present disclosure.

When images of the patient are superimposed onto live data seen through the head mounted display, in many embodiments image segmentation can be desirable. Any known algorithm in the art can be used for this purpose, for example thresholding, seed point techniques, live wire, deformable models, statistical models, active shape models, level set methods, marching cubes algorithms, artificial neural networks, deep learning techniques, or combinations thereof and the like. Many of these algorithms are available is part of open-source or commercial libraries, for instance the Insight Segmentation and Registration Toolkit (ITK), the Open Source Computer Vision Library OpenCV, G'MIC (GREYC's Magic for Image Computing), Caffe, or MATLAB (MathWorks, Natick, Mass.). A non-limiting representative workflow for segmentation and subsequent is provided in FIG. 2. An optional pre-operative imaging study 40 can be obtained. An optional intra-operative imaging study 41 can be obtained. The pre-operative 40 or intra-operative 41 imaging study can be segmented 42, extracting, for example, surfaces, volumes or key features. An optional 3D reconstruction or 3D rendering 43 can be generated. The pre-operative 40 or intra-operative 41 imaging study and any 3D reconstruction or 3D rendering 43 can be registered in a common coordinate system 44. The pre-operative 40 or intra-operative 41 imaging study and any 3D reconstruction or 3D rendering 43 can be used for generating a virtual surgical plan 45. The virtual surgical plan 45 can be registered in the common coordinate system 44. The surgical site 46 can be registered in the common coordinate system 44. Intra-operative measurements 47 can be obtained and can be used for generating a virtual surgical plan 45. An ARDD (e.g. HMD) 48 can project or display digital holograms of virtual data or virtual data 49 superimposed onto and aligned with the surgical site. The HMD 48 is configured to use a built-in camera or image capture or video capture system 50 to optionally detect and/or measure the position and/or orientation and/or alignment of one or more optical markers 51, which can be used for the coordinate measurements 52, which can be part of the intra-operative measurements 47.

Software and Algorithms for Registration

Registration of virtual data with live data can be performed using a variety of techniques know in the art. These include, but are not limited to, surface registration algorithms such as the Iterative Closest Point algorithm, statistical models, Active Shape Models, mutual information-based or other volume registration algorithms, object recognition, pattern recognition or computer vision techniques, deep learning or other artificial intelligence methods. The processed data can, for example, consist of mesh data, parametric surface data, point cloud data, volume data or a combination thereof. These methods are known in the art and have been implemented in publicly and/or commercially available code libraries and application programming interfaces (API's), such as the Insight Segmentation and Registration Toolkit (ITK), the open-source computer vision library OpenCV, Elastix, Plastimatch, or the Medical Image Registration Toolkit (MIRTK).

Superimposition of Virtual Data and Live Data by the HMD

In some embodiments, segmented data or raw data can be superimposed on the patient's live data seen through the head mounted display. This superimposition can occur in unregistered form, i.e. the patient's virtual data may not be aligned with the live data seen through the optical head mounted display. In this case, the operator who is wearing the OHMD may move his/her head in a direction of orientation that will superimpose corresponding features of virtual data and live patient data. The surgeon or operator can also move and re-orient the virtual data using other means, e.g. a trackball or a virtual display interface displayed in the OHMD, unrelated to the surgeon/operator head movement. The operator can adjust the magnification of the live data so that the size, shape, length, thickness of certain features of the virtual data matches that of the live data for a given distance to the object/patient.

For example, during brain surgery, the surgeon may visually in live data look at the exposed gyri and sulci of the patient's brain. The OHMD can display a virtual 3D model of the gyri and sulci of the patient. The surgeon can optionally adjust the magnification of the 3D model so that the model will match the size or width or the length of the corresponding gyri and sulci in the live data. The surgeon can optionally adjust the transparency or opacity of the virtual data displayed in the OHMD. The ratio of virtual vs. live data transmitted through the OHMD can be 1:10, 1:9, 1:8, 1:5, 1:2, 1:1, 2:1, 3:1, 5:1, 8:1, 10:1, as well as fractions or multiples thereof. Any combination of transparency or opacity of virtual data and live data is possible. The surgeon can move his/her head in a direction or orientation that will superimpose virtual features, e.g. the patient's gyri and sulci, with the live patient data. Once the data have been superimposed, the surgeon can optionally register the virtual data with the live data. This registration can be as simple as described here, e.g. a visual confirmation from the surgeon that virtual and live data are substantially matching or substantially superimposed. At this time, the surgeon can optionally reference the virtual data and/or the coordinate system of the virtual data in 2, 3 or more dimensions with the live data and/or the coordinate system of the live data. Once the data are registered, the surgeon can move his/her head into any desired position or orientation, for example for viewing the patient's brain or a lesion and adjacent, e.g. sensitive, anatomy from different view angles. The IMU of the OHMD will register the head movement, the direction of the head movement, the new head position and head orientation. The change in location and orientation of the surgeon's head can be simultaneously or, if desired, non-simultaneously applied to the virtual data which can now be superimposed with the resultant new position and orientation in relationship to the live data. In addition, when the surgeon moves his/her head or body further away from the target anatomy, the change in position and the increase in distance from the target anatomy can be measured by the IMU. Depending on the distance from the IMU, a magnification or minification factor can be applied to the virtual data so that the size, shape and dimensions of the virtual data will, in some embodiments, be close to or match the size, shape and dimensions of the live data, irrespective of the distance, location and orientation of the surgeon's head.

For purposes of registration of virtual data and live data, the ARDD (e.g. OHMD) can be optionally placed in a fixed position, e.g. mounted on a stand or on a tripod. While the ARDD is placed in the fixed position, live data can be viewed by the surgeon and they can be, optionally recorded with a camera and/or displayed on a monitor. Virtual data can then be superimposed and the matching and registration of virtual data and live data can be performed. At this point, the surgeon or an operator can remove ARDD from the fixed position and the surgeon can wear the ARDD during the surgical procedure.

The virtual data can optionally be displayed using a different color, e.g. red, green, yellow etc. Optionally, only the outline of select features of the virtual data may be displayed. For example, these features can be the sulci of the patient's brain (e.g. with a black line or black or lines with other colors), with no visualization of the gyri that these sulci border. Or, for example, only a lesion, e.g. a tumor such as, in the example of the brain, glioblastoma, can be displayed. Or combinations of virtual data of normal tissue and pathologic tissue can be displayed.

The virtual data can be registered with the live data seen through the optical head mounted display. The registration can occur using any method known in the art for registering or cross-referencing virtual and live data, in 2, 3, or more dimensions.

In some embodiments, the registration of the virtual data and the live data will be maintained through the surgical procedure. In some embodiments, the registration of the virtual data and the live data will be maintained during select portions of the surgical procedure or the surgical plan, which can be or can include a virtual, e.g. a preoperatively generated, surgical plan.

In some embodiments, the superimposition of the virtual data and the live data by the ARDD (e.g. OHMD) occurs simultaneously. In some embodiments, the superimposition of the virtual data and the live data by the ARDD is not simultaneous. For example, the virtual data can be superimposed intermittently.

Virtual data can be transparent, translucent or opaque. If virtual data are opaque, they may be displayed intermittently so that the operator or surgeon can see how they project in relationship to the live data of the patient.

If combinations of virtual data are displayed simultaneously with the live data, the different types of virtual data can be displayed with different colors. Representative combinations of virtual and live data are provided below. The following is only illustrative in nature and by no means meant to be limiting:

- Live data: the patient's brain; surgically exposed gyri and sulci.
- Live data: surgical instrument, e.g. biopsy needle or cutting tool
- Virtual data: the patient's brain with gyri and sulci derived and optionally segmented from an imaging modality, e.g. a CT scan or an MRI scan
- Virtual data: a brain tumor, deep seated inside the brain
- Virtual data: the same surgical instrument currently used by the surgeon, in a virtual representation of the instrument, the virtual data indicating the desired orientation, location or direction of the surgical instrument.

Any of the foregoing virtual data can be displayed in two dimensions or three dimensions. Multi-dimensional displays as outlined in other sections of the disclosure are possible.

For example, the patient's normal tissue, e.g. normal brain tissue, can optionally be displayed in two dimensions, e.g. using grey level images, while the patient's abnormal tissue, e.g. a stroke, a hemorrhage or a tumor, can be displayed in three dimensions. Any combination of 2D, 3D, and multi-dimensional images is possible for display by the ARDD; any combination of 2D, 3D, and multi-dimensional images can be superimposed on live patient data by the ARDD.

The virtual 2D, 3D, and multi-dimensional data can be generated or acquired by different data acquisition technologies, e.g. different imaging tests etc.

Locking or Moving of Virtual Data

In some embodiments, virtual data can be locked in relationship to the surgeon or operator or in relationship to the patient or a certain target anatomy within a patient. This means even if the surgeon moves his or her head or the body or parts of the patient's anatomy are being moved, the virtual data will not move in the HMD display. For example, once registration has occurred, the HMD can display a virtual image of a target tissue or adjacent tissue. The virtual image of the target tissue or adjacent tissue can be, for example, an image through a tumor or other type of pathologic tissue. As the surgeon or operator moves his or her head or body during the surgical procedure, the virtual data will not move, but are being displayed within the same location.

In some embodiments, virtual data can move in relationship to the surgeon or operator or in relationship to the patient or a certain target anatomy within a patient. This means if the surgeon moves his or her head, and with that the HMD, or the body or parts of the patient's anatomy are being moved, the virtual data can move in the HMD display. This can include an adjustment of the focal plane or focal point or a selection of a different focal plane or focal point for the virtual display of the virtual data by the one or more HMDs. For example, once registration has occurred, the HMD can display a virtual image of a target tissue or adjacent tissue. The virtual image of the target tissue or adjacent tissue can be, for example, an image through a tumor or other type of pathologic tissue. As the surgeon or operator moves his or her head or body during the surgical procedure, A computer processor can be configured to move and change the location and orientation of the virtual data and can adjust or change focal plane or focal point to the extent and reflecting how the surgeon moves his/her head or body, typically reflecting the change in perspective or view angle that the surgeon obtained by moving his or her head or body.

Optionally the moving of the virtual data can be at greater virtual distance or greater angle or lesser virtual distance or lesser angle than the movement of the surgeon's head or body.

Improving the Accuracy of Moving or Re-Orienting Virtual Data

Once registration between virtual data and physical data has occurred, the moving or re-orienting of virtual data to follow, for example, the surgeon's head movements or body movements or operating arm or hand movements, or the movements of the patient or certain body parts of the patient can be accomplished, for example, by monitoring the movement and change in location and/or orientation of the surgeon's head using the IMU of the HMD.

In some embodiments, optical or RF tracker's or other tracking devices known in the art can be applied to the HMD and/or the patient including select body parts or target tissues of the patient, e.g. the patient's knee. Using standard surgical navigation techniques known in the art, the spatial location of the optical or RF trackers can be recorded, for example for a starting pose or position or location. Movement of the trackers, e.g. induced by movement of the surgeon's head or body or by movement of at least a part of the patient, can then be tracked using the navigation system. The information on positional change, orientational change or movement direction of the surgeon's head or the patient or both can then be used to update the virtual data, or the display of the virtual data in the HMD, or both correspondingly. In this manner, the virtual data and the live data can be superimposed by the HMD, typically in an accurate manner.

Optionally, positional, orientational, directional data and the like generated by the IMU can be used in conjunction with such data generated by a surgical navigation system. A combination of data can be beneficial for more accurate measurement of changes in position or orientation of the surgeon's head, body, operating arm, hand, or the patient.

The head mounted display can be of optical see-through type, with the anatomic structures directly visible to the user's eye through the transparent or partially transparent OHMD. The head mounted display can be of video see through type, with the anatomic structure imaged using one or more video cameras, optionally stereoscopic, attached to the head mounted display, with the anatomic structures imaged with the video cameras and then displayed by the head mounted display, but typically not directly visible to the user's eye. In some embodiments, hybrid applications of both can be used, for example with a partially transparent OHMD that receives also feed from one or more video cameras for display by the OHMD.

The following embodiments describe in detail how tracking information acquired during surgery can be used to determine head mounted display parameters for convergence, focal plane, focal point and/or scale for the overlay display or superimposition of virtual data on live surgery data or live images including anatomic data or structures of the patient. The focal plane, focal point, scale/magnification, or convergence of virtual data, e.g. a virtual surgical guide, displayed by a first display unit for the left eye and a second display unit for the right eye of the HMD, e.g. an optical see through head mounted display or a video see through head mounted display, can be adjusted continuously or intermittently based on a distance determined between a target anatomic site or structure, a target surgical site (e.g. with one or more anatomic structures, a marker attached to the patient (e.g. attached to an anatomic structure, e.g. at or near a surgical site) and the HMD, e.g. the first display unit for the left eye and the second display unit for the right eye; the refresh rate or the frequency of such adjustments can be, for example, a frequency of 0.01 Hz, 0.05 Hz, 0.1 Hz, 0.5 Hz, 1.0 Hz, 3.0 Hz, 5.0 Hz, 8.0 Hz, 10 Hz, 15 Hz or 20 Hz, or at the refresh rate of the HMD or at a refresh rate of a navigation system or inside out tracking system or any combinations thereof.

The adjusting of a focal plane, focal point, scale/magnification, or convergence of virtual data, e.g. a virtual surgical guide, displayed by a first display unit for the left eye and a second display unit for the right eye of the HMD can be effected, for example, by moving the virtual data displayed by the first display unit for the left eye and the virtual data displayed by the second display unit for the right eye by 0.01 mm, 0.05 mm, 0.1 mm, 0.5 mm, 1.0 mm, 3.0 mm, 5.0 mm, or any other number including fractional number. The moving of the virtual data, e.g. the virtual surgical guide, can be effected with a deformable lens or deformable mirror. The moving can be a translation, rotation and/or pivoting.

The adjusting of a focal plane, focal point, scale/magnification, or convergence of virtual data, e.g. a virtual surgical guide, displayed by a first display unit for the left eye and a second display unit for the right eye of the HMD can be effected, for example, by moving the first display unit for the left eye and the second display unit for the right eye by 0.01 mm, 0.05 mm, 0.1 mm, 0.5 mm, 1.0 mm, 3.0 mm, 5.0 mm, or any other number including fractional number. The moving can be a translation, rotation and/or pivoting. The moving of the first and second display units can be effected with mechanical, electrical, electromagnetic and/or piezoelectric adjustment effectors, means, mechanism, or systems including active optical elements known in the art. The moving of the first and second display units can be effected with a deformable lens or deformable mirror.

In some embodiments, the system, e.g. comprising a head mounted display, one or more computer processors, optionally one or more cameras, optionally one or more markers, e.g. attached to a patient, can be configured so that one or more processors are configured to determine the distance between one or more predetermined coordinates of virtual data, e.g. a virtual surgical guide, and a head mounted display during movement of a marker (e.g. attached to a patient (for example a surgical site or anatomic structure), movement of the head mounted display, or movement of the marker and the head mounted display, wherein the one or more processors can be configured to adjust the focal plane, focal point, convergence or combination thereof based on the change in the determined distance.

In some embodiments, the distance between the virtual data projected onto, superimposed onto, aligned with or projected inside an anatomic structure and the viewpoint of the user/operator can be used to adjust convergence, focal plane, focal point and/or scale display parameters. Virtual data can, for example, consist of pre- or intra-operative imaging data of the patient, virtual surgical guides (e.g. virtual planes, virtual axes, virtual cut guides), virtual tools, virtual instruments, virtual implants, and virtual devices. The virtual data is commonly registered into a common coordinate system with the live surgery data, e.g. with a corresponding anatomical structure, physical tool, physical instrument, physical implant or physical device using a suitable registration method, for example using the methods and system disclosed throughout the disclosure. After this registration of the virtual data in a common coordinate system with the live surgical data, e.g. the anatomic structures, the position and pose of the virtual data relative to the live surgical data, e.g. the anatomic structures, is known, and therefore tracking information about the live surgical data can be used to determine the distance between virtual data and the HMD and/or the viewpoint of the user/operator and the virtual data and any physical instruments, physical tools, physical implants, or physical devices. The following embodiments therefore include a description of different methods to track live surgical data, e.g. anatomic structures (including, for example anatomic and or biomechanical axes), and how they relate to determining convergence, focal plane, focal point and/or scale parameters for display of the virtual data in the HMD. Any of the registration and tracking techniques described in the disclosure or known in the art can be used.

Convergence

In some embodiments, a video see-through or an optical see-through head mounted display can be configured to account for convergence and/or accommodation of the user's eye(s). Convergence can be the convergent rotation of the eyes where the visual axes of the two eyes are being brought into intersection at a 3D location in space. The head mounted display can, for example, be configured to account for convergence by measuring the inter-pupillary or inter-ocular distance. The inter-pupillary or inter-ocular distance can be measured using a ruler or an inter-ocular measurement device, for example, or any other technique known in the art. The head mounted display can, for example, be configured to account for convergence by measuring the amount of convergence using eye tracking, e.g. using systems or methods described in the disclosure for eye tracking or gaze tracking or known in the art, and by moving, e.g. rotating the left and right eye display unit of the head mounted display so that the display unit of each eye is substantially vertical to the visual axis of the left eye and the right eye, and/or by adjusting or moving the virtual data displayed by the HMD for the left eye and the right eye.

The head mounted display can, for example, be configured to account for convergence by measuring, with a computer system, the distance between a head mounted display and an anatomic structure, for example using an image capture, a video capture, a 3D scanner, a laser scanner, a navigation system, and/or using any of the techniques described in the disclosure or known in the art.

Outside-In Tracking

With outside-in tracking an image capture or video capture system using, for example, optical markers, e.g. with geometric patterns, calibration phantoms or reference phantoms can be used for coordinate determination in the common coordinate system and distance measurements\. One or more external cameras can be installed in a stationary location, e.g. on the ceiling, the wall or a stand or attached to the OR table. One or more optical markers can be applied to the ARDD for tracking the coordinates and/or the position and/or orientation of the ARDD. One or more optical markers can be applied to the surgeon for tracking the coordinates and/or the position and/or orientation of the surgeon. One or more optical markers can be applied to the anatomic structure or near the anatomic structure tracking the coordinates and/or the position and/or orientation of the anatomic structure. One or more optical markers can be applied to a physical tool, physical instrument, physical implant or physical device tracking the coordinates and/or the position and/or orientation of the physical tool, physical instrument, physical implant or physical device.

Figure 20:
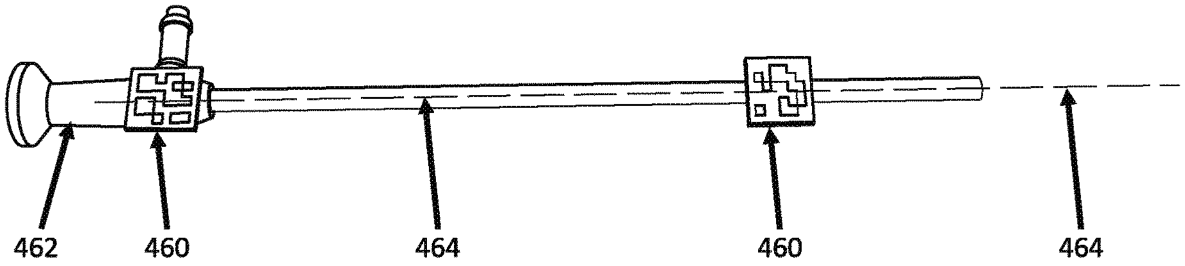
FIG. 20 shows an illustrative, non-limiting example of a surgical instrument with multiple optical markers attached for tracking the surgical instrument according to some embodiments of the present disclosure.

Multiple different technical approaches are possible to track the surgical instruments in the surgeon's live view of the patient through the OHMD and to project the invisible parts of an instrument hidden by the tissue and its direction with the OMHD. None of these approaches are meant to be limiting, but are only exemplary in nature. Someone skilled in the art can recognize other approaches for tracking surgical instruments using embodiments of the present disclosure. Multiple optical markers 460 can be attached to a surgical instrument 462 as shown in FIG. 20. For example, the markers can be fixed at defined positions on the instrument. With the geometry of the instrument known, the position and orientation of the instrument can be calculated, e.g. for an instrument like an awl with a tip for which its rotary orientation is aligned with the pointing axis only two markers 460 are needed as shown in FIG. 20. More markers can be used, e.g. in different geometric locations on the instrument with overlapping or separate, distinct x, y, and z coordinates. The markers' 3D coordinates are recognized by the RDD (e.g. OHMD) using the methods described in the preceding sections. Using the coordinates of a first and second marker, a vector 464, line in FIG. 20 pointing in the direction of the tip is calculated and displayed by the ARDD to indicate the direction of the hidden portions of the instrument superimposed onto the surgical site, enabling the surgeon to align the physical awl or pedicle screw including its hidden portions with the intended path defined using the standard or virtual planning interface and also projected by the ARDD. Rather than using two or more markers, a single marker can be used, for example with sufficient geometric information, e.g. along the long axis or other axis of the instrument, for accurate coordinate determination, e.g. 2, 3, 4, 5, 6, 7, 8, 9 or 10 cm long and, for example, 1, 2, 3, 4, 5, 6, or 7 or other cm wide, depending also on the spatial resolution of the camera system. In general, the greater the spatial resolution of the camera or video system, the smaller the marker size that can be used for accurate coordinate and/or vector determination. In addition, smaller marker sizes can be possible when markers are stationary, e.g. rigidly attached to a non-moving anatomic part of the patient or the OR table. Larger marker sizes can be used, for example, when markers are attached to a moveable anatomic landmark, e.g. a distal femoral condyle or a proximal tibial plateau, or a humerus, or a humeral tuberosity, or when they are attached to the ARDD and are thus, for example, subject to movement as the surgeon moves his or her head.

Another approach uses pivoting, a mathematical technique for determining the position of the tip. With pivoting, the instruments tip is fixed in one position on the tissue while the whole instrument is moved. The attached optical markers move on a spherical surface. This leads, for example, to an accurate registration of an entry point.

With outside-in tracking a camera, e.g. using visible light or infrared light, a 3D scanner or a laser scanner using, for example, optical markers, e.g. with geometric patterns, navigation markers, RF markers, LED's, IMU's, calibration phantoms or reference phantoms can be used for coordinate determination in the common coordinate system and distance measurements. One or more external camera, 3D scanners or laser scanners can be installed in a stationary location, e.g. on the ceiling, the wall or a stand or attached to the OR table. One or more optical markers, e.g. with geometric patterns, navigation markers, RF markers, LEDs, IMUs, calibration phantoms or reference phantoms can be applied to the ARDD for tracking the coordinates and/or the position and/or orientation of the ARDD. One or more optical markers, e.g. with geometric patterns, navigation markers, RF markers, LEDs, IMUs, calibration phantoms or reference phantoms can be applied to the surgeon for tracking the coordinates and/or the position and/or orientation of the surgeon. One or more optical markers, e.g. with geometric patterns, navigation markers, RF markers, LEDs, IMUs, calibration phantoms or reference phantoms can be applied to the anatomic structure or near the anatomic structure tracking the coordinates and/or the position and/or orientation of the anatomic structure. One or more optical markers, e.g. with geometric patterns, navigation markers, RF markers, LEDs, IMUs, calibration phantoms or reference phantoms can be applied to a physical tool, physical instrument, physical implant or physical device tracking the coordinates and/or the position and/or orientation of the physical tool, physical instrument, physical implant or physical device. The distance between the ARDD and an anatomic structure and/or the distance between the ARDD and a physical tool, physical instrument, physical implant or physical device, and/or the distance between virtual data projected onto, superimposed onto, aligned with or projected inside an anatomic structure and the ARDD and/or the distance between virtual data projected onto, superimposed onto, aligned with or projected inside an anatomic structure and a physical tool, physical instrument, physical implant or physical device can be determined using this approach and the convergence between the left eye and the right eye display can be computed, for example for a given inter-pupillary or inter-ocular distance. Optionally, eye or gaze tracking can also be used for estimating or determining the convergence, for example when the surgeon is looking at an anatomic structure through the optical or video see through head mounted display or when the surgeon is looking at a physical tool, physical instrument, physical implant or physical device through the optical or video see through head mounted display. Optionally a combination of coordinate measurements and/or distance measurements and eye or gaze tracking can be used for estimating or determining the convergence.

With outside-in tracking a surgical navigation system using, for example, navigation markers, e.g. infrared markers, RF markers, passive markers or active markers can be used for coordinate determination in the common coordinate system and distance measurements. One or more external surgical navigation cameras can be installed in a stationary location, e.g. on the ceiling, the wall or a stand or attached to the OR table. One or more navigation markers, e.g. infrared markers, RF markers, passive markers or active markers can be applied to the ARDD for tracking the coordinates and/or the position and/or orientation of the ARDD. One or more navigation markers, e.g. infrared markers, RF markers, passive markers or active markers can be applied to the surgeon for tracking the coordinates and/or the position and/or orientation of the surgeon. One or more navigation markers, e.g. infrared markers, RF markers, passive markers or active markers can be applied to the anatomic structure or near the anatomic structure tracking the coordinates and/or the position and/or orientation of the anatomic structure. One or more navigation markers, e.g. infrared markers, RF markers, passive markers or active markers can be applied to a physical tool, physical instrument, physical implant or physical device tracking the coordinates and/or the position and/or orientation of the physical tool, physical instrument 1150, physical implant or physical device. The distance between the ARDD and an anatomic structure and/or the distance between the ARDD and a physical tool, physical instrument, physical implant or physical device, and/or the distance between virtual data projected onto, superimposed onto, aligned with or projected inside an anatomic structure and the ARDD and/or the distance between virtual data projected onto, superimposed onto, aligned with or projected inside an anatomic structure and a physical tool, physical instrument, physical implant or physical device can be determined using this approach and the convergence between the left eye and the right eye display can be computed, for example for a given inter-pupillary or inter-ocular distance. Optionally, eye or gaze tracking can also be used for estimating or determining the convergence, for example when the surgeon is looking at an anatomic structure through the optical or video see through head mounted display or when the surgeon is looking at a physical tool, physical instrument, physical implant or physical device through the optical or video see through head mounted display. Optionally a combination of coordinate measurements and/or distance measurements and eye or gaze tracking can be used for estimating or determining the convergence.

With outside-in tracking one or more depth sensors using, for example, markers, calibration phantoms or reference phantoms can be used for coordinate determination in the common coordinate system and distance measurements. One or more external depth sensors can be installed in a stationary location, e.g. on the ceiling, the wall or a stand or attached to the OR table. One or more markers, calibration phantoms or reference phantoms can be applied to the ARDD for tracking the coordinates and/or the position and/or orientation of the ARDD. One or more markers, calibration phantoms or reference phantoms can be applied to the surgeon for tracking the coordinates and/or the position and/or orientation of the surgeon. One or more markers, calibration phantoms or reference phantoms can be applied to the anatomic structure or near the anatomic structure tracking the coordinates and/or the position and/or orientation of the anatomic structure. One or more markers, calibration phantoms or reference phantoms can be applied to a physical tool, physical instrument, physical implant or physical device tracking the coordinates and/or the position and/or orientation of the physical tool, physical instrument, physical implant or physical device. Optionally, the depth sensor can determine the coordinates of the ARDD, the surgeon, the anatomic structure, the physical tool or physical instrument, the physical implant or physical device without use of markers, calibration phantoms or reference phantoms. The distance between the ARDD and an anatomic structure and/or the distance between the ARDD and a physical tool, physical instrument, physical implant or physical device, and/or the distance between virtual data projected onto, superimposed onto, aligned with or projected inside an anatomic structure and the ARDD and/or the distance between virtual data projected onto, superimposed onto, aligned with or projected inside an anatomic structure and a physical tool, physical instrument, physical implant or physical device can be determined using this approach and the convergence between the left eye and the right eye display can be computed, for example for a given inter-pupillary or inter-ocular distance. Optionally, eye or gaze tracking can also be used for estimating or determining the convergence, for example when the surgeon is looking at an anatomic structure through the optical or video see through head mounted display or when the surgeon is looking at a physical tool, physical instrument, physical implant or physical device through the optical or video see through head mounted display. Optionally a combination of coordinate measurements and/or distance measurements and eye or gaze tracking can be used for estimating or determining the convergence.

Inside-Out Tracking

With inside-out tracking, one or more an image capture or video capture systems can be attached to the ARDD or the user's head or integrated with the ARDD for coordinate determination in the common coordinate system and distance measurements. The image capture or video capture system can be dedicated to the tracking functionality. Information gathered by the image capture or video capture systems can be used to determine the ARDDs position and/or orientation and/or coordinates in 3D space in the common coordinate system as well as the position and/or orientation and/or coordinates of the surgeon, the anatomic structure(s), the physical tool or physical instrument, and/or the physical implant or device. This can be done, for example, by detecting optical markers, active or passive markers, LEDs, IMUs, calibration phantoms or reference phantoms attached to the external environment, e.g. the ceiling, the wall, the OR table, a stand, or a tripod, the surgeon, the anatomic structure(s), the physical tool or physical instrument, and/or the physical implant or device. Changes in the relative position of the optical markers, active or passive markers, LEDs, IMUs, calibration phantoms or reference phantoms relative to the image capture or video capture system attached to or integrated into the ARDD can be used to intermittently, continuously, or in real time determine the position and/or orientation and/or coordinates of the ARDD, the surgeon, the anatomic structure(s), the physical tool or physical instrument, and/or the physical implant or device. Changes in the position of the image capture or video capture system attached to or integrated into the ARDD relative to the optical markers, active or passive markers, LEDs, IMUs, calibration phantoms or reference phantoms attached to the external environment, e.g. the ceiling, the wall, the OR table, a stand, or a tripod, can also be used to intermittently, continuously, or in real time determine the position and/or orientation and/or coordinates of the ARDD, the surgeon, the anatomic structure(s), the physical tool or physical instrument, and/or the physical implant or device. The distance between the ARDD and an anatomic structure and/or the distance between the ARDD and a physical tool, physical instrument, physical implant or physical device, and/or the distance between virtual data projected onto, superimposed onto, aligned with or projected inside an anatomic structure and the ARDD and/or the distance between virtual data projected onto, superimposed onto, aligned with or projected inside an anatomic structure and a physical tool, physical instrument, physical implant or physical device can be determined using this approach and the convergence between the left eye and the right eye display can be computed, for example for a given inter-pupillary or inter-ocular distance. Optionally, eye or gaze tracking can also be used for estimating or determining the convergence, for example when the surgeon is looking at an anatomic structure through the optical or video see through head mounted display or when the surgeon is looking at a physical tool, physical instrument, physical implant or physical device through the optical or video see through head mounted display. Optionally a combination of coordinate measurements and/or distance measurements and eye or gaze tracking can be used for estimating or determining the convergence.

With inside-out tracking, one or more an 3D scanners or laser scanners can be attached to the ARDD or the user's head or integrated with the ARDD 1125 for coordinate determination in the common coordinate system and distance measurements. The 3D scanner or laser scanner can be dedicated to the tracking functionality. Information gathered by the 3D scanner or laser scanner can be used to determine the ARDDs position and/or orientation and/or coordinates in 3D space in the common coordinate system as well as the position and/or orientation and/or coordinates of the surgeon, the anatomic structure(s), the physical tool or physical instrument, and/or the physical implant or device. This can be done, for example, by detecting optical markers, e.g. with geometric patterns, LEDs, IMUs, calibration phantoms or reference phantoms attached to the external environment, e.g. the ceiling, the wall, the OR table, a stand, or a tripod, the surgeon, the anatomic structure(s), the physical tool or physical instrument, and/or the physical implant or device. Changes in the relative position of the optical markers, e.g. with geometric patterns, LEDs, IMUs, calibration phantoms or reference phantoms relative to the 3D scanner or laser scanner attached to or integrated into the ARDD can be used to intermittently, continuously, or in real time determine the position and/or orientation and/or coordinates of the ARDD, the surgeon, the anatomic structure(s), the physical tool or physical instrument, and/or the physical implant or device. Changes in the position of the 3D scanner or laser scanner attached to or integrated into the ARDD relative to the optical markers, e.g. with geometric patterns, LEDs, IMUs, calibration phantoms or reference phantoms attached to the external environment, e.g. the ceiling, the wall, the OR table, a stand, or a tripod, can also be used to intermittently, continuously, or in real time determine the position and/or orientation and/or coordinates of the ARDD, the surgeon, the anatomic structure(s), the physical tool or physical instrument, and/or the physical implant or device. The distance between the ARDD and an anatomic structure and/or the distance between the ARDD and a physical tool, physical instrument, physical implant or physical device, and/or the distance between virtual data projected onto, superimposed onto, aligned with or projected inside an anatomic structure and the ARDD and/or the distance between virtual data projected onto, superimposed onto, aligned with or projected inside an anatomic structure and a physical tool, physical instrument, physical implant or physical device can be determined using this approach and the convergence between the left eye and the right eye display can be computed, for example for a given inter-pupillary or inter-ocular distance. Optionally, eye or gaze tracking can also be used for estimating or determining the convergence, for example when the surgeon is looking at an anatomic structure through the optical or video see through head mounted display or when the surgeon is looking at a physical tool, physical instrument, physical implant or physical device through the optical or video see through head mounted display. Optionally a combination of coordinate measurements and/or distance measurements and eye or gaze tracking can be used for estimating or determining the convergence.

With inside-out tracking, one or more navigation systems can be attached to the ARDD or the user's head or integrated with the ARDD for coordinate determination in the common coordinate system and distance measurements. The navigation system can be dedicated to the tracking functionality. The cameras attached or integrated into the ARDD as part of the navigation system can include infrared cameras. Infrared LED's or emitters can also be included in the ARDD. Information gathered by the navigation system can be used to determine the ARDDs position and/or orientation and/or coordinates in 3D space in the common coordinate system as well as the position and/or orientation and/or coordinates of the surgeon, the anatomic structure(s), the physical tool or physical instrument, and/or the physical implant or device. This can be done, for example, by detecting navigation markers, e.g. infrared markers, RF markers, passive markers or active markers attached to the external environment, e.g. the ceiling, the wall, the OR table, a stand, or a tripod, the surgeon, the anatomic structure(s), the physical tool or physical instrument, and/or the physical implant or device. Changes in the relative position of the navigation markers, e.g. infrared markers, RF markers, passive markers or active markers relative to the navigation system attached to or integrated into the ARDD can be used to intermittently, continuously, or in real time determine the position and/or orientation and/or coordinates of the ARDD, the surgeon, the anatomic structure(s), the physical tool or physical instrument, and/or the physical implant or device. Changes in the position of the navigation system attached to or integrated into the ARDD relative to the navigation markers, e.g. infrared markers, RF markers, passive markers or active markers attached to the external environment, e.g. the ceiling, the wall, the OR table, a stand, or a tripod, can also be used to intermittently, continuously, or in real time determine the position and/or orientation and/or coordinates of the ARDD, the surgeon, the anatomic structure(s), the physical tool or physical instrument, and/or the physical implant or device. The distance between the ARDD and an anatomic structure and/or the distance between the ARDD and a physical tool, physical instrument, physical implant or physical device, and/or the distance between virtual data projected onto, superimposed onto, aligned with or projected inside an anatomic structure and the ARDD and/or the distance between virtual data projected onto, superimposed onto, aligned with or projected inside an anatomic structure and a physical tool, physical instrument, physical implant or physical device can be determined using this approach and the convergence between the left eye and the right eye display can be computed, for example for a given inter-pupillary or inter-ocular distance. Optionally, eye or gaze tracking can also be used for estimating or determining the convergence, for example when the surgeon is looking at an anatomic structure through the optical or video see through head mounted display or when the surgeon is looking at a physical tool, physical instrument, physical implant or physical device through the optical or video see through head mounted display. Optionally a combination of coordinate measurements and/or distance measurements and eye or gaze tracking can be used for estimating or determining the convergence.

With inside-out tracking, one or more depth sensors can be attached to the ARDD or the user's head or integrated with the ARDD for coordinate determination in the common coordinate system and distance measurements. The depth sensor can be dedicated to the tracking functionality. Information gathered by the depth sensor can be used to determine the ARDD's position and/or orientation and/or coordinates in 3D space in the common coordinate system as well as the position and/or orientation and/or coordinates of the surgeon, the anatomic structure(s), the physical tool or physical instrument, and/or the physical implant or device. This can be done, for example, by 3D surface mapping or depth mapping of the different structures and objects, e.g. the surgeon, the anatomic structure(s), the physical tool or physical instrument, and/or the physical implant or device. This can be done, for example, by detecting markers, calibration phantoms or reference phantoms attached to the external environment, e.g. the ceiling, the wall, the OR table, a stand, or a tripod, the surgeon, the anatomic structure(s), the physical tool or physical instrument, and/or the physical implant or device. Changes in the relative position of the markers, calibration phantoms or reference phantoms relative to the depth sensor(s) attached to or integrated into the ARDD can be used to intermittently, continuously, or in real time determine the position and/or orientation and/or coordinates of the ARDD, the surgeon, the anatomic structure(s), the physical tool or physical instrument, and/or the physical implant or device. Changes in the position of the depth sensor(s) attached to or integrated into the ARDD relative to the markers, calibration phantoms or reference phantoms attached to the external environment, e.g. the ceiling, the wall, the OR table, a stand, or a tripod, can also be used to intermittently, continuously, or in real time determine the position and/or orientation and/or coordinates of the ARDD, the surgeon, the anatomic structure(s), the physical tool or physical instrument, and/or the physical implant or device. Optionally, the depth sensor can determine the coordinates of the ARDD, the surgeon, the anatomic structure, the physical tool or physical instrument, the physical implant or physical device without use of markers, calibration phantoms or reference phantoms. The distance between the ARDD and an anatomic structure and/or the distance between the ARDD and a physical tool, physical instrument, physical implant or physical device, and/or the distance between virtual data projected onto, superimposed onto, aligned with or projected inside an anatomic structure and the ARDD and/or the distance between virtual data projected onto, superimposed onto, aligned with or projected inside an anatomic structure and a physical tool, physical instrument, physical implant or physical device can be determined using this approach and the convergence between the left eye and the right eye display can be computed, for example for a given inter-pupillary or inter-ocular distance. Optionally, eye or gaze tracking can also be used for estimating or determining the convergence, for example when the surgeon is looking at an anatomic structure through the optical or video see through head mounted display or when the surgeon is looking at a physical tool, physical instrument, physical implant or physical device through the optical or video see through head mounted display. Optionally a combination of coordinate measurements and/or distance measurements and eye or gaze tracking can be used for estimating or determining the convergence.

With the distance between the anatomic structure and the optical head mounted display and the inter-pupillary or inter-ocular distance known, the computer system with one or more computer processors can compute the amount of convergence needed for a given distance between the anatomic structure and the optical head mounted display and, optionally, for a given inter-pupillary or inter-ocular distance, and it can account for the convergence by moving, e.g. rotating, the left and right eye display unit of the optical head mounted display so that the display unit of each eye is substantially vertical to the visual axis of the left eye and the right eye, and/or by adjusting or moving the virtual data displayed by the HMD for the left eye and the right eye.

The rotating and/or translating of the left and right eye display of the HMD can be executed by rotating the left and right eye display unit, e.g. using mechanical actuation, an electric motor, an electromagnetic mechanism, and/or a piezoelectric mechanism. The amount of rotation and/or translation can also be adjusted based on the inter-ocular distance of the operator. The position, orientation, position and orientation of the at least left and the at least right eye display of the HMD can be adjusted based on the inter-ocular distance of the operatory, gaze or eye tracking data, data generated by outside-in-tracking, data generated by inside-out tracking, or any combination thereof.

The rotating and/or translating of the left and right eye display of the HMD can be executed by rotating and/or translating the virtual data displayed for the left eye and for the right eye, e.g. using eye tracking data on eye position and/or gaze direction, and/or as a function of the distance of the physical data, e.g. an anatomic structure (e.g. a spinal element, a spinal structure, a knee structure, a hip structure, a shoulder structure, an ankle structure, a dental structure (a tooth, gum, root), a vessel, a vascular structure, an internal organ, a brain) to the ARDD display, and/or the virtual data projected onto or inside the anatomic structure using the registration and coordinate information, and/or also the inter-pupillary or inter-ocular distance of the user. The amount of rotation and/or translation can be adjusted based on the inter-pupillary or inter-ocular distance of the operator. Thus, one or more of an inter-pupillary or inter-ocular distance, eye tracking data, e.g. with measurement of gaze direction, gaze tracking data, or the distance 170 of the physical data, e.g. an anatomic structure (e.g. a spinal element, a spinal structure, a knee structure, a hip structure, a shoulder structure, an ankle structure, a dental structure (a tooth, gum, root), a vessel, a vascular structure, an internal organ, a brain) to the ARDD display can be used to determine, using a computer processor, the adjusting of the convergence, e.g. using rotation and/or translation of the left and right eye display, for example by rotating and/or translating the physical display unit or by rotating and/or translating the virtual data displayed by the ARDD or both. One or more of an inter-pupillary or inter-ocular distance, eye tracking data, e.g. with measurement of gaze direction, gaze tracking data, or the distance of the physical tool, physical instrument, physical implant or physical device to the ARDD display can be used to determine, using a computer processor, the adjusting of the convergence, e.g. using rotation and/or translation of the left and right eye display, for example by rotating and/or translating the physical display unit or by rotating and/or translating the virtual data displayed by the ARDD or both. The computer system can be configured to provide visualization or display of the virtual data displayed by the ARDD with a convergence of the eyes for the virtual data displayed to the left and right eye that is substantially similar to the convergence of the eyes when looking at the anatomic structure, and/or the physical tool, physical instrument, physical implant or physical device, visible directly through an optical see through head mounted display, without the need for adjustments in convergence when looking at the anatomic structure, and/or the physical tool, physical instrument, physical implant or physical device, and the virtual data displayed by the ARDD.

In some embodiments, the computer system can be configured to update the convergence of the display of the virtual data displayed by the HMD for the left eye and the right eye continuously or intermittently. The intermittent updates can, for example, occur at a frequency of 0.01 Hz, 0.05 Hz, 0.1 Hz, 0.5 Hz, 1.0 Hz, 3.0 Hz, 5.0 Hz, 8.0 Hz, 10 Hz, 15 Hz or 20 Hz, or at the refresh rate of the HMD. Any frequency is possible. In any of the embodiments throughout the disclosure, the computer system can be configured to update the convergence of the display of the virtual data displayed by the HMD for the left eye and the right eye in real time. The real time updates can, for example, occur at a frequency of 30 Hz, 40 Hz, 50 Hz, 60 Hz, 70 Hz, 80 Hz 90 Hz, 100 Hz or greater. Other frequencies are possible for real time updating the convergence of the display of the virtual data by the HMD.

With intermittent, near real time or real time updating of the convergence of the display of the virtual data displayed by the HMD for the left eye and the right eye, the computer system can adjust the convergence of the display of the virtual data displayed by the HMD for the left eye and the right eye with movement of the HMD, and/or movement of the anatomic structure, and/or movement of the physical tool, physical instrument, physical implant or physical device. With intermittent, near real time or real time updating of the convergence of the display of the virtual data displayed by the HMD for the left eye and the right eye, the computer system can adjust the convergence of the display of the virtual data displayed by the HMD for the left eye and the right eye with movement of one or more of the HMD, the anatomic structure, the physical tool, physical instrument, or the physical implant or physical device. The movement of the anatomic structure can, for example, be the movement of a spinal element, a spinal structure, a knee structure, a hip structure, a shoulder structure, an ankle structure, a joint movement, e.g. a flexion, extension, abduction, adduction, rotation, elevation, a dental structure, a vessel, a vascular structure, a pulsation of a vessel or vascular structure, a surgically altered surface or structure. The computer system can adjust the convergence of the display of the virtual data displayed by the HMD for the left eye and the right eye with movement of an anatomic structure so that the convergence of the virtual data displayed by the HMD for the left eye and the right eye is maintained with the same or substantially the same portion or region or surface or anatomic features of the anatomic structure.

The convergence between a first view displayed by a first display unit of an HMD (for example for the left eye) and a second view displayed by the second display unit of the HMD (for example for a right eye) can also be adjusted by adjusting at least one of a size, dimension, position, orientation or combination thereof of the first and second views on the first and second display units based on a determined distance, e.g. determined between an anatomic structure and the HMD.

Accommodation

Accommodation refers to the focus action of the eye where the shape of the lens is adjusted to objects depending on their distance from the eye. In some embodiments, an optical head mounted display can use a fixed focal distance or a range of fixed focal distances forcing accommodation and accommodation cues to be tied with a fixed focal distance or a range of fixed focal distances. In these embodiments, virtual data regardless of their distance from the eye or their location in the common coordinate system are seen in focus if the viewer focuses on the focal plane or focal point of the virtual data. If the focal plane or focal point of the virtual data coincides with an anatomic structure (e.g. a spinal element, a spinal structure, a knee structure, a hip structure, a shoulder structure, an ankle structure, a dental structure (a tooth, gum, root), a vessel, a vascular structure, an internal organ, a brain), e.g. the surface of an anatomic structure, the eyes can focus on the anatomic structure as seen through the optical or video see through head mounted display and the display of the virtual data can be in focus (i.e. sharp) also, since the effective focal distance between the anatomic structure and the HMD and the display of the virtual data and the HMD are the same or similar.

If the focal plane or focal point does not coincide with or is substantially different from an anatomic structure (e.g. a spinal element, a spinal structure, a knee structure, a hip structure, a shoulder structure, an ankle structure, a dental structure (a tooth, gum, root), a vessel, a vascular structure, an internal organ, a brain), e.g. the surface of an anatomic structure, the eyes can focus on the anatomic structure as seen through the optical or video see through head mounted display; however, the display of the virtual data will not be in focus (which means it can be unsharp or blurred).

If the focal plane or focal point does not coincide with or is substantially different from an anatomic structure (e.g. a spinal element, a spinal structure, a knee structure, a hip structure, a shoulder structure, an ankle structure, a dental structure (a tooth, gum, root), a vessel, a vascular structure, an internal organ, a brain), e.g. the surface of an anatomic structure, the eyes can focus on the focal plane or focal point of the virtual data displayed by the HMD alternatively; however, the anatomic structure as seen through the optical see through head mounted display may not be in focus (which means it can be unsharp or blurred). In some embodiments, if a video see through HMD system is used, the video cameras can still focus on the anatomic structure in this embodiment and both the virtual data and the display of the anatomic structure in the video see through system can be displayed in the same or similar focal plane or with the same or similar focal point of the HMD and can be sharp.

In some embodiments, the difference in focal distance and/or focal planes or focal points between anatomic structures and virtual data displayed by the HMD can be addressed using a volumetric display in which all voxels within a volumetric space have to be rendered by the HMD; in these embodiments, the volumetric display of the virtual data can coincide with the focal distance between the HMD and the anatomic structure.

In some embodiments, spatial multiplexed and time multiplexed techniques can be used for adjusting and/or selecting the focal plane or focal point of virtual data displayed by the HMD.

Multi-Focal Display of Virtual Data

In some embodiments, a multi-focal HMD system can be used. A multi-focal HMD with multi-focal display of virtual data can, for example, be spatial multiplexed and can use, for example, a stack of planar or non-planar HMD display units (e.g. combiners, multiple mirrors or a stack of LCD's or stacked waveguides) to form focal planes in an HMD display that divide a volumetric space, for example at focal distances of 10, 20, 30, 40, 50, 60 and/or 70 cm, or at focal planes or focal distances of 10, 15, 20, 25, 30, 35, 40, 45, 50, 55, and/or 60 cm. Any other increments are possible. Increments can optionally extend into infinity. Increments can be even spaced. Increments can have irregular spacing, e.g. 10, 20, 25, 27, 29, 30, 31, 33, 35, 40, 50 cm, or 10, 20, 25, 27, 29, 30, 31, 40, 50 cm. Any combination of increments is possible. The separation of the planar displays can, for example, take visual acuity, typical range of focal distances for a particular activity, e.g. surgery, visual acuity, pupil size and inter-pupillary or inter-ocular distance into account.

One or more planar or non-planar display units can be configured, e.g. by selecting an appropriate spacing, to match or be similar to the determined distance between an anatomic structure and an HMD so that a focal plane, focal point or combination thereof of virtual data derived based on the determined distance can coincide or be similar with at least one of the planar or non-planar display units in the stack.

Similarly, one or more planar or non-planar display units can be configured, e.g. by selecting an appropriate spacing, to match or be similar to the determined distance between an anatomic structure and an HMD so that a range of focal planes, focal points or combination thereof of virtual data displayed by the stack of planar or non-planar display units includes a range of focal planes, focal points or combination thereof of virtual data derived based on one or more determined distances or near one or more determined distances between an anatomic structure and the HMD.

With a multi-focal HMD display of virtual data, a display of the virtual data can be selected that is similar to or that substantially matches the focal plane or the focal point(s) of the anatomic structure seen by the surgeon through the HMD. The selection of the focal plane or the focal points can be performed based on coordinate data obtained using tracking techniques including, for example, markers (e.g. markers that reflect or emit light, markers with geometric patterns, RF markers, active markers, passive markers, etc.), image capture, video capture, 3D scanners, laser scanner and surgical navigation systems. The coordinate data in the coordinate system of the ARDD, and the patient, e.g. the surgical site or anatomic structure and, optionally, any physical tools, physical instruments, physical implants or physical device can be used to determine the distance between the ARDD (and, optionally, the surgeon's pupil) and the patient, e.g. the surgical site or anatomic structure, and/or the ARDD (and, optionally, the surgeon's pupil) and/or the one or more physical tools, physical instruments, physical implants or physical device. The coordinate data of the patient, e.g. the surgical site or anatomic structure and, optionally, any physical tools, physical instruments, physical implants or physical device, can be referenced to or can be based on a marker attached to the patient, e.g. attached to an anatomic structure, for example an anatomic structure within the surgical site or near the surgical sites, and/or can be referenced to or based on a marker attached to the OR table or a structure or device in the operating room. One or more coordinates of a virtual surgical guide can be predetermined, for example at a predetermined position, predetermined orientation or combination thereof of a physical surgical tool or instrument and can be referenced to or based on a marker attached to the surgical site or anatomic structure. For example, the marker attached to the patient can be used to reference or to determine a common coordinate system. The determined distance between the ARDD and the patient, e.g. the surgical site or anatomic structure, (and/or optionally a marker attached to the patient, e.g. attached to an anatomic structure, for example an anatomic structure within the surgical site or near the surgical sites) and/or the ARDD and the one or more physical tools, physical instruments, physical implants or physical devices can be used to select a focal plane or focal point or to adjust a focal plane or focal point within the multifocal display of the virtual data that can match or can be similar to the measured distance, e.g. between the ARDD and the patient, e.g. the surgical site or anatomic structure, and/or the ARDD and the one or more physical tools, physical instruments, physical implants or physical device.

The distance between the ARDD and the patient, e.g. the surgical site or anatomic structure, and/or the ARDD and the one or more physical tools, physical instruments, physical implants or physical device can be measured continuously or intermittently, e.g. with a frequency of 0.2 Hz, 0.5 Hz, 1 Hz, 2 Hz, 5 Hz, 10 Hz, 20 Hz, or any other frequency, or it can be measured in real time, e.g. with frequencies greater than 30 Hz, 50 Hz, 100 Hz or more. If the anatomic structure or the ARDD moves or if both move, the determined distance can be updated accordingly between the ARDD and the patient, e.g. the surgical site or anatomic structure, and/or the ARDD and the one or more physical tools, physical instruments, physical implants or physical device, and the selection of the focal plane or focal point(s) within the multifocal display of the virtual data can be updated or changed to match or be similar to the measured or determined distance, e.g. between the ARDD and the patient, e.g. the surgical site or anatomic structure seen through the ARDD, and/or the ARDD and the one or more physical tools, physical instruments, physical implants or physical device, and/or the distance between virtual data projected onto, superimposed onto, aligned with or projected inside an anatomic structure and the ARDD and/or the distance between virtual data projected onto, superimposed onto, aligned with or projected inside an anatomic structure and a physical tool, physical instrument, physical implant or physical device, and to maintain a focal plane or focal point of the virtual data that is the same or similar to the measured or determined distance between the ARDD and the patient, e.g. the surgical site or anatomic structure seen through the ARDD, and/or the ARDD and the one or more physical tools, physical instruments, physical implants or physical device.

For example, if the OHMD moves, the selection of the focal plane or focal point(s) within the multifocal display of the virtual data can be updated or changed to match or be similar to the measured distance, e.g. between the OHMD and the patient, e.g. the surgical site or anatomic structure, seen through the OHMD and/or the OHMD and the one or more physical tools, physical instruments, physical implants or physical device, and to maintain a focal plane or focal point of the virtual data that is the same or similar to the measured distance between the OHMD and the patient, e.g. the surgical site or anatomic structure, seen through the OHMD and/or the OHMD and the one or more physical tools, physical instruments, physical implants or physical device.

For example, if the anatomic structure moves, the selection of the focal plane or focal point(s) within the multifocal display of the virtual data can be updated or changed to match or be similar to the measured distance, e.g. between the OHMD and the patient, e.g. the surgical site or anatomic structure, seen through the OHMD and/or the OHMD and the one or more physical tools, physical instruments, physical implants or physical device, and to maintain a focal plane or focal point of the virtual data that is the same or similar to the measured distance between the OHMD, microscope or endoscope and the patient, e.g. the surgical site or anatomic structure, seen through the OHMD and/or the OHMD and the one or more physical tools, physical instruments, physical implants or physical device.

For example, if the physical tools, physical instruments, physical implants or physical device move, the selection of the focal plane or focal point(s) within the multifocal display of the virtual data can be updated or changed to match or be similar to the measured distance, e.g. between the OHMD, microscope, endoscope and the patient, e.g. the surgical site or anatomic structure, seen through the OHMD and/or the OHMD and the one or more physical tools, physical instruments, physical implants or physical device, and to maintain a focal plane or focal point of the virtual data that is the same or similar to the measured distance between the OHMD and the patient, e.g. the surgical site or anatomic structure, seen through the OHMD, and/or the OHMD and the one or more physical tools, physical instruments, physical implants or physical device.

Any combination is possible, thereby accounting also for simultaneous movement of one or more of the OHMD, the anatomic structure, the physical tools, physical instruments, physical implants or physical devices.

Varifocal Display of Virtual Data

In some embodiments, a varifocal HMD can be used, for example using a time multiplexed approach. With a varifocal HMD, a single-plane 2D display device can, for example, be used and can be controlled using a computer processor through a mechanical, electrical, electromagnetic and/or piezoelectric adjustment effectors, means, mechanism, or systems or through an active optical element for focusing adjustment. For example, a relay lens can be moved in the HMD unit for focusing adjustment. Alternatively, a display unit can be axially translated within the HMD unit using a microcontroller controlled by a computer processor, for example with mechanical, electrical, electromagnetic and/or piezoelectric actuators effecting the axial translation. Different types of translation, e.g. axial, superior, inferior, medial, lateral, are possible. Rotation and/or translation and/or pivoting of the display unit (also, for example, for convergence adjustment) can be performed. Combinations of translation, rotation and pivoting of the display unit can be implemented.

With traditional mechanical lenses, the focal plane can be adjusted or changed for a varying focal distance by translating the optical elements within the lens against each other. Deformable lenses or deformable mirrors can be an alternative to traditional mechanical lenses or mirrors that can allow focusing over a range of distances and that can be small requiring optionally less space than mechanical systems. Deformable lenses or deformable mirrors can use, for example, electro-optical, electromechanical, thermo-optical, and acousto-mechanical techniques. Electro-optical devices can incorporate electrowetting or liquid-crystal cells to perform the deformation function. Electromechanical techniques can use servomotors, MEMS micropumps, and piezoelectric devices to achieve lens deformation. Heat and sound can also be used to achieve lens deformation. Liquid lenses that use electrowetting technology can perform focusing with use of a lens that comprises two immiscible fluids of different refractive indexes. These can consist of an electrically conducting water solution and electrically non-conducting oil. Due to the index difference of the two liquids, the interface between these liquids can form a natural diopter. An electric field can be applied across the hydrophobic coating to control the shape of the lens, so that it becomes less hydrophobic; this process called electrowetting results from an electrically induced change in surface tension. As a result of the changes in hydrophobic properties, the aqueous solution can begin to wet the sidewalls of a tube, altering the radius of curvature of the meniscus between the two fluids and thus the lens' focal length. The surface of an initially convex lens can be made completely flat or even concave by increasing the electric field. The lens can range from convergent to divergent in configuration.

Liquid crystals can be used in electro-optical adaptive lens or mirror designs to perform adjusting and changing the focal length. For example, a voltage can be applied to change the rotation of molecules in a liquid-crystal cell, thereby achieving a change in refractive index. The differential rotation of the liquid-crystal molecules from the center to the periphery of the element can be changed by applying the voltage, thereby adjusting or changing the focal distance. By tuning the voltage through a range of voltages, the focal distance can be adjusted or changed from infinity to near field.

Electromechanical techniques can be used for lens deformation. Electroactive polymers can be employed for an electrically focusable lens. These techniques can use a dielectric elastomer actuator. Applying a voltage to two electrodes connected to either side of the dielectric elastomer actuator can result in an expansion of the polymer which can be used to form a lens that can bend as an electric field is applied. Alternatively, mechanically tunable liquid lenses can be used in which the lens fluid can be pumped into or out of the lens enclosure, and the lens contracts or expands to form a concave or convex shape to adjust the focal length and, optionally, to zoom in or out.

Piezoelectric actuators can also be used for lens deformation, for example using a two-chamber approach with two immiscible liquids connected by a circular hole. The liquid-liquid interface that is formed at the hole can act as the aperture of the lens. Due to the different refractive indices of the two liquids, the interface can operate as a refractive surface.

Thermally tunable lenses can also adjust the focal length. Thermally tunable microlenses can use, for example, polydimethylsiloxane (PDMS), a silicon-based organic polymer in conjunction with a microarray heating system. By increasing the temperature of the microarray heating system underneath the PDMS lens, the radius of curvature can change due to the thermal expansion of the PDMS causing a change in the lens' focal length.

Acousto-optical lenses can also be used for adjusting and changing the focal length. Acousto-optical lenses can use water droplets acting as oscillators when confined in defined spaces; water droplets can oscillate back and forth with the rate of oscillation and the resultant refraction determined by the frequency of the sound.

In some embodiments, deformable mirrors can be used for adjusting the focal length of the virtual data displayed by the HMD. Deformable mirrors can include multiple flat mirror segments which can, for example, be moved with three degrees of freedom. Deformable mirrors with a continuous faceplate can utilize a thin deformable reflective membrane or surface with multiple actuators attached to the backside of the faceplate. The actuators can be mechanical, electric, electromagnetic and/or piezoelectric. Other concepts for deformable mirrors include, for example, thin conductive and reflective membranes, that can be deformed by applying controlled voltages to electrostatic actuators connected to the membrane. Bimorph mirrors can be deformable, having two or more layers of different materials, for example one made of a piezoelectric material and one made of an electro-restrictive material. Liquid deformable mirrors can be utilized, for example using ferromagnetic nanoparticles which can align with an electric field applied so that the mirror shape can be a function of magnetic, gravitational and surface tension forces present.

With a varifocal approach, the distance between an anatomic structure (e.g. a spinal element, a spinal structure, a knee structure, a hip structure, a shoulder structure, an ankle structure, a dental structure (a tooth, gum, root), a vessel, a vascular structure, an internal organ, a brain) and the HMD can be determined and the focal plane or focal point of the virtual data displayed by the HMD can be dynamically moved or adjusted and can be matched to the distance between the anatomic structure and the HMD. The distance between an anatomic structure (e.g. a spinal element, a spinal structure, a knee structure, a hip structure, a shoulder structure, an ankle structure, a dental structure (a tooth, gum, root), a vessel, a vascular structure, an internal organ, a brain) and the HMD can be determined and the focal plane or focal point of the virtual data displayed by the HMD can be dynamically moved and can be matched to the distance between the anatomic structure and the HMD.

Adjusting or Moving the Display Unit

The adjusting and moving the focal plane or focal point and maintaining the focal plane or focal point focused or fixated on the anatomic structure and/or one or more physical tools, physical instruments, physical implants or physical device can be performed by the computing system using one or more computer processors by adjusting and/or moving including translating, rotating and/or pivoting the display units (e.g. combiners, mirrors, LCD's) for the left eye and for the right eye so that the focal plane or focal point can be maintained relative to the anatomic structure and/or one or more physical tools, physical instruments, physical implants or physical device for a given distance between the ARDD, microscope, and/or endoscope and the anatomic structure and/or the ARDD, microscope, and/or endoscope and the one or more physical tools, physical instruments, physical implants or physical device, even with movement of the ARDD and/or movement of the anatomic structure and/or movement of the one or more physical tools, physical instruments, physical implants or physical device. The focal plane or focal point can be adjusted or moved continuously or intermittently e.g. with a frequency of 0.1 Hz, 0.2 Hz, 0.5 Hz, 1 Hz, 2 Hz, 5 Hz, 10 Hz, 20 Hz, or any other frequency, or it can be adjusted or moved in real time, e.g. with frequencies greater than 30 Hz, 50 Hz, 100 Hz or more. By adjusting or moving the focal plane or focal point frequently or in real time with movement of the ARDD and/or the anatomic structure and/or the physical tools, instruments, implants or devices, the display of the virtual data can be maintained in focus or focused, while the user or operator is observing and focusing his or her eyes on the anatomic structure and/or the physical tools, instruments, implants or devices directly visible through the see through optical head mounted display, irrespective of any movement of the ARDD and/or the anatomic structure and/or the physical tools, instruments, implants or devices.

Adjusting or Moving or Deforming the Lens or Mirror

The adjusting and moving the focal plane or focal point and maintaining the focal plane or focal point focused or fixated on the anatomic structure and/or one or more physical tools, physical instruments, physical implants or physical device can also be performed by the computing system using one or more computer processors by adjusting and/or moving one or more traditional mechanical lenses and/or by adjusting and/or moving and/or deforming one or more deformable lenses, adjustable lenses, deformable mirrors and/or adjustable mirrors of the ARDD using any of the techniques described in the disclosure or known in the art for the left eye and for the right eye so that the focal plane or focal point can be maintained relative to the anatomic structure and/or one or more physical tools, physical instruments, physical implants or physical device for a given distance between the ARDD, microscope and/or endoscope and the anatomic structure and/or the ARDD, microscope and/or endoscope and the one or more physical tools, physical instruments, physical implants or physical device, even with movement of the ARDD, microscope, and/or endoscope and/or movement of the anatomic structure and/or movement of the one or more physical tools, physical instruments, physical implants or physical device. The focal plane or focal point can be adjusted or moved continuously or intermittently e.g. with a frequency of 0.1 Hz, 0.2 Hz, 0.5 Hz, 1 Hz, 2 Hz, 5 Hz, 10 Hz, 20 Hz, or any other frequency, or it can be adjusted or moved in real time, e.g. with frequencies greater than 30 Hz, 50 Hz, 100 Hz or more. By adjusting or moving the focal plane or focal point frequently or in real time with movement of the ARDD and/or the anatomic structure and/or the physical tools, instruments, implants or devices, the display of the virtual data can be maintained in focus or focused, while the user or operator is observing and focusing his or her eyes on the anatomic structure and/or the physical tools, instruments, implants or devices directly visible through the see through optical head mounted display, irrespective of any movement of the ARDD and/or the anatomic structure and/or the physical tools, instruments, implants or devices.

Any of the foregoing embodiments related to volume, multifocal or varifocal approaches can be used with outside-in tracking and inside-out tracking, as described, for example, in the disclosure or as known in the art.

In any of the embodiments throughout the disclosure, the computer system can be configured to update the focal plane or focal point of the virtual data displayed by the ARDD in real time to coincide with or intersect with or be tangent with or be at a predetermined angle with the anatomic structure, and/or the virtual data projected onto or inside the anatomic structure using the registration and coordinate information or a focal plane of a microscope or endoscope, and/or the physical tool, physical instrument, physical implant or physical device. The real time updates can, for example, occur at a frequency of 30 Hz, 40 Hz, 50 Hz, 60 Hz, 70 Hz, 80 Hz 90 Hz, 100 Hz or greater. Other frequencies are possible for real time updating of the focal plane or focal point of the virtual data.

With intermittent, near real time or real time updating of the focal plane or focal point of the virtual data, the computer system can adjust or maintain the focal plane or focal point of the virtual data displayed by the ARDD to remain or to be maintained coinciding with or intersecting with or being tangent with or being at a predetermined angle with the anatomic structure, and/or the physical tool, physical instrument, physical implant or physical device even with movement of the ARDD, and/or movement of the anatomic structure, and/or movement of the physical tool, physical instrument, physical implant or physical device, and/or movement of a focal plane of a microscope or endoscope. With intermittent, near real time or real time updating of the focal plane or focal point of the virtual data, the computer system can adjust or maintain the focal plane or focal point of the virtual data displayed by the ARDD to remain or to be maintained coinciding with or intersecting with or being tangent with or being at a predetermined angle with the anatomic structure, and/or the physical tool, physical instrument, physical implant or physical device even with movement of one or more of the ARDD, the anatomic structure the physical tool or physical instrument, or the physical implant or physical device. The movement of the anatomic structure can, for example, be the movement of a spinal element, a spinal structure, a knee structure, a hip structure, a shoulder structure, an ankle structure, a joint movement, e.g. a flexion, extension, abduction, adduction, rotation, elevation, a dental structure, a vessel, a vascular structure, a pulsation of a vessel or vascular structure, a surgically altered surface or structure.

The computer system can adjust or maintain the focal plane or focal point of the virtual data displayed by the ARDD to remain or to be maintained coinciding with or intersecting with or tangent with or at a predetermined angle with the anatomic structure with movement of the anatomic structure so that the focal plane or focal point of the virtual data is maintained coinciding with or intersecting with or tangent with or at a predetermined angle with the same or substantially the same portion or region or surface or anatomic features of the anatomic structure. The computer system can adjust or maintain the focal plane or focal point of the virtual data displayed by the ARDD to remain or to be maintained coinciding with tangent with or parallel with the focal plane or focal point of a microscope or endoscope. The computer system can adjust or maintain the focal plane or focal point of the virtual data displayed by the ARDD to remain or to be maintained coinciding with or intersecting with or tangent with or at a predetermined angle with the anatomic structure with movement of the anatomic structure so that the focal plane or focal point of the virtual data remains fixated with the same or substantially the same portion or region or surface or anatomic features of the anatomic structure during movement.

Adjustment or Selection of Scale and/or Magnification of Virtual Data

The ARDD can, for example, be configured to adjust the scale and/or magnification of the virtual data by measuring, with a computer system, the distance between an optical head mounted display and an anatomic structure, for example using an image capture, a video capture, a 3D scanner, a laser scanner, a navigation system, and/or using any of the techniques described in the disclosure or known in the art, or by replicating the magnification (or minification) of a microscope or endoscope.

In some embodiments, the computer processor can be configured to maintain the 2D imaging slice or imaging cross-section projected by the HMD superimposed and/or aligned with the physical tissue of the patient always in a constant or the same position relative to the physical tool, physical instrument, physical implant, e.g. intersecting with the tip or located at the tip, while maintaining a fixed anatomic orientation, e.g. sagittal, coronal, axial, oblique sagittal, oblique coronal, oblique axial, curved sagittal, curved coronal, curved axial. This can be advantageous, for example, when a biopsy needle or a tissue harvester is moved or advanced through soft-tissue or hard tissue, e.g. during a brain, heart, lung, thyroid, parathyroid, liver, spleen, kidney, adrenal, prostate, ovary, bone, cartilage or any other biopsy. This can also be advantageous, for example, for any surgical procedure where a physical surgical tool, physical surgical instrument, physical implant or any other physical surgical device is moved or advanced through soft-tissue or hard tissue, e.g. through a brain, heart, lung, thyroid, parathyroid, liver, spleen, kidney, adrenal, prostate, ovary, bone, cartilage or any other tissue. For example, as a surgeon moves and advances a physical needle, physical awl, physical screw through a vertebra or a portion of a vertebra, e.g. a pedicle [for example for a spinal fusion], the computer processor can be configured to move and/or advance 2D imaging slices through the vertebra, portion of the vertebra, e.g. the pedicle, and the imaging slices can always be located at the tip of the tracked physical needle, physical awl or physical screw and can always be in a fixed anatomic orientation, e.g. in a sagittal, coronal, axial, oblique sagittal, oblique coronal, oblique axial, curved sagittal, curved coronal, or curved axial plane. Thus, as the surgeon moves the physical needle, physical awl or physical screw from a first position with a first set of coordinates to a second position with a second set of coordinates, the HMD can display a first 2D imaging slice through the pedicle at the first position, with the 2D imaging slices intersecting with or located at the tip of the physical needle, physical awl or physical screw and, for example, oriented in a coronal plane or a sagittal plane or an axial plane at the first position or first coordinates and the HMD can then display a second 2D imaging slice through the pedicle at the second position, with the 2D imaging slices intersecting with or located at the tip of the physical needle, physical awl or physical screw and, for example, oriented in a coronal plane or a sagittal plane or an axial plane at the second position or second coordinates. In this manner, the surgeon can always monitor the location of the physical needle, physical awl or physical screw inside the physical tissue of the patient and relative to the 2D images obtained pre- or intra-operatively from the patient. This can be beneficial, for example, when complex 3D structures, e.g. a spine reconstructed in 3D from a CT scan or MRI scan, can potentially obscure fine anatomic detail inside the patient due to superimposition of multiple structures. This can also be beneficial during spinal fusion surgery with pedicle screws since the cortex of the pedicle and the inner pedicle wall or endosteum can be difficult to see on a superimposed and/or aligned 3D display of the spine, e.g. reconstructed from a CT scan, while it can be readily visible on the superimposed and/or aligned 2D imaging, e.g. a CT slice superimposed and/or aligned with the corresponding physical tissue/pedicle slice of the patient. In some embodiments, the 2D image(s) displayed by the HMD can be maintained by the computer processor in a fixed location, e.g. the center of a pedicle, while the physical tool, physical instrument, physical implant or physical device is moved, e.g. inside the pedicle.

In some embodiments, more than one 2D slice can be displayed by the HMD, for example at least two or more of a sagittal, coronal, axial, oblique sagittal, oblique coronal, oblique axial, curved sagittal, curved coronal, or curved axial slices or images. The two or more 2D slices can be moved through the tissue, e.g. anterior, posterior, medial, lateral, superior, inferior, by the computer processor of the HMD display following the movement of a tracked physical tool, physical instrument, physical implant or physical device so that the two or more 2D slices displayed by the computer processor of the HMD display are always superimposed onto and/or aligned with a corresponding slice of the patient's physical tissue in the coordinate system while the physical tool, physical instrument, physical implant or physical device is moved in the patient's tissue and in the coordinate system and their position and/or orientation relative to the physical tool, physical instrument, physical implant or physical device can be maintained during the movement. The two or more 2D slices or cross-sections can intersect in the display of the HMD. The intersection can be, for example, centered around an anatomic structure or maintained [e.g. during movement of the patient, the surgical site, the HMD, the physical tool, physical instrument, physical implant or physical device] at or over an anatomic structure or site, e.g. the center of a pedicle or a line through the pedicle. The intersection can be centered around or maintained at or around a physical surgical tool, physical surgical instrument, physical implant or any other physical surgical device, e.g. around a long axis or other portion of the physical surgical tool, physical surgical instrument, physical implant or any other physical surgical device. The maintaining of the intersection of the two or more imaging planes over a portion of the physical surgical tool, physical surgical instrument, physical implant or any other physical surgical device can be performed by the computer processor while the tracked physical surgical tool, physical surgical instrument, physical implant or any other physical surgical device are moved inside the physical tissue of the patient, e.g. while an awl is advanced inside a pedicle.

2D imaging data or imaging slices or cross-sections as well as 3D displays, e.g. a 3D reconstruction from a CT or MRI scan [e.g. of a spine, or a hip, or a knee] and any virtual data, e.g. a predetermined path, predetermined start or end point, predetermined virtual axis, virtual tool, virtual instrument, virtual implant, virtual device, displayed by the HMD can be magnified by the HMD display in any of the embodiments throughout the disclosure. The magnification can be centered around an anatomic structure, e.g. the center of a pedicle or a line through the pedicle, e.g. a center line of a pedicle. The magnification can be centered around the center of a left pedicle, the center of a right pedicle, the center of both pedicles, a left facet joint, a right facet joint, a lamina, a spinous process, a posterior vertebral wall or an anterior vertebral wall. Other locations are possible, e.g. an anterior third of a pedicle, a posterior third of a pedicle. The magnification can be centered around a physical surgical tool, physical surgical instrument, physical implant or any other physical surgical device, e.g. around a long axis of the physical surgical tool, physical surgical instrument, physical implant or any other physical surgical device. The magnification can be centered around a virtual surgical guide [e.g. a virtual axis], a virtual surgical tool, virtual surgical instrument, virtual implant or any other virtual surgical device, e.g. around a long axis of the virtual surgical tool, virtual surgical instrument, virtual implant or any other virtual surgical device.

In surgery employing a surgical microscope, 2D or 3D images [e.g. pre- or intra-operatively obtained images] and any virtual data, e.g. a predetermined path, predetermined start or end point, predetermined virtual axis, virtual tool, virtual instrument, virtual implant, virtual device, can be magnified in the HMD display by a computer processor, optionally matching the magnification of the microscope. Optionally, the magnification of the 2D or 3D imaging studies and any virtual data, e.g. a predetermined path, predetermined start or end point, predetermined virtual axis, virtual tool, virtual instrument, virtual implant, virtual device, displayed by the HMD can be greater than that of the microscope and the microscopic view of the physical tissue of the patient or it can be less than that of the microscope and the microscopic view of the physical tissue of the patient. The magnification of the 2D or 3D imaging studies and any virtual data, e.g. a predetermined path, predetermined start or end point, predetermined virtual axis, virtual tool, virtual instrument, virtual implant, virtual device, displayed by the HMD can be centered around the center of the microscopic view or the central axis of the lens system of the microscopy system. The magnification of the 2D or 3D imaging studies and any virtual data, e.g. a predetermined path, predetermined start or end point, predetermined virtual axis, virtual tool, virtual instrument, virtual implant, virtual device, displayed by the HMD can be centered around an anatomic structure, e.g. the center of a pedicle or a line through the pedicle, e.g. a center line of a pedicle. The magnification can be centered around the center of a left pedicle, the center of a right pedicle, the center of both pedicles, a left facet joint, a right facet joint, a lamina, a spinous process, a posterior vertebral wall or an anterior vertebral wall. Other locations are possible, e.g. an anterior third of a pedicle, a posterior third of a pedicle. The magnification can be centered around a physical surgical tool, physical surgical instrument, physical implant or any other physical surgical device, e.g. around a long axis of the physical surgical tool, physical surgical instrument, physical implant or any other physical surgical device. The magnification can be centered around a virtual surgical guide [e.g. a virtual axis], a virtual surgical tool, virtual surgical instrument, virtual implant or any other virtual surgical device, e.g. around a long axis of the virtual surgical tool, virtual surgical instrument, virtual implant or any other virtual surgical device.

Use of Virtual Data in 3 or More Dimensions

In some embodiments, the HMD can display a 3D virtual image of the patient. A 3D representation of the patient can include a 3D display of different types of anatomy, for example in an area of intended surgery or a surgical site.

A 3D reconstruction of image data or other data of the patient can be generated preoperatively, intraoperatively and/or postoperatively. A virtual 3D representation can include an entire anatomic area or select tissues or select tissues of an anatomic area. Different tissues can be virtually displayed by the HMD in 3D using, for example, different colors. Normal tissue(s) and pathologic tissue(s) can be displayed in this manner.

Normal tissue can, for example, include brain tissue, heart tissue, lung tissue, liver tissue, vascular structures, bone, cartilage, spinal tissue, intervertebral disks, nerve roots. Any tissue can be visualized virtually by the HMD.

Registration of Virtual Data and Live Data of a Patient, for Example Over a Surgical Site In some embodiments, virtual data of a patient displayed by an OHMD and live data of a patient seen through an OHMD are spatially registered in relationship to each other, for example in a common coordinate system, for example with one or more optical OHMDs in the same common coordinate system. Virtual and physical surgical instruments and implant components can also be registered in the common coordinate system. Spatial co-registration can have the benefit that the simultaneous display of virtual and live data of the patient is not affected or less affected when the surgeon moves his or her head or body, when the OHMD moves or when the patient moves. Thus, the view perspective of the live data of the patient seen by the surgeon's eyes through the OHMD, e.g. the live surgical field, can stay the same as the view perspective of the virtual data of the patient seen by the surgeon's eyes through the display of the OHMD unit, e.g. the virtual surgical field, virtual surgical plane, virtual paths, virtual cut paths or planes, projected into the surgeon's eyes, even as the surgeon moves his or her head or body. In this manner, the surgeon does not need to re-think or adjust his hand eye coordination since live data of the patient seen through the surgeon's eye and virtual data of the patient seen through the OHMD display are superimposed, which is fundamentally different from other approaches such as surgical navigation which employ a separate computer monitor in the OR with a view angle for the surgeon that is different than his or her view angle for the live data of the patient and the surgical field. Also, with surgical navigation, a first virtual instrument can be displayed on a computer monitor which is a representation of a physical instrument tracked with navigation markers, e.g. infrared or RF markers, and the position and/or orientation of the first virtual instrument can be compared with the position and/or orientation of a corresponding second virtual instrument generated in a virtual surgical plan. Thus, with surgical navigation the positions and/or orientations the first and the second virtual instruments are compared.

With guidance in mixed reality environment, e.g. with stereoscopic display like an electronic holographic environment, a virtual surgical guide, tool, instrument or implant can be superimposed onto the joint, spine or surgical site. Further, the physical guide, tool, instrument or implant can be aligned with the 2D or 3D representation of the virtual surgical guide, tool, instrument or implant. Thus, guidance in mixed reality environment does not need to use a plurality of virtual representations of the guide, tool, instrument or implant and does not need to compare the positions and/or orientations of the plurality of virtual representations of the virtual guide, tool, instrument or implant.

In some embodiments, virtual data can move in relationship to the surgeon or operator or in relationship to the patient or a certain target anatomy within a patient. This means if the surgeon moves his or her head or the body or parts of the patient's anatomy are being moved, the virtual data will move in the ARDD display. For example, once registration of the ARDD, the virtual data of the patient and the live data of the patient in a common coordinate system has occurred, the ARDD can display a virtual image of a target tissue or adjacent tissue. The virtual image of the target tissue or adjacent tissue can be, for example, an image of or through a tumor or other type of pathologic tissue or a spine or a spinal pedicle. As the surgeon or operator moves his or her head or body during the surgical procedure, the virtual data will move and change location and orientation the same way how the surgeon moves his/her head or body, typically reflecting the change in perspective or view angle that the surgeon obtained by moving his or her head or body. The virtual data can include a 3D representation of a surgical tool or instrument such as a needle for kyphoplasty or vertebroplasty, where the virtual representation of the needle shows its intended location, orientation or path in relationship to the spine and/or a pedicle. The virtual data can also include a medical device, such as a pedicle screw, wherein the virtual data of the pedicle screw shows its intended location, orientation or path in relationship to the spine, and/or a pedicle, and/or a vertebral body.

In some embodiments, registration is performed with at least three or more points that can be superimposed or fused into a common object coordinate system for virtual data and live data. Registration can also be performed using a surface or a 3D shape of an anatomic structure present in both virtual data and live data of the patient. In this case the virtual surface can be moved until it substantially matches the live surface of the patient or the virtual shape can be moved until it substantially matches the live shape of the patient.

Registration of virtual data of a patient and live data of a patient can be achieved using different means. The following is by no means meant to by limiting, but is only exemplary in nature.

Registration of Virtual Patient Data and Live Patient Data Using Directly or Indirectly Connected Object Coordinate Systems Registration of virtual and live data of the patient can be performed if the virtual data, e.g. imaging data of the patient, are acquired with the patient located in a first object coordinate system and the live data, e.g. during surgery, are observed or acquired with the patient located in a second object coordinate system, wherein the first and the second object coordinate system can be connected by direct, e.g. physical, or indirect, e.g. non-physical, means. A direct connection of the first and second object coordinate system can be, for example, a physical connection between the first and second object coordinate system. For example, the patient can be moved from the first to the second object coordinate system along the length of a tape measure. Or the patient can be scanned inside a scanner, e.g. a CT scanner or MRI scanner, and the scanner table can be subsequently moved out of the scanner for performing a surgical procedure with the patient still located on the scanner table. In this case, the scanner table can be a form of physical connection between the first and the second object coordinate system and the length of the table movement between the scan position and the outside the scanner position (for the live data, e.g. the surgical procedure) can define the coordinate transformation from the first to the second object coordinate system.

An indirect connection between the first (virtual data) and second (live data) object can be established if the patient is moved between the acquiring the virtual data, e.g. using an imaging test, and the live data, e.g. while performing a surgical procedure, along a defined path, wherein the direction(s) and angle(s) of the path are known so that the first and the second object coordinate system can be cross-referenced and an object coordinate transfer can be applied using the known information of the defined path and virtual data of the patient, live data of the patient and the HMD can be registered in a common coordinate system. Virtual and physical surgical instruments and implant components can also be registered in the common coordinate system.

Registration of virtual patient data and live patient data is also possible without directly or indirectly connected object coordinate systems using other means and methods as will be explained in the following paragraphs and columns, for example when the patient performed one or more movements of unknown direction, length or magnitude. Combinations of all different registration methods described in the disclosure are possible, e.g. for switching registration methods during a procedure or for simultaneously using multiple registration methods, e.g. for enhancing the accuracy of the registration.

Registration Using Spatial Mapping

Live data, e.g. live data of the patient, the position and/or orientation of a physical instrument, the position and/or orientation of an implant component, the position and/or orientation of one or more HMDs, can be acquired or registered, for example, using a spatial mapping process. This process creates a three-dimensional mesh describing the surfaces of one or more objects or environmental structures using, for example and without limitation, a depth sensor, laser scanner, structured light sensor, time of flight sensor, infrared sensor, or tracked probe. These devices can generate 3D surface data by collecting, for example, 3D coordinate information or information on the distance from the sensor of one or more surface points on the one or more objects or environmental structures. The 3D surface points can then be connected to 3D surface meshes, resulting in a three-dimensional surface representation of the live data. The surface mesh can then be merged with the virtual data using any of the registration techniques described in the disclosure.

The live data can be static, or preferably, it can be intermittently, continuously, or in real time updated with additional information to incorporate changes in the position or surface of the one or more objects or environmental structures. The additional information can, for example be acquired by a depth sensor, laser scanner, structured light sensor, time of flight sensor, infrared sensor, or tracked probe.

For initial spatial mapping and updating of mapping data, commonly available software code libraries can be used. For example, this functionality can be provided by the Microsoft HoloToolkit or the Google Project Tango platform. Various techniques have been described for spatial mapping and tracking including those described in U.S. Pat. No. 9,582,717, which is expressly incorporated by reference herein in its entirety.

Registration of Virtual Patient Data and Live Patient Data Using Visual Anatomic Features a) Visual registration of virtual patient data in relationship to live patient data by the surgeon or operator In some embodiments, a surgeon or operator can visually align or match virtual patient data with live patient data. Such visually aligning or matching of virtual patient data and live patient data can, for example, be performed by moving the HMD, for example via movement of the head of the operator who is wearing the HMD. In this example, the virtual patient data can be displayed in a fixed manner, not changing perspective as the operator moves the HMD. The operator will move the HMD until the live patient data are aligned or superimposed onto the fixed projection of the virtual patient data. Once satisfactory alignment, matching or superimposition of the live patient data with the virtual patient data has been achieved, the surgeon can execute a registration command, for example via a voice command or a keyboard command or using a user interface. The virtual patient data and the live patient data are now registered. At this point, upon completion of the registration, the virtual patient data will move corresponding to the movement of the HMD, for example as measured via the movement of an integrated IMU, image and field of view tracking, e.g. using anchor points in an image or field of view using an image and/or video capture system, and/or an attached navigation system with optical or RF or other trackers, which can be attached to the patient, the surgical site, a bone or any other tissue of the patient, the surgeon, the surgeon's arm, the surgeon's head or an HMD worn by the surgeon.

Thus, once a satisfactory alignment or match has been achieved the surgeon can execute a command indicating successful registration. The registration can include changes in at least one of position, orientation, and magnification of the virtual data and the live data in order to achieve the alignment or match. Magnification applied to the virtual data can be an indication of the distance from the HMD or the surgeon's head to the matched tissue. As a means of maximizing the accuracy of the registration, the estimated distance between the HMD and the target tissue or the skin surface or other reference tissue can be confirmed with an optional physical measurement of the distance, in particular if the HMD is, for example, in a fixed position, e.g. on a stand or tripod, which may be used optionally during the initial registration. Upon successful alignment or matching, the surgeon command can register, for example, the virtual patient data and the live patient data or images and the HMD in the same common coordinate system. Virtual and physical surgical instruments and implant components can also be registered in the common coordinate system.

In some embodiments, the visual anatomic data can be, for example, gyri of the brain or osteophytes or bone spurs or pathologic bone deformations or tumor nodes or nodules, e.g. on the surface of a liver or a brain.

Figure 3:
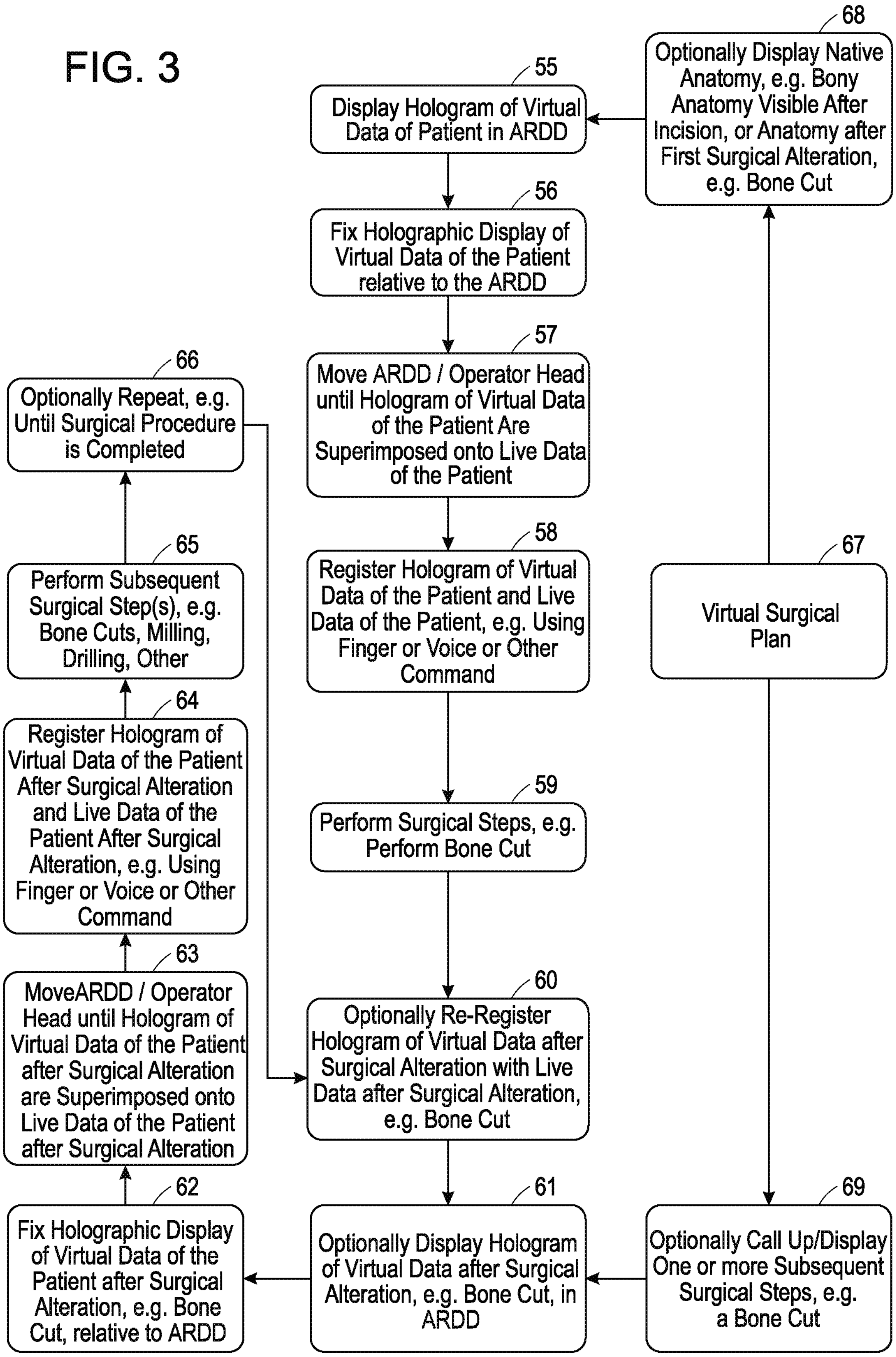
FIG. 3 illustrates an example of registering a digital hologram for an initial surgical step, performing the surgical step and re-registering one or more digital holograms for subsequent surgical steps according to some embodiments of the present disclosure.

In some embodiments, the registration of virtual patient data and live patient data using the methods described herein can be repeated after one or more surgical steps have been performed. In this case, the surgically altered tissue or tissue surface or tissue contour or shape, e.g. shape of a bone after milling or reaming, or tissue perimeter, e.g. perimeter of a bone cut, or tissue volume or other tissue features in the live patient can be matched to, superimposed onto and/or registered with the surgically altered tissue or tissue surface or tissue contour or tissue perimeter or tissue volume or other tissue features in the virtual data of the patient, e.g. in a virtual surgical plan developed for the patient, with substantially identical view angle of the virtual data of the patient seen by the surgeon's eyes through the display of the HMD unit and the live data of the patient seen by the surgeon's eyes through the HMD unit. The matching, superimposing and/or registering of the live data of the patient and the virtual data of the patient after the surgical tissue alteration can be performed using the same methods described in the foregoing or any of the other registration methods described in the disclosure or any other registration method known in the art. Referring to FIG. 3, FIG. 3 illustrates an example of registering a digital hologram or virtual data for an initial surgical step, performing the surgical step and re-registering one or more holograms for subsequent surgical steps. An ARDD can project or display a digital hologram of virtual data or virtual data of the patient 55. The digital hologram can optionally be fixed to the ARDD so that it will move with the movement of the ARDD 56. The operator can move the ARDD until digital hologram of the virtual data or virtual data of the patient is superimposed and aligned with the live data of the patient, e.g. the surgical site 57. The digital hologram of the virtual data or virtual data can then be registered using the same or similar coordinates as those of the live data with which the digital hologram is superimposed 58. The surgeon can then perform one or more predetermined surgical steps, e.g. bone cuts 59. A digital hologram of the virtual data or virtual data can optionally be registered or re-registered after the surgical alteration with the live data 60. The digital hologram of the virtual data or virtual data after the surgical alteration can optionally be displayed by the ARDD 61. The digital hologram of the virtual data or virtual data after the surgical alteration can optionally be fixed relative to the ARDD so that it will move with the movement of the ARDD 62. The operator can move the ARDD until digital hologram of the virtual data or virtual data of the patient after the surgical alteration is superimposed and aligned with the live data of the patient after the surgical alteration 63. The digital hologram of the virtual data or virtual data can then be registered using the same or similar coordinates as those of the live data after the surgical alteration with which the digital hologram is superimposed 64. The surgeon can then perform one or more predetermined subsequent surgical steps, e.g. bone cuts, milling or drilling 65. The preceding steps can optionally be repeated until the surgical procedures are completed 66. A virtual surgical plan 67 can be utilized. Optionally, the native anatomy of the patient including after a first surgical alteration can be displayed by the ARDD 68. The ARDD can optionally display digital holograms of subsequent surgical steps 69.

b) Automatic or semi-automatic registration of virtual patient data in relationship to live patient data using image processing and/or pattern recognition and matching techniques c) In some embodiments, image processing techniques, pattern recognition techniques or deep learning/artificial neural-network based techniques can be used to match virtual patient data and live patient data. Optionally, image processing and/or pattern recognition algorithms can be used to identify certain features, e.g. gyri or sulci on the brain surface of virtual data of a patient. An ear including its unique shape can also be used for the purpose of matching virtual patient data and live patient data.

For example, with brain surgery, the patient can be placed on the operating table. Optionally, cleaning or sterilization fluid can be applied to the shaved skull, for example using betadine. The HMD can be placed over the patient, either on a tripod or worn by the operator, for example with the head of the patient turned sideways over the live patient's ear and lateral skull. The HMD will be placed over an area of the live patient that includes the virtual data of the patient to be displayed.

Virtual data of the patient can be displayed in the HMD. The virtual data of the patient can include, for example, a visualization of the patient's skin or other data, e.g. the patient's ear or nose, for example derived from preoperative MRI data. The virtual data of the patient's skin or other structures, e.g. the patient's ear or nose, can be displayed simultaneously with the live patient data. The virtual data of the patient can then be moved, re-oriented, re-aligned and, optionally, magnified or minified until a satisfactory alignment, match or superimposition has been achieved. Optionally, the HMD can be moved also during this process, e.g. to achieve a satisfactory size match between virtual data and live data of the patient, optionally without magnification or minification of the virtual data of the patient.

Once a satisfactory alignment, match or superimposition has been achieved between virtual data and live data of the patient, the operator can execute a command indicating successful registration. Changes in position, orientation, or direction of the HMD, for example as measured via an integrated IMU, image and field of view tracking, e.g. using anchor points in an image or field of view using an image and/or video capture system, and/or a navigation system attached to the HMD, can be used to move the virtual patient data with the view of the live patient data through the HMD, with substantially identical object coordinates of the virtual data of the patient and the live data of the patient, thereby maintaining registration during the course of the surgery irrespective of any movements of the HMD, e.g. head movement by the operator wearing the HMD, and ensuring that the virtual data of the patient is correctly superimposed with the live data of the patient when projected into the surgeon's view.

After successful registration of the virtual patient data to the patient's skin or other structures, e.g. an ear or a nose, the operator or an assistant can apply a marker or calibration or registration phantom or device on the patient, for example close to the intended site of a craniotomy. The marker or calibration or registration phantom or device will not be covered by any drapes or surgical covers that will be placed subsequently. A secondary registration of the virtual patient data to the live patient data can then occur, by registering the virtual patient data to the live patient data, using the live marker or calibration or registration phantom or device placed on the patient and by cross-referencing these to the live data of the patient's skin or other structures, e.g. an ear or a nose. This can be achieved, for example, by registering the patient's skin or other structures, e.g. an ear or a nose, in the same coordinate system as the marker or calibration or registration phantom or device placed on the patient, e.g. by co-registering the virtual patient data of the patient's skin or other structures, e.g. an ear or a nose or an osteophyte or bone spur or other bony anatomy or deformity, with the live data of the marker or calibration or registration phantom or device. The distance, offset, angular offset or overall difference in coordinates between the patient's skin or other structures, e.g. an ear or nose or an osteophyte or bone spur or other bony anatomy or deformity, to the marker or calibration or registration phantom or device attached to the patient can be measured and can be used to switch the registration of the virtual patient data to the live patient data from the live data of the patient's skin or other structures, e.g. an ear or a nose, to the live data of the marker or calibration or registration phantom or device. Optionally, registration can be maintained to both the live data of the patient's skin or other structures, e.g. an ear or a nose, and the live data of the marker or calibration or registration phantom or device. Optionally, the system can evaluate if registration to the live data of the patient's skin or other structures, e.g. an ear or a nose, or to the live data of the marker or calibration or registration phantom or device is more accurate and the system can switch back and forth between either. For example, if the distance increases or decreases from the HMD to the patient's skin or other structure, e.g. an ear or a nose, beyond a certain level, e.g. a threshold, which can be optionally predefined, or if some of them is partially covered by a drape, the system can switch the registration to the live data of the marker or calibration or registration phantom or device. The reverse is possible. Or, if the angle from the HMD increases or decreases beyond a certain level, e.g. a threshold, which can be optionally predefined, to the patient's skin or other structure, e.g. an ear or a nose or an osteophyte or bone spur or other bony anatomy or deformity, the system can switch the registration to the live data of the marker or calibration or registration phantom or device. The reverse is possible.

The operator or the assistants can then place sterile drapes or surgical covers over the site, however preferably not covering the marker or calibration or registration phantom or device. Registration can be maintained via the live data of the marker or calibration or registration phantom or device attached to the patient, e.g. adjacent to or inside a craniotomy site.

Image processing and/or pattern recognition of the live data of the patient can then be performed through the HMD, e.g. using a built-in image capture apparatus and/or a 3D scanner for capturing the live data of the patient or image and/or video capture systems and/or a 3D scanner attached to, integrated with or coupled to the HMD.

Virtual and live data features or patterns can then be matched. The matching can include a moving and/or reorienting and/or magnification and/or minification of virtual data for successful registration with the live data of the patient and superimposition of both. Virtual and live data can include an osteophyte or bone spur or other bony anatomy or deformity. Combination of (a) and (b), e.g. automatic registration with manual adjustment option, e.g. by moving the virtual image data in relation to the live image data after image processing software and/or pattern recognition software and/or matching software have identified a potential match or performed an initial matching, which can then be followed by manual/operator-based adjustments. Alternatively, manual/operator-based matching and registration can be performed first, followed then by fine-tuning via software or algorithm (image processing, pattern recognition, etc.) based matching and registration. Virtual and live data can include an osteophyte or bone spur or other bony anatomy or deformity.

In some embodiments, the registration of virtual patient data and live patient data using the methods described herein can be repeated after one or more surgical steps have been performed. In this case, the surgically altered tissue or tissue surface or tissue contour or tissue perimeter or tissue volume or other tissue features in the live patient can be matched to, superimposed onto and/or registered with the surgically altered tissue or tissue surface or tissue contour or tissue perimeter or tissue volume or other tissue features in the virtual data of the patient, e.g. in a virtual surgical plan developed for the patient. The matching, superimposing and/or registering of the live data of the patient and the virtual data of the patient after the surgical tissue alteration can be performed using the same methods described in the foregoing or any of the other registration methods described in the disclosure or any other registration method known in the art.

Registration of Virtual Patient Data and Live Patient Data Using Anatomic Landmarks In some embodiments, a surgeon can identify select anatomic landmarks on virtual data of the patient, e.g. on an electronic preoperative plan of the patient, and on live data of the patient. For example, the surgeon can identify a landmark by placing a cursor or a marker on it on an electronic image of the virtual data of the patient and by clicking on the landmark once the cursor or marker is in the desired location. In a spine, such a landmark can be, for example, the posterior tip of a spinous process, a spinal lamina, an inferior facet on the patient's left side, a superior facet on the patient's left side, an inferior facet on the patient's right side, a superior facet on the patient's right side, a tip of a facet joint, a bone spur, an osteophyte etc. In a hip, such landmarks can be the most anterior point of the acetabulum, an osteophyte, e.g. on the acetabular rim, in the acetabulum, adjacent to the acetabulum, on the femoral head, on the femoral neck or the neck shaft junction, the center of the femoral head in a 2D or 3D image, the most anterior point of the femoral head, an anterosuperior iliac spine, an anteroinferior iliac spine, a symphysis pubis, a greater trochanter, a lesser trochanter etc. In a knee, such landmarks can be a femoral condyle, a femoral notch, an intercondylar space, a medial or lateral epicondyle, a femoral axis, an epicondylar axis, a trochlear axis, a mechanical axis, a trochlear groove, a femoral osteophyte, a marginal femoral osteophyte, a central femoral osteophyte, a dome of the patella, a superior, medial, lateral, inferior edge of the patella or the femur or femoral articular surface, a patellar osteophyte, an anterior tibia, a tibial spine, a medial, lateral, anterior, posterior edge of the tibia, a tibial osteophyte, a marginal tibial osteophyte, a central tibial osteophyte. The surgeon can then identify the same landmarks live in the patient. For example, as the surgeon looks through the OHMD, the surgeon can point with the finger or with a pointing device at the corresponding anatomic landmark in the live data. The tip of the pointer or the tip of the finger can, optionally, include a tracker which locates the tip of the pointer or the finger in space. Such locating can also be done visually using image and/or video capture and/or a 3D scanner, e.g. in a stereoscopic manner through the OHMD for more accurate determination of the distance and location of the pointer or finger in relationship to the OHMD. An image and/or video capture system and/or a 3D scanner can also be attached to, integrated with or coupled to the OHMD. Virtual and live data can include an osteophyte or bone spur or other bony anatomy or deformity.

Representative anatomic landmarks that can be used for registration of virtual and live data of the patient can include (but are not limited to):

- In Spine: A portion or an entire spinous process; A portion or an entire spinal lamina; A portion or an entire spinal articular process; A portion of or an entire facet joint; A portion of or an entire transverse process; A portion of or an entire pedicle; A portion of or an entire vertebral body; A portion of or an entire intervertebral disk; A portion of or an entire spinal osteophyte; A portion of or an entire spinal bone spur; A portion of or an entire spinal fracture; A portion of or an entire vertebral body fracture or Combinations of any of the foregoing
- Hip: A portion of or an entire acetabulum; A portion of or an entire edge of an acetabulum; Multiple portions of an edge of an acetabulum; A portion of an iliac wall; A portion of a pubic bone; A portion of an ischial bone; An anterior superior iliac spine; An anterior inferior iliac spine; A symphysis pubis; A portion of or an entire greater trochanter; A portion of or an entire lesser trochanter; A portion of or an entire femoral shaft; A portion of or an entire femoral neck; A portion of or an entire femoral head; A fovea capitis; A transverse acetabular ligament; A pulvinar; A ligamentum teres; A labrum; One or more osteophytes, femoral and/or acetabular or Combinations of any of the foregoing
- Knee: A portion or an entire medial femoral condyle; A portion or an entire lateral femoral condyle; A portion or an entire femoral notch; A portion or an entire trochlea; A portion of an anterior cortex of the femur; A portion of an anterior cortex of the femur with adjacent portions of the trochlea; A portion of an anterior cortex of the femur with adjacent portions of the trochlea and osteophytes when present; One or more osteophytes femoral and/or tibial; One or more bone spurs femoral and/or tibial; An epicondylar eminence; A portion or an entire medial tibial plateau; A portion or an entire lateral tibial plateau; A portion or an entire medial tibial spine; A portion or an entire lateral tibial spine; A portion of an anterior cortex of the tibia; A portion of an anterior cortex of the tibia and a portion of a tibial plateau, medially or laterally or both; A portion of an anterior cortex of the tibia and a portion of a tibial plateau, medially or laterally or both and osteophytes when present; A portion or an entire patella; A medial edge of a patella; A lateral edge of a patella; A superior pole of a patella; An inferior pole of a patella; A patellar osteophyte; An anterior cruciate ligament; A posterior cruciate ligament; A medial collateral ligament; A lateral collateral ligament; A portion or an entire medial meniscus; A portion or an entire lateral meniscus or Combinations of any of the foregoing
- Shoulder: A portion or an entire glenoid; A portion or an entire coracoid process; A portion or an entire acromion; A portion of a clavicle; A portion or an entire humeral head; A portion or an entire humeral neck; A portion of a humeral shaft; One or more humeral osteophytes; One or more glenoid osteophytes; A portion or an entire glenoid labrum; A portion or an entire shoulder ligament, e.g. a coracoacromial ligament, a superior, middle, or inferior glenohumeral ligament; A portion of a shoulder capsule or Combinations of any of the foregoing
- Skull and brain: A portion of a calvarium; A portion of an occiput; A portion of a temporal bone; A portion of a occipital bone; A portion of a parietal bone; A portion of a frontal bone; A portion of a facial bone; A portion of a facial structure; A portion or an entire bony structure inside the skull; Portions or all of select gyri; Portions or all of select sulci; A portion of a sinus; A portion of a venous sinus; A portion of a vessel; A portion of an ear; A portion of an outer auditory canal or combinations of any of the foregoing.
- Organs: A portion of an organ, e.g. a superior pole or inferior pole of a kidney; An edge or a margin of a liver, a spleen, a lung; A portion of a hepatic lobe; A portion of a vessel; A portion of a hiatus, e.g. in the liver or spleen; A portion of a uterus.

Someone skilled in the art can identify other anatomic landmarks of hard tissues, soft-tissues and or organs including brain that can be used for registration of virtual data (including optionally including virtual surgical plans) and live data of the patient and the ARDD (e.g. HMD) in a common coordinate system. Virtual and physical surgical instruments and implant components can also be registered in the common coordinate system.

In some embodiments, the HMD can display an arbitrary virtual plane over the surgical field. The arbitrary virtual plane can be moveable using a virtual or other interface. For example, the arbitrary virtual plane can include a "touch area", wherein gesture recognition software, for example the one provided by Microsoft with the Microsoft Hololens including, for example, the integrated virtual "drag function" for holograms can be used to move the arbitrary virtual plane. For example, one or more cameras integrated or attached to the HMD can capture the movement of the surgeon's finger(s) in relationship to the touch area; using gesture tracking software, the virtual plane can then be moved by advancing the finger towards the touch area in a desired direction.

The HMD can display the arbitrary virtual plane in any location initially, e.g. projected onto or outside the surgical field, e.g. a hip joint, knee joint, shoulder joint, ankle joint, or a spine. The HMD can optionally display the arbitrary virtual plane at a defined angle, e.g. orthogonal or parallel, relative to a fixed structure in the operating room, which can, for example, be recognized using one or more cameras, image capture or video capture systems and/or a 3D scanner integrated into the HMD and spatial recognition software such as the one provided by Microsoft with the Microsoft Hololens or which can be recognized using one or more attached optical markers or navigation markers including infrared or RF markers. For example, one or more optical markers can be attached to an extension of the operating table. The HMD can detect these one or more optical markers and determine their coordinates and, with that, the horizontal plane of the operating room table. The arbitrary virtual plane can then be displayed perpendicular or at another angle relative to the operating room table.

For example, in a hip replacement, the HMD can display a virtual arbitrary plane over the surgical site. The virtual arbitrary plane can be perpendicular to the operating table or at another predefined or predetermined angle relative to the OR table. Using a virtual interface, e.g. a touch area on the virtual surgical plane and gesture tracking, the HMD can detect how the surgeon is moving the virtual arbitrary plane. Optionally, the virtual arbitrary plane can maintain its perpendicular (or of desired other angle) orientation relative to the OR table while the surgeon is moving and/or re-orienting the plane; a perpendicular orientation can be desirable when the surgeon intends to make a perpendicular femoral neck cut. A different angle can be desirable, when the surgeon intends to make the femoral neck cut with another orientation.

Using the touch area or other virtual interface, the surgeon can then move the arbitrary virtual plane into a desired position, orientation and/or alignment. The moving of the arbitrary virtual plane can include translation and rotation or combinations thereof in any desired direction using any desired angle or vector. The surgeon can move the arbitrary virtual plane to intersect with select anatomic landmarks or to intersect with select anatomic or biomechanical axes. The surgeon can move the arbitrary virtual plane to be tangent with select anatomic landmarks or select anatomic or biomechanical axes.

Figure 4A:
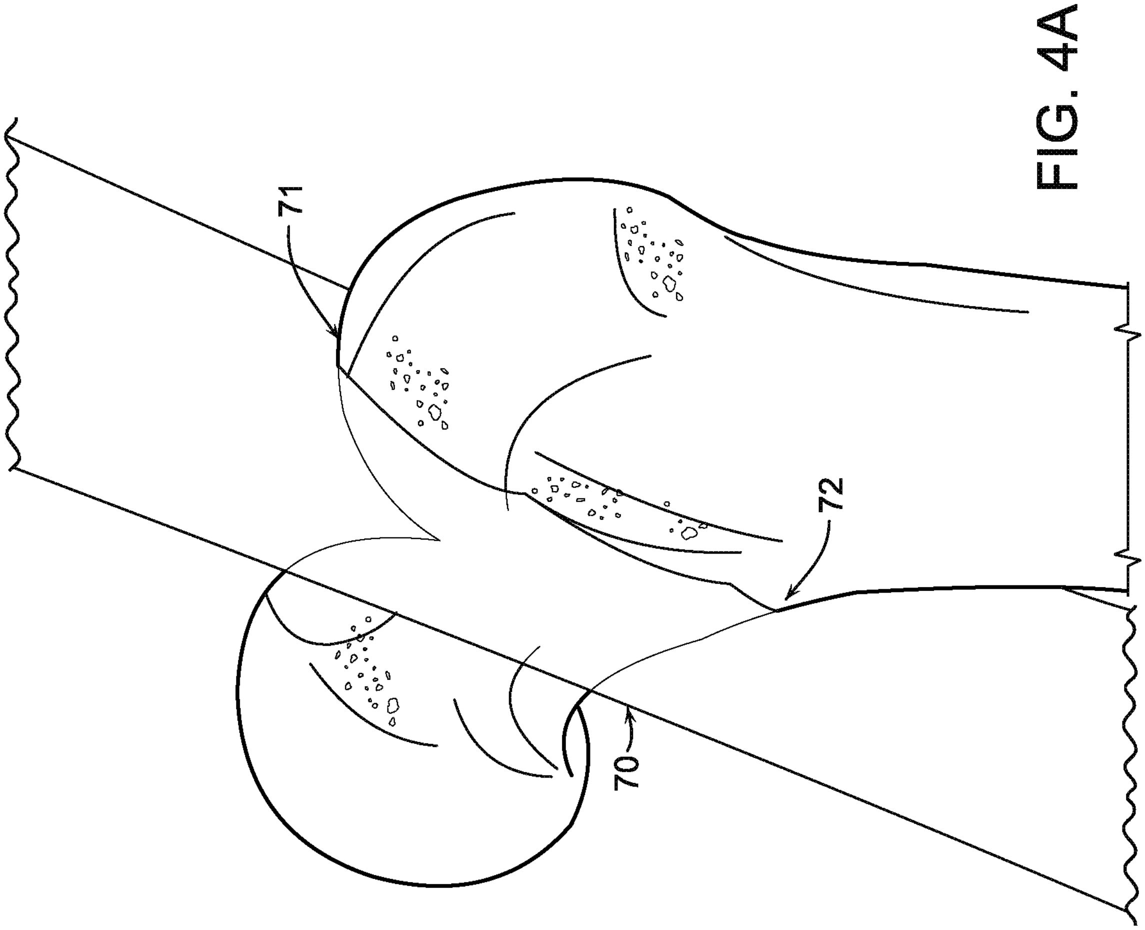
FIGS. 4A, 4B and 4C are illustrative examples of arbitrary virtual planes in the hip and a femoral neck cut plane according to some embodiments of the present disclosure.
Figure 4B:
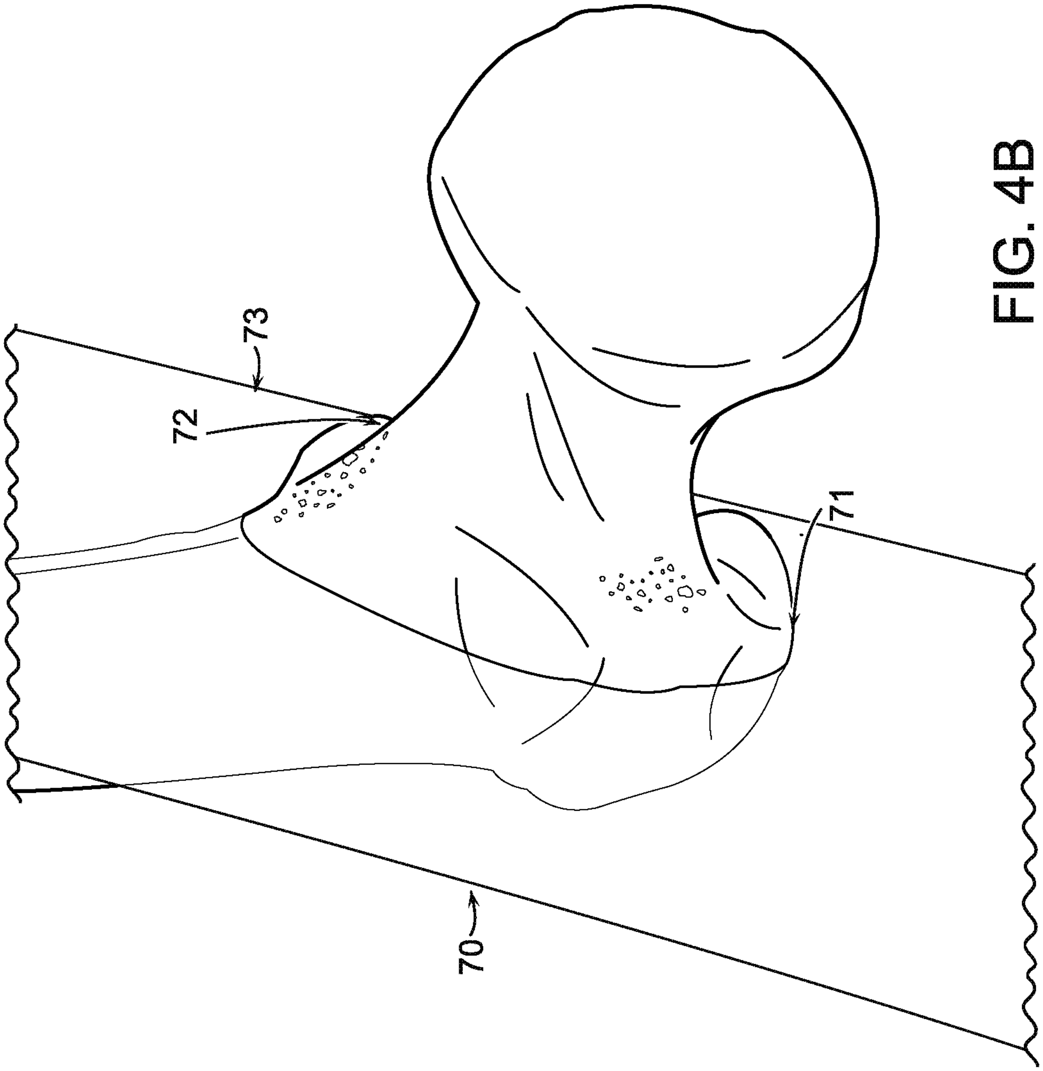

For example, in a hip replacement, the surgeon can move the arbitrary virtual plane to be tangent with the most superior aspect of the greater trochanter and the most superior aspect of the lesser trochanter. FIG. 4A shows an illustrative example of a virtual plane 70 that a primary surgeon has moved and aligned to be tangent with the most superior aspect of the greater trochanter 71 and the most superior aspect of the lesser trochanter 72. FIG. 4B shows an illustrative example of the same virtual plane 70 that the primary surgeon has moved and aligned to be tangent with the most superior aspect of the greater trochanter 71 and the most superior aspect of the lesser trochanter 72, now with the view from the optical head mounted display or head mounted display of a second surgeon or surgical assistant, e.g. on the other side of the OR table.

Figure 4C:
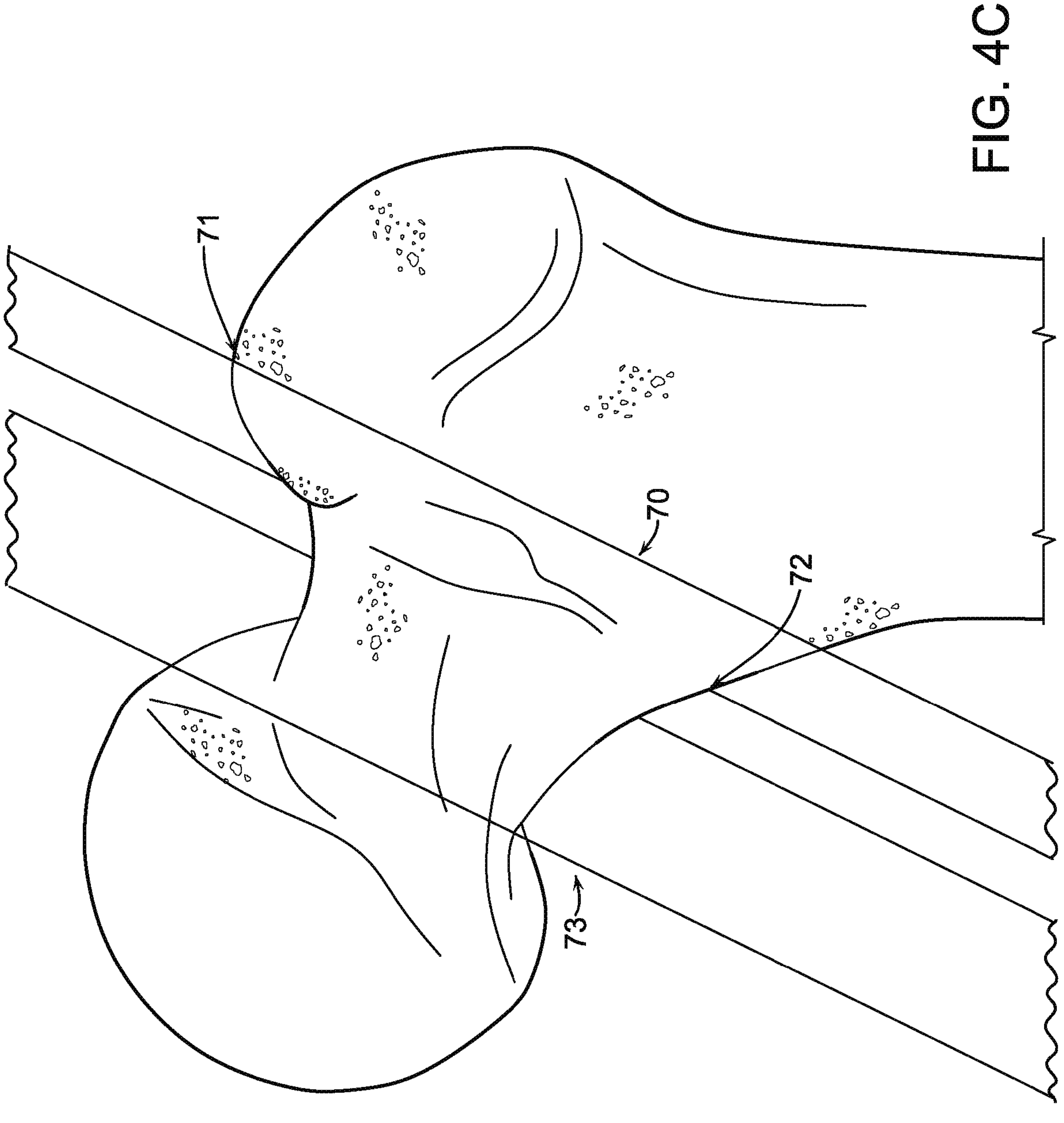

Optionally, for example with a pointer with an attached optical marker or an attached navigation marker, or with his finger detected using an image or video capture system integrated into the HMD and gesture recognition software such as the one provided by Microsoft with the Hololens, or with his finger with an attached optical marker or navigation marker, the surgeon can point at and identify the sulcus point, e.g. the lowest point between the greater trochanter and the femoral neck, which can be an additional reference. The line connecting the most superior aspect of the greater trochanter and the most superior aspect of the lesser trochanter can then be determined on a pre-operative or intra-operative AP radiograph of the hip; optionally, the sulcus point can also be detected on the AP radiograph. The AP radiograph can include a template used by the surgeon for selecting and sizing, for example, the femoral and acetabular component, as well as the liner and/or femoral heads. The radiographic template can include an indication for the femoral neck cut. The angle between the line connecting the most superior aspect of the greater trochanter and the most superior aspect of the lesser trochanter and the indication for the femoral neck cut can be determined. FIG. 4C is an illustrative example that shows that a second virtual plane 73, the virtual femoral neck cut plane 73, can then be projected or displayed by the ARDD, also perpendicular to the OR table like the arbitrary virtual plane 70, the latter tangent with the most superior aspect of the greater trochanter 71 and the most superior aspect of the lesser trochanter 72, and the femoral neck cut plane 73 at the same angle and/or distance to the arbitrary virtual plane as the angle and distance between the line connecting the most superior aspect of the greater trochanter and the most superior aspect of the lesser trochanter and the indication for the femoral neck cut on the radiograph. In this manner, the femoral neck cut plane can be defined using a second virtual plane prescribed or predetermined based on the intra-operatively placed arbitrary virtual plane, moved by the operator to be tangent with the most superior aspect of the greater trochanter and the most superior aspect of the lesser trochanter. The virtual femoral neck cut plane prescribed and projected or displayed in this manner can also be a virtual guide, e.g. a virtual cut block that projects, for example, a virtual slot for guiding a physical saw. The virtual guide or virtual cut block can have one or more dimensions identical to a physical guide or cut block, so that the physical guide or cut block can be aligned with the virtual guide or cut block. The virtual guide or cut block can be an outline, 2D or 3D, partial or complete, of the physical guide or cut block, with one or more identical dimensions, so that the surgeon can align the physical guide or cut block with the virtual guide or cut block. The virtual guide or cut block can include placement indicia for the physical guide or cut block.

If radiographic magnification is a concern for prescribing a second virtual plane, e.g. a virtual cut plane, based on a first virtual plane, e.g. a plane tangent with or intersecting one or more anatomic landmarks or one or more anatomic or biomechanical axes, at an angle incorporated from or derived from a pre-operative radiograph, optionally, distance measurements can be incorporated and magnification correction can be applied. For example, the distance between one or more landmarks, e.g. the ones with which the virtual plane is tangent with or that the virtual plane intersects, can be measured in the live data of the patient and can be measured on the radiograph. If the radiographic distance is larger or smaller than the distance in the live patient, a magnification correction can be applied and, for example, the distance between the first virtual plane, e.g. a plane tangent with or intersecting one or more anatomic landmarks or one or more anatomic or biomechanical axes, and the second virtual plane, e.g. a virtual cut plane, can be corrected based on the radiographic magnification factor.

In addition to virtual planes, the surgeon can place one or more virtual points, e.g. with a pointer with an attached optical marker or an attached navigation marker, or with his or her finger detected using an image or video capture system integrated into the ARDD (e.g. HMD) and gesture recognition software such as the one provided by Microsoft with the Hololens, or with his or her finger with an attached optical marker or navigation marker. The surgeon can point at and identify an anatomic landmark, e.g. a medial epicondyle of a knee or a sulcus point in a proximal femur or a medial malleolus, using any of the foregoing methods and/or devices. Optionally, the surgeon can then fixate optical markers to the virtual point and the underlying or corresponding anatomic landmark, for example using a screw or pin. By identifying two or more virtual points the surgeon can define a virtual axis or vector. For example, by identifying, e.g. with use of one or more optical markers applied to the anatomic landmark, a medial epicondyle of the knee and a lateral epicondyle of the knee, the transepicondylar axis can be determined in a patient. By identifying three or more virtual points, the surgeon can define a virtual plane. For example, by identifying, e.g. with use of one or more optical markers applied to the anatomic landmark, a left anterior superior iliac spine, a right anterior superior iliac spine and a symphysis pubis, the system can determine an anterior pelvic plane in a patient.

Figure 5:
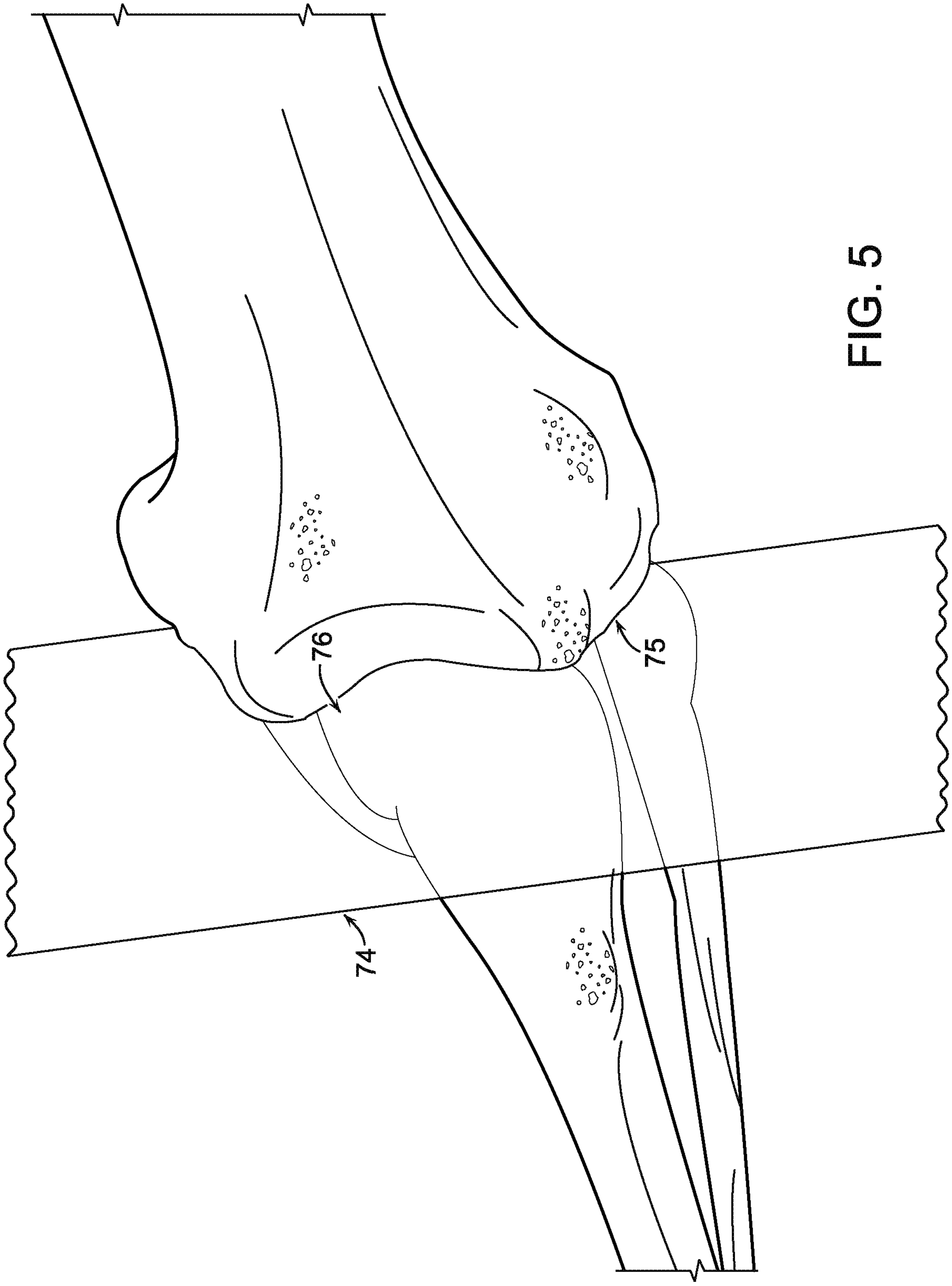
FIG. 5 is an illustrative example of an arbitrary virtual plane in the knee extending through the medial and lateral joint space according to some embodiments of the present disclosure.

In another example, an arbitrary virtual plane can be projected or displayed outside of or over the surgical field in a knee replacement. Optionally, the arbitrary virtual plane can be, at least initially, perpendicular to the OR table or at a defined angle to the OR table. If the mechanical axis of the leg has been determined in a preceding step, e.g. using an intra-operative measurement, for example with optical markers applied to the thigh and one or more optical markers applied to the ankle joint, for determining the center of rotation of the hip joint and the center of the ankle joint using an image capture or video capture system and/or a 3D scanner integrated into, attached to or separate from the HMD, the arbitrary virtual plane can be configured to be perpendicular to the mechanical axis of the leg. Using a virtual interface, e.g. a touch area, and an image or video capture system integrated or attached to the HMD and optional gesture tracking software, the surgeon can move and/or re-align the arbitrary virtual plane, for example to intersect with the medial and lateral joint space of the exposed knee joint, for example in extension or at 5, 10, 15, 20, 30, 45, or more degrees of flexion. FIG. 5 is an illustrative example of an arbitrary virtual plane 74 in the knee that intersects with the medial 76 and lateral 75 joint space in extension.

One or more additional arbitrary virtual planes can then optionally be projected, for example perpendicular or at another angle relative to the operating table or using a desired femoral component flexion angle or a desired tibial slope. The surgeon can optionally move these one or more arbitrary virtual planes to coincide with one or more anatomic axes, for example the anatomic femoral shaft axis or the anatomic tibial shaft axis in the live patient. The surgeon can also move a virtual arbitrary plane to be placed and oriented in the center of the femoral notch, parallel to the notch walls and extending centered between the medial and the lateral femoral shaft cortex as a means of estimating the anatomic femoral shaft axis.

Once the anatomic femoral and/or tibial axes have been determined or estimated, a virtual surgical plan with femoral and tibial resections designed to achieve a desired femoral mechanical axis correction, e.g. from the patient's mechanical axis alignment, e.g. 5, 10, 15 degrees of varus or valgus, to normal mechanical axis alignment or any desired residual, e.g. congenital varus or valgus, can be developed or generated. Implant size and desired polyethylene thickness can be factored into the virtual surgical plan. The ARDD can then, for example, project virtual surgical cut planes based on the virtual surgical plan and/or the intra-operative measurements, the desired varus and/or valgus correction, desired slope, and/or desired implant rotation. The surgeon can then align the physical saw blade with the projected or displayed virtual saw blade or cut plane. Alternatively, the ARDD can display a virtual guide or virtual cut block with at least one or more dimensions identical to the physical guide or physical cut block and the surgeon can align the physical cut guide or cut block with the virtual guide or cut block, in the physical guide or cut block, insert the saw blade into the physical guide or cut block and execute the one or more blocks.

The foregoing concepts of projecting arbitrary virtual planes and aligning them with one or more anatomic landmarks, anatomic axes or biomechanical or mechanical axes can be applied to any joint and also the spine. Similarly, these concepts can be applied to brain surgery, where one or more virtual planes can be projected or displayed and moved to be tangent with or intercept one or more landmarks, e.g. gyri, pons, cerebellum etc. Similarly, these concepts can be applied to organ surgery, where one or more virtual planes can be projected or displayed and moved to be tangent with or intercept one or more landmarks, e.g. liver portal, anterior liver edge, one or more cardiac valves etc.

Other arbitrary 2D and/or 3D virtual shapes or outlines or surfaces, e.g. cubes, cuboids, prisms, cones, cylinders, spheres, ellipsoid derived 3D shapes, irregular shapes, 2D and/or 3D virtual shapes or outlines or surfaces of virtual instruments and/or virtual implant components can be virtually projected or displayed and automatically or using a virtual or other user interface moved, oriented or aligned to coincide, to be tangent with, to intersect, to be offset with, to be partially or completely superimposed with internal, subsurface, or hidden patient anatomy, internal, subsurface, or hidden pathology, internal, subsurface, or hidden anatomic axes, internal, subsurface, or hidden biomechanical including mechanical axes, internal, subsurface, or hidden anatomic planes, internal, subsurface, or hidden 3D shapes, internal, subsurface, or hidden 2D and/or 3D geometries, internal, subsurface, or hidden 3D surfaces, and/or internal, subsurface, or hidden 3D volumes of any organs, soft-tissues or hard tissues of the patient. Arbitrary 2D and/or 3D virtual shapes or outlines or surfaces, e.g. cubes, cuboids, prisms, cones, cylinders, spheres, ellipsoid derived 3D shapes, irregular shapes, 2D and/or 3D virtual shapes or outlines or surfaces of virtual instruments and/or virtual implant components can be virtually projected or displayed and automatically or using a virtual or other user interface moved, oriented or aligned to coincide, to be tangent with, to intersect, to be offset with, to be partially or completely superimposed with external patient anatomy, external pathology, external anatomic axes, external biomechanical including mechanical axes, external anatomic planes, external 3D shapes, external 2D and/or 3D geometries, external 3D surfaces, and/or external 3D volumes of any organs, soft-tissues or hard tissues of the patient. Arbitrary 2D and/or 3D virtual shapes or outlines or surfaces, e.g. cubes, cuboids, prisms, cones, cylinders, spheres, ellipsoid derived 3D shapes, irregular shapes, 2D and/or 3D virtual shapes or outlines or surfaces of virtual instruments and/or virtual implant components can be virtually projected or displayed and automatically or using a virtual or other user interface moved, oriented or aligned to coincide, to be tangent with, to intersect, to be offset with, to be partially or completely superimposed with patient anatomy directly visible to the operator's eye, e.g. without using a display of an HMD, pathology directly visible to the operator's eye, e.g. without using a display of an HMD, anatomic axes directly visible to the operator's eye, e.g. without using a display of an HMD, biomechanical including mechanical axes directly visible to the operator's eye, e.g. without using a display of an HMD, anatomic planes directly visible to the operator's eye, e.g. without using a display of an HMD, 3D shapes directly visible to the operator's eye, e.g. without using a display of an HMD, 2D and/or 3D geometries directly visible to the operator's eye, e.g. without using a display of an HMD, 3D surfaces directly visible to the operator's eye, e.g. without using a display of an HMD, and/or 3D volumes directly visible to the operator's eye, e.g. without using a display of an HMD, of any organs, soft-tissues or hard tissues of the patient. Patient anatomy can include an implantation site, a bone for implanting a medical device, a soft-tissue for implanting a medical device, an anatomic structure adjacent to an implantation site, e.g. an adjacent tooth with which a dentist can virtually align a virtual implant component.

After the moving, orienting or aligning, the coordinate information of the 2D and/or 3D virtual shapes or outlines or surfaces can then be measured. Optionally, based on the coordinate information, additional intraoperative measurements can be performed and/or, optionally, a virtual surgical plan can be developed or modified using the information.

Figure 6:
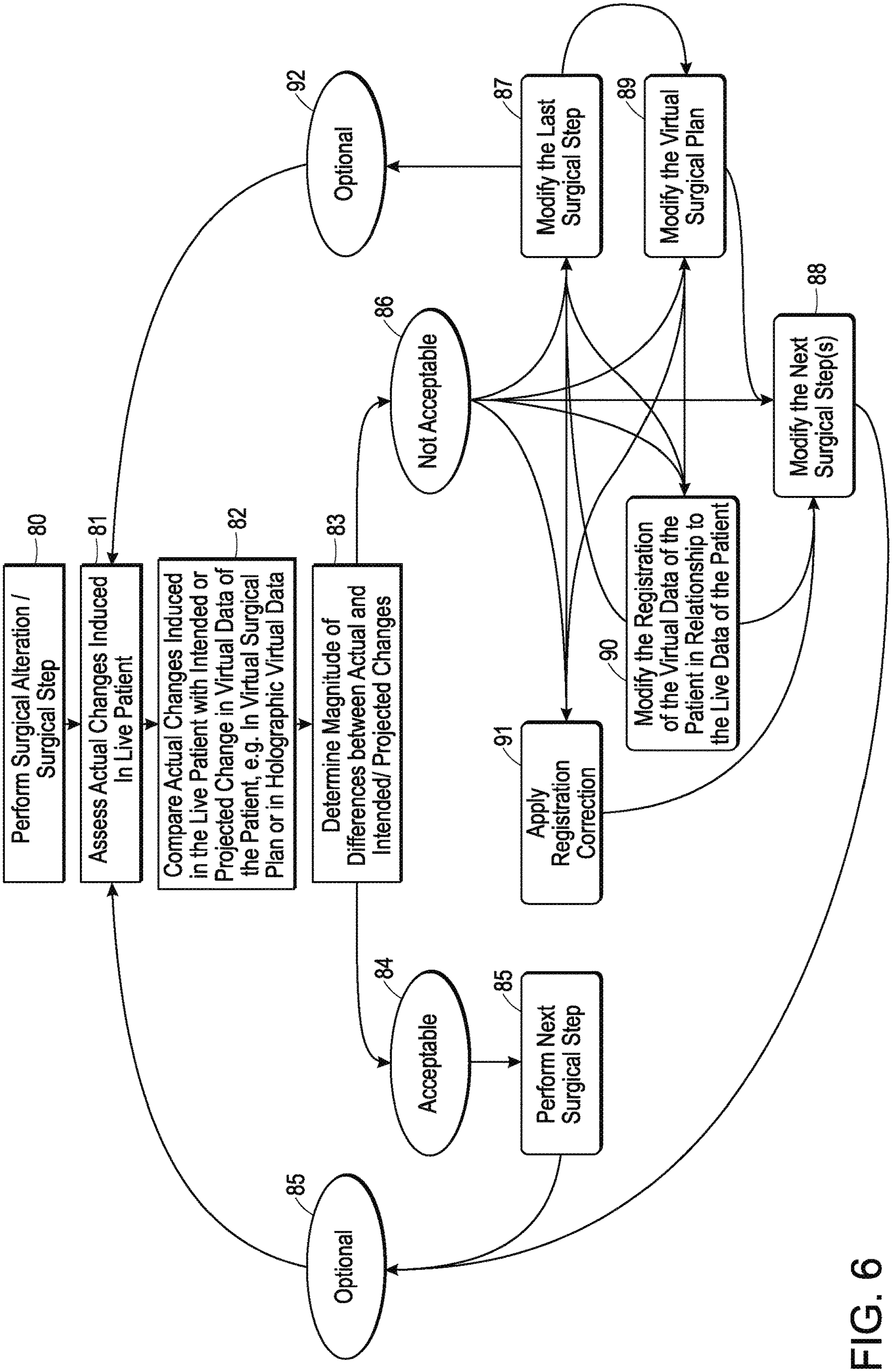
FIG. 6 is an illustrative flow chart that shows different methods of addressing inaccuracies between the changes induced by a surgical step and the intended, projected or predetermined changes in the virtual data of the patient according to some embodiments of the present disclosure.

FIG. 6 is an illustrative flow chart that shows different methods of addressing inaccuracies between the changes induced by a surgical step and the intended, projected or predetermined changes in the virtual data of the patient according to some embodiments of the present disclosure.

Systems, methods and techniques for superimposing and/or aligning one or more of virtual surgical guides, e.g. a virtual axis or a virtual plane (e.g. for aligning a saw), virtual tools, virtual instruments, and/or virtual trial implants are described in International Patent Application No. PCT/US17/21859 and U.S. Pat. No. 9,861,446 which are incorporated herein by reference in their entireties.

In any of the embodiments, the HMD display of virtual data, e.g. of one or more of virtual surgical tool, virtual surgical instrument including a virtual surgical guide or cut block, virtual trial implant, virtual implant component, virtual implant or virtual device, all optionally selected from a virtual library, a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration can be performed in relationship to and/or with a predetermined location, orientation, and/or alignment to a normal, damaged and/or diseased cartilage, cartilage surface, and/or cartilage shape, and/or a subchondral bone, subchondral bone surface and/or subchondral bone shape and/or cortical bone, cortical bone surface and/or cortical bone shape. The predetermined location, orientation, and/or alignment can be external and/or internal to a normal, damaged and/or diseased cartilage, cartilage surface, and/or cartilage shape, and/or a subchondral bone, subchondral bone surface and/or subchondral bone shape, and/or cortical bone, cortical bone surface and/or cortical bone shape. The predetermined location, orientation, and/or alignment can be tangent with and/or intersecting with a normal, damaged and/or diseased cartilage, cartilage surface, and/or cartilage shape, and/or a subchondral bone, subchondral bone surface and/or subchondral bone shape, and/or cortical bone, cortical bone surface and/or cortical bone shape. The intersecting can be at one or more predetermined angles. The predetermined location, orientation, and/or alignment can be at an offset to a normal, damaged and/or diseased cartilage, cartilage surface, and/or cartilage shape, and/or a subchondral bone, subchondral bone surface and/or subchondral bone shape, and/or cortical bone, cortical bone surface and/or cortical bone shape, e.g. an offset of 0.5, 1.0, 1.5, 2.0, 3.0, 4.0, 5.0, 7.0, 10.0, 15.0, 20.0 mm, or a range from 0.1 to 50 mm in x, y and/or z-direction relative to the normal, damaged and/or diseased cartilage, cartilage surface, and/or cartilage shape, and/or a subchondral bone, subchondral bone surface and/or subchondral bone shape, and/or cortical bone, cortical bone surface and/or cortical bone shape. For example, a virtual surgical guide and/or any virtual placement indicators for a physical surgical guide can be projected by one or more HMDs so that at least portions of the virtual surgical guide and/or virtual placement indicators are tangent with, intersecting with and/or offset with a normal, damaged and/or diseased cartilage, cartilage surface, and/or cartilage shape, and/or a subchondral bone, subchondral bone surface and/or subchondral bone shape, and/or cortical bone, cortical bone surface and/or cortical bone shape of the patient.

In embodiments, the HMD display of virtual data, e.g. of one or more of virtual surgical tool, virtual surgical instrument including a virtual surgical guide or cut block, virtual trial implant, virtual implant component, virtual implant or virtual device, all optionally selected from a virtual library, a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration, can be superimposed onto and/or aligned with the corresponding anatomic structure, e.g. a target tissue or an exposed joint surface, e.g. an exposed articular surface, seen directly through the see-through head mounted display (as they would be seen by the surgeon without wearing an HMD). The surgeon can then, for example, move a physical instrument, surgical guide, surgical tool, implant, implant component, device to align with the virtual projection.

Orienting, Aligning, Projecting and/or Superimposing Virtual Data Relative to Anatomic Structures and/or Surfaces In embodiments, the HMD display of virtual data, e.g. of one or more of virtual surgical tool, a virtual surgical instrument, a virtual surgical guide, which can be one or more of a virtual plane, a virtual axis, or a virtual cut block, a virtual trial implant, a virtual implant component, a virtual implant or a virtual device, all optionally selected from a virtual library, a virtual predetermined start point, a virtual predetermined start position, a virtual predetermined start orientation or alignment, a virtual predetermined intermediate point(s), a virtual predetermined intermediate position (s), a virtual predetermined intermediate orientation or alignment, a virtual predetermined end point, a virtual predetermined end position, predetermined end orientation or alignment, a virtual predetermined path, a virtual predetermined plane, a virtual predetermined cut plane, a virtual predetermined contour or outline or cross-section or surface features or shape or projection, a virtual predetermined depth marker or depth gauge, a virtual predetermined stop, a virtual predetermined angle or orientation or rotation marker, a virtual predetermined axis, e.g. rotation axis, flexion axis, extension axis, a virtual predetermined axis of the virtual surgical tool, non-visualized portions for one or more devices or implants or implant components or surgical instruments or surgical tools, and/or one or more of a virtual predetermined tissue change or alteration, can be projected onto and/or superimposed onto and/or aligned with and/or oriented with the surface of an anatomic structure seen directly through the see-through head mounted display (as they would be seen by the surgeon without wearing an HMD). The one or more of virtual surgical tool, a virtual surgical instrument, a virtual surgical guide, which can be one or more of a virtual plane, a virtual axis, or a virtual cut block, a virtual trial implant, a virtual implant component, a virtual implant or a virtual device, all optionally selected from a virtual library, a virtual predetermined start point, a virtual predetermined start position, a virtual predetermined start orientation or alignment, a virtual predetermined intermediate point(s), a virtual predetermined intermediate position(s), a virtual predetermined intermediate orientation or alignment, a virtual predetermined end point, a virtual predetermined end position, predetermined end orientation or alignment, a virtual predetermined path, a virtual predetermined plane, a virtual predetermined cut plane, a virtual predetermined contour or outline or cross-section or surface features or shape or projection, a virtual predetermined depth marker or depth gauge, a virtual predetermined stop, a virtual predetermined angle or orientation or rotation marker, a virtual predetermined axis, e.g. rotation axis, flexion axis, extension axis, a virtual predetermined axis of the virtual surgical tool, non-visualized portions for one or more devices or implants or implant components or surgical instruments or surgical tools, and/or one or more of a virtual predetermined tissue change or alteration can be projected onto and/or superimposed onto and/or aligned with and/or oriented with so that at least portions of them are tangent with, intersecting with, orthogonal to, at a defined angle to, and/or offset with, e.g. at a predetermined distance or angle, with the surface of the anatomic structure.

The surface of the anatomic structure can be at least a portion of one or more of a cartilage, a damaged or diseased cartilage, a subchondral bone, a cortical bone, any combination of a cartilage, a damaged or diseased cartilage, a subchondral bone, or a cortical bone, an articular surface, a weight-bearing zone of an articular surface, a non-weight bearing zone of an articular surface, a periosteum, a soft-tissue, a fascia, a muscle, a tendon, a ligament, a meniscus, a labrum, an intervertebral disk, a skin, a subcutaneous tissue (e.g. in an incision), a subcutaneous fat (e.g. in an incision), a mucosa or mucosal surface (e.g. of an oral cavity, a sinus, a nose, a nasopharyngeal area, a pharynx, a larynx, a gut, a small or large bowel, a colon, a rectum an intestine, a stomach, an esophagus, a bile duct, a pancreatic duct, a gallbladder, a gallbladder duct, or a bladder), a mucosal fold, a gingiva, a gingival fold, a marginal gum, an attached gum, an interdental gum, an enamel, a tooth, an epithelium or epithelial surface (e.g. in a lumen), a synovial membrane (e.g. in an exposed joint), a peritoneum or peritoneal surface (e.g. in an abdominal cavity or a pelvis, e.g. lining a mesentery or internal organs or a liver surface or a spleen), a capsule (e.g. a Glisson capsule of a liver or a renal capsule, an adrenal capsule, a thyroid capsule or a parathyroid capsule), a diaphragm, a pleura, a pericardium, a meninx (e.g. a dura mater, arachnoid mater, pia mater), a sinus (e.g. a cavernous sinus or a sigmoid or other sinus), a calvarium, a facial structure (e.g. a nose, an ear, an earlobe), a surface of an eye (e.g. a cornea, a lens, a sclera), an eyelid.

In some embodiments, one or more physical surgical tools or physical surgical instruments can be configured to effect a tissue removal in a patient. The tissue removal can be, for example, a removal of bone or a removal of cartilage or combinations thereof, e.g. using an awl, a drill, a tap, a screw, a pin, a mill, a reamer, a burr, an impactor, a broach, a saw, a saw blade.

The surface(s) of these one or more anatomic structures can be exposed during surgery, e.g. using an incision or tissue removal, and the one or more of virtual surgical tool, a virtual surgical instrument, a virtual surgical guide, which can be one or more of a virtual plane, a virtual axis, or a virtual cut block, a virtual trial implant, a virtual implant component, a virtual implant or a virtual device, all optionally selected from a virtual library, a virtual predetermined start point, a virtual predetermined start position, a virtual predetermined start orientation or alignment, a virtual predetermined intermediate point(s), a virtual predetermined intermediate position(s), a virtual predetermined intermediate orientation or alignment, a virtual predetermined end point, a virtual predetermined end position, predetermined end orientation or alignment, a virtual predetermined path, a virtual predetermined plane, a virtual predetermined cut plane, a virtual predetermined contour or outline or cross-section or surface features or shape or projection, a virtual predetermined depth marker or depth gauge, a virtual predetermined stop, a virtual predetermined angle or orientation or rotation marker, a virtual predetermined axis, e.g. rotation axis, flexion axis, extension axis, a virtual predetermined axis of the virtual surgical tool, and/or one or more of a virtual predetermined tissue change or alteration can be projected, aligned and/or superimposed by one or more HMDs onto the surface(s) of the one or more anatomic structures so that at least portions of the virtual data and/or virtual display(s) are tangent with, intersecting with, orthogonal to, at a defined angle to, and/or offset with, e.g. at a predetermined distance or angle, with the surface(s) of the one or more anatomic structures. Once the anatomic surface(s) is (are) exposed, the one or more of virtual surgical tool, a virtual surgical instrument, a virtual surgical guide, which can be one or more of a virtual plane, a virtual axis, or a virtual cut block, a virtual trial implant, a virtual implant component, a virtual implant or a virtual device, all optionally selected from a virtual library, a virtual predetermined start point, a virtual predetermined start position, a virtual predetermined start orientation or alignment, a virtual predetermined intermediate point(s), a virtual predetermined intermediate position(s), a virtual predetermined intermediate orientation or alignment, a virtual predetermined end point, a virtual predetermined end position, predetermined end orientation or alignment, a virtual predetermined path, a virtual predetermined plane, a virtual predetermined cut plane, a virtual predetermined contour or outline or cross-section or surface features or shape or projection, a virtual predetermined depth marker or depth gauge, a virtual predetermined stop, a virtual predetermined angle or orientation or rotation marker, a virtual predetermined axis, e.g. rotation axis, flexion axis, extension axis, a virtual predetermined axis of the virtual surgical tool, non-visualized portions for one or more devices or implants or implant components or surgical instruments or surgical tools, and/or one or more of a virtual predetermined tissue change or alteration can be projected, aligned and/or superimposed by one or more HMDs onto the surface(s) of the one or more anatomic structures and the surgeon or a robot can then, for example, move and/or align and/or superimpose a physical tool, a physical instrument, a physical surgical guide, physical implant component, a physical implant and/or a physical device to align and/or superimpose it with the virtual projection(s).

Using Light Sources for Referencing Live Anatomic Landmarks

The tracker or pointing device can also be a light source, which can, for example, create a red point or green point created by a laser on the patient's tissue highlighting the anatomic landmark intended to be used for registration. A light source can be chosen that has an intensity and/or a color that will readily distinguish it from the live tissue of the patient.

The laser or other light source can optionally be integrated into or attached to the HMD. For example, the laser or the light source can be integrated into or attached to a bridge connecting the frame pieces between the left and the right eye portion of the HMD, for example over the nasal region.

Image and/or video capture and/or a 3D scanner, for example integrated into or attached to or coupled to the HMD, can be used to identify the location of the light on the patient's tissue or the patient's anatomic landmark. Once the light has been directed to the desired location on the live data of the patient, specifically, the live landmark of the patient, registration can be performed by executing a registration command, registering the live data of the patient with the virtual data of the patient, e.g. the live landmark with the laser or other light being reflected of it and the corresponding virtual landmark of the patient. This process can be repeated for different anatomic landmarks, e.g. by pointing the light source at the next live anatomic landmark of the patient, confirming accurate placement or pointing, the light, e.g. a red or green laser point being reflected from the live patient landmark can be captured via the image and/or video capture device and/or 3D scanner, and the next anatomic live landmark can be registered with the corresponding virtual anatomic landmark of the patient. Virtual and live data can include an osteophyte or bone spur or other bony anatomy or deformity. In this manner, the HMD, live data of the patient and virtual data of the patient can be registered in a common coordinate system. Virtual and physical surgical instruments and implant components can also be registered in the common coordinate system.

In some embodiments, more than one live and virtual anatomic landmark of the patient will be used, e.g. two, three or more.

In some embodiments, ultrasound or a radiofrequency transmitter can be used to pinpoint certain live anatomic landmarks. For example, an ultrasonic transmitter or a radiofrequency transmitter can be integrated into a point device, for example the tip of a pointing device. When the tip touches the desired live anatomic landmark, the transmitter can transmit and ultrasonic or RF signal which can be captured at a receiving site, optionally integrated into the HMD. Optionally, for example as a means of increasing the accuracy of live data registration, multiple receiving sites can be used in spatially different locations. Virtual and live data can include an osteophyte or bone spur or other bony anatomy or deformity.

In some embodiments, the dimensions of the pointer have been previously scanned and registered with the HMD. The image and/or video capture system attached to, integrated with or coupled to the HMD can recognize the pointer in the live data and can identify the tip of the pointer. When the tip of the pointer touches the live landmark on the patient that corresponds to the landmark in the virtual data, the surgeon can, for example, click to indicate successful cross-referencing. The two data points can then optionally be fused or superimposed in a common coordinate system. Virtual and live data and data points can include or can be generated from an osteophyte or bone spur or other bony anatomy or deformity. Virtual and physical surgical instruments and implant components can also be registered in the common coordinate system.

Anatomic landmarks can include an unaltered surface shape, e.g. skin, facial features, e.g. the tip of the nose, a distance between both eyes, the location of an ear, the shape of the ear. Anatomic landmarks can also be bony landmarks, e.g. a medial or lateral malleolus, a tibial tuberosity, a medial or lateral epicondyle, a trochlear notch, a spinous process etc. Virtual and live data and virtual and live anatomic landmarks can include an osteophyte or bone spur or other bony anatomy or deformity.

Optionally, a live anatomic surface can be used for registration purposes. In this embodiment, the live anatomic surface can be derived, for example, using a light scanning, infrared scanning or ultrasound technique, or ultrasonic scanning technique during the surgery. The live surfaces of the patient that are detected and generated in this manner can be matched or aligned with virtual surfaces of the patient, for example obtained preoperatively using an imaging test such as x-ray imaging, ultrasound, CT or MRI or any other technique known in the art. Virtual and live data and anatomic surfaces can include an osteophyte or bone spur or other bony anatomy or deformity.

In some embodiments, the registration of virtual patient data and live patient data using the methods described herein can be repeated after one or more surgical steps have been performed. In this case, the surgically altered tissue or tissue surface or tissue contour or tissue perimeter or tissue volume or other tissue features in the live patient can be matched to, superimposed onto and/or registered with the surgically altered tissue or tissue surface or tissue contour or tissue perimeter or tissue volume or other tissue features in the virtual data of the patient, e.g. in a virtual surgical plan developed for the patient. The matching, superimposing and/or registering of the live data of the patient and the virtual data of the patient after the surgical tissue alteration can be performed using the same methods described in the foregoing or any of the other registration methods described in the disclosure or any other registration method known in the art.

Registration of Virtual Patient Data and Live Patient Data using Implantable or Attachable Markers or Calibration or Registration Phantoms or Devices Including Optical Markers In some embodiments, a surgeon is optionally using implantable or attachable markers to register virtual data of the patient with live data of the patient. This embodiment can, for example, be useful if the surgery is very extensive and results in the removal of tissue in the surgical site, as can be the case during brain surgery, e.g. removal of a brain tumor, liver surgery, e.g. removal of a liver tumor, joint replacement surgery and many other types of surgery. Virtual and live data can include an osteophyte or bone spur or other bony anatomy or deformity.

The terms implantable markers, attachable markers, skin markers, soft-tissue markers, calibration or registration phantoms or devices, and image capture markers as used throughout the application can include optical markers, e.g. optical markers with different geometric shapes or patterns, with QR codes, with bar codes, with alphanumeric codes. Implantable or attachable markers or calibration or registration phantoms or devices can be implanted prior to the actual surgery and can be included in pre-, intra- and/or postoperative imaging. Implantable or attachable markers or calibration or registration phantoms or devices can be implanted on or attached to osteophytes or bone spurs or other bony anatomy or deformity.

If the implantable or attachable markers or calibration or registration phantoms or devices are present in the virtual image data, the surgeon can optionally identify the implantable or attachable markers or calibration or registration phantoms or devices after an incision as he or she gains access to the target tissue and the implantable markers placed next to the target tissue or inside the target tissue. Such implantable or attachable markers or calibration or registration phantoms or devices can, for example, include radiation beets or metallic beets, for example also used for stereographic imaging or registration.

Alternatively, implantable or attachable markers or calibration or registration phantoms or devices can be placed during the surgery and, for example using an image and/or video capture system and/or 3D scanner attached to, integrated with or coupled to the HMD, the location of the implantable or attachable markers or calibration or registration phantoms or devices can be determined. The location of the implantable or attachable markers or calibration or registration phantoms or devices on the patient in the live data of the patient can then be matched with the location of the anatomic structure to which the implantable or attachable markers or calibration or registration phantoms or devices is attached in the virtual data of the patient. For example, the anatomic structure in the virtual and live data can include an osteophyte or bone spur or other bony anatomy or deformity. In some embodiments, a pointer or pointing device can optionally include implantable or attachable markers or calibration or registration phantoms or device or optical markers followed by image capture through the HMD or other image and/or video capture device and/or 3D scanner attached to, integrated with or coupled to the HMD and registration of the tip of the pointer. In this manner, the HMD, the implantable or attachable markers or calibration or registration phantoms or devices including optical markers and, through the use of the implantable or attachable markers or calibration or registration phantoms or devices including optical markers, the anatomic structures, pathologic structures, instruments, implant components and any other objects to which one or more implantable or attachable markers or calibration or registration phantoms or devices including optical markers can be attached, as well as the virtual data of the patient can be registered in a common coordinate system. Virtual and physical surgical instruments and implant components can also be registered in the common coordinate system.

Implantable or attachable markers or calibration or registration phantoms or devices can include rigid or fixed registration markers. Such rigid or fixed registration markers can be used to maintain registration as surgical field is being altered. A rigid or fixed registration marker can, for example, be a screw or a pin. Virtual and live data can include an osteophyte or bone spur or other bony anatomy or deformity. The rigid or fixed registration marker can be attached to the osteophyte or bone spur or other bony anatomy or deformity. In some embodiments, the medical device that is being implanted or a component thereof that has been, for example, already temporarily or permanently attached to the patient's tissue, e.g. an osteophyte or bone spur or bony anatomy or deformity, or the anatomic site or the surgical site can be used as an implantable or attachable marker or calibration or registration phantom or device during the surgery, for example while subsequent steps of the surgery are being completed. Such subsequent steps can, for example, include the implantation of additional components of the medical device. For example, in spinal fusion surgery, a first pedicle screw can be implanted. Live data and virtual data of the first pedicle screw can be registered. Subsequent pedicle screws or other components can be virtually displayed in the HMD including their intended path, position, location or orientation, by maintaining registration between live and virtual data using the registered first pedicle screw. Any other rigid or fixed registration marker or implantable device can be used in this manner for different types of surgeries of the human body.

The one or more implantable or attachable markers or calibration or registration phantoms or devices can be attached to bone, cartilage, soft-tissues, organs or pathologic tissues such as osteophytes or bone spur or other bony anatomy or deformity, etc.

The one or more implantable or attachable markers or calibration or registration phantoms or devices can optionally include optical markers, retroreflective markers, infrared markers, or RF markers or any other marker device described in the art.

Optical markers can be markers that can emit or reflect light within the visible spectrum, i.e. the portion of the electromagnetic spectrum that is visible to the human eye, with wavelengths from about 390 to 700 nm or a frequency band from about 430-770 THz. Optical markers can also emit or reflect light that includes a mix of different wavelengths within the visible spectrum. The light reflected by the optical markers can be detected by an image and/or video capture system integrated into, attached to or separate from the HMD. Optical markers can be detected with regard to their location, position, orientation, alignment and/or direction of movement and/or speed of movement with use of an image and/or video capture system integrated into, attached to or separate from the HMD with associated image processing and, optionally, pattern recognition software and systems. Optical markers can include markers with select geometric patterns and/or geometric shapes that an image and/or video capture system, for example integrated into, attached to or separate from the HMD, can recognize, for example using image processing and/or pattern recognition techniques. Optical markers can include markers with select alphabetic codes or patterns and/or numeric codes or patterns and/or alphanumeric codes or patterns or other codes or patterns, e.g. bar codes or QR codes, that an image and/or video capture system, for example integrated into, attached to or separate from the HMD, can recognize, for example using image processing and/or pattern recognition techniques. QR codes or quick response codes include any current or future generation matrix code including barcode. Barcodes and QR codes are machine readable optical labels that can include information, for example, about the patient including patient identifiers, patient condition, type of surgery, about the surgical site, the spinal level operated if spine surgery is contemplated, the patient's side operated, one or more surgical instruments, one or more trial implants, one or more implant components, including type of implant used and/or implant size, type of polyethylene, type of acetabular liner (e.g. standard, lipped, offset, other) if hip replacement is contemplated. A QR code can use different standardized encoding modes, e.g. numeric, alphanumeric, byte/binary, and/or kanji to store data. Other encoding modes can be used. Any current and/or future version of QR codes can be used. QR codes using single or multi-color encoding can be used. Other graphical markers, such as the ones supported by the Vuforia (PTC, Needham, Mass.) augmented reality platform, can be used as well.

A bar code, QR code or other graphical marker can be the optical marker. A bar code, QR code or other graphical marker can be part of an optical marker or can be integrated into an optical marker. The same QR code or bar code or other graphical marker can contain

- information related to the patient and/or the surgical site, e.g. patient identifiers, age, sex, BMI, medical history, risk factors, allergies, site and side (left, right), spinal level to be operated
- information related to inventory management, e.g. of surgical instruments and/or implants or implant components, e.g. left vs. right component, selected component size (match against virtual surgical plan and/or templating and/or sizing)

and can be used to obtain information about the location, position, orientation, alignment and/or direction of movement, and/or speed of movement, if applicable, of the surgical site, surgically altered tissue, one or more surgical instruments and one or more trial implants and/or implant components.

Geometric patterns, geometric shapes, alphabetic, numeric, alphanumeric, and other codes or patterns including bar codes and QR codes included in or part of one or more optical markers can be predefined and, optionally, stored in database accessible by an image and/or video capture system and associated image processing software and pattern recognition software. Geometric patterns, geometric shapes, alphabetic, numeric, alphanumeric, and other codes or patterns including bar codes and QR codes included in or part of one or more optical markers can be in 2D and some of it in 3D. For example, one or more planar or 2D patterns can be used in select embodiments. Alternatively, select 3D geometric shapes can be used, e.g. cubes, cuboids, prisms, cones, cylinders, spheres. Any 3D shape can be used including irregular shapes and/or asymmetric shapes. The 3D geometric shape can include 2D geometric patterns and/or alphabetic, numeric, alphanumeric, and other codes or patterns including bar codes and QR codes on one or more surfaces. For example, if a cuboid or other 3D shape is used for an optical marker, the same or different geometric patterns and/or alphabetic, numeric, alphanumeric, and other codes or patterns including bar codes and QR codes can be included in, affixed to or integrated into one or more of its surfaces or faces, e.g. two opposing surfaces or two adjacent surfaces oriented, for example, perpendicularly. 2D geometric patterns and/or alphabetic, numeric, alphanumeric, and other codes or patterns including bar codes and QR codes included in, affixed to or integrated into one or more surfaces or faces of a 3D geometric shape can be used to determine the orientation of select surfaces or faces of the geometric shape including the optical marker and, with that, the orientation and/or alignment of the surface or face and with that the geometric shape, for example in relationship to a surgical site, a surgical alteration, e.g. a cut bone surface or a reamed bone surface, a surgical instrument and/or one or more implant components including trial implants. In this manner, movement of a limb or surgical site can be tracked in embodiments. For example, an optical marker with a 3D shape can be attached to a trochlea or an anterior tibia. The optical marker can have a first surface with a first geometric pattern. The optical marker can have a second surface with a second geometric pattern. The first surface with the first geometric pattern can, for example, be anteriorly facing. The second surface with the second geometric pattern can, for example, be medially or laterally facing. When the operator looks through the OHMD, optionally with one or more video systems integrated into, attached to or separate from the OHMD, at the optical marker and the video system, in this example, detects predominantly the first surface, the information can be used to indicate that the knee is in a frontal, e.g. non-rotated position; if the video system detects a different ratio of first vs. second surface visible or detectable, e.g. with a larger portion of the second surface visible or detectable, the information can be used to indicate that the knee is in a somewhat or more rotated position. Similarly, a third surface with a third geometric pattern can be superior or inferior facing. If the video detects that a greater portion of the third surface is visible or detectable, the information can indicate that the knee is in a more flexed position. Any combination is possible.

A 3D optical marker can, optionally, not have distinct surfaces with distinct geometric patterns, but can include a continuum of the same or, optionally changing, geometric patterns along its 3D surface or 3D surfaces. The location and/or or position and/or orientation and/or coordinates of the changing, different portions of the geometric pattern along the 3D surface(s) can be known, e.g. prior to tracking a surgical site, a surgical instrument, an implant, a medical device or a limb or bone, e.g. during movement. A video system integrated into, attached to or separate from the HMD can detect the location and/or position and/or orientation and/or coordinates of one or more of the different portions of the geometric patterns and can use the information to track a surgical site, a surgical instrument, an implant, a medical device or a limb or bone, e.g. during movement.

The detection of one or more surfaces with geometric patterns or one or more portions of geometric patterns, e.g. on a 2D optical marker or a 3D optical marker, can be used to trigger one or more computer demands. Similarly, the disappearance of one or more surfaces with geometric patterns or one or more portions of geometric patterns or an entire geometric pattern can be used to trigger one or more computer demands. Such computer commands can, for example, include activating a motion tracking mode, de-activating a motion tracking mode, activating an HMD display, de-activating an HMD display, displaying a surgical step, e.g. a next surgical step or a prior surgical step, displaying a proposed correction for a surgical step, initiating an alarm, terminating an alarm, displaying a surgical instrument, tracking a surgical instrument, displaying a next surgical instrument, displaying an implant component, displaying a medical device, tracking any of the foregoing, terminating any of the foregoing commands. Someone skilled in the art can recognize other commands that can be initiated or executed in this manner. Such commands can also be used, for example, to initiate action by a robot, e.g. activating a bone saw, guiding a robot or executing a bone cut or bone removal with a robot. The robot can be configured for use with a robotic arm. The robot can be handheld. An actuator, e.g. a drill or a saw, can be handheld and can be simultaneously attached to a robotic arm.

In another embodiment, one or more video systems or cameras integrated into, attached to or separate from an HMD can detect a change in angular orientation of a 2D or 3D optical marker and/or geometric pattern and/or portions of one or more of the foregoing; the change in angular orientation detected in this manner can also be used to trigger or execute one or more commands.

Geometric patterns and/or geometric shapes, alphabetic, numeric, alphanumeric, and other codes or patterns including bar codes and QR codes can be in color or black and white. Geometric patterns and/or geometric shapes and/or alphabetic, numeric, alphanumeric, and other codes or patterns including bar codes and QR codes can include portions that include color and black and white sections, portions that include only color and portions that are only black and white. Geometric shapes can include faces or surfaces that include color and black and white, faces or surfaces that include only black and white, and faces or surfaces that include only color. Different colors and different color codes can be used for different faces or surfaces of a geometric shape part of an optical marker. Different colors and different color codes can be used for different geometric patterns and/or geometric shapes and/or alphabetic, numeric, alphanumeric, and other codes or patterns including bar codes and QR codes. Different colors and different color codes can be used for different optical markers. Different colors, e.g. red, blue, green, orange, cyan etc., can be used for different geometric patterns and/or geometric shapes and/or alphabetic, numeric, alphanumeric, and other codes or patterns including bar codes and QR codes. Different colors, e.g. red, blue, green, orange, yellow, pink, cyan can be used for different optical markers. Different optical markers can optionally be associated with different surgical steps and/or different surgical instruments and/or different implant components; the use of a particular marker can be recognized by an image and/or video capture system integrated into, attached to or separate from the HMD using standard image processing and/or pattern recognition software, including, optionally a database of patterns, e.g. with their associations with a particular surgical step and/or surgical instruments. As the image and/or video capture system recognizes a particular optical marker in the field of view, for example based on a particular geometric pattern and/or geometric shape and/or alphabetic, numeric, alphanumeric, and other codes or patterns including bar codes and QR codes used, it can then optionally display the corresponding surgical step and/or surgical instrument and/or implant component associated with that optical marker.

2D geometric patterns, alphabetic, numeric, alphanumeric, and other codes or patterns including bar codes and QR codes or combinations thereof, optionally with color and/or black and white coding, included in, affixed to or integrated into one or more surfaces or faces of a 3D geometric shape can be used to determine the orientation and/or alignment of select surfaces or faces of the geometric shape and, with that, the orientation and/or alignment of the geometric shape and/or the optical marker, for example in relationship to an anatomic landmark, a surgical site, a surgical alternation, e.g. a cut bone surface or a reamed bone surface, a surgical instrument and/or one or more implant components including trial implants. One or more 2D geometric patterns, alphabetic, numeric, alphanumeric, and other codes or patterns including bar codes and QR codes, optionally with color and/or black and white coding, included in, affixed to or integrated into an optical marker can be used to determine the orientation and/or alignment of the optical marker, which can, for example, be affixed to or integrated into an anatomic landmark, a surgical site, a surgical alternation, e.g. a cut bone surface or a reamed bone surface, a surgical instrument and/or one or more implant components including trial implants. Optical markers can be affixed to an anatomic landmark, a surgical site, a surgical alteration, e.g. a cut bone surface or a reamed bone surface, or a drill hole of the patient and the corresponding anatomic landmark, surgical site, or surgical alternation can be identified in the virtual data of patient thereby enabling registration of the virtual data and the live data of the patient in the same coordinate system.

Optical markers on HMDs: Optical markers can also be attached to an HMD including multiple HMDs if multiple HMDs are used during a surgery. Optionally, optical markers, e.g. with QR codes, can be used to differentiate a first from a second, third, fourth and/or more HMDs. One or more optical markers can optionally be attached to the operating room (OR) table and they can be registered in a coordinate system, for example the same coordinate system in which the one or more HMDs, the patient, and portions of the surgical site can be registered. One or more optical markers can optionally be attached to other structures in the operating room including fixed structures, e.g. walls, and movable structures, e.g. OR lights, and they can be registered in a coordinate system, for example the same coordinate system in which the one or more HMDs, the patient, and portions of the surgical site can be registered. In this example, optical markers can also be mounted to fixed structures on holding arms or extenders, optionally moveable and, for example, of known dimensions, orientations, lengths and angles.

Optical markers attached to fixed structures such as OR walls can be used to enhance the accuracy of room recognition and spatial mapping, in particular when the coordinates and/or the angles and/or distances between different optical markers are known. Optical markers attached to fixed structures such as OR walls can also be used to enhance the determination of the location and pose and change in location or pose or the coordinates and change in coordinates of one or more ARDDs (e.g. OHMD), which can assist with increasing the accuracy of the display of virtual data and their superimposition on corresponding live data.

Optical markers attached to movable structures can be used to track their location in the operating room. Optical markers attached to OR lights can be used to estimate the direction of light and the orientation and/or trajectory of shadows in the OR or a room. If the orientation and/or trajectory of shadows in the OR or the room is known, virtual shadowing or shading with the same or similar orientation or trajectory can be applied to virtual data display by the HMD.

Different coordinate systems can be used. For example, a global coordinate system, can include one or more of a femoral coordinate system, tibial coordinate system, ankle coordinate system, hip coordinate system, acetabular coordinate system, humeral coordinate system, glenoid coordinate system, vertebral coordinate system etc. Someone skilled in the art can readily recognize other sub-coordinate systems in the global coordinate system.

In one example, one or more optical markers including one or more geometric shapes, geometric patterns, alphabetic, numeric, alphanumeric, and other codes or patterns including bar codes and QR codes or combinations thereof can be attached to a medial femoral epicondyle, for example using a pin or a screw or an adhesive. An image and/or video capture system integrated into, attached to or separate from the HMD can be used to monitor the position, and/or orientation and/or alignment and/or direction of movement and/or speed of movement of the optical marker in relationship to the image and/or video capture system and/or the coordinate system, e.g. a femoral coordinate system, a tibial coordinate system or a global coordinate system or combinations thereof; as the distal femur moves, the image and/or video capture system can detect the marker, for example based on its pre-programmed geometric shape, geometric pattern, alphabetic, numeric, alphanumeric, and other codes or patterns including bar codes and QR codes, and can monitor and, optionally, record the movement. If a second optical marker, including one or more geometric shapes, geometric patterns, alphabetic, numeric, alphanumeric, and other codes or patterns including bar codes and QR codes or combinations thereof is attached to the lateral femoral condyle in the same example, the image and/or video capture system can also monitor and, optionally record the position, and/or orientation and/or alignment and/or direction of movement and/or speed of movement of the second optical marker in relationship to the image and/or video capture system and/or the coordinate system, e.g. a femoral coordinate system, a tibial coordinate system or a global coordinate system or combinations thereof; by monitoring the position, and/or orientation and/or alignment and/or direction of movement and/or speed of movement of the first optical marker on the medial femoral epicondyle and the position, and/or orientation and/or alignment and/or direction of movement and/or speed of movement of the second optical marker on the lateral femoral epicondyle, the image and/or video capture system and related image processing and pattern recognition software can also monitor and, optionally, record the movement, e.g. direction of movement or speed of movement, of the femoral epicondylar axis, for example during flexion and extension of the knee. One or more optical markers including one or more geometric shapes, geometric patterns, alphabetic, numeric, alphanumeric, and other codes or patterns including bar codes and QR codes or combinations thereof can be attached to a proximal tibia, e.g. an anterior tibial rim, a medial and/or lateral tibial spine, a lowest point of a medial plateau and/or a highest point of a lateral tibial plateau, for example in the same example. The image and/or video capture system integrated into, attached to or separate from the HMD can be used to monitor the position, and/or orientation and/or alignment and/or direction of movement and/or speed of movement of the optical marker(s) attached to the tibia in relationship to the image and/or video capture system and in relationship to one or more femoral optical markers and/or the coordinate system, e.g. a femoral coordinate system, a tibial coordinate system or a global coordinate system or combinations thereof, thereby monitoring and, optionally recording, tibiofemoral motion, e.g. during a surgery. One or more optical markers including one or more geometric shapes, geometric patterns, alphabetic, numeric, alphanumeric, and other codes or patterns including bar codes and QR codes or combinations thereof can be attached to a patella, e.g. a most superior aspect, a most inferior aspect, a most lateral aspect and/or a most medial aspect, for example in the same example. The image and/or video capture system integrated into, attached to or separate from the HMD can be used to monitor the position, and/or orientation and/or alignment and/or direction of movement and/or speed of movement of the optical marker(s) attached to the patella in relationship to the image and/or video capture system and in relationship to one or more femoral optical markers and/or the coordinate system, e.g. a femoral coordinate system, a tibial coordinate system, a patellar coordinate system or a global coordinate system or combinations thereof, thereby monitoring and, optionally recording, patellofemoral motion, e.g. during a surgery. The image and/or video capture system integrated into, attached to or separate from the HMD can be used to monitor the position, and/or orientation and/or alignment and/or direction of movement and/or speed of movement of the optical marker(s) attached to the patella in relationship to the one or more tibial optical markers, thereby monitoring and, optionally recording, patellar motion in relationship to the tibia, e.g. during tibial adduction or abduction.

In some embodiments, an optical marker, for example with one or more specific geometric shapes, geometric patterns, alphabetic, numeric, alphanumeric, and other codes or patterns including bar codes and QR codes or combinations thereof, can be assigned to a virtual surgical step. The marker can, for example, include written text defining the surgical step or corresponding to the surgical step, which can be the immediately preceding surgical step or the next surgical step, for example in a virtual surgical plan. In some embodiments, the text can be a number, for example a number corresponding to a particular surgical step, e.g. 1—for distal femoral cut, 2—for anterior femoral cut, 3—for posterior femoral cut, 4—for first chamfer cut, 5—for second chamfer cut. The number can be recognized by the image and/or video capture system, which can then display the virtual view for the corresponding surgical step, e.g. for 1—a cut plane for the distal femoral cut or a virtual outline of the corresponding physical distal femoral cut block. A combination of numbers and text can be used and the image and/or video capture system and associated software and optional pattern recognition software and systems can recognize the numbers and text and trigger a command to display the corresponding virtual view of the corresponding virtual surgical step, e.g. 1F—distal femoral cut, 2F—anterior femoral cut, 1T—proximal tibial cut, 2T—tibial keel punch etc.

In another example, an optical marker with one or more specific geometric shapes, geometric patterns, alphabetic, numeric, alphanumeric, and other codes or patterns including bar codes and QR codes or combinations thereof can be assigned to the step "distal femoral cut" in a virtual surgical plan for a total knee replacement in a patient; the optical marker can include the text "distal femoral cut". The surgeon can, for example, affix the marker to the cut bone surface of the distal femur or somewhere adjacent to it. An image and/or video capture system and/or 3D scanner integrated into, attached to or separate from an HMD can detect the optical marker with the one or more specific geometric patterns and/or specific geometric shapes assigned to "distal femoral cut", indicating that the distal femoral cut has been completed; the image capture signal and/or 3D scanner signal can then initiate a command to the HMD to display the next surgical step, e.g. an anterior cut plane or an outline of an anterior cut block or cut guide, as the surgeon prepares to perform the next cut, e.g. the anterior femoral cut in this example.

In some embodiments, an optical marker, for example with one or more specific geometric shapes, geometric patterns, alphabetic, numeric, alphanumeric, and other codes or patterns including bar codes and QR codes or combinations thereof, can be integrated into, included in, or attached to a surgical instrument used for a surgical step in a virtual surgical plan. For example, the optical marker can be included in, integrated into or attached to a surgical cut block or cutting tool, e.g. for a proximal tibial cut. Optionally, the marker can include written text defining the surgical step or corresponding to the surgical step, e.g. in a virtual surgical plan. In the immediately foregoing example, an optical marker with one or more specific geometric shapes, geometric patterns, alphabetic, numeric, alphanumeric, and other codes or patterns including bar codes and QR codes or combinations thereof can be assigned to the step "proximal tibial cut" in a virtual surgical plan for a total knee replacement in a patient; the optical marker can include the text "proximal tibial cut" which the surgeon can read and ensure that the correct marker is used for the next surgical step that he or she is contemplating, in this example a proximal tibial cut.

As the optical marker enters the surgeon's field of view, an image and/or video capture system integrated into or attached to the HMD on the surgeon's head can detect the optical marker and display the next virtual surgical step, e.g. an outline of a virtual proximal tibial cut block corresponding to the physical proximal tibial cut block, so that the surgeon can align or superimpose the physical surgical cut block or instrument onto the outline of the virtual surgical cut block or instrument. Alternatively, as the optical marker enters the surgeon's field of view, an image and/or video capture system integrated into or attached to the HMD on the surgeon's head can detect the optical marker and display the next virtual surgical step, e.g. a virtual cut plane with a predetermined resection level, varus or valgus angle and/or slope, so that the surgeon can align or superimpose the physical surgical cut block and/or the physical surgical saw with the virtual cut plane. Once the surgical step is completed, e.g. a proximal tibial cut, and the surgeon removes the physical surgical instrument with the integrated, included or attached optical markers from the surgical field and/or the field of view of the image and/or video capture system, the image and/or video capture system can detect that the optical marker is not present in the field of view anymore and software can generate a command to turn off the display of HMD, e.g. as a means of preserving battery power in the HMD, or the display of the completed virtual surgical step. Optionally, a command can be generated at this time, optionally automatically, to display the next surgical step, e.g. a tibial keel punch including, for example, setting tibial rotation. Alternatively, the display of the HMD unit can display the next surgical step as the next surgical instrument with the corresponding optical marker for the next surgical step enters the field of view, e.g. in the surgeon's hand.

In a similar example, an optical marker can be attached to an acetabular reamer used for hip replacement. An image and/or video capture system integrated into or attached to an HMD can detect the optical marker as it enters the surgeon's field of view triggering a command to display the reaming axis or a virtual display of the reamer with the intended alignment and/or direction for the reaming step; as the optical marker with the surgical instruments exits the surgeon's field of view, the image and/or video capture system can detect it triggering a command to stop the display of the reaming axis or virtual display of the reamer, optionally switching to the next surgical step.

In some embodiments, one or more optical markers can be included in, integrated into or attached to an insert for a cutting block or guide. The insert can be configured to fit into one or more slots or guides within the cutting block or guide for guiding a saw blade. Representative cutting blocks or guides are, for example, cutting blocks or guides used in knee replacement, shoulder replacement, hip replacement, and ankle replacement. These cutting blocks or guides are, for example, used to remove bone at the articular surface to fit the patient's bone to the bone facing side of an implant or implant component. The insert can be designed to partially or substantially fill the entire slot or guide, e.g. in x and y direction or x and z direction or y and z direction depending on the shape and/or design of the cutting block or guide. If the insert partially fills or substantially fills the slot or guide in x and y direction, the insert can be configured to extend beyond the slot or guide in z direction. If the insert partially fills or substantially fills the slot or guide in x and z direction, the insert can be configured to extend beyond the slot or guide in y direction. If the insert partially fills or substantially fills the slot or guide in y and z direction, the insert can be configured to extend beyond the slot or guide in x direction. Any direction is possible including oblique directions, orthogonal directions and non-orthogonal directions depending on the configuration of the cutting block or guide and the associated slots or guides. Oblique slots can, for example, be used for chamfer cuts in total knee replacement or oblique talar cuts in total ankle replacement.

The portion(s) of the insert that extend beyond the slot or guide can, for example, include one or more integrated or attached optical markers. If more than one optical marker is used, the optical markers can be arranged at predefined angles and locations, e.g. 90 degrees or less than 90 degrees or more than 90 degrees. The insert can have similar dimensions to a representative saw blade used with the cutting block or guide. The insert can indicate the position, location, orientation, alignment and direction of travel for a saw blade that will subsequently be inserted. The surgeon can place the insert inside the slot or guide of the physical cutting block or guide and align the insert, for example, with a virtual cut plane or a virtual outline of the insert or cutting block or guide projected by the HMD onto the surgical site, e.g. a distal femur in total knee replacement or a proximal femur in total hip replacement. Once the insert is substantially aligned and/or superimposed with the virtual cut plane, the virtual outline of the insert or cutting block or guide, the surgeon can pin the physical cutting block or guide onto the bone, thereby affixing the cutting block or guide to the bone in a position where the virtual surgical plan, e.g. the virtual cut plane or virtual outline of the insert or cutting block or guide is substantially aligned with the physical cut plane and or the physical insert or cutting block or guide. The surgeon can then insert the physical saw blade and perform the physical cut. The insert can be configured to have a shape substantially similar to the physical saw blade, serving as a dummy saw blade.

Alternatively, the surgeon can place the physical saw blade inside the slot or guide of the physical cutting block or guide and the surgeon can align the physical saw blade, for example, with a virtual cut plane or a virtual outline of the saw blade or cutting block or guide projected by the HMD onto the surgical site, e.g. a distal femur in total knee replacement or a proximal femur in total hip replacement. Once the physical saw blade is substantially aligned and/or superimposed with the virtual cut plane, the virtual outline of the saw blade or cutting block or guide, the surgeon can pin the physical cutting block or guide onto the bone, thereby affixing the cutting block or guide to the bone in a position where the virtual surgical plan, e.g. the virtual cut plane or virtual outline of the saw blade or cutting block or guide is substantially aligned with the physical cut plane and or the physical saw blade or cutting block or guide. The surgeon can then advance the physical saw blade and perform the physical cut. Optical markers can be included in, integrated into or attached to the cutting block or guide or the insert, e.g. a dummy saw blade. Optical markers can also be attached or affixed the saw blade. The optical markers can include a text or alphanumeric code for the surgeon that designates, for example, a specific surgical step, e.g. 1F—distal femoral cut, 2F—anterior femoral cut, 1T—proximal tibial cut, 2T—tibial keel punch etc. The optical markers can also include one or more specific geometric shapes, geometric patterns, alphabetic, numeric, alphanumeric, and other codes or patterns including bar codes and QR codes or combinations thereof. The one or more specific geometric shapes, geometric patterns, alphabetic, numeric, alphanumeric, and other codes or patterns including bar codes and QR codes or combinations thereof can be specific for the surgical step, corresponding, for example, to the lettering or alphanumeric code that indicates the surgical step to the surgeon. An image and/or video capture system integrated into, attached to or separate from the HMD can detect the one or more specific geometric shapes, geometric patterns, alphabetic, numeric, alphanumeric, and other codes or patterns including bar codes and QR codes or combinations thereof as the optical marker(s) enters the field of view; the specific geometric shapes, geometric patterns, alphabetic, numeric, alphanumeric, and other codes or patterns can be recognized using image processing and/or pattern recognition software triggering, for example, a command to display corresponding virtual surgical step in the HMD superimposed onto the surgical field with the view angle for the surgeon aligned with the surgical field or target anatomy or bone cut. When the cutting block or guide, the insert, e.g. a dummy saw blade, or the physical saw blade with the optical marker is removed, the image and/or video capture system can detect that the optical marker is not present in the field of view any longer, triggering, for example a command to turn off the HMD display, e.g. as a means of preserving battery power, or the display of the completed surgical step or to switch to the display of the next surgical step and corresponding virtual display.

In some embodiments, one or more optical markers, e.g. at select angles, e.g. 90 degrees or less or more or parallel or on one axis, can be included in, integrated into or attached to a cutting block or guide.

In some embodiments, one or more optical markers can be used in conjunction with a spinal surgery, e.g. a vertebroplasty, a kyphoplasty, a posterior spinal fusion, an anterior spinal fusion, a lateral spinal fusion and/or a disk replacement. For example one or more optical markers can be included in, integrated into, or attached to a needle, a pin, an awl, a feeler probe, a ball handle probe, a straight probe, a curved probe, a tap, a ratchet, a screw driver, a rod template, a rod inserter, a rod gripper, a bender, a plug starter, a compressor, a distractor, a break off driver, an obturator, a counter torque, a quick connector, a driver, a retractor, a retracting frame, an implant positioner, a caliper, a plate holder, a plate bender, a forceps and the like. The foregoing list is only exemplary and not to be construed limiting. The one or more optical markers can be used to designate the patient's left side and the patient's right side and/or they can be used to designate the patient's spinal level, using, for example, one or more geometric shapes, geometric patterns, alphabetic, numeric, alphanumeric, and other codes or patterns that can be detected with an image and/or video capture system integrated into, attached to or separate from the HMD and that can be recognized using image processing and/or pattern recognition.

One or more optical markers can be used to determine the position, location, orientation, alignment and/or direction of a needle, a pin, an awl, a feeler probe, a ball handle probe, a straight probe, a curved probe, a tap, a ratchet, a screw driver, a rod template, a rod inserter, a rod gripper, a bender, a plug starter, a compressor, a distractor, a break off driver, an obturator, a counter torque, a quick connector, a driver, a retractor, a retracting frame, an implant positioner, a caliper, a plate holder, a plate bender, a forceps, a mill, a saw, a reamer, a broach, an impactor, a cutting or drilling block, and/or other surgical instrument and/or trial implant and/or implant component with use of an image and/or video capture system integrated into, attached to or separate from the HMD. For example, after the initial registration or any subsequent registration of the patient, the surgical site, the HMD, optionally an image and/or video capture system integrated into, attached to or separate from the HMD, the virtual data and/or the live data of the patient have been performed, the image and/or video capture system can detect an optical marker included in, integrated into, and/or attached to the surgical instrument. Since the location, position, alignment and/or orientation of the optical marker on the surgical instrument are known and the dimensions, e.g. at least one of them, or geometry of the surgical instrument are known, the image and/or video capture system can track the optical marker and the surgical instrument with regard to its location, position, orientation, alignment and/or direction of movement.

In another example, two or more optical markers can be integrated into or attached to different, optionally defined locations along the long axis of a needle, a pin, an awl, a feeler probe, a ball handle probe, a straight probe, a curved probe, a tap, a ratchet, a screw driver, a rod template, a rod inserter, a rod gripper, a bender, a plug starter, a compressor, a distractor, a break off driver, an obturator, a counter torque, a quick connector, a driver, a retractor, a retracting frame, an implant positioner, a caliper, a plate holder, a plate bender, a forceps, a mill, a saw, a reamer, a broach, an impactor, a cutting or drilling block, and/or other surgical instrument and/or trial implant and/or implant component, for example instruments or trial implants or implant components in knee replacement or hip replacement. An image and/or video capture system can detect the two or more optical markers and their respective location can be determined. With the location of the two or more optical markers captured and defined by the image and/or video capture system, the long axis of the needle, pin, awl, probe, tap, mill, saw, reamer, broach, impactor, and/or other surgical instrument and/or trial implant and/or implant component can be determined; other axes can be determined in addition to the long axis or instead of the long axis. With the location of the optical markers on the needle, pin, awl, probe, tap, mill, saw, reamer, broach, impactor, and/or other surgical instrument and/or trial implant and/or implant component known, the long axis or other axis of the needle, pin, awl, probe, tap, mill, saw, reamer, broach, impactor, and/or other surgical instrument and/or trial implant and/or implant component known and the dimensions of the needle, pin, awl, probe, tap, mill, saw, reamer, broach, impactor, and/or other surgical instrument and/or trial implant and/or implant component known, any portions of the needle, pin, awl, probe, tap, mill, saw, reamer, broach, impactor, and/or other surgical instrument and/or trial implant and/or implant component hidden by the tissue, e.g. below the skin and/or inside or within muscle or the cartilage or the bone, can be estimated and can optionally be displayed by the HMD in addition to the virtual or intended path or projected path or any other aspects of a virtual surgical plan. Rather than using two or more optical markers in the foregoing embodiment, an optical marker long enough or wide enough or deep enough to define one or more axes of a needle, pin, awl, probe, tap, mill, saw, reamer, broach, impactor, and/or other surgical instrument and/or trial implant and/or implant component can also be used.

Optionally, when two or more optical markers are used included in, integrated into or attached to a surgical instrument, the optical markers, can be arranged at the same angles, e.g. parallel or on the same axis, or at different angles, e.g. orthogonal angles or non-orthogonal angles. Similarly, in determining an axis of a joint, e.g. an epicondylar axis, optical markers, e.g. optical markers attached to a medial or a lateral femoral epicondyle, can be arranged at the same angles, e.g. parallel or on the same axis, or at different angles, e.g. orthogonal angles or non-orthogonal angles. This can be particularly useful, when the optical markers include one or more of a geometric shape, geometric pattern, alphabetic, numeric, alphanumeric, and other codes or patterns including bar codes and QR codes or combinations thereof. By arranging the optical markers and any associated geometric shapes, geometric patterns, alphabetic, numeric, alphanumeric, and other codes or patterns including bar codes and QR codes or combinations thereof in this manner, the angular orientation of the surgical instrument or an axis can be determined in a more accurate manner. For example, at certain view angles from an image and/or video capture system integrated into or attached to an HMD select geometric shapes, geometric patterns, alphabetic, numeric, alphanumeric, and other codes or patterns including bar codes and QR codes or combinations thereof of a first optical marker on a surgical instrument or an anatomic landmark may be only partially visualized or not visualized at all due to the angular orientation; when a second optical marker is oriented at a different angle, location and/or orientation on the same surgical instrument or an anatomic landmark, the view angle from the image and/or video capture system integrated into or attached to the HMD to the second optical marker can allow for a complete or a more complete visualization of the one or more geometric shapes, geometric patterns, alphabetic, numeric, alphanumeric, and other codes or patterns including bar codes and QR codes or combinations thereof, thereby allowing a more accurate determination of the angular orientation of the second optical marker and, with that, the surgical instrument. In addition, the respective projections of the first optical marker and/or the second optical marker measured by the image and/or video capture system, optionally paired with any parallax information when two or more cameras are used, e.g. one positioned near the left eye and another positioned near the right eye, can be used to more accurately determine their relative position and the position of the surgical instrument.

An image and/or video capture system integrated into or attached to or separate from an HMD can detect an optical marker included in, integrated into or attached to a needle, a pin, an awl, a feeler probe, a ball handle probe, a straight probe, a curved probe, a tap, a ratchet, a screw driver, a rod template, a rod inserter, a rod gripper, a bender, a plug starter, a compressor, a distractor, a break off driver, an obturator, a counter torque, a quick connector, a driver, a retractor, a retracting frame, an implant positioner, a caliper, a plate holder, a plate bender, a forceps, a mill, a saw, a reamer, a broach an impactor, a cutting or drilling block, and/or other surgical instrument and/or trial implant and/or implant component as it enters the surgeon's field of view triggering a command to display the predetermined path or plane or a virtual display of the a needle, a pin, an awl, a feeler probe, a ball handle probe, a straight probe, a curved probe, a tap, a ratchet, a screw driver, a rod template, a rod inserter, a rod gripper, a bender, a plug starter, a compressor, a distractor, a break off driver, an obturator, a counter torque, a quick connector, a driver, a retractor, a retracting frame, an implant positioner, a caliper, a plate holder, a plate bender, a forceps, a mill, a saw, a reamer, a broach, an impactor, a cutting or drilling block, and/or other surgical instrument and/or trial implant and/or implant component or other display mode or type of the virtual surgical plan, for example with the intended position, location and/or alignment and/or direction for the intended surgical step; as the optical marker with the surgical instrument exits the surgeon's field of view, the image and/or video capture system can detect it triggering a command to stop the display of the predetermined path or the virtual display of the surgical instrument or other aspects of the virtual surgical plan, optionally switching to the next surgical step and corresponding virtual display. In a spinal procedure as well as select other procedures, the next surgical step can involve the same side of the patient or the opposite side of the patient at the same spinal level, where the corresponding virtual display for the next surgical step for a given level and side can be initiated by the ARDD. The next surgical step can involve the same side of the patient or the opposite side of the patient at an adjoining or different spinal level, where the corresponding virtual display for the next surgical step for a given level and side can be initiated by the ARDD.

Optical markers can include one or more QR codes. QR codes can be part of or can be embedded in a geometric pattern or geometric shape included in an optical marker. Optical markers can be a QR code.

If an optical marker is attached to a surgical instrument, the attachment can occur in a defined location and/or position and/or alignment, for example at an end of the surgical instrument. The attachment can include, for example, an opening with a stop thereby defining the location and/or position and/or alignment of the optical marker on the surgical instrument. For example, the optical marker can have an opening with a stop that is large enough to accommodate the surgeon facing end of a pin or drill, for example inserted into a spinous process or a facet joint or a portion of a pedicle. With this type of attachment and other attachments that secure the marker in a defined location, position and/or orientation on the surgical instrument, an image and/or video capture system can detect the optical marker and its location, position and/or orientation can be used to determine the location, position, and/or orientation of the surgical instrument, e.g. a pin, including its tip or frontal portion inside the patient due to their defined spatial relationship and due to the known geometry of the surgical instrument.

In some embodiments, an optical marker can be used to determine or identify the position, location, orientation, alignment, dimensions, axis or axes, plane or planes of a surgical alteration. For example, if a bone cut has been performed in a surgical step, one or more optical markers can be attached to the cut bone to determine one or more of its position, location, orientation, alignment, dimensions, shape, geometry, axis or axes, plane or planes. For example, one, two or more optical markers can be placed near or attached to the periphery or the edge of the cut bone or surgical alteration; an image and/or video capture system integrated into, attached to or separate from the ARDD can detect the location, position, and/or orientation of the optical markers and software can be used, for example, to analyze the location, position, and/or orientation information of the optical markers to derive information on the periphery and/or edge and/or shape of the cut bone or surgical alteration. One, two or more optical markers can be placed near or attached to the cut bone or surgical alteration; an image and/or video capture system integrated into, attached to or separate from the ARDD can detect the location, position, and/or orientation of the optical markers and software can be used, for example, to analyze the location, position, and/or orientation information of the optical markers to derive information on the shape or geometry of the cut bone or surgical alteration. If the bone cut is planar, one or more optical markers with a planar bone facing surface or one or more optical markers attached to a carrier or instrument, e.g.

a plastic piece, with a planar bone facing surface can be held against, affixed to or attached to the cut bone surface; an image and/or video capture system integrated into, attached to or separate from an ARDD can then be used to detect the one or more optical markers and software can be used, for example, to analyze the location, position and/or orientation information of the one or more optical markers to derive information on the location and/or position and/or orientation and/or alignment of the plane of the bone cut, including for example in relationship to other anatomic landmarks and/or other optical markers. The carrier or instrument for the optical marker can be transparent or semi-transparent so that the surgeon can check or confirm that the carrier or instrument and the attached optical marker(s) are flush against the bone cut prior to determining or confirming, for example, the plane of the bone cut. Once the plane of the bone cut has been determined or confirmed in this manner, the optical marker(s) attached to the cut bone and/or the determined plane of the bone cut can be used to plan the next surgical alteration, e.g. the next bone cut or surgical alteration, e.g. an anterior or posterior femoral cut after the distal femoral cut in knee replacement, or a chamfer cut after the anterior and posterior femoral cuts in knee replacement, or a cut on an opposing articular surface. By determining, confirming and/or referencing a preceding surgical alteration, e.g. a bone cut, in this manner, the accuracy of subsequent surgical steps can be improved thereby ultimately improving the overall accuracy of the surgical procedure.

Optical markers on fixed structures in the OR: In some embodiments, one or more optical marker and/or LEDs can be attached to an operating room (OR) table. If the optical marker is parallel to the OR table, a single marker can be sufficient to determine the principal plane of the OR table, e.g. the horizontal plane, which can be the plane on which the patient is resting, for example in supine, prone, lateral or oblique or other positions known in the art. This can be aided by using optical marker and/or LEDs that include a surface or plane that is parallel or perpendicular or at a defined angle to the OR table and that is large enough to be detected by the camera, image or video capture system integrated into, attached to or separate from the ARDD. For example, such a plane of the optical marker can measure 1×1 cm, 2×2 cm, 2×3 cm, 4×4 cm, 4×6 cm and so forth. Alternatively, multiple, e.g. two, three or more, optical marker and/or LEDs can be used to determine a plane through the markers corresponding to the principal plane of the OR table or a plane parallel to the principal plane of the OR table or, for example, a plane vertical to the OR table or, for example, a plane at a defined angle to the OR table. If the OR table is hidden by surgical drapes, one or more magnetic or otherwise attachable bases can be attached to the OR table prior to placing the drapes. After the drapes have been placed, one or more magnetic or otherwise attachable optical marker and/or LEDs can be affixed to the magnetic bases or attachment mechanisms with the interposed surgical drapes. The magnetic base can be radiopaque which can help identify the location, orientation and/or coordinates of the optical marker(s) in radiographic images or other images using ionizing radiation. Alternatively, one or more holding arms or extenders of known geometry can be attached to the OR table and one or more optical marker and/or LEDs can be attached to or can be integrated into the holding arms or extenders. An image and/or video capture system integrated into, attached to or separate from the ARDD can then identify the location, position, orientation and/or alignment of the one or more optical marker and/or LEDs. The resultant information can be used to determine the principal plane of the OR table on which the patient is lying. One or more ARDDs can be referenced using, for example, an image and/or video capture system integrated into or attached to the ARDD relative to the OR table and/or the attached optical marker and/or LEDs. Once the principal plane of the OR table is determined in the system, virtual surgical steps can be planned in the virtual surgical plan of the patient in relationship to the principal plane of the OR table. For example, one or more bone cuts can be planned and/or performed perpendicular to the principal plane of the OR table, for example with the patient in supine or prone position or any other desired position. One or more bone cuts can be planned and/or performed at defined angles other than 90 degrees relative to the horizontal plane of the OR table, for example with the patient in supine or prone position or any other desired position. One or more bone cuts can be planned and/or performed at a non-orthogonal plane or orientation relative to the principal plane or horizontal plane of the OR table, for example with the patient in supine or prone position or any other desired position, optionally referencing a plane vertical to the OR table, displayed by the ARDD. The principal plane of the OR table can be used as a reference in this manner including for comparing or referencing virtual data of the patient and live data of the patient and including for comparing or referencing a virtual surgical plan. Such bone cuts at orthogonal angles or non-orthogonal angles, e.g. relative to the OR table or relative to anatomy, anatomic landmarks, anatomic or biomechanical axes of the patient, can be executed using one or more virtual surgical guides or cut blocks and/or one or more physical surgical guides or cut blocks. Virtual surgical guides or cut blocks can include one or more dimensions corresponding to physical surgical guides or cut blocks. One or more anatomic axes or biomechanical axes or combinations thereof can also be referenced to the OR table in this manner, e.g. the principal plane of the OR table, a plane parallel to the OR table, a plane perpendicular to the OR table, a plane oblique to the OR table or combinations thereof.

One or more optical marker and/or LEDs attached to or referencing the OR table can also serve as a fixed reference for the one or more ARDDs during a surgical procedure. This can be useful, for example, when the patient and/or the extremity and/or the surgical site moves during the procedure. A fixed reference to the OR table can aid in maintaining registration of the one or more ARDDs and the virtual surgical plan and the live data of the patient and/or OR.

In some embodiments, one or more optical marker and/or LEDs can be placed on or attached to the patient in the area of the surgical field and/or in an area away from the surgical field. An image and/or video capture system integrated into, attached to or separate from the ARDD can be used to identify the one or more optical marker and/or LEDs and to determine their location, position, orientation and/or alignment. The image and/or video capture system can also, optionally, determine the location, position, orientation and/or alignment of one or more optical marker and/or LEDs attached to or referencing the OR table. The system can reference the coordinates and/or the spatial relationship of the one or more optical marker and/or LEDs attached to the patient in the area of the surgical field and/or in an area away from the surgical field and the one or more optical marker and/or LEDs attached to or referencing the OR table. In this manner, if the patient's body moves during the procedure, e.g. during a broaching of a proximal femur or an acetabular reaming during hip replacement, or a femoral or tibial component impacting during knee replacement, or during a pinning or cutting of a bone, or during a placement of a spinal device, e.g. a cage or a pedicle screw, the movement between the one or more optical marker and/or LEDs attached to the patient in the area of the surgical field and/or in an area away from the surgical field and the one or more optical marker and/or LEDs attached to or referencing the OR table and the change in coordinates of the one or more optical marker and/or LEDs attached to the patient in the area of the surgical field and/or in an area away from the surgical field can be detected and the amount of movement, direction of movement and magnitude of movement can be determined; the resultant information can, for example, be used to update or adjust or modify a virtual surgical plan or to update or adjust or modify the display of the virtual surgical plan or virtual surgical steps or virtual displays for the movement of the patient, including for example by updating, moving or adjusting one or more aspects or components of the virtual surgical plan including one or more of a virtual surgical tool, virtual surgical instrument including a virtual surgical guide or cut block, virtual trial implant, virtual implant component, virtual implant or virtual device, a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration using the new patient coordinates or the new coordinates of the surgical field.

Radiopaque optical markers: In some embodiments, portions of the optical marker or the entire optical marker can be radiopaque, so that the optical marker can also be visible on a radiograph or other imaging studies that utilize ionizing radiation including, for example, fluoroscopy, digital tomosynthesis, cone beam CT, and/or computed tomography. Different levels or degrees of radiopacity can be present in different portions or areas of the optical marker. Different levels or degrees of radiopacity can be utilized to encode information. For example, different levels of radiopacity can be used to encode information also contained, for example, in an optically readable alphanumeric code, bar code or QR or other code. The different levels of radiopacity can optionally be arranged in a bar like thickness distribution, which can optionally mirror portions or all of the information contained in a bar code. The different levels of radiopacity can optionally be arranged in a point or square like thickness distribution, which can optionally mirror portions of the information contained in a QR code. Different radiopacity can be obtained by varying the thickness of the metal, e.g. lead. Radiopaque optical marker and/or LED's with information encoded in such manner can, for example, be manufactured using 3D metal printers. They can also be CNC machined, e.g. from bar stock or cast blanks. Optical markers can include portions that are radiopaque and portions that are not radiopaque. Radiopaque portions can include radiopaque elements, e.g. radiopaque struts, disks, sphere and/or other shapes. Any shape known in the art can be used. The optical marker can be attached to the radiopaque elements and/or radiopaque portions. The optical marker can be integrated into the radiopaque elements and/or radiopaque portions. The optical marker can be separate from the radiopaque elements and/or radiopaque portions, e.g. at a defined or known distance, defined or known angle and/or defined or known geometric and/or spatial arrangement.

A radiopaque marker can be included in an imaging study, e.g. a CT scan or cone beam CT. The radiopaque marker can be in a defined geometric relationship (e.g. a fixed relationship or rigidly attached) to an optical marker, a navigation marker, an RF marker, an IMU, an LED, a fiducial array (e.g. of navigation markers) attached to an anatomic structure, which can be tracked in a coordinate system, e.g. by a camera or 3D scanner. In this manner, a computer processor can detect the radiopaque marker in the imaging study and can register the imaging study in the coordinate system. Surgical instruments can be tracked in the same coordinate system, e.g. using an optical marker, a navigation marker, an RF marker, an IMU, an LED, a fiducial array attached to the surgical instrument. The surgical instruments can then be displayed by an ARDD in relationship to the imaging study and the anatomic structures displayed in the imaging study in the coordinate system.

In some embodiments, a radiopaque marker comprises an optical marker, a navigation marker, an RF marker, an IMU, an LED, a fiducial array (e.g. of navigation markers) which can be tracked in a coordinate system, e.g. by a camera or 3D scanner. A separate optical marker, a navigation marker, an RF marker, an IMU, an LED, a fiducial array (e.g. of navigation markers) attached to an anatomic structure, e.g. a spinous process, can also be tracked in the coordinate system and the imaging study with the radiopaque marker and the separate optical marker, a navigation marker, an RF marker, an IMU, an LED, a fiducial array (e.g. of navigation markers) attached to the anatomic structure can be cross-referenced and tracked in the coordinate system. In this manner, the imaging study can be displayed in the coordinate system of the separate optical marker, a navigation marker, an RF marker, an IMU, an LED, a fiducial array (e.g. of navigation markers) attached to the anatomic structure along with any surgical instruments tracked in the coordinate system.

Other reference phantoms, e.g. an MRI visible phantoms (for example including Vitamin E capsules or Gadolinium-doped water), a PET visible phantom (e.g. positron emitting phantoms), a radiation emitting (e.g. Gamma-radiation) phantom for SPECT or nuclear scintigraphy imaging, an ultrasound visible phantom (e.g. containing ultrasound visible bubbles or water or fat) can be included in the field of view of an imaging study, e.g. an MRI scan, PET scan, SPECT scan, nuclear scan, an ultrasound scan etc., The reference phantom can be in a defined geometric relationship (e.g. a fixed relationship or rigidly attached) to an optical marker, a navigation marker, an RF marker, an IMU, an LED, a fiducial array (e.g. of navigation markers) attached to an anatomic structure, which can be tracked in a coordinate system, e.g. by a camera or 3D scanner; any other tracking means described in the disclosure or known in the art can be used. In this manner, a computer processor can detect the reference phantom in the imaging study and can register the imaging study in the coordinate system. Surgical instruments can be tracked in the same coordinate system, e.g. using an optical marker, a navigation marker, an RF marker, an IMU, an LED, a fiducial array attached to the surgical instrument or other tracking means described in the disclosure or known in the art. The surgical instruments can then be displayed by an ARDD in relationship to the imaging study and the anatomic structures displayed in the imaging study in the coordinate system.

In some embodiments, a reference phantom comprises an optical marker, a navigation marker, an RF marker, an IMU, an LED, a fiducial array (e.g. of navigation markers) which can be tracked in a coordinate system, e.g. by a camera or 3D scanner; any other tracking means described in the disclosure, e.g. electromagnetic sensors, or known in the art can be used. A separate optical marker, a navigation marker, an RF marker, an IMU, an LED, a fiducial array (e.g. of navigation markers) or any other tracking means attached to an anatomic structure, e.g. a spinous process, can also be tracked in the coordinate system and the imaging study with the radiopaque marker and the separate optical marker, a navigation marker, an RF marker, an IMU, an LED, a fiducial array (e.g. of navigation markers) attached to the anatomic structure can be cross-referenced and tracked in the coordinate system. Other tracking means such as 3D scanning of an anatomic structure or surface of the patient can be used. In this manner, the imaging study can be displayed in the coordinate system of the separate optical marker, a navigation marker, an RF marker, an IMU, an LED, a fiducial array (e.g. of navigation markers) attached to the anatomic structure or the coordinate system established with any other tracking means described in the disclosure or known in the art, along with any surgical instruments tracked in the coordinate system.

The radiopaque portions of the optical marker can include information on laterality, e.g. L for left and R for right, visible on the radiograph, for example through different material thicknesses, e.g. lead; the same information can be included in an attached alphanumeric code or text, bar code or QR code which can be read by a bar code or QR code reader or an image and/or video capture system integrated into, attached to or separate from the ARDD. The radiopaque portions of the optical marker can include information on anatomical site, e.g. L5 or L4, T1 or T2, C3 or C7, knee, hip, visible on the radiograph, for example through different material thicknesses, e.g. lead; the same information can be included in an attached alphanumeric code or text, bar code or QR code which can be read by a bar code or QR code reader or an image and/or video capture system integrated into, attached to or separate from the ARDD. Image processing techniques and/or software can be applied to the radiographic information including the optical marker and radiographically encoded information such as laterality and/or site and the information included in the radiograph can be compared against the information included on the optical scan. If any discrepancies are detected, an alert can be triggered, which can, for example, be displayed in the ARDD.

Multiple partially or completely radiopaque optical markers can be used. The radiopaque optical markers can be applied at different locations and in different planes around the surgical site. In spinal surgery, for example, one, two, three or more radiopaque optical markers can be applied to the skin around the spinal levels for the intended surgery; one, two, three or more radiopaque optical markers can be attached to a pin, drill or screw inserted into a spinous process and/or a pedicle or other spinal element; one, two, three or more radiopaque optical markers can be applied to the patient's flank or abdomen. In hip replacement surgery, one, two, three or more radiopaque optical markers can be applied to the anterior superior iliac spine on the patient's intended surgical side, e.g. with an adhesive to the skin or attached to a pin or drill to the bone; one, two, three or more radiopaque optical markers can be applied to the anterior superior iliac spine on the patient's contralateral side, e.g. with an adhesive to the skin or attached to a pin or drill to the bone; one, two, three or more radiopaque optical markers can be applied to the symphysis pubis, e.g. with an adhesive to the skin or attached to a pin or drill to the bone; one, two, three or more radiopaque optical markers can be applied to the acetabulum on the patient's intended surgical side, e.g. attached to a pin or drill to the bone; one, two, three or more radiopaque optical markers can be applied to the greater trochanter on the patient's intended surgical side, e.g. attached to a pin or drill to the bone. By using multiple radiopaque optical markers in multiple different locations and in different planes around the surgical site, the accuracy of any three-dimensional spatial registration and cross-reference of the optical markers in different modalities, e.g. radiographs, image capture, can be increased, for example by obtaining multiple x-rays at different angles, e.g. AP, lateral and/or oblique, and/or by imaging the radiopaque optical markers from multiple view angles using an image and/or video capture system integrated into, attached to or separate from the ARDD or by imaging the radiopaque optical markers from multiple view angles using multiple image and/or video capture system integrated into, attached to or separate from the ARDD leveraging information from multiple view angles or leveraging parallax information. By using multiple optical markers in multiple different locations and in different planes around the surgical site, the accuracy of any three-dimensional spatial registration of the optical markers can be increased, for example by imaging the optical markers from multiple view angles using an image and/or video capture system integrated into, attached to or separate from the ARDD. In addition, the accuracy of the registration can be better maintained as the view angle or radiographic angle changes, for example during the course of the surgical procedure or due to patient movement.

In some embodiments, the system performance can be tested. System performance tests can, for example, measure a phantom including two or more optical markers at known locations, positions, orientations and/or alignment. With the coordinates of the two or more optical markers known along with the distance(s) and angle(s) between the markers, the accuracy of performing distance measurements and/or angle measurements and/or area measurements and/or volume measurements using an image and/or video capture system integrated into, attached to or separate from the ARDD can be determined. In addition, by repeating the measurements, the reproducibility and/or precision of performing distance measurements and/or angle measurements and/or area measurements and/or volume measurements using an image and/or video capture system integrated into, attached to or separate from the ARDD can be determined. The accuracy and/or the reproducibility and/or the precision of performing distance measurements and/or angle measurements and/or area measurements and/or volume measurements using an image and/or video capture system integrated into, attached to or separate from the ARDD can be determined for static and dynamic conditions. Static conditions can be conditions where a patient, a spine, an extremity, a joint and/or a bone do not move. Dynamic conditions can be conditions where a patient, a spine, an extremity, a joint and/or a bone move during the image capture. Dynamic conditions can, for example, be useful in determining the center of rotation of a joint. Measurements for static conditions and for dynamic conditions can be performed for different view angles and distances of the image and/or video capture system integrated into, attached to or separate from the ARDD. More than one image and/or video capture system integrated into, attached to or separate from the ARDD can be used leveraging information from multiple view angles or leveraging parallax information. Measurements for static conditions and for dynamic conditions can be performed with the ARDD at rest, not moving. Measurements for static conditions and for dynamic conditions can be performed with the ARDD not at rest, but moving, for example moving with the operator's head.

TABLE 2 shows exemplary tests with various combinations of test conditions and test parameters for which the accuracy and the reproducibility and/or the precision of the measurements can be determined. Any combination is possible. Other parameters, e.g. reproducibility of color temperature (e.g. in Kelvin), can be measured. Other statistical tests can be applied. All measurements and all statistical determinations and parameters can be assessed for static, dynamic, HMD at rest and HMD moving conditions including at different angles and distances of the image and/or video capture system to the target anatomy and/or test apparatus and/or phantom.

TABLE 2

| | Coordinates of optical markers | Distance between optical markers | Angle between optical markers | Area enclosed by optical markers | Volume of optical marker(s) | Volume enclosed by multiple optical markers | Axis defined by two or more optical markers | Speed of movement of optical marker | Direction of movement of optical marker |
|---|---|---|---|---|---|---|---|---|---|
| Accuracy | X | X | X | X | X | X | X | X | X |
| Reproducibility | X | X | X | X | X | X | X | X | X |
| Static | X | X | X | X | X | X | X | • | • |
| Dynamic | X | X | X | X | X | X | X | X | X |
| OHMD at rest | X | X | X | X | X | X | X | X | X |
| OHMD moving | X | X | X | X | X | X | X | X | X |

Once the accuracy and/or the reproducibility and/or the precision of performing distance measurements and/or angle measurements and/or area measurements and/or volume measurements and/or coordinate measurements using one or more image and/or video capture system integrated into, attached to or separate from the HMD has been determined, threshold values can, for example, be defined that can indicate when the system is operating outside a clinically acceptable performance range. The threshold values can be determined using standard statistical methods known in the art. For example, when a view angle and/or a distance or a movement speed of an image and/or video capture system integrated into an HMD indicate that a measurement value can fall outside two standard deviations of the system performance including overall system performance, it can trigger an alert to the surgeon that the display of virtual data, e.g. portions of a virtual surgical plan, virtual projected paths or virtual planes, e.g. virtual cut planes, may not be accurate. A binary, e.g. yes, no, system can be used for triggering an alert that the image and/or video capture system and/or the HMD display are operating outside a clinically acceptable performance range, e.g. exceeding certain view angles, exceeding or being below certain distances to the target anatomy, or exceeding an acceptable movement speed. Alternatively, a sliding scale can be used as the system enters progressively into a range outside the clinically acceptable performance range. The sliding scale can, for example, be a color scale from green to red with mixed colors in between. The sliding scale can be an acoustic signal that increases in intensity or frequency the further the system operates outside the clinically acceptable range. The sliding scale can be a vibration signal that increases in intensity or frequency the further the system operates outside the clinically acceptable range. In some embodiments, the HMD can optionally turn off the display of any virtual data of the patient, e.g. virtual plan information, virtual surgical guides or cut blocks or virtual planes or intended paths, or one or more desired or predetermined alignment axes, anatomical axes, biomechanical axes and/or rotation axes when one or more test data indicate that the system is operating outside its clinically acceptable performance range. When test data indicate that the system is operating again inside the clinically acceptable performance range, the HMD display can turn back on. System tests including accuracy tests and reproducibility tests can be performed intermittently, e.g. every 3 seconds, 5 seconds, 10 seconds, 20 seconds, 30 seconds, 1 minutes, 2 minutes and so forth. System tests can be performed continuously. System tests can be performed intermittently or continuously but limited to times when virtual data are displayed by the HMD. System tests can be performed intermittently or continuously but limited to times when surgical steps that require high accuracy or reproducibility are being performed. Such steps requiring high accuracy or high reproducibility can be identified for example by the surgeon through voice commands or other commands or they can be identified in the virtual surgical plan, e.g. automatically or by surgeon choice.

In some embodiments, radiopaque and non-radiopaque optical markers can optionally be attached to or applied to extenders that increase the distance of the optical marker from the patient's skin. Such extenders can, for example, be anchored in a spinous process, a pedicle or other spinal element or a femoral condyle or tibial tubercle via a pin, drill or screw. The use of extenders with attached radiographic optical markers can increase the accuracy of registration between radiographic data and image capture data, for example when AP and lateral radiographs are used. The use of extenders with attached optical markers can help define anatomic or instrument axes and other information when image capture is used. When two or more markers are used with extenders and the markers are separated by a distance greater than the spatial resolution of the image and/or video capture system, the accuracy in determining, for example, an axis between the two markers can increase, for example as the length of the extender and the distance between the markers increases. Optical markers can be visible with other imaging modalities, e.g. MRI, nuclear scintigraphy, SPECT or PET. Optical markers can, for example, be doped with an MRI contrast agent such as Gadolinium-DTPA so that they are MRI visible. Optical markers can, for example, be doped with an isotope or positron emitter so that they are SPECT or PET visible.

Registration of Virtual Patient Data and Live Patient Data Using Patient Specific Markers or Templates Various techniques have been described for registering virtual patient data with live patient data using patient specific markers or templates including those described in WO9325157A1, which is expressly incorporated by reference herein.

In some embodiments, pre-operative imaging is performed to acquire 3D data of the patient. The pre-operative imaging can, for example, entail ultrasound, CT or MRI, any of the foregoing, optionally with administration of a contrast agent.

The pre-operative imaging can include a single area or region, such as a lumbar spine or portions of a lumbar spine or one or more spinal segments, or a single joint, such as a knee joint, hip joint, ankle joint, shoulder joint, elbow joint or wrist joint. Alternatively, the pre-operative imaging can include scanning through portions or all of one or more adjacent joints. This approach can be beneficial when information about a length of an extremity or axis alignment or rotational alignment is desirable. For example, in planning a hip replacement surgery, it can be beneficial to have image information through the distal femur and, optionally, the knee joint and/or the ankle joint available to determine, for example, leg length. In planning a knee replacement surgery, it can be beneficial to have image information through the hip joint and the ankle joint available. In this manner, the center of the hip and the ankle joint can be, for example, determined. This information can be used to determine the mechanical axis alignment of the patient and, optionally, to plan for any mechanical axis correction.

The pre-operative imaging can also entail imaging in one or more positions, e.g. prone, supine, upright, flexion, extension, lateral bending. Data obtained from scans with the patient in different positions can optionally be combined or fused. For example, an upright standing weight-bearing partial or full leg x-ray can be used to determine the mechanical axis alignment of the leg. 3D data of the knee, e.g. from CT or MRI can be used to obtain detailed anatomic information about the joint, for example to derive a surface shape and to design a patient specific marker or template. The information from the upright scan can be used to align the patient specific marker or template or aspects of it in relationship to the mechanical axis. The information from the 3D knee scan can be used to derive one or more patient specific surfaces that fit to the unique shape of the patient.

In a patient with spinal symptoms, 3D data of the spine can be obtained, for example, with a CT or MRI scan or a rotational fluoroscopy or C-arm scan. Upright imaging, for example in flexion and extension, can be used to determine the presence and degree of spinal instability, for example prior to an intended spinal fusion surgery with pedicle screws and/or cages. The degree of instability or slippage can be determined and used to decide on the degree of intended correction, if any, or the degree of a required foraminotomy, both of which can be optionally planned on the 3D data. Lateral bending views can optionally be used to determine the degree and angle of a partial vertebral corpectomy and the desired placement and/or height of intervertebral cages. Thus, data from upright imaging studies can be combined or optionally fused with data from supine or prone imaging studies. Data from 2D imaging studies can be combined or fused with data from 3D imaging studies. The 3D data can be used to derive one or more patient specific surfaces that fit to the unique shape of the patient, e.g. to the unique shape of one or more of the patient's spinous processes, one or more of the patient's transverse processes, one or more of the patient's laminae, one or more of the patient's articular processes, one or more of the patient's vertebral body.

The patient specific marker or template can include one or more surfaces that are designed and manufactured to fit the corresponding surface of the patient, typically like a negative or substantially a negative. Optional smoothing of the surface can be performed. Alternatively, the surface can be intentionally "roughened" to include more surface features than the segment 3D surface of the patient's target anatomy. Such surface features can, for example, include spike or pin-like structures to allow for enhanced fixation of the patient specific marker or template on the patient's tissue surface.

The patient specific marker or template can be developed from CT, MRI or ultrasound scans as well as x-ray imaging. Principally, any multi-planar 2D or 3D imaging modality is applicable, in particular when it provides information on surface shape or provides information to derive estimates of surface shape of an anatomic region. The patient specific marker or template can include one or more surfaces that are designed or manufactured to fit in any joint or in a spine or other anatomic locations a corresponding Cartilage surface of a patient; Subchondral bone surface of a patient; Cortical bone surface of a patient; Osteophyte or bone spur of a patient; Bone defect of a patient; Exuberant bone formation of a patient; Subchondral cyst of a patient; Soft-tissue shape, e.g. the shape of a thigh or calf or lower back, or thoracic region, or neck region, or foot or ankle region, or shoulder region; Soft-tissue shape in different body poses or positions, e.g. in prone position or in supine position or in lateral position; Ligament of a patient; Labrum of a patient; Meniscus of a patient; Organ shape of a patient; Organ rim or edge of a patient, e.g. a liver edge or spleen edge.

Different imaging tests can be particularly amenable for a given tissue. For example, if the patient specific marker or template is designed to fit the cartilage shape of the patient, MRI and ultrasound or CT arthrography are ideally suited to provide the surface information. If the patient specific marker or template is intended to fit the subchondral bone shape or cortical bone shape, CT can be used, although MRI and ultrasound can also provide information on bone shape.

Patient specific markers or templates can be manufactured using different materials, e.g. ABS or nylon or different types of plastics or metals. They can be machined, e.g. from a blank, wherein a CAD/CAM process transfers the patient specific shape information into the milling machines. They can also be produced using stereolithography or 3D printing techniques known in the art. If 3D printing is used, any residual powder can be removed using an air cleaning operation and/or a water bath. 3D printing can be performed using powder based or liquid resin based approaches, including, but not limited to continuous liquid interface production.

Patient specific markers or templates can include or incorporate optical markers, e.g. optical markers with different geometric shapes or patterns, with QR codes, with bar codes, with alphanumeric codes. Optionally, geometric shapes or patterns, QR codes, bar codes, alphanumeric codes can be printed, for example when 3D printing is used for manufacturing patient specific markers or templates. 3D printing can be performed with software, e.g. Materialise Magics (Materialise, Leuven, Belgium), and hardware known in the art, e.g. 3D printers from 3D Systems, Rock Hill, SC, or Concept Laser, Lichtenfels, Germany.

Patient specific markers or templates can be made with different material properties. For example, they can be non-elastic, semi-elastic or elastic. They can be hard. They can be solid or include hollow spaces or openings. They can be opaque. Patient specific markers or templates can be semi-opaque. Patient specific markers can be transparent. In some embodiments, a patient specific marker or template can be semi-opaque or semi-transparent. However, when the patient specific marker or templates comes in contact with the patient and the patient specific surface(s) of the marker or template achieves a good fit with the corresponding surface of the patient, the patient specific marker or template becomes transparent due to the tissue moisture on the corresponding surface of the patient.

One or more patient specific markers or templates can be used on a first surface of a joint. One or more patient specific markers can be used on a second surface of a joint. The first and second surface can be on the same weight-bearing side of the joint. The first and second surface can be on opposite sides of the joint. The one or more patient specific markers or templates on the first surface of the joint cannot be connected to the one or more patient specific markers or templates on the second surface of the joint. In some embodiments, the one or more patient specific markers or templates on the first surface of the joint can, optionally, be connected or linked to the second surface of the joint. Thus, one or more patient specific markers or templates can optionally be cross-referenced.

Patient specific markers or templates can be designed for any joint, any portion of a spine, and any tissue of the human body. Patient specific markers or templates typically include one or more surfaces or shapes designed to fit a corresponding surface or shape of a patient. Representative, non-limiting examples of patient surfaces to which patient specific markers or templates can be designed and/or fitted include:

Spine:
- A portion or an entire spinous process
- A portion or an entire spinal lamina
- A portion or an entire spinal articular process
- A portion of or an entire facet joint
- A portion of or an entire transverse process
- A portion of or an entire pedicle
- A portion of or an entire vertebral body
- A portion of or an entire intervertebral disk
- A portion of or an entire spinal osteophyte
- A portion of or an entire spinal bone spur
- A portion of or an entire spinal fracture
- A portion of or an entire vertebral body fracture
- Combinations of any of the foregoing Hip:
- A portion of or an entire acetabulum
- A portion of or an entire edge of an acetabulum
- Multiple portions of an edge of an acetabulum
- A portion of an iliac wall
- A portion of a pubic bone
- A portion of an ischial bone
- A portion of or an entire greater trochanter
- A portion of or an entire lesser trochanter
- A portion of or an entire femoral shaft
- A portion of or an entire femoral neck
- A portion of or an entire femoral head
- A fovea capitis
- A transverse acetabular ligament
- A pulvinar
- A ligamentum teres
- A labrum
- One or more osteophytes, femoral and/or acetabular
- Combinations of any of the foregoing Knee:
- A portion or an entire medial femoral condyle
- A portion or an entire lateral femoral condyle
- A portion or an entire femoral notch
- A portion or an entire trochlea
- A portion of an anterior cortex of the femur
- A portion of an anterior cortex of the femur with adjacent portions of the trochlea
- A portion of an anterior cortex of the femur with adjacent portions of the trochlea and osteophytes when present
- One or more osteophytes femoral and/or tibial
- One or more bone spurs femoral and/or tibial
- An epicondylar eminence
- A portion or an entire medial tibial plateau
- A portion or an entire lateral tibial plateau
- A portion or an entire medial tibial spine
- A portion or an entire lateral tibial spine
- A portion of an anterior cortex of the tibia
- A portion of an anterior cortex of the tibia and a portion of a tibial plateau, medially or laterally or both
- A portion of an anterior cortex of the tibia and a portion of a tibial plateau, medially or laterally or both and osteophytes when present
- A portion or an entire patella
- A medial edge of a patella
- A lateral edge of a patella
- A superior pole of a patella
- An inferior pole of a patella
- A patellar osteophyte
- An anterior cruciate ligament
- A posterior cruciate ligament
- A medial collateral ligament
- A lateral collateral ligament
- A portion or an entire medial meniscus
- A portion or an entire lateral meniscus
- Combinations of any of the foregoing Shoulder:
- A portion or an entire glenoid
- A portion or an entire coracoid process
- A portion or an entire acromion
- A portion of a clavicle
- A portion or an entire humeral head
- A portion or an entire humeral neck
- A portion of a humeral shaft
- One or more humeral osteophytes
- One or more glenoid osteophytes
- A portion or an entire glenoid labrum
- A portion or an entire shoulder ligament, e.g. a coracoacromial ligament, a superior, middle, or inferior glenohumeral ligament
- A portion of a shoulder capsule
- Combinations of any of the foregoing Skull and Brain:
- A portion of a calvarium
- A portion of an occiput
- A portion of a temporal bone
- A portion of an occipital bone
- A portion of a parietal bone
- A portion of a frontal bone
- A portion of a facial bone
- A portion or an entire bony structure inside the skull
- Portions or all of select gyri Portions or all of select sulci
A portion of a sinus
A portion of a venous sinus
A portion of a vessel Organs:
A portion of an organ, e.g. a superior pole or inferior pole of a kidney
An edge or a margin of a liver, a spleen, a lung
A portion of a hepatic lobe
A portion of a vessel
A portion of a hiatus, e.g. in the liver or spleen
A portion of a uterus The patient specific marker or template can be designed or fitted to any of the previously mentioned tissues, if applicable for a particular anatomic region, e.g. cartilage, subchondral bone, cortical bone, osteophytes etc. The patient specific marker or template can be designed or fitted to normal tissue only. The patient specific marker or template can be designed or fitted to abnormal or diseased tissue only. The patient specific marker or template can be designed or fitted to combinations of normal and abnormal or diseased tissue. For example, the patient specific marker can be designed to normal cartilage, or to diseased cartilage, or to combinations of normal and diseased cartilage, e.g. on the same or opposing joint surfaces. Patient specific markers can be used to register one or more normal or pathologic tissues or structures in a common coordinate system, for example with one or more ARDD and virtual data of the patient. Virtual and physical surgical instruments and implant components can also be registered in the common coordinate system.

The patient specific marker or template can be designed using virtual data of the patient, e.g. from a pre-operative imaging study such as a CT scan, MRI scan or ultrasound scan. The patient specific marker or template includes one or more surfaces that are designed and/or manufacture to achieve a close fit with a corresponding surface of the patient.

In some embodiments, a surgeon or an operator can apply the patient specific marker or template to the corresponding tissue of the patient. Once a satisfactory fit has been achieved and the two corresponding surfaces are substantially in contact, the patient specific marker or template can be used to register the virtual data of the patient and an optional virtual surgical plan with the live data of the patient. By applying the patient specific marker or template to its corresponding surface(s) on the patient, the surgeon is effectively identifying corresponding structures or surfaces in the virtual data and the live data of the patient.

The position, location and/or orientation of the patient specific marker or template can then be determined in relationship to the ARDD. Any of the embodiments described herein can be applied for determining the position, location and/or orientation of the patient specific marker or template in relationship to the ARDD. For example, the side of the patient specific marker or template that is opposite the patient specific surface can include certain standardized geometric features, e.g. rectangles, triangles, circles and the like, that can be readily recognized by an image and/or video capture system integrated into or attached to or coupled to the ARDD. In alternative embodiments, the patient specific marker or template can include one or more IMU's, including, for example, accelerometers, magnetometers, and gyroscopes, similar, for example, to the ARDD. In some embodiments, the patient specific marker or template can include one or more radiofrequency tags or markers or retroreflective markers and its position, location and/or orientation can be captured by a surgical navigation system. Radiofrequency tags can be active or passive. Optionally, the ARDD may also include one or more radiofrequency tags or markers or retroreflective markers and its position, location and/or orientation can also be captured by the surgical navigation system and cross-referenced to the patient specific marker or template. The patient specific marker or template can also include light sources, such as lasers or LED's. A laser can be projected, for example, on a wall or a ceiling and the ARDD can be referenced in relationship to that. An LED attached to or integrated into the patient specific marker or template can be recognized, for example, by an image and/or video capture system integrated into or attached to coupled to the ARDD. In an additional embodiment, one or more of the surgical instruments and/or one or more of the implantable devices used during the surgery can include certain standardized geometric features, e.g. rectangles, triangles, circles and the like, that can be readily recognized by an image and/or video capture system integrated into or attached to or coupled to the ARDD. In alternative embodiments, one or more of the surgical instruments and/or one or more of the implantable devices used during the surgery can include one or more IMUs, including, for example, accelerometers, magnetometers, and gyroscopes, similar, for example, to the ARDD. In some embodiments, one or more of the surgical instruments and/or one or more of the implantable devices used during the surgery can include one or more radiofrequency tags or markers or retroreflective markers and its position, location and/or orientation can be captured by a surgical navigation system. Optionally, the ARDD may also include one or more radiofrequency tags or markers or retroreflective markers and its position, location and/or orientation can also be captured by the surgical navigation system and cross-referenced to the patient specific marker or template and/or the one or more of the surgical instruments and/or one or more of the implantable devices used during the surgery. One or more of the surgical instruments and/or one or more of the implantable devices used during the surgery can also include light sources, such as lasers or LEDs. A laser can be projected, for example, on a wall or a ceiling and the ARDD and the patient can be referenced in relationship to that. An LED attached to or integrated into the one or more of the surgical instruments and/or one or more of the implantable devices used during the surgery can be recognized, for example, by an image and/or video capture system integrated into or attached to or coupled to the ARDD. Optionally, multiple LEDs can be used. Optionally, two or more of the multiple LEDs emit light with different wavelength or color. The two or more LEDs can be located in spatially defined locations and orientations, e.g. at a pre-defined or fixed distance and at one or more pre-defined or fixed angles. In this manner, the two or more LEDs can be located by an image and/or video capture system integrated into, attached to or separate from the ARDD and their measured distance and/or angles as seen through the image and/or video capture system can, for example, be used to determine the distance and or orientation of the operator to the target anatomy, e.g. when the image and/or video capture system is close to the operator's eyes. By using LEDs with different wavelength or color, the image and/or video capture system can differentiate between different LEDs; when the LEDs are arranged in a known spatial orientation, this information can be helpful for increasing the accuracy of the registration and/or for obtaining accurate distance, angle, direction and/or velocity measurements. The use of two or more LEDs with different wavelength and color and measurements or registration as described above are applicable throughout the disclosure in all embodiments that incorporate the use of LEDs or that are amenable to using LEDs.

Optionally, the patient specific marker or template and, optionally, one or more of the surgical instruments and/or one or more of the implantable devices used during the surgery can also include color markings, optionally with different geometric shapes or located or oriented at different, known locations and different, known angles, that can be used, for example, by an image and/or video capture system integrated into or attached to or coupled to an ARDD to recognize such patterns and, for example, to estimate distances and angles, e.g. from the surgical site to the ARDD, or distances and angles between two markings, two surgical instruments or medical device components.

Optionally, the patient specific marker or template and, optionally, one or more of the surgical instruments and/or one or more of the implantable devices used during the surgery can also include scales, e.g. of metric distances, inches, or angles that can be used, for example, by an image and/or video capture system integrated into or attached to or coupled to an ARDD to recognize such scales or angles and, for example, to estimate distances and angles, e.g. from the surgical site to the ARDD, or distances and angles between two surgical instruments or medical device components.

In some embodiments, the patient specific marker or template can be attached to the corresponding surface of the patient or to an adjacent surface of the patient, for example using tissue glue such as fibrin glue or a pin or a staple.

In some embodiments, the patient specific marker or template can include openings or guides, for example for accepting a surgical instrument or tool such as a bur, a saw, a reamer, a pin, a screw and any other instrument or tool known in the art.

By cross-referencing virtual patient data and live patient data with use of a patient specific marker or template and, optionally, one or more of the surgical instruments and/or one or more of the implantable devices used during the surgery and an ARDD, any coordinate information, distance information, axis information, functional information contained in the virtual patient data can now be available and used during the surgery.

In some embodiments, the registration of virtual patient data and live patient data using the techniques described herein can be repeated after one or more surgical steps have been performed. In this case, the surgically altered tissue or tissue surface or tissue contour or tissue perimeter or tissue volume or other tissue features in the live patient can be matched to, superimposed onto and/or registered with the surgically altered tissue or tissue surface or tissue contour or tissue perimeter or tissue volume or other tissue features in the virtual data of the patient, e.g. in a virtual surgical plan developed for the patient. The matching, superimposing and/or registering of the live data of the patient and the virtual data of the patient after the surgical tissue alteration can be performed using the same techniques described in the foregoing or any of the other registration techniques described in the disclosure or any other registration technique known in the art.

Registration of Virtual Patient Data and Live Patient Data Using Intraoperative Imaging In some embodiments, intraoperative imaging, for example using x-ray imaging or CT imaging and/or ultrasound imaging, can be performed. Virtual patient data obtained intraoperatively using intraoperative imaging can be used to register virtual patient data obtained preoperatively, for example using preoperative x-ray, ultrasound, CT or MRI imaging. The registration of preoperative and intraoperative virtual data of the patient and live data of the patient in a common coordinate system with one or more HMDs can be performed, for example, by identifying and, optionally, marking corresponding landmarks, surfaces, object shapes, e.g. of a surgical site or target tissue, in the preoperative virtual data of the patient, the intraoperative virtual data of the patient, e.g. on electronic 2D or 3D images of one or more of the foregoing, and the live data of the patient. Virtual preoperative, virtual intraoperative and live data can include an osteophyte or bone spur or other bony anatomy or deformity. Virtual and physical surgical instruments and implant components can also be registered in the common coordinate system.

This embodiment can be advantageous when the amount of information obtained with intraoperative imaging is, for example, anatomically or in other ways more limited than the amount of information available with preoperative imaging or vice versa.

For example, intraoperative imaging may be performed using x-ray imaging, which is commonly only two-dimensional in nature. X-ray imaging can be augmented through image acquisition in more than one plane, e.g. orthogonal planes or one or more planes separated by a defined angle. Intraoperative x-ray images can be used to identify certain landmarks or shapes that can then be registered to preoperative imaging and/or live data of the patient during surgery. Preoperative imaging can, optionally, include 3D image data, for example obtained with CT or MRI. Acquisition of intraoperative images in multiple planes can be helpful to more accurately define the location of certain landmarks, contours or shapes intended for use in a registration of preoperative virtual data, intraoperative virtual data and live data of the patient. For purposes of clarification, intraoperative virtual data of the patient can be intraoperative images of the patient in 2D or 3D.

For example, in a spinal procedure such as vertebroplasty, kyphoplasty, pedicle screw placement, or placement of anterior spinal device including artificial disks or cages, intraoperative x-ray imaging can be used to identify, for example, the spinal level targeted for the surgery, in an AP projection certain landmarks or contours, e.g. the tip of a spinous process, a facet joint, the superior or inferior tip of a facet joint, the cortical edge of a lamina, a superior or inferior endplate or an osteophyte or bone spur or other bony anatomy or deformity. Optionally, the distance of the x-ray tube from the patient resulting in x-ray magnification can be factored into any registration in order to improve the accuracy of the registration of virtual preoperative data of the patient and virtual intraoperative data of the patient or live data of the patient. The intraoperative x-ray images can then be registered and, optionally, superimposed onto the preoperative data of the patient or the live data of the patient in the projection by the ARDD. The intraoperative virtual data of the patient, e.g. the tip of a spinous process, a facet joint, the superior or inferior tip of a facet joint, the cortical edge of a lamina, a superior or inferior endplate, can be registered to the live data of the patient, for example by touching the corresponding anatomic landmarks with a pointing device or a needle or a pin inserted through the skin and by cross-referencing the location of the tip of the live data pointing device with the intraoperative virtual data of the patient. In this manner, any one of preoperative virtual data of the patient, intraoperative virtual data of the patient, and live data of the patient and combinations thereof can be co-registered. Two or three of these data sets, preoperative virtual data of the patient, intraoperative virtual data of the patient, and live data of the patient, can optionally be seen in the ARDD. However, in many embodiments, intraoperative imaging may only be used for enhancing the accuracy of the registration of preoperative virtual data of the patient and live data of the patient and, for example, preoperative virtual data of the patient and/or a medical device intended for placement in a surgical site will be displayed by the ARDD together with the view of the live data of the patient or the surgical site.

In some embodiments, the registration of virtual patient data and live patient data using the techniques described herein can be repeated after one or more surgical steps have been performed and, optionally, intraoperative imaging can be repeated. In this case, the surgically altered tissue or tissue surface or tissue contour or tissue perimeter or tissue volume or other tissue features in the live patient or in the intraoperative repeat imaging data of the patient can be matched to, superimposed onto and/or registered with the surgically altered tissue or tissue surface or tissue contour or tissue perimeter or tissue volume or other tissue features in the virtual data of the patient, e.g. in a virtual surgical plan developed for the patient. The matching, superimposing and/or registering of the live data of the patient and the virtual data of the patient after the surgical tissue alteration can be performed using the same techniques described in the foregoing or any of the other registration techniques described in the disclosure or any other registration technique known in the art.

Registration of Virtual Patient Data and Live Patient Data Using Skin Markers or Soft-Tissue Markers In some embodiments, skin markers and soft-tissue markers, calibration or registration phantoms or devices can be used for registering preoperative virtual data, optionally intraoperative virtual data such as data obtained from intraoperative x-ray imaging, and live data seen through the OHMD in a common coordinate system with one or more OHMDs. Virtual and physical surgical instruments and implant components can also be registered in the common coordinate system. For example, an initial registration between preoperative virtual data and live data of the patient can happen at the beginning of the procedure. The initial registration can, for example, be performed using corresponding anatomic landmarks, surfaces or shapes, or using intraoperative imaging resulting in intraoperative virtual data or any of the other embodiments described in the present disclosure. The registration can be used, for example, to place the virtual data and the live data and the ARDD (e.g. OHMD) into a common coordinate system. Skin markers, calibration or registration phantoms or devices can then be applied. Virtual and physical surgical instruments and implant components can also be registered in the common coordinate system. Alternatively, or in addition, soft-tissue markers, calibration or registration phantoms or devices can be applied. Typically, more than one, such as two, three, four or more skin markers and soft-tissue markers, calibration or registration phantoms or devices will be applied. For clarity, the terms implantable markers, attachable markers, skin markers, soft-tissue markers, calibration or registration phantoms or devices as used through the application can include optical markers, e.g. optical markers with different geometric shapes or patterns, with QR codes, with bar codes, with alphanumeric codes. Skin markers and soft-tissue markers, calibration or registration phantoms or devices can, for example, be applied to the skin or the soft-tissue using a form of tissue compatible adhesive, including fibrin glue and the like. In some embodiments, one, two, three, four or more skin markers and soft-tissue markers, calibration or registration phantoms or devices can be included in a surgical drape or dressing or a transparent film applied to the skin prior to the procedure. The skin markers and soft-tissue markers, calibration or registration phantoms or devices can then be registered in the live data and cross-referenced to virtual data. The skin markers and soft-tissue markers, calibration or registration phantoms or devices can subsequently be used, for example, when the surgical site is altered and the landmarks, surface or shape that was used for the initial registration of virtual and live data have been altered or removed and cannot be used or cannot be used reliably for maintaining registration between virtual data and live data. Virtual preoperative, virtual intraoperative and live data can include an osteophyte or bone spur or other bony anatomy or deformity.

In some embodiments, the registration of virtual patient data and live patient data using the techniques described herein can be repeated after one or more surgical steps have been performed. In this case, the surgically altered tissue or tissue surface or tissue contour or tissue perimeter or tissue volume or other tissue features in the live patient can be matched to, superimposed onto and/or registered with the surgically altered tissue or tissue surface or tissue contour or tissue perimeter or tissue volume or other tissue features in the virtual data of the patient, e.g. in a virtual surgical plan developed for the patient. The matching, superimposing and/or registering of the live data of the patient and the virtual data of the patient after the surgical tissue alteration can be performed using the same techniques described in the foregoing or any of the other registration techniques described in the disclosure or any other registration technique known in the art.

The same skin markers or soft-tissue markers or calibration phantoms or registration phantoms can be used after one or more surgical steps have been performed if the markers or phantoms are still in place. Alternatively, re-registration of the live data of the patient and virtual data of the patient can be performed after one or more surgical steps or surgical alterations. Following re-registration, one or more new skin markers or soft-tissue markers or calibration phantoms or registration phantoms can be applied and cross-referenced to the re-registered live and virtual data after the surgical step or alteration. The skin markers or soft-tissue markers or calibration phantoms or registration phantoms can then be used for subsequent matching, superimposition, movement and registration of live patient data and virtual patient data.

Registration of Virtual Patient Data and Live Patient Data Using Calibration or Registration Phantoms with Defined Dimensions or Shapes In some embodiments, calibration or registration phantoms with defined dimensions or shapes can be used to perform the registration of virtual data of the patient and live data of the patient. The calibration or registration phantoms can be of primarily two-dimensional or three-dimensional nature. For example, a calibration or registration phantom can be arranged or located primarily in a single plane. Other calibration phantoms can be located in multiple planes, thereby creating the opportunity for registration using more than one planes. For clarity, the terms calibration or registration phantoms, implantable markers, attachable markers, skin markers, soft-tissue markers, or devices as used through the application can include optical markers, e.g. optical markers with different geometric shapes or patterns, with QR codes, with bar codes, with alphanumeric codes.

Such calibration or registration phantoms can be, for example, attached to the patient's skin. The calibration or registration phantom can be integrated or attached to a surgical drape. The calibration or registration phantom can be attached to the patient's tissue. The calibration or registration phantom can be part of or a component of a medical device. The part or component of the medical device will typically have known dimensions. By using calibration or registration phantoms, as well as other markers, the live data of a patient and the virtual data of the patient can be registered in a common coordinate system, for example with one or more HMDs. Virtual and physical surgical instruments and implant components can also be registered in the common coordinate system.

In some embodiments, the calibration or registration phantom includes known dimensions, angles or geometric 2D or 3D shapes. For example, the calibration or registration phantom can include structures such as

- circles, ovoids, ellipses, squares, rectangles, complex 2D geometries, 2D geometries with one or more defined distances, 2D geometries with one or more defined angles
- spheres, egg shaped structures, cylinders, cubes, cuboids, complex 3D geometries or shapes, 3D geometries with one or more defined distances, 3D geometries with one or more defined angles, 3D geometries with one or more defined surfaces Optionally, the calibration or registration phantoms can be radiopaque if pre-operative or intra-operative imaging is performed using an imaging modality with ionizing radiation, e.g. x-ray imaging, fluoroscopy in 2D or 3D, CT, cone beam CT etc.

In some embodiments, the calibration or registration phantom can be MRI visible or nuclear scintigraphy or SPECT visible or PET visible, for example by including portions or containers in the phantom containing Gadolinium-DTPA doped or radionuclide doped or PET isotope emitting water. Any contrast agent or MRI or nuclear scintigraphy or SPECT or PET visible agent known in the art can be used in this fashion.

In some embodiments, the calibration or registration phantom includes retroreflective markers or features which facilitate detection by an image and/or video capture system. The calibration or registration phantom can also be highlighted against the patient's tissue(s) including blood as well as surgical drapes through a choice of select colors, e.g. a bright green, bright blue, bright yellow, bright pink etc. Color combinations are possible. Any color or color combination known in the art can be used.

The calibration or registration phantom can optionally include LEDs, optionally battery powered. More than one LED can be used. The LEDs can emit a light of a known color, hue and intensity, preferably selected to be readily identifiable by the image and/or video capture system and any segmentation techniques or algorithms used for detecting the location, position and/or orientation of the LEDs.

The LEDs can be arranged in a spatially defined way, with two or more LEDs arranged at a defined distance or distances, at a defined angle or angles, in substantially the same plane or different planes. If LEDs are arranged in different planes, the spatial orientation of the planes is for example known and defined.

When two or more LEDs are used, the two or more LEDs can emit light utilizing different wavelengths, colors, intensity and, optionally also, blinking frequency. In this manner, an image and/or video capture system integrated into, attached to or separate from the HMD can recognize each different LED based on one or more of their different wavelength, color, intensity and/or blinking frequency. When the LEDs are arrange in a spatially defined and known manner, e.g. using known distances or angles within the same plane or different planes, the identification of each individual LED and the change in distances and angles measured by the image and/or video capture system can be used to determine the position, location and/or orientation of the HMD and/or the operator's head (e.g. if the image and/or video capture system is integrated into the HMD or attached to the HMD) or, in some applications, the movement of the patient or body part to which the calibration or registration phantom and LEDs are attached.

LEDs used throughout the disclosure can be re-useable. LEDs used throughout the disclosure can also be disposable, optionally with integrated, disposable battery cells/batteries. LEDs can be operated utilizing wires, e.g. connected to a power supply and/or connected to a wired user interface or control unit. LEDs can be wireless, e.g. without attached power supply (e.g. battery operated) and/or connected to a wireless (e.g. WiFi, Bluetooth) control unit.

LEDs can be connected and/or organized in LIF networks. One or more LIF networks can be used, for example, to transmit or receive data or information back and forth from the one or more HMDs to a control unit or computer, optionally with a user interface. In this example, LEDs participating or connected in the one or more LIF networks can be integrated into or attached to the HMD. LEDs participating or connected in the one or more LIF networks can be attached to or, when applicable, integrated into any location or site on the surgeon, the OR staff, the patient, the surgical site, one or more HMDs, one or more navigation systems, one or more navigation markers, e.g. retroreflective markers, infrared markers, RF markers; one or more optical markers, calibration or registration phantoms.

An LIF network can also be used to transmit or receive data or information about the spatial position, orientation, direction of movement, speed of movement etc. of individual LEDs. The same LEDs whose relative position, orientation, direction of movement, speed of movement, e.g. in relationship to the surgeon or the patient or the surgical site, is being measured, e.g. using an image and/or video capture system, can be used to transmit or receive information in the LIF network, optionally using different wavelengths, color, frequency, blinking patterns depending on the type of data being transmitted. The information can be about the position, orientation, direction of movement, speed of movement of individual LEDs. The information can also be data that are being transmitted or received by the HMD. The information can be the information or data that are being displayed by the HMD. The information can be information generated or received by navigation markers, RF markers. The information can be information captured by one or more image and/or video capture systems or cameras. 1, 2, 3, 4 or more LEDs can be connected to or attached to the patient, the target anatomy, the surgical site, the surgical site after a first, second or more surgical alterations, for example executed using a virtual surgical plan, the HMD, a second, third and/or additional HMDs, for example worn by a second surgeon, a scrub nurse, other OR personnel, the hand, forearm, upper arm and or other body parts of the surgeon/operator.

The relative position, orientation, movement, direction of movement, velocity of movement of each LED can be determined, for example using one or more image and/or video capture systems, e.g. integrated into, attached to or separate from the one or more HMDs, e.g. when the one or more LED's emit light utilizing different wavelengths, colors, intensity and, optionally also, blinking frequency.

The calibration or registration phantom can optionally include one or more lasers, optionally battery powered. More than one laser can be used. The laser can emit a light of a known color, hue and intensity, for example selected to be readily identifiable by the image and/or video capture system and any segmentation techniques or algorithms used for detecting the location, position and/or orientation of the laser.

The laser can be arranged in a spatially defined way, with two or more lasers arranged at a defined distance or distances, at a defined angle or angles, in substantially the same plane or different planes. If lasers are arranged in different planes, the spatial orientation of the planes can be known and defined.

The calibration or registration phantom can optionally include radiofrequency (RF) transmitters, optionally battery powered. More than one RF transmitter can be used. The RF transmitters can transmit a signal or signals selected to be readily identifiable by an RF receiver system used for detecting the location, position and/or orientation of the RF transmitters. One or more RF transmitters can transmit signals with different frequency and intensity, thereby permitting differentiation of the different RF transmitters by the RF receiver system.

The RF transmitters can be arranged in a spatially defined way, with two or more RF transmitters arranged at a defined distance or distances, at a defined angle or angles, in substantially the same plane or different planes. If RF transmitters are arranged in different planes, the spatial orientation of the planes is can be known and defined.

The calibration or registration phantom can optionally include ultrasound (US) transmitters, optionally battery powered. More than one US transmitter can be used. The US transmitters can transmit a signal or signals selected to be readily identifiable by an US receiver or transducer system used for detecting the location, position and/or orientation of the US transmitters. One or more US transmitters can transmit signal with different frequency and intensity, thereby permitting differentiation of the different US transmitters by the US receiver or transducer system.

The US transmitters can be arranged in a spatially defined way, with two or more US transmitters arranged at a defined distance or distances, at a defined angle or angles, in substantially the same plane or different planes. If US transmitters are arranged in different planes, the spatial orientation of the planes is can be known and defined.

Calibration phantoms or registration phantoms can be used for pre-operative imaging and/or for intraoperative imaging and/or image capture of live data, for example using an image and/or video capture system attached to or integrated into the HMD or coupled to the HMD or separate from the HMD. Virtual preoperative, virtual intraoperative and live data can include an osteophyte or bone spur or other bony anatomy or deformity.

If the same calibration or registration phantom is used for pre-operative imaging and for intra-operative imaging, optionally, the imaging can be performed using the same imaging modality, e.g. x-ray imaging, and, for example, using the same orientation of the patient in relationship to the x-ray source and the detector system and, for example using the same distance of the patient in relationship to the x-ray source and the detector system. Using this approach, the anatomic structures visualized on the pre-operative imaging and intra-operative imaging can be superimposed and registered, optionally in the same coordinate system.

In the event, the calibration or registration phantom has been positioned differently on the patient for the pre-operative imaging and for the intraoperative imaging data acquisition, the difference in location or position or coordinates can be determined using the co-registration of the anatomic data visualized on the pre-operative imaging and intra-operative imaging. An adjustment for the difference in phantom location from the pre-operative to the intraoperative data can be performed; this adjustment can optionally be defined as a phantom offset between pre-operative and intra-operative data. Virtual preoperative, virtual intraoperative and live data can include an osteophyte or bone spur or other bony anatomy or deformity.

As an alternative to the anatomic registration from the anatomic structures visualized on the pre-operative imaging and intra-operative imaging, the registration between pre-operative imaging data and intra-operative live data visualized through the HMD or an attached, integrated or separate image and/or video capture system can be performed alternatively now using the calibration or registration phantom as visualized or as identified optically during the surgery, for example using the phantom offset between pre-operative and intra-operative data.

In general, the initial registration of virtual data and live data is possible using any of the techniques described herein, e.g. using anatomic features, anatomic landmarks, intraoperative imaging etc. Then co-registration of the calibration or registration phantom, e.g. in the same coordinate system, can be performed. If initial registration fails during the surgical procedure, registration can be maintained using the calibration or registration phantom. For this purpose, the position, location, orientation and/or alignment of the calibration or registration phantom will be continuously or intermittently monitored using an image and/or video capture system, which can be integrated into or attached to the HMD or coupled to the HMD or separate from the HMD.

In some embodiments, the preoperative imaging can entail a cross-sectional imaging modality, e.g. computed tomography, which can optionally generate 3D data of the patient, e.g. in the form of a spiral or a helical CT scan and, optionally, a 3D reconstruction. The 3D data of the patient, e.g. the spiral or helical CT scan or 3D reconstruction, can be re-projected into a 2D image, creating an x-ray like transmission image of the patient, e.g. of the bony structures of the patient including, but not limited to an osteophyte or bone spur or other bony anatomy or deformity. Optionally, this 2D re-projection of the 3D data, e.g. CT data, can be performed using the same plane or projection or view angle and, for example, the same or similar magnification as can be used subsequently during surgery with an intraoperative x-ray imaging test. The film-focus and, optionally, object distance of the x-ray system used for the intraoperative imaging part can be known at the time of the re-projection of the preoperative 3D data, so that the magnification of the patient or anatomic data resulting for a given intraoperative film-focus and optionally object distance will be matched or reflected in the re-projected pre-operative data. If the film-focus and, optionally, object distance of the x-ray system used for the intraoperative imaging part is not known at the time of the re-projection of the preoperative 3D data, the magnification of the re-projected data can be adjusted when they are visualized with and optionally superimposed onto the 2D intraoperative imaging data of the patient or anatomic data resulting for a given intraoperative film-focus and optionally object distance so that the magnification of both re-projected and intraoperative imaging data will be matched or substantially similar. Such matching in magnification can be achieved, for example, by aligning certain features or anatomic landmarks or pathologic tissues including an osteophyte or bone spur or other bony anatomy or deformity in the pre-operative re-projected data with the intraoperative data and adjusting the magnification until the feature or landmarks are substantially superimposed or substantially matching. With this approach, pre-operative imaging data can use the benefit of 3D data including, for example, more accurate three-dimensional placement of an implant component such as a spinal component or a component for joint replacement or fracture repair. Similarly, certain anatomic landmarks or features can be detected and utilized for surgical planning in the 3D data set. When the 3D data are then re-projected into a 2D re-projection or view, anatomic landmarks, features or data or pathologic data can be readily matched up or aligned with corresponding anatomic landmarks, features or data or pathologic data in the corresponding portions of the intraoperative 2D imaging study, e.g. intraoperative x-rays. Thus, while different 3D preoperative and 2D intraoperative imaging modalities can be used, 2D re-projection allows for cross-referencing and, optionally, co-registration of the 2D and 3D data sets. Any 2D and 3D imaging modality known in the art can be used in this manner.

In additional embodiments, the calibration/registration phantom can be used

1.) To estimate distance, position, orientation of HMD from the patient, for primary or back-up registration, for example used in conjunction with an image and/or video capture system integrated into, attached to or coupled to or separate from the HMD
2.) To estimate distance, position, orientation of target tissue or surgical site underneath the patient's skin, e.g. after cross-registration with pre-operative and/or intra-operative imaging data
3.) To estimate the path of a surgical instrument or to estimate the location of a desired implantation site for a medical device or implant or transplant
4.) To update a surgical plan The calibration or registration phantom can be used in physical time mode, using physical time registration, for example using an image and/or video capture system integrated into, attached to, coupled to, or separate from the HMD, which can optionally operate in physical time mode. Physical time mode can, for example, mean that image capture is performed with more than 5 frames/second, 10 frames/second, 15 frames/second, 20 frames/second, 30 frames/second etc.

If images generated with the image and/or video capture system are segmented or, for example, image processing or pattern recognition is performed, this can optionally be performed on each frame generated with the image and/or video capture system. Alternatively, segmentation or image processing or pattern recognition can be performed on a subset of the image frames captured with the image and/or video capture system. Segmentation, image processing or pattern recognition data can be averaged between frames. The foregoing embodiments are applicable to all embodiments in this disclosure that utilize image capture.

Image processing can be performed to include data from one or more osteophytes or bone spurs or other bony anatomy or deformity. The one or more osteophytes or bone spurs or other bony anatomy or deformity can be used for purposes of registration of virtual and live data, including virtual preoperative and virtual intraoperative imaging or virtual functional data. Image processing can also be performed to exclude data from one or more osteophytes or bone spurs or other bony anatomy or deformity. The one or more osteophytes or bone spurs or other bony anatomy or deformity can be excluded or omitted from any data used for purposes of registration of virtual and live data, including virtual preoperative and virtual intraoperative imaging or virtual functional data. The inclusion or exclusion of one or more osteophytes or bone spurs or other bony anatomy or deformity can be selected based on the anatomic site, the surgical site, and/or the desired accuracy of the segmentation or the registration of virtual data and live data.

The calibration or registration phantom can be used in non-physical time mode, e.g. an intermittent mode, for example using an image and/or video capture system integrated into, attached to, coupled to, or separate from the HMD, which can optionally operate in intermittent mode. Intermittent mode use of the calibration or registration phantom can be performed, for example, by using a timer or timing device, wherein image capture and registration is performed every 10 seconds, 8 seconds, 5 seconds, 3 seconds, 2 seconds, 1 second etc.

In some embodiments, real-time and intermittent registration using the calibration or registration phantom will be selected or designed so that the data generated will for example not exceed the temporal resolution of the image and/or video capture system and/or the temporal resolution of the segmentation or image processing or pattern recognition used for the registration.

In any of the foregoing embodiments, the accuracy of registration can optionally be improved by using multiple registration points, patterns, planes or surfaces. In general, the accuracy of registration will improve with an increasing number of registration points, patterns, planes or surfaces. These may, in some embodiments, not exceed the spatial resolution of the image and/or video capture system. In some embodiments, these may exceed the spatial resolution of the image and/or video capture system. In that situation, optionally, down-sampling of data can be performed, e.g. by reducing the effective spatial resolution in one, two or three planes or by reducing the spatial resolution in select areas of the field of view seen through the HMD or visualized in the virtual data. Virtual preoperative, virtual intraoperative and live data can include an osteophyte or bone spur or other bony anatomy or deformity.

In some embodiments, the registration of virtual patient data and live patient data using the techniques described herein can be repeated after one or more surgical steps have been performed. In this case, the surgically altered tissue or tissue surface or tissue contour or tissue perimeter or tissue volume or other tissue features in the live patient can be matched to, superimposed onto and/or registered with the surgically altered tissue or tissue surface or tissue contour or tissue perimeter or tissue volume or other tissue features in the virtual data of the patient, e.g. in a virtual surgical plan developed for the patient. The matching, superimposing and/or registering of the live data of the patient and the virtual data of the patient after the surgical tissue alteration can be performed using the same techniques described in the foregoing or any of the other registration techniques described in the disclosure or any other registration technique known in the art.

The same skin markers or soft-tissue markers or calibration phantoms or registration phantoms can be used after one or more surgical steps have been performed if the markers or phantoms are still in place. Alternatively, re-registration of the live data of the patient and virtual data of the patient can be performed after one or more surgical steps or surgical alterations. Following re-registration, one or more new skin markers or soft-tissue markers or calibration phantoms or registration phantoms can be applied and cross-referenced to the re-registered live and virtual data after the surgical step or alteration. The skin markers or soft-tissue markers or calibration phantoms or registration phantoms can then be used for subsequent matching, superimposition, movement and registration of live patient data and virtual patient data.

To Estimate Distance, Position, Orientation of HMD from the Patient

If registration of virtual patient data and live patient data has occurred using any of the techniques or techniques described in this disclosure and if the calibration or registration phantom is also registered in relationship to the live patient data, the calibration or registration phantom or any other registration technique described in the disclosure or known in the art can be used to maintain registration, for example on an intermittent or a real-time basis, including while the surgeon or operator moves his or her head or body. The calibration or registration phantom can, for example, not be moved during the surgery. If the calibration or registration phantom needs to be moved, it may optionally be re-registered in relationship to any live patient data, virtual patient data, pre-operative data and intra-operative data.

In this and related embodiments, the calibration or registration phantom will be identified with regard to its location, position, orientation, alignment, surfaces or shape using an image and/or video capture system and, optionally, segmentation, image processing or pattern recognition and any other techniques known in the art for identifying an object in image data. The image and/or video capture system can be integrated into or attached to the HMD. The image and/or video capture system can be coupled to or separate from the HMD. The image and/or video capture system will be used to determine the location, position, orientation, alignment, surfaces or shape of the calibration or registration phantom in relationship to the patient, the operator and/or the HMD.

Any other techniques known in the art, including as described in this disclosure, that can be used to determine the location, position, orientation, alignment, surfaces or shape of the calibration or registration phantom in relationship to the patient, the operator and/or the HMD, can be used, including, but not limited to surgical navigation including optical or RF tracking, laser based distance measurements and the like.

The calibration or registration phantom can be used for primary or back-up registration. Optionally, synchronized registration can be used, wherein, for example, more than one technique of registration is used simultaneously to maintain registration between virtual patient data and live patient data, for example by simultaneously maintaining registration between virtual patient data and live patient data using one or more calibration or registration phantoms in conjunction with maintaining registration using corresponding anatomic landmarks or surfaces between virtual patient data and live patient data. If synchronized registration is used, optionally, rules can be applied to resolve potential conflicts between a first and a second registration technique for registering virtual and live patient data.

For example, with an image and/or video capture system integrated into or attached to the HMD or coupled to the HMD, any change in the position, location or orientation of the surgeon's or operator's head or body will result in a change in the perspective view and visualized size and/or shape of the calibration or registration phantom. The change in perspective view and visualized size and/or shape of the calibration or registration phantom can be measured and can be used to determine the change in position, location or orientation of the surgeon's or operator's head or body, which can then be used to maintain registration between the virtual patient data and the live patient data, by moving the virtual patient data into a position, location, orientation and/or alignment that ensures that even with the new position location or orientation of the surgeon's or operator's head or body the registration is maintained and the virtual and the live patient data are, for example, substantially superimposed or matched where desired. Similarly, when more than one HMD is used, e.g. one for the primary surgeon, a second HMD for an assistant, a third HMD for a resident, a fourth HMD for a scrub nurse and a fifth HMD for a visitor, with an image and/or video capture system integrated into or attached to each of the different HMDs or coupled to each of the different HMDs, any change in the position, location or orientation of the user's or viewer's head or body will result in a change in the perspective view and visualized size and/or shape of the calibration or registration phantom. The change in perspective view and visualized size and/or shape of the calibration or registration phantom can be measured and can be used to determine the change in position, location or orientation of the user's or viewer's head or body, which can then be used to maintain registration between the virtual patient data and the live patient data, by moving the virtual patient data into a position, location, orientation and/or alignment that ensures that even with the new position location or orientation of the user's or viewer's head or body the registration is maintained and the virtual and the live patient data are, for example, substantially superimposed or aligned or matched where desired, with substantially identical view angle of the virtual data of the patient seen by the viewer's left eye through the display of the HMD unit and the live data of the patient seen by the viewer's left eye through the HMD unit and substantially identical view angle of the virtual data of the patient seen by the viewer's right eye through the display of the HMD unit and the live data of the patient seen by the viewer's right eye through the HMD unit for each of the HMDs used.

In some embodiments, the calibration or registration phantom can be used to check the accuracy of an integrated or attached or coupled or separate image and/or video capture system.

In a further embodiment, the calibration or registration phantom can be used to calibrate an integrated or attached or coupled or separate image and/or video capture system.

In some embodiments, the calibration or registration phantom can be used to calibrate the IMU, e.g. for distance measurements, movement, distance to object, since calibration or registration phantom includes known geometries, e.g. known distances or angles.

Registration of Virtual Patient Data and Live Patient Data Accounting for Tissue Deformation In some embodiments, tissue deformation, a shape change or removal of tissue caused by the surgery or surgical instruments can be simulated in the virtual data. The resultant simulated virtual data can then be registered related to the live patient data, either before and/or after deformation, alteration of shape or removal of tissue of the live patient. The tissue deformation, shape change or removal of tissue caused by the surgery or surgical instruments can include the shape alteration or removal of one or more osteophytes or bone spurs or other bony anatomy or deformity. The virtual data of the patient and the live data of the patient can be registered in a common coordinate system, for example with one or more HMDs. Virtual and physical surgical instruments and implant components can also be registered in the common coordinate system.

In some embodiments, the registration of virtual patient data and live patient data using the techniques described herein can be repeated after one or more surgical steps have been performed. In this case, the surgically altered tissue or tissue surface or tissue contour or tissue perimeter or tissue volume or other tissue features in the live patient can be matched to, superimposed onto and/or registered with the surgically altered tissue or tissue surface or tissue contour or tissue perimeter or tissue volume or other tissue features in the virtual data of the patient, e.g. in a virtual surgical plan developed for the patient. The matching, superimposing and/or registering of the live data of the patient and the virtual data of the patient after the surgical tissue alteration can be performed using the same techniques described in the foregoing or any of the other registration techniques described in the disclosure or any other registration technique known in the art. Re-registration of live patient data and virtual patient data can be particularly helpful if the surgical alteration or surgical step has led to some tissue deformation. For example, the re-registration can be performed by matching, superimposing, and/or registering tissues that have not been performed by the surgical step or surgical alteration. Alternatively, the re-registration can be performed by matching, superimposing and/or registering deformed live patient data, e.g. from surgically deformed tissue, with virtual patient data that simulate the same tissue deformation after the virtual surgical step, e.g. an osteophyte or tissue removal.

Registration of Virtual Patient Data and Live Patient Data at Multiple Time Points, for Example at Different Stages of a Surgical Procedure In some embodiments, registration of virtual patient data and live patient data can occur at multiple time points, for example during different phases of tissue removal or implantation of a medical device. For select or each time point, e.g. for select or all stages of the surgical procedure, the live data of the patient and the virtual data of the patient can be registered in a common coordinate system, for example with one or more HMDs. Virtual and physical surgical instruments can also be registered in the common coordinate system.

In knee replacement surgery or hip replacement surgery, for example, registration of virtual patient data and live patient data can be performed using, for example, the femoral or tibial or acetabular surface shape or using femoral or tibial or acetabular landmarks prior to the resection of any tissue. Optionally pins or other rigid fixation markers can be placed, for example in an area that will not be surgically resected during at least part of the surgical procedure. The registration of virtual and live patient data can be repeated using different registration sites, surfaces or landmarks after tissue has been removed, e.g. after a burring of the articular surface has occurred or after a bone cut has been performed or after reaming has been performed or after one or more osteophytes or bone spurs or other bony anatomy or deformity have been removed. The registration can now occur to a newly created landmark, created by the surgical procedure, or, for example, a newly created surface, e.g. created by the surgical procedure. Such a newly created surface can be, for example, a planar surface on the residual femur or tibia created by a bone cut. Optionally implanted pins or rigid fixation markers can be used to aid with the registration of the virtual data after surgical alteration and the live data of the patient altered by the surgery. Thus, aspects of the present disclosure allow for multiple time point registration of virtual patient data and live patient data, for example by registered virtual patient data to the live patient data prior to surgical alteration and after one or more surgical alterations. In this manner, it is possible to re-register multiple times as surgical field changes.

The registration of virtual patient data and live patient data using the techniques described herein can be repeated after one or more surgical steps have been performed. In this case, the surgically altered tissue or tissue surface or tissue contour or tissue perimeter or tissue volume or other tissue features in the live patient can be matched to, superimposed onto and/or registered with the surgically altered tissue or tissue surface or tissue contour or tissue perimeter or tissue volume or other tissue features in the virtual data of the patient, e.g. in a virtual surgical plan developed for the patient. The matching, superimposing and/or registering of the live data of the patient and the virtual data of the patient after the surgical tissue alteration can be performed using the same techniques described in the foregoing or any of the other registration techniques described in the disclosure or any other registration technique known in the art.

Registration of Virtual Patient Data and Live Patient Data Using CAD Files or Data or 3D Files or Data, e.g. of a Medical Device In some embodiments, a CAD file or CAD data of a medical device can be displayed by the HMD and superimposed on live data of the patient. The CAD file or CAD data can be a medical device intended for use or implantation during the surgical procedure. Any type of CAD file or CAD data or any type of 3D file or 3D data of a medical device, a surgical instrument or an implantable device can be superimposed and registered in relationship to the live data of the patient including normal anatomy or pathologic tissue, e.g. one or more osteophytes or bone spurs or other bony anatomy or deformity or soft-tissue or neoplastic tissue or abnormality in a common coordinate system, for example with one or more HMDs. Physical surgical instruments and implant components can also be registered in the common coordinate system.

Medical devices can include non-biologic as well as biologic devices, e.g. tissue scaffolds, cells, cell matrices etc. that can be implanted in a human body.

In some embodiments, multiple CAD files and/or 3D files of virtual data can be superimposed onto the live data of the patient. For example, CAD files can be CAD files of a medical device available in different sizes or shapes. Virtual 2D or 3D data of the patient, for example obtained from a preoperative imaging test, can be superimposed onto live data of the patient, e.g. a surgical site. The surgeon can then optionally introduce a 3D CAD file of a medical device into the display by the HMD. The surgeon can check the size or shape of the medical device in relationship to the virtual 2D or 3D data of the patient and/or the live data of the patient. If the surgeon is not satisfied with the projected size or shape of the medical device in relationship to the virtual 2D or 3D data of the patient and/or the live data of the patient, the surgeon can select a different CAD file of a medical device with a different size and/or shape, project the CAD file optionally onto the virtual 2D or 3D data of the patient and the live data of the patient in the HMD display and repeat the process as many times as needed until the surgeon is satisfied with the resultant size or shape of the selected medical device in relationship to the virtual 2D or 3D data of the patient and/or the live data of the patient.

The registration of virtual patient data and live patient data using the techniques described herein can be repeated after one or more surgical steps have been performed. In this case, the surgically altered tissue or tissue surface or tissue contour or tissue perimeter or tissue volume or other tissue features in the live patient can be matched to, superimposed onto and/or registered with the surgically altered tissue or tissue surface or tissue contour or tissue perimeter or tissue volume or other tissue features in the virtual data of the patient, e.g. in a virtual surgical plan developed for the patient. The matching, superimposing and/or registering of the live data of the patient and the virtual data of the patient after the surgical tissue alteration can be performed using the same techniques described in the foregoing or any of the other registration techniques described in the disclosure or any other registration technique known in the art. For example, CAD files simulating the virtual surgical step or surgical alteration in the virtual patient data can be matched, superimposed or registered with live patient data after the physical surgical step or surgical alteration in the live patient. In this manner, live and virtual data can be re-registered after the surgical step or surgical alteration.

Registration of Virtual Patient Data and Live Patient Data Using Non-Anatomic Data Registration of virtual data of the patient and live data of the patient can be performed using data other than anatomic or pathologic structures. Registration can be performed, for example, based on motion data, kinematic data (for example to determine the center of rotation of a joint in the live data which can then be registered to an estimate or simulated center of rotation in the virtual data of the patient). Registration can be performed using metabolic data, for example using an area of high 18 FDG-PET uptake in a PET scan or PET-MRI or PET CT, which can be, for example matched to an area of increased body temperature in a target surgical site. Registration can be performed using functional data, e.g. using functional MRI studies. Virtual data and live data of the patient can be registered in a common coordinate system, for example with one or more HMDs. Virtual and physical surgical instruments and implant components can also be registered in the common coordinate system.

Optionally, different types of data, e.g. anatomic, motion, kinematic, metabolic, functional, temperature and/or vascular flow data can be used alone or in combination for registered virtual and live data of the patient.

The registration of virtual patient data and live patient data using the techniques described herein can be repeated after one or more surgical steps have been performed using non-anatomic data. In this case, the surgically altered tissue or tissue surface or tissue contour or tissue perimeter or tissue volume or other tissue features in the live patient can be matched to, superimposed onto and/or registered with the surgically altered tissue or tissue surface or tissue contour or tissue perimeter or tissue volume or other tissue features in the virtual data of the patient, e.g. in a virtual surgical plan developed for the patient, optionally using non-anatomic data. The matching, superimposing and/or registering of the live data of the patient and the virtual data of the patient after the surgical tissue alteration can be performed using the same techniques described in the foregoing or any of the other registration techniques described in the disclosure or any other registration technique known in the art.

Virtual Surgical Plans

Virtual and physical surgical instruments and implant components can be registered in a common coordinate system, for example with one or more HMDs and live data of the patient. When pre-operative imaging studies, intra-operative imaging studies or intra-operative measurements are registered in a common coordinate system with one or more HMDs using, for example, anatomic features, anatomic landmarks, implantable and attachable markers, calibration and registration phantoms including optical markers, LEDs with image capture, navigation markers, infrared markers, RF markers, IMUs, or spatial anchors and spatial recognition, one or more of an instrument or implant position, orientation, alignment can be predetermined using the information from the pre- and intra-operative imaging studies and/or the intra-operative measurements.

In some embodiments, a surgeon or an operator can develop a virtual surgical plan. The virtual surgical plan can include the virtual removal of select tissues, e.g. bone or cartilage or soft-tissue, e.g. for installing or implanting a medical device. The virtual surgical plan can include removal of a tumor or other tissues. The virtual surgical plan can include placing a graft or a transplant. Any surgical procedure known in the art can be simulated in a virtual surgical plan, for example spinal fusion including anterior and posterior, spinal disk replacement using motion preservation approaches, hip replacement, knee replacement, ankle replacement, shoulder replacement, ACL repair or reconstruction, ligament reconstruction.

A virtual surgical plan can be developed using intra-operative data or measurements, including measurements obtained using one or more optical markers which can, for example, be detected using one or more cameras, an image capture system, a video capture system and/or 3D scanner integrated into, attached to or separate from an HMD. The one or more cameras, an image capture system, a video capture system and/or 3D scanner integrated into, attached to or separate from an HMD can, for example, detect the coordinates of one or more optical markers attached to the surgical site, e.g. a bone or cartilage, an altered surgical site, e.g. a bone cut, the operating room table, an extension of the operating room table, and/or fixture structures in the operating room, e.g. walls. The one or more cameras, an image capture system, a video capture system and/or 3D scanner integrated into, attached to or separate from an HMD can detect the one or more optical markers in static positions and/or dynamic, moving positions. The coordinates (x, y, z) of the optical markers can be measured in static and dynamic conditions.

Any other sensor described in the disclosure, e.g. IMUs, navigation markers, e.g. infrared markers and/or RF markers, LED's, can be used for obtaining intraoperative measurements and can be combined, for example with optical marker measurements, for deriving intra-operative measurements and for generating and/or developing a virtual surgical plan.

Intra-operative measurements using one or more cameras, an image capture system, a video capture system and/or 3D scanner integrated into or attached to an HMD can be beneficial when measurements are desired to be obtained from the view angle of the surgeon or, when multiple HMDs are used, from the view angle of a surgical assistant or second surgeon. Intra-operative measurements using one or more cameras, an image capture system, a video capture and/or 3D scanner separate from an HMD can be advantageous when measurements are desired to be obtained from a view angle other than the surgeon or, when multiple HMDs are used, from a view angle other than of a surgical assistant or second surgeon.

Pre-operative data, e.g. pre-operative imaging studies or kinematic studies of a patient, e.g. with the joint or the spine measured or imaged in motion, can also be incorporated into a virtual surgical plan. Pre-operative data alone can be used to develop a virtual surgical plan.

The virtual surgical plan can be developed with use of a computer or computer workstation as well as a local or remote computer or computer network. The computer or computer workstation can include one or more displays, keyboard, mouse, trackball, mousepad, joystick, human input devices, processor, graphics processors, memory chips, storage media, disks, and software, for example for 3D reconstruction, surface displays, volume displays or CAD design and display, as well as optional CAM output. The software can include one or more interfaces for CAD design, for displaying the patient's anatomy, for displaying virtual surgical instruments and for displaying virtual implants, implant components, medical devices and/or medical device components.

The different anatomic and pathologic structures as well as the different virtual instruments, e.g. virtual surgical guides including drill guides or cut blocks, virtual implants, implant components, medical devices and/or medical device components can optionally be displayed simultaneously on the same screen or screen section or non-simultaneously, e.g. on different screens, on the same screen at different times, or no different screen sections. The different anatomic and pathologic structures including hidden and/or obscured or partially hidden and/or obscured anatomic and pathologic structures as well as the different virtual instruments, e.g. virtual surgical guides including drill guides or cut blocks, virtual implants, implant components, medical devices and/or medical device components can optionally be displayed using different colors or different shading. Some of the different anatomic and pathologic structures as well as the different virtual instruments, e.g. virtual surgical guides including drill guides or cut blocks, virtual implants, implant components, medical devices and/or medical device components can optionally be displayed in a form of outline mode or pattern mode, where only the outline or select features or patterns of the anatomic and pathologic structures as well as the virtual instruments, e.g. virtual surgical guides including drill guides or cut blocks, different virtual implants, implant components, medical devices and/or medical device components are being displayed, for example with solid, dotted or stippled lines or geometric patterns.

Figure 7:
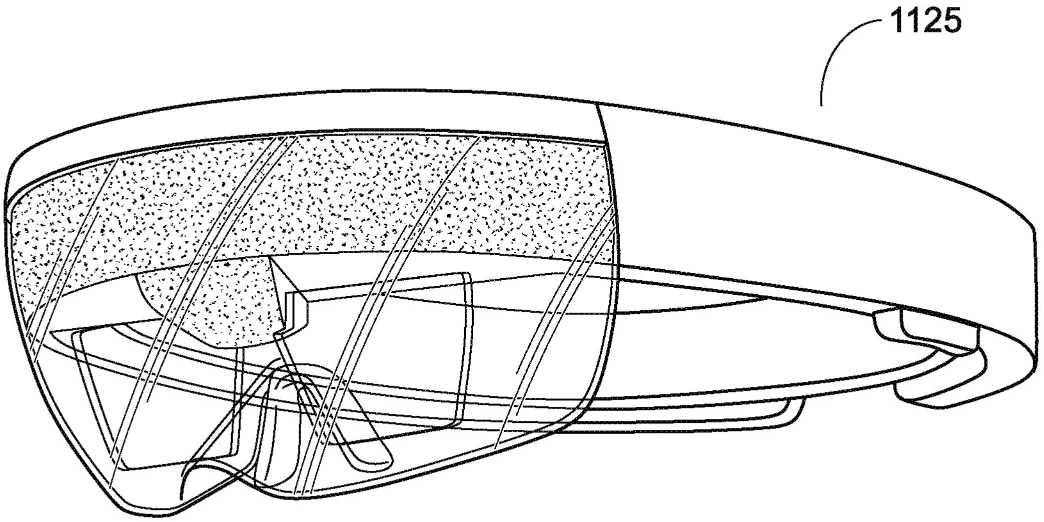
FIG. 7 is an example of a head mounted display, in this particular example a see-through optical head mounted display.

FIG. 7 is another exemplary workflow for generating a virtual surgical plan. Imaging data of a patient are acquired, e.g. at a site remote from the operating room 290. The imaging data can be transferred to a computer or workstation, e.g. via electronic data transfer routines such as ftp or internet 291. The imaging data of the patient can be reconstructed in three dimensions 292. The imaging data can be displayed in two or three dimensions on a computer display 293 or HMD.

Figure 8:
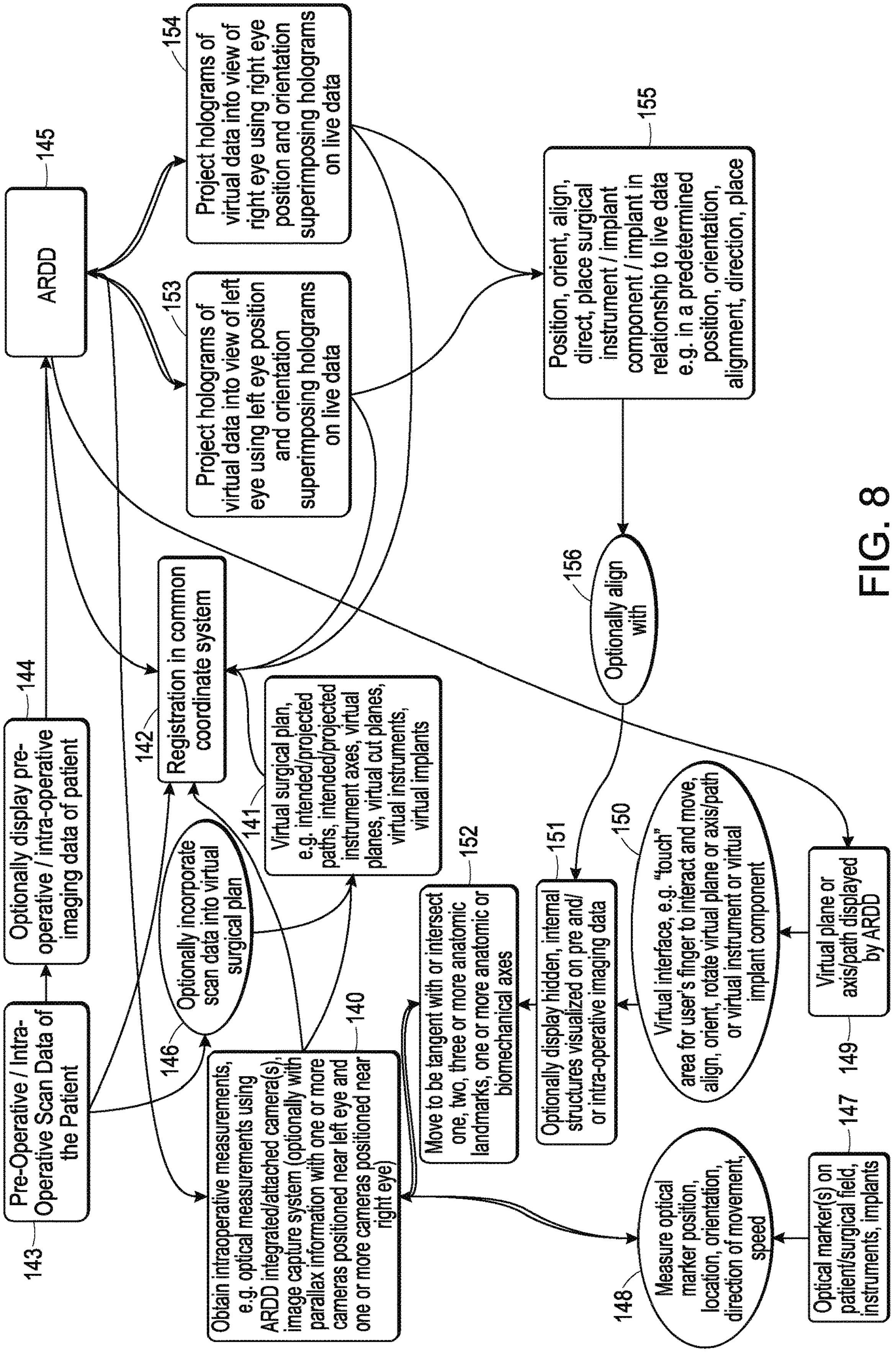
FIG. 8 is an illustrative example how a virtual surgical plan can be generated using intraoperative data, e.g. intra-operative measurements, for example measurements obtained with one or more cameras, an image capture system or a video capture system and/or a 3D scanner integrated into, attached to or separate from an optical head mount display according to some embodiments of the present disclosure.

FIG. 8 shows an example how a virtual surgical plan 157 can be modified using intraoperative data, e.g. intraoperative measurements 140. The virtual surgical plan 157 can be developed using pre-operative and intra-operative imaging data of the patient 143. The virtual surgical plan 157 can be registered in a common coordinate system 142. Preoperative and/or intraoperative scan data 143 can be generated and can be optionally displayed 144 in two or three dimensions in an ARDD (e.g. OHMD) 145. Preoperative and/or intraoperative scan data 143 can be used to develop the virtual surgical plan 157 which can be optionally displayed 158 by the ARDD (e.g. OHMD) 145. Optical markers 147 can be present on the patient, the surgical field, surgical instruments or implants and can be measured with regard to their position, location, orientation, direction of movement and/or speed 148. A virtual plane or path or axis 149 can be displayed by the ARDD (e.g. OHMD) 145 and, using a virtual interface 150, the plane or path or axis, as well as optionally virtual implants or instruments, can be moved by the surgeon. Optionally, the ARDD (e.g. OHMD) 145 can display hidden or internal structures 151, e.g. visualized on preoperative or intraoperative imaging studies or combinations of both, and the surgeon can align the planes, axis or path, as well as optionally virtual implants or instruments, relative to the hidden or internal structures 149. The plane, axis or path or virtual surgical instruments or virtual implants can be moved to be tangent with or intersect anatomic landmarks, and/or anatomical axes and/or biomechanical axes 152, for example for alignment purposes or to achieve a predetermined position and/or orientation of an instrument or an implant. The ARDD (e.g. OHMD) can project stereoscopic views for the left eye and right eye by displaying virtual data superimposing the virtual data using the left eye position and orientation on the live data for the left eye 153 and superimposing the virtual data using the right eye position and orientation on the live data for the right eye 154. The projected virtual data in 153 and 154 can be used to position, orient, align, direct or place one or more of a surgical instrument, an implant component and an implant in relationship to the live data of the patient, e.g. in a predetermined position, orientation, alignment direction or place 155. The position, orientation, alignment direction or place of the one or more of a surgical instrument, an implant component and an implant can optionally be aligned with hidden anatomy or internal structures 151, optionally using a virtual interface 150. Intraoperative measurements 140 can be utilized to generate or modify a virtual surgical plan 157. The virtual surgical plan 157 and/or a modified virtual surgical plan 162 can optionally be superimposed on preoperative and intraoperative imaging data of the patient 159. The virtual surgical plan 157 and/or a modified virtual surgical plan 162 can optionally be superimposed on preoperative and intraoperative imaging data of the patient 159. The modified virtual surgical plan 162 can be further modified based on visual or optical feedback or input 161 and it can be used to position, orient, align, direct, place one or more virtual or physical instruments, implant components and/or implants in a predetermined position 155. Someone skilled in the art can recognize that multiple coordinate systems can be used instead of a common coordinate system. In this case, coordinate transfers can be applied from one coordinate system to another coordinate system, for example for registering the ARDD (e.g. OHMD), live data of the patient including the surgical site, virtual instruments and/or virtual implants and physical instruments and physical implants.

In some embodiments, one or more of a virtual surgical tool, virtual surgical instrument including a virtual surgical guide or cut block, virtual trial implant, virtual implant component, virtual implant or virtual device, one or more of a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration can be moved, re-oriented and/or re-aligned by the surgeon using a virtual or other interface. For example, the virtual representation of the one or more of a virtual surgical tool, virtual surgical instrument including a virtual surgical guide or cut block, virtual trial implant, virtual implant component, virtual implant or virtual device, one or more of a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration can include a “touch area”, wherein an image or video capture system and/or 3D scanner and gesture recognition software, for example the one provided by Microsoft with the Microsoft Hololens including, for example, the integrated virtual “drag function” for holograms can be used to move the virtual data. For example, one or more cameras integrated or attached to the ARDD (e.g. OHMD) can capture the movement of the surgeon’s finger(s) in relationship to the touch area; using gesture tracking software, the hologram(s) can then be moved by advancing the finger towards the touch area in a desired direction. A surgeon can, for example, also “hold” the hologram(s) by closing two fingers, e.g. thumb and index finger, over the touch area and then moving the fingers in the desired direction.

In some embodiments, the virtual surgical plan can start out with the initial surgical step as defined, for example, in the surgical technique. This can be followed optionally by each or some of the subsequent surgical steps, for example only the major steps. The virtual surgical plan can then continue up to the selection and/or design and placement of the implant in the virtual data of the patient. If the resultant selection and/or design and/or placement of the implant, implant component or medical device differs from the desired result, for example as defined in the surgical plan or as desired by the surgeon, any of the foregoing surgical steps, the placement and/or the selection or the design of the implant, implant component or medical device can be modified. This process can be iterative, manual, semi-automatic or automatic until the desired virtual surgical plan, implant, implant component or medical device selection and/or design or placement are achieved.

Figure 9:
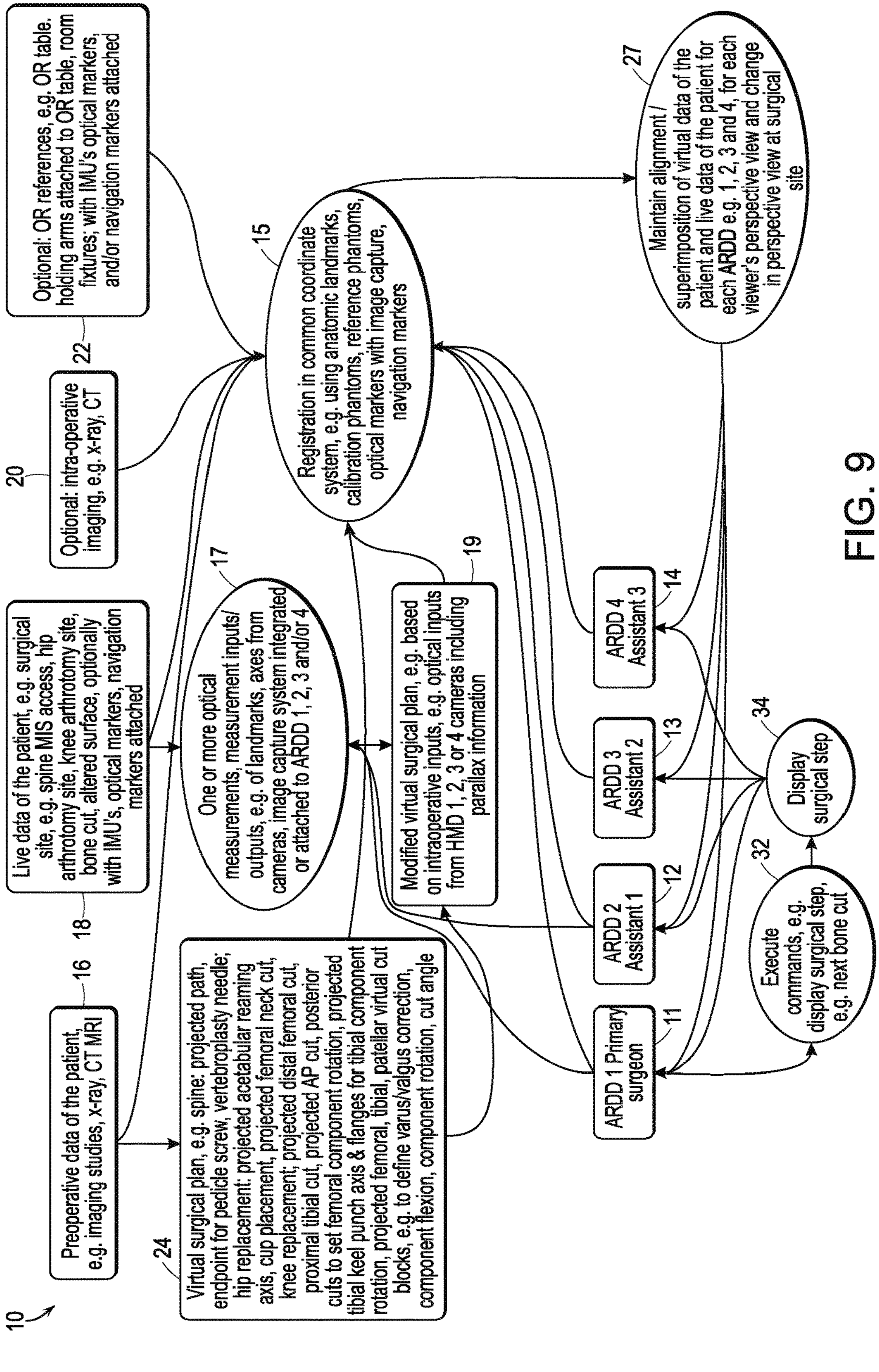
FIG. 9 shows an illustrative example how multiple HMD's can be used during a surgery, for example by a first surgeon, a second surgeon, a surgical assistant and/or one or more nurses and how a surgical plan can be modified and displayed during the procedure by multiple HMD's while preserving the correct perspective view of virtual data and corresponding live data for each individual operator according to some embodiments of the present disclosure.

FIG. 9 shows an illustrative example how multiple ARDD (e.g. OHMD) can be used during a surgery, for example by a first surgeon, a second surgeon, a surgical assistant and/or one or more nurses and how a surgical plan can be modified and displayed during the procedure by multiple ARDD (e.g. OHMD) while preserving the correct perspective view of virtual data and corresponding live data for each individual operator. A system 10 for using multiple ARDD (e.g. OHMD) 11, 12, 13, 14 for multiple viewer’s, e.g. a primary surgeon, second surgeon, surgical assistant(s) and/or nurses (s) is shown. The multiple ARDD (e.g. OHMD) can be registered in a common coordinate system 15 using anatomic structures, anatomic landmarks, calibration phantoms, reference phantoms, optical markers, navigation markers, and/or spatial anchors, for example like the spatial anchors used by the Microsoft Hololens. Pre-operative data 16 of the patient can also be registered in the common coordinate system 15. Live data 18 of the patient, for example from the surgical site, e.g. a spine, optionally with minimally invasive access, a hip arthrotomy site, a knee arthrotomy site, a bone cut, an altered surface can be measured, for example using one or more IMUs, optical markers, navigation markers, image or video capture systems and/or 3D scanner and/or spatial anchors. The live data 18 of the patient can be registered in the common coordinate system 15. Intra-operative imaging studies 20 can be registered in the common coordinate system 15. OR references, e.g. an OR table or room fixtures can be registered in the common coordinate system 15 using, for example, optical markers IMUs, navigation markers or spatial mapping 22. The pre-operative data 16 or live data 18 including intra-operative measurements or combinations thereof can be used to develop, generate or modify a virtual surgical plan 24. The virtual surgical plan 24 can be registered in the common coordinate system 15. The ARDD (e.g. OHMD) 11, 12, 13, 14 can maintain alignment and superimposition of virtual data of the patient and live data of the patient for each ARDD (e.g. OHMD) 11, 12, 13, 14 for each viewer’s perspective view and position and head position and orientation 27. Using a virtual or other interface, the surgeon wearing ARDD (e.g. OHMD) 1 11 can execute commands 32, e.g. to display the next predetermined bone cut, e.g. from a virtual surgical plan or an imaging study or intra-operative measurements, which can trigger the ARDD (e.g. OHMD) 11, 12, 13, 14 to project virtual data of the next surgical step 34 superimposed onto and aligned with the surgical site in a predetermined position and/or orientation. Any of the ARDD (e.g. OHMD) 11, 12, 13, 14 can acquire one or more optical measurements or measurement inputs, e.g. of anatomic landmarks, axes from cameras, anatomic axes, biomechanical axes, a mechanical axis of a leg 17, using for example an integrated or attached camera, image capture or video system. By using multiple ARDD (e.g. OHMD) 11, 12, 13, 14 from different view angles with multiple cameras, image capture or video systems, the accuracy of the measurements can optionally be improved. Optionally, parallax measurements can be performed using the multiple ARDD (e.g. OHMD) 11, 12, 13, 14 from different view angles with multiple cameras, image capture or video systems. The one or more optical measurements can be used to modify the virtual surgical plan 19, optionally using the information from multiple ARDD (e.g. OHMD) 11, 12, 13, 14. Someone skilled in the art can recognize that multiple coordinate systems can be used instead of a common coordinate system. In this case, coordinate transfers can be applied from one coordinate system to another coordinate system, for example for registering the ARDD (e.g. OHMD), live data of the patient including the surgical site, virtual instruments and/or virtual implants and physical instruments and physical implants.

Virtual Data and Live Data Seen Through One or More ARDD (e.g. OHMD)

A virtual surgical plan using, for example, virtual data of the patient, can be used to develop or determine any of the following for placing or directing a surgical tool, a surgical instrument, a trial implant component, a trial implant, an implant component, an implant, a device including any type of biological treatment or implant or matrix known in the art:

- Predetermined start point
- Predetermined start position.
- Predetermined start orientation/alignment
- Predetermined intermediate point(s)
- Predetermined intermediate position(s)
- Predetermined intermediate orientation/alignment
- Predetermined end point
- Predetermined end position
- Predetermined intermediate orientation/alignment
- Predetermined path
- Predetermined plane (e.g. for placing or orienting a surgical instrument or an implant component)
- Predetermined cut plane (e.g. for directing a saw or other surgical instruments (e.g. drills, pins, cutters, reamers, rasps, impactors, osteotomes) and/or for placing or orienting an implant component or a trial implant component)
- Projected contour/outline/cross-section/surface features/shape/projection
- Predetermined depth marker or depth gauge, predetermined stop, optionally corresponding to a physical depth marker or depth gauge on the physical surgical tool, surgical instrument, trial implant, implant component, implant or device
- Predetermined angle/orientation/rotation marker, optionally corresponding to a physical angle/orientation/rotation marker on the physical surgical tool, surgical instrument, trial implant, implant component, implant or device
- Predetermined axis, e.g. rotation axis, flexion axis, extension axis
- Predetermined axis of the physical surgical tool, surgical instrument, trial implant, implant component, implant or device, e.g. a long axis, a horizontal axis, an orthogonal axis, a drilling axis, a pinning axis, a cutting axis
- Estimated/projected non-visualized portions of device/implant/implant component/surgical instrument/surgical tool, e.g. using image capture or markers attached to device/implant/implant component/surgical instrument/surgical tool with known geometry
- Predetermined virtual tissue change/alteration.

Any of the foregoing, e.g. a cut plane or an outline, e.g. an outline of an implant or a surgical instrument, can be displayed in 2D and/or in 3D, optionally alternatingly. For example, a 2D visualization, e.g. a line, of a cut plane can be used when a surgeon looks substantially on end on a bone, e.g. a distal femur, for orienting and/or directing a cutting instrument, e.g. a saw or a saw blade. When the surgeon looks from the side, e.g. at an angle, the visualization can optionally switch to a 3D display to show the desired angular orientation of the cut and/or the blade in relationship to the bone. The display can also remain in 2D mode. The switching between 2D and 3D display can be manual, e.g. through a voice command or a command on a virtually projected keyboard or a virtually projected user interface, or automatic, e.g. based on the position and/or orientation of the operator's head and/or the ARDD in relationship to the surgical site (e.g. operator head/ARDD in frontal orientation relative to surgical site, or close to including 90 degree side (near orthogonal) orientation, or angular, non-90 degree side orientation, e.g. 30, 40, 50, 60, 70 degree angles). A 2D or 3D display of a cut plane can help determine/display the desired angular orientation of the intended cut. The angular orientation can, for example, be a reflection of a planned/intended mechanical axis correction in a knee replacement, a planned/intended femoral component flexion or extension in a knee replacement, a planned/intended tibial slope in a knee replacement or a planned/intended femoral neck resection for a planned/intended leg length in a hip replacement.

A 2D or 3D display can also include multiple cut planes, e.g. two or more femoral neck cuts in a hip replacement procedure, as can be used in hip replacement procedures involving, for example, an anterior approach and using a "napkin ring" like dual cut through the femoral neck. In this example, the 3D cut plane can include the distal cut plane at its inferior pointing surface and the proximal cut plane at its superior surface. These "napkin ring" inferior, distal facing, and superior, proximal facing cuts can be parallel or non-parallel, e.g. for easier extraction of the femoral head. Any cut planes visualized in 2D or 3D using the ARDD display can be parallel or non-parallel, using stereoscopic or non-stereoscopic display.

If the surgeon elects to change or adjust any of a virtual surgical tool, virtual surgical instrument including a virtual surgical guide or cut block, virtual trial implant, virtual implant component, virtual implant or virtual device, a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration used in the one or more virtual surgical plans using, for example, a virtual interface displayed by the ARDD display, e.g. a finger slider or finger tab to move and/or rotate a virtual cut plane by virtually touching it, or any other interface, including, for example, a finger command or a voice command, the virtual representation of the virtual data can move accordingly and the virtual data displayed in the ARDD can be updated accordingly in the surgeon's display. The change in position and/or orientation of the virtual representation of the virtual data can also be seen in other ARDDs, e.g. worn by a second surgeon, a resident, a scrub nurse or a PA, and the projection of the virtual data can also be updated accordingly in a second, third or any additional ARDD units used, for example, by a second surgeon, a resident, a scrub nurse or a PA during the surgery. Optionally, the virtual interface or any other interface to change or adjust one or more of the virtual data can only be available for the surgeon's ARDD unit, i.e. the lead ARDD unit, while the other ARDD units can operate as slave units that simply follow the display of the lead ARDD unit. In this manner, potential intraoperative errors, for example with a non-surgeon modifying virtual data or aspects of the virtual surgical plan, can be avoided. Optionally, the lead can be passed over to any of the other units, in which case the surgeon's ARDD unit can operate as a slave unit. This can be beneficial when complex changes are required to the virtual surgical plan and/or the virtual data of the patient, which may require a separate person to implement such changes, while the surgeon is managing the physical operation in the live patient. In some embodiments, the ARDD unit of the surgeon can capture the live data of the patient using one or more image and/or video capture systems and/or 3D scanners integrated into or attached to the ARDD. The captured live data of the patient can then be transmitted in electronic, digital form as live stream to slave ARDD units, optionally together with the virtual data of the patient, e.g. superimposed onto or co-displayed with the virtual data of the patient. Alternatively, the slave units in this example can be non-see-through virtual reality (VR) systems such as the Google Daydream system or the Zeiss VR One system and others known in the art.

Any intended cut plane displayed by the ARDD can optionally include or account for the thickness of the saw blade to reflect bone last during the sawing step. Any intended path for a drill or pin or other surgical instrument can include or account for the thickness of the surgical instrument to reflect bone lost during the surgical step. In addition, any bone lost due to movement of a surgical instrument, e.g. movement not in the primary direction of the surgical step such as saw blade flutter or saw vibration or a slightly eccentric drill or drill vibration can be included in the virtual surgical plan, for example through estimations of saw blade flutter or saw vibrations in addition to a known saw blade thickness, and can be accounted for in the virtual resection planning and in the resultant display of one or more 2D or 3D cut planes by the ARDD.

Someone skilled in the art can readily recognize that accounting for the thickness of a saw blade or dimensions of other bone removing instruments as well as related instrument or device movement or vibration induced bone loss can be accounted for in one, two, three or more bone removing steps, if a surgical procedure involves multiple bone removing steps, such as the femoral preparation of a partial or total knee replacement, which can include two, three or more bone cuts.

When the ARDD is used to display the estimated/projected non-visualized portions of a device, an implant, an implant component, a surgical instrument and/or a surgical tool, the display of the non-visualized portion of the device, implant, implant component, surgical instrument and/or surgical tool can also account for any bone loss that may have been or will be induced by the device, implant, implant component, surgical instrument and/or surgical tool. By accounting for the bone loss induced by the device, implant, implant component, surgical instrument and/or surgical tool, the virtual surgical plan and the display of any surgical steps including subsequent surgical steps by the ARDD can be more accurate.

A virtual surgical plan can be used to define a predetermined start point for a surgical tool, a surgical instrument, a trial implant component, a trial implant, an implant component, an implant, a device. A start point can be, for example, the entry at the patient's skin. If pre-operative imaging, e.g. ultrasound, CT and/or MRI, is used for developing the surgical plan, the skin can be located in the imaging data and the start point can be defined at an area typically near the intended surgical site. A start point can also be defined at a select soft-tissue depth, e.g. 5, 8 or 10 cm into the soft-tissue, e.g. subcutaneous tissue or muscle or other tissues or organ tissue. A start point can be defined at the surface of an organ, e.g. a liver or a spleen or a kidney or a bladder or a brain. A start point can be defined at an anatomic landmark or in relationship to an anatomic landmark of an organ, e.g. a rim of a liver, a liver portal, an entry of an inferior vena cava into the liver, an entry of a portal vein into the liver, a superior or inferior pole of a kidney, a renal hilum. A start point can be defined at a bone surface or bony landmark.

The one or more of a virtual surgical tool, virtual surgical instrument including a virtual surgical guide or cut block, virtual trial implant, virtual implant component, virtual implant or virtual device, one or more a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration used in the one or more virtual surgical plans can be highlighted in the one or more ARDD displays using various techniques known in the art, including but not limited to: Colored display; Grey scale display; Shaded display; Patterned display, e.g. squares, lines, bars; Line display, e.g. solid, stippled, dotted; Arrow display; Target like display; Intermittent display, e.g. blinking or flashing; Appearing or disappearing display; Magnified display; Minified display.

For example, a virtual surgical tool, virtual surgical instrument including a virtual surgical guide or cut block, virtual trial implant, virtual implant component, virtual implant or virtual device, a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration is displayed by the ARDD multiple colors can be chosen.

For example, a virtual surgical tool, virtual surgical instrument including a virtual surgical guide or cut block, virtual trial implant, virtual implant component, virtual implant or virtual device, a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration can be highlighted using an arrow display. The arrows can be aligned with the direction of the one or more surgical tools, surgical instruments, implant components, implants or devices. The arrows can also not be aligned with the direction of the one or more surgical tools, surgical instruments, implant components, implants or devices. The arrows can be orthogonal to the direction of the one or more surgical tools, surgical instruments, implant components, implants or devices. The arrows can be aligned with the one or more surgical tools, surgical instruments, implant components, implants or devices. The arrows cannot be orthogonal with the one or more surgical tools, surgical instruments, implant components, implants or devices.

One or more arrows can directly point at the one or more of a virtual surgical tool, virtual surgical instrument including a virtual surgical guide or cut block, virtual trial implant, virtual implant component, virtual implant or virtual device, one or more a predetermined start point, predetermined start position, predetermined start orientation or alignment, predetermined intermediate predetermined point(s), intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration. The one or more arrows can optionally be magnified or minified. The one or more arrows can optionally be displayed intermittently, e.g. blinking or flashing. The one or more arrows can optionally be appearing or disappearing. For example, the one or more arrows can disappear when the predetermined end point is reached by the physical surgical tool, surgical instrument, implant component, implant or device.

The one or more of a virtual surgical tool, virtual surgical instrument including a virtual surgical guide or cut block, virtual trial implant, virtual implant component, virtual implant or virtual device, one or more predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration can be highlighted using a target like display. More than one target-like display can be used.

The target-like display can, for example, be positioned over a starting point, one or more intermediate points, an end point, a starting position, one or more intermediate positions, an end position, an intended path, predetermined plane, predetermined cut plane, a predetermined axis of the physical surgical tool, surgical instrument, trial implant, implant component, implant or device. A line or an axis oriented in orthogonal fashion through the target and passing through the center of one or more targets can optionally be aligned with a predetermined path, predetermined plane, predetermined cut plane, or predetermined axis of the physical surgical tool, surgical instrument, trial implant, implant component, implant or device, and/or one or more of a predetermined tissue change/alteration.

An intermittent, e.g. blinking or flashing display can be used to show one or more of a virtual surgical tool, virtual surgical instrument including a virtual surgical guide or cut block, virtual trial implant, virtual implant component, virtual implant or virtual device, one or more of a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration. An intermittent display can, for example, highlight if and when one or more of the surgical tool, surgical instrument, trial implant, implant component, implant or device are not aligned with one or more of the virtual surgical tool, virtual surgical instrument including a virtual surgical guide or cut block, virtual trial implant, virtual implant component, virtual implant or virtual device, one or more of the predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration. An intermittent display can, for example, highlight if and when one or more of the surgical tool, surgical instrument, trial implant, implant component, implant or device are aligned with one or more of the one or more of a virtual surgical tool, virtual surgical instrument including a virtual surgical guide or cut block, virtual trial implant, virtual implant component, virtual implant or virtual device, a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration.

An intermittent display can optionally change colors or have intermittent, varying color schemes. For example, a blinking or flashing red color can turn into solid, not intermittent green color when one or more of the physical surgical tool, surgical instrument, trial implant, implant component, implant and/or devices are aligned with one or more of a virtual surgical tool, virtual surgical instrument including a virtual surgical guide or cut block, virtual trial implant, virtual implant component, virtual implant or virtual device, or one or more of the predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration.

An intermittent display can, for example, highlight if and when one or more of the surgical tool, surgical instrument, trial implant, implant component, implant or device are not aligned with one or more of the predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration in the ARDD can turn from a solid color, e.g. green or blue, to a blinking or flashing red color. Different colors can be chosen for intermediate versus final, end positions, e.g. blue for intermediate and green for final/end.

An appearing or disappearing display can be used to show one or more of a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide or cut block, virtual trial implant, virtual implant component, implant or device inside the ARDD. An appearing or disappearing display can, for example, highlight if and when one or more of the surgical tool, surgical instrument, trial implant, implant component, implant or device are not aligned with one or more of a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide or cut block, virtual trial implant, virtual implant component, implant or device. In this example, the one or more of a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide or cut block, virtual trial implant, virtual implant component, implant or device can appear in the ARDD display when the physical surgical tool, surgical instrument, trial implant, implant component, implant, and/or device are not aligned, e.g. with the surgical plan or the one or more of the predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide or cut block, virtual trial implant, virtual implant component, implant or device. The one or more of a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide or cut block, virtual trial implant, virtual implant component, implant or device can disappear in the ARDD display when alignment is achieved again. The reverse can be possible, e.g. with the one or more of a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide or cut block, virtual trial implant, virtual implant component, implant or device disappearing when alignment is not achieved and appearing when alignment is achieved.

A magnified or minified display can be used to show one or more of a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide or cut block, virtual trial implant, virtual implant component, implant or device. The ARDD can also, optionally, provide or superimpose a magnified or minified display of the virtual anatomy or virtual data of the patient, for example after registration with the live anatomy/live data of the patient. The unmagnified, magnified or minified virtual anatomy or virtual data of the patient can be displayed by the ARDD simultaneously, e.g. with use of different colors, grey scale or patterns, or alternatingly with the unmagnified, magnified or minified display by the ARDD of the one or more of a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide or cut block, virtual trial implant, virtual implant component, implant or device. In some embodiments, the magnification (including no magnification) or minification of the display of the virtual anatomy or virtual data of the patient can be the same as the magnification (including no magnification) or minification of the one or more of a predetermined start point, predetermined start position, predetermined start orientation or alignment, predetermined intermediate point(s), predetermined intermediate position(s), predetermined d intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide or cut block, virtual trial implant, virtual implant component, implant or device. Virtual anatomy or virtual data of the patient as used in the foregoing includes all virtual data of the patient, including, for example, data from vascular flow studies, metabolic imaging, kinematic data and the like.

A magnified or minified display by the ARDD can, for example, highlight if and when one or more of the surgical tool, surgical instrument, trial implant, implant component, implant or device are not aligned with one or more of a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide or cut block, virtual trial implant, virtual implant component, implant or device. In this example, the predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide or cut block, virtual trial implant, virtual implant component, implant or device can be magnified or minified in the ARDD display when the physical surgical tool, surgical instrument, trial implant, implant component, implant, and/or device are not aligned, e.g. with the surgical plan or the one or more of the predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide or cut block, virtual trial implant, virtual implant component, implant or device. The one or more of a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide or cut block, virtual trial implant, virtual implant component, implant or device can be set to zero magnification or minification or can go from magnified to minified or from minified to magnified in the ARDD display when alignment is achieved again.

If more than one a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide or cut block, virtual trial implant, virtual implant component, implant or device are displayed by the ARDD, any combination of display styles or techniques, e.g. multi-colored, grey scale, shaded, patterned, line, arrow, target, intermittent, appearing, disappearing, magnified, minified is possible. In some embodiments, different display styles or techniques can be chosen for different predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide or cut block, virtual trial implant, virtual implant component, implant or device.

Any of the foregoing display types for the display of virtual data by one or more ARDD's can be performed using adjustment or selection of the focal plane or focal point for the display of the virtual data, for example based on coordinates of the ARDD and/or the coordinates of the surgical site or anatomic structure(s) on which surgery is contemplated to be performed or is being performed on and/or the coordinates of one or more physical surgical tools, instruments, implants or devices.

Two-Dimensional and Three-Dimensional Displays

One or more of a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide or cut block, virtual trial implant, virtual implant component, implant or device can be displayed by the ARDD in two dimensions.

One or more of a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide or cut block, virtual trial implant, virtual implant component, implant or device can be displayed by the ARDD in three dimensions.

One or more of a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide or cut block, virtual trial implant, virtual implant component, implant or device can be displayed by the ARDD in two dimensions and/or three dimensions, for example alternatingly or as triggered by voice commands or other commands. Simultaneous display of one or more of a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide or cut block, virtual trial implant, virtual implant component, implant or device in three dimensions can be possible.

Any of the foregoing two-dimensional or three-dimensional display types for the display of virtual data by one or more ARDDs can be performed using adjustment or selection of the focal plane or focal point for the display of the virtual data, for example based on coordinates of the ARDD and/or the coordinates of the surgical site or anatomic structure(s) on which surgery is contemplated to be performed or is being performed on and/or the coordinates of one or more physical surgical tools, instruments, implants or devices.

Stereoscopic and Non-Stereoscopic Displays

One or more of a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide or cut block, virtual trial implant, virtual implant component, implant or device can be displayed by the HMD in a non-stereoscopic manner in three dimensions, with similar view angle of the virtual data of the patient seen by the surgeon's eyes through the display of the HMD unit and the live data of the patient seen by the surgeon's eyes through the HMD unit.

One or more of a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide or cut block, virtual trial implant, virtual implant component, implant or device can be displayed by the HMD in a stereoscopic manner in three dimensions.

One or more of a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide or cut block, virtual trial implant, virtual implant component, implant or device can be displayed by the HMD in a stereoscopic and/or a non-stereoscopic display, for example alternatingly or as triggered by voice commands or other commands. Simultaneous display of one or more of a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide or cut block, virtual trial implant, virtual implant component, implant or device in a non-stereoscopic manner with display of one or more of a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide or cut block, virtual trial implant, virtual implant component, implant or device in a stereoscopic manner can be possible.

In some embodiments, one or more of a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide or cut block, virtual trial implant, virtual implant component, implant or device can be located in a spine, more specifically a vertebral body, a pedicle, a vertebral fracture, a posterior element, a facet joint depending on the virtual surgical plan and the anatomy and clinical condition of the patient. The predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide or cut block, virtual trial implant, virtual implant component, implant or device can be located in the posterior elements of a spine, a pedicle and a vertebral body, for example, if spinal fusion with pedicle screws or vertebroplasty of kyphoplasty are contemplated.

If spinal fusion with pedicle screws is planned, the predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide or cut block, virtual trial implant, virtual implant component, implant or device can coincide with, be parallel with, or be aligned and/or superimposed with the long axis of the pedicle screw in its intended virtual placement position from the virtual surgical plan, optionally using placement criteria, e.g. distance from cortex, as used in the virtual surgical plan.

If vertebroplasty or kyphoplasty or spinal biopsy is planned, the predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide or cut block, virtual trial implant, virtual implant component, implant or device can coincide with, be parallel with, or be aligned and/or superimposed with the long axis of the vertebroplasty, kyphoplasty or biopsy needle or needle set in its intended virtual placement position from the virtual surgical plan, optionally using placement criteria, e.g. distance from cortex, as used in the virtual surgical plan.

When stereoscopic projection is used by the HMD, the display for the left eye and the right eye can be adjusted for the surgeon's or operator's inter-ocular distance, including, for example, the inter-pupillary distance. For example, the distance between the left pupil and the right pupil can be measured prior to operating the HMD. Such measurements can be performed using an image and/or video capture system and/or 3D scanner integrated into, attached to or separate from the HMD. Such measurements can also be performed using any other technique known in the art, including, for example, mechanical rulers, optical measurement tools and standard tools used by optometrists.

Any of the foregoing stereoscopic or non-stereoscopic displays for the display of virtual data by one or more HMDs can be performed using adjustment or selection of the focal plane or focal point for the display of the virtual data, for example based on coordinates of the HMD and/or the coordinates of the surgical site or anatomic structure(s) on which surgery is contemplated to be performed or is being performed on and/or the coordinates of one or more physical surgical tools, instruments, implants or devices.

Adjusting the ARDD (e.g. HMD) Unit Including the Display

In some embodiments, once the inter-ocular, e.g. the inter-pupillary distance, of the surgeon or operator is known, it can be entered into the display system interface and/or software and the 3D projection of the left and the right eye can be adjusted for the user. For example, with a narrow inter-ocular or inter-pupillary distance, the projection for the left eye and the right eye can be moved closer to the nose so that the center of the left and the right projections will be aligned with the center of the left eye/pupil and the right eye/pupil. With a wide inter-ocular or inter-pupillary distance, the projection for the left eye and the right eye can be moved further away from the nose so that the center of the left and the right projections will be aligned with the center of the left eye/pupil and the right eye/pupil. Different user settings can be stored in the system, e.g. by user name. In this manner, when a different user is placing the HMD on his or her head, the user or the system can call up their preferred user settings, including their respective inter-ocular or inter-pupillary distance. User settings can be called up, for example, using a visual or optical keyboard interface, projected by the HMD, where the operator can select virtual buttons. User settings can also be called up using voice commands, keyboards and any other known technique or technique for executing user commands.

Refresh Rates, Addressing Image Flicker

In many embodiments of the present disclosure, a fast refresh rate can be desirable, e.g. 15 Hz, 20 Hz, 25 Hz, or 30 Hz, 50 Hz, 70 Hz, 80 Hz, 100 Hz, 120 Hz, 150 Hz, 175 Hz, 200 Hz or greater. When higher refresh rates are used, the spatial resolution of the display of the virtual data can optionally be reduced if bandwidth and transmission speed and/or display speed reach their limits. Alternatively, there can be an alternating of a high-resolution display, e.g. 1920×1080 pixel resolution, and lower resolution, e.g. 1024×768 pixel resolution. The ratio of high to lower resolution images can be 1:1, 2:1, 3:1, 1:2, 1:3, with any other combination possible.

Some users physicalize no flicker with refresh rates of 30 Hz, sometimes less. Other users can feel or experience flicker with refresh rates of 70 Hz or faster. If a user is experiencing flicker effects or a flicker feeling with the display of virtual data, the user can have the option of increasing the refresh rate and, optionally, decreasing the display resolution if necessary, for example for reasons of bandwidth or transmission speed. The user can also select alternating resolutions, e.g. 1920×1080 pixel resolution intermixed with 1024×768 pixel resolution; any other pixel resolution and combination of pixel resolutions is possible. In this manner, the user can select the setting that will yield a pleasant, substantially flicker free display while at the same time maintaining sufficient spatial and/or temporal resolution to enable an accurate physical/virtual work environment.

In some embodiments, the display will automatically turn off and, optionally, turn on depending where the user and/or operator and/or surgeon directs the view.

Managing Display, Hardware, Software or Bandwidth Limitations

In some embodiments, the display of the HMD unit can display a subset of the data and/or images representing a smaller portion of the field of view visible through the HMD or displayable by the display of the HMD unit, using, for example, only a portion of the available display. If data from a pre-operative or intra-operative imaging study, e.g. x-rays, a CT scan, an MRI scan, are displayed, the data or images displayed by the HMD can also be targeted to a volume smaller than the original scan volume or area covered by the imaging study in order to decrease the amount of data displayed. In addition, the data or images displayed by the HMD can also be targeted to a volume or area smaller than the volume or area to be operated or smaller than the volume or area of the surgical site. This embodiment can, for example, be useful, when the software environment limits the amount of surface points or nodes displayed or limits the size or amount of the data displayed by the HMD. This embodiment can also be useful when a WiFi or Bluetooth or other wireless connection is used with the HMD with limitations in bandwidth and/or data transmission, thereby limiting the amount of data being transmitted to the HMD and, ultimately, displayed, in particular when this limitation implies a limitation in the amount of data available for the display of the data and/or images by the HMD.

This smaller portion of the field of view visible through the HMD or displayable by the display of the HMD unit, smaller, targeted volume from an imaging study, or the volume or area smaller that the volume or area of the surgical site can be targeted to portions of the surgical site or to anatomic landmarks. For example, in a knee replacement, this smaller portion of the field of view can be targeted to the distal femur or portions of the distal femur while the surgeon is contemplating surgical steps on the femur, e.g. a distal femoral cut or an anterior or posterior cut or chamfer cuts; it can be targeted to the proximal tibia or portions thereof while the surgeon is contemplating surgical steps on the tibia, e.g. a proximal tibial cut or a tibial keel preparation and punch; it can be targeted to the patella, while the surgeon is contemplating surgical steps on the patella, e.g. a milling or cutting of the patella. In a hip replacement, the smaller portion of the field of view can be targeted to the proximal femur or portions thereof, while the surgeon is contemplating steps on the proximal femur, e.g. a femoral neck cut; it can be targeted to the acetabulum, while the surgeon is contemplating surgical steps on the acetabulum, e.g. an acetabular reaming or an impaction of an acetabular cup; it can be re-focused or re-targeted on the proximal femur when the surgeon contemplates femoral broaching or reaming, optionally followed by femoral component impaction. In a pedicle screw placement or a vertebroplasty or kyphoplasty, the smaller portion of the field of view can be targeted to the level and/or the side where the surgeon contemplates the next surgical step, e.g. insertion of an awl, a pedicle screw, a needle, a vertebra- or kyphoplasty needle.

A targeted area or smaller portion of the field of view visible through the OHMD or displayable by the display of the OHMD, a smaller, targeted volume from an imaging study, or a volume or area smaller that the volume or area of the surgical site can also be defined with use of one or more anatomic landmarks, e.g. in a hip a most inferior point, e.g. sulcus point, between the greater trochanter and the femoral neck, a most superior point on the greater trochanter, a most superior point on a lesser trochanter, an acetabular rim or portions thereof, an acetabular center, or in a knee, a most medial point on a medial condyle, a most lateral point on a lateral condyle, a center of a trochlear notch, a tibial spine, a most anterior point of a tibia, a central point of a patella. One or more of the same landmarks that have been/are being used for registration of virtual data and live data of the patient can be used for defining or identifying a target area or a smaller portion of the field of view visible through the OHMD or displayable by the display of the OHMD. The landmarks can be identified using, for example, an image and/or video capture system and/or 3D scanner integrated into, attached to or separate from an OHMD. The landmarks can be identified by attaching optionally one or more optical markers, navigation markers including infrared markers, retroreflective markers, RF markers, surgical navigation, LEDs, reference phantoms, calibration phantoms, or marks. A target area can be enclosed by landmarks, e.g. by three or more landmarks. A target area can extend beyond one or more landmarks, e.g. by 2, 4, 5, 6, 8, 10 cm or more or any other distance or radius, e.g. selected by the surgeon or operator.

By limiting the display to such a smaller portion of the field of view visible through the OHMD or displayable by the display of the OHMD or target area, a smaller, targeted volume from an imaging study, or a volume or area smaller than the volume or area of the surgical site the amount of data displayed can be reduced. In addition, the amount of data transmitted, e.g. using a Wifi, Bluetooth or LiF network can also be reduced.

Viewing 2D Computer Monitors Through an ARDD (e.g. OHMD) Unit

In some embodiments, the ARDD system (e.g. OHMD) can detect, e.g. automatically, if the surgeon or operator is looking at a computer or display monitor separate from the ARDD, for example, with use of an image and/or video capture system and/or 3D scanner integrated into, attached to or separate from the ARDD. The standalone or separate computer or display monitor can be used, for example, to display image data, e.g. of a patient, or to concurrently display virtual data displayed by the ARDD. The image and/or video capture system and/or 3D scanner can, for example, capture the outline of the computer or display monitor, e.g. round, square or rectangular, and the software can, optionally, automatically match, superimpose or align the items or structures displayed by the ARDD with the items or structures displayed by the standalone or separate computer or display monitor. Alternatively, the user, operator and/or surgeon can execute a command, e.g. a voice command or a command using a virtual finger/keyboard interface, indicating that he or she is looking at the standalone or separate computer or display monitor and the software can then match, superimpose or align the items or structures displayed by the ARDD with the items or structures displayed by the standalone or separate computer or display monitor. The ARDD system can match, superimpose, or align all of the structures displayed by the standalone or separate computer monitor. The ARDD system can match, superimpose or align a portion of the structures displayed by the standalone or separate computer monitor.

The ARDD can display the structures displayed by the standalone or separate computer monitor using the same color. The ARDD can display the structures displayed by the standalone or separate computer monitor using different colors. The ARDD can display structures not displayed by the standalone or separate computer monitor using a different color or greyscale or contrast than that used by the standalone or separate computer monitor.

The ARDD can display the structures displayed by the standalone or separate computer monitor using the same greyscale and/or contrast used by the standalone or separate computer monitor. The ARDD can display the structures displayed by the standalone or separate computer monitor using a different greyscale and/or contrast used by the standalone or separate computer monitor.

The ARDD can display the structures displayed by the standalone or separate computer monitor using the same image intensity used by the standalone or separate computer monitor. The ARDD can display the structures displayed by the standalone or separate computer monitor using a different image intensity used by the standalone or separate computer monitor, e.g. brighter or less bright.

In some embodiments, a standalone or separate computer or display monitor located in a user area, e.g. an operating room or a surgical suite, can be used as a calibration or reference or registration phantom for the ARDD unit including the frame and display position, orientation and/or alignment and/or direction of movement. The monitor can have a round, rectangular or square shape of known dimensions. An image and/or video capture system and/or 3D scanner integrated into, attached to or separate from the ARDD can be used to capture one or more images of the monitor. Since the dimensions of the monitor are known, the size, shape or dimensions, for example along its edges, or the area of the monitor on the captured image(s) can be used to determine the distance of the ARDD to the monitor; the shape of the circle, oval, rectangle or square can be used to determine the angle of the ARDD relative to the monitor. If the image and/or video capture system and/or 3D scanner integrated into or attached to the ARDD uses two or more cameras, the difference in shape of the circle, oval, rectangle or square detected between a first, second and any additional cameras can be used to increase the accuracy of any estimates of the angular orientation of the ARDD to the display monitor, e.g. by calibrating the measurement of a first camera against a second camera against a third camera and so forth. If two or more cameras are used integrated into or attached to different portions of the ARDD frame, e.g. the left side of the frame and the right side of the frame, the difference in projection of the monitor circle, oval, rectangle or square between the two cameras can also be used to estimate the user's head position and/or orientation and/or alignment and/or the position and/or orientation and/or alignment of the ARDD frame in relationship to the user's head and/or face.

In some embodiments, the user and/or surgeon can optionally look at the display monitor through the ARDD while maintaining his or her head in a neutral position, e.g. with no neck abduction, adduction, flexion, extension or rotation. This head position can be used to calibrate the position of the ARDD display in relationship to the target area and/or the patient and/or the surgical site, e.g. during an initial registration or a subsequent registration. This head position can also be used to calibrate the position of the ARDD unit/frame in relationship to the user's and/or the surgeon's head and face. Optionally, the user and/or surgeon can place his or her head on a chin stand or head holder for purposes of this calibration or registration. This process of using an external computer or display monitor as a reference for calibration and/or registration purposes can be performed at the beginning of an activity and/or a surgical procedure, e.g. as part of an initial registration process. This process of using an external display monitor as a reference for calibration and/or registration purposes can also be performed during an activity or after an activity and/or surgical procedure, for example when there is concern that the ARDD unit may have moved relative to the user's and/or surgeon's face.

In some embodiments, the position, location, orientation, and/or alignment of the outline of the standalone or separate computer or display monitor can be monitored, for example using an image and/or video capture system and/or 3D scanner integrated into, attached to or separate from the ARDD. Optionally, the position, location, orientation and/or alignment of the outline of the standalone or separate computer or display monitor can be monitored using attached optical markers, navigation markers including infrared markers, retroreflective markers, RF markers, LEDs and/or IMUs as well as any other techniques described in the disclosure or known in the art for determining and/or tracking the position, location, orientation and/or alignment of an object. With the position, location, orientation and/or alignment of the standalone or external computer or display monitor known, the position, location, orientation, alignment and/or direction of movement of the ARDD unit can be tracked in relationship to it, e.g. via an image and/or video capture system and/or 3D scanner integrated into or attached to the ARDD or optical markers, navigation markers including infrared markers, retroreflective markers, RF markers, LEDs and/or IMUs integrated into it or attached to it. As the position, location, orientation, alignment and/or direction of movement of the ARDD unit can be tracked, the display of the ARDD unit can at all times or, if preferred, intermittently, display the same structures, or at least a portion or subset thereof, displayed by the standalone or separate computer or display monitor, spatially matched. If the standalone or separate computer or display monitor occupies only a portion of the visual field covered by the ARDD display, the ARDD display can match the displayed structures with the structures displayed by the standalone or separate computer or display monitor only for the portion of the visual field occupied by the standalone or separate computer or display monitor. Optionally, the ARDD display can display structures extending beyond the portion of the visual field occupied by the standalone or separate computer or display monitor. The structures extending beyond the portion of the visual field occupied by the standalone or separate computer or display monitor can be continuous with the structures displayed by the standalone or separate computer or display monitor. The structures outside the portion of the visual field occupied by the standalone or separate computer or display monitor can be separate and/or from the structures displayed by the standalone or separate computer or display monitor. For example, in addition to displaying one or more structures matching or corresponding to what is displayed by the standalone or separate computer or display monitor, the ARDD display can display items such as vital signs or patient demographics, or pre-operative imaging studies in those portions of the visual field that do not include the standalone or separate computer or display monitor. This can be useful when the user, operator and/or surgeon is not looking at the patient.

In some embodiments, the ARDD can display surgical field related information, e.g. details or aspects of a virtual surgical plan, e.g. intended/projected cut planes, or anatomic information of the patient, e.g. from a pre-operative imaging study, when the user or surgeon is looking at the surgical field; the ARDD can display portions of information or all of the information displayed by a standalone or separate computer or display monitor, for example in 3D while the standalone or separate computer or display monitor display can be in 2D, when the user or surgeon is looking at the standalone or separate computer or display monitor; the ARDD can display non-surgical field related information and non-standalone or separate computer or display monitor related or displayed information when the user or surgeon is neither looking at the surgical field nor at the standalone or separate computer or display monitor or when the surgical field and/or the standalone or separate computer or display monitor occupy only a portion of the visual field covered by the ARDD display. The switching or toggling between surgical field related information, standalone or separate computer or display monitor information and other information by the ARDD display can be automatic, for example via image capture and related image processing and recognition which area the user or surgeon is currently looking at, e.g. optionally demarcated by optical markers, navigation markers including infrared markers, retroreflective markers, RF markers, and/or LED's, or it can be via commands executed by the user or surgeon, e.g. voice commands or finger/keyboard commands, for example using a virtual keyboard displayed by the ARDD display.

The ARDD can display information related to the information displayed on the standalone or separate computer display or monitor in two dimensions or three dimensions, the latter stereoscopically or non-stereoscopically. Any number of combinations of displays can be applied between the display by the ARDD display and the display by the standalone or separate computer or monitor display. For example, when the computer or monitor displays shows a pre-operative or intra-operative imaging study of the patient, these can be displayed in 2D (e.g. cross-sectional) or 3D using pseudo-3D display techniques, for example with surface reconstruction and shading. Overlaying or superimposing, for example, a true 3D, e.g. stereoscopic 3D, view of the anatomy from the pre- or intra-operative imaging study and/or virtual surgical plan of the patient using the ARDD display onto the same anatomic structures and/or virtual surgical plan displayed in 2D or pseudo 3D by the standalone or separate computer or display monitor can be beneficial for the surgeon as he or she executes surgical plans or plans next surgical plans during a procedure.

In some embodiments, the display of the ARDD unit or the standalone or separate computer or display monitor can display functional and/or time studies of the patient, e.g. the surgeon moving a leg or an arm of the patient using real-time fluoroscopic imaging, while the other of the two display modalities can simultaneously display and/or superimpose static images. For example, the standalone or separate computer or display monitor can display 2D or 3D function and/or time studies, e.g. of knee motion captured using real-time 2D single or biplane fluoroscopy or captured using 3D CT fluoroscopy, while the display of the ARDD unit can superimpose 2D or 3D non-stereoscopic or 3D stereoscopic images of the corresponding anatomy.

The following is an exemplary list of select possible combinations of 2D, 3D non-stereoscopic and stereoscopic displays by the ARDD and 2D and pseudo 3D displays of the standalone or separate computer or display monitor. The list in Table 3 is in no way meant to be limiting.

Table 3: Examples of possible combinations of display modes or types by the display of the ARDD unit and the display of the standalone or separate computer or display monitor.

TABLE 3

| | | | | | Standalone or Separate Computer or Display Monitor | | | |
|---|---|---|---|---|---|---|---|---|
| OHMD Display 2D | 3D Non-Stereoscopic | 3D Stereoscopic | 3D Non-Stereoscopic with Function/Time | 3D Stereoscopic with Function/Time | 2D | Pseudo 3D | 2D with Function/Time | Pseudo 3D with Function/Time |
| X | | | | | X | | | |
| X | | | | | | X | | |
| X | | | | | | | X | |
| X | | | | | | | | X |
| | X | | | | X | | | |
| | X | | | | | X | | |
| | X | | | | | | X | |
| | X | | | | | | | X |
| | | X | | | X | | | |
| | | X | | | | X | | |
| | | X | | | | | X | |
| | | X | | | | | | X |
| | | | X | | X | | | |
| | | | X | | | X | | |
| | | | X | | | | X | |
| | | | X | | | | | X |
| | | | | X | X | | | |
| | | | | X | | X | | |
| | | | | X | | | X | |
| | | | | X | | | | X |

X denotes type of display mode used

The ARDD display can optionally display some virtual data, e.g. pre-operative images and/or image reconstructions, of the patient in 2D, while it can display other virtual data, e.g. aspects or components of the virtual plan, e.g. intended cut planes, in 3D. Similarly, the ARDD display can optionally display some virtual data, e.g. pre-operative images and/or image reconstructions, of the patient in 3D, while it can display other virtual data, e.g. aspects or components of the virtual plan, e.g. intended pin or drill placement, in 2D, e.g. as a line.

The standalone or separate computer or display monitor can optionally display some virtual data, e.g. pre-operative images and/or image reconstructions, of the patient in 2D, while it can display other virtual data, e.g. aspects or components of the virtual plan, e.g. intended cut planes, in pseudo 3D, e.g. with perspective views and shading. Similarly, the standalone or separate computer or display monitor can optionally display some virtual data, e.g. pre-operative images and/or image reconstructions, of the patient in 3D, while it can display other virtual data, e.g. aspects or components of the virtual plan, e.g. intended pin or drill placement, in 2D, e.g. as a line.

Aspects or components of the virtual surgical plan can, for example, include one or more of the following: a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide or cut block, virtual trial implant, virtual implant component, implant or device.

In an additional embodiment, the ARDD display can optionally display some of the aspects or components of the virtual surgical plan in 2D and other aspects and components in 3D, stereoscopic or non-stereoscopic. For example, the ARDD display can display an intended cut plane in 3D stereoscopic or non-stereoscopic, while it can display a virtual cut block as an outline in 2D, for example projected with a stereoscopic 3D view of the underlying tissue to be cut, e.g. a femoral neck for a hip replacement. The ARDD display can display a virtual surgical instrument, e.g. a reamer in 3D, e.g. stereoscopic or non-stereoscopic, and it can project the intended reaming axis in 2D or in 3D.

The standalone or separate computer or display monitor can optionally co-display some of the aspects or components of the virtual surgical plan in 2D and other aspects and components in pseudo 3D, optionally with different colors. For example, the standalone or separate computer or display monitor can display an intended cut plane in pseudo 3D, while it can display a virtual cut block as an outline in 2D, for example projected on a pseudo 3D view of the underlying tissue to be cut, e.g. a distal femur for a knee replacement. The standalone or separate computer or display monitor can display a virtual implant or trial implant in pseudo 3D, and it can project its intended central axis, e.g. a femoral shaft axis for a femoral component of a hip replacement, in 2D.

The different 2D and 3D displays by the ARDD display and the standalone or separate computer or display monitor can be displayed and viewed simultaneously, in many embodiments substantially or partially superimposed. Since the user or surgeon can view the standalone or separate computer or display monitor through the ARDD display, the user or surgeon can experience a combination of 2D and 3D display information, e.g. of virtual anatomy of the patient and/or aspects of the virtual surgical plan, not previously achievable.

Table 4: Further examples of possible combinations for simultaneous viewing of display modes or types by the display of the ARDD unit and the display of the standalone or separate computer or display monitor for virtual data of the patient including anatomy, e.g. pre-operative imaging, and/or aspects and/or components of a virtual surgical plan, and/or virtual surgical instruments and/or virtual implants or implant components and/or intra-operative imaging of the patient.

TABLE 4

| | Standalone or Separate Computer or Display Monitor | | | | | | | | | | | |
|---|---|---|---|---|---|---|---|---|---|---|---|---|
| | Virtual Anatomic Data of the Patient | | | | Components of Virtual Surgical Plan of the Patient | | | | Virtual Surgical Instruments | | | |
| | 2D | Pseudo 3D | 2D with Function/Time | Pseudo 3D with Function/Time | 2D | Pseudo 3D | 2D with Function/Time | Pseudo 3D with Function/Time | 2D | Pseudo 3D | 2D with Function/Time | Pseudo 3D with Function/Time |
| OHMD Display<br>Virtual Anatomic Data of the Patient | | | | | | | | | | | | |
| 2D | X | X | X | X | X | X | X | X | X | X | X | X |
| 3D Non-Stereoscopic | X | X | X | X | X | X | X | X | X | X | X | X |
| 3D Stereoscopic | X | X | X | X | X | X | X | X | X | X | X | X |
| 3D Non-Stereoscopic with Function/Time | X | X | X | X | X | X | X | X | X | X | X | X |
| 3D Stereoscopic with Function/Time | X | X | X | X | X | X | X | X | X | X | X | X |
| Components of Virtual Surgical Plan of the Patient | | | | | | | | | | | | |
| 2D | X | X | X | X | X | X | X | X | X | X | X | X |
| 3D Non-Stereoscopic | X | X | X | X | X | X | X | X | X | X | X | X |
| 3D Stereoscopic | X | X | X | X | X | X | X | X | X | X | X | X |
| 3D Non-Stereoscopic with Function/Time | X | X | X | X | X | X | X | X | X | X | X | X |
| 3D Stereoscopic with Function/Time | X | X | X | X | X | X | X | X | X | X | X | X |
| Virtual Surgical Instruments | | | | | | | | | | | | |
| 2D | X | X | X | X | X | X | X | X | X | X | X | X |
| 3D Non-Stereoscopic | X | X | X | X | X | X | X | X | X | X | X | X |
| 3D Stereoscopic | X | X | X | X | X | X | X | X | X | X | X | X |
| 3D Non-Stereoscopic with Function/Time | X | X | X | X | X | X | X | X | X | X | X | X |
| 3D Stereoscopic with Function/Time | X | X | X | X | X | X | X | X | X | X | X | X |
| Virtual Implant or Trial Implant Components | | | | | | | | | | | | |
| 2D | X | X | X | X | X | X | X | X | X | X | X | X |
| 3D Non-Stereoscopic | X | X | X | X | X | X | X | X | X | X | X | X |
| 3D Stereoscopic | X | X | X | X | X | X | X | X | X | X | X | X |
| 3D Non-Stereoscopic with Function/Time | X | X | X | X | X | X | X | X | X | X | X | X |
| 3D Stereoscopic with Function/Time | X | X | X | X | X | X | X | X | X | X | X | X |
| Intra-Operative Imaging of the Patient | | | | | | | | | | | | |
| 2D | X | X | X | X | X | X | X | X | X | X | X | X |
| 3D Non-Stereoscopic | X | X | X | X | X | X | X | X | X | X | X | X |
| 3D Stereoscopic | X | X | X | X | X | X | X | X | X | X | X | X |
| 3D Non-Stereoscopic with Function/Time | X | X | X | X | X | X | X | X | X | X | X | X |
| 3D Stereoscopic with Function/Time | X | X | X | X | X | X | X | X | X | X | X | X |

TABLE 4-continued

| | Standalone or Separate Computer or Display Monitor | | | | | | | |
|---|---|---|---|---|---|---|---|---|
| | Virtual Implant or Trial Implant Components | | | | Intra-Operative Imaging of the Patient | | | |
| | 2D | Pseudo 3D | 2D with Function/Time | Pseudo 3D with Function/Time | 2D | Pseudo 3D | 2D with Function/Time | Pseudo 3D with Function/Time |
| **OHMD Display** | | | | | | | | |
| **Virtual Anatomic Data of the Patient** | | | | | | | | |
| 2D | X | X | X | X | X | X | X | X |
| 3D Non-Stereoscopic | X | X | X | X | X | X | X | X |
| 3D Stereoscopic | X | X | X | X | X | X | X | X |
| 3D Non-Stereoscopic with Function/Time | X | X | X | X | X | X | X | X |
| 3D Stereoscopic with Function/Time | X | X | X | X | X | X | X | X |
| **Components of Virtual Surgical Plan of the Patient** | | | | | | | | |
| 2D | X | X | X | X | X | X | X | X |
| 3D Non-Stereoscopic | X | X | X | X | X | X | X | X |
| 3D Stereoscopic | X | X | X | X | X | X | X | X |
| 3D Non-Stereoscopic with Function/Time | X | X | X | X | X | X | X | X |
| 3D Stereoscopic with Function/Time | X | X | X | X | X | X | X | X |
| **Virtual Surgical Instruments** | | | | | | | | |
| 2D | X | X | X | X | X | X | X | X |
| 3D Non-Stereoscopic | X | X | X | X | X | X | X | X |
| 3D Stereoscopic | X | X | X | X | X | X | X | X |
| 3D Non-Stereoscopic with Function/Time | X | X | X | X | X | X | X | X |
| 3D Stereoscopic with Function/Time | X | X | X | X | X | X | X | X |
| **Virtual Implant or Trial Implant Components** | | | | | | | | |
| 2D | X | X | X | X | X | X | X | X |
| 3D Non-Stereoscopic | X | X | X | X | X | X | X | X |
| 3D Stereoscopic | X | X | X | X | X | X | X | X |
| 3D Non-Stereoscopic with Function/Time | X | X | X | X | X | X | X | X |
| 3D Stereoscopic with Function/Time | X | X | X | X | X | X | X | X |
| **Intra-Operative Imaging of the Patient** | | | | | | | | |
| 2D | X | X | X | X | X | X | X | X |
| 3D Non-Stereoscopic | X | X | X | X | X | X | X | X |
| 3D Stereoscopic | X | X | X | X | X | X | X | X |
| 3D Non-Stereoscopic with Function/Time | X | X | X | X | X | X | X | X |
| 3D Stereoscopic with Function/Time | X | X | X | X | X | X | X | X |

X denotes type of display mode combinations used or possible

Virtual data of the patient including anatomy, e.g. pre-operative imaging, and/or aspects and/or components of a virtual surgical plan, and/or virtual surgical instruments and/or virtual implants or implant components and/or intra-operative imaging of the patient can be displayed using different colors, greyscale values and image intensities by the display of the ARDD unit and the display of the standalone or separate computer or display monitor.

Intra-operative imaging of the patient can include, for example, x-ray imaging, laser scanning, 3D scanning or mechanical probe scanning of a joint, e.g. hip joint, knee joint, shoulder joint, or a spine. Intra-operative X-ray images, laser scans, 3D scans, mechanical probe scans, pre-operative imaging data of the patient including 2D and 3D reconstructions, aspects or components of a virtual surgical plan, virtual surgical instruments, and/or virtual implants and implant components can be displayed simultaneously and, optionally, superimposed by the display of the ARDD unit and the display of the standalone or separate computer or display monitor. If two or more imaging modalities or pre-operative and intra-operative imaging studies are co-displayed, they can optionally be anatomically matched and they can optionally be displayed using the same projection plane or, optionally, different projection planes.

If 2D views are co-displayed with 3D views or pseudo 3D views by the ARDD display alone, by the standalone or separate computer or display monitor alone, or the two together and partially or completely superimposed, the 2D views can optionally be displayed using certain standard projections, e.g. AP, lateral, oblique; the standard projection, e.g. AP, lateral and oblique, can optionally be referenced to the live data of the patient, e.g. the corresponding planes with the patient positioned on the OR table, or to the data of the patient displayed on the standalone or separate computer or display monitor. Standard projections or standard views can also include view angles from the patient's side, front, top, bottom, or oblique views.

Dynamic views or functional views, for example with two or three spatial dimensions and a time dimension can be displayed by the display of the ARDD unit and/or the display of the standalone or separate computer or display monitor, optionally superimposed onto or co-displayed with static images, e.g. 2D or 3D, by the second display unit, e.g. the display of the ARDD unit or the display of the standalone or separate computer or display monitor. Such dynamic views or functional views can include kinematic studies of a joint, e.g. obtained with an intraoperative laser or 3D scanner, which can be used by a surgeon to obtain scans of the knee, hip, shoulder an any other joint at different flexion angles, extensions angles, rotation angles, abduction angles, adduction angles, e.g. 0, 10, 15, 20, 30, 40, 45, 50, 60, 70, 80, 90, 100, 110, 120, 130, 140, 150 degrees etc. Any other type of dynamic scan, which can include a time element or time dimension or a functional element or functional dimension can be displayed by the display of the ARDD unit and/or the display of the standalone or separate computer or display monitor.

In some embodiments, the display of the ARDD unit can be used for displaying lower resolution data and/or images, while the display of the display of the standalone or separate computer or display monitor can be used for displaying corresponding or matching or overlapping higher resolution data and/or images. This embodiment can be particularly useful when, for example, the maximum available display resolution of the ARDD is lower than desirable for a particular application or surgical procedure. This embodiment can also be useful, when the software environment limits, for example, the amount of surface points or nodes displayed or limits the available resolution. This embodiment can also be useful when a WiFi or Bluetooth or other wireless connection is used with the ARDD with limitations in bandwidth and/or data transmission, thereby limiting the amount of data being transmitted to the ARDD and, ultimately, displayed, in particular when this limitation implies a limitation in available spatial resolution for the display of the data and/or images by the ARDD. By viewing the lower resolution data and/or images through the ARDD such as an OHMD, the user can have, for example, the benefit of stereoscopic visualization or the benefit of viewing components or aspects of the surgical plan, e.g. a virtual resection line, a virtual cut plane, a virtual instrument and/or a virtual implant, while by viewing simultaneously and/or with partial or complete superimposition the higher resolution data and/or images on the display of the standalone or separate computer or display monitor the viewer can have the concurrent benefit of viewing the data and/or images in high resolution.

In some embodiments, the display of the ARDD unit can be used for displaying static data and/or images, while the display of the standalone or separate computer or display monitor can be used for displaying corresponding or matching or overlapping dynamic data and/or images, e.g. images demonstrating a function, e.g. kinematic movement of a joint, and/or a time element or dimension including a change in condition or function monitored over a time period. This embodiment can be particularly useful when, for example, the refresh rate of the ARDD display is lower than desirable for a particular application or surgical procedure. This embodiment can also be useful, when the software environment limits, for example, the amount of data and/or images displayed. This embodiment can also be useful when a WiFi or Bluetooth or other wireless connection is used for connecting the ARDD with limitations in bandwidth and/or data transmission, thereby limiting the amount of data being transmitted to the ARDD and, ultimately, displayed, in particular when this limitation implies a limitation in available temporal and/or spatial resolution for the display of the data and/or images by the ARDD. By viewing the static data and/or images through the ARDD such as an OHMD, the user can have, for example, the benefit of stereoscopic visualization or the benefit of viewing components or aspects of the surgical plan, e.g. a virtual resection line, a virtual cut plane, a virtual instrument and/or a virtual implant, while by viewing simultaneously and/or with partial or complete superimposition the dynamic data and/or images on the display of the standalone or separate computer or display monitor the viewer can have the concurrent benefit of viewing the dynamic data and/or images, optionally in high resolution.

In some embodiments, the display of the ARDD unit can be used for displaying a subset of the data and/or images representing a smaller portion of the field of view displayed by the standalone or separate computer or display monitor, while the display of the display of the standalone or separate computer or display monitor can be used for displaying corresponding or matching or overlapping higher data and/or images using the full intended field of view of patient data. This embodiment can, for example, be useful, when the software environment limits the amount of surface points or nodes displayed or limits the size of the data displayed by the ARDD. This embodiment can also be useful when a WiFi or Bluetooth or other wireless connection is used with the ARDD with limitations in bandwidth and/or data transmission, thereby limiting the amount of data being transmitted to the ARDD and, ultimately, displayed, in particular when this limitation implies a limitation in the amount of data available for the display of the data and/or images by the ARDD. By viewing data and/or images with a smaller, more narrow field of view through the ARDD such as an OHMD, the user can have, for example, the benefit of stereoscopic visualization or the benefit of viewing components or aspects of the surgical plan, e.g. a virtual resection line, a virtual cut plane, a virtual instrument and/or a virtual implant, while by viewing simultaneously and/or with partial or complete superimposition the data and/or images with the full field of view on the display of the standalone or separate computer or display monitor the viewer can have the concurrent benefit of viewing the data and/or images using the full intended field of view of patient data.

When 3D views are superimposed onto or co-displayed with 2D views by the display of the ARDD unit and the display of the standalone or separate computer or display monitor or when multiple 2D views are superimposed or co-displayed by the display of the ARDD unit and the display of the standalone or separate computer or display monitor, they can be anatomically matched, for example using corresponding landmarks and/or using common coordinates. They can also have different view angles, e.g. a view angle as the patient is positioned on the OR table, a view angle from the side, front, top, bottom, or oblique views. Thus, the ARDD display can, for example, show a stereoscopic 3D view of the patient's virtual anatomy, e.g. from a pre-operative imaging study, while the standalone or separate computer or display monitor can show a matching AP or lateral intra-operative radiographic view or a matching pseudo 3D laser view of the patient.

The matching of data displayed by the display of the ARDD unit and the display of the standalone or separate computer or display monitor can be achieved in different ways, e.g. using matching of data and/or image using coordinates; matching of data and/or image using content or combinations of matching of data and/or image coordinates and data and/or image content.

In some embodiments, data and/or images displayed by the ARDD and data and/or images displayed by the standalone or separate computer or display monitor can be matched using known image coordinates and can then optionally be partially or completely superimposed, e.g. as the user and/or surgeon moves his or her head and/or body while looking at the standalone or separate computer or display monitor. For example, if the ARDD is registered in space, e.g. with regard to the patient and/or the surgical site and/or the standalone computer or display monitor and/or the image data displayed on the standalone computer or display monitor, data and/or images displayed by the ARDD and/or displayed by the standalone computer or display monitor can be in the same or a common coordinate system, which can allow the matching or superimposition of the display by the ARDD with the display by the standalone or separate computer or display monitor, when portions or all of the separate computer or display monitor are included in the field of view of the user or surgeon through the ARDD such as an OHMD.

In some embodiments, when both the display of the ARDD and the display of the separate computer or display monitor are registered in the same coordinate system, which can include that the image data displayed by the one or more ARDDs and the image data displayed by the separate computer or display monitor are registered in the same coordinate system, the ARDD can display then a set of data and/or images at least partially matching the coordinates and/or anatomic features, e.g. in 2D or 3D, of the data and/or images of the separate computer or display monitor. For example, the ARDD can display stereoscopic 3D views that share common coordinates and/or anatomic features, e.g. in 2D or 3D, with a pseudo 3D visualization displayed by the standalone or separate computer or display monitor. Such common coordinates can, for example, be corner points or edges or select geometric features and/or locations which can be superimposed then in the resultant composite ARDD/standalone monitor view that the user or surgeon sees. The ARDD can also, for example, display a stereoscopic 3D view of live data of the patient or virtual data of the patient or both, while the standalone or separate computer or display monitor displays a 2D view, e.g. a pre-operative imaging study, of the patient. The 2D plane or view display by the standalone or separate computer or display monitor can have the same or common coordinates and/or anatomic features, e.g. in 2D or 3D, with the corresponding 2D plane embedded in or contained in the 3D data and/or images displayed by the ARDD which can be matched or superimposed then in the resultant composite ARDD/standalone monitor view that the user or surgeon sees. Alternatively, in a similar example, if the ARDD provides only a surface display, for example, the periphery or outline or select peripheral points of the 2D plane displayed by the standalone or separate computer or display monitor can have the same or common coordinates and/or anatomic features, e.g. in 2D or 3D, with corresponding surface points and/or anatomic features, e.g. in 2D or 3D, in the location corresponding to the 2D plane in the 3D data and/or images displayed by the ARDD.

The data and/or images displayed by the ARDD can be matched to the data displayed by the standalone or separate computer or display monitor, e.g. by identifying common coordinates and superimposing them and/or by defining a common coordinate system. Alternatively, the data and/or images displayed by the standalone or separate computer or display monitor can be matched to the data displayed by the ARDD, e.g. by identifying common coordinates and superimposing them and/or by defining a common coordinate system. When the data and/or images displayed by the ARDD are superimposed with the data and/or images displayed by the standalone or separate display monitor, the data and/or images displayed by the ARDD and the data and/or images displayed by the standalone or separate display monitor can be displayed with the same magnification in order to optimize the superimposition or matching.

In some embodiments, the surgical table can be moved. The movement of the surgical table can translate into a comparable movement of the patient and/or the surgical site in x, y, and/or z direction. When the magnitude and direction of the table movement is known, it can be used to move the common coordinate system by a corresponding amount or direction for matching or superimposing the data and/or images displayed by the ARDD and the data and/or images displayed by the standalone or separate display monitor. For example, if the ARDD displays live data of the patient, e.g. captured through an image and/or video capture system and/or 3D scanner integrated into, attached to or separate from the ARDD, and/or virtual data of the patient and/or virtual data of the patient superimposed onto live data of the patient and the standalone or separate computer or display monitor displays a pre-operative imaging study of the patient, the surgical table and the patient can be moved and the display of the live or virtual data by the ARDD can be moved by a corresponding amount, thereby maintaining registration including registration to the data displayed on the standalone or separate computer or display monitor.

In some embodiments, the data and/or images displayed by the ARDD and the data and/or images displayed by the standalone or separate computer or display monitor can be cross-registered and, for example, moved into a shared or common coordinate system with use of an image and/or video capture system and/or 3D scanner integrated into, attached to, or separate from the ARDD (e.g OHMD), capturing the data displayed by the standalone or separate computer or display monitor. For example, the standalone or separate computer or display monitor can display data from a real-time intra-operative imaging study of the patient, including, for example, imaging during movement of the patient or surgical table or both. Standard image processing techniques can, for example, recognize anatomic landmarks or features on the data or images displayed on the standalone or separate computer or display monitor and match these with the corresponding anatomic landmarks or features in the data and/or images available for display by the ARDD. The ARDD can then display the corresponding data and/or images, optionally superimposing the data based on landmark matching. The landmark matching can, for example, occur by moving and/or translating the data or images available for display by the ARDD by an amount that will superimpose or match in a common coordinate system corresponding anatomic landmarks and/or features.

In embodiments, the process can be applied with use of an image capture or video capture system or a 3D scanner capturing the information from the standalone or separate computer monitor or display, by comparing, registering, matching, moving, aligning and/or superimposing images acquired with the intra-operative imaging system, e.g. displayed by the standalone or separate computer monitor or display, with data and/or images obtained in a pre-operative imaging study, e.g. displayed by the ARDD. In embodiments, the process can be applied directly, i.e. without use of an image capture or video capture system or a 3D scanner, using, for example, a computer workstation, optionally connected to the standalone or separate computer monitor or display, by comparing, registering, matching, moving, aligning and/or superimposing images acquired with the intra-operative imaging system, e.g. displayed by the standalone or separate computer monitor or display, with data and/or images obtained in a pre-operative imaging study, e.g. displayed by the ARDD.

In embodiments, the process can be applied with use of an image capture or video capture system or a 3D scanner capturing the information from the standalone or separate computer monitor or display, by comparing, registering, matching, moving, aligning and/or superimposing images obtained in a pre-operative imaging study, e.g. displayed by the ARDD, with data and/or images acquired with an intra-operative imaging system, e.g. displayed by the standalone or separate computer monitor or display. In embodiments, the process can be applied directly, i.e. without use of an image capture or video capture system or a 3D scanner, using, for example, a computer workstation, optionally connected to the standalone or separate computer monitor or display, by comparing, registering, matching, moving, aligning and/or superimposing images obtained in a pre-operative imaging study, e.g. displayed by the ARDD, with data and/or images acquired with an intra-operative imaging system, e.g. displayed by the standalone or separate computer monitor or display.

Image processing techniques can, for example, recognize anatomic landmarks or features on the data or images acquired by the real-time imaging system and match these with the corresponding anatomic landmarks or features in the data and/or images available for display by the ARDD. The ARDD can then display the corresponding data and/or images, optionally superimposing the data based on landmark matching. The landmark matching can, for example, occur by moving and/or translating the data or images available for display by the ARDD by an amount that will superimpose or match in a common coordinate system corresponding anatomic landmarks and/or features.

In the foregoing embodiments, the data and/or images displayed by the ARDD can be matched to the data displayed by the standalone or separate computer or display monitor, e.g. by identifying common coordinates and superimposing them and/or by defining a common coordinate system. Alternatively, the data and/or images displayed by the standalone or separate computer or display monitor can be matched to the data displayed by the ARDD, e.g. by identifying common coordinates and superimposing them and/or by defining a common coordinate system. When the data and/or images displayed by the ARDD are superimposed with the data and/or images displayed by the standalone or separate display monitor, the data and/or images displayed by the ARDD and the data and/or images displayed by the standalone or separate display monitor can be displayed with the same magnification in order to optimize the superimposition or matching.

Matching of images displayed by the ARDD and a standalone or separate computer or display monitor can also be performed by combining coordinate based matching, e.g. using the same coordinate system for both displays, and landmark based matching using any of the foregoing techniques. Someone skilled in the art will readily recognize other means of coordinate matching and landmark matching.

In some embodiments, the magnification of the items displayed by the ARDD can be adjusted so that it is reflective of, corresponds to, is smaller or larger than the magnification used by the standalone or separate computer or display monitor. Alternatively, the standalone or separate computer or display monitor can have one or more markers, e.g. one or more LED's, that an image and/or video capture system and/or 3D scanner, e.g. integrated into, attached to or separate from the ARDD, can detect which, in turn, can then trigger the adjustment of the magnification of the items displayed by the ARDD, e.g. based on the distance of the ARDD to the monitor. In some embodiments, an image and/or video capture system and/or 3D scanner integrated into, attached to or separate from the ARDD can visualize the size and shape (round, oval, ellipsoid, rectangular, square) of the standalone or separate computer or display monitor; using standard image processing techniques and geometry, the size and shape can then be used to derive the distance and angle of the ARDD relative to the standalone or separate computer or display monitor. If more than one camera is used, additional parallax information (difference in size and/or shape of the standalone or separate computer or display monitor) can be used to further estimate or improve the estimation of the distance or angle of the ARDD to the standalone or separate computer or display monitor. The resultant estimation of the distance and/or angle of the ARDD display to the standalone or separate computer or display monitor can then optionally be used to match the magnification of the data displayed by the standalone or separate computer or display monitor or to display at a higher or lower magnification than the data display by the standalone or separate computer or display monitor.

Similarly, the ARDD can detect, e.g. automatically, if the surgeon or operator is not looking at the standalone or separate computer or display monitor, for example, with use of an image and/or video capture system and/or 3D scanner integrated into, attached to or separate from the ARDD. The image and/or video capture system and/or 3D scanner can, for example, detect that the outline of the standalone or separate computer or display monitor (e.g. round, square, rectangular) is not present in the captured image data and the software can the automatically adjust the magnification of the items displayed by the ARDD so that it is reflective of or corresponds to the distance of the ARDD (e.g. OHMD) or the surgeon's eyes to the patient's surgical site, or is smaller or larger than that. Alternatively, a standalone or separate computer or display monitor can have one or more markers, e.g. one or more LED's or optical markers, that the image and/or video capture system and/or 3D scanner can detect; in this case, when the image captures system notices that the one or more LED's or optical markers are not included in the image capture data, the software can then automatically adjust the magnification of the items displayed by the ARDD so that it is reflective of or corresponds to the distance of the ARDD (e.g. OHMD) or the surgeon's eyes to the patient's surgical site, or is smaller or larger than that. Similarly, markers or LED's placed on the patient's surgical site can be detected by the ARDD including an image and/or video capture system and/or 3D scanner integrated into, attached to or separate from the ARDD thereby triggering an adjustment in magnification so that it is reflective of, corresponds to the distance of the ARDD (e.g. OHMD) or the surgeon's eyes to the patient's surgical site, or is smaller or larger than that when the surgeon or operator is looking at the patient's surgical site.

In some embodiments, the ARDD can be used to display data and/or images instead of a standalone or separate computer or display monitor. Optionally, the ARDD can replace the standalone or separate computer or display monitor. In some embodiments, the ARDD can display the live data from the patient's surgical site and project them for the surgeon and superimpose them with virtual data. The ARDD can also display one or more aspects or components of the virtual surgical plan, e.g. projected paths for one or more surgical instruments, or it can display one or more virtual implants or implant components. In this embodiment, the ARDD can optionally match the magnification of the one or more projected paths, and/or one or more surgical instruments and/or one or more virtual implants or implant components relative to the magnification of the live data from the patient. The ARDD can also apply a larger or smaller magnification and/or size than the magnification of the live data from the patient for the one or more projected paths and/or virtual surgical instruments, and/or one or more virtual implants or implant components. The live data of the patient can be seen through the transparent display of the OHMD. Alternatively, the display can be partially or completely opaque and the live data can be capture through an image and/or video capture system and/or 3D scanner integrated into, attached to or separate from the ARDD (e.g. OHMD) and then subsequently be displayed by the ARDD (e.g. OHMD) display.

In some embodiments, for example when the OHMD is the primary display unit, the OHMD can be non-transparent to light or minimally transparent to light reflected from the patient's surgical field and can display, for example, live (electronic) images collected by the image and/or video capture system and/or 3D scanner and, optionally, it can display, in addition, aspects or components of the virtual surgical plan, e.g. one or more projected paths for one or more physical surgical instruments, probes, pointers, and/or one or more virtual instruments and/or one or more virtual implants or implant components (optionally with various chosen matching or non-matching magnifications). In this setting, the OHMD can also display electronic images of the physical surgical instruments and or devices and their respective movements, for example captured with an image and/or video capture system and/or 3D scanner integrated into, attached to, or separate from the OHMD (with various chosen matching or non-matching magnifications).

The OHMD can be permanently non-transparent to light or minimally transparent to light reflected from the patient's surgical field. Alternatively, the degree of transparency can be variable, for example with use of one or more optical filters, e.g. polarizing light filters, in front of or integrated into the OHMD or electronic, e.g. LCD, or optical filters in front or integrated into the OHMD, or via intensity adjustments. The OR theater can optionally use light sources, e.g. polarized or filtered light that will support modulation or aid with adjustments of the transparency of the OHMD to light reflected from the patient's surgical field.

Any of the foregoing display types for the display of virtual data by one or more ARDD (e.g. OHMD) superimposed onto a 2D computer monitor can be performed using adjustment or selection of the focal plane or focal point for the display of the virtual data, for example based on coordinates of the ARDD (e.g. OHMD) and/or the coordinates of the computer monitor and/or the coordinates of the surgical site or anatomic structure(s) on which surgery is contemplated to be performed or is being performed on and/or the coordinates of one or more physical surgical tools, instruments, implants or devices.

Magnified Displays

Magnified displays of the following structures and/or devices can be shown with an HMD for example for one or more of the following, simultaneously or non-simultaneously:

- Physical anatomy (e.g. using intra-operative imaging with optional magnification or demagnification)
- Static
- Dynamic, e.g. with functional or time element or dimension
- Virtual anatomy, e.g. from pre-operative or intra-operative imaging study [optionally displayed as a 3D reconstruction [optionally with stereoscopic display by the HMD] and/or as 2D cross-section or image slices [optionally with stereoscopic display by the HMD]]
- Aspects or components of a virtual surgical plan, e.g. a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide [e.g. a virtual axis, virtual plane or virtual cut block], virtual trial implant, virtual implant component, implant or device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide [e.g. a virtual axis, virtual plane or virtual cut block], virtual trial implant, virtual implant component, implant or device
- Virtual surgical instrument(s)
- Virtual implant(s) or implant component(s)

In some embodiments, the ARDD display can display live data of the patient captured through an image and/or video capture system and/or 3D scanner integrated into, attached to or separate from the ARDD with higher magnification than the live data seen through transparent portions of an ARDD by the user's or surgeon's eye. Thus, the live data of the patient captured through an image and/or video capture system and/or 3D scanner integrated into, attached to or separate from the ARDD can be displayed in a magnified manner for a given distance of the ARDD display to the surgical field. This has the benefit that select structures can be seen with greater detail, for example offering a low power microscopic, magnified view of portions or all of the surgical field. The distance of the ARDD to the surgical field can be determined using techniques described in the disclosure, e.g. optical markers, navigation markers including infrared markers, retroreflective markers, RF markers, IMUs, LEDs and any other technique known in the art. The distance of the ARDD, e.g. an HMD in this example, to a separate or standalone computer monitor or display can be considered in addition to the magnification of any images displayed using the standalone computer monitor or display in order to match the structures and the magnification of the structures displayed by the separate or standalone computer monitor with the ARDD display. The magnified display of live data can be performed while partially or completely blending out live data seen through the OHMD, e.g. with the OHMD turned partially or completely opaque to light emitted from the surgical field and primarily or only data displayed captured through the image and/or video capture system and/or 3D scanner. The magnified display of live data captured through the image and/or video capture system and/or 3D scanner can be superimposed on live data seen through one or more partially or completely transparent portions of the OHMD. In this example, the magnified display of the live data can be a portion of the surgical field seen through the OHMD.

Optionally, a declining gradient of magnification can be applied to the live data so that the magnified live data can blend in seamlessly or near seamlessly with the non-magnified live data, e.g. the live data seen through one or more partially or completely transparent portions of the OHMD.

The magnification of a portion or all of the live data captured through an image and/or video capture system and/or 3D scanner can be at preset levels, e.g. 1.5×, 2.0×, 3.0×, 4.0×, or 5.0× or any other magnification level, e.g. a range from 0-1×, 0-5×, 0-10×, 0-20×. The magnification can be continuous, e.g. on a sliding scale. The magnification can be selected by the user and/or surgeon, for example using voice commands, eye commands or using a virtual keyboard interface displayed by the OHMD.

Virtual data [including, for example, any 2D or 3D imaging studies obtained pre- or intra-operatively] can optionally be displayed with the same magnification as the live data. Optionally, virtual data can be displayed with no magnification or lesser or greater magnification than live data.

In some embodiments, the HMD display can display virtual data of the patient and, principally any virtual data, e.g. portions of a virtual surgical plan, a predetermined start point, a predetermined start position, a predetermined start orientation or alignment, a predetermined intermediate point(s), a predetermined intermediate position(s), a predetermined intermediate orientation or alignment, a predetermined end point, a predetermined end position, a predetermined end orientation or alignment, a predetermined path, a predetermined plane, a predetermined cut plane, a predetermined contour or outline or cross-section or surface features or shape or projection, a predetermined depth marker or depth gauge, a predetermined stop, a predetermined angle or orientation or rotation marker, a predetermined axis, e.g. rotation axis, flexion axis, extension axis, a predetermined axis of a virtual surgical tool, a virtual surgical instrument, a virtual surgical guide [e.g. a virtual axis, virtual plane or virtual cut block], a virtual trial implant, a virtual implant component, implant or device, non-visualized portions for one or more devices or implants or implant components or surgical instruments or surgical tools, and/or one or more of a predetermined tissue change or alteration, and/or one or more of a predetermined position and/or orientation of a virtual surgical tool, virtual surgical instrument, virtual surgical guide [e.g. a virtual axis, virtual plane or virtual cut block], a virtual trial implant, a virtual implant component, implant or device, with higher magnification than the live data seen through transparent portions of the HMD by the user's or surgeon's eye. Thus, the virtual data of the patient can be displayed in a magnified manner for a given distance of the HMD display to the surgical field. This has the benefit that select structures or aspects of components of a virtual surgical plan or virtual data can be seen with greater detail, for example offering a low power microscopic, magnified view of portions or all of the virtual data. The distance of the HMD to the surgical field can be determined using techniques described in the disclosure, e.g. optical markers, navigation markers including infrared markers, retroreflective markers, RF markers, IMU's, LED's and any other technique known in the art.

The magnified display of virtual data can be performed while partially or completely blending out live data seen through the HMD, e.g. with the OHMD turned partially or completely opaque to light emitted from the surgical field and primarily or only virtual data displayed. The magnified display of virtual data captured through the image and/or video capture system and/or 3D scanner can be superimposed on live data seen through one or more partially or completely transparent portions of the OHMD. In this example, the magnified display of the virtual data can be a portion of the surgical field seen through the OHMD. Optionally, a declining gradient of magnification can be applied to the virtual data so that the magnified virtual data can blend in seamlessly or near seamlessly with the non-magnified live data, e.g. the live data seen through one or more partially or completely transparent portions of the OHMD.

The magnification of a portion or all of the virtual data can be at preset levels, e.g. 1.5×, 2.0×, 3.0×, 4.0×, or 5.0× or any other magnification level, e.g. a range from 0-1×, 0-2×, 0-3×, 0-5×, 0-10×, 10-20×. The magnification can be continuous, e.g. on a sliding scale. The magnification can be selected by the user and/or surgeon, for example using voice commands, eye commands or using a virtual keyboard interface displayed by the OHMD.

Both portions or all of live data and virtual data can be displayed using magnification or no magnification. Non-limiting examples of possible magnification combinations between live data and virtual data are provided below.

TABLE 5

Exemplary, non-limiting combinations of magnifications of live data and/or virtual data.

| Virtual data | Live data, e.g. as captured by image capture system and displayed by OHMD: Original size | Portions magnified | All magnified | Portions minified | All minified |
|---|---|---|---|---|---|
| Original size | X | X | X | X | X |
| Portions magnified | X | X | X | X | X |
| All magnified | X | X | X | X | X |
| Portions minified | X | X | X | X | X |
| All minified | X | X | X | X | X |

X denotes type of magnification mode combinations used or possible

The magnification of live data and virtual data can be the same. The magnification of live data and virtual data can be different. Virtual data can be partially, e.g. affecting only part of the displayed virtual data, or all magnified. Live data can be partially, e.g. affecting only part of the displayed live data, or all magnified. Virtual data can be magnified while live data are not magnified. Live data can be magnified while virtual data are not magnified. Any combination is possible.

The term magnification includes also displays wherein the live data or the virtual data are displayed in a format or with a magnification that is smaller than live data seen through transparent portions of the OHMD for a given distance or seen through one or more image or video capture systems with display by a virtual reality HMD (e.g. non-see-through).

The magnification of live data (e.g. video images) and/or virtual data [e.g. virtual data of the patient and, principally any virtual data, e.g. portions of a virtual surgical plan, a predetermined start point, a predetermined start position, a predetermined start orientation or alignment, a predetermined intermediate point(s), a predetermined intermediate position(s), a predetermined intermediate orientation or alignment, a predetermined end point, a predetermined end position, a predetermined end orientation or alignment, a predetermined path, a predetermined plane, a predetermined cut plane, a predetermined contour or outline or cross-section or surface features or shape or projection, a predetermined depth marker or depth gauge, a predetermined stop, a predetermined angle or orientation or rotation marker, a predetermined axis, e.g. rotation axis, flexion axis, extension axis, a predetermined axis of a virtual surgical tool, a virtual surgical instrument, a virtual surgical guide [e.g. a virtual axis, virtual plane or virtual cut block], a virtual trial implant, a virtual implant component, implant or device, non-visualized portions for one or more devices or implants or implant components or surgical instruments or surgical tools, and/or one or more of a predetermined tissue change or alteration, and/or one or more of a predetermined position and/or orientation of a virtual surgical tool, virtual surgical instrument, virtual surgical guide [e.g. a virtual axis, virtual plane or virtual cut block], a virtual trial implant, a virtual implant component, implant or device] can be applied around a central point, e.g. an anchor point, an anatomic landmark, a pin entry into a bone, a screw head, or central axis of the field of view of the OHMD, a pin axis or a screw axis or any other axis, e.g. an anatomic axis (e.g. through a portion or the center of a pedicle) or a biomechanical axis or around an anchor point or a central point or an axis, e.g. a long axis, of a virtual and/or physical tool, instrument, implant and/or device. A central axis or axis around which the live and/or virtual data can be magnified can be an anatomic axis (e.g. through a portion or the center of a pedicle) or a biomechanical axis or an axis, e.g. a long axis, of a virtual and/or physical tool, instrument, implant and/or device, or a virtual axis, e.g. derived in a virtual surgical plan.

When a central point is used, the coordinates of the central point in the live data of the patient as seen by the surgeon's right eye through the OHMD unit will be the same as the view coordinates of the central point in the virtual data of the patient seen by the surgeon's right eye projected by the display of the OHMD unit; the coordinates of the central point in the live data of the patient as seen by the surgeon's left eye through the OHMD unit will be the same as the view coordinates of the central point in the virtual data of the patient seen by the surgeon's left eye projected by the display of the OHMD unit. When a central axis or any other axis is used, the coordinates of the central axis or other axis in the live data of the patient as seen by the surgeon's right eye through the OHMD unit will be the same as the view coordinates of the central or other axis in the virtual data of the patient seen by the surgeon's right eye projected by the display of the OHMD unit; the coordinates of the central axis or other axis in the live data of the patient as seen by the surgeon's left eye through the OHMD unit will be the same as the view coordinates of the central axis or other axis in the virtual data of the patient seen by the surgeon's left eye projected by the display of the OHMD unit. When stereoscopic projection is used with the left and right displays of the OHMD unit, the view coordinates for the left display and the right display of the OHMD unit will be different for the left eye and the right eye; the difference in view coordinates is a reflection of the parallax. For example, when the user or surgeon elects to turn on magnification of live and/or virtual data, the magnification can be applied around a central point or axis, e.g. an anatomic or other axis, of the last unmagnified field of view. The system including its software can optionally apply the magnification automatically around the central point or axis, e.g. an anatomic or other axis, of the last field of view. Alternatively, the user and/or surgeon can use a different central point or central axis or other axis as the center around which the live and/or virtual data are being magnified. The central point or central axis can, for example, coincide with the center of a pedicle, when spinal surgery is contemplated. The central axis can coincide with an acetabular or femoral axis, e.g. an anteversion axis, or a predetermined reaming axis, e.g. in hip or shoulder joint replacement. The central axis can, for example, be a predetermined path. The central point, can, for example, be an endpoint. The central point or central axis can, for example, be the center of an acetabulum when hip replacement or other hip surgery is contemplated. The central point or central axis can, for example, be the center of a glenoid when shoulder surgery is contemplated. The central point or central axis or other axis for magnification can be pre-selected for various anatomic sites or surgical fields or surgeries contemplated, e.g. hip replacement, knee replacement surgery, knee arthroscopy or spinal fusion. Using, for example, one or more image and/or video capture systems and/or 3D scanner integrated into, attached to or separate from the ARDD (e.g. OHMD) or using intra-operative imaging, one or more anatomic structures can optionally be identified using standard image processing techniques (e.g. the acetabulum and its center) and the central point or central axis for any magnified views can optionally be set or defined automatically.

Any of the foregoing magnified display types for the display of virtual data by one or more ARDD (e.g. OHMD) can be performed using adjustment or selection of the focal plane or focal point for the display of the virtual data, for example based on coordinates of the ARDD (e.g. OHMD) and/or the coordinates of the surgical site or anatomic structure(s) on which surgery is contemplated to be performed or is being performed on and/or the coordinates of one or more physical surgical tools, instruments, implants or devices.

Displaying Surgical Instruments and/or Medical Devices/Implantables

In some embodiments, surgical instruments or medical devices or implantables can be displayed virtually with the live data of the patient. The virtual data surgical instrument or virtual implantable can be shown by the HMD superimposed onto the live data of the patient including the live data surgical instrument.

The HMD can show the virtual surgical instrument or the virtual implantable indicating the desired orientation or direction or placement of the virtual surgical instrument or the virtual implantable, for example using a virtual surgical plan. Optionally, the HMD can display directional markers such as an intended path derived from a surgical plan to help guide the surgeon direct the physical surgical instrument or the physical implantable.

The physical surgical instrument or physical implantable can be scanned preoperatively to derive its shape and/or dimensions for subsequent display of a derived shape or dimension of a virtual representation of the surgical instrument or the implantable by the HMD. Alternatively, a CAD file or 3D file of the surgical instrument or the implantable can be used. Preoperative scanning of the surgical instrument or the implantable can be performed using any technique known in the art. Scanning of the surgical instrument or the implantable can be performed by the HMD, for example using a built-in image capture device. Scanning of the surgical instrument or the implantable can be performed by a separate image capture device.

In some embodiments, scanning of the surgical instrument or the implantable can occur in two or more dimensions. The more dimensions are used typically the more accurate the resultant virtual representation of the surgical instrument or the implantable.

If an image capture device is used, e.g. one attached to or integrated into the HMD or coupled to or separate from the HMD, the surgical instrument or the implantable can be scanned in one, two or more projections, positions or orientation, e.g. by moving the HMD or the surgical instrument or implantable into different positions or orientations. In some embodiments, the surgical instrument or the implantable can be placed on a tray or fixture for this purpose, which allows to move the surgical instrument or the implantable into different positions and, optionally, to rotate the surgical instrument or the implantable. In some embodiments, the distance between the surgical instrument or the implantable and the image capture device, including an image capture device attached to or integrated into the HMD or coupled to or separate from the HMD, is fixed, while the surgical instrument or the implantable are being scanned.

Scans of the physical surgical instrument or implantable can then be used to derive a virtual 2D or 3D representation of the surgical instrument or the implantable.

By scanning the surgical instrument or the implantable intraoperatively, the surgeon has great flexibility in using different surgical instruments or implantables which he can change and modify and, optionally, integrate into his physical or virtual surgical plan.

The surgeon can optionally store each surgical instrument or implantable that has been scanned in this manner in a virtual library of surgical instruments or implantables. The virtual surgical instruments or implantables stored in this manner can be named and stored for future use in subsequent surgical procedures in other patients. By storing the virtual surgical instruments or implantables the need for repeat scans of the same surgical instrument or same type or shape of implantable is obviated.

In some embodiments, the surgeon can use the virtual data of the surgical instrument or implantables that were previously generated in a new surgical plan for another, new patient. The surgeon can select a desired virtual surgical instrument or implantable from the virtual library and use the virtual surgical instrument or the virtual implantable in his or her virtual surgical plan.

When the surgeon performs the physical surgery and the HMD displays optionally the virtual surgical instrument or implantable, optionally superimposed onto or displayed near the physical surgical instrument or implantable, the software can optionally compare the size and shape of the physical surgical instrument or implantable with that of the previously selected virtual surgical instrument or implantable. Alternatively, the surgeon can visually compare the size and/or shape of the virtual and the physical surgical instrument or implantable.

If a size and/or shape mismatch is detected, the software can send an alert or alarm to the surgeon, e.g. visual or audible, that indicates a mismatch. A mismatch can indicate to the surgeon that the accuracy of registration of virtual data and live data has been compromised and that re-registration may be required. A mismatch can also indicate to the surgeon that the wrong physical surgical instrument or implantable has been selected in comparison to the previously identified virtual surgical instrument or implantable. In this case, the surgeon can check the virtual surgical plan or the physical surgical plan and modify either or both, for example by selecting a different size or shape virtual or live surgical instrument or implantable.

Stereoscopic and Non-Stereoscopic 3D Display of Virtual Data of the Patient with Superimposition on Live Data of the Patient In some embodiments, the HMD can display a virtual 2D or 3D image of the patient's normal or diseased tissue or an organ or a surgical site or target tissue with a view angle or a perspective or projection that is different for the display for the left eye compared to the display for the right eye resulting in a stereoscopic projection of the anatomy or the pathologic tissue. The virtual data of the patient is thus superimposed on the live data of the patient, e.g. the surgical site, for the left and right eye of the surgeon, respectively, using both the left and the right view angle for the surgeon. This means that two separate views are rendered from the virtual 2D or 3D data sets, one for the left eye and one for the right eye. Multidimensional views exceeding three dimensions generated for the left eye and the right eye are possible. For example, in addition to the virtual anatomy of the patient vascular flow or joint motion can be displayed separately for the left eye and the right eye. The difference in perspective between the left eye and the right eye projection of virtual data or parallax can be selected or programmed so that it will change, for example, with the distance of the HMD, the surgeon's head or the surgeon's eye in relationship to the target site, surgical site or target tissue. The distance between the surgeon's or operator's eyes can also be taken into account. In some embodiments, the difference in perspective or parallax will be selected or programmed so that a 3D effect is generated in a stereoscopic 3D manner or effect. The difference in perspective or parallax can change depending on any changes in the distance of the HMD, the surgeon's or operator's head or the surgeon's or operator's eye in relationship to the target site, surgical site or target tissue. For example, as the surgeon or operator moves away from the target site, surgical site or target tissue, the difference in perspective or parallax can decrease. As the surgeon or operator moves towards the target site, surgical site or target tissue, the difference in perspective or parallax can increase. The decrease or increase can be linear, non-linear, exponential or algorithmic. Any other mathematical function is possible. In some embodiments, the difference in perspective or parallax will change similar to the change experienced by the human eye as the surgeon or operator moves towards or away from a target.

The distance of the HMD, the surgeon's or operator's head or the surgeon's or operator's eye in relationship to the target site, surgical site or target tissue can be measured via image capture, anatomic landmark embodiments, image capture used in conjunction with calibration or registration phantoms, surgical navigation or any of the other embodiments described in this disclosure and or spatial mapping. The distance and any changes in distance of the HMD, the surgeon's or operator's head or the surgeon's or operator's eye in relationship to the target site, surgical site or target tissue can be used to change the difference in perspective views or parallax in views for the left eye and the right eye.

FIGS. 11A-11B are flow charts summarizing model generation, registration and view projection for one or more ARDD (e.g. OHMD), e.g. by a primary surgeon, second surgeon, surgical assistant nurse, or others. Pre-operative, intra-operative or post-operative images of the patient can be acquired 240. The image data can optionally be segmented 241. 3D reconstructions of the patient's anatomy or pathology including multiple different tissues, e.g. using different colors or shading, can be generated 242. Virtual 3D models of surgical instruments and devices components can be generated which can include their predetermined position, location, rotation, orientation, alignment and/or direction 243. The virtual 3D models can be registered, for example in relationship to the ARDD (e.g. OHMD) and the patient 244. The virtual 3D models can be registered relative to the live patient data 245. Optionally, adjustments can be made for different view perspectives, parallax, skin, skin movement and other tissue specific issues 246. Different perspective views can be generated for the user's left eye and right eye to facilitate a stereoscopic viewing experience, e.g. like an electronic hologram, of the virtual models of subsurface or hidden anatomic or pathologic tissues 247 and the virtual 3D models of tools, instruments, implants and devices 248. Virtual patient data 249 and virtual 3D models of tools, instruments, implants and devices 250 can be displayed in the ARDD (e.g. OHMD), optionally with different view perspectives adjusted for the left and the right eye of the user 251 and 252. Left eye and right eye offsets or parallax can optionally be adjusted based on the distance from the ARDD (e.g. OHMD), surgeon head or surgeon eyes to the surgical site using, for example, depth sensors or spatial mapping or other registration techniques and also based on inter-ocular distance 253. Polarization or color techniques for stereoscopic views 254 can be combined with electronic holograms such as those provided by the Microsoft Hololens.

Figure 11C:
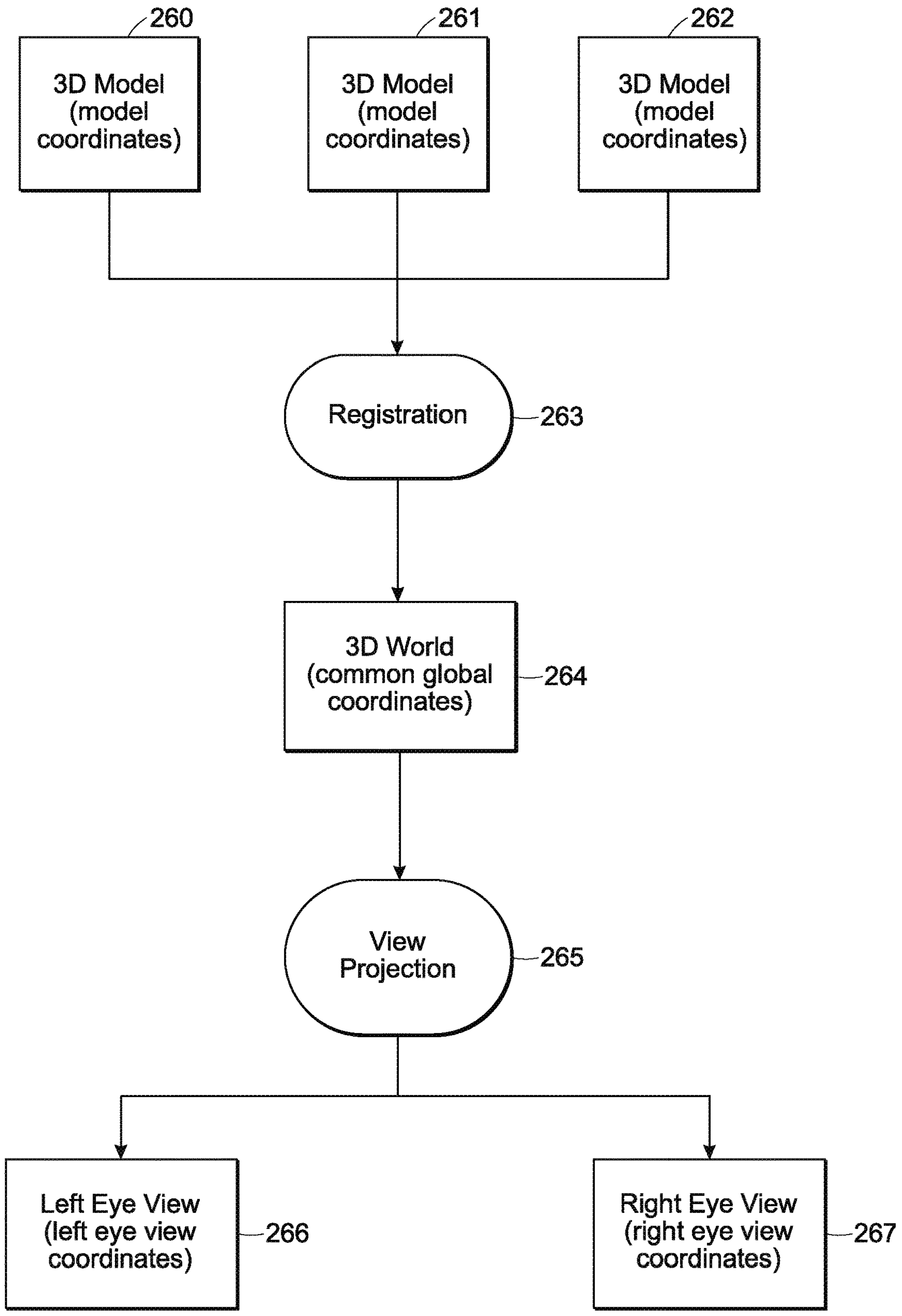

In an alternative description in FIG. 11C, multiple 3D models 260, 261, 262 can be generated, e.g. one for subsurface anatomic or pathologic structures of the patient, one for virtual surgical tools or instruments and one for virtual surgical implant components. These can be registered, e.g. in a common coordinate system or multiple coordinate systems using coordinate transfers, also with the ARDD (e.g. OHMD) 263. Using shared coordinates for the different virtual 3D models 260, 261, 262 multiple viewers using multiple ARDD (e.g. OHMD) can share a 3D World 264 with projection or display of one or more of the models onto the live data of the patient 265. The display can be generated separately for the left eye of each user using the user's left eye coordinates 266 and the right eye of each user using the user's right eye coordinates 267.

Stereoscopic views or different perspective views or views with a parallax for the left eye and the right eye can be generated for multiple virtual data sets or data volumes of the patient. Any of the dimensions listed in Table 1 or virtual structures, tissues or data mentioned in the application can be displayed separately for the left eye and the right eye using stereoscopic views or different perspective views or views with a parallax, simultaneously, non-simultaneously, or sequentially. In addition, any of the virtual data in Table 6 can be displayed using stereoscopic views or different perspective views or views with a parallax for the left eye and the right eye. Multiple of the data listed in Table 6 can be displayed simultaneously, non-simultaneously or sequentially, for example also with the live data or images of the patient seen through the ARDD, stereoscopically or non-stereoscopically:

TABLE 6: Exemplary, non-limiting list of virtual data of the patient, surgical sites and alterations to surgical sites, surgical instruments and surgical steps or procedures, and medical devices that can be displayed, optionally simultaneously, using stereoscopic views or different perspective views or views with a parallax for the left eye and the right eye or non-stereoscopically. Virtual data are typically displayed in conjunction with viewing or displaying live data of the patient. Virtual data can be displayed stereoscopically or non-stereoscopically or combinations thereof if multiple virtual data sets are displayed in the ARDD.

TABLE 6A: Exemplary virtual data of the patient that can be displayed stereoscopically or non-stereoscopically

- Native anatomy, e.g.
  - Gyri of the brain
  - Venous sinus of the brain
  - Arterial structures of the brain
  - Brain lesion
  - Brain tumor
  - Features of the face
  - Features of an ear
  - Liver margin
  - Liver lobes
  - Spleen margin
  - Kidney, renal outline
  - One or more osteophytes
  - Bone spurs
  - Bony anatomy
  - Bony deformity
  - Acetabular rim of a hip
  - Tri-radiate cartilage region
  - Fovea capitis
  - Anterior superior iliac spine
  - Anterior inferior iliac spine
  - Symphysis pubis
  - Femoral head of a hip
  - Femoral neck
  - Greater trochanter
  - Lesser trochanter
  - Condyles of a knee
  - Trochlea of a knee
  - Patella of a knee
  - Tibial plateau of a knee
  - Medial tibial plateau of a knee
  - Lateral tibial plateau of a knee
  - Anterior cruciate ligament of a knee
  - Posterior cruciate ligament of a knee
  - Distal tibia of an ankle joint
  - Distal fibula of an ankle joint
  - Talus of an ankle joint
  - Any ligament or ligamentous structure of a patient
  - Glenoid rim of a shoulder
  - Glenoid of a shoulder
  - Humeral head or neck of a shoulder
  - Facet joint of a spine
  - Spinous process
  - Pedicle of a spine
  - Vertebral endplate
  - Intervertebral disk
  - Herniated disk
  - Any tumor affecting the human body
  - Any of the foregoing tissues on an exposed surface, e.g. surgically exposed
  - Any of the foregoing tissues in a hidden location or a subsurface location
  - Any of the foregoing tissues visualized using an imaging test TABLE 6B: Exemplary virtual surgical sites and alterations to a surgical site that can be displayed stereoscopically or non-stereoscopically

- Alterations planned to surgical site, e.g.
  - Tissue removal
  - Removal of normal tissue
  - Removal of diseased tissue
  - Removal of neoplastic tissue
  - Bone cuts
  - Reaming (e.g. in proximal femur)
  - Broaching (e.g. in proximal femur)
  - Impacting (e.g. in a femur or a tibia)
  - Milling
  - Drilling
  - Tissue transplants
  - Organ transplants
  - Partial or complete resections, e.g. of organs
  - Placement of a medical device
  - Placement of a stent TABLE 6C: Exemplary virtual surgical instruments and surgical steps or procedures that can be displayed stereoscopically or non-stereoscopically

- Tissue cutters,
  - e.g. scalpels, blades, drills, saws, burrs, reamers, broaches
- Tissue ablation devices
  - e.g. heat or cryotherapy
- Handheld robots
- Robotic arms
- Instruments attached to a robot
- Handheld instruments attached to a robotic arm
- Endoscopy devices
- Endoscopic cameras
- Endoscopic cutting devices
- Endoscopic ablation devices
- A predetermined surgical path or predetermined placement or position, location, rotation, orientation, alignment, or direction of one surgical instrument
- A predetermined surgical path or predetermined placement or position, location, rotation, orientation, alignment, or direction of more than one surgical instrument
- A predetermined surgical path or predetermined placement or position, location, rotation, orientation, alignment, or direction of more than one surgical instrument used simultaneously
- A predetermined surgical path or predetermined placement or position, location, rotation, orientation, alignment, or direction of more than one surgical instrument used non-simultaneously
- A predetermined surgical path or predetermined placement or position, location, rotation, orientation, alignment, or direction of more than one surgical instrument used in succession
- A predetermined surgical path or predetermined placement or position, location, rotation, orientation, alignment, or direction of more than one surgical instrument not used in succession
- A predetermined surgical path or predetermined placement or position, location, rotation, orientation, alignment, or direction of more than one surgical instrument used on the same side of a joint
- A predetermined surgical path or predetermined placement or position, location, rotation, orientation, alignment, or direction of more than one surgical instrument used on one or more opposing sides of a joint
- A predetermined surgical path or predetermined placement or position, location, rotation, orientation, alignment, or direction of more than one surgical instrument used on the same vertebral levels
- A predetermined surgical path or predetermined placement or position, location, rotation, orientation, alignment, or direction of more than one surgical instrument used on adjacent vertebral levels
- A predetermined surgical path or predetermined placement or position, location, rotation, orientation, alignment, or direction of more than one surgical instrument used on non-adjacent vertebral levels
- A predetermined surgical path or predetermined placement or position, location, rotation, orientation, alignment, or direction of one surgical instrument used on a vertebral endplate
- A predetermined surgical path or predetermined placement or position, location, rotation, orientation, alignment, or direction of more than one surgical instrument used on a superior vertebral endplate and on an adjacent, inferior vertebral endplate
- A predetermined surgical path or predetermined placement or position, location, rotation, orientation, alignment, or direction of an instrument used for disk removal TABLE 6D: Exemplary virtual medical devices and implants that can be displayed stereoscopically or non-stereoscopically

- Hip replacement components
  - Acetabular cup including predetermined placement or position, location, rotation, orientation, alignment, anteversion, retroversion, inclination, offset, location in relationship to the safe zone
  - Acetabular liner including predetermined placement or position, location, rotation, orientation, alignment, anteversion, retroversion, inclination, offset, location in relationship to the safe zone
  - Femoral head including predetermined placement or position, location, rotation, orientation, alignment, anteversion, retroversion, inclination, offset, location in relationship to the safe zone
  - Femoral neck including predetermined placement or position, location, rotation, orientation, alignment, anteversion, retroversion, inclination, offset, location in relationship to the safe zone (optionally with modular necks)
  - Femoral stem including predetermined placement or position, location, rotation, orientation, alignment, anteversion, retroversion, inclination, offset, location in relationship to the femoral neck cut, the calcar, the greater or the lesser trochanter, the acetabulum
- Knee replacement components
  - Femoral component including predetermined placement or position, location, internal or external rotation, orientation, alignment, flexion, extension, position in relationship to anterior cortex, or mechanical axis or other axis alignment, all optionally through the range of motion
  - Tibial component including predetermined placement or position, location, internal or external rotation, orientation, alignment, flexion, extension, slope, position in relationship to cortical rim, or mechanical axis or other axis alignment, all optionally through the range of motion
  - Polyethylene or other inserts including predetermined placement or position, location, internal or external rotation, orientation, alignment, flexion, extension, slope, position in relationship to cortical rim, or mechanical axis or other axis alignment, all optionally through the range of motion
  - Patellar component including predetermined placement or position, location, internal or external rotation, orientation, alignment, position in relationship to patellar cortical rim, position in relationship to trochlea, optionally in flexion and/or extension and/or through the range of motion, position in relationship to mechanical axis, trochlear axis, trochlear groove, epicondylar axis or other axis alignment
  - Trial femoral component including predetermined placement or position, location, internal or external rotation, orientation, alignment, flexion, extension, position in relationship to anterior cortex, or mechanical axis or other axis alignment, all optionally through the range of motion
  - Trial tibial component including predetermined placement or position, location, internal or external rotation, orientation, alignment, flexion, extension, slope, position in relationship to cortical rim, or mechanical axis or other axis alignment, all optionally through the range of motion

- Trial inserts including predetermined placement or position, location, internal or external rotation, orientation, alignment, flexion, extension, slope, position in relationship to cortical rim, or mechanical axis or other axis alignment, all optionally through the range of motion
- Trial patellar component including predetermined placement or position, location, internal or external rotation, orientation, alignment, position in relationship to patellar cortical rim, position in relationship to trochlea, optionally in flexion and/or extension and/or through the range of motion, position in relationship to mechanical axis, trochlear axis, trochlear groove, epicondylar axis or other axis alignment Spinal screws including predetermined placement or position, location, rotation, orientation, alignment, location in relationship to the pedicle, the cortical bone of the pedicle, the endosteal bone of the pedicle, the posterior cortical bone of the vertebral body, the anterior cortical bone of the vertebral body, the lateral cortical bone of the vertebral body, the superior endplate, the inferior endplate, the intervertebral disk, the vertebral body, the trabecular bone of the vertebral body, any fracture components or fragments, e.g. involving a pedicle, a facet joint or a vertebral body Pedicle screws including predetermined placement or position, location, rotation, orientation, alignment, location in relationship to the pedicle, the cortical bone of the pedicle, the endosteal bone of the pedicle, the posterior cortical bone of the vertebral body, the anterior cortical bone of the vertebral body, the lateral cortical bone of the vertebral body, the superior endplate, the inferior endplate, the intervertebral disk, the vertebral body, the trabecular bone of the vertebral body, any fracture components or fragments, e.g. involving a pedicle, a facet joint or a vertebral body Spinal rods including predetermined placement or position, location, rotation, orientation, alignment, location in relationship to one or more pedicles, the cortical bone of the pedicle, the posterior cortical bone of the vertebral body, the anterior cortical bone of the vertebral body, the lateral cortical bone of the vertebral body, the superior endplate, the inferior endplate, the intervertebral disk, the vertebral body, any fracture components or fragments, e.g. involving a pedicle, a facet joint or a vertebral body, a scoliotic deformity, and predetermined correction for a scoliotic deformity Artificial spinal disks including predetermined placement or position, location, rotation, orientation, alignment, location in relationship to one or more pedicles, the cortical bone of the pedicle, the posterior cortical bone of the vertebral body, the anterior cortical bone of the vertebral body, the lateral cortical bone of the vertebral body, the superior endplate, the inferior endplate, the intervertebral disk, the vertebral body, any fracture components or fragments, e.g. involving a pedicle, a facet joint or a vertebral body, a scoliotic deformity, and predetermined correction for a scoliotic deformity Metal screws, pins, plates, rods for trauma including predetermined placement or position, location, rotation, orientation, alignment, location in relationship to one or more pedicles, the cortical bone of the pedicle, the posterior cortical bone of the vertebral body, the anterior cortical bone of the vertebral body, the lateral cortical bone of the vertebral body, the superior endplate, the inferior endplate, the intervertebral disk, the vertebral body, any fracture components or fragments, e.g. involving a pedicle, a facet joint or a vertebral body, a long bone, a joint, an articular surface, and any predetermined correction for a fracture or fracture deformity Intramedullary nails including predetermined placement or position, location, rotation, orientation, alignment, location in relationship to one or more fracture components or fragments, e.g. a long bone, a joint, an articular surface, and any predetermined correction for a fracture or fracture deformity Vascular stents

- Coronary stents including predetermined placement or position, location, rotation, orientation, alignment, for example in relationship to an area of stenosis, an area of vascular occlusion, a thrombus, a clot, a plaque, an ostium, two or more ostia, an aneurysm, a dissection, an intimal flap, adjacent vessels, adjacent nerves
- Carotid stents including predetermined placement or position, location, rotation, orientation, alignment, for example in relationship to an area of stenosis, an area of vascular occlusion, a thrombus, a clot, a plaque, an ostium, two or more ostia, an aneurysm, a dissection, an intimal flap, adjacent vessels, adjacent nerves
- Aortic stents including predetermined placement or position, location, rotation, orientation, alignment, for example in relationship to an area of stenosis, an area of vascular occlusion, a thrombus, a clot, a plaque, an ostium, two or more ostia, an aneurysm, a dissection, an intimal flap, adjacent vessels, adjacent nerves
- Femoral stents including predetermined placement or position, location, rotation, orientation, alignment, for example in relationship to an area of stenosis, an area of vascular occlusion, a thrombus, a clot, a plaque, an ostium, two or more ostia, an aneurysm, a dissection, an intimal flap, adjacent vessels, adjacent nerves Cochlear implants including predetermined placement or position, location, rotation, orientation, alignment, for example in relationship to osseous structures, neural structures, auditory structures, the labyrinth Retinal implants including predetermined placement or position, location, rotation, orientation, alignment, for example in relationship to osseous structures, neural structures, vascular structures Neural implants including predetermined placement or position, location, rotation, orientation, alignment, for example in relationship to neural structures, vascular structures, osseous structures Neuroprosthetics including predetermined placement or position, location, rotation, orientation, alignment, for example in relationship to neural structures, vascular structures, osseous structures Implants for deep brain stimulation, e.g. for treatment of Parkinson's disease including predetermined placement or position, location, rotation, orientation, alignment, for example in relationship to neural structures, vascular structures, osseous structures.

The list in Tables 6A-6D is only exemplary and is not meant to be limiting. Any of the exemplary virtual data of the patient listed in Table 6A, exemplary virtual surgical sites and alterations to a surgical site listed in Table 6B, exemplary virtual surgical instruments and surgical steps or procedures listed in Table 6C, and exemplary virtual medical devices and implants listed in Table 6D can be displayed by the ARDD in two, three or more dimensions (e.g. as described also in Table 4), using stereoscopic as well as non-stereoscopic projections or view. Thus, the present disclosure is not limited to stereoscopic displays and/or 2D displays and/or 3D displays. Any combination of virtual displays is possible, e.g. 3D stereoscopic patient anatomy or surgical site with 2D surgical instrument displays and/or 2D medical device displays, or 3D patient anatomy, with 3D non-stereoscopic surgical instrument display and/or 3D stereoscopic medical device display.

Any of the foregoing display types for the display of virtual data, e.g. virtual tools, virtual instruments, virtual implants, and/or virtual devices, by one or more ARDD can be performed using adjustment or selection of the focal plane or focal point for the display of the virtual data, for example based on coordinates of the ARDD and/or the coordinates of the surgical site or anatomic structure(s) on which surgery is contemplated to be performed or is being performed on and/or the coordinates of one or more physical surgical tools, instruments, implants or devices.

Tissue Morphing Including Bone Morphing, Cartilage Morphing

In some embodiments, the shape of one or more of the patient's tissues, such as a bone, a cartilage, a joint or an organ, can be estimated or morphed in three dimensions intra-operatively, e.g. during the surgery. The estimating or morphing of the patient's tissue shape, e.g. bone shape, cartilage shape, joint shape or organ shape, can help reduce or obviate the need for pre-operative imaging and, in select embodiments, intra-operative imaging.

In some embodiments, 2D preoperative data can be used and the shape of one or more of the patient's tissues, such as a bone, a cartilage, a joint or an organ, can be estimated or morphed in three dimensions pre-operatively, e.g. prior to surgery.

Bone Morphing and/or Cartilage and/or Tissue Morphing Using Pre-Operative Imaging or Intra-Operative Imaging In some embodiments, one or more two-dimensional images of the patient can be obtained. These images can, for example, include one or more x-rays of the patient. X-rays can be obtained using digital acquisition techniques. X-rays can also be obtained using conventional film based technique, in which case the x-rays can be subsequently digitized using a scanner. Exemplary x-ray images can include:

- Spine: AP, PA, lateral, oblique views, and/or angled views, flexion, extension views, lateral bending views; upright, supine or prone
- Hip: AP, PA, lateral, oblique views, angled views, and/or frogleg view; standing or lying, weight-bearing or non-weight-bearing
- Knee: AP, PA, lateral, oblique views, angled views, tunnel view, and/or Merchant view, sunrise view and the like, any other patellar, femoral or tibial views known in the art; standing or lying, weight-bearing or non-weight-bearing
- Full leg x-rays films; standing or lying, weight-bearing or non-weight-bearing
- Full femur x-rays; standing or lying, weight-bearing or non-weight-bearing
- Full tibia x-rays; standing or lying, weight-bearing or non-weight-bearing
- Selective leg x-rays films, e.g. hip, knee, ankle; standing or lying, weight-bearing or non-weight-bearing X-rays can be obtained with the patient in upright, supine and/or prone position. X-rays can be obtained with the patient in weight-bearing and in non-weight-bearing position. In some embodiments, x-rays are obtained intra-operatively, for example with the patient already positioned and placed for the intended surgical procedure.

The x-ray data of the patient can be transferred into a computer. Optionally, image processing can be applied to segment select patient tissues, such as a bone or vertebra or vertebral structure, subchondral bone, cortical bone, osteophytes. Image processing can, for example, also be applied to determine the edge of select patient tissues, such as a bone or vertebra or vertebral structure, subchondral bone, cortical bone, osteophytes. When subchondral bone has been identified and/or derived from the images, including a subchondral bone curvature and/or geometry and/or shape, a cartilage shape, curvature or geometry can be superimposed or added to the subchondral bone shape. The cartilage shape, curvature or geometry can assume a standard cartilage thickness for a given joint and/or a given patient, e.g. 1.0 mm, 1.5 mm, 2.0 mm, 2.5 mm, 3.0 mm, 3.5 mm. The cartilage geometry can also assume a variable cartilage thickness, e.g. depending on the location of the cartilage in the joint and/or on the articular surface and/or based on the patient's age, gender, race, body weight, and/or BMI, as well as underlying deformity, e.g. *varus* or valgus deformity.

In some embodiments, the 2D x-rays images can be used to derive information about the dimensions and shape of the anatomic structure(s) included in the x-ray. Some of this information can be, for example:

- Anatomic landmark(s)
- Distances and/or dimensions between two or more known landmarks/structures
- Angles between landmarks
- Anatomic axes
- Biomechanical axes
- Curvature information
- Curvature information of a bone surface
- Curvature information of a subchondral bone surface
- Curvature information of an articular surface
- Change in curvature from convex to concave
- Change in curvature from concave to convex
- Surface information
- Edge information
- Shape information, e.g. when information from multiple x-rays images obtained with different projection or beam angles is combined or aggregated
- Length information, e.g. in AP, ML, SI direction, AP, ML, SI plane, oblique planes
- Width information, e.g. in AP, ML, SI direction, AP, ML, SI plane, oblique planes
- Depth information, e.g. in AP, ML, SI direction, AP, ML, SI plane, oblique planes Any of the foregoing information can be external on the surgical field, e.g. directly visible through a see-through ARDD or the eye of a surgeon without an ARDD and/or on an accessible surface. Any of the information can be internal to the surgical field, e.g. not directly visible through a see-through ARDD display or the eye of a surgeon without an ARDD and/or not on an accessible surface and/or hidden by other tissue, e.g. bone, cortical bone and/or soft-tissue.

Examples of landmarks, distances, dimensions, surfaces, edges, angles, axes, curvatures, shapes, lengths, widths, depths and/or other features for the spine, the hip, the knee and the shoulder joint that can be used for bone morphing and 3D model selection, development, derivations, and deformations in any surgeries of these or to these areas are provided below in Table 7. These examples are in no way meant to be limiting, but are only exemplary in nature. Someone skilled in the art will readily recognize other landmarks, distances, dimensions, surfaces, edges, angles, axes, curvatures, shapes, lengths, widths, depths and/or other features for these joints as well as any other joint in the human body. These landmarks, distances, dimensions, surfaces, edges, angles, axes, curvatures, shapes, lengths, widths, depths and/or other features for the spine, the hip, the knee and the shoulder joint can be obtained using, for example, a pointer, a 3D scanner, a video system and/or an image capture system, or an imaging technique, e.g. x-ray, cone beam CT, CT, O-arm, MRI, ultrasound, or combinations thereof. Landmarks, distances, dimensions, surface point, edges, angles, axes, curvatures, shapes, lengths, widths, depths and/or other features for the spine, the hip, the knee and the shoulder joint can be used to generate 3D surfaces based on data obtained with a pointer, a 3D scanner, a video system and/or an image capture system, or an imaging technique, e.g. x-ray, cone beam CT, CT, O-arm, MRI, ultrasound, or combinations thereof. Surface points, 3D surfaces obtained with at least one of a pointer, a 3D scanner, a video system and/or an image capture system, or an imaging technique, e.g. x-ray, cone beam CT, CT, O-arm, MRI, ultrasound, or combinations thereof can be combined.

For any of the embodiments, landmarks, distances, dimensions, surfaces, edges, angles, axes, curvatures, shapes, lengths, widths, depths and/or other features can be external on the surgical field, e.g. directly visible through a see-through ARDD or the eye of a surgeon without an ARDD and/or on an accessible surface; landmarks, distances, dimensions, surfaces, edges, angles, axes, curvatures, shapes, lengths, widths, depths and/or other features can be internal to the surgical field, e.g. not directly visible through a see-through ARDD display or the eye of a surgeon without an ARDD and/or not on an accessible surface and/or hidden by other tissue, e.g. bone, cortical bone and/or soft-tissue.

TABLE 7. Examples of landmarks, distances, dimensions, surfaces, edges, angles, axes, curvatures, shapes, lengths, widths, depths and/or other features for the spine, the hip, the knee and the shoulder joint that can be used for bone morphing and/or 3D model selection, development, derivations, and deformations in any surgeries of these or to these areas.

Spine:

Cortical bone of a pedicle; Endosteal bone of a pedicle; Posterior cortical bone of a vertebral body; Anterior cortical bone of a vertebral body; Lateral cortical bone of a vertebral body; Superior endplate; Inferior endplate; Intervertebral disk; Vertebral body; Trabecular bone of the vertebral body; Superior facet; Inferior facet; Spinous process; Any fracture components or fragments, e.g. involving a pedicle, a facet joint or a vertebral body; Endplate shape, e.g. sagittal plane; Endplate shape, e.g. coronal plane; Schmorl's node(s); Interpedicular distance; Intervertebral height or disk height; AP length of vertebral body, e.g. at level of inferior endplate, superior endplate, mid-portion; ML width of vertebral body, e.g. at level of inferior endplate, superior endplate, mid-portion; Oblique width vertebral body, e.g. at level of inferior endplate, superior endplate, mid-portion; Vertebral body height, e.g. anterior, mid-portion, posterior; Pedicle length; Pedicle width; Pedicle height; Pedicle angle; Spinous process SI thickness, e.g. anterior, mid-portion, tip; Spinous process width, e.g. anterior, mid-portion, tip; Spinous process inferior angle from origin; Facet dimensions, AP, ML, SI; Facet angle, e.g. angle of joint formed between inferior facet of superior vertebra and superior facet of inferior vertebra; Lamina SI height; Lamina AP width; Lamina ML radius, diameter; Spinal canal AP diameter, ML diameter; Lordosis; Kyphosis; Scoliosis; Side bending, e.g. left lateral, right lateral; Cobb angle; Lumbosacral angle Hip:

Lateral acetabular point or edge; Medial acetabular point or edge; Superior acetabular point or edge; Anterior acetabular point or edge; Posterior acetabular point or edge; Triradiate cartilage and region; Acetabular labrum, medial, lateral, anterior, posterior (e.g. when x-ray contrast has been injected into the joint); Fovea capitis; Femoral head subchondral bone, contour, outline; Femoral head-neck/junction, curvature, convex, concave; Greater trochanter, e.g. lateral cortex, superior cortex, anterior cortex, posterior cortex; Sulcus point (lowest point between greater trochanter and femoral neck), e.g. as seen on a frontal or AP x-ray; Sulcus curvature; Greater trochanter/sulcus transition, curvature, convex, concave; Lesser trochanter; Lesser trochanter/femoral neck transition, curvature; Lesser trochanter/femoral shaft transition; Femoral shaft, anterior cortex, posterior cortex, medial cortex, lateral cortex; Anterior cortex, posterior cortex, medial cortex, lateral cortex for any of the foregoing structures as applicable; Endosteal bone, anterior, posterior, medial, lateral for any of the foregoing structures as applicable; Femoral neck angle; Femoral shaft angle; Acetabular angle; Acetabular anteversion; Femoral anteversion; Femoral shaft angle; Pelvic tilt; Femoral offset; Shenton's line; Hilgenreiner line; Perkin line; Acetabular index Knee:

Medial wall of the femoral notch; Lateral wall of the femoral notch; Roof of the femoral notch; Femoral notch geometry; Femoral notch shape; Distance/line/plane from roof of femoral notch to lowest point or other point or surface on medial femoral condyle; Distance/line/plane from roof of femoral notch to lowest point or other point or surface on lateral femoral condyle; Medial wall of the medial condyle; Lateral wall of medial condyle; Medial wall of lateral condyle; Lateral wall of the lateral condyle; Medial edge of the medial condyle; Lateral edge of medial condyle; Medial edge of lateral condyle; Lateral edge of the lateral condyle; Medial edge of the medial condyle after one or more bone resections or bone removals; Lateral edge of medial condyle after one or more bone resections or bone removals; Medial edge of lateral condyle after one or more bone resections or bone removals; Lateral edge of the lateral condyle after one or more bone resections or bone removals; Medial epicondylar eminence; Lateral epicondylar eminence; Medial femoral condyle shape, e.g. radii, convexities, concavities, curvatures, e.g. sagittal J-curve; Lateral femoral condyle shape, e.g. radii, convexities, concavities curvatures, e.g. sagittal J-curve; Intercondylar notch shape; Intercondylar notch surface features; Medial tibial spine; Lateral tibial spine; Anteromedial tibial rim; Anterolateral tibial rim; Medial tibial rim; Lateral tibial rim; Posterior tibial rim; Anteromedial tibial edge; Anterolateral tibial edge; Medial tibial edge; Lateral tibial edge; Posterior tibial edge; Anteromedial tibial edge after one or more bone resections or bone removals; Anterolateral tibial edge after one or more bone resections or bone removals; Medial tibial edge after one or more bone resections or bone removals; Lateral tibial edge after one or more bone resections or bone removals; Posterior tibial edge after one or more bone resections or bone removals; Lowest point of the medial plateau; Lowest point of the lateral plateau; Highest point of the medial plateau; Highest point of the lateral plateau; Medial tibial plateau shape; Lateral tibial plateau shape; Medial tibial plateau sagittal curvature; Lateral tibial plateau sagittal curvature; Medial tibial plateau coronal curvature; Lateral tibial plateau coronal curvature; Medial tibial plateau surface features, e.g. radii, convexities, concavities; Lateral tibial plateau surface features, e.g. radii, convexities, concavities; Femoral osteophytes; Tibial osteophytes; Patellar osteophytes; Femoral subchondral cysts; Tibial subchondral cysts; Patellar osteophytes; Patellar subchondral cysts; Trochlea osteophytes; Trochlea subchondral cysts; Patellar sagittal curvature; Patellar coronal curvature; Patellar axial curvature; Patellar surface features, e.g. radii, convexities, concavities; Patellar surface features, e.g. radii, convexities, concavities; Patellar circumference shape; Patellar rise; Patellar thickness; Trochlear depth; Trochlear sagittal curvature; Trochlear axial curvature; Trochlear coronal curvature; Trochlea sagittal shape; Trochlea axial shape; Trochlea coronal shape; Trochlear angle; Trochlear sulcus depth; Epicondylar axis; Posterior femoral axis; Trochlear rotation axis; Mechanical axis; Q-angle Shoulder:

Clavicle; AC joint; Acromion; Glenoid; Scapula; Coracoid; Humeral head; Humeral neck; Humeral shaft; Glenoid osteophytes; Humeral osteophytes; AC joint osteophytes; Glenoid subchondral cysts; Humeral subchondral cysts; AC joint subchondral cysts; Acromio-humeral distance; Acromio-humeral space; Deepest point of glenoid; Most anterior point or edge of glenoid; Most posterior point or edge of glenoid; Most superior point or edge of glenoid; Most inferior point or edge of glenoid; Glenoid shape; Humeral head shape; Glenoid sagittal curvature, e.g. radii, convexities, concavities; Glenoid axial curvature, e.g. radii, convexities, concavities; Glenoid coronal curvature, e.g. radii, convexities, concavities; Humeral head sagittal curvature, e.g. radii, convexities, concavities; Humeral head axial curvature, e.g. radii, convexities, concavities; Humeral head coronal curvature, e.g. radii, convexities, concavities; Mechanical axis; Anatomical axis; Angle of inclination; Axis of head and neck; Axis through epicondyles; Angle of retroversion.

These landmarks, distances, dimensions, surfaces, edges, angles, axes, curvatures, shapes, lengths, widths, depths and/or other features for the spine, the hip, the knee and the shoulder joint can also be used for the virtually placing a device and/or implant component and/or instrument, virtually evaluating and/or selecting a good fitting or the best fitting device and/or implant component and/or instrument, evaluating the virtual shape and/or selecting a virtual device and/or implant component and/or instrument with a preferred shape, evaluating the virtual function and/or selecting a device and/or implant component and/or instrument with a preferred virtual function, virtually determining the preferred position of a device and/or implant component and/or instrument, virtually determining the preferred orientation of a device and/or implant component and/or instrument, virtually determining the preferred alignment of a device and/or implant component and/or instrument, and/or virtually determining and/or selecting a preferred virtual anchor and/or attachment and/or fixation member. These landmarks, distances, dimensions, surfaces, edges, angles, axes, curvatures, shapes, lengths, widths, depths and/or other features for the spine, the hip, the knee and the shoulder joint can also be used for other applications throughout the application that utilize anatomic information, e.g. measurements, developments of virtual surgical plans, ARDD projection of virtual data onto such landmarks, distances, dimensions, surfaces, edges, angles, axes, curvatures, shapes, lengths, widths, depths and/or other features etc.

By measuring any of the foregoing landmarks, distances, dimensions, surfaces, edges, angles, axes, curvatures, shapes, lengths, widths, depths and/or other features, including external on the surgical field, e.g. directly visible through a see-through ARDD or the eye of a surgeon without an ARDD and/or on an accessible surface and/or internal to the surgical field, e.g. not directly visible through a see-through ARDD display or the eye of a surgeon without an ARDD and/or not on an accessible surface and/or hidden by other tissue, e.g. bone, cortical bone and/or soft-tissue, it is possible to estimate a 3D shape, volume or surface(s) of a bone, e.g. a proximal femur, a distal femur, a proximal tibia, an acetabulum, a vertebral body and spinal elements and a glenoid and/or a proximal humerus. The more landmarks, distances, dimensions, surfaces, edges, angles, axes, curvatures, shapes, lengths, widths, depths and/or other features are being measured, the more accurate can the estimation of the 3D shape, volume or surface(s) of the bone be. In addition, the more 2D images are being taken or acquired from different view angles, projection angles, beam angles, optionally with the same magnification or different magnifications, optionally with or without magnification correction applied, the more accurate can the estimation of the 3D shape, volume or surface(s) of the bone be.

The 3D shape, volume or surface or curvature of the bone can, for example, be estimated by filling in the information, e.g. intermediate or connecting landmarks, distances, dimensions, surfaces, edges, angles, axes, curvatures, shapes, lengths, widths, depths and/or other features between known landmarks, distances, dimensions, surfaces, edges, angles, axes, curvatures, shapes, lengths, widths, depths and/or other features derived from the one, two, three or more x-ray images. The 3D shape, volume or surface or curvature of the bone can, for example, be estimated by interpolating surfaces between multiple points or by fitting splines.

In some embodiments, a standard model of the bone can be used and can be deformed using one or more of the known landmarks, distances, dimensions, surfaces, edges, angles, axes, curvatures, shapes, lengths, widths, depths and/or other features derived from the x-ray images, including using landmarks, distances, dimensions, surfaces, edges, angles, axes, curvatures, shapes, lengths, widths, depths and/or other features external on the surgical field, e.g. directly visible through a see-through ARDD or the eye of a surgeon without an ARDD and/or on an accessible surface and/or landmarks, distances, dimensions, surfaces, edges, angles, axes, curvatures, shapes, lengths, widths, depths and/or other features internal to the surgical field, e.g. not directly visible through a see-through ARDD display or the eye of a surgeon without an ARDD and/or not on an accessible surface and/or hidden by other tissue, e.g. bone, cortical bone and/or soft-tissue. Such deformations can be performed using various statistical models known in the art.

In some embodiments, a database or library of bone models and tissue models can be used. The one or more of these anatomic landmarks, distances, dimensions, surfaces, edges, angles, axes, curvatures, shapes, lengths, widths, depths and/or other features, e.g. external and/or internal, can be used to identify a standard bone shape and/or a standard cartilage shape by comparing the one or more landmarks, distances, dimensions, surfaces, edges, angles, axes, curvatures, shapes, lengths, widths, depths and/or other external and/or internal features with data in a reference database of reference patients and/or reference bone and/or cartilage shapes and by selecting a 3D model that most closely matches the selected landmarks, distances, dimensions, surfaces, edges, angles, axes, curvatures, shapes, lengths, widths, depths and/or other features. In this manner, the 3D shape of the patient's bones and/or cartilage, e.g. the distal femur and/or the proximal tibia and/or the acetabulum and/or the proximal femur, and/or the vertebral body and/or the spinal elements and/or the glenoid and/or the proximal humerus, can be estimated without the need acquire 3D data or without the need of segmentation of the 3D data or limiting the amount of segmentation needed from available 3D data, e.g. a CT scan or an MRI scan of the patient. The reference database can be, for example, an anatomic reference database from cadaver data. The reference database can also be, for example, scan data, e.g. acquired in the NIH Osteoarthritis Initiative or acquired from imaging data to generate patient specific instruments for knee replacement.

Such scan data can be used to generate a database of 3D shapes of patients with different age, gender, ethnic background, race, weight, height and/or BMI.

Of note, the use 2D imaging data or 3D imaging data, e.g. x-ray, ultrasound, CT or MRI, in combination with one or more reference databases of 3D shape(s) of select anatomic structures, such as a bone, a cartilage, an organ for reducing or limiting or obviating the need for acquiring 3D data or for segmenting 2D or 3D data is applicable to any embodiment described herein including for all other clinical applications, e.g. hip replacement, knee replacement, shoulder replacement spinal surgery, spinal fusion, vertebroplasty, kyphoplasty, ACL repair, ACL reconstruction, fracture fixation, brain surgery, liver surgery, cancer surgery etc.

In some embodiments, a standard model, optionally already deformed using the patient's landmarks, distances, dimensions, surfaces, edges, angles, axes, curvatures, shapes, lengths, widths, depths and/or other features, can be combined or fused with a model selected from a database using the patient's landmarks, distances, dimensions, surfaces, edges, angles, axes, curvatures, shapes, lengths, widths, depths and/or other features. In some embodiments, the model selected from the database can be deformed and/or adapted using the patient's landmarks, distances, dimensions, surfaces, edges, angles, axes, curvatures, shapes, lengths, widths, depths and/or other features. Such deformations can be performed using various statistical models known in the art.

If one or more x-rays are used, they can, for example, be obtained in an AP projection of the knee (or PA), and a lateral projection of the knee. Other views are possible, as known in the art, e.g. a tunnel view, Merchant view, patellar view, oblique views, standing views, supine views, prone views. Optionally, the medial and lateral femoral condyles can be identified on the AP/PA and/or lateral and/or oblique views; optionally, the medial and lateral tibial plateau can be identified on the AP/PA and/or lateral and/or oblique views. Other landmarks, distances, dimensions, surfaces, edges, angles, axes, curvatures, shapes, lengths, widths, depths and/or other features, e.g. external and/or internal, can be identified.

A lateral knee x-ray can, for example, be used to derive curvature information about the medial and the lateral condyle. Two distinct curves can be seen on a lateral knee radiograph, one representing the medial condyle and the other representing the lateral condyle. In most instances, the lateral condyle has a smaller radius than the medial condyle, for example in the central weight-bearing zone. Software can identify and/or segment each curve using, for example, some of the software packages described in Data Segmentation. This can be followed by a curvature analysis assessing the radii of each curve. In some embodiments, the curve with the smaller radii, e.g. in the central weight bearing area, can be assigned as the lateral condyle. Other combinations are possible. If the position of the leg is known relative to the x-ray source and detector panel, e.g. medial side or lateral side of the knee closer to the detector panel, e.g. with lower magnification, the dimensions or magnification of a first condyle can be compared to the dimensions or magnification of the second condyle and the difference in measured dimensions, and, optionally, estimated magnification, can be used to identify the condyle closer to the detector panel on the x-ray, e.g. less magnified, and the condyle further away from the detector panel, e.g. more magnified. The identification of the medial and/or lateral condyle can be manual, e.g. by the operator or surgeon, semi-automatic or automatic.

The foregoing description of techniques to estimate or morph the three-dimensional shape of a patient's bone is only exemplary in nature and is in no way meant to be limiting. Someone skilled in the art will readily recognize other means to estimate the shape of the patient's bone in three dimensions. Any technique known in the art for determining or estimating the three-dimensional shape of a bone from two-dimensional data can be used. Any technique known in the art for modeling and displaying the three-dimensional shape of a bone from two-dimensional data can be used. The resultant 3D model of the patient's bone using any of these techniques can then be displayed by one or more ARDD's, e.g. superimposed onto the patient's live, physical anatomy or surgical site.

Bone and/or Tissue Morphing Using Mechanical Probes and/or Opto-Electronic and/or RF Probes In some embodiments, a mechanical probe can be used to determine the three-dimensional shape of a patient's tissue, e.g. cartilage or bone or organ tissue, intra-operatively. The tissue probe can be attached to a stand or holder. The tissue probe can also be handheld.

The tissue probe can be configured similar to a mechanical detection device known in the art and used, for example, for industrial shape inspection purposes, e.g. coordinate measuring machines (CMM) known in the art, such as, for example, the Faro arm system.

In some embodiments, a mechanical probe can be used that has at least one of an optical marker, e.g. with one or more geometric patterns, e.g. one or more barcodes or QR codes, navigation marker, including infrared markers, retroreflective markers, RF markers, LED and/or IMU attached. The position and/or orientation and/or alignment and/or direction of movement of the probe can be determined then, for example, using a navigation system and/or an image and/or video capture system and/or 3D scanner integrated into, attached to or separate from the ARDD. In embodiments, the mechanical probe is tracked directly, for example using an image or video capture system or 3D scanner integrated into, attached to or separate from the ARDD.

By moving the mechanical probe along the bone, cartilage, tissue and/or organ surface, the position of the tip of the probe can, for example, be registered and, for example, a point cloud can be generated which can be used to generate a 3D surface. Standard techniques known in the art, e.g. tessellation, can be used for this purpose. The point cloud generated by tracking the movement of the mechanical probe, e.g. with one or more attached optical markers with geometric patterns, can be used to generate a 3D model of one or more surface of the patient, e.g. the surgical site. The point cloud can optionally be used to select a 3D model of the patient, e.g. from a pre-existing library of models. The point cloud can optionally be used to deform a 3D model.

Bone and/or Tissue Morphing Using Optical Probes and/or 3D Scanners and/or Image and/or Video Capture Systems In some embodiments, an image and/or video capture system and/or 3D scanner integrated into, attached to or separate from the ARDD can be used to image the patient's bone and/or cartilage and/or tissue and/or ligaments and/or menisci and/or organ surface. With the position, orientation, alignment and/or direction of movement of the image and/or video capture system(s) and/or 3D scanner(s) optionally known, e.g. in a common coordinate system, for example using optical markers, navigation markers including infrared markers, retroreflective markers, RF markers, LEDs and/or IMUs, spatial mapping, and/or depth mapping, images of the patient's bone and/or cartilage and/or tissue and/or ligaments and/or menisci and/or organ surface can be acquired from multiple viewpoints or continuously and, using software and image processing as described in Data Segmentation or spatial mapping techniques as described in Spatial Mapping, images can be used to derive one or more 3D volumes, 3D surfaces and/or 3D shapes of the patient's bone and/or cartilage and/or tissue and/or ligaments and/or menisci and/or organ. The accuracy of such image acquisitions and reconstruction of 3D volumes, 3D surfaces and/or 3D shapes can optionally be enhanced with image and/or video capture systems and/or 3D scanners that use two or more cameras and/or scanners, which can be used to generated parallax information and/or stereoscopic information of the same structures, wherein, for example, the parallax and/or stereoscopic information can be used to enhance the accuracy of the reconstructions. Alternatively, the information from two or more cameras can be merged by averaging the 3D coordinates or detected surface points or other geometric structures such as planes or curved surfaces.

In some embodiments, 3D laser scanners or depth sensors known in the art, such as, for example, the Structure laser scanner provided by Occipital Inc., can be used to image the surface of the patient's bone and/or cartilage and/or tissue and/or ligaments and/or menisci and/or organ. Other 3D scanners known in the art can be used. Any laser scanning, optical or light scanning technique known in the art for determining, estimating or deriving the 3D volume, 3D surface or 3D shape of a structure known in the art can be used.

In some embodiments, the 3D scanner or image and/or video capture system and/or 3D scanner can be attached to an arm or tripod. Images of the patient's bone and/or cartilage and/or tissue and/or ligaments and/or menisci and/or organ can be acquired at a constant distance. Images of the patient's bone and/or cartilage and/or tissue and/or ligaments and/or menisci and/or organ can be acquired at a variable distance. The laser or optical scanner can optionally be used to measure the distance to the patient's bone and/or cartilage and/or tissue and/or ligaments and/or menisci and/or organ during the image acquisition. Using the laser's starting position or the starting position of the image and/or video capture system and/or 3D scanner and/or at least one of an optical marker, navigation marker including infrared markers, retroreflective markers, RF markers, LED and/or IMU, the position, orientation, alignment and/or direction of movement of the image and/or video capture system and/or 3D scanner can be known throughout the acquisition allowing for magnification correction and optional view angle adjustments and/or projection and/or surface generation calculation and/or adjustments and/or corrections.

Combining Pre-Operative and Intra-Operative Data

In some embodiments, 2D or 3D data obtained intra-operatively with a mechanical probe, opto-electronic probe, RF probe, optical probe, image and/or video capture system, laser scanner and/or 3D scanner can be combined with pre-operative data, e.g. pre-operative imaging data and/or a virtual surgical plan.

The 2D or 3D information obtained pre-operatively can, for example, include mechanical axis information, e.g. of the knee and/or lower extremity (e.g. obtained using a standing x-ray), rotation axis information, e.g. of a hip or a knee, e.g. using epicondylar axis information, posterior condylar axis information, tibial tubercle information, one or more AP dimensions of a joint, one or more ML dimensions of a joint, one or more SI dimensions of a joint, a medial condyle curvature and/or a lateral condyle curvature, e.g. as seen on a lateral and/or an AP radiograph, a medial tibial curvature and/or a lateral tibial curvature, e.g. as seen on a lateral and/or an AP radiograph, joint line information, e.g. the location of a medial and/or a lateral joint line in a knee, offset information, e.g. an offset in a hip or an offset between a medial and/or a lateral condyle.

The 2D or 3D data obtained intra-operatively can, for example, include dimensional information, geometric information, curvature information, volume information, shape information, and/or surface information of the tissue, organ, e.g. cartilage and/or bone. The 2D or 3D data obtained intra-operatively can, for example, include information about joint line location, e.g. medial and/or lateral, femoral offsets and/or tibial offsets, measured based on cartilage and/or subchondral bone.

Optionally, adjustments or corrections can be applied to data obtained pre-operatively and/or intra-operatively. For example, osteophytes and/or subchondral cysts can be virtually removed from the pre-operative and/or intra-operative 2D or 3D data. Flattening of a joint surface seen on any of the data can be optionally corrected, e.g. by applying a corrected shape, e.g. using spline surfaces or smoothing functions or averaging functions.

In some embodiments, 2D or 3D pre-operative data can be combined with 2D or 3D intra-operative data. For example, mechanical axis information obtained from a pre-operative standing x-ray can be combined with an intra-operative 3D scan of a joint, e.g. a knee joint or a hip joint. A virtual surgical plan can be developed or derived based on the combined data, for example with resections that are planned to maintain or restore normal mechanical axis alignment or any other alignment desired by the surgeon, e.g. 5% or less of *varus* or valgus alignment of a joint. If a virtual surgical plan has already been developed pre-operatively, the virtual surgical plan can be modified intra-operatively using intra-operative 3D scan information of one or more joints, for example using more accurate intra-operative surface information of the joint or organ.

In some embodiments, 3D surfaces morphed from 2D pre-operative data, e.g. using one or more pre-operative x-rays, can be combined with 3D surfaces derived intra-operatively, e.g. derived using an intra-operative mechanical and/or opto-electronic and/or laser and/or 3D scanner. For example, the pre-operative morphed surfaces of a femoral head can be matched, aligned, superimposed or merged in this manner with the intra-operative surfaces. Or the pre-operative morphed surfaces of one or both femoral condyles and/or tibial plateaus can be matched, aligned superimposed or merged in this manner with their corresponding intraoperative surfaces. By matching, aligning, superimposing or merging surfaces derived from pre-operative and intra-operative data, axis information obtained on pre-operative data, e.g. standing x-rays can be readily superimposed or merged with intra-operative data. The resultant model can be used to develop, derive and/or modify a virtual surgical plan, for example with subsequent display of one or more cut planes or tissue resections or axes by an ARDD.

2D data obtained pre-operatively and/or intra-operatively using 2D to 3D tissue morphing, e.g. bone morphing, for example as described in the disclosure, and morphed into a 3D model can be displayed stereoscopically and/or non-stereoscopically using one or more ARDD displays. In addition, any of a virtual surgical tool, virtual surgical instrument including a virtual surgical guide or cut block, virtual trial implant, virtual implant component, virtual implant or virtual device, a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration can be displayed by the ARDD concurrent with the 2D to 3D morphed 3D model, e.g. bone model, stereoscopically or non-stereoscopically. The one or more of a virtual surgical tool, virtual surgical instrument including a virtual surgical guide or cut block, virtual trial implant, virtual implant component, virtual implant or virtual device, predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration can be planned using the 2D to 3D morphed 3D model, for example using a virtual surgical plan.

In some embodiments, at least one or more of the same landmarks, distances, dimensions, surfaces, edges, angles, axes, curvatures, shapes, lengths, widths, depths and/or other features used for 2D to 3D tissue morphing, e.g. bone morphing, can be used for intra-operative registration of live data and virtual data, e.g. pre-operative data, of the patient by identifying the at least one or more of the corresponding landmarks, distances, dimensions, surfaces, edges, angles, axes, curvatures, shapes, lengths, widths, depths and/or other features in the live data, using, for example, some of the techniques described in the disclosure. In this manner, the accuracy of registration can, for example, by improved by using real, physical data used for 2D to 3D tissue morphing, as compared to morphed data, for registration of the physical patient anatomy, e.g. a surgical site, with the virtual data.

Figure 10:
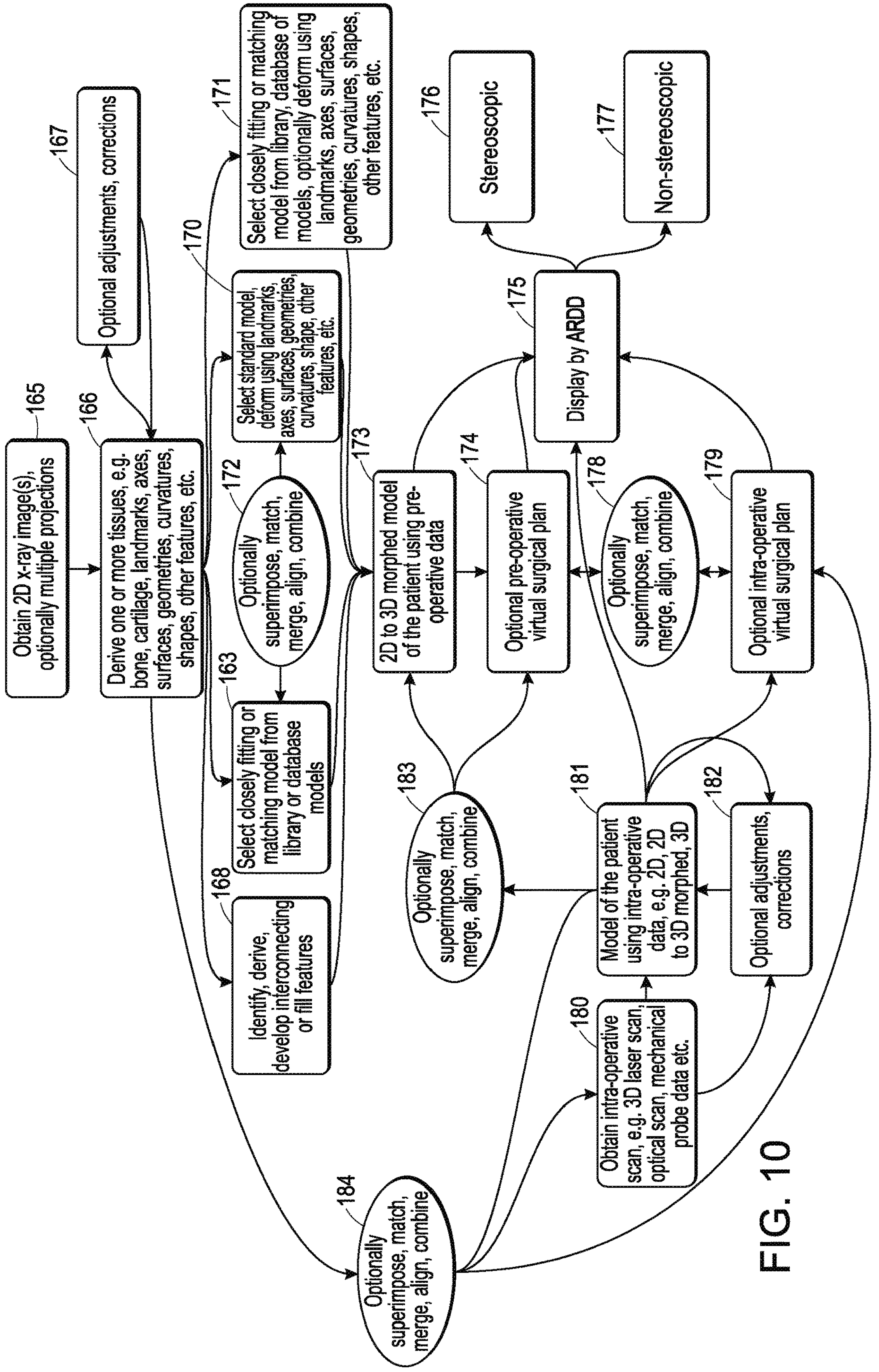
FIG. 10 is an example how 2D to 3D morphed data can be used or applied.

FIG. 10 is an example how 2D to 3D morphed data can be used or applied. The example is in no way meant to be limiting. In this example, 2D x-ray images can be obtained, optionally with multiple projections 165. One or more tissues, e.g. bone, cartilage, their landmarks, shapes and or geometries or other features can be derived 166 and can be optionally adjusted 167. Interconnecting or fill features can be determined 168, a closely fitting or matching model can be selected from a library or database of models 169, a standard model can be selected and optionally be deformed 170 using the shapes, geometries or features 166, a closely fitting or matching model can be selected from a library or database of models 171 and deformed using the information in 166. Steps and processes in 168, 169, 170, and 171 can optionally be combined 172. Steps and processes 168, 169, 170, 171, and 172 can be used to generate a 2D to 3D morphed model 173, which can be used to generate pre-operative virtual surgical plan 174. The morphed model 173 and the pre-operative virtual surgical plan 174 can be displayed by one or more ARDD 175, optionally stereoscopic 176 or non-stereoscopic 177. An intra-operative virtual surgical plan 179 can optionally be superimposed, merged, matched or aligned with the pre-operative virtual surgical plan 174. An intra-operative scan or probe data 180 can be used to generate a model of the patient using intra-operative data, e.g. 2D, 2D to 3D morphed, 3D 181, which can optionally be superimposed, matched, merged or aligned 173 with the morphed model of the patient using pre-operative data 173 or the pre-operative virtual surgical plan 174. Optional adjustments to the model of the patient using intra-operative data 181 can be made 182.

The following examples show representative applications of various embodiments of the disclosure. The examples are not meant to be limiting. Someone skilled in the art will recognize other applications or modifications of the methods, techniques, devices and systems described. Any embodiment described for one joint or anatomic region, e.g. a spine or pedicle, can be applied to other joints or other regions, e.g. a hip, hip replacement, knee, knee replacement, vascular imaging study, angiography etc.

In some embodiments, when a physical guide, tool, instrument or implant is aligned with or superimposed onto a virtual surgical guide, tool, instrument or implant displayed or projected by the ARDD, the aligning or superimposing can be performed with a location accuracy of about 10 mm, about 9 mm, about 8 mm, about 7 mm, about 6 mm, about 5 mm, about 4 mm, about 3 mm, about 2 mm, about 1 mm, about 0.5 mm, about 0.25 mm, or less, 0.25 mm to 0.5 mm, 0.25 mm to 1 mm, 0.25 mm to 2 mm, 0.25 mm to 3 mm, 0.25 mm to 4 mm, 0.25 mm to 5 mm, 0.25 mm to 6 mm, 0.25 mm to 7 mm, 1 mm to 2 mm, 1 mm to 3 mm, 1 mm to 4 mm, 1 mm to 5 mm, 1 mm to 6 mm, 1 mm to 7 mm, 2 mm to 3 mm, 2 mm to 4 mm, 2 mm to 5 mm, 2 mm to 6 mm, 2 mm to 7 mm, 3 mm to 4 mm, 3 mm to 5 mm, 3 mm to 6 mm, 3 mm to 7 mm, 4 mm to 5 mm, 4 mm to 6 mm, 4 mm to 7 mm, 5 mm to 6 mm, 5 mm to 7 mm, 6 mm to 7 mm or as needed depending on the clinical application, in one, two or three directions, x, y, z. When the physical guide, tool, instrument or implant is aligned with or superimposed onto the virtual surgical guide, tool, instrument or implant displayed or projected by the ARDD, the aligning or superimposing can be performed with an orientation or angle accuracy of about 10°, about 9°, about 8°, about 7°, about 6°, about 5°, about 4°, about 3°, about 2°, about 1°, about 0.5°, about 0.25° or less, 0.25-10°, 0.25 to 9°, 0.25-8°, 0.25-7°, 0.25-6°, 0.25-5°, 0.25-4°, 0.25-3°, 0.25-2°, 0.25-1°, 0.25-0.5°, 0.5 to 9°, 0.5-8°, 0.5-7°, 0.5-6°, 0.5-5°, 0.5-4°, 0.5-3°, 0.5-2°, 0.5-1°, 1 to 9°, 1-8°, 1-7°, 1-6°, 1-5°, 1-4°, 1-3°, 1-2°, 2-9°, 2-8°, 2-7°, 2-6°, 2-5°, 2-4°, 2-3°, 3-9°, 3-8°, 3-7°, 3-6°, 3-5°, 3-4°, 4-9°, 4-8°, 4-7°, 4-6°, 4-5°, 5-9°, 5-8°, 5-7°, 5-6°, 6-9°, 6-8°, 6-7°, 7-9°, 7-8°, 8-9° or as needed depending on the clinical application, in one, two or three directions, x, y, z.

The mechanical axis of the lower extremity is determined by drawing a line from the center of the femoral head to the center of the ankle joint, which corresponds typically to an approximately 3° slope compared with that of the vertical axis. This can be subdivided into the femoral mechanical axis, which runs from the head of the femur to the intercondylar notch of the distal femur, and the tibial mechanical axis, which extends from the center of the proximal tibia to the center of the ankle. The medial angle formed between the mechanical axis of the femur and the mechanical axis of the tibia is called the hip-knee-ankle angle, which represented the overall alignment of the lower extremity and is usually about or slightly less than 180° in normal knees, also called normal mechanical axis alignment. The position of the mechanical axis causes it to usually pass just medial to the tibial spine, but this can vary widely based on the patient height and pelvic width.

Augmented Reality Guidance of Robots and Robotic Arms

Display of a Virtual Surgical Guide, e.g. A Virtual Plane, for Detecting Deviation of a Saw Blade, a Saw, and/or Robot or Robotic Arm from its Predetermined Path In some embodiments, an ARDD, optionally a see-through ARDD or a non-see-through ARDD using a video camera with live stream of video images of the surgical field into the ARDD display, can display a virtual surgical guide, e.g. a virtual plane, superimposed onto and/or aligned with a bone of a patient, e.g. a distal femur or a proximal tibia exposed during a knee replacement procedure. The virtual surgical guide, e.g. a virtual plane, can be at a predetermined position, predetermined orientation and/or predetermined position and/or orientation, e.g. for a predetermined or intended anteversion and/or offset and/or rotation and/or flexion and/or extension and/or slope, for an intended bone cut for an implant component, e.g. a femoral component in a knee replacement, a tibial component in a knee replacement, a femoral component in a hip replacement, a humeral component in a shoulder replacement, a tibial or talar component in an ankle replacement. The predetermined position, predetermined orientation and/or predetermined position and/or orientation can be selected to define or determine, for example, a leg length, e.g. in a hip replacement and a proximal femoral bone cut, an implant component varus or valgus position, an implant component rotation, an implant component flexion or extension position, an implant component slope, e.g. in a proximal tibial plateau in a knee replacement. The virtual surgical guide, e.g. a virtual plane, can be derived, for example, using data from an imaging test, e.g. an x-ray, an ultrasound, a CT scan, an MRI scan. The virtual surgical guide, e.g. a virtual plane, can be derived, for example, by touching select landmarks of a joint, e.g. portions of an articular surface or osteophytes, or by "painting" portions of the joint, e.g. portions of an articular surface, e.g. of a distal femur with a pointer, e.g. with one or more attached optical markers, navigation markers and/or IMU's and/or by generating a point cloud and surface of an articular surface. A bone cut can then be referenced in relationship to the articular surface, e.g. for a given implant component geometry, e.g. a planar surface on the implant. A bone cut can be referenced, e.g. in relationship to an articular surface, using a CAD file of an implant component. A bone cut can be referenced, e.g. in relationship to an articular surface, using a CAD file of a cut block. A bone cut can be referenced, e.g. in relationship to an articular surface, using any combination of the foregoing.

In some embodiments, a bone cut can be executed by a saw attached to or integrated into a robot. In any of the embodiments throughout the disclosure, a robot can be active, e.g. with an actively guided robotic arm and attached or integrated saw, actively cutting the bone, or semi-active, e.g. letting a surgeon perform the cut, but stopping a movement of the saw blade or covering the saw blade, if the saw blade is moved outside a predetermined or intended area of cutting or volume of cutting or coordinates for cutting, or passive, e.g. positioning a guide for the surgeon making the cut. A robot can be attached to an arm or to a base via an arm. A robot can be handheld. A robot can be attached to an arm and handheld. Any saw or saw mechanism known in the art can be used, e.g. reciprocating saws or oscillating saws.

A bone cut can be executed using a robot, for example using a predetermined virtual surgical plan. The predetermined virtual surgical plan can be generated using an imaging study, e.g. an ultrasound, CT or MRI scan of the patient. The predetermined virtual surgical plan can be generated by touching select landmarks of a joint, e.g. portions of an articular surface or osteophytes, or by "painting" portions of the joint, e.g. portions of an articular surface, e.g. of a proximal tibia, followed by optional point cloud generation. The predetermined virtual surgical plan can be generated using augmented reality techniques described in the disclosure, for example by virtually placing, fitting, sizing, selecting and/or aligning a virtual implant component on the live physical joint of the patient and/or by utilizing one or more coordinates of the virtually placed virtual implant component; and/or by deriving the plane and/or coordinates of the bone cut surface or plane using the virtually placed implant component, including its coordinates and geometry, including the geometry of a planar surface of the implant facing the bone cut. Information and/or data from pre- or intra-operative imaging study, touching of landmarks, surface painting and/or point cloud generation and/or augmented reality techniques can be combined.

When the robot executes the bone cut or, in case of a semi-active or passive robot, assists the surgeon in executing the bone cut, the saw blade attached to the saw and/or robotic system can deviate from the predetermined and/or intended cut, for example in the presence of sclerotic bone, which can cause the saw blade to deviate from its predetermined or intended path and/or which can cause the saw blade to bend and/or to deviate from its predetermined or intended path ("saw blade skiving'). Saw blade deviation (saw blade skiving) can be difficult to detect for a surgeon. Thus, it is possible that a surgeon trusts the surgical plan and bone cuts executed by the robot or with assistance by the robot, while in fact the actual cuts in the physical bone can deviate significantly from the predetermined and/or intended cut.

In some embodiments, one or more ARDDs can display and/or project a virtual surgical guide, e.g. a virtual plane, onto the surface of the joint, e.g. an articular surface, for example a cartilage and/or bone and/or subchondral bone and/or an osteophyte, with the predetermined position, predetermined location and/or predetermined orientation, e.g. from the virtual surgical plan, e.g. the virtual plan developed for or by the robotic system, e.g. using imaging data and/or painting of one or more articular surfaces using a pointer or combinations thereof, and the ARDD can maintain the display of the virtual surgical guide, e.g. a virtual plane, relative to one or more anatomic structures of the joint, e.g. an articular surface and/or an osteophyte, while the robot executes the bone cut with the saw or assists in executing the bone cut with the saw. In any of the embodiments throughout the disclosure, the ARDD or multiple ARDDs can be registered in the same coordinate system as the robot or robotic arm, e.g. a common coordinate system. In the event of a deviation of the saw blade, the difference between the actual saw path and/or the actual saw blade position, location and/or orientation and the virtual surgical guide, e.g. a virtual plane, including its predetermined position, predetermined location and/or predetermined orientation can be detected.

In some embodiments, the ARDD display can be configured using a computer system and/or computer processor to display or project a virtual surgical guide, e.g. a virtual plane, in a predetermined position, predetermined location, predetermined orientation superimposed onto the surface of a joint, e.g. a cartilage, a bone, a subchondral bone, a cortical bone, and to allow for superimposition and/or alignment of a physical saw, saw blade, and/or robot, e.g. a robotic arm. The ARDD display of the virtual surgical guide, e.g. a virtual plane, can be configured so that a deviation of the physical saw, saw blade, and/or robot from the virtual surgical guide, e.g. a virtual plane, can be readily detected. For example, display colors and transparencies can be selected by the computer system that support visual distinction between the virtual surgical guide, e.g. a virtual plane, and the physical saw, saw blade, and/or robot. The virtual surgical guide, e.g. a virtual plane, can be maintained by the one or more ARDDs superimposed onto the joint, for example in fixed position and/or orientation relative to one or more anatomic landmarks of the joint, while the physical saw, saw blade, and/or robot is/are moving. The virtual surgical guide, e.g. a virtual plane, can be maintained by the one or more ARDDs superimposed onto the joint, for example in fixed position and/or orientation relative to one or more anatomic landmarks of the joint, while the physical joint moves or is being moved. The virtual surgical guide, e.g. a virtual plane, can be maintained by the one or more ARDDs superimposed onto the joint, for example in fixed position and/or orientation relative to one or more anatomic landmarks of the joint, while the physical saw, saw blade, and/or robot are moving and while the physical joint, e.g. one or more articular surfaces, moves or is being moved.

Optionally, a saw blade can be tracked using, for example, optical markers, e.g. with geometric patterns, navigation markers, e.g. using infrared or RF markers, or IMU's or any other marker or tracking mechanism known in the art or described in the disclosure. The saw blade can be tracked using a 3D scanner, a laser scanner and/or a video imaging system. The saw blade can be attached to a bone saw or other power instrument. The saw blade can be attached to or integrated into an active, semi-active or a passive robot. Any deviation of the physical saw blade from its predetermined position, location, and/or orientation and/or predetermined or intended path can be detected, e.g. automatically or semi-automatically and can, optionally, trigger an alert, e.g. an acoustic or visual alert, e.g. displayed by the ARDD, to the surgeon. Thus, physical saw blade deviation from its intended or predetermined path can be detected using the display of a virtual surgical guide, e.g. a virtual plane, by one or more ARDDs, for example, configured to visualize deviation of the physical saw blade from the virtual surgical guide, e.g. a virtual plane; physical saw blade deviation from its intended or predetermined path can also be detected using tracking and measurement of the coordinates of the saw blade, or any combination of both. Physical saw blade deviation from its intended or predetermined path can be detected using the display of a virtual surgical guide, e.g. a virtual plane, by one or more ARDDs and using tracking and measurement of the coordinates of the physical saw blade.

With the physical saw blade or cutting tool (e.g. a pin, a drill, a mill, a reamer), e.g. attached to a robotic arm, being tracked, the percent superimposition of the physical saw blade or cutting tool with the virtual surgical guide, e.g. a virtual plane or virtual axis, can be determined. The percent superimposition can be displayed on a computer monitor or via the ARDD display. The percent superimposition can be color coded, e.g. with the color changing from red to green when greater than 90, 95, 97, 98, 99 or any other percentage of superimposition is achieved. When the percent superimposition of the physical saw blade or cutting tool (e.g. a pin, a drill, a mill, a reamer), e.g. attached to a robotic arm, with the virtual surgical guide, e.g. a virtual plane or a virtual axis, falls below a predefined or predetermined threshold value, an alarm can be generated, which can be visual, acoustic, vibratory or haptic feedback. A computer processor tracking the coordinates of the physical saw blade or cutting tool, e.g. held by a robotic arm, and comparing the coordinates of the physical saw blade or cutting tool with the coordinates of the virtual surgical guide, e.g. a virtual plane or a virtual axis, can also determine the absolute time or percentage of time of the total "on-time" of the physical saw or cutting tool, e.g. a drill or a burr, when the physical saw or cutting tool is operating above a predefined or predetermined percentage superimposition, e.g. 90, 95, 97, 98, or 99% or any other percentage.

Display of a Virtual Axis for Detecting Deviation of a Pin, Drill, Mill, Reamer, and/or Robot or Robotic Arm from its Predetermined Path In some embodiments, an ARDD, optionally a see-through ARDD or a non-see-through ARDD using a video camera with live stream of video images of the surgical field into the ARDD display, can display a virtual axis superimposed onto and/or aligned with a bone of a patient, e.g. a distal femur or a proximal tibia exposed during a knee replacement procedure. The virtual axis can, for example, be used for placing a first and, optionally, a second pin or screw for attaching a cut block and performing a bone cut. The virtual axis can, for example, be used for burring or milling a first and, optionally, a second hole in a bone for attaching or inserting at least portions of a cut block (for example with a corresponding peg) and performing a bone cut. The virtual axis can be at a predetermined position, predetermined orientation and/or predetermined position and/or orientation, e.g. for a predetermined or intended anteversion and/or offset and/or rotation and/or flexion and/or extension and/or slope, for an intended bone cut for an implant component, e.g. a femoral component in a knee replacement, a tibial component in a knee replacement, a femoral component in a hip replacement, a humeral component in a shoulder replacement, a tibial or talar component in an ankle replacement. The predetermined position, predetermined orientation and/or predetermined position and/or orientation can be selected to define, for example, a leg length, e.g. in a hip replacement and a proximal femoral bone cut, an implant component varus or valgus position, an implant component rotation, an implant component flexion or extension position, an implant component slope, e.g. in a proximal tibial plateau in a knee replacement. The virtual axis can be derived, for example, using data from an imaging test, e.g. an x-ray, an ultrasound, a CT scan, an MRI scan. The virtual axis can be derived, for example, by touching select landmarks of a joint, e.g. portions of an articular surface or osteophytes, or by "painting" portions of the joint, e.g. portions of an articular surface, e.g. of a distal femur, with a pointer, e.g. with one or more attached optical markers, navigation markers and/or IMU's and/or by generating a point cloud and surface of an articular surface. A bone cut can then be referenced in relationship to the articular surface, e.g. for a given implant component geometry, e.g. a planar surface on the implant. A bone cut can be referenced, e.g. in relationship to an articular surface, using a CAD file of an implant component. A bone cut can be referenced, e.g. in relationship to an articular surface, using a CAD file of a physical cut block with, for example, holes for pin placement (and ARDD display of a corresponding virtual axis) or pegs (and ARDD display of a corresponding virtual axis for burring, milling or drilling one or more holes in the bone). Any combination of embodiments is possible.

In some embodiments, a hole or void can be created by a pin or a drill or a burr or a mill or a reamer attached to or integrated into a robot. The robot can be active, e.g. with an actively guided robotic arm and attached or integrated pin, or drill, or burr, or mill or reamer, actively pinning or drilling or burring or milling or reaming the bone, or semi-active, e.g. letting a surgeon perform the pinning or drilling or burring or milling or reaming, but stopping a movement of the pin or drill or burr or mill or reamer or covering the pin, or drill, or burr, or mill or reamer, if the pin, or drill, or burr, or mill or reamer is moved outside a predetermined or intended area of pinning or drilling or burring or milling or reaming or volume of pinning or drilling or burring or milling or reaming or coordinates for pinning or drilling or burring or milling or reaming, or passive, e.g. positioning a guide for the surgeon to perform a pinning or drilling or burring or milling or reaming. The robot can be attached to an arm or to a base via an arm. The robot can be handheld. The robot can be attached to an arm and handheld. Any pinning or drilling or burring or milling or reaming mechanism known in the art can be used.

The pinning or drilling or burring or milling or reaming can be executed using a robot, for example using a predetermined virtual surgical plan. The predetermined virtual surgical plan can be generated using an imaging study, e.g. an ultrasound, CT or MRI scan of the patient. The predetermined virtual surgical plan can be generated using touching of landmarks, surface painting of a joint followed by optional point cloud generation. The predetermined virtual surgical plan can be generated using augmented reality techniques described in the disclosure, for example by virtually placing, fitting, sizing, selecting and/or aligning a virtual implant component on the live physical joint of the patient and/or by using one or more coordinates of the virtually placed implant component. Information and/or data from pre- or intra-operative imaging study, touching of landmarks, surface painting and/or optional point cloud generation and/or augmented reality techniques, e.g. virtual placement of virtual implant components on the live physical joint of the patient, can be combined.

When the robot executes the pinning or drilling or burring or milling or reaming or, in case of a semi-active or passive robot, assists the surgeon in executing the pinning or drilling or burring or milling or reaming, the pin or drill or burr or mill or reamer can deviate from the predetermined and/or intended pinning or drilling or burring or milling or reaming, for example in the presence of sclerotic bone, which can cause the pin or drill or burr or mill or reamer to deviate from its predetermined or intended path and/or which can cause the pin or drill or burr or mill or reamer to bend and/or to deviate from its predetermined or intended path. Pin or drill or burr or mill or reamer deviation can be difficult to detect for a surgeon. Thus, it is possible that a surgeon trusts the surgical plan and pinning or drilling or burring or milling or reaming executed by the robot or with assistance by the robot, while in fact the actual pinning or drilling or burring or milling or reaming in the physical bone can deviate significantly from the predetermined and/or intended pinning or drilling or burring or milling or reaming and related holes in the bone or bone voids.

In some embodiments, one or more ARDDs can display and/or project a virtual surgical guide, e.g. a virtual axis, onto the surface of the joint, e.g. an articular surface, for example a cartilage and/or bone and/or subchondral bone and/or an osteophyte, with the predetermined position, predetermined location and/or predetermined orientation, e.g. from the virtual surgical plan, and the ARDD can maintain the display of the virtual axis relative to one or more anatomic structures of the joint, e.g. an articular surface and/or an osteophyte, while the robot executes the pinning or drilling or burring or milling or reaming or assists in executing the pinning or drilling or burring or milling or reaming. In the event of a deviation of the pin or drill or burr or mill or reamer from its predetermined or intended path and/or axis, the difference between the actual pin or drill or burr or mill or reamer path and/or the actual pin or drill or burr or mill or reamer position, location and/or orientation and the virtual surgical guide, e.g. the virtual axis or a 2D or 3D placement indicator of the pin or drill or burr or mill or reamer, including its predetermined position, predetermined location and/or predetermined orientation can be detected.

In some embodiments, the ARDD display can be configured using a computer system and/or computer processor to display a virtual surgical guide, e.g. a virtual axis, in a predetermined position, predetermined location, predetermined orientation superimposed onto the surface of a joint, e.g. a cartilage, a bone, a subchondral bone, a cortical bone, and to allow for superimposition and/or alignment of a physical pin, or drill, or mill or robot and/or robot. The ARDD display of the virtual surgical guide, e.g. a virtual axis, can be configured so that a deviation of the physical drill or pin or mill or reamer and/or robot from the virtual axis can be readily detected. For example, display colors and transparencies can be selected by the computer system that support visual distinction between the virtual surgical guide, e.g. a virtual axis, and the physical pin or drill or burr or mill or reamer and/or robot. The virtual surgical guide, e.g. a virtual axis, can be maintained by the one or more ARDDs superimposed onto the joint, for example in fixed position and/or orientation relative to one or more anatomic landmarks of the joint, while the physical pin, or drill, or mill, or reamer, and/or robot are moving. The virtual surgical guide, e.g. a virtual axis, can be maintained by the one or more ARDDs superimposed onto the joint, for example in fixed position and/or orientation relative to one or more anatomic landmarks of the joint, while the physical joint moves or is being moved. The virtual surgical guide, e.g. a virtual axis, can be maintained by the one or more ARDDs superimposed onto the joint, for example in fixed position and/or orientation relative to one or more anatomic landmarks of the joint, while the physical pin, or drill, or mill, or reamer, and/or robot are moving and while the physical joint moves or is being moved. Optionally, a pin or drill or burr or mill or reamer can be tracked using, for example, optical markers, e.g. with geometric patterns, navigation markers, e.g. using infrared or RF markers, or IMU's or any other marker or tracking mechanism known in the art or described in the disclosure. The pin or drill or burr or mill or reamer can be tracked using a 3D scanner, a laser scanner and/or a video imaging system. The pin or mill or drill or burr or reamer can be attached to a power instrument. The pin or mill or drill or burr or reamer and/or power instrument can be attached to or integrated into an active, semi-active or a passive robot. Any deviation of the physical saw pin or drill or burr or mill or reamer from its predetermined position, location, and/or orientation and/or predetermined or intended path can be detected, e.g. automatically or semi-automatically and can, optionally, trigger an alert, e.g. an acoustic or visual alert, e.g. displayed by the ARDD, to the surgeon. Thus, deviation of the pin or drill or burr or mill or reamer from its intended or predetermined path can be detected using the display of a virtual surgical guide, e.g. a virtual axis, by one or more ARDDs configured to visualize deviation of the physical pin or mill or drill or reamer and/or robot from the virtual surgical guide, e.g. a virtual axis; the deviation from its intended or predetermined path can also be detected using tracking and measurement of the coordinates of the physical pin or drill or burr or mill or reamer and/or robot, e.g. robot arm. Deviation of the physical pin or drill or burr or mill or reamer from its intended or predetermined path can be detected using the display of a virtual surgical guide, e.g. a virtual axis, by one or more ARDDs and using tracking and measurement of the coordinates of the physical pin or drill or burr or mill or reamer and/or robot, including robotic arm or portions thereof. With the physical saw blade or cutting tool (e.g. a pin, a drill, a mill, a reamer), e.g. attached to a robotic arm, being tracked, the percent superimposition of the physical saw blade or cutting tool with the virtual surgical guide, e.g. a virtual plane or virtual axis, can be determined. The percent superimposition can be displayed on a computer monitor or via the ARDD display. The percent superimposition can be color coded, e.g. with the color changing from red to green when greater than 90, 95, 97, 98, 99 or any other percentage of superimposition is achieved. When the percent superimposition of the physical saw blade or cutting tool (e.g. a pin, a drill, a mill, a reamer), e.g. attached to a robotic arm, with the virtual surgical guide, e.g. a virtual plane or a virtual axis, falls below a predefined or predetermined threshold value, an alarm can be generated, which can be visual, acoustic, vibratory or haptic feedback. A computer processor tracking the coordinates of the physical saw blade or cutting tool, e.g. held by a robotic arm, and comparing the coordinates of the physical saw blade or cutting tool with the coordinates of the virtual surgical guide, e.g. a virtual plane or a virtual axis, can also determine the absolute time or percentage of time of the total "on-time" of the physical saw or cutting tool, e.g. a drill or a burr, when the physical saw or cutting tool is operating above a predefined or predetermined percentage superimposition, e.g. 90, 95, 97, 98, or 99% or any other percentage.

ARDD Displays for Projecting One or More Virtual Portions of a Robot or Placement Indicators of a Robot, Augmented Reality Guidance of Robots or Robotic Arms In some embodiments, a physical surgical instrument or a physical surgical tool can include a robotic arm, e.g. for bone removal, e.g. with an attached drill, mill, burr, reamer, impactor, broach, and/or saw and/or saw blade. The robotic arm can, for example, move with 2, 4 or 6 degrees of freedom and can be attached to a stand. At least portions of the robot can be handheld. The robot can optionally provide haptic feedback, e.g. when a surgeon is holding a portion of a robot and the robot operates within or outside an intended or predetermined perimeter, area or volume of bone removal, slowing or stopping, for example the advancement of the robot or robotic arm if the robot operates outside the intended or predetermined perimeter, area or volume of bone removal. In some embodiments, a sharp tool for bone removal, e.g. a drill, a mill, a burr, a reamer, a broach, a saw, can be exposed by the robot when the user is advancing the robot within a predetermined surgical plan, e.g. within a perimeter or area or volume predetermined for bone removal; the sharp tool for bone removal can be covered by a protective sleeve when the robot or robotic arm is advanced outside a predetermined surgical plan, e.g. outside a perimeter or area or volume predetermined for bone removal.

One or more optical head mounted displays can display a virtual surgical instrument, e.g. a virtual representation or a virtual display of portions of a robot, e.g. a robotic arm, or virtual images or a virtual representation or a virtual display of a robotic arm, including, for example, any handheld portions, for example with an attached drill, mill, burr, reamer, impactor, broach, and/or saw and/or saw blade. The virtual display or virtual representation can be a 2D or a 3D display. The 2D or 3D display can be an outline of the robot or robotic arm or portions thereof. The 2D or 3D display can be a placement indicator of the virtual surgical instrument, e.g. a robot or robotic arm or portions thereof. The 2D or 3D display can be based on an STL file of the robot or robotic arm or portions thereof. The 2D or 3D display can be based on a CAD file of the robot or robotic arm or portions thereof. One or more portions of the robot or robotic arm and/or its virtual display can include one or more of a drill, mill, burr, reamer, impactor, broach, and/or saw and/or saw blade. One or more portions of the robot or robotic arm displayed by the ARDD, e.g. in form of a virtual surgical instrument, can include one or more of a handheld portion of a robot and/or at least a portion of a robotic arm.

The one or more optical head mounted displays can be registered in a coordinate system, e.g. a common coordinate system. The robot or robotic arm or at least portions of the robot can be registered in the same coordinate system. One or more anatomic sites, e.g. a knee exposed during knee replacement surgery, or an acetabulum or a proximal femur exposed during hip replacement surgery, or a spine, e.g. a spinous process, a facet joint, a pedicle, a vertebral body, or any other joint or portion of the body can be registered in the same coordinate system.

A physical surgical instrument and/or the physical surgical tool can be or can include a physical robotic arm or portions thereof, including, for example, with an attached physical drill, mill, burr, reamer, impactor, broach, and/or saw and/or saw blade, or a physical portion of a robot to which one or more of a drill, mill, burr, reamer, impactor, broach, and/or saw and/or saw blade are attached, or a physical handheld portion of a robot or a robotic arm or any other physical component of a robot, including, for example, one or more physical optical markers, e.g. using one or more geometric patterns, navigation markers, e.g. using RF or infrared markers, calibration phantoms, IMU's and/or any other marker known in the art or described, for example, in U.S. provisional application No. 62/700,096, filed Jul. 18, 2018, which is incorporated herein by reference in its entirety.

In some embodiments, the at least one optical head mounted display can be configured to display a virtual surgical instrument, a virtual surgical tool, a virtual display, or virtual representation, e.g. of a robot or portions thereof, superimposed onto a physical joint, e.g. the surface of the physical joint, for example a cartilage, subchondral bone or cortical bone, or spine based, for example, at least in part on coordinates of a predetermined position and/or orientation or combinations thereof of the virtual surgical instrument, virtual surgical tool, virtual display, or virtual representation, and the virtual surgical instrument, virtual surgical tool, virtual display, or virtual representation can configured to allow for superimposing and/or aligning the physical surgical instrument or physical surgical tool, e.g. portions of a physical robot, with the virtual surgical instrument, virtual surgical tool, virtual display, or virtual representation to guide a bone cut and/or bone and/or cartilage removal of the joint, e.g. using a pin, a drill, a mill, a burr, a reamer, a broach and/or an impactor, e.g. attached to or integrated into the robot.

The virtual surgical instrument, virtual surgical tool, virtual display, or virtual representation, e.g. of at least a portion of a robot or any components thereof, including, for example, an attached or integrated pin, drill, burr, mill, reamer, broach and/or impactor, can be at a predetermined position, predetermined orientation and/or predetermined position and/or orientation, e.g. for a predetermined or intended anteversion and/or offset and/or rotation and/or flexion and/or extension and/or slope and/or leg length and/or arm length, for an intended bone cut for an implant component, e.g. a femoral component in a knee replacement, a tibial component in a knee replacement, a femoral component in a hip replacement, an acetabular component in a hip replacement, a humeral component in a shoulder replacement, a tibial or talar component in an ankle replacement or a femoral and/or tibial tunnel or intended graft site for an ACL or other ligament reconstruction. The predetermined position, predetermined orientation and/or predetermined position and/or orientation can be selected to define, for example, a leg length, e.g. in a hip replacement and a proximal femoral bone cut, an implant component varus or valgus position, an implant component rotation, an implant component flexion or extension position, an implant component slope, e.g. in a proximal tibial plateau in a knee replacement. The predetermined position, predetermined orientation and/or predetermined position and/or orientation of the virtual surgical instrument, virtual surgical tool, virtual display, or virtual representation, e.g. of at least a portion of a robot or any components thereof, including, for example, an attached or integrated pin, drill, burr, mill, reamer, broach and/or impactor, can be derived, for example, using data from an imaging test, e.g. an x-ray, an ultrasound, a CT scan, an MRI scan. In any of the embodiments throughout the disclosure, the data from the imaging test can, for example, include data generated by placing and/or fitting and/or sizing and/or selecting and/or aligning a virtual implant component, e.g. an STL file or CAD file of an implant component, in imaging data or using imaging data of the patient. The virtual surgical instrument, virtual surgical tool, virtual display, or virtual representation, e.g. of at least a portion of a robot or any components thereof, including, for example, an attached or integrated pin, drill, burr, mill, reamer, broach and/or impactor, can be derived, for example, by touching select landmarks of a joint, e.g. portions of an articular surface or osteophytes, or by "painting" portions of the joint, e.g. portions of an articular surface, e.g. of a distal femur, with a pointer, e.g. with one or more attached optical markers, navigation markers and/or IMU's and/or by generating a point cloud and surface of an articular surface. A bone cut or bone removal, e.g. using a pin, a drill, a burr, a mill, a reamer, a broach, and/or an impactor and/or a saw, can then be referenced in relationship to the articular surface, e.g. for a given implant component geometry, e.g. a planar surface on the implant. A bone cut can be referenced, e.g. in relationship to an articular surface, using a CAD file of an implant component. A bone cut or bone removal, e.g. using a pin, a drill, a burr, a mill, a reamer, a broach, and/or an impactor and/or a saw, can be referenced, e.g. in relationship to an articular surface, using a CAD file of a physical cut block with, for example, holes for pin placement (and optional ARDD display of a corresponding virtual surgical guide, virtual surgical instrument, virtual surgical tool, virtual display or virtual representation, e.g. a virtual axis) or pegs (and optional ARDD display of a corresponding virtual surgical guide, virtual surgical instrument, virtual surgical tool, virtual display or virtual representation, e.g. a virtual axis for burring, milling or drilling one or more holes in the bone). A bone cut or bone removal, e.g. using a pin, a drill, a burr, a mill, a reamer, a broach, and/or an impactor and/or a saw, can be referenced in relationship to coordinates of a virtually placed, fitted, sized, selected and/or aligned virtual implant component, placed, for example, on portions of a physical joint of the patient. Any combination of embodiments is possible.

In some embodiments, the at least one optical head mounted display can be configured to display the virtual surgical instrument, virtual surgical tool, virtual display or virtual representation, e.g. of a robot or a robotic arm or portions thereof, including, for example, an attached or integrated pin, drill, burr, mill, reamer, broach and/or impactor and/or saw or saw blade, superimposed onto and/or aligned with a physical joint, e.g. the surface of the physical joint including a surgically exposed surface, or onto a spine, e.g. an exposed surface of the spine, for example, a spinous process or a lamina, and to maintain the display of the virtual surgical instrument, virtual surgical tool, virtual display or virtual representation superimposed onto and/or aligned with one or more anatomic landmarks and/or the surface of the physical joint or spine when the one or more physical surgical instrument, e.g. portions of a physical robot or robotic arm, for example a handheld portion of the robot or a robotic arm, physical surgical tool, physical medical device, e.g. an implant, move, e.g. in the coordinate system.

In some embodiments, the at least one optical head mounted display can be configured to display the virtual surgical instrument, virtual surgical tool, virtual display or virtual representation, e.g. of a robot or a robotic arm or portions thereof, including, for example, an attached or integrated pin, drill, burr, mill, reamer, broach and/or impactor and/or saw or saw blade, superimposed onto and/or aligned with a physical joint, e.g. the surface including a surgically exposed surface, or spine, e.g. a surface and/or anatomic landmark, including surgically exposed surfaces or anatomic landmarks, and to maintain the display of the virtual surgical instrument, virtual surgical tool, virtual display or virtual representation superimposed onto and/or aligned with one or more anatomic landmarks and/or surfaces of the physical joint or spine when at least portions of the physical joint or spine move, e.g. in the coordinate system. The portions of the physical joint can, for example, be a first and/or a second articular surface, which can, for example move into different degrees of flexion and/or extension and/or rotation and/or abduction and/or adduction. The portions of the physical spine can, for example, be a first vertebral level, a second vertebral level, a portion of or all of posterior elements, e.g. at one or more spinal levels, a portion of a vertebral body or vertebral bodies, e.g. at one or more spinal levels, a portion of or all of a facet joint, e.g. at one or more spinal levels.

In some embodiments, the at least one optical head mounted display can be configured to display the virtual surgical instrument, virtual surgical tool, virtual display or virtual representation, e.g. of a robot or portions thereof, including, for example, an attached or integrated pin, drill, burr, mill, reamer, broach and/or impactor and/or saw or saw blade, superimposed onto and/or aligned with a physical joint or spine and to maintain the display of the virtual surgical instrument, virtual surgical tool, virtual display or virtual representation superimposed onto and/or aligned with one or more anatomic landmarks of the physical joint or spine when the one or more physical surgical tool or physical surgical instrument, e.g. portions of a physical robot, for example a handheld portion of the robot or a robotic arm, or a physical implant or device move, e.g. in the coordinate system, and when also at least portions of the physical joint or spine move, e.g. in the coordinate system.

ARDD Displays for Projecting One or More Virtual Active Boundaries or Planes and/or One or More Safety Boundaries and/or Safety Planes for a Robot or Robotic Arm In some embodiments, a physical surgical instrument or a physical surgical tool can include a robotic arm, e.g. for bone removal, e.g. with an attached drill, mill, burr, reamer, impactor, broach, and/or saw and/or saw blade. The robotic arm can, for example, move with 2, 4 or 6 degrees of freedom and can be attached to a stand. At least portions of the robot can be handheld. The robot can optionally provide haptic feedback, e.g. when a surgeon is holding a portion of a robot and the robot operates within or outside an intended or predetermined perimeter, area or volume of bone removal, slowing or stopping, for example the advancement of the robot or robotic arm if the robot operates outside the intended or predetermined perimeter, area or volume of bone removal. In some embodiments, a sharp tool for bone removal, e.g. a drill, a mill, a burr, a reamer, a broach, a saw, can be exposed by the robot when the user is advancing the robot within a predetermined surgical plan, e.g. within a perimeter or area or volume predetermined for bone removal; the sharp tool for bone removal can be covered by a protective sleeve when the robot or robotic arm is advanced outside a predetermined surgical plan, e.g. outside a perimeter or area or volume predetermined for bone removal.

In some embodiments, an active zone or boundary or plane can be defined or predetermined for a robot. The active zone or boundary or plane can, for example, be the zone or boundary or plane of a perimeter or area or volume within which the robot can be active, e.g. with an active sharp tool or cutting tool such as a saw, a drill, a mill, a reamer, or the zone or boundary or plane of a perimeter or area or volume within which a sharp tool for bone removal, e.g. a drill, a mill, a burr, a reamer, a broach, a saw, can be exposed by the robot when the user is advancing the robot or robotic arm.

In some embodiments, a safety zone or boundary or plane can be defined or predetermined for a robot. The safety zone or boundary or plane can, for example, be the zone or boundary or plane of a perimeter or area or volume within which the robot can be deactivated or slowed down, e.g. with a deactivated or slowed down sharp tool or cutting tool such as a saw, a drill, a mill, a reamer, or the zone or boundary or plane of a perimeter or area or volume within which a sharp tool for bone removal, e.g. a drill, a mill, a burr, a reamer, a broach, a saw, can be covered by the robot when the user is operating or moving the robot or robotic arm within the safety zone. Other zones, boundaries or planes can be defined based on the operating characteristics of the robot. One or more computer processors can be programmed for different robot functions so that the virtual robot operating zone, virtual robot operating boundary or virtual robot plane is a visual 3D indicator of operating within the boundaries of that robot function or outside boundaries of that function. One or more optical head mounted displays can display a virtual active zone, virtual active boundary or virtual active plane, a virtual safety zone, virtual safety boundary or virtual safety zone, or a virtual robot operating zone, virtual robot operating boundary or virtual robot plane, for example superimposed onto a joint (e.g. an articular surface), e.g. a knee joint, hip joint, shoulder joint or ankle joint. The virtual active zone, virtual active boundary or virtual active plane, a virtual safety zone, virtual safety boundary or virtual safety zone, or a virtual robot operating zone, virtual robot operating boundary or virtual robot plane can be a 2D or a 3D display.

In some embodiments, the virtual active zone, virtual active boundary or virtual active plane, the virtual safety zone, virtual safety boundary or virtual safety zone, or the virtual robot operating zone, virtual robot operating boundary or virtual robot plane can be defined or determined using one or more pre-operative scans of the patient, e.g. an ultrasound, CT or MRI scan. One or more computer processors can generate a graphical user interface providing for tools, e.g. segmentation tools, to determine the one or more virtual active zone, virtual active boundary or virtual active plane, a virtual safety zone, virtual safety boundary or virtual safety zone, or a virtual robot operating zone, virtual robot operating boundary or virtual robot plane.

The one or more optical head mounted displays can be registered in a coordinate system, e.g. a common coordinate system. The robot or robotic arm or at least portions of the robot can be registered in the same coordinate system. The virtual active zone, virtual active boundary or virtual active plane, a virtual safety zone, virtual safety boundary or virtual safety zone, or a virtual robot operating zone, virtual robot operating boundary or virtual robot plane can be registered in the same coordinate system. One or more anatomic sites, e.g. a knee exposed during knee replacement surgery, or an acetabulum or a proximal femur exposed during hip replacement surgery, or a spine, e.g. a spinous process, a facet joint, a pedicle, a vertebral body, or any other joint or portion of the body can be registered in the same coordinate system.

A physical surgical instrument and/or the physical surgical tool can be or can include a physical robotic arm or portions thereof, including, for example, with an attached physical drill, mill, burr, reamer, impactor, broach, and/or saw and/or saw blade, or a physical portion of a robot to which one or more of a drill, mill, burr, reamer, impactor, broach, and/or saw and/or saw blade are attached, or a physical handheld portion of a robot or a robotic arm or any other physical component of a robot, including, for example, one or more physical optical markers, e.g. using one or more geometric patterns, navigation markers, e.g. using RF or infrared markers, calibration phantoms, IMU's and/or any other marker known in the art or described, for example, in U.S. provisional application No. 62/700,096, filed Jul. 18, 2018, which is incorporated herein by reference in its entirety. The physical surgical instrument and/or the physical surgical tool can be registered in the coordinate system, for example using the markers.

In some embodiments, the at least one optical head mounted display can be configured to display a virtual active zone, virtual active boundary or virtual active plane, a virtual safety zone, virtual safety boundary or virtual safety zone, or a virtual robot operating zone, virtual robot operating boundary or virtual robot plane superimposed onto a physical joint, e.g. the surface of the physical joint, for example a cartilage, subchondral bone or cortical bone, or spine based, for example, at least in part on coordinates of a predetermined position and/or orientation or combinations thereof of the virtual surgical instrument, virtual surgical tool, virtual display, or virtual representation or of the virtual active zone, virtual active boundary or virtual active plane, a virtual safety zone, virtual safety boundary or virtual safety zone, or a virtual robot operating zone, virtual robot operating boundary or virtual robot plane, and the virtual active zone, virtual active boundary or virtual active plane, a virtual safety zone, virtual safety boundary or virtual safety zone, or a virtual robot operating zone, virtual robot operating boundary or virtual robot plane can be configured to allow for superimposing and/or aligning the physical surgical instrument or physical surgical tool, e.g. portions of a physical robot, within or outside one or more of the virtual active zone, virtual active boundary or virtual active plane, a virtual safety zone, virtual safety boundary or virtual safety zone, or a virtual robot operating zone, virtual robot operating boundary or virtual robot plane.

The virtual active zone, virtual active boundary or virtual active plane, a virtual safety zone, virtual safety boundary or virtual safety zone, or a virtual robot operating zone, virtual robot operating boundary or virtual robot plane can be at a predetermined position, predetermined orientation and/or predetermined position and/or orientation for an intended bone cut or bone removal for an implant component, e.g. a femoral component in a knee replacement, a tibial component in a knee replacement, a femoral component in a hip replacement, an acetabular component in a hip replacement, a humeral component in a shoulder replacement, a tibial or talar component in an ankle replacement or a femoral and/or tibial tunnel or intended graft site for an ACL or other ligament reconstruction.

The predetermined position, predetermined orientation and/or predetermined position and/or orientation of the virtual active zone, virtual active boundary or virtual active plane, a virtual safety zone, virtual safety boundary or virtual safety zone, or a virtual robot operating zone, virtual robot operating boundary or virtual robot plane can be derived, for example, using data from an imaging test, e.g. an x-ray, an ultrasound, a CT scan, an MRI scan. In any of the embodiments throughout the disclosure, the data from the imaging test can, for example, include data generated by placing and/or fitting and/or sizing and/or selecting and/or aligning a virtual implant component, e.g. an STL file or CAD file of an implant component, in imaging data or using imaging data of the patient. The predetermined position, predetermined orientation and/or predetermined position and/or orientation of the virtual active zone, virtual active boundary or virtual active plane, a virtual safety zone, virtual safety boundary or virtual safety zone, or a virtual robot operating zone, virtual robot operating boundary or virtual robot plane can be derived, for example, by touching select landmarks of a joint, e.g. portions of an articular surface or osteophytes, or by "painting" portions of the joint, e.g. portions of an articular surface, e.g. of a distal femur, with a pointer, e.g. with one or more attached optical markers, navigation markers and/or IMU's and/or by generating a point cloud and surface of an articular surface. A bone cut or bone removal, e.g. using a pin, a drill, a burr, a mill, a reamer, a broach, and/or an impactor and/or a saw, can be referenced in relationship to the articular surface, e.g. for a given implant component geometry, e.g. a planar surface on the implant. A bone cut can be referenced, e.g. in relationship to an articular surface, using a CAD file of an implant component. A bone cut or bone removal, e.g. using a pin, a drill, a burr, a mill, a reamer, a broach, and/or an impactor and/or a saw, can be referenced, e.g. in relationship to an articular surface, using a CAD file of a physical cut block with, for example, holes for pin placement (and optional ARDD display of a corresponding virtual surgical guide, virtual surgical instrument, virtual surgical tool, virtual display or virtual representation, e.g. a virtual axis) or pegs (and optional ARDD display of a corresponding virtual surgical guide, virtual surgical instrument, virtual surgical tool, virtual display or virtual representation, e.g. a virtual axis for burring, milling or drilling one or more holes in the bone). A bone cut or bone removal, e.g. using a pin, a drill, a burr, a mill, a reamer, a broach, and/or an impactor and/or a saw, can be referenced in relationship to coordinates of a virtually placed, fitted, sized, selected and/or aligned virtual implant component, placed, for example, on portions of a physical joint of the patient. A predetermined position, predetermined orientation and/or predetermined position and/or orientation of the virtual active zone, virtual active boundary or virtual active plane, a virtual safety zone, virtual safety boundary or virtual safety zone, or a virtual robot operating zone, virtual robot operating boundary or virtual robot plane can be derived using any of the foregoing information including the coordinates of a bone cut or bone removal. Any combination of embodiments is possible. In some embodiments, the at least one optical head mounted display can be configured to display the virtual active zone, virtual active boundary or virtual active plane, a virtual safety zone, virtual safety boundary or virtual safety zone, or a virtual robot operating zone, virtual robot operating boundary or virtual robot plane superimposed onto and/or aligned with a physical joint, e.g. the surface of the physical joint including a surgically exposed surface, or onto a spine, e.g. an exposed surface of the spine, for example, a spinous process or a lamina, and to maintain the display of the virtual active zone, virtual active boundary or virtual active plane, a virtual safety zone, virtual safety boundary or virtual safety zone, or a virtual robot operating zone, virtual robot operating boundary or virtual robot plane superimposed onto and/or aligned with one or more anatomic landmarks and/or the surface of the physical joint or spine when the one or more physical surgical instrument, e.g. portions of a physical robot or robotic arm, for example a handheld portion of the robot or a robotic arm, physical surgical tool, physical medical device, e.g. an implant, move, e.g. in the coordinate system.

In some embodiments, the at least one optical head mounted display can be configured to display the virtual active zone, virtual active boundary or virtual active plane, a virtual safety zone, virtual safety boundary or virtual safety zone, or a virtual robot operating zone, virtual robot operating boundary or virtual robot plane superimposed onto and/or aligned with a physical joint, e.g. the surface including a surgically exposed surface, or spine, e.g. a surface and/or anatomic landmark, including surgically exposed surfaces or anatomic landmarks, and to maintain the display of the virtual active zone, virtual active boundary or virtual active plane, a virtual safety zone, virtual safety boundary or virtual safety zone, or a virtual robot operating zone, virtual robot operating boundary or virtual robot plane superimposed onto and/or aligned with one or more anatomic landmarks and/or surfaces of the physical joint or spine when at least portions of the physical joint or spine move, e.g. in the coordinate system. The portions of the physical joint can, for example, be a first and/or a second articular surface, which can, for example move into different degrees of flexion and/or extension and/or rotation and/or abduction and/or adduction. The portions of the physical spine can, for example, be a first vertebral level, a second vertebral level, a portion of or all of posterior elements, e.g. at one or more spinal levels, a portion of a vertebral body or vertebral bodies, e.g. at one or more spinal levels, a portion of or all of a facet joint, e.g. at one or more spinal levels.

In some embodiments, the at least one optical head mounted display can be configured to display the virtual active zone, virtual active boundary or virtual active plane, a virtual safety zone, virtual safety boundary or virtual safety zone, or a virtual robot operating zone, virtual robot operating boundary or virtual robot plane superimposed onto and/or aligned with a physical joint or spine and to maintain the display of the virtual active zone, virtual active boundary or virtual active plane, a virtual safety zone, virtual safety boundary or virtual safety zone, or a virtual robot operating zone, virtual robot operating boundary or virtual robot plane superimposed onto and/or aligned with one or more anatomic landmarks of the physical joint or spine when the one or more physical surgical tool or physical surgical instrument, e.g. portions of a physical robot, for example a handheld portion of the robot or a robotic arm, or a physical implant or device move, e.g. in the coordinate system, and when also at least portions of the physical joint or spine move, e.g. in the coordinate system.

Tracking Physical Robots, Measuring Percent Superimposition Between Physical Robots or Portions Thereof and Virtual Surgical Guides, e.g. Virtual Placement Indicators In some embodiments, portions of a robot or the entire robot, including, for example, an attached or integrated pin, drill, burr, mill, reamer, broach and/or impactor and/or saw or saw blade, can be tracked, e.g. by measuring one or more coordinates, for example using optical markers integrated or attached to the robot or portions thereof, e.g. with geometric patterns, detected by a video system, e.g. integrated into, attached to, or separate from an ARDD, navigation markers integrated or attached to the robot or portions thereof, e.g. RF or infrared markers, detected by a navigation system, calibration phantoms integrated or attached to the robot or portions thereof, IMU's integrated or attached to the robot or portions thereof. Portions of a robot or the entire robot, including, for example, an attached or integrated pin, drill, burr, mill, reamer, broach and/or impactor and/or saw or saw blade, can be tracked using direct imaging techniques, for example with optional feature or contour detection, or 3D scanners, e.g. laser scanners, as described, for example, in U.S. provisional application No. 62/700,096, filed Jul. 18, 2018, which is incorporated herein by reference in its entirety.

As the physical surgical guide, physical surgical instrument and/or physical surgical tool, e.g. at least a portion of a robot, for example including a pin, a drill, a burr, a mill, a reamer, a broach, an impactor, a saw blade and/or a saw, is moved, for example actively or passively, to align it and/or superimpose it with a virtual surgical guide, virtual surgical instrument, and/or virtual surgical tool, e.g. a virtual portion of the robot or a virtual placement indicator of the robot or portions thereof, including, for example, an attached or integrated pin, drill, burr, mill, reamer, broach and/or impactor and/or saw or saw blade, the superimposition can be indicated as a percent or graphical volume superimposition between the physical and the virtual surgical guide, or the physical and the virtual surgical instrument and/or the physical and the virtual surgical tool, or the physical and the virtual portion of the robot or portions thereof, a percent or graphical surface superimposition, a percent or graphical area superimposition, a percent or graphical superimposition in a first, second, and/or third direction, e.g. x-, y- and z-, e.g. in mm, a percent or graphical superimposition with regard to angular alignment, e.g. in x-, y-, and z-direction, e.g. in degrees (e.g. for slope or flexion), a percent or graphical coordinate superimposition, e.g. in mm (all optionally indicated in graphical, color coded and/or numerical form). The superimposition can be visualized using color coding, for example from red (e.g. "poor"), to orange (e.g. "medium") to green (e.g. "good"). When the physical surgical guide, physical surgical instrument, physical surgical tool or physical device is sufficiently well or completely superimposed onto the virtual surgical guide, virtual surgical instrument, virtual surgical tool or virtual device (e.g. 100% match or >90% match or >95% match, or any other amount), the physical robot can, for example, be activated and/or a cover can be removed from a pin, drill, burr, mill, reamer, broach, impactor and/or saw and/or saw blade, and a bone removal can be initiated or continued; the bone removal can be a pinning, drilling, burring, milling, reaming, broaching, impacting, and/or cutting. The foregoing embodiments on tracking and/or displaying and/or determining and/or measuring superimposition can be applied to many different embodiments throughout the application using robots including handheld robots, e.g. for spinal surgery, spinal fusion, hip replacement, shoulder replacement, ankle replacement, ACL reconstruction or repair, dental surgery, root canals, dental implant placement, etc.

In other embodiments, the at least one ARDD can be configured to display the surgical plan. The surgical plan can, for example, consist of virtual models of the patient's anatomy, such as the femoral or tibial bone, or spinal bone, which can be derived from the preoperative images, and/or implants and/or implant geometries, e.g. derived using STL or CAD files, to be inserted or placed into the patient. The surgical plan can also include virtual surgical guides, e.g. virtual cut guides, virtual axes, virtual cut planes. Areas or portions of bone to be resected, removed, cut or milled can be highlighted in the virtual model, for example in a different color.

The surgical plan and the virtual anatomical models can be registered and superimposed with the patient's anatomy, for example to enable the surgeon to compare the surgical plan derived from preoperative images with the real intraoperative anatomy of the patient, e.g. a physical joint or spine or vertebral level or portions thereof. The surgeon can then make updates to the surgical plan based on the intraoperative assessment and comparison between virtual anatomical model and live physical patient anatomy. For example, the surgeon can assess the tracking of the patella relative to the planned internal/external rotation of the femoral implant and adjust the planned rotation of the femoral implant. In another embodiment, the surgeon can adjust the tibial slope angle based on the intraoperative assessment. Any changes in the surgical plan can then be translated into updated control commands for the robot and updated display of virtual data by one or more ARDDs.

In another embodiment, the progress of a robotic milling procedure, for example with a semi-active robot, can be displayed in real time to the surgeon. For example, the section or volume of bone to be removed by drilling, pinning, burring, milling, reaming, broaching, impacting and/or sawing and/or cutting can be marked in a different color and/or transparency, for example, in a virtual anatomical model, which can be superimposed onto and/or aligned with the patient's intraoperative anatomy by the one or more ARDDs. The pathway of the bone removal, e.g. from a pin, drill, burr, mill, reamer, broach, impactor, and/or saw can be tracked continuously or intermittently, and the pinned, drilled, burred, milled, reamed, broached, impacted and/or cut bone can optionally be virtually removed from the virtual anatomical model displayed by the one or more ARDDs. In this manner, the surgeon can easily see which parts of the bone still need to be removed, and direct the robot, e.g. a tip or edge or bone removing portion of a robotic pin, drill, burr, mill, reamer, broach, impactor, and/or saw, accordingly. Thus, the one or more ARDDs can be configured using a computer processor so that the display facilitates visualization of areas of bone removed and areas of bone remaining to be removed and/or targeted for removal and/or highlighted for removal superimposed onto and/or aligned with corresponding anatomic structures of the physical patient, e.g. the physical joint, e.g. the physical articular surface. One or more ARDDs can also display any areas of over-resection, i.e. areas where too much bone has been removed, superimposed onto and/or aligned with the joint, e.g. the articular surface, subchondral bone, marrow bone and/or cortical bone. Thus, one or more ARDDs can display a virtual display or virtual anatomic 3D model of the section or volume of bone and/or cartilage to be removed, the pathway of bone and/or cartilage removal, the bone and/or cartilage removed, the area of volume of over-resection, an osteophyte to be removed, an area of over-resection of an osteophyte.

In some embodiments, the at least one optical head mounted display can be configured to display a virtual display or virtual anatomic 3D model of the section or volume of bone and/or cartilage to be removed, the pathway of bone and/or cartilage removal, the bone and/or cartilage removed, the area of volume of over-resection, an osteophyte to be removed, an area of over-resection of an osteophyte superimposed onto a physical joint, e.g. the surface of the physical joint, for example a cartilage, subchondral bone or cortical bone, or spine based, for example, at least in part on coordinates of a predetermined position and/or orientation or combinations thereof of a virtual surgical instrument, virtual surgical tool, virtual display, or virtual representation or of the virtual display or virtual anatomic 3D model of the section or volume of bone and/or cartilage to be removed, the pathway of bone and/or cartilage removal, the bone and/or cartilage removed, the area of volume of over-resection, an osteophyte to be removed, an area of over-resection of an osteophyte.

The virtual display or virtual anatomic 3D model of the section or volume of bone and/or cartilage to be removed, the pathway of bone and/or cartilage removal, the bone and/or cartilage removed, the area of volume of over-resection, an osteophyte to be removed, an area of over-resection of an osteophyte can be at a predetermined position, predetermined orientation and/or predetermined position and/or orientation for an intended bone cut or bone removal for an implant component, e.g. a femoral component in a knee replacement, a tibial component in a knee replacement, a femoral component in a hip replacement, an acetabular component in a hip replacement, a humeral component in a shoulder replacement, a tibial or talar component in an ankle replacement or a femoral and/or tibial tunnel or intended graft site for an ACL or other ligament reconstruction.

The predetermined position, predetermined orientation and/or predetermined position and/or orientation of the virtual display or virtual anatomic 3D model of the section or volume of bone and/or cartilage to be removed, the pathway of bone and/or cartilage removal, the bone and/or cartilage removed, the area of volume of over-resection, an osteophyte to be removed, an area of over-resection of an osteophyte can be derived, for example, using data from an imaging test, e.g. an x-ray, an ultrasound, a CT scan, an MRI scan. In any of the embodiments throughout the disclosure, the data from the imaging test can, for example, include data generated by placing and/or fitting and/or sizing and/or selecting and/or aligning a virtual implant component, e.g. an STL file or CAD file of an implant component, in imaging data or using imaging data of the patient. The predetermined position, predetermined orientation and/or predetermined position and/or orientation of the virtual display or virtual anatomic 3D model of the section or volume of bone and/or cartilage to be removed, the pathway of bone and/or cartilage removal, the bone and/or cartilage removed, the area of volume of over-resection, an osteophyte to be removed, an area of over-resection of an osteophyte can be derived, for example, by touching select landmarks of a joint, e.g. portions of an articular surface or osteophytes, or by "painting" portions of the joint, e.g. portions of an articular surface, e.g. of a distal femur, with a pointer, e.g. with one or more attached optical markers, navigation markers and/or IMU's and/or by generating a point cloud and surface of an articular surface. A bone cut or bone removal, e.g. using a pin, a drill, a burr, a mill, a reamer, a broach, and/or an impactor and/or a saw, can be referenced in relationship to the articular surface, e.g. for a given implant component geometry, e.g. a planar surface on the implant. A bone cut can be referenced, e.g. in relationship to an articular surface, using a CAD file of an implant component. A bone cut or bone removal, e.g. using a pin, a drill, a burr, a mill, a reamer, a broach, and/or an impactor and/or a saw, can be referenced, e.g. in relationship to an articular surface, using a CAD file of a physical cut block with, for example, holes for pin placement (and optional ARDD display of a corresponding virtual surgical guide, virtual surgical instrument, virtual surgical tool, virtual display or virtual representation, e.g. a virtual axis) or pegs (and optional ARDD display of a corresponding virtual surgical guide, virtual surgical instrument, virtual surgical tool, virtual display or virtual representation, e.g. a virtual axis for burring, milling or drilling one or more holes for pegs in the bone). A bone cut or bone removal, e.g. using a pin, a drill, a burr, a mill, a reamer, a broach, and/or an impactor and/or a saw, can be referenced in relationship to coordinates of a virtually placed, fitted, sized, selected and/or aligned virtual implant component, placed, for example, on portions of a physical joint of the patient. A predetermined position, predetermined orientation and/or predetermined position and/or orientation of the virtual display or virtual anatomic 3D model of the section or volume of bone and/or cartilage to be removed, the pathway of bone and/or cartilage removal, the bone and/or cartilage removed, the area of volume of over-resection, an osteophyte to be removed, an area of over-resection of an osteophyte can be derived using any of the foregoing information including the coordinates of a bone cut or bone removal. Any combination of embodiments is possible.

In some embodiments, the at least one optical head mounted display can be configured to display the virtual display or virtual anatomic 3D model of the section or volume of bone and/or cartilage to be removed, the pathway of bone and/or cartilage removal, the bone and/or cartilage removed, the area of volume of over-resection, the osteophyte to be removed, the area of over-resection of an osteophyte superimposed onto and/or aligned with a physical joint, e.g. the surface of the physical joint including a surgically exposed surface, or onto a spine, e.g. an exposed surface of the spine, for example, a spinous process or a lamina, and to maintain the virtual display or virtual anatomic 3D model of the section or volume of bone and/or cartilage to be removed, the pathway of bone and/or cartilage removal, the bone and/or cartilage removed, the area of volume of over-resection, the osteophyte to be removed, the area of over-resection of an osteophyte superimposed onto and/or aligned with one or more anatomic landmarks and/or the surface of the physical joint or spine when the one or more physical surgical instrument, e.g. portions of a physical robot or robotic arm, for example a handheld portion of the robot or a robotic arm, physical surgical tool, physical medical device, e.g. an implant, move, e.g. in the coordinate system.

In some embodiments, the at least one optical head mounted display can be configured to display the virtual display or virtual anatomic 3D model of the section or volume of bone and/or cartilage to be removed, the pathway of bone and/or cartilage removal, the bone and/or cartilage removed, the area of volume of over-resection, the osteophyte to be removed, the area of over-resection of an osteophyte superimposed onto and/or aligned with a physical joint, e.g. the surface including a surgically exposed surface, or spine, e.g. a surface and/or anatomic landmark, including surgically exposed surfaces or anatomic landmarks, and to maintain the virtual display or virtual anatomic 3D model of the section or volume of bone and/or cartilage to be removed, the pathway of bone and/or cartilage removal, the bone and/or cartilage removed, the area of volume of over-resection, the osteophyte to be removed, the area of over-resection of an osteophyte superimposed onto and/or aligned with one or more anatomic landmarks and/or surfaces of the physical joint or spine when at least portions of the physical joint or spine move, e.g. in the coordinate system. The portions of the physical joint can, for example, be a first and/or a second articular surface, which can, for example move into different degrees of flexion and/or extension and/or rotation and/or abduction and/or adduction. The portions of the physical spine can, for example, be a first vertebral level, a second vertebral level, a portion of or all of posterior elements, e.g. at one or more spinal levels, a portion of a vertebral body or vertebral bodies, e.g. at one or more spinal levels, a portion of or all of a facet joint, e.g. at one or more spinal levels.

In some embodiments, the at least one optical head mounted display can be configured to display the virtual display or virtual anatomic 3D model of the section or volume of bone and/or cartilage to be removed, the pathway of bone and/or cartilage removal, the bone and/or cartilage removed, the area of volume of over-resection, the osteophyte to be removed, the area of over-resection of an osteophyte superimposed onto and/or aligned with a physical joint or spine and to maintain the virtual display or virtual anatomic 3D model of the section or volume of bone and/or cartilage to be removed, the pathway of bone and/or cartilage removal, the bone and/or cartilage removed, the area of volume of over-resection, the osteophyte to be removed, the area of over-resection of an osteophyte superimposed onto and/or aligned with one or more anatomic landmarks of the physical joint or spine when the one or more physical surgical tool or physical surgical instrument, e.g. portions of a physical robot, for example a handheld portion of the robot or a robotic arm, or a physical implant or device move, e.g. in the coordinate system, and when also at least portions of the physical joint or spine move, e.g. in the coordinate system.

The techniques and examples and any modifications thereof for using and optimizing optical markers, for optimizing geometric patterns of optical markers, for optimizing the shape of optical markers, for aligning optical markers and/or geometric patterns with radiopaque elements, for registering fluoroscopic images with the patient's live anatomy, for utilizing pre-existing information on the known size, shape and/or dimensions of one or more optical markers, for networks of ARDDs and combining multiple spatial maps, for various interfaces including virtual interfaces and for tracking surgical instruments are applicable to any type of surgical procedure, surgical instruments and implants and implant components, including trial components, including, but not limited to partial and total knee replacement, partial and total hip replacement, partial and total shoulder replacement, partial and total ankle replacement, partial and total elbow replacement, partial and total wrist replacement, partial and total mid-foot and forefoot joint replacement, partial and total small joint replacement in hand and feet, arthroscopy of the knee, hip, shoulder, ankle, elbow, wrist and other joints, ligament repair including ACL and/or PCL repair, ligament repair in the knee, hip, shoulder, elbow, ankle or wrist joint, spinal fusion, anterior and/or posterior, spinal disk replacement, spinal motion preservation surgery, different types of spinal surgery approaches and procedures, e.g. PLIF, TLIF, ALIF and others known in the art.

Hip Replacement

Any of the registration techniques and/or techniques described in the embodiments can be applied for hip replacement surgery, including resurfacing, partial and total hip replacement including implantable and attachable markers, calibration and registration phantoms including optical markers, navigation markers, infrared markers, RF markers, patient specific markers, LED's with image capture and IMU's. Optical markers and/or LED's and/or calibration and/or reference phantoms and/or other markers can, for example, be detected and/or tracked using an optical imaging system and/or a 3D scanner, for example integrated into, attached to or separate from an ARDD. For example, one or more markers, e.g. optical markers, navigation markers, patient specific markers or templates, can be applied to the edge of the acetabulum, the inside of the acetabulum or a pelvic wall. Similarly, one or more markers, e.g. optical markers, navigation markers, e.g. infrared or radiofrequency markers, patient specific markers or templates, can be applied to a greater trochanter, a lesser trochanter, a femoral shaft or a femoral neck. By applying the one or more patient specific markers or templates and/or optical markers, for example, to the corresponding structures on the patient, virtual data and live data can be effectively cross-referenced and/or registered in a common coordinate system, for example with one or more ARDD's. By registering the patient specific marker or template and/or optical marker in relationship to the ARDD also or by using any of the other registration techniques or techniques described herein or known in the art, the ARDD can display or superimpose the desired position, location, orientation, alignment and/or trajectory of any surgical instrument used during hip replacement. For example, an acetabular reamer can be applied at a predetermined angle, with the long axis of the reamer typically matching the desired acetabular cup angle, offset, medial or lateral position and/or anteversion and/or inclination, e.g. from a virtual surgical plan for the patient. Registration can be performed using anatomic structures such as the anterior superior iliac spine, the symphysis pubis, the greater trochanter, the lesser trochanter, the anterior, posterior, medial or lateral surface of the femoral neck, the anterior, posterior, medial or lateral surface of the femoral head, the anterior, posterior, medial or lateral surface of the femoral shaft, the anterior, posterior, superior or inferior acetabular margin or the center of the acetabulum or the center of rotation of the hip joint, the ilioischial line, the iliopectineal line, the anterior, posterior, medial or lateral surface of the sacrum or coccyx, the superior surface or endplate of the sacrum, and any other anatomic structure within the hip and pelvic region. One or more patient specific markers or templates and/or optical markers and/or navigation markers can be applied to one or more of these anatomic structures and can be registered within a common coordinate system, for example along with one or more ARDD's, the patient and, optionally, the OR table. Optionally, a pin or screw can be attached to or introduced into the bony anatomic structure and one or more optical markers and/or navigation markers and/or IMU's can be attached to the pin or screw.

In the hip joint, one or more ARDD's, one or more virtual data sets or virtual data can be registered in a common coordinate system. In a hip joint, two opposing articular surfaces, e.g. with opposing cartilage surfaces and underlying subchondral bone, can be registered separately and/or optionally jointly in a coordinate system, e.g. a common coordinate system. A first articular surface can be located on the pelvic side, i.e. on the acetabulum, a second articular surface can be located on the proximal femur. Registering the first articular surface and/or or associated bones and/or structures and the second articular surface and/or or associated bones and/or structures separately in a common coordinate system can have the benefit of allowing movement, e.g. flexion and/or extension and/or rotation and/or abduction, and/or adduction, and/or elevation and/or other movements, e.g. translation, of the first articular surface and/or or associated bones and/or structures, e.g. on the acetabular side, in relationship to the second articular surface and/or or associated bones and/or structures, e.g. on the proximal femoral side, while maintaining registration of the first articular surface and/or associated bones and/or structures, e.g. on the acetabular side, and/or the second articular surface and/or or associated bones and/or structures, e.g. on the proximal femoral side, e.g. in a common coordinate system or a subcoordinate system, for example optionally along with one or more ARDD's and/or fixed structures in the operating room, e.g. the OR table, and/or other structures or anatomic landmarks of the patient, e.g. irrespective movement of the individual portions of the joint; the foregoing applies to any joint in the human body, e.g. a shoulder, elbow, wrist, finger, knee, ankle, foot or toe joint or a temporomandibular joint. In this manner, the hip joint or any other joint can be placed in different positions, e.g. flexion, extension, rotation, abduction, adduction, e.g. a degree of hip abduction, e.g. 20, 30, 40 or other degrees, e.g. during placement of a femoral component, and a degree of hip abduction, e.g. 30, 40, or 50 or other degrees, during placement of the acetabular component, or any other degrees for either component placement depending on surgical technique and surgeon preference, while the registration of the acetabular and/or the registration of the proximal femoral side and the display of any virtual data, e.g. a virtual surgical guide, a virtual cut plane, a virtual implant component on the acetabular side and/or the proximal femoral side can be maintained and superimposed onto the corresponding anatomic area, e.g. the area intended for implant component placement, irrespective of the movement of individual portions of the joint, thereby allowing the one or more ARDD's to maintain anatomically registered displays of virtual data superimposed onto the corresponding portions of the physical joint anatomy, e.g. an articular surface, including a normal, damaged and/or diseased cartilage and/or subchondral bone and/or cortical bone, e.g. in a tangent, intersecting and/or offset manner, e.g. external and/or internal to the normal, damaged and/or diseased cartilage and/or subchondral bone and/or cortical bone.

Figure 13A:
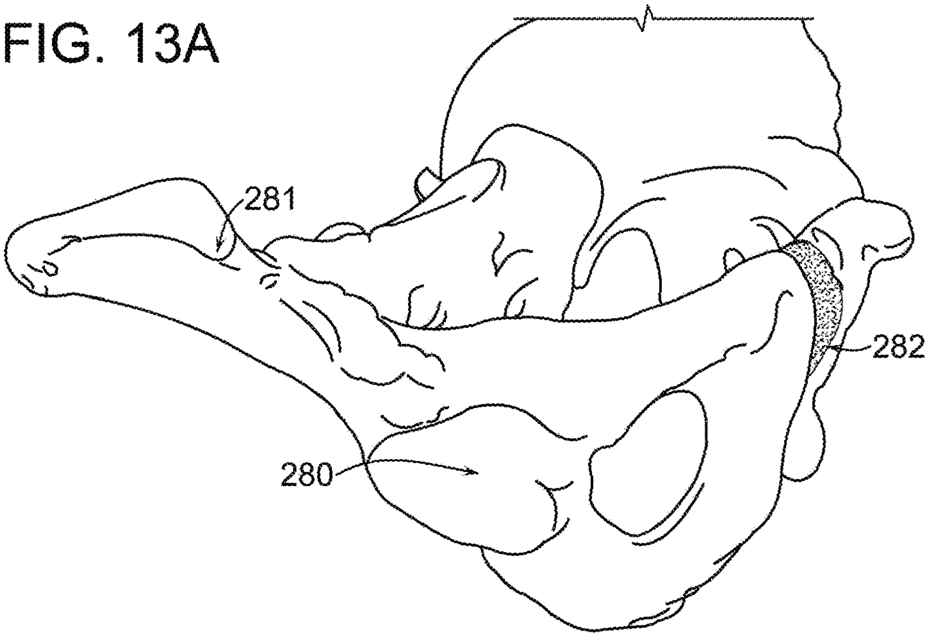
FIGS. 13A-13F are illustrative examples of displaying a virtual acetabular reaming axis using one or more ARDD (e.g. HMD) and aligning a physical acetabular reamer with the virtual reaming axis for placing an acetabular cup with a predetermined cup angle, offset, medial or lateral position and/or anteversion according to some embodiments of the present disclosure.
Figure 13B:
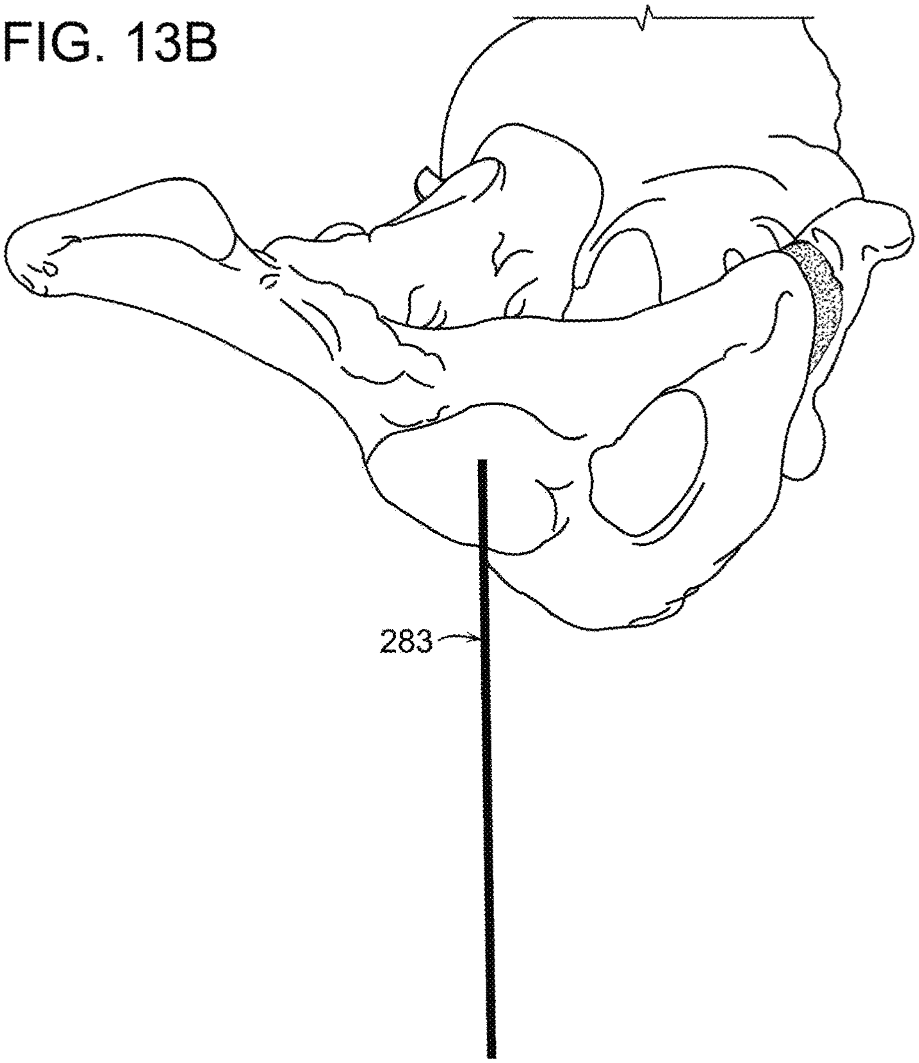
Figure 13C:
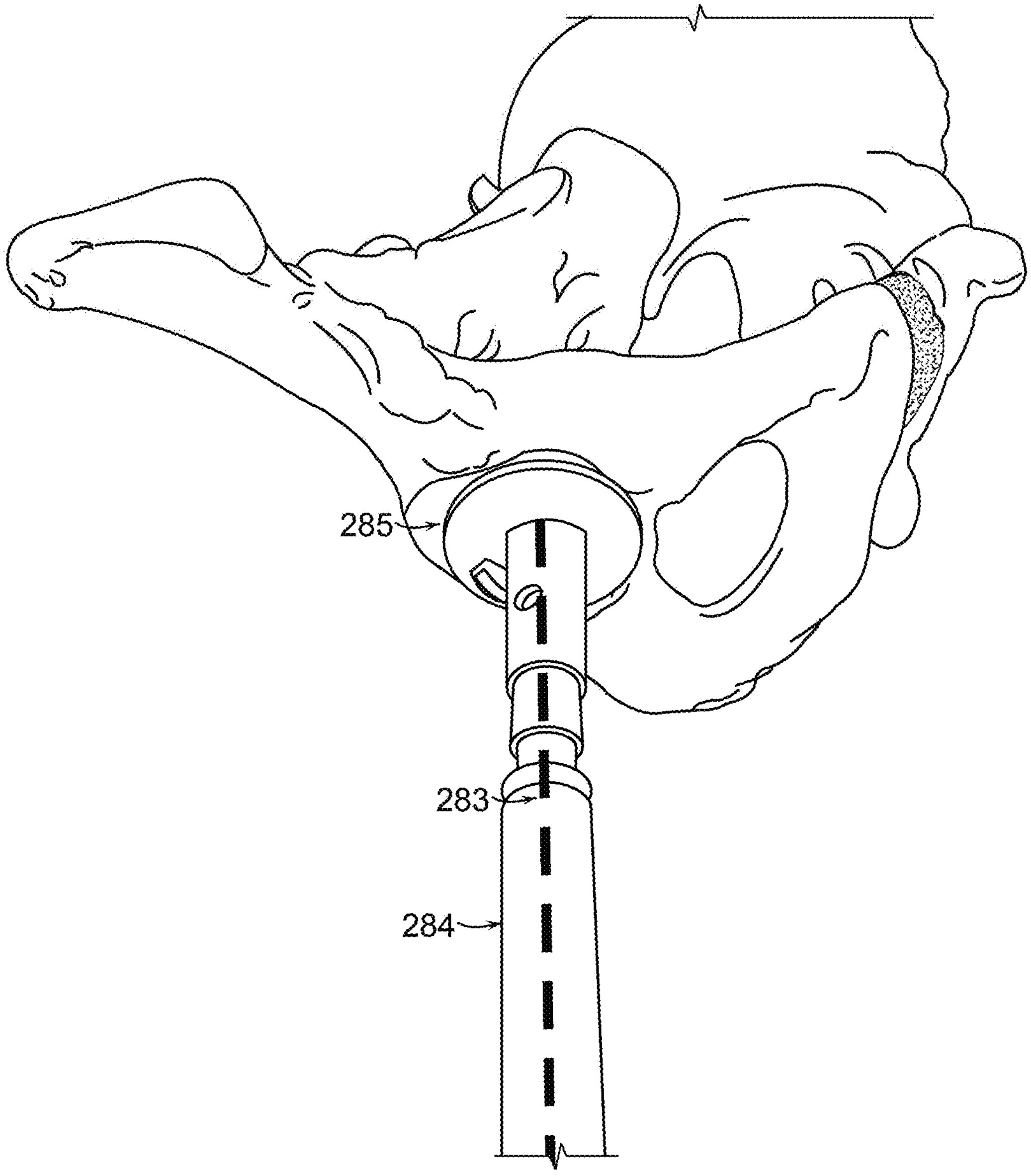

FIGS. 13A-13F are illustrative examples of displaying a virtual acetabular reaming axis using one or more see through optical head mounted displays (ARDD) and aligning a physical acetabular reamer with the virtual reaming axis for placing an acetabular cup with a predetermined cup angle, offset, medial or lateral position and/or anteversion and/or inclination. FIG. 13A shows a first surgeon's view, e.g. through an ARDD, onto the patient's exposed acetabulum 280. Note also the anterior superior iliac spine 281 and the symphysis pubis 282, which can optionally be used for registration purposes, for example using attached optical markers or navigation markers. In FIG. 13B, the first surgeon can see a virtual acetabular reaming axis 283 through the ARDD, which can be oriented in a predetermined manner to achieve a predetermined acetabular cup angle, offset, medial or lateral position and/or anteversion and/or inclination, e.g. from a virtual surgical plan for the patient. In FIG. 13C, the first surgeon aligns the physical acetabular reamer shaft 284 so that its central axis is aligned or superimposed with the virtual acetabular reaming axis thereby placing the reamer head 285 in the acetabulum in a predetermined position and orientation for a predetermined acetabular cup angle, offset, medial or lateral position and/or anteversion and/or inclination.

Figure 13D:
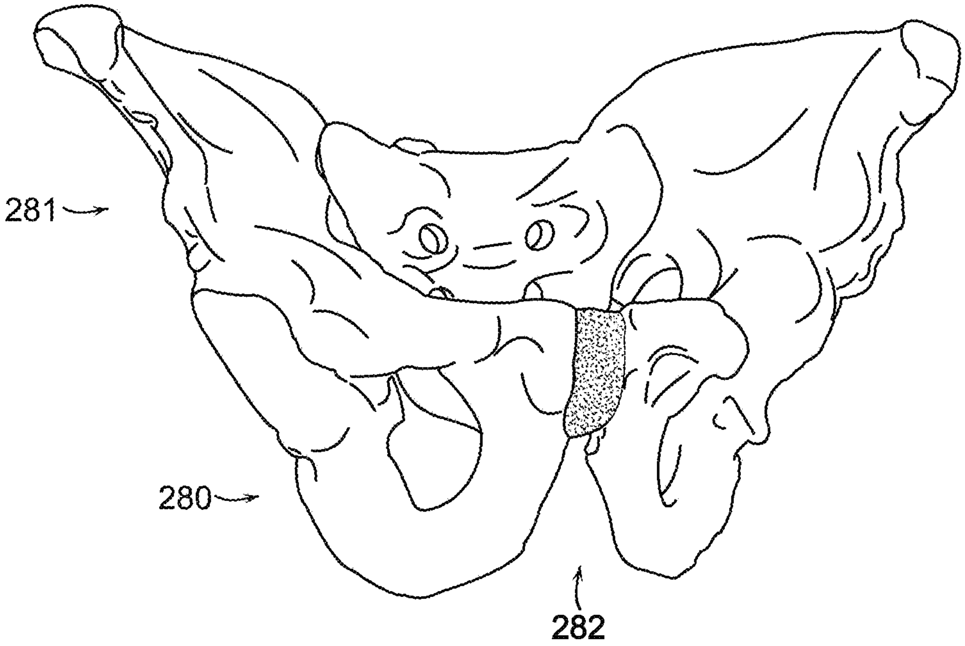
Figure 13E:
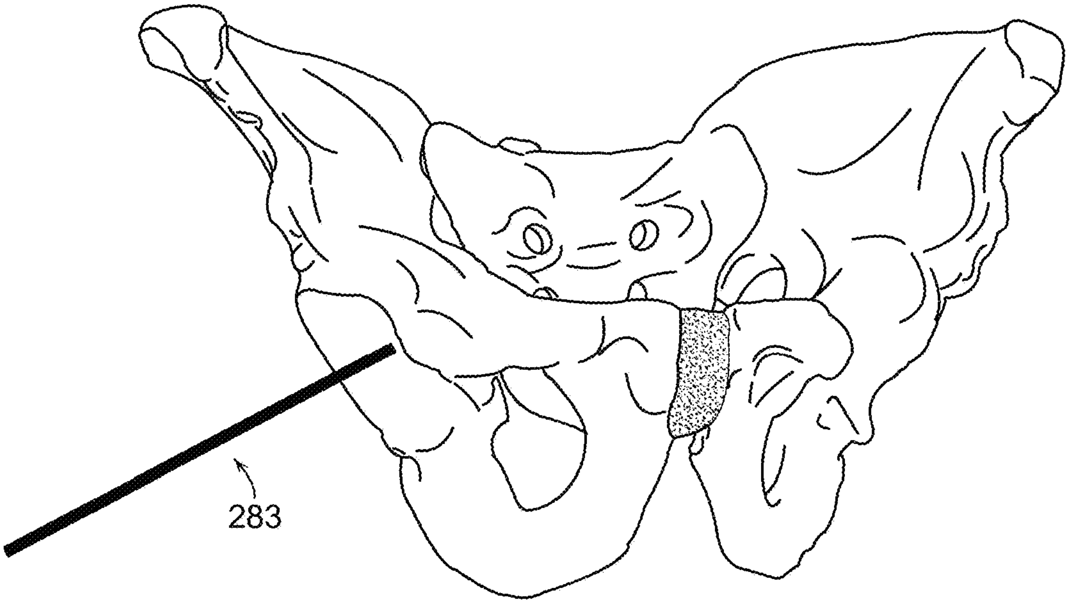
Figure 13F:
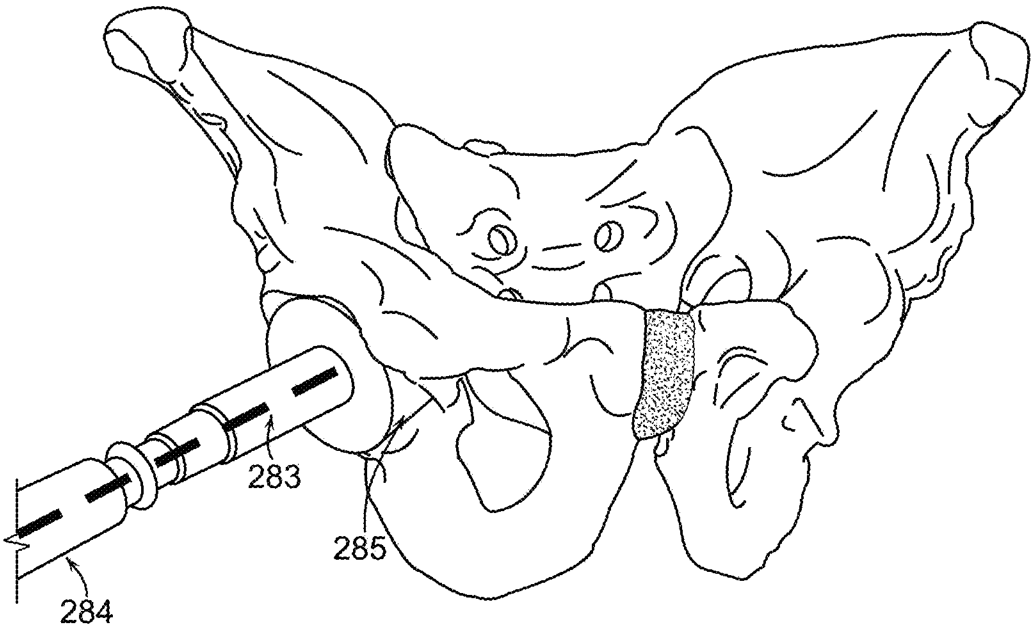

FIG. 13D shows a second surgeon's view with his or her respective view perspective of live data and virtual data through the ARDD onto the patient's exposed acetabulum 280. Note also the anterior superior iliac spine 281 and the symphysis pubis 282, which can optionally be used for registration purposes, for example using attached optical markers or navigation markers. In FIG. 13E, the second surgeon can see the virtual acetabular reaming axis 283 through the ARDD, which can be oriented in a predetermined manner to achieve a predetermined acetabular cup angle, offset, medial or lateral position and/or anteversion and/or inclination, e.g. from a virtual surgical plan for the patient. The virtual acetabular reaming axis is projected with a view angle or view perspective matching the view angle or view perspective of the live data of the patient seen by the second surgeon. In FIG. 13F, the second surgeon can see how the physical acetabular reamer shaft 284 is aligned by the first surgeon so that its central axis is aligned or superimposed with the virtual acetabular reaming axis thereby placing the reamer head 285 in the acetabulum in a predetermined position and orientation for a predetermined acetabular cup angle, offset, medial or lateral position and/or anteversion and/or inclination.

Thus, the surgeon can hold the physical acetabular reamer seeing the live data through the ARDD; at the same time, the OHDM can display or project a digital hologram of the corresponding virtual acetabular reamer with the virtual acetabular reamer aligned and oriented to achieve a desired acetabular cup position, e.g. anteversion, inclination, as optionally defined in a virtual surgical plan. Alternatively, the ARDD can display a partial (e.g. broken or dotted) or complete 2D or 3D outline of the virtual acetabular reamer or one or more placement indicators, e.g. lines indicating the predetermined placement position and orientation of the acetabular reamer, e.g. a virtual predetermined medial border or placement or position, a virtual predetermined lateral border or placement or position, a virtual predetermined anterior border or placement or position, a virtual predetermined posterior border or placement or position, a virtual predetermined superior border or placement or position and/or a virtual predetermined inferior border or placement or position and/or or virtual predetermined rim position and/or a virtual predetermined central axis orientation or position and/or a virtual predetermined anteversion.

The surgeon can now align the physical acetabular reamer with the virtual acetabular reamer or its 2D or 3D outline or placement indicator or predetermined or virtual reaming axis displayed by the ARDD so that the physical acetabular reamer is substantially superimposed or aligned with or oriented along the virtual acetabular reamer or its 2D or 3D outline or placement indicator or virtual reaming axis. The ARDD can also indicate the desired or predetermined reaming depth as optionally defined in a virtual surgical plan, for example derived from one or more intra-operative measurement and/or a pre- or intra-operative scan, e.g. a CT or MRI scan [optionally displayed by the ARDD as one or more 2D slices or a 3D reconstruction of the anatomy]. The desired or predetermined reaming depth can be displayed by the ARDD, e.g. as a virtual red border to which the physical reamer can be advanced. If the reaming surface of the physical reamer is not visible since it is hidden by tissue, e.g. soft-tissue or bone, it can be estimated based on the visible portions of the physical reamer and it can be optionally displayed by the ARDD, e.g. using a different color than the display of the virtual reamer or the virtual "red border" for the reaming depth. The physical reaming depth of the physical reamer can also be measured, for example via image capture or mechanical data capture of a numeric scale on the physical reamer which indicates reaming depth, or by attaching IMU's or one or more optical markers, RF tags or retro-reflective markers for navigation to the reamer and by comparing physical measured reaming depth to the virtual surgical plan. The ARDD can indicate when the desired or predetermined reaming depth has been achieved, for example with a visual or acoustic signal. One or more optical markers can also be attached to the shaft of the acetabular reamer. By measuring the position of the one or more optical markers, e.g. two optical markers in two different locations along the shaft of the reamer, the long axis of the physical acetabular reamer can be determined using image or video capture and can be compared to the predetermined virtual reaming axis to achieve a desired or predetermined cup placement, including a desired or predetermined offset and/or cup angle and/or anteversion.

By attaching or integrating one or more optical markers, navigation markers, infrared markers, RF markers, patient specific markers, LED's with image capture and IMU's to a reamer or a broach or an impactor in hip replacement or any other instrument or tool in other joint replacement procedures or arthroscopic procedures in the hip, knee, shoulder, ankle, elbow, wrist or any other joint, e.g. a cut block, drill, pin, mill, reamer, broach, impactor, drill tower, template, or patient specific instrument, the instruments or tools can be tracked in regards to their position, location, orientation, direction of movement, speed of movement and/or coordinates in the coordinate system. Similarly, a video system or a 3D scanner can be used for tracking the instruments and their position, location, orientation, direction of movement, speed of movement and/or coordinates in the coordinate system. The position, location, orientation, direction of movement, speed of movement and/or coordinates in the coordinate system of the tracked instruments or tools can be compared to the predetermined or intended position, location, orientation, direction of movement, speed of movement and/or coordinates in the coordinate system of the instruments or tools in a virtual surgical plan. If an instrument or tool deviates from the predetermined or intended position, location, orientation, direction of movement, speed of movement and/or coordinates in the coordinate system this can be indicated or displayed in the ARDD. For example, if the instrument or tool deviates from the predetermined or intended position, location, orientation, direction of movement, speed of movement and/or coordinates in the coordinate system the ARDD can display an optical warning, optionally color coded, e.g. red, or optionally blinking or flashing. The ARDD can also emit an acoustic or any other signal, e.g. a vibration. The tracked instrument or tool can optionally be displayed with a color highlighting the deviation from the predetermined or intended position, location, orientation, direction of movement, speed of movement in the coordinate system, e.g. a red color. The optical, acoustic, or other warning signals can stop when the instrument or tool is in or returns to the predetermined or intended position, location, orientation, direction of movement, speed of movement and/or coordinates in the coordinate system, or is within a certain range of the predetermined or intended position, location, orientation, direction of movement, speed of movement and/or coordinates in the coordinate system, e.g. 1%, 2%, 3%, 5%, 10%, 15%, 20%, 30% etc., or 1 degree, 2 degrees, 3 degrees, 5 degrees, 10 degrees, 15 degrees, 20 degrees etc., or 0.5 mm, 1.0 mm, 2.0 mm, 3.0 mm, 5.0 mm, 10.0 mm, 15.0 mm, 20.0 mm etc. Any value can be used. Optionally, the system can measure the percentage time the instrument or tool was outside the predetermined or intended position, location, orientation, direction of movement, speed of movement and/or coordinates in the coordinate system. Optionally, the system can measure the average deviation from the predetermined or intended position, location, orientation, direction of movement, speed of movement and/or coordinates in the coordinate system, e.g. in %, degrees or mm. Optionally, the system can generate a warning or a report if the instrument or tool deviated from the predetermined or intended position, location, orientation, direction of movement, speed of movement and/or coordinates in the coordinate system for more than a defined percentage of time or average or median or other statistical value, e.g. in %, degrees or mm. Optionally, when the instrument or tool is in or returns to the predetermined or intended position, location, orientation, direction of movement, speed of movement and/or coordinates in the coordinate system, the display including the color of the instrument or tool can change in the ARDD, e.g. from red to green, or from blinking or flashing to steady or disappearing.

In another embodiment, the percentage overlap or alignment of a virtual implant, instrument or tool with a physical implant, instrument or tool can be shown in the form of a numeric display, e.g. 10%, 20%, 30%, 40%, 50%, 60%, 70%, 80%, 90%, 95%, 98%, 99%, 100%. The percentage overlap or alignment can be computed by comparing the tracked physical implant, instrument, or tool against the virtual implant, instrument or tool, e.g. in the virtual surgical plan. The percentage overlap or alignment can be based on coordinates, an outline of the implant, instrument or tool, a placement indicator, an area or a volume of overlap, e.g. between the virtual implant, virtual instrument or virtual tool and the physical implant, physical instrument or physical tool.

In certain circumstances, the percentage overlap or alignment of a virtual implant, instrument or tool with a tracked physical implant, instrument or tool can be greater than 90%, greater than 95%, greater than 98%, greater than 99% or can be 100%, but the physical implant, instrument or tool seen through a see through optical head mounted display may not appear to be aligned with the virtual implant, instrument or tool, contrary to the indication based on the tracking data. This can happen, for example, if the ARDD moves on the surgeon's head, for example after an initial calibration or registration in the coordinate system. Thus, it can be possible that the virtual display can be offset relative to the surgeon's eyes or pupils, for example similar to the amount of movement of the optical head mounted display on the surgeon's head or face. If a discrepancy between the percentage overlap or alignment of a virtual implant, instrument or tool with a tracked physical implant, instrument or tool between the tracking data and the visible superimposition of the two is apparent, the registration and/or calibration can optionally be repeated for the one or more optical head mounted displays to ensure accurate registration of the ARDD in the coordinate system.

Figure 18:
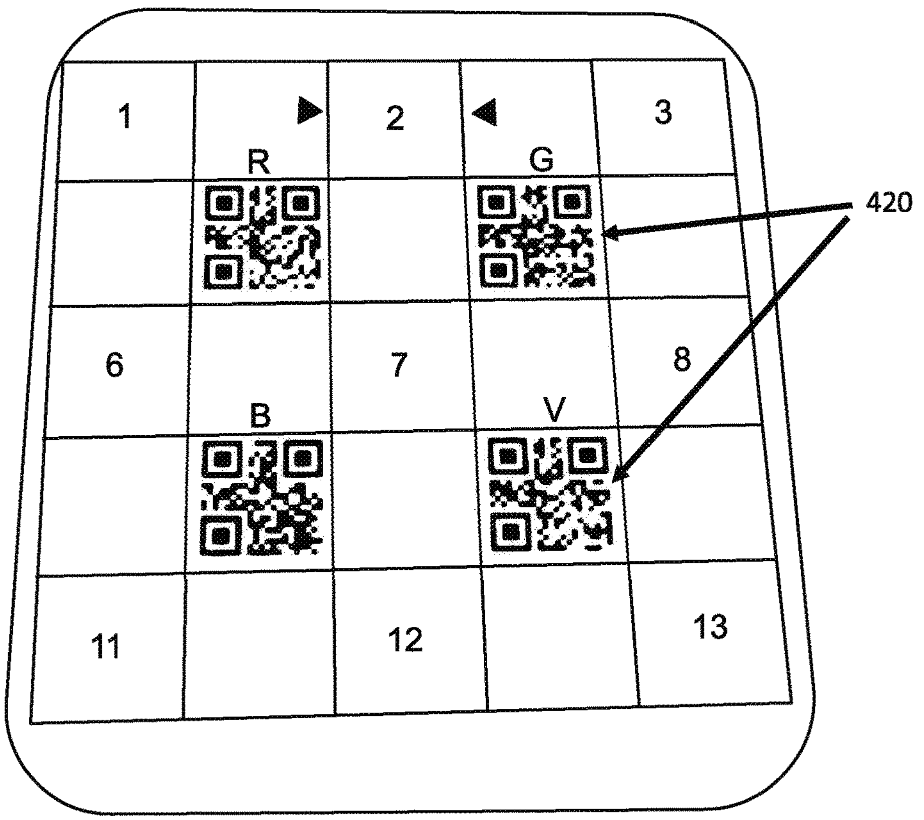
FIG. 18 shows a wooden board with 25 squares and four 4.0×4.0 cm optical markers according to some embodiments of the present disclosure.
Figure 19:
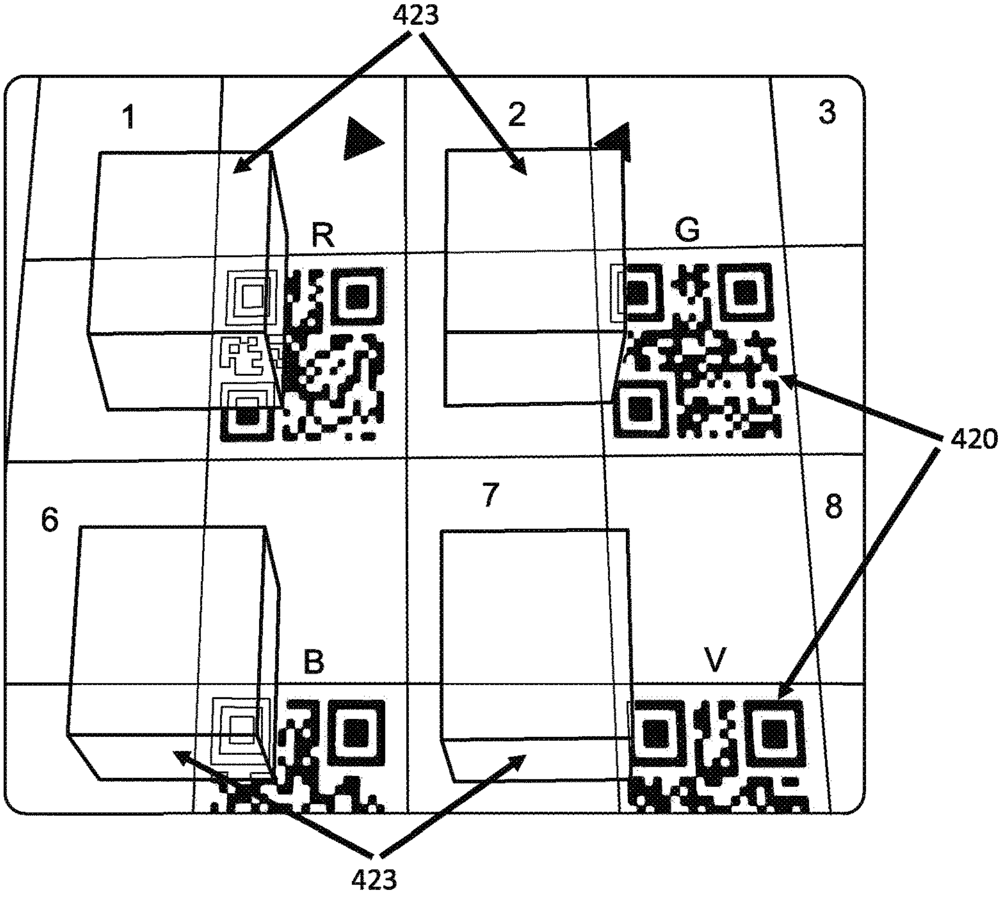
FIG. 19 shows an illustrative, non-limiting example of registration of four cubes in relationship to four optical markers using the image capture system of an ARDD (e.g. HMD) according to some embodiments of the present disclosure.

In some embodiments, a calibration structure, a reference phantom, an optical marker, a navigation marker [e.g. an RF or IR marker], or an LED can be applied to a portion of the surgical site and/or a fixed structure in the operating room. A computer processor can then display a virtual reference body superimposed onto the one or more calibration structure, reference phantom, optical marker, navigation marker [e.g. an RF or IR marker], or LED; the superimposition can be at or near 100%. If the virtual reference body is not superimposed onto or aligned with the one or more calibration structure, reference phantom, optical marker, navigation marker [e.g. an RF or IR marker], or LED, it can be an indication that the ARDD can have moved on the surgeon's face or head. FIG. 19 can be an example of a virtual reference body, e.g. a virtual cube 423, superimposed onto a calibration structure, reference phantom, optical marker, navigation marker [e.g. an RF or IR marker], or LED, in this example an optical marker 420 (FIG. 18). When the virtual reference body is not aligned with the marker, it can be an indication that the registration is not accurate or has been lost, which can, for example, be an indication of a technical problem or an indication that the ARDD can have moved on the surgeon's face at some point after the initial registration. Thus, the use of a calibration structure or reference phantom, for example applied to portions of the surgical site or a fixed structure in the OR, e.g. the OR table, with virtual projection and superimposition of a corresponding virtual calibration structure or virtual reference phantom can be useful for detecting potential registration and/or tracking issues, including problems related to the registration of one or more ARDD's in the coordinate system. This can, in turn, be used to initiate or trigger a re-registration. In some embodiments, the surgeon can visually observe the virtual calibration structure or virtual and reference phantom in relationship to the physical calibration structure or physical reference phantom; the surgeon can decide if there is a registration issue. In other embodiments, one or more cameras can be positioned near one or both eyes of the surgeon, and the cameras can obtain an image or video projection of the physical calibration structure or reference phantom. A computer processor can then compare the position and/or location and/or alignment and/or alignment of the physical calibration phantom or reference structure with the position and/or location and/or alignment and/or coordinates of the virtual calibration phantom or reference structure. Optionally the images or video obtained from the one or more cameras positioned near one or both eyes of the surgeon can be corrected for parallax relative to the surgeon's eye. For this purpose, two, three, four or more cameras can be used, for example at defined positions and/or orientations relative to the eye or the pupil of the surgeon. If the computer processor detects a significant discrepancy, e.g. in mm, degrees, or percentage superimposition (e.g. area or volume) between the position and/or location and/or alignment and/or coordinates of the physical calibration phantom or reference structure with the position and/or location and/or alignment and/or coordinates of the virtual calibration phantom or reference structure, the system can trigger an alarm, initiating, for example, a re-calibration or re-registration, e.g. of the ARDD, one or more tracked instruments, tools or implants, the surgical site and/or the one or more physical calibration structures or reference phantoms in the coordinate system.

In another embodiment, one or more cameras directed at the eye(s) of the surgeon can image both the position and/or location and/or alignment and/or coordinates of the physical calibration phantom or reference structure and the position and/or location and/or alignment and/or coordinates of the virtual calibration phantom or reference structure visible on and/or reflected from the lens or cornea or other structures of the eye of the surgeon or user. If the two reflections are not aligned and/or superimposed, it can be an indication that the registration is not accurate. The system can then determine the discrepancy, e.g. in mm, degrees, or percentage superimposition, between the position and/or location and/or alignment and/or coordinates of the physical calibration phantom or reference structure with the position and/or location and/or alignment and/or coordinates of the virtual calibration phantom or reference structure, and the system can trigger an alarm, initiating, for example, a re-calibration or re-registration, e.g. of the ARDD, one or more tracked instruments, tools or implants, the surgical site and/or the one or more physical calibration structures or reference phantoms in the coordinate system.

The physical acetabular cup can be placed by obtaining substantial or near substantial superimposition with the virtual acetabular cup or its 2D or 3D outline or placement indicator(s) projected by the ARDD using, for example, the virtual surgical plan for the patient, whereby the virtual acetabular cup or its 2D or 3D outline or placement indicator(s) show the desired anteversion and inclination. Depending on the surgical approach, e.g. anterior, posterior or posterolateral, only those portions of the virtual acetabular cup can be displayed that correspond to the portions of the physical acetabular cup which would be visible for the surgical approach or surgical site. Optionally, the physical values, e.g. numerical values in degrees, of anteversion and inclination can be numerically displayed, e.g. by the ARDD, showing, for example, the desired values for the patient from the virtual surgical plan and the physical values based on the physical cup or trial cup position, location, orientation, and/or alignment. If there is a visual discrepancy, i.e. incomplete superimposition between virtual cup displayed by the ARDD and the physical or trial cup, or a numeric discrepancy, e.g. in virtual cup anteversion and/or inclination from the virtual surgical plan versus physical cup anteversion and/or inclination, the surgeon can correct the position, location, orientation, and/or alignment of the physical cup prior to impaction. The surgeon can also monitor the visual alignment and the numeric alignment or discrepancy between the virtual and the physical acetabular cup, e.g. during impaction, or the surgeon can also monitor the numeric concordance or discrepancy between the virtual and the physical acetabular impactor.

Figure 21:
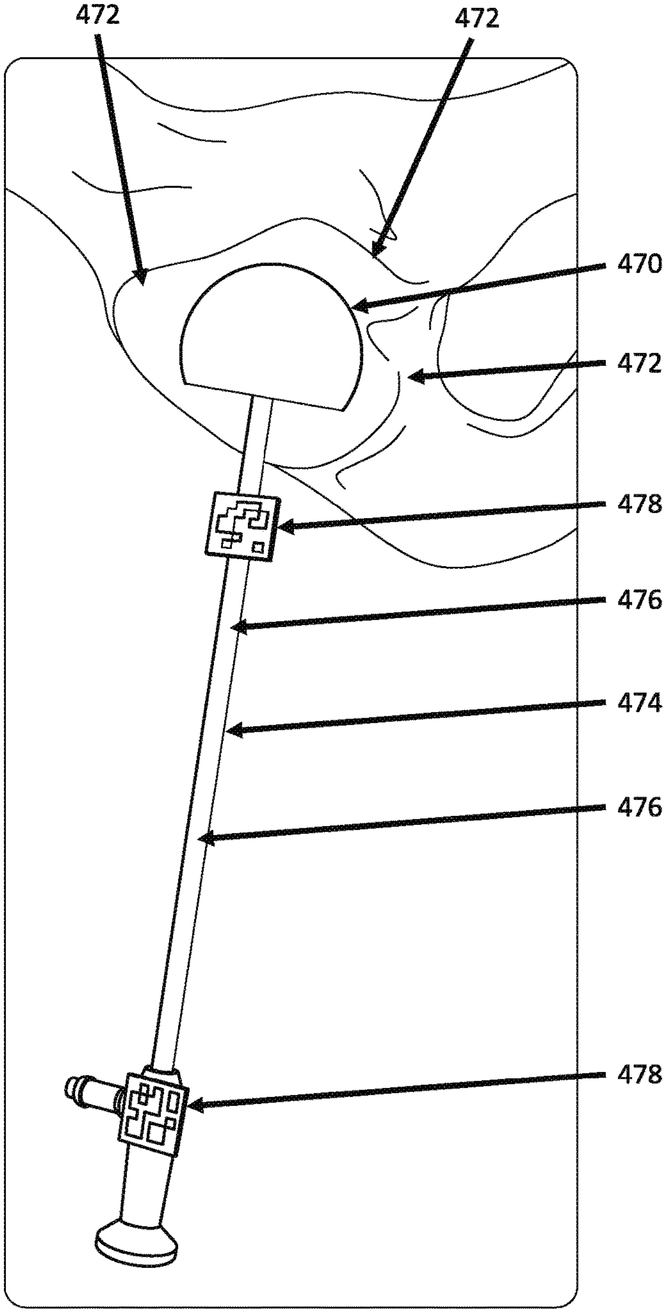
FIG. 21 shows an illustrative, non-limiting example of an acetabular placement instrument or tool with attached optical markers according to some embodiments of the present disclosure.
Figure 22A:
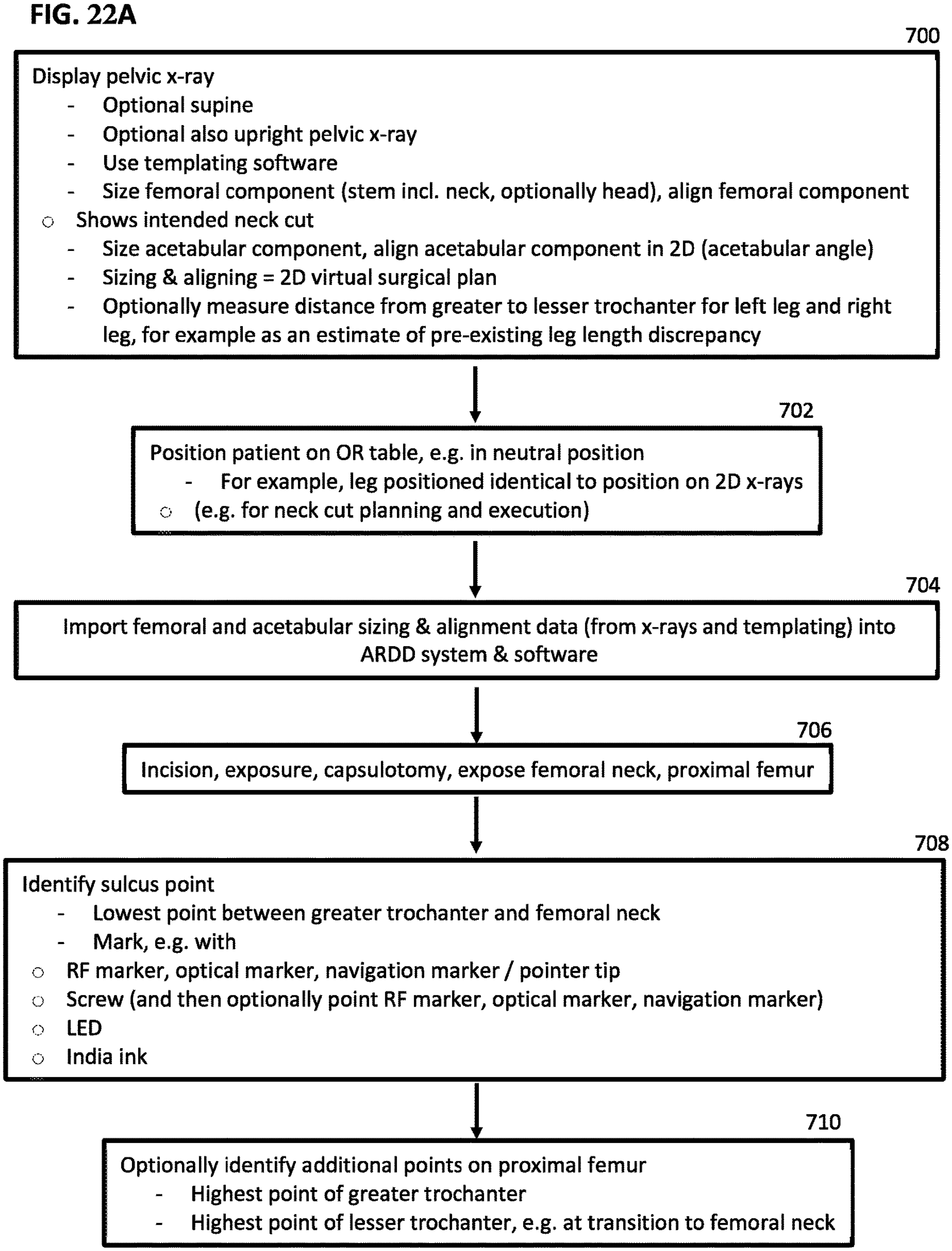
Figure 22G:
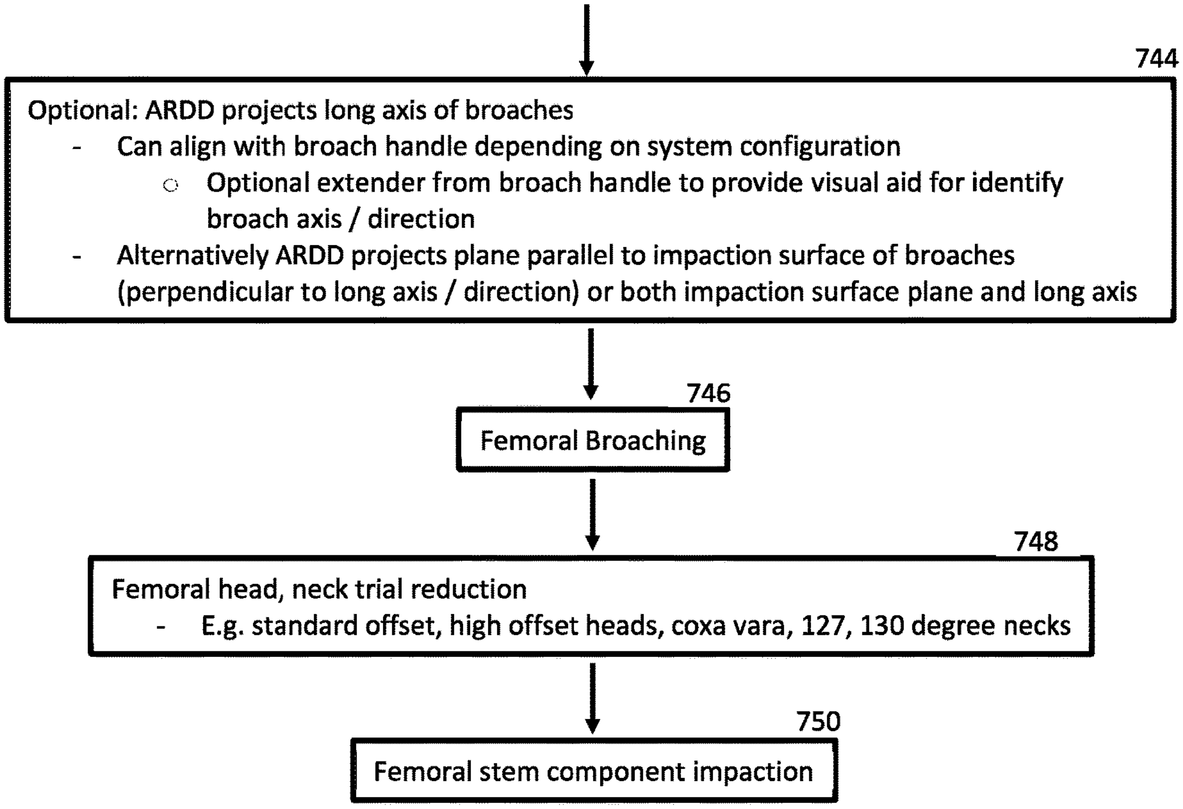

In another example, an acetabular placement instrument 470 can be placed by the surgeon in the exposed acetabular fossa as shown in an illustrative example in FIG. 21. The acetabular placement instrument can have the same shape and/or dimensions and/or radius and/or radii on the acetabular fossa facing surface as the acetabular cup or trial cup selected for implantation. The acetabular placement instrument can have a shape and/or dimensions and/or radius and/or radii on the acetabular fossa facing surface matching the shape and/or dimensions and/or radius of the patient's acetabular fossa. The acetabular placement tool 470 can also have a similar or a smaller shape and/or dimensions and/or radius and/or radii than the acetabular cup or trial cup or than the patient's acetabular fossa as seen in FIG. 21. By placing the acetabular placement instrument under visual control equidistant from the anterior, posterior, superior and inferior acetabular margin 472 of the patient, the surgeon can determine the patient's acetabular inclination and anteversion. The surgeon can choose the use the same cup inclination and anteversion during the surgery for the implantation of the prosthetic acetabular cup. Alternatively, the surgeon can choose a different position, e.g. by medializing the position of the acetabular placement instrument or by changing the anteversion of the acetabular placement instrument.

The acetabular placement instrument can have a handle 474 with a central axis 476 (FIG. 21). Two or more optical markers 478 can be integrated into or attached to the handle 474. The position of the optical markers 478 can be detected with a video camera integrated into, attached to or separate from the ARDD (e.g. OHMD). With the optical markers located, for example, at defined positions on the acetabular placement instrument and with the geometry of the instrument known, the position and orientation of the instrument can be calculated, including the location of the acetabulum facing portion of the instrument. More markers 478 can be used, e.g. in different geometric locations on the instrument with overlapping or separate, distinct x, y, and z coordinates. Alternatively, navigation markers, e.g. infrared or RF, can be used in conjunction with a surgical navigation system. The 3D coordinates of the optical markers or, alternatively any other markers, e.g. LED's, are recognized by the image and/or video capture system and/or 3D scanner integrated into or attached to the ARDD (e.g. OMHD) or separate from the ARDD (e.g. OHMD) using the methods described in the disclosure including the examples. Using the coordinates of a first and second marker, a central axis and vector 476, FIG. 21, is calculated. The acetabular placement instrument can then be removed from the acetabular fossa. The surgeon can optionally make adjustments to the acetabular inclination and anteversion or the reaming axis determined in this manner, for example on a standalone or separate computer in the operating room which can host a virtual surgical plan, e.g. determined pre-operatively or intra-operatively, e.g. based on x-rays and x-ray templates, or based on intra-operative measurements including measurements using the acetabular placement instrument. The surgeon can also use a virtual interface to change the orientation of the vector and with that the acetabular inclination and anteversion and the intended reaming axis. The ARDD can subsequently display the intended acetabular reaming axis, which can be the axis or vector measured with the acetabular placement tool or which can be an axis modified or derived based on the axis or vector measured with the acetabular placement tool or which can be any other axis, e.g. a predetermined axis or an axis with a fixed angle, e.g. relative to the OR table.

By utilizing the 3D anatomic information of the patient from the pre-operative data or by using intra-operative measurements, for example optical markers for determining a center of rotation of a hip joint or for determining a desired anteversion, the surgeon can work more accurately in this manner, thereby reducing, for example, the need for offset or asymmetric liners.

In another embodiment, the dimensions and/or shape of the resected bone can be measured and the information can be combined with information obtained using optical markers, IMU's, navigation markers and/or calibration phantoms. For example, in a hip replacement, the surgeon can determine the center of a resected femoral head and the anteversion of the resected femoral head and neck as well as the neck length, combined head-neck length and neck resection angle. Measurements on resected bone specimens can be performed using mechanical devices, including but not limited to rulers, calipers and angle measurement tools as well as more sophisticated instruments such as CMM machines, e.g. a Faro arm (Faro, Warwickshire, UK). Alternatively, optical scanners and laser scanners can be used to measure the resected bone specimens. A representative scanner is, for example, the Structure 3D scanner by Occipital, Inc., San Francisco, CA. Bone lost from cutting, e.g. by the thickness of the saw blade can be accounted for in any of the measurements. If more than one bone cut was performed, e.g. in case of "napkin ring" resection of the femoral neck in an anterior hip replacement, the bone lost by the two bone cuts can also be accounted for. The napkin ring dimensions and thickness can also be measured. By measuring the resected bone in this manner, any deviations of the actual surgery including the actual, physical bone cuts from the virtual surgical plan can be detected and can be accounted for in subsequent surgical steps or with use of different implant components, e.g. in a hip replacement by using plus or minus size heads or various liner thicknesses or stem components with different neck angles.

Of note, the same steps and ARDD guided acetabular procedures are also possible using the ARDD with any of the registration and cross-referencing techniques described in the disclosure and known in the art, such as, for example, registration using anatomic landmarks or registration or calibration phantoms including optical markers or image capture, optionally using optical markers, or surgical navigation or patient specific markers or intra-operative imaging.

Any of the registration techniques or techniques described herein including implantable and attachable markers, calibration and registration phantoms including optical markers, navigation markers, infrared markers, RF markers, patient specific markers, LED's with image capture and IMU's can be applied for registering the patient's proximal femur in relationship to, for example, one or more ARDD worn by the surgeon and/or is assistants, and/or in relationship to one or more surgical instruments, pins, drills, saws, reamers, impactors, broaches and the like and/or in relationship to one or more femoral or acetabular implants, including metal and/or polyethylene components. For example, by applying one or more optical markers and/or patient specific markers or templates to a greater trochanter, a lesser trochanter, a femoral shaft or a femoral neck, or femoral osteophytes, virtual and physical live patient data can be cross-referenced on the femoral side. Optionally, a pin or a screw can be inserted into the proximal femur, e.g. in a greater trochanter, which can be used as a reference for registration, for example if an optical marker or patient specific marker moves. Optical markers can be optionally attached to the pin or screw. Multiple pins or screws can be used in this manner. The virtual surgical plan can include a desired neck cut location for a particular femoral component. The neck cut can be designed or selected to avoid any offset issues and to maintain the patient's leg length in the virtual surgical plan. By registering the optical marker and/or patient specific marker or template in relationship to the ARDD also, e.g. in a common coordinate system with the ARDD, the surgical site, the proximal femur, the ARDD can display or superimpose and/or project digital holograms with different view coordinates for the left eye and the right eye of the user wearing the ARDD showing the desired or predetermined position, location, orientation, alignment and/or trajectory or predetermined plane of any surgical instrument including a saw for performing the femoral neck cut. After successful registration of virtual and live data of the patient using any of the techniques or techniques described herein, the ARDD can show the desired 3D trajectory including the desired location, entry point and angles in x, y and z direction for the femoral neck cut or the ARDD can display one or more digital holograms of a virtual cut plane and/or a virtual saw or saw blade in the position, location, angular orientation, and trajectory (e.g. as a dotted line or arrow) defined in the surgical plan which the surgeon can then match with the physical saw, i.e. the surgeon can orient and align the physical saw so that it will be aligned with or substantially superimposed onto the virtual saw (see also FIGS. 4A-4C).

Alternatively, the ARDD can show a digital hologram of a partial (e.g. broken or dotted) or complete 2D or 3D outline of the virtual saw or placement indicators, e.g. lines indicating the predetermined placement position and orientation of the saw, e.g. a virtual predetermined medial placement or position, a virtual predetermined lateral placement or position, a virtual predetermined anterior placement or position, a virtual predetermined posterior placement or position, a virtual predetermined superior placement or position and/or a virtual predetermined inferior placement or position. Alternatively, the ARDD can show a digital hologram of a virtual femoral neck cut plane.

Optionally, for example once the entry point on the femoral neck has been defined or the desired location, orientation and/or direction of the saw has been determined with assistance from the ARDD, the surgeon can apply a standard saw guide to the femoral neck to facilitate the neck cut. Alternatively, the ARDD can display a digital hologram of a virtual femoral neck saw guide or its corresponding 2D or 3D outline or placement indicators in its desired position or location on the femoral neck. The physical saw guide can then be aligned with the corresponding virtual saw guide or its corresponding 2D or 3D outline or placement indicators placed in the desired position, orientation and angulation based on the virtual surgical plan of the patient. The virtual saw guide can have the same or similar shape and/or one or more dimensions or planes as the physical saw guide. Once the physical saw guide is substantially superimposed in position with the virtual saw guide or its corresponding 2D or 3D outline or placement indicators displayed by the ARDD, the surgeon can optionally pin the physical saw guide in place and perform the neck cut. By executing the neck cut using one of these approaches which utilize accurate 3D anatomic information of the patient from the preoperative scan and/or intra-operative measurements including registration, e.g. using optical markers, leg length and offset can be more accurately preserved or addressed.

Similarly, the ARDD can project the desired position, location, orientation and trajectory of any virtual femoral reamers and impactors. Alternatively, the ARDD can only show a partial (e.g. broken or dotted) or complete 2D or 3D outline of the virtual femoral reamers or impactors or placement indicators, e.g. lines indicating the predetermined placement position and orientation of the reamers or impactors, e.g. a virtual predetermined medial placement or position, a virtual predetermined lateral placement or position, a virtual predetermined anterior placement or position, a virtual predetermined posterior placement or position, a virtual predetermined superior placement or position or a virtual predetermined inferior placement or position or a virtual reaming axis, e.g. a central axis through the reamer shaft. The ARDD can also display a digital hologram of a predetermined virtual reaming and/or broaching axis, which can provide a desired femoral component position including one or more of an offset and/or anteversion including, for example, composite anteversion for both femoral and acetabular components. The virtual femoral reamers and impactors can have the same or similar shape and dimensions as the physical femoral reamers and impactors. The surgeon can then match the position, location, orientation and trajectory (e.g. indicated by a dotted line or an arrow in the virtual data) of the physical femoral reamers and impactors with the virtual reamers and impactors or their corresponding 2D or 3D outlines or placement indicators or a virtual reaming or broaching axis, thereby reducing the possibility of mal-seating of the femoral stem and possibly incorrect femoral anteversion, incorrect femoral offset or femoral component angulation or leg length discrepancy. In some embodiments, the surgeon can align the ARDD so that the view angle is perpendicular to the femoral shaft axis or, alternatively, the femoral neck axis. The ARDD can then display a bulls-eye or target like structure whereby the surgeon will aim the femoral reamers, impactors, femoral trials and the physical femoral component to be located in the center of the bulls-eye or target. The ARDD can display the desired entry point, e.g. with regard to medial or lateral, anterior or posterior location on the cut femoral neck, and/or entry angle based on the virtual surgical plan including, for example, the virtual femoral component placement. The ARDD can also display the desired femoral version, for example via a solid or dotted line or arrows on the cut femoral neck surface or in relationship to the cut femoral neck surface. The desired femoral version can also be displayed by the ARDD by displaying one or more digital holograms of the femoral reamers, impactors, femoral trials and the final femoral component or their respective 2D or 3D outlines or placement indicators in the desired virtual location and orientation including femoral version based on the virtual surgical plan. In this manner, the surgeon can align the physical femoral reamers, physical impactors, physical femoral trials and the physical final femoral component to be substantially aligned or superimposed with the digital holograms of the one or more virtual femoral reamers, virtual impactors, virtual femoral trials and virtual final femoral component thereby achieving a result near the desired femoral version and, optionally, leg length based on the virtual surgical plan.

All of the foregoing steps and ARDD guided femoral procedures are also possible using the ARDD with any of the other registration and cross-referencing techniques described in the disclosure or known in the art, such as, for example, registration using anatomic landmarks or implantable and attachable markers, calibration and registration phantoms including optical markers, navigation markers, infrared markers, RF markers, patient specific markers, LED's with image capture and IMU's.

In some embodiments, an ultrasound scan can be used to derive the shape information used for designing and producing the patient specific template, e.g. for use on the acetabular side or the femoral side. Optionally, the ultrasound scan can be obtained in supine and/or upright position. By obtaining the ultrasound scan in upright position, information about femoro-acetabular alignment and orientation can be obtained under weight-bearing positions including, for example, femoral or acetabular anteversion, femoral/acetabular/hip flexion, extension, abduction, adduction and/or rotation. By obtaining the ultrasound scan in supine position, information about femoro-acetabular alignment and orientation can be obtained under non-weight-bearing positions including, for example, femoral or acetabular anteversion, femoral/acetabular/hip flexion, extension, abduction, adduction and/or rotation. By comparing data from one or more upright and one or more supine ultrasound scans, e.g. by comparing the relative movement of corresponding anatomic landmarks, information can be obtained about pelvic tilt. The information from the upright and/or supine scan can be used for selecting the desired femoral and acetabular components including, for example, the shape and length of the femoral neck, the offsets, the femoral head component, as well as the shape of the acetabular component, including, for example, offset, mesialized, lateralized, or rimmed acetabular components. The information from the upright and/or supine scan can be used for developing or adjusting the virtual surgical plan, for example by changing the predetermined cup position based on the upright scan information or based on information on pelvic tilt. Similar information can be obtained using supine and upright x-rays studies.

Optionally, the information from the upright and/or supine imaging data can be used to assess information on pelvic tilt, which in turn can be introduced into the surgical plan and component selection in order to avoid or minimize the risk of postoperative complications such as component dislocation.

Thus, by performing hip replacement using the different embodiments, it is possible for the surgeon to conduct the surgery with high accuracy thereby reducing the possibility of common complications in hip replacement such as offset error or wrong acetabular or femoral anteversion leading to hip dislocation or leg length discrepancy. Optionally, the ARDD can also display sensitive vascular or neural structures, thereby reducing the possibility of vascular injury or, for example, sciatic nerve injury.

In some embodiments, the registration of virtual patient data and live patient data using the techniques described herein can be repeated after one or more surgical steps have been performed in an ARDD guided hip replacement procedure. In this case, the surgically altered tissue or tissue surface or tissue contour or tissue perimeter or tissue volume or other tissue features in the live patient can be matched to, superimposed onto and/or registered with the surgically altered tissue or tissue surface or tissue contour or tissue perimeter or tissue volume or other tissue features in the virtual data of the patient, e.g. in a virtual surgical plan developed for the patient. The matching, superimposing and/or registering of the live data of the patient and the virtual data of the patient after the surgical tissue alteration can be performed using the same techniques described in the foregoing or any of the other registration techniques described in the disclosure or any other registration technique known in the art. For example, the re-registration can be performed using a cut bone surface, e.g. a cut femoral neck using the surface shape, surface area or perimeter or other feature, optionally measured with image capture or mechanical or physical probes, to match, superimpose and/or register the live patient data and the virtual patient data prior to performing subsequent surgical steps, e.g. a reaming, milling or impacting of the femoral canal for placement of a femoral component. For example, the re-registration can be performed using a milled bone surface, e.g. a milled acetabulum using the surface shape, surface area or perimeter or other feature, optionally measured with image capture or mechanical or physical probes, to match, superimpose and/or register the live patient data and the virtual patient data prior to performing subsequent surgical steps, e.g. a placement of an acetabular component including trial components.

FIGS. 22A-22G are an illustrative, non-limiting exemplary flow chart demonstrating some of the foregoing examples and embodiments as well as additional examples and embodiments. In step 700, one or more pelvic x-rays are displayed, for example on an ARDD or a standalone computer monitor for templating and/or sizing of a femoral and/or acetabular component. Optionally, the x-rays can be obtained with the patient in supine and/or upright position. In step 702, the patient is positioned on the OR table, for example in neutral position or any other position. Optionally, the leg can be positioned in the same position in which it was when the x-rays were obtained, e.g. for templating and sizing. This can, for example, be helpful for planning and execution of the femoral neck cut. In step 704, the femoral and/or acetabular sizing and alignment data, e.g. from x-rays and templating, can be imported into an ARDD system. Optionally, the templating and/or sizing can be performed on a cross-sectional imaging study, e.g. a CT scan or MRI scan or can be obtained using upright imaging with an EOS or similar system (EOS, Paris, France). The system can comprise the ARDD display unit, one or more processors or computer chips, software, memory, e.g. RAM memory, sensors, e.g. depth sensors or acoustic sensors, and/or one or more cameras. Optionally, the data can also reside or be imported into a standalone computer, e.g. a PC, or server, in the OR or outside the OR and, optionally, computationally intensive steps, e.g. virtually moving, fitting, sizing, aligning implant components on the physical joint of the patient via a user interface, e.g. a graphical user interface, acoustic interface, optical interface, virtual interface, gesture recognition interface or any other interface known in the art, can occur on the standalone computer or server; alternatively, they can occur on the ARDD or a network of ARDD sharing computational and processor power and capacity. In step 706, the surgeon can perform the incision, exposure, capsulotomy, and expose the femoral neck and proximal femur. In step 708, the surgeon can optionally identify the sulcus point, e.g. the lowest point between the greater trochanter and the femoral neck. The sulcus or any other point or anatomic landmark can optionally be marked, e.g. with an optical marker, a navigation marker, e.g. an IR or RF marker, a pointer, e.g. with one or more optical markers and/or one or more navigation markers, a screw, and LED marker and/or India ink or any other marker known in the art. In step 710, the surgeon can identify additional points on the proximal femur, e.g. the highest point or multiple points on the greater trochanter, the highest or lowest point or multiple points on the lesser trochanter, one or more points on the femoral neck, one or more points on the femoral shaft, one or more points on the femoral head, one or more points on osteophytes. These points can be used for registration of virtual data and physical data. These points can be used for generating point clouds, e.g. for surface matching of virtual data, e.g. a preoperative ultrasound, CT or MRI scan, and physical surfaces on the proximal femur and, similarly, the acetabulum, acetabular edge and ilium or pubis. In step 712, one or more of the foregoing points, e.g. the sulcus point or any other points, or one or more of the point clouds or surfaces can be used for computing the femoral neck cut. For example, corresponding points can be identified intraoperatively on the live surgical site, e.g. the exposed femoral neck, greater trochanter or lesser trochanter, and in pre-operative or intra-operative imaging studies, e.g. x-rays, CT, MRI or ultrasound scans. For example, the highest point on the greater trochanter and the lesser trochanter can be identified intra-operatively on the physical joint or bone of the patient and on a pre- or intra-operative imaging study. If the imaging study is two-dimensional, e.g. x-rays, a first plane can be defined intersecting these two points and being, for example, orthogonal or at a defined angle relative to the OR table. Since the femoral neck cut plane can be visualized as part of the templating software and display, the angle and distance of the first plane to the femoral neck cut plane can be determined. Accounting for x-ray magnification, the angle and distance between the first plane and the femoral neck cut plane identified on the imaging study can be applied to the first plane, the plane intersecting the greater and lesser trochanter in this example, and a virtual femoral neck cut plane can be computed for projecting onto the physical proximal femur of the patient. One or more ARDD's can then project the femoral neck cut plane onto the surgical site, e.g. the uncut proximal femur in this example. The femoral neck cut plane can be oriented to be orthogonal to the coronal plane or the OR table; the femoral neck cut plane can be at any other angle relative to the coronal plane or the OR table, e.g. depending on the surgical approach, e.g. anterior vs. posterior vs. posterolateral, or surgeon preference. If a napkin ring cut approach is used, e.g. in anterior hip replacement, with two femoral neck cuts, the ARDD can optionally project the two femoral neck cuts. Optionally, an outline of a femoral neck cut tool or a virtual femoral neck cut tool can be displayed by the ARDD. In step 714, the surgeon can perform the one or more femoral neck cuts and expose the acetabulum, by removing the femoral head with optional resection of the acetabular labrum, pulvinar, fat, osteophytes. In step 716, the center of the acetabulum can be defined. A partial or full radius acetabular placement took can be used, e.g. with radius ½ or ⅔ or 1/1 of acetabular radius of the patient, e.g. on x-ray, and/or of the implant and optional central stem/extender indicating the center of the acetabulum and/or anteversion if the placement tool is placed substantially centered in the acetabulum of the patient. The central stem or extender can include one or more optical markers or navigation markers or LED's or other markers. Alternatively, or additionally, direct image capture and image analysis by a computer processor can be performed for identifying the center of the acetabulum. For this purpose, the image capture apparatus or system, e.g. video camera(s), can be registered in a common coordinate system, e.g. with the patient and/or one or more ARDD's. In some embodiments, a laser scan or 3D scan of the acetabulum can also be obtained, for example with the laser or 3D scanner also registered in the common coordinate system. Mechanical probes, e.g. a pointer probe with attached RF markers, IR markers for navigation, optical markers, LED's and/or IMU's can be used to determine one or more points on the acetabulum and, for example, to generate a point cloud. The points can be used for identifying the geometric center of the acetabulum. Optionally, the center of the acetabulum can be medialized or lateralized, e.g. by moving the partial acetabular placement tool medially or laterally or by moving the center of the acetabulum for reaming and/or impacting medially or laterally on the point cloud with subsequent medialized or lateralized guidance of the reamer and/or impactor in the one or more ARDD'displays. Alternatively, the acetabular cup and with it the center of the acetabulum can be moved medially or laterally on a graphical user interface, e.g. using a computer display or an ARDD, and the virtual surgical plan can utilize the new, adjusted medialized or lateralized center. In step 718, the surgeon can select the acetabular component, e.g. with use of x-rays and/or intra-operative physical trials and/or intra-operative virtual trial components projected by one or more ARDD's onto the acetabulum. In step 720, the center of rotation of the hip joint can be determined, for example, using the patient's center of the acetabulum, measured, for example, using the partial or full radius acetabular placement tool, measured by estimating or determining the rim location, or derived either based on the selected acetabular component or derived from the femoral head radius/center of femoral head measured on an AP and/or frogleg radiograph, or measured on the excised femoral head of the patient. In step 722, the resected femoral head and neck portion can be measured to determine, for example, femoral anteversion and/or offset. The measurements can be used to adjust the reaming or broaching or selection of implant components, e.g. the femoral component or the head component including head offsets and to adjust the reaming or broaching and/or implant components for under-resection or over-resection. Optionally, saw blade thickness can be considered in the calculation and adjustments. Optionally, pre-existing leg length discrepancy and optional correction thereof can be considered in the calculation and adjustment(s). In step 724, the surgeon, the software and/or the system can check if the center of rotation is maintained for a combination of acetabular component and acetabular liner; optionally, different liner(s) can be selected or the virtual surgical plan and/or physical surgical plan can be modified or changed. In step 726, the surgeon, the software and/or the system can check if the center of rotation is maintained for select medialization or lateralization of the cup, which can, for example, be performed during reaming or impacting; optionally, different liner(s) can be selected or the virtual surgical plan and/or physical surgical plan can be modified or changed. In step 728, optionally a desired or predetermined reaming depth can be determined in the virtual surgical plan, e.g. based on pre-operative x-rays or imaging studies, e.g. a pre- or intra-operative CT scan or MRI scan, which can optionally be co-displayed by the one or more ARDD's or based on intra-operative findings. In step 730, an acetabular component central axis and/or an acetabular component reaming axis can be projected onto the surface of the acetabulum and onto the surface of the surgical site. The acetabular component central axis and/or acetabular component reaming axis can account for a predetermined anteversion, e.g. from a pre- or intra-operative imaging study, e.g. a CT scan or one or more x-rays. The acetabular component central axis and/or acetabular component reaming axis can account for a desired medialization or lateralization and/or offset. Optionally, the ARDD can display a pre- or intra-operative imaging study projected onto the surface of the acetabulum as well as subjacent to the surface of the acetabulum. The imaging study can be an x-ray, e.g. projected through an anterior portion, central portion, posterior portion, medial portion or lateral portion of the acetabulum, optionally registered with corresponding anatomic structures, e.g. the acetabular rim or edge or the anterior inferior iliac spine. The x-ray(s) can be parallel in projection to the OR table or parallel to the coronal plane of the patient or any other plane of the patient, or it/they can be perpendicular or at any other defined angle to the OR table or the coronal plane of the patient or any other plane of the patient. Alternatively, volumetric data can be displayed, e.g. from a CT scan or an MRI scan. The volumetric data can be registered to corresponding landmarks and/or surfaces in the physical patient, e.g. an acetabular edge or rim, an acetabular articular surface, an iliac wing surface, a symphysis pubis etc. By display the imaging study, optionally multiple 2D or 3D imaging studies, superimposed onto the live, physical anatomy of the patient, the ARDD can facilitate display of the underlying bone stock as well as display of hidden structures, e.g. nerves, nerve roots or vascular structures. Thus, the ARDD display of the imaging data can be used to guide the direction, speed and depth of any steps involving bone removal, e.g. reaming or broaching. In this manner, the ARDD display can facilitate the surgical procedure ensuring that no over-reaming of an acetabular fossa can occur since the underlying bone stock can be displayed. The imaging studies, e.g. one or more x-rays, a CT scan or MRI scan [optionally displayed by the ARDD as one or more 2D slices or a 3D reconstruction of the anatomy], and/or the underlying bone stock, and/or the acetabular component central axis and/or acetabular component reaming axis can be displayed concurrently thereby facilitating guidance of the reamer or other surgical instrument and determination of the reaming depth. For example, a computer processor can display one or more x-rays, a CT scan or MRI scan [optionally displayed by the ARDD as one or more 2D slices or a 3D reconstruction of the anatomy] using the ARDD superimposed onto and/or aligned with the corresponding anatomic structures of the patient, e.g. an acetabular rim or acetabular fossa [or, in a shoulder joint, a glenoid rim or glenoid fossa]. The display by the ARDD can include a display of the underlying bone stock, e.g. in the patient's pubic, iliac or ischial bone or an area of a tear drop, which can be used to determine a desired or predetermined reaming depth or which can be used to determine a desired or predetermined residual bone thickness, area of volume following the reaming or other forms of bone removal. Optionally the acetabular component central axis and/or acetabular component reaming axis can be displayed onto the surface of the acetabulum and underneath the surface of the acetabulum, e.g. extending into the one or more imaging studies, e.g. one or more x-rays, a CT scan or MRI scan [optionally displayed by the ARDD as one or more 2D slices or a 3D reconstruction of the anatomy], displayed by the ARDD. Optionally, one or more pre- or intra-operative imaging studies, e.g. one or more x-rays, a CT scan or MRI scan [optionally displayed by the ARDD as one or more 2D slices or a 3D reconstruction of the anatomy], can be used to determine a predetermined reaming depth, e.g. using a graphical user interface or virtual or other interface, which can optionally be displayed, e.g. in the form of a virtual stop for the physical reamer. The virtual stop can be a virtual indicator which shows how far the surgeon can advance a corresponding physical portion of the reamer in order to achieve the predetermined reaming depth. In some embodiments a reaming depth, e.g. for reaming an acetabulum, a proximal femur, a glenoid, or a proximal humerus, a patella or any other bone, or a depth for a bone removal can be determined using a pre- or intra-operative imaging test, e.g. one or more x-rays, a CT scan or MRI scan [optionally displayed by the ARDD as one or more 2D slices or a 3D reconstruction of the anatomy], which can show the bone in and underneath or subjacent to the area of intended reaming or bone removal [e.g. milling, drilling, burring, impacting] and which can also be used to determine the thickness, area or volume of the bone in and underneath or subjacent to the area of intended reaming or bone removal. The amount of bone removal can also be a predetermined fixed value, e.g. with a predetermined fixed depth [e.g. 0.5, 1.0, 2.0, 3.0, 4.0 mm etc.] or with a predetermined fixed area [e.g. 0.5, 1.0, 2.0, 3.0, 4.0 $mm^2$ etc.] or volume [e.g. 0.5, 1.0, 2.0, 3.0, 4.0 $mm^3$ etc.]. The surface, e.g. an articular or bone surface, of the area of intended reaming or bone removal [e.g. milling, drilling, burring, impacting] can then be detected using any of the techniques described in the disclosure or known in the art, e.g. using an intra-operative scan, e.g. an ultrasound scan, optionally with a tracked ultrasound probe, a mechanical probe or pointer applied to multiple points of the surface while tracking the probe in a coordinate system and generating a point cloud [e.g. for generating a surface from the point cloud] or an image or video capture system or a 3D scanner, e.g. a laser scanner. A computer processor can then display the predetermined reaming depth or depth of bone removal (e.g. for drilling, burring, milling, reaming, impacting) with use of the ARDD, e.g. superimposed onto and/or aligned with the surface of the area of intended reaming or bone removal and/or subjacent to or underneath the surface of the area of intended reaming or bone removal. For example, the depth can be displayed subjacent to the area of intended reaming or bone removal, e.g. subjacent to a glenoid articular surface [e.g. inside the glenoid or glenoid vault] or subjacent to an acetabular articular surface, e.g. inside the acetabular bone or bone structures of the patient; the depth can optionally be displayed as a 2D or 3D depth indicator. The depth can be displayed in the ARDD as a virtual 2D or 3D outline of the outer surface of the physical instrument or physical tool used for the bone removal, e.g. the outer surface of a drill, a burr, a reamer, a mill, an impactor, e.g. in their final desired or predetermined position and/or orientation and/or alignment and/or coordinates. The depth can be displayed in the ARDD as a graphical, virtual representation of the physical instrument or physical tool used for the bone removal, e.g. the outer surface of a drill, a burr, a reamer, a mill, an impactor, e.g. in their final desired or predetermined position and/or orientation and/or alignment and/or coordinates. A surgeon can advance the tool or instrument for bone removal, e.g. a drill, a burr, a reamer, a mill, an impactor, which can be optionally tracked using any of the techniques described in the disclosure or known in the art, and a computer processor can display virtually the portions of the tool or instrument for bone removal hidden inside the tissue using the registration and tracking data in the ARDD display superimposed onto the corresponding anatomic structures, e.g. the bone underneath an acetabular or glenoid surface, of the patient and it can also display the predetermined depth. The physical tool or physical instrument for bone removal, e.g. a drill, a burr, a reamer, a mill, an impactor, can then be advanced until the ARDD display indicates superimposition of the hidden portions of the physical tool or instrument hidden inside the tissue and the predetermined depth, e.g. a virtual 2D or 3D outline of the outer surface of the physical instrument or physical tool used for the bone removal or a graphical, virtual representation of the physical instrument or physical tool used for the bone removal, e.g. the outer surface of a drill, a burr, a reamer, a mill, an impactor, e.g. in their final desired or predetermined position and/or orientation and/or alignment and/or coordinates.

In step 732, the surgeon can ream the acetabulum, for example by aligning the physical reamer with the projected virtual reaming axis or a projected virtual reamer. In step 734, an intended or predetermined virtual acetabular reaming depth can be displayed and the physical reamer can be advanced until the virtual reaming depth reference is reached by a corresponding physical part of the physical reamer. Alternatively or additionally, the ARDD can also display an imaging study, e.g. registered with the patient, [e.g. one or more x-rays, a CT scan or MRI scan [optionally displayed by the ARDD as one or more 2D slices or a 3D reconstruction of the anatomy] to show the underlying bone stock so that the surgeon can monitor the remaining bone stock while advancing the reamer. The reamer can be tracked, e.g. using optical markers, navigation markers, a video system or a 3D scanner, and the position, e.g. x, y, z coordinates, and known geometry of the reamer can be used to determine how far the reamer has advanced into the bone. This information, in turn, can be used to compute or display the residual bone stock, e.g. in the acetabular wall [or, in a shoulder replacement, a glenoid fossa or the underlying bone, e.g. in the glenoid vault], by subtracting the reamer advancement, e.g. the distance travelled from the articular surface into the bone, from the overall acetabular bone stock, e.g. in mm or $mm^3$. In step 736, optionally an acetabular impaction axis can be projected by the ARDD. The acetabular impaction axis, acetabular component central axis and/or acetabular component reaming axis can be the same. In step 738, the acetabular component can be impacted, for example by aligning the impactor with the acetabular component impaction or reaming axis. In step 740, optionally, the position of the physical position and/or orientation of the femoral shaft of the patient can be determined, e.g. prior to reaming or broaching. For this purpose, for example, a screw placed in the proximal femur, e.g. with an attached optical marker or navigation marker, can be used for determining the position, orientation and/or coordinates of the proximal femur, e.g. at the level of the neck resection. In step 742, the ARDD can project a predetermined virtual entry or a virtual placement indicator, e.g. an outline, of an entry, e.g. an entry box, for a box osteotome for a given femoral shaft position and/or orientation and a desired femoral stem placement. The virtual entry or placement indicator can facilitate in guiding to a medial or lateral position, e.g. of reamer or broaches. Alternatively, a drill can be used instead of using a box osteotome. In step 744, the ARDD can optionally project the long axis of one or more broaches. The physical broach(es) can then be aligned with the virtual broach axis projected by the ARDD. Optionally, the physical broach can include extenders, e.g. from the broach handle; optionally the ARDD can display one or more virtual extenders to which the physical extenders can be aligned to. In step 746, femoral broaching can be performed. In step 748, optional trial reduction can be performed, e.g. for standard or different offsets, or different femoral stem or neck configurations. In step 750, femoral stem component impaction can be performed. The foregoing sequence or order can be modified based on surgeon preference. The sequence or order can be modified based on anterior vs. posterior approach. Select steps can be added or omitted based on surgeon preference. Select steps can be added or omitted based on anterior vs. posterior approach. Pelvic tilt, pelvic incidence and sacral slope can be introduced into the virtual surgical plan. In addition to supine pelvic x-rays, upright, standing pelvic x-rays can also be used. In a preferred embodiment, additional x-ray views, e.g. lateral view or sacral view can also be used to provide additional information. Pelvic tilt, pelvic incidence and/or sacral slope can be measured on supine and upright x-rays. The difference in pelvic tilt between supine and upright x-rays can, for example, be used to modify the virtual surgical plan, e.g. by changing the acetabular and/or femoral anteversion and/or the offset. When frontal, e.g. AP, x-rays of the pelvis are used in supine and upright position, the change in pelvic position, e.g. outline of acetabulum, width of ellipse, obliquity, change in shape and size of the obturator foramen can be applied to a standard model of a pelvis, which can optionally be deformed using statistical models and patient landmarks obtained from one or more x-rays, in order to estimate the difference in pelvic tilt between the supine and upright position.

Knee Replacement, Partial or Total

With knee replacement general alignment and orientation recommendations exist, some of which have been summarized in a review (Gromov et al. Acta Orthop 2014, 85, 5, 480-487): Neutral overall coronal alignment is currently the gold standard, and a neutral mechanical axis of the leg or 2-7° valgus anatomical tibial femoral axis can be targeted. The femoral component can be placed in 2-8° coronal valgus with respect to the femoral anatomic axis (e.g., 2°, 3°, 4°, 5°, 6°, 7°, 8°, 2-3°, 2-4°, 2-5°, 2-6°, 2-7°, 2-8°, 3-4°, 3-5°, 3-6°, 3-7°, 3-8°, 4- 5°, 5-6°, 5-7°, 5-8°, 6-7°, 6-8°,) 7-8° and >3 mm of implant component overhang over the bone should be avoided. The tibial component can be placed in neutral coronal alignment (90°) with maximum bone coverage and minimal, if any, implant component overhang. In the sagittal plane, the femoral component can be placed with 0-3° of flexion (e.g. 0°, 1°, 2°, 3°, 0-1°, 0-2°, 0-3°, 1-2°, 1-3°, 2-3°), and the tibial slope can be 0-7° (e.g. 0°, 1°, 2°, 3°, 4°, 5°, 6°, 7°, 0-1°, 0-2°, 0-3°, 0-4°, 0-5°, 0-6°, 0-7°, 1-2°, 1-3°, 1-4°, 1-5°, 1-6°, 1-7°, 2-3°, 2-4°, 2-5°, 2-6°, 2-7°, 3-4°, 3-5°, 3-6°, 3-7°, 4-5°, 4-6°, 4-7°, 5-6°, 5-7°, 6-7°). Internal rotation of the femoral component should be avoided, as the femoral component should be placed in 2-5° of external rotation in relation to surgical transepicondylar axis (e.g. 2°, 3°, 4°, 5°, 2-3°, 2-4°, 2-5°, 3-4°, 3-5°, 4-5°). Excessive tibial rotation with respect to neutral transverse axis of the tibia, tibial tubercle axis and also combined internal tibiofemoral rotation should also be avoided.

Any of the registration techniques and/or techniques described in the embodiments can be applied for knee replacement, e.g. resurfacing, partial and total knee replacement procedures, including implantable and attachable markers, calibration and registration phantoms including optical markers, navigation markers, infrared markers, RF markers, patient specific markers, LED's with image capture, e.g. using an optical imaging system and/or a 3D scanner, e.g. integrated into, attached to or separate from an ARDD, and IMU's. For example, one or more optical marker and/or patient specific markers or templates or other markers and/or LED's and/or IMU's or combinations thereof can be applied to the distal femur, for example the distal anterior cortex and/or the superior trochlea, optionally along with any osteophytes when present. Similarly, one or more optical markers and/or patient specific markers or templates or other markers and/or LED's and/or IMU's or combinations thereof can be applied to the proximal tibia, e.g. the anterior tibial cortex, for example in the tibial plateau area, optionally along with any osteophytes when present, or a tibial spine. One or more optical markers and/or patient specific markers or templates or other markers and/or LED's and/or IMU's or combinations thereof can be applied to the proximal tibia, e.g. the anterior tibial cortex By applying the one or more optical markers and/or patient specific markers or templates or any of the other registration techniques including implantable and attachable markers, calibration and registration phantoms, navigation markers, infrared markers, RF markers, LED's with image capture and IMU's to the corresponding structures on the patient, virtual data, e.g. derived from pre-operative imaging, and live data can be effectively cross-referenced for knee replacement surgery and can be, for example registered in a common coordinate system, e.g. with one or more ARDD worn by the surgeon and his or her surgical assistants and nurses. By registering optical marker and/or the patient specific marker or template in relationship to the ARDD also, the ARDD can display or superimpose the desired position, location, orientation, alignment and/or axes and/or trajectory of any surgical instrument used during knee replacement.

The patient's joint, one or more ARDD, one or more virtual data sets or virtual data can be registered in a common coordinate system. In a knee joint, two or more opposing articular surfaces, e.g. with opposing cartilage surfaces and underlying subchondral bone, can be registered separately and/or optionally jointly in a coordinate system, e.g. a common coordinate system. A first articular surface can be located on the distal femur, a second articular surface can be located on the proximal tibia, a third articular surface can be located on the patella. Registering the first articular surface and/or or associated bones and/or structures and the second articular surface and/or or associated bones and/or structures separately can have the benefit of allowing movement, e.g. flexion and/or extension and/or rotation and/or abduction, and/or adduction, and/or elevation and/or other movements, e.g. translation, of the first articular surface and/or or associated bones and/or structures, e.g. the distal femur, in relationship to the second articular surface and/or or associated bones and/or structures, e.g. the proximal tibia, while maintaining registration of the first articular surface and/or associated bones and/or structures, e.g. on the distal femur, and/or the second articular surface and/or or associated bones and/or structures, e.g. on the proximal tibia, e.g. in a common coordinate system or a subcoordinate system, optionally along with one or more ARDD's and/or fixed structures in the operating room, e.g. the OR table, and/or other structures or anatomic landmarks of the patient, e.g. irrespective movement of the individual portions of the joint. In this manner, the knee joint can be placed in different positions, e.g. flexion, extension, rotation, abduction, adduction, e.g. a degree of knee flexion, e.g. 90, 100, 110, 120 degrees, e.g. during placement of a femoral component, and a degree of knee flexion, e.g. 60, 70, 80 or other degrees, during placement of the tibial component, while the registration of the distal femur and/or the registration of the proximal tibia and the display of any virtual data, e.g. a virtual surgical guide, a virtual cut plane, a virtual implant component on the distal femur and/or the proximal tibia can be maintained and superimposed onto the corresponding anatomic area, e.g. the area intended for implant component placement, irrespective of the movement of individual portions of the joint, thereby allowing the one or more ARDD's to maintain anatomically registered displays of virtual data superimposed onto the corresponding portions of the physical joint anatomy, e.g. an articular surface, including a normal, damaged and/or diseased cartilage and/or subchondral bone and/or cortical bone, e.g. in a tangent, intersecting and/or offset manner, e.g. external and/or internal to the normal, damaged and/or diseased cartilage and/or subchondral bone and/or cortical bone.

In some embodiments, an ultrasound scan can be used to obtain the shape information of the distal femur and/or the proximal tibia and/or the patella, for example for designing, selecting or manufacturing a patient specific marker or template. For example, a handheld ultrasound or an ultrasound probe attached to a holding device, stand, tripod or the like can be used to image the distal anterior cortex and the superior trochlea of the femur, optionally along with any osteophytes when present. The ultrasound device can then be used to optionally image the proximal tibia, e.g. the anterior tibial cortex, for example in the tibial plateau area, optionally along with any osteophytes when present. The ultrasound device can then be used to optionally image the patella, e.g. the patellar surface, the whole patella or portions of the patella, for example the superior pole or inferior pole, medial or lateral edge, optionally along with any osteophytes when present. The ultrasound data can optionally be segmented. For example, bone shape and/or cartilage shape as well as, optionally, meniscal shape, when present, can be derived. Moreover, information about ligament location and/or morphometry, including, but not limited to, the origin, insertion, location, length, movement with flexion, extension, rotation of the knee, of the medial collateral ligament, lateral collateral ligament, anterior cruciate ligament, posterior cruciate ligament, patellofemoral ligament or tendon and quadriceps insertion can optionally also be captured with ultrasound. In some embodiments, the shape information derived from the ultrasound data can optionally be used to design, select and/or manufacture a patient specific marker or template, for example one that fits on the distal anterior cortex and the superior trochlea of the femur of the patient, optionally along with any osteophytes when present; or one that fits on the proximal tibia of the patient, e.g. the anterior tibial cortex, for example in the tibial plateau area, optionally along with any osteophytes when present; or one or more that fits on the patella of the patient, e.g. the patellar surface, the whole patella or portions of the patella, for example the superior pole or inferior pole, medial or lateral edge, optionally along with any osteophytes when present.

Optionally, the ultrasound probe can also be used to image portions of the patient's hip joint, for example, to identify the center of the hip joint. Optionally, the ultrasound probe can also be used to image portions of the patient's ankle joint, for example to identify the ankle mortise or the center of the ankle joint or the ⅓ or ⅔ equidistant distance of the ankle joint in the coronal plane or select radii or distance from the medial or lateral ankle mortise. Optionally, the ultrasound scan(s) of the knee, optionally the hip and optionally the ankle can be obtained in supine or in upright position. By obtaining the ultrasound scan or scans in upright position, optionally more accurate information on mechanical axis alignment, in particular during weight-bearing, can be obtained. For example, varus or valgus deformity of the knee can be more pronounced under weight-bearing conditions. Correction of varus or valgus deformity using mechanical axis information under weight-bearing conditions can be more accurate than correction of varus or valgus deformity based on non-weight-bearing information. This information can be beneficial when planning any desired mechanical axis corrections.

Optionally, the location of the ultrasound probe can be captured while performing the hip scan and/or the ankle scan and, optionally, the knee scan, for example using optical markers with image capture or video capture, retro-reflective markers, infrared markers or RF markers or other tracking means used in conjunction with a surgical navigation system or, for example, using image capture, e.g. integrated into, attached to, coupled to or separate from an ARDD, or using one or more IMU's. By imaging the hip joint and the ankle joint, and, optionally, the knee joint in this manner and by capturing information of the ultrasound probe location and orientation, e.g. by tracking the coordinates of the ultrasound probe including its location, position, orientation, alignment and/or direction of movement and/or speed of movement, using one or more attached markers or any of the registration and/or tracking techniques described in the disclosure or known in the art, including 3D scanning or image or video capture, during the ultrasound scan, it is possible to derive information on the mechanical axis and/or the anatomic axis of the patient's leg and knee joint.

Of note, an ultrasound probe or ultrasound transducer used in any of the embodiments throughout the disclosure can be registered and/or tracked in a coordinate system, e.g. a common coordinate system in which, for example, the surgical site, and/or physical tissue of the patient, and/or one or more ARDD and/or one or more virtual tools, virtual instruments, virtual implants, virtual devices, a virtual surgical plan or portions thereof, and/or physical tools, physical instruments, physical implants, physical devices can also be registered and, optionally, be tracked. By tracking the ultrasound probe, the images generated by the probe or transducer and ultrasound system, e.g. 2D slices or cross-sections or 3D images, can be registered also, optionally in real time, in the coordinate system and can be simultaneously displayed by the ARDD superimposed onto and/or aligned with the corresponding physical tissue or tissue slice or tissue volume of the patient, with the proper position, orientation, alignment of the ultrasound image displayed by the ARDD for a given viewer's perspective through the ARDD and for a given transducer position, orientation, alignment. Thus, when an operator moves the tracked transducer, e.g. with the left hand, and, with that, the ultrasound imaging plane or direction or orientation inside the patient, the computer processor can move the imaging plane or data or volume superimposed onto or aligned with the corresponding physical tissue of the patient in real time in the ARDD display. In some embodiments, the geometry of a tracked physical biopsy needle, surgical tool, instrument, implant or device, can be known and can be stored, for example, in a CAD file, and/or accessed by a computer processor associated with the ARDD display. As portions of the tracked physical biopsy needle, surgical tool, instrument, implant or device, disappear below the surface or inside the patient's tissue, a computer processor can display using the ARDD the hidden portions of the tracked physical biopsy needle, surgical tool, instrument, implant or device, e.g. hidden inside the tissue or underneath an organ surface.

In some embodiments, when an operator moves a tracked transducer, e.g. with the left hand, and, with that, the ultrasound imaging plane or direction or orientation inside the patient or the patient's tissue, and moves simultaneously, e.g. with the right hand, a physical biopsy needle, surgical tool, instrument, implant or device, the computer processor associated with the ARDD display can display both the ultrasound image and the tracked hidden portions of the physical biopsy needle, surgical tool, instrument, implant or device hidden inside the tissue [e.g. displayed using known geometries, e.g. using a CAD file of the physical biopsy needle, surgical tool, instrument, implant or device] in the ARDD display. If the tracked hidden portions of the physical biopsy needle, surgical tool, instrument, implant or device hidden inside the tissue are not within the imaging range or field of view of the ultrasound probe, the computer processor can display in the ARDD display the tracked hidden portions of the physical biopsy needle, surgical tool, instrument, implant or device using the tracking data while the ARDD display simultaneously can show the ultrasound image. Using the ARDD display and the tracking, the physical biopsy needle, surgical tool, instrument, implant or device can then be moved inside the tissue until it approaches the ultrasound beam and associated field of view and appears in the ultrasound image, displayed by the computer processor in the ARDD. This embodiment can, for example, be advantageous if it is desirable to maintain the ultrasound probe and image(s) over a lesion, e.g. a tumor, while advancing the physical biopsy needle, surgical tool, instrument, implant or device towards the ultrasound imaging field or volume and, ultimately, using ultrasound visualization into the lesion.

In some embodiments, information from an ultrasound, e.g. of the distal femur, proximal tibia, and/or patella, can be combined or fused with information from another imaging modality, e.g. an MRI, CT or x-ray. X-rays can include x-rays in prone, supine, non-weight-bearing position or in standing, weight-bearing position. X-rays can be limited to the knee only. X-rays can be obtained in different poses of the knee, e.g. in extension and at different flexion angles, weight-bearing or non-weight-bearing. Flexion/extension x-rays can, for example, be used to derive information about the rotational axes of the knee, e.g. an epicondylar or trochlear axis. X-rays can also include other portions of the lower extremity or the entire lower extremity, such as a standing full-length x-ray of the leg in weight-bearing position. A standing full-length x-ray of the leg in weight-bearing position can be used to identify the center of the hip joint as well as the ankle mortise, for example to estimate or derive a mechanical axis and/or an anatomic axis of the knee. In some embodiments, mechanical axis and/or anatomic axis and/or rotational axis information of the knee obtained from x-rays can be included in a patient specific marker or template derived from ultrasound. For example, a patient specific, ultrasound derived surface of the patient-specific marker can fit to a select anatomic region of the patient, e.g. a distal femur including portions of the superior trochlea or an anterior tibial cortex, for example in the tibial plateau area. One or more external facing surfaces of the patient specific marker or template can have a standard shape and can, optionally, include markers or indicators to show an anatomic axis of the knee of the patient, a mechanical axis of the knee of the patient, a desired new mechanical axis of the knee of the patient after the surgery is performed, e.g. as defined in an optional virtual surgical plan, and/or a rotational axis of the knee of the patient and/or a desired new rotational axis of the knee of the patient after the surgery is performed, e.g. as defined in an optional virtual surgical plan. These external markers or indicators including optical markers can then optionally be used during the surgery to confirm, for example, a desired mechanical axis correction or rotational axis correction or combinations thereof. An image and/or video capture system and/or 3D scanner attached to, integrated with, coupled to or separate from an ARDD can optionally be used to identify such corrections using, for example, one or more of the optical markers or indicators on the patient specific marker or template and, optionally to compare them to a virtual surgical plan. Any deviations or differences from the virtual surgical plan can be identified and the surgeon or operator can optionally perform modifications to the surgical technique, e.g. using additional ligament releases, bone cuts or different implant components including, for example, different medial, lateral or combined insert heights, insert shapes, spacers, and augments.

In some embodiments, the accuracy of the placement of an optical marker or a patient specific marker can be checked during the surgery. For example, in a knee replacement, the optical marker or patient specific marker can be placed on a distal femur or a proximal tibial or combinations thereof. A visual or an optical marker, e.g. an LED or a laser light, can indicate a mechanical axis of the patient, e.g. by projecting an arrow or a beam towards the center of the hip and/or the ankle. Alternatively, a mechanical marker, e.g. a femoral alignment rod pointing towards the hip or a tibial alignment rod pointing towards the ankle, can be used to indicate the mechanical axis of the patient as determined using the optical marker or patient specific marker. The femoral and/or tibial alignment rod can be integral, attachable or physically or visually linkable to the optical marker or patient specific marker. One or more optical markers can be integrated into or attached to a femoral and/or tibial alignment rod. An intraoperative x-ray or an intra-operative ultrasound or an intra-operative CT can then be used to determine the physical center of the hip and/or the physical center of the ankle in the live patient on the OR table and, optionally, the patient's physical mechanical axis prior to any corrections. If the projected mechanical axis from optical marker or the patient specific marker coincides with the physical center of the hip and/or the physical center of the ankle, the placement or the information from the optical marker or patient specific marker is accurate. If the projected mechanical axis from the optical marker and/or patient specific marker does not coincide with the physical center of the hip and/or the physical center of the ankle, the placement of the optical marker and/or patient specific marker is not accurately placed and can be repositioned. The degree or amount of difference between the physical and the projected center of the hip and/or the ankle can be used to determine the amount of correction of placement needed. Alternatively, the optical marker and/or patient specific marker can remain in place; however, a correction can be applied to any subsequent registration, wherein the correction is based on the degree or amount of difference between the physical (from the intra-operative imaging study) and the projected center of the hip and/or the ankle (from the optical marker(s) and/or patient specific marker(s)). Someone skilled in the art can recognize that these types of corrections in placement or corrections can be applied to other measurements, e.g. rotational axes, and other joints.

Once any correction of placement inaccuracies of the optical markers and/or patient specific markers has been performed, if applicable, the intended axis correction, e.g. a correction of the patient's abnormal mechanical or rotational axis or both, can be executed on.

Femur

In some embodiments, once the femur is registered using any of the techniques described in the disclosure and/or any of the other registration techniques described in the disclosure or known in the art, including implantable and attachable markers, calibration and registration phantoms including optical markers, navigation markers, infrared markers, RF markers, patient specific markers, LED's with image capture and IMU's, the ARDD can display a virtual distal femoral cut block for performing the distal femoral cut.

Figure 14A:
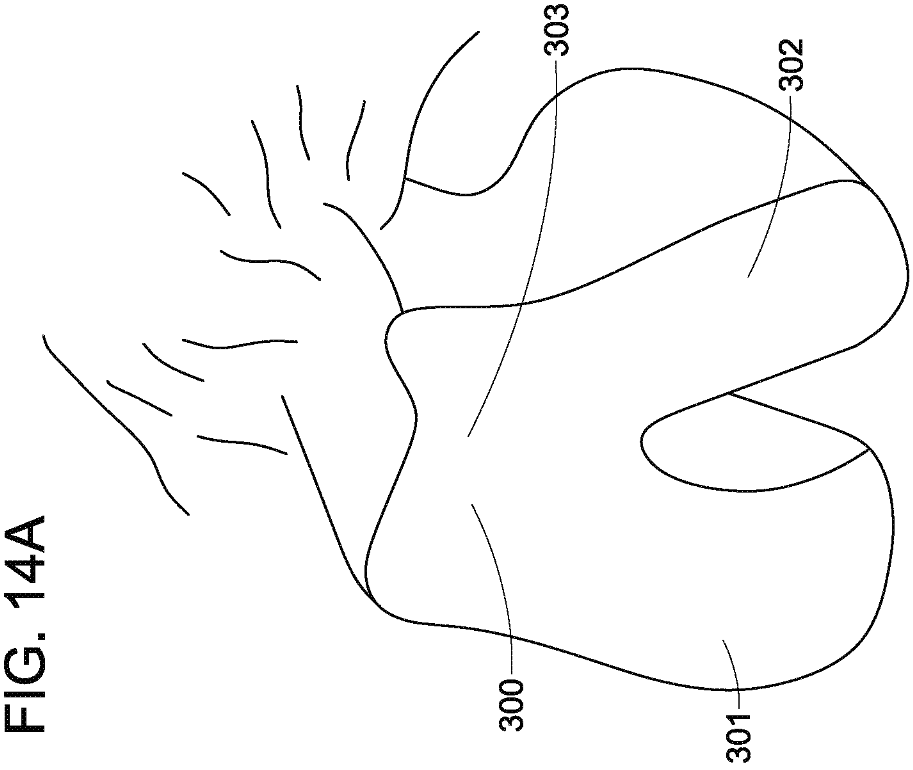
FIGS. 14A-14D provide an illustrative, non-limiting example of the use of virtual surgical guides such as a distal femoral cut block displayed by an ARDD (e.g. HMD) and physical surgical guides such as physical distal femoral cut blocks for knee replacement according to some embodiments of the present disclosure.
Figure 14B:
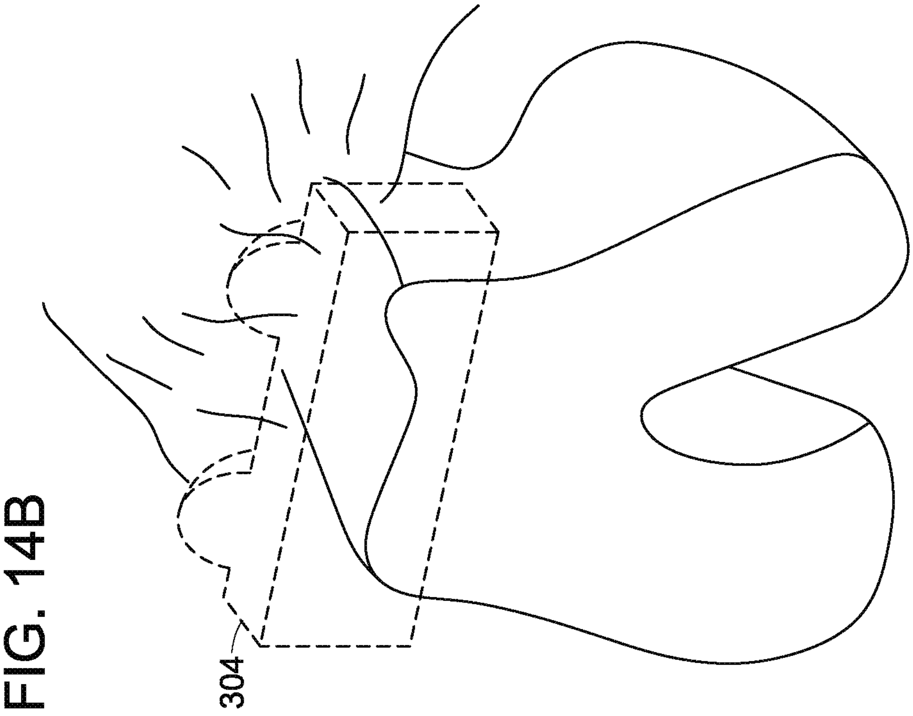
Figure 14D:
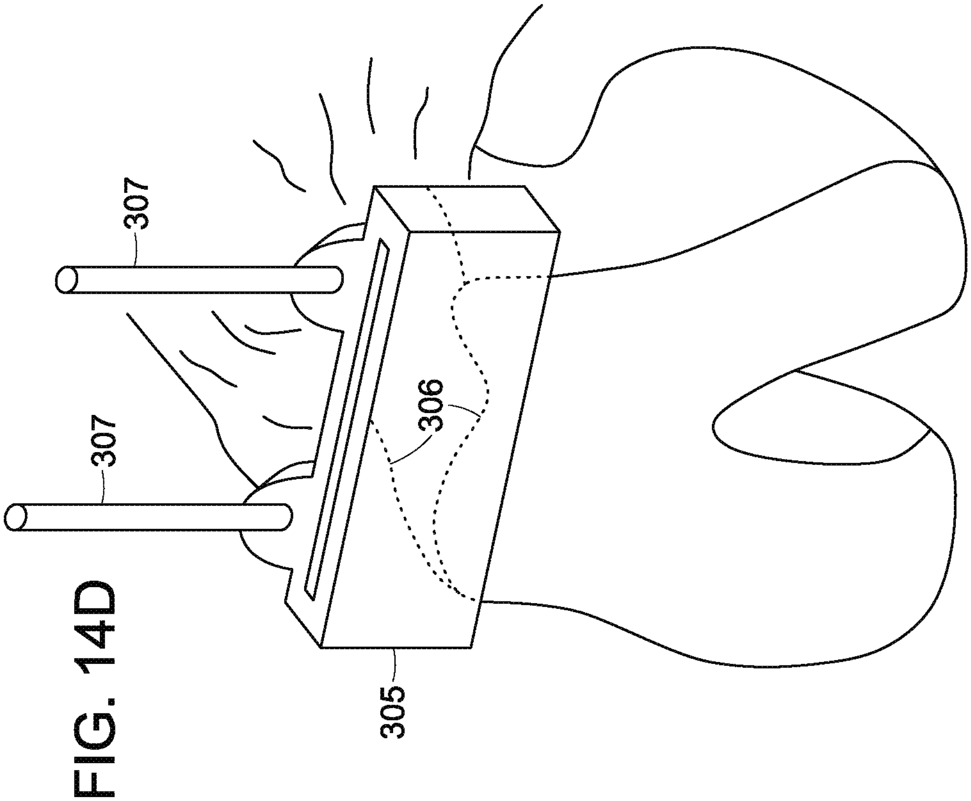
Figure 14C:
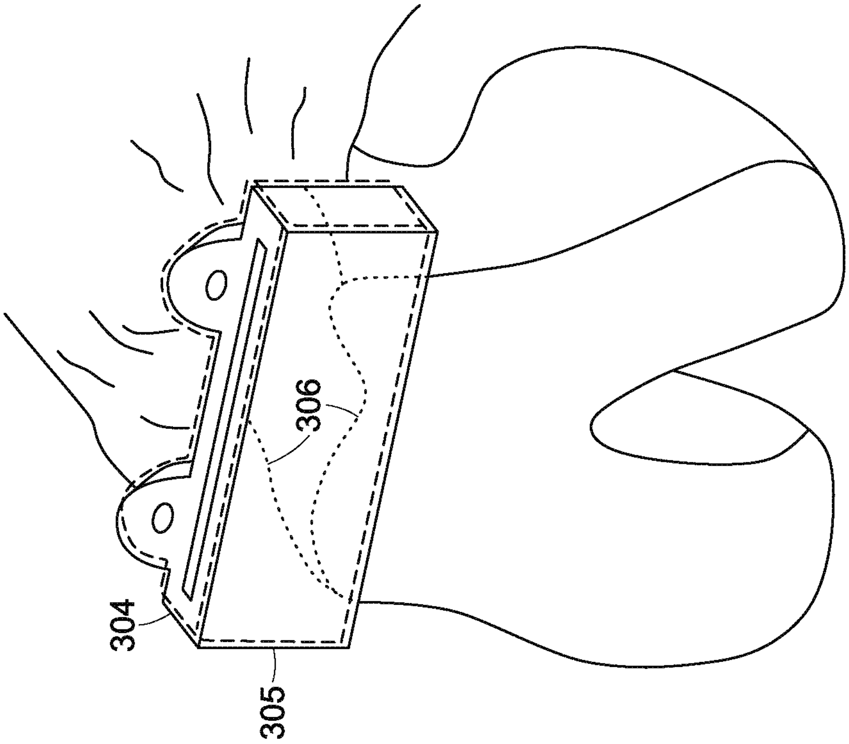

FIGS. 14A-14D provide an illustrative, non-limiting example of the use of virtual surgical guides such as a distal femoral cut block displayed by an optical see through head mounted display (ARDD) and physical surgical guides such as physical distal femoral cut blocks. FIG. 14A shows live data of a patient with a distal femur 300 exposed during knee replacement surgery, a medial condyle 301, a lateral condyle 302 and a trochlea 303. In FIG. 14B, one or more ARDD's can display a virtual distal femoral cut block, e.g. in a stereoscopic manner for the left eye and the right eye of the surgeon(s) creating a form of electronic hologram of the virtual surgical guide, i.e. the virtual distal cut block. The virtual distal femoral cut block 304 in this example is an outline of the physical distal femoral cut block with substantially similar dimensions as those of the physical distal femoral cut block. The virtual distal femoral cut block 304 is aligned based at least in part on coordinates of a predetermined position for guiding the distal femoral cut, for example for achieving a predetermined varus or valgus correction and/or a predetermined femoral component flexion relative to the distal femur and, for example, its anatomic or biomechanical axes. In FIG. 14C, the physical surgical guide 305, i.e. the physical distal femoral cut block 305 (solid line) in this example, can be moved and aligned to be substantially superimposed with or aligned with the virtual surgical guide 304, i.e. the virtual distal femoral cut block 304 (broken line) in this example. The hidden areas of the knee joint 306, obscured or hidden by the physical distal femoral cut block 305, can optionally also be displayed by the optical see through head mounted display. In FIG. 14D, the physical distal femoral cut block 305 can be attached to the distal femoral bone using two pins 307. These pins 307 can be used for subsequent surgical steps, for example for referencing a flexion gap or an extension gap or for ligament balancing. The optical see through head mounted display can stop display the virtual surgical guide, i.e. the virtual distal femoral cut block in this example, but can optionally continue display the hidden anatomy 306.

Figure 15A:
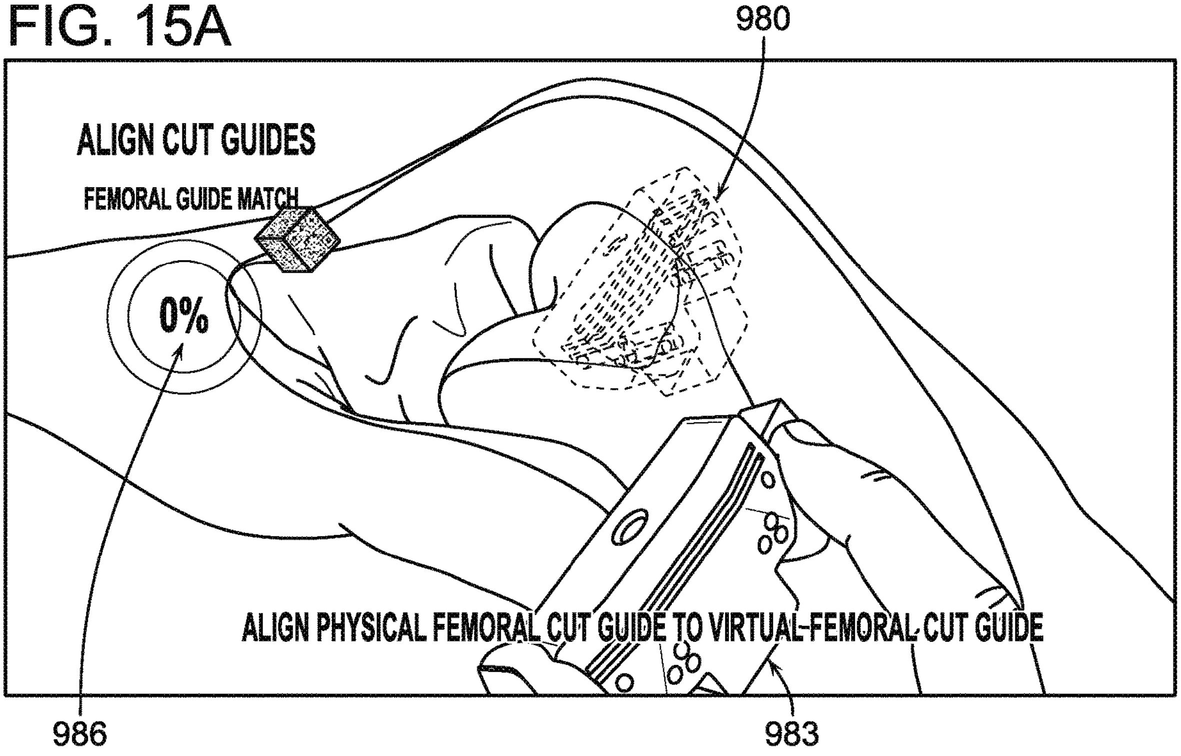
FIGS. 15A-15B provide an illustrative, non-limiting example of the use of virtual surgical guides such as a distal femoral cut block displayed by an ARDD (e.g. HMD) and physical surgical guides such as physical distal femoral cut blocks for knee replacement according to some embodiments of the present disclosure.
Figure 15B:
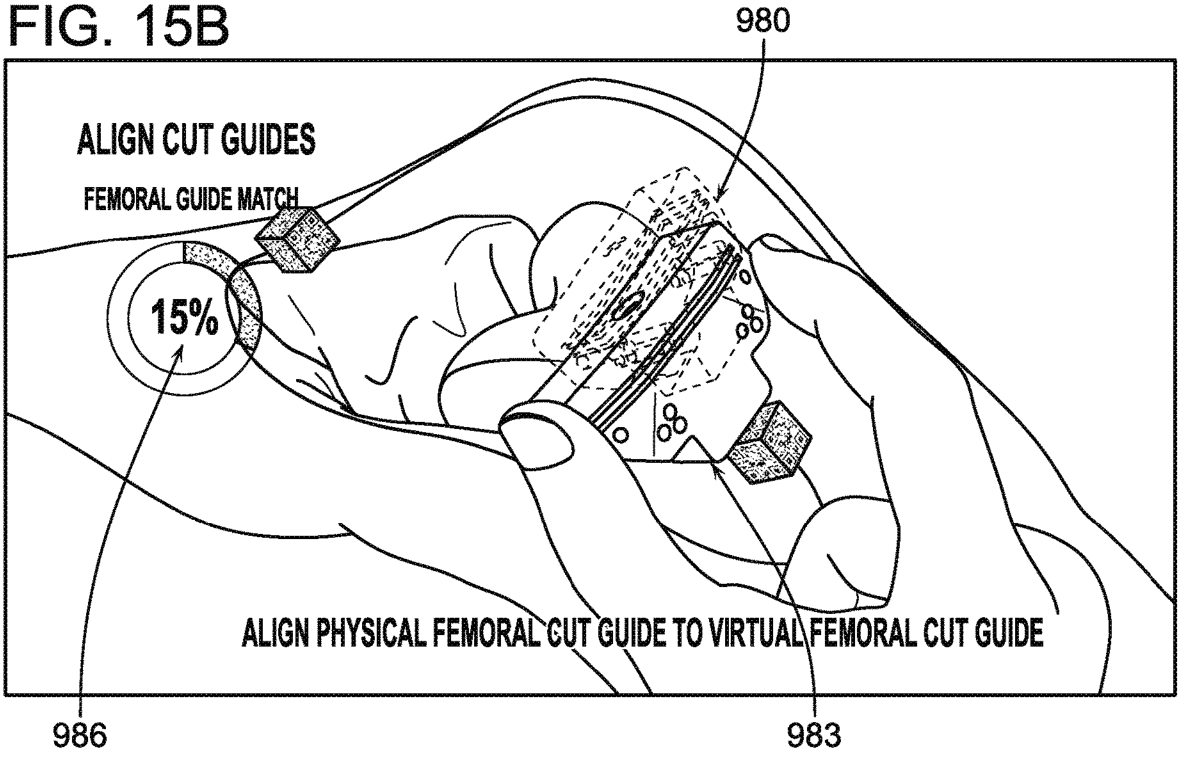

FIGS. 15A-15B shows an example of an optical see through head mounted display projecting a virtual surgical guide 980 onto the surface of the joint. A physical surgical guide 983 can then be superimposed onto and aligned with the virtual surgical guide. A computer processor can track the physical surgical guide 983, for example using direct video detection or one or more markers, e.g. navigation markers or optical markers (not shown), e.g. with a navigation system and/or image capture system, and can track the percentage superimposition 986 of the physical surgical guide 983 with the virtual surgical guide 980. The superimposition can be indicated as a percent volume superimposition between the physical and the virtual surgical guide, percent surface superimposition, percent area superimposition, percent superimposition in a first, second, and/or third direction, e.g. x-, y- and z-, e.g. in mm, percent superimposition with regard to angular alignment, e.g. in x-, y-, and z-direction, e.g. in degrees (e.g. for slope or flexion), percent coordinate superimposition, e.g. in mm (all optionally indicated in graphical, color coded and/or numerical form). The superimposition can be visualized using color coding, for example from red (e.g. "poor"), to orange (e.g. "medium") to green (e.g. "good"). When the physical surgical guide is completely superimposed onto the virtual surgical guide (e.g. 100% match or >90% match or >95% match, or any other amount), the physical surgical guide can be pinned to the bone (not shown). The foregoing embodiments on tracking and/or displaying and/or determining and/or measuring superimposition can be applied to many different embodiments throughout the application, e.g. for spinal surgery, spinal fusion, hip replacement, shoulder replacement, ankle replacement, ACL reconstruction or repair, dental surgery, root canals, dental implant placement, etc.

The virtual distal femoral cut block can have the same or similar shape and one or more dimensions and one or more planes as the physical distal femoral cut block. Alternatively, the ARDD can only show a partial (e.g. broken or dotted) or complete 2D or 3D outline of the virtual distal femoral cut block or placement indicators, e.g. lines or planes indicating the predetermined placement position and orientation of the distal femoral cut block, e.g. a virtual predetermined medial border or placement or position, a virtual predetermined lateral border or placement or position, a virtual predetermined anterior border or placement or position, a virtual predetermined posterior border or placement or position, a virtual predetermined superior border or placement or position and/or a virtual predetermined inferior border or placement or position. In the virtual surgical plan, the distal femoral cut will typically be perpendicular to the mechanical axis of the femur in order to restore mechanical axis alignment, unless the surgeon desires to preserve a mild varus deformity, for example, as can be the case with partial or some total knee replacements, or unless the surgeon uses a different alignment approach, e.g. kinematic alignment, or unless the surgeon desires to maintain a certain amount of pre-existing varus or valgus alignment in a patient. The surgeon can then take the physical distal femoral cut block and substantially align or superimpose the physical distal femoral cut block with the virtual distal femoral cut block or its 2D or 3D outline or its placement indicators displayed by the ARDD. Once adequate alignment or superimposition of the physical distal femoral cut block with the virtual distal femoral cut block or its 2D or 3D outline or its placement indicators displayed by the ARDD based on the patient's virtual surgical plan is achieved, the surgeon can pin or attach the physical distal femoral cut block to the bone and perform the cut. By utilizing preoperative 3D data information or intra-operative measurements of combinations of both for the alignment of the physical distal femoral cut block with the assistance of the ARDD, the surgeon can perform the distal femoral cut in an accurate manner, without the need for intramedullary rods or patient specific instrumentation for performing the cut. Alternatively, the ARDD can display a digital hologram of a virtual cut plane corresponding to the distal femoral cut and the surgeon can align the saw blade with the digital hologram of the virtual distal femoral cut plane.

The display of a virtual surgical guide, which can be a virtual plane or a predetermined path for guiding a bone cut or a tissue cut, using an ARDD is applicable to any surgical procedure that includes placing one or more bone cuts or tissue cuts. In some embodiments, the display of a virtual plane or a predetermined path for guiding a bone cut, e.g. with a bone saw, using an ARDD display can be used to evaluate the accuracy of a cut that is being executed using another guidance or cutting technique, for example with surgical navigation and/or a robot.

The ARDD can display the predetermined virtual plane or the predetermined path for the cut, for example imported into a computer processor associated with the ARDD from a virtual surgical plan used by a surgical navigation system and/or a robot. If the surgical navigation system and/or the robot fail to execute the physical bone cut according to its predetermined location, position, orientation, and/or alignment, the difference between the actual, physical bone cut and the predetermined virtual plane or the predetermined path for the bone cut can be visible through the see-through optical head mounted display and/or also an optical head mounted VR display, e.g. non see-through, using one or more cameras for imaging the live data of the patient and/or the physical saw blade. If the surgical navigation system and/or the robot fail to direct or move the bone saw according to its predetermined location, position, orientation, and/or alignment and/or direction, the difference between the actual, physical location, position, orientation, and/or alignment of the physical bone saw and the predetermined virtual plane or the predetermined path can be visible through the see-through optical head mounted display and/or also an optical head mounted VR display, e.g. non see-through, using one or more cameras for imaging the live data of the patient and/or the physical saw blade. For example, bone saws can bend or skive when they hit or enter hard bone, e.g. cortical bone or sclerotic bone as can be present in an arthritic joint. As the bone saw bends or skives, the deviation of the bone saw from the virtual surgical plane and/or its predetermined path can be visualized in the see-through optical head mounted display and/or also an optical head mounted VR display, e.g. non see-through, using one or more cameras for imaging the live data of the patient and/or the physical saw blade. Similarly, as the bone cut deviates from the virtual surgical plane and/or its predetermined path as a result of the bending or skiving of the saw blade, the deviation or difference of the physical bone cut from the virtual surgical plane can be visualized in the see-through optical head mounted display and/or also an optical head mounted VR display, e.g. non see-through, using one or more cameras for imaging the live data of the patient and/or the physical saw blade.

Similarly, when physical gut guides or cut blocks are used, for example in conjunction with a virtual surgical plan developed for ARDD guided surgery, as the bone saw bends or skives, the deviation of the bone saw from the virtual surgical plane and/or its predetermined path can be visualized in the see-through optical head mounted display and/or also an optical head mounted VR display, e.g. non see-through, using one or more cameras for imaging the live data of the patient and/or the physical saw blade. Similarly, as the bone cut deviates from the virtual surgical plane and/or its predetermined path as a result of the bending or skiving of the saw blade, the deviation or difference of the physical bone cut from the virtual surgical plane can be visualized in the see-through optical head mounted display and/or also an optical head mounted VR display, e.g. non see-through, using one or more cameras for imaging the live data of the patient and/or the physical saw blade. This can be particularly apparent when there is a gap between the exit portion of a slot of the physical surgical guide, e.g. a physical cut block, and the joint, e.g. the articular surface of the joint, which can be frequently present for physical femoral and/or tibial cut guides, for example due to the variable shape and curvature of the joints of different patients.

Optionally, the ARDD can display a digital hologram of a virtual femoral alignment rod or a placement indicator thereof, e.g. indicating a central axis for an alignment rod, which can extend from the distal femur to the hip joint. The surgeon can compare the alignment of the virtual femoral alignment rod or placement indicator with the physical femoral alignment rod in the live patient and assess if both align with the center of the hip joint of the live patient. If the virtual (including a placement indicator) and the physical femoral alignment rod are not aligned with each other and/or the center of the hip joint, the surgeon can check the accuracy of alignment of the physical alignment rod in the live patient, the accuracy of registration of live data of the patient and virtual data of the patient and/or the accuracy of the virtual surgical plan. The surgeon can then optionally make adjustments to the alignment of the physical alignment rod in the live patient, the registration or the virtual surgical plan.

The surgeon can then, for example, select to display or project a digital hologram of the virtual femoral AP cut block in the ARDD. The virtual femoral AP cut block can have the same or similar shape and dimensions as the physical femoral AP cut block. The ARDD can display the virtual femoral AP cut block or a partial (e.g. broken or dotted) or complete 2D or 3D outline of the virtual distal femoral cut block or placement indicators, e.g. planes or lines indicating the predetermined placement position and orientation of the AP femoral cut block, e.g. a virtual predetermined medial border or placement or position, a virtual predetermined lateral border or placement or position, a virtual predetermined anterior border or placement or position, a virtual predetermined posterior border or placement or position, a virtual predetermined superior border or placement or position and/or a virtual predetermined inferior border or placement or position. The virtual surgical plan can include the predetermined position and rotation for the virtual femoral AP cut block. The rotation of the femoral AP cut block can determine the rotation of the resultant anterior and posterior femoral cuts in relationship to, for example, a femoral rotation axis or other axis or anatomic landmark, and, with that, can determine the femoral component implant rotation. The ARDD can display the virtual femoral AP cut block or its 2D or 3D outline or one or more placement indicators.

Figure 16A:
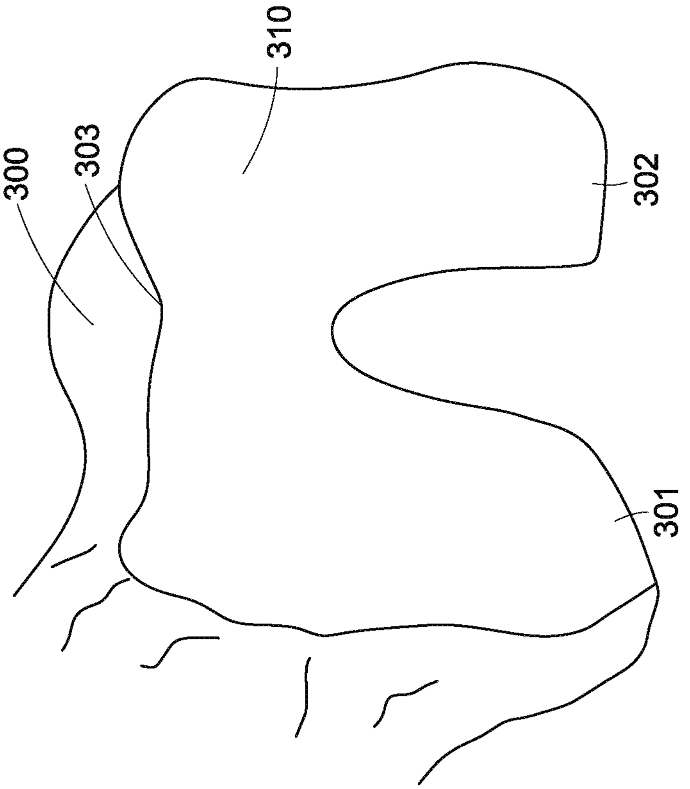
FIGS. 16A-16C provide an illustrative, non-limiting example of the use of virtual surgical guides such as an AP femoral cut block displayed by an ARDD (e.g. HMD) and physical surgical guides such as physical AP cut blocks for knee replacement according to some embodiments of the present disclosure.
Figure 16B:
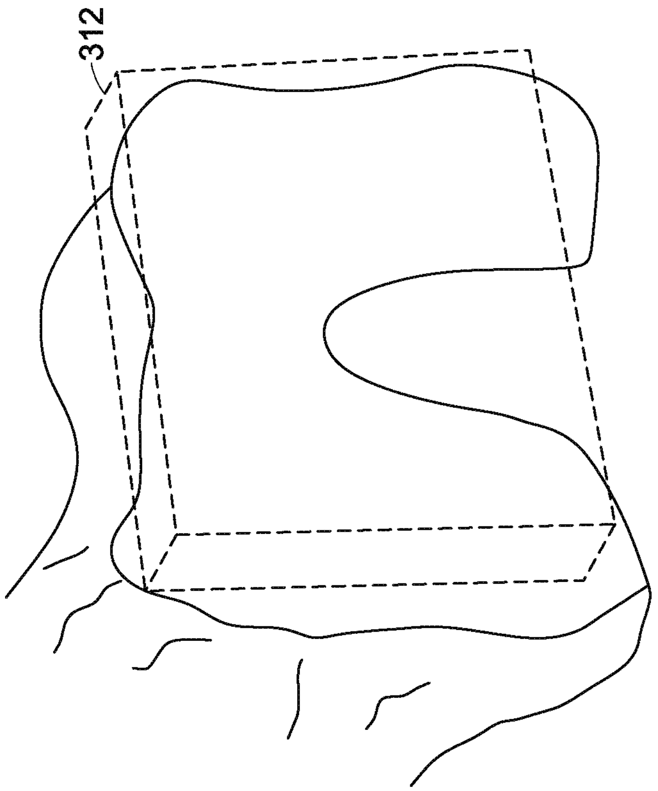
Figure 16C:
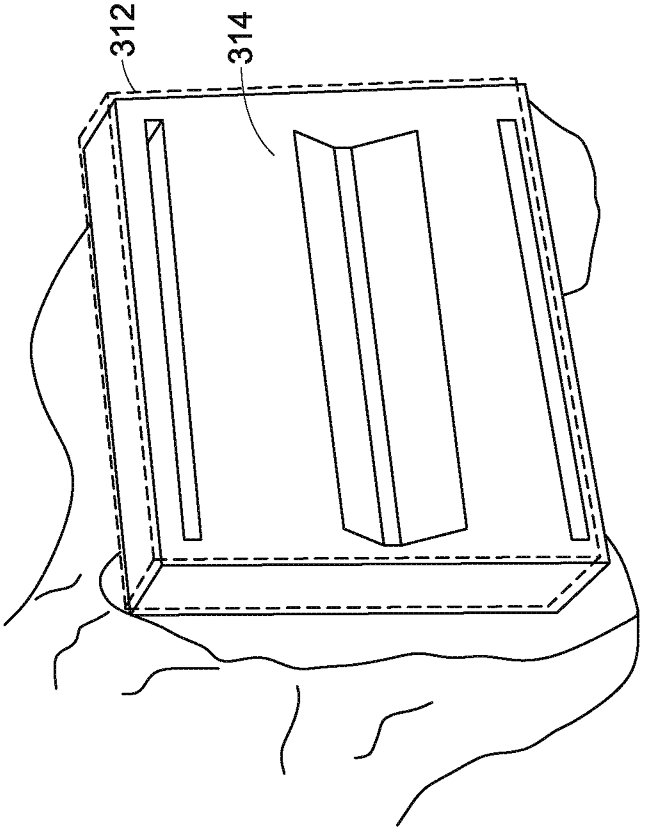

FIGS. 16A-16C provide an illustrative, non-limiting example of the use of virtual surgical guides such as an AP femoral cut block displayed by an ARDD and physical surgical guides such as physical AP cut blocks for knee replacement. FIG. 16A shows live data of a patient with a distal femur 300 exposed during knee replacement surgery after a distal femoral cut creating a planar distal surface 310, a medial condyle 301, a lateral condyle 302 and a trochlea 303. In FIG. 16B, one or more ARDD can display a virtual femoral AP cut block 312, e.g. in a stereoscopic manner for the left eye and the right eye of the surgeon(s) creating a form of electronic or digital hologram of the virtual surgical guide, i.e. the virtual femoral AP cut block 312. The virtual femoral AP cut block 312 in this example is an outline of the physical femoral AP cut block with similar dimensions, edges, or planes as those of the physical femoral AP cut block. The virtual femoral AP cut block 312 is aligned based at least in part on coordinates of a predetermined position for guiding the different bone cuts, e.g. an anterior cut, posterior cut and/or chamfer cuts depending on the configuration of the physical femoral AP cut block, for example for achieving a predetermined femoral component rotation. In FIG. 16C, the physical surgical guide 314, i.e. the physical femoral AP cut block 314 (solid line) in this example, can be moved and aligned to be substantially superimposed with or aligned with the virtual surgical guide 312, i.e. the virtual femoral AP cut block 312 (broken line) in this example. The physical femoral AP cut block can be attached to the distal femoral bone using pins (not shown) and the cuts can be performed. Subsequent surgical steps can optionally be referenced based on one or more of the cuts executed using the physical femoral AP cut block. The surgeon can align or substantially superimpose the physical femoral AP cut block with the digital hologram of the virtual femoral AP cut block or its 2D or 3D outline or one or more placement indicators projected by the ARDD. Once adequate alignment or superimposition of the physical AP cut block with the virtual AP cut block or its 2D or 3D outline or one or more placement indicators displayed by the ARDD has been achieved, the surgeon can pin the physical AP cut block and perform the cuts. By utilizing preoperative 3D data information or intra-operative information, e.g. from optical marker and image or video capture measurements, for the position, alignment and rotation of the physical femoral AP cut block with the assistance of the ARDD, the surgeon can perform the anterior and posterior femoral cuts in a highly accurate manner, thereby achieving accurate rotational alignment of the femoral component. The same approaches and display options, e.g. virtual cut blocks, 2D or 3D outline or one or more placement indicators, can be applied to all subsequent femoral preparation steps including chamfer cuts and chamfer cut blocks.

Of note, similar steps and ARDD guided femoral procedures are also possible using the ARDD with any of the other registration and cross-referencing techniques described in the disclosure or known in the art, for example intraoperative image guidance.

Tibia

In some embodiments, once the tibia is registered using any of the techniques described in the disclosure or known in the art, including, for example, implantable and attachable markers, calibration and registration phantoms including optical markers, navigation markers, infrared markers, RF markers, patient specific markers, LED's with image capture and IMU's, the ARDD can display a virtual proximal tibial cut block for performing the proximal tibial cut. Alternatively, the ARDD can only show a partial (e.g. broken or dotted) or complete 2D or 3D outline of the virtual proximal tibial cut block or placement indicators, e.g. planes or lines indicating the predetermined placement position and orientation of the proximal tibial cut block, e.g. a virtual predetermined medial border or placement or position, a virtual predetermined lateral border or placement or position, a virtual predetermined anterior border or placement or position, a virtual predetermined posterior border or placement or position, a virtual predetermined superior border or placement or position and/or a virtual predetermined inferior border or placement or position. The virtual proximal tibial cut block can have the same or similar shape and dimensions as the physical proximal tibial cut block or it can have at least one or more dimensions or planes that are identical to the physical proximal tibial cut block or guide.

Figure 17A:
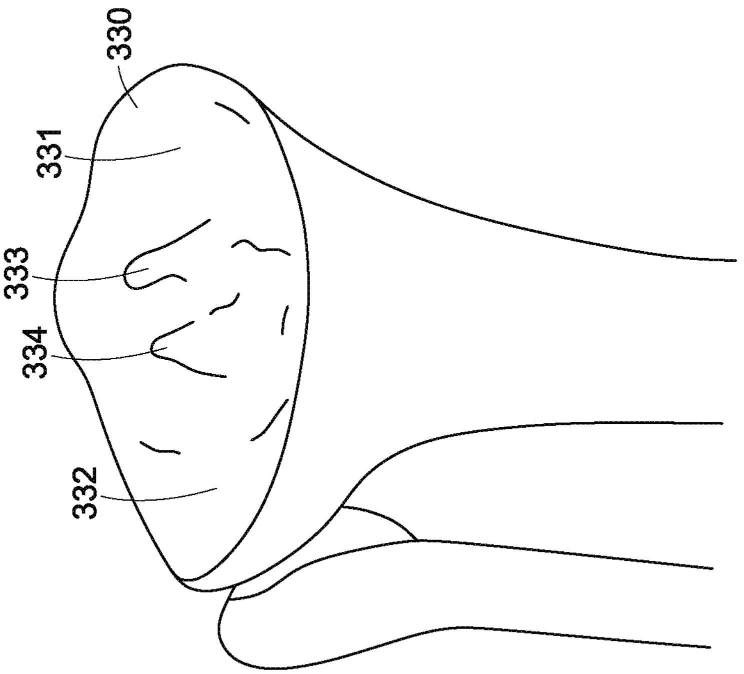
FIGS. 17A-17F provide an illustrative, non-limiting example of the use of virtual surgical guides such as a virtual proximal tibial cut guide displayed by an ARDD (e.g. HMD) and physical surgical guides such as physical proximal tibial cut guide according to some embodiments of the present disclosure.
Figure 17C:
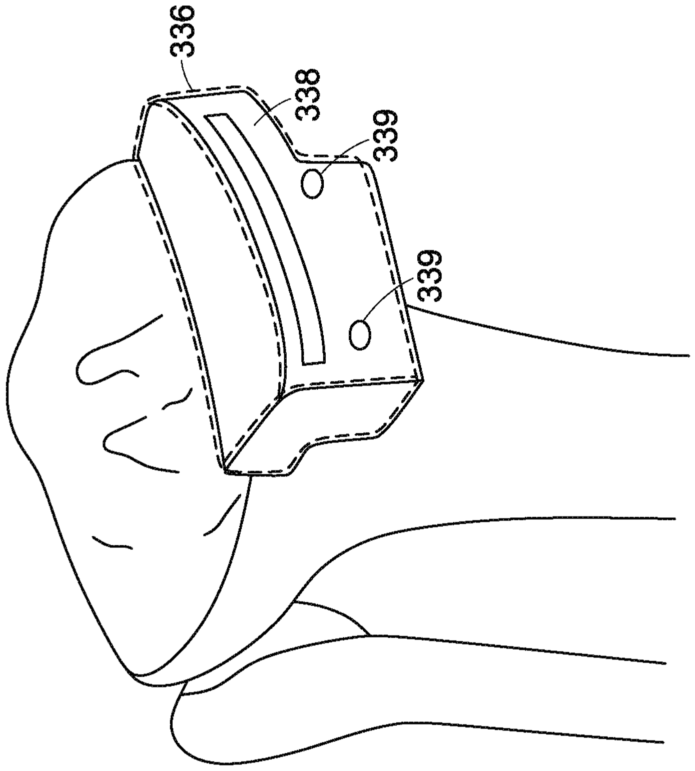
Figure 17B:
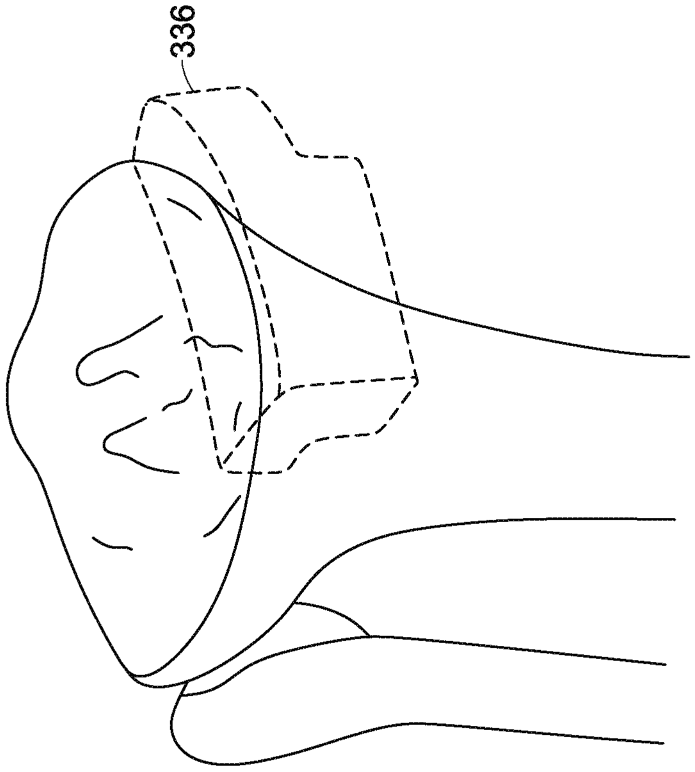
Figure 17E:
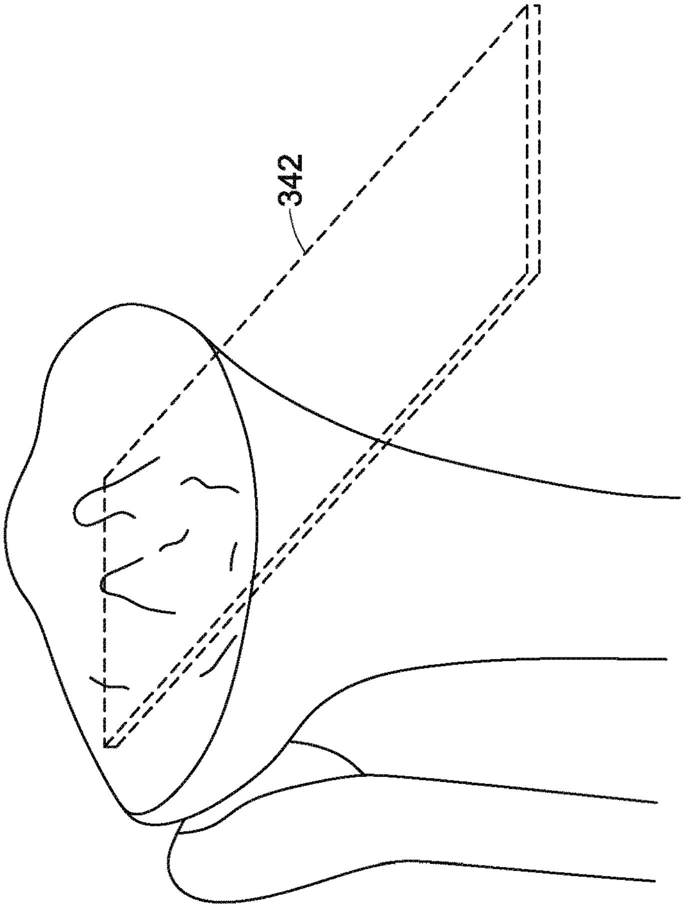
Figure 17D:
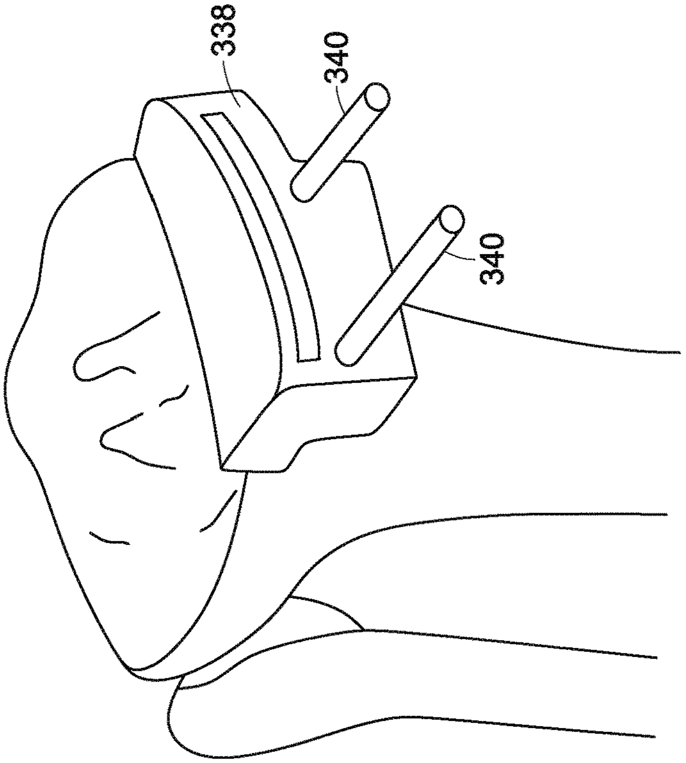
Figure 17F:
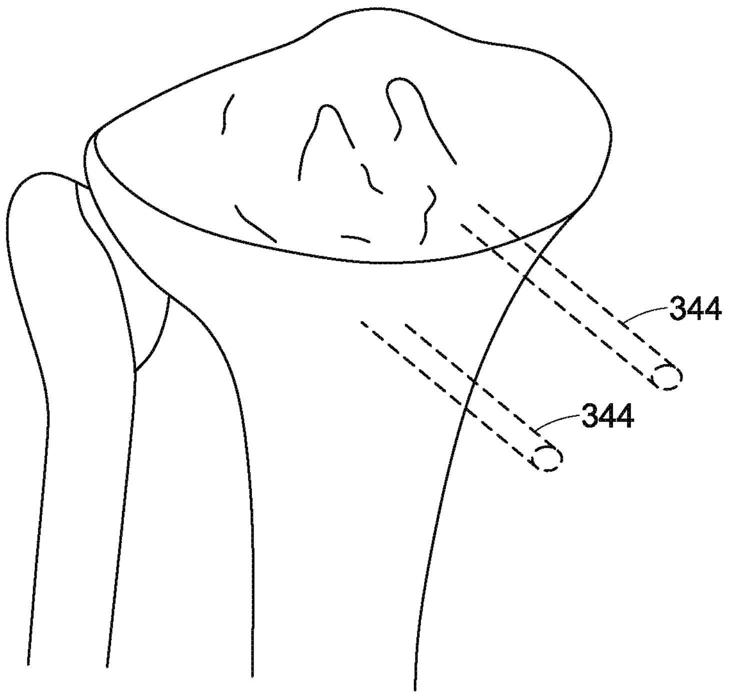

FIGS. 17A-17F provide an illustrative, non-limiting example of the use of virtual surgical guides such as a virtual proximal tibial cut guide displayed by an ARDD and physical surgical guides such as physical proximal tibial cut guide. FIG. 17A shows live data of a patient with a proximal tibia 330 exposed during knee replacement surgery, a medial tibial plateau 331, a lateral tibial plateau 332 and a medial tibial spine 333 and a lateral tibial spine 334. In FIG. 17B, one or more ARDD can display a virtual proximal tibial cut guide, e.g. in a stereoscopic manner for the left eye and the right eye of the surgeon(s), creating a form of electronic hologram of the virtual surgical guide, i.e. the virtual proximal tibial cut guide. The virtual proximal tibial cut guide 336 in this example can be an outline of the physical proximal tibial cut guide with substantially similar dimensions as those of the physical proximal tibial cut guide. The virtual proximal tibial cut guide 336 is aligned based at least in part on coordinates of a predetermined position for guiding the proximal tibial cut, for example for achieving a predetermined varus or valgus correction and/or a predetermined slope relative to the proximal tibia and, for example, its anatomic or biomechanical axes. In FIG. 17C, the physical surgical guide 338, i.e. the physical proximal tibial cut guide 338 (solid line) in this example, can be moved and aligned to be substantially superimposed with or aligned with the virtual surgical guide 336, i.e. the virtual proximal tibial cut guide 336 (broken line) in this example. Note two pin holes 339 in the physical proximal tibial cut guide 338. In FIG. 17D, the physical proximal tibial cut guide 338 can be attached to the proximal tibia bone using two pins 340. These pins 307 can be used for subsequent surgical steps, for example for referencing a flexion gap or an extension gap or for ligament balancing. In FIG. 17E, an alternative embodiment is shown to FIG. 17B. One or more ARDD can display a virtual proximal tibial cut plane 342, e.g. in a stereoscopic manner for the left eye and the right eye of the surgeon(s), creating a form of electronic hologram of the virtual tibial cut plane. The virtual proximal tibial cut plane 342 in this example is parallel with and substantially aligned and superimposed with the predetermined cut plane for the physical proximal tibial cut guide. The virtual proximal tibial cut plane 342 is aligned based at least in part on coordinates of a predetermined position for guiding the proximal tibial cut, for example for achieving a predetermined varus or valgus correction and/or a predetermined slope relative to the proximal tibia and, for example, its anatomic or biomechanical axes. A physical saw blade or a slot for aligning the physical saw blade in a physical proximal tibial cut guide or an open guide area for accommodating the saw blade in a physical proximal tibial cut guide can then be aligned and at least partially superimposed with the virtual proximal tibial cut plane 342. In FIG. 17F, an alternative embodiment is shown to FIG. 17B. One or more ARDD's can display two or more virtual drills or pins 344 for placement in the proximal tibia, e.g. in a stereoscopic manner for the left eye and the right eye of the surgeon(s), creating a form of electronic hologram of the virtual tibial pins or drills. The virtual drills or pins 344 in this example can be an outline or a projected path of the physical pins or drills that can be used to fixate a physical proximal tibial cut guide to the proximal tibia. The virtual drills or pins 344 are aligned based at least in part on coordinates of a predetermined position for guiding the proximal tibial cut, for example for achieving a predetermined *varus* or valgus correction and/or a predetermined slope relative to the proximal tibia and, for example, its anatomic or biomechanical axes. The physical drills or pins (not shown) can then be aligned and superimposed with the virtual drills or pins 344 and placed in the proximal tibia. A physical proximal tibial cut guide can then be attached to the physical pins and the proximal tibial cut can be executed.

In some embodiments, a physical and a corresponding virtual proximal tibial guide or a physical and a corresponding virtual distal femoral guide can also be pin guides, wherein the physical guide can be used to place two or more pins in the bone for attaching physical cut guides for subsequent surgical steps. The embodiments for aligning physical with virtual guides, as shown for example in FIG. 17B and FIG. 17C, can also be applied to pin guides. Someone skilled in the art can recognize that the use of virtual and physical surgical guides, including cut guides and pin guides, can be applied to any joint of the human body and the spine.

In the virtual surgical plan, the proximal tibial cut can be perpendicular to the mechanical axis of the tibia in order to restore neutral mechanical axis alignment, unless the surgeon desires to preserve a mild varus deformity, for example, as can be the case with partial or some total knee replacements, or unless the surgeon uses a different alignment approach, e.g. kinematic alignment, or unless the surgeon desires to maintain a certain amount of pre-existing varus or valgus alignment in a patient. The surgeon can then take the physical proximal tibial cut block and substantially align or superimpose the physical proximal tibial cut block with the virtual proximal tibial cut block or its 2D or 3D outline or its placement indicators displayed by the ARDD. The virtual surgical plan and/or the intraoperative measurements can optionally determine not only the alignment of the proximal tibial cut in relationship to the mechanical axis of the leg, but can also determine the anterior-posterior slope with which the proximal tibia is cut in sagittal direction. In some embodiments, the surgeon, the operator or semi-automatic or automatic software may elect to cut the proximal tibia with a fixed sagittal slope, e.g. 5 degrees or 7 degrees or 3 degrees, for example with a Cruciate Retaining (CR) knee replacement system. Or the surgeon, the operator or semi-automatic or automatic software may elect to cut the proximal tibia with a fixed sagittal slope, e.g. 0 degrees or 2 degrees or 3 degrees, for example with a Posterior Substituting (PS) knee replacement system. Or the surgeon, the operator or semi-automatic or automatic software may elect to cut the proximal tibia with a patient specific slopes, which can be identical to or derived from the medial slope of the native, un-operated medial tibial plateau, the lateral slope of the native, un-operated lateral tibial plateau, or combinations or averages thereof. Once adequate alignment or superimposition of the physical proximal tibial cut block with the virtual representation of the virtual proximal tibial cut block or its 2D or 3D outline or its placement indicators displayed by the ARDD based on the patient's virtual surgical plan and/or intra-operative measurements is achieved, the surgeon can pin the physical proximal tibial cut block and perform the cut, which can then reflect an alignment with the desired mechanical axis correction and the desired tibial slope. By utilizing preoperative 3D data information and/or intraoperative measurements and/or information for the alignment of the physical proximal tibial cut block with the assistance of the ARDD, the surgeon can perform the proximal tibial cut in an accurate manner, without the need for intramedullary rods or patient specific instrumentation for performing the cut. At the same time, the surgeon retains the ability to perform intraoperative adjustments, which can be as simple as manually moving the distal or other femoral cut blocks or moving the proximal tibial cut block or other tibial cut blocks, for example also with use of a stylus like device, e.g. for checking and measuring slope. Any such adjustment can be checked against the virtual surgical plan and/or the intraoperative measurements, by displaying in the ARDD, for example, the final desired implant position or the predetermined position of the corresponding virtual surgical instruments for which the adjustment is contemplated in the physical surgical instrument. Any difference in alignment between any virtual surgical instrument and any physical surgical instrument can be indicated in numeric values by the ARDD, e.g. distance in millimeters or angles in degrees, e.g. difference in external rotation of the femoral component. Any subsequent steps in the virtual surgical plan can be modified in the event the surgeon or operator elected to perform an adjustment, e.g. of tibial slope or femoral or tibial resection levels.

Of note, the same steps and ARDD guided tibial procedures are also possible using the ARDD with any of the other registration and cross-referencing techniques described in the disclosure or known in the art, for example using intraoperative image guidance and implantable and attachable markers, calibration and registration phantoms including optical markers, navigation markers, infrared markers, RF markers, patient specific markers, LED's with image capture and IMU's.

A tibial template or tibial base trial can be used to prepare the proximal tibia for accepting the tibial implant component. A drill can be used to remove the bone in the center of the proximal tibia to accept the central bore of the keel of the tibial component. A keel punch can be used to punch out the space to accept the keel wings of the tibial component. The final seating and orientation of the tibial keel and keel wings can determine tibial implant rotation.

Accurate tibial rotation, for example aligned with the rotation axis of the native knee, is an important objective for avoiding postoperative pain.

In some embodiments, the ARDD can display a digital hologram of a virtual tibial template or virtual tibial base trial as well as virtual tibial drill towers and virtual keel punches. Other virtual tibial preparation instruments can be displayed depending on the configuration and surgical technique of the knee replacement system used. Alternatively, the ARDD can only show a partial (e.g. broken or dotted) or complete 2D or 3D outline of the virtual tibial template or virtual tibial base trial as well as virtual tibial drill towers and virtual keel punches or other virtual tibial preparation instruments or placement indicators, e.g. planes or lines indicating the predetermined placement position and orientation of the tibial template or tibial base trial as well as tibial drill towers and keel punches or other tibial preparation instruments, e.g. a virtual predetermined medial border or placement or position, a virtual predetermined lateral border or placement or position, a virtual predetermined anterior border or placement or position, a virtual predetermined posterior border or placement or position, a virtual predetermined superior border or placement or position and/or a virtual predetermined inferior border or placement or position. The virtual tibial template or tibial base trial as well as virtual tibial drill towers and virtual keel punches and other virtual tibial preparation instruments can have the same or similar shape and dimensions as the physical tibial template or physical tibial base trial as well as physical tibial drill towers and physical keel punches and physical tibial preparation instruments. In the virtual surgical plan, the virtual tibial template or tibial base trial as well as virtual tibial drill towers and virtual keel punches and virtual tibial preparation instruments can be aligned in a manner to achieve close to zero tibial rotation error of the final, physical tibial tray implanted in relationship to the native rotation axis of the tibia of the un-operated knee, if intended. The surgeon or operator has the option to deviate from zero rotation and can add optionally 1, 2, 3 or more degrees of internal or external tibial component rotation to the virtual surgical plan and/or the intra-operative measurements.

For each step of the tibial preparation, the ARDD can display digital holograms of the virtual tibial instrument(s) used or its (their) 2D or 3D outline or its (their) placement indicators along with its (their) desired alignment and rotation based on the virtual surgical plan. The surgeon can then align or superimpose the corresponding physical tibial instrument with the virtual tibial instrument(s) or its (their) 2D or 3D outline or its (their) placement indicators thereby achieving the desired alignment and/or rotation of the physical tibial instrument in relationship to the virtual surgical plan and/or the intraoperative measurements. All virtual tibial preparation tools and instruments including virtual tibial templates or virtual tibial base trials as well as virtual tibial drills, drill towers or saws and keel punches can be displayed using digital holograms by the ARDD if desired. Alternatively, the ARDD can display digital holograms of a 3D contour or placement indicators of the virtual tibial instruments. Optionally, the ARDD can only display the key instruments used for setting tibial component alignment and rotation. By utilizing preoperative 3D data information and/or intra-operative measurements and/or information for the position, alignment and rotation of the virtual tibial preparation instruments, the tibial trials and final tibial components or their respective 2D or 3D outlines or placement indicators displayed with the assistance of the ARDD, the surgeon can perform the physical tibial preparation in an accurate manner by matching physical instruments and components with the alignment and rotation of the virtual instruments and components or their respective 2D or 3D outlines or placement indicators, thereby achieving accurate rotational alignment of the tibial component.

Optionally, the ARDD can display a digital hologram of a virtual tibial alignment rod, which can extend from the proximal tibia to the ankle joint. The surgeon can compare the alignment of the virtual tibial alignment rod with the physical tibial alignment rod in the live patient and assess if both align with the desired location in the ankle joint of the live patient. If the virtual and the physical tibial alignment rod are not aligned with each other and/or the desired location in the ankle joint, the surgeon can check the accuracy of alignment of the physical alignment rod in the live patient, the accuracy of registration of live data of the patient and virtual data of the patient and/or the accuracy of the virtual surgical plan and/or the intra-operative measurements. The surgeon can then optionally make adjustments to the alignment of the physical alignment rod in the live patient, the registration or the virtual surgical plan.

Of note, the same steps and ARDD guided tibial procedures are also possible using the ARDD with the other registration and cross-referencing techniques described in the disclosure or known in the art including implantable and attachable markers, calibration and registration phantoms including optical markers, navigation markers, infrared markers, RF markers, patient specific markers, LED's with image capture and IMU's.

Figure 23A:
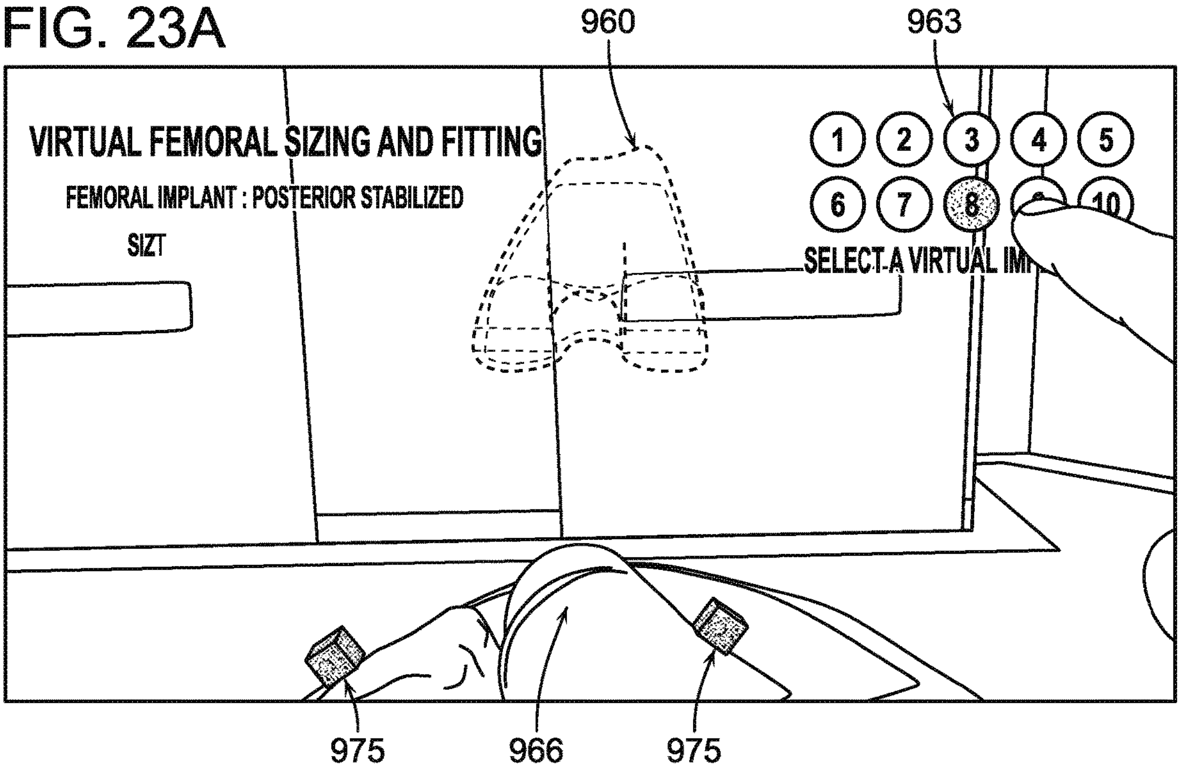
FIGS. 23A-23B provide illustrative, non-limiting examples of one or more augmented reality HMD displays for virtual placing, sizing, fitting, selecting and aligning of implant components.
Figure 23B:
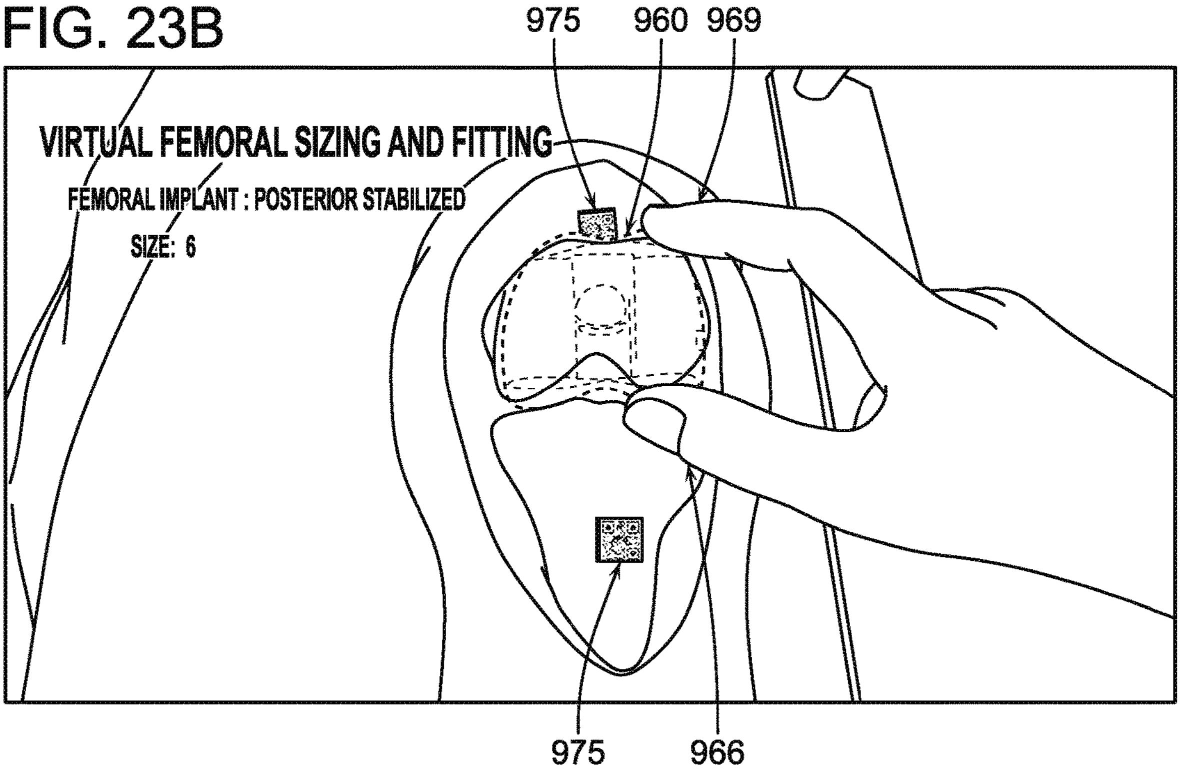

FIGS. 23A-23B provide illustrative, non-limiting examples of one or more augmented reality ARDD displays for virtual placing, sizing, fitting, selecting and aligning of implant components. A virtual femoral component 960 can be displayed by one or more ARDD displays. A virtual user interface 963 can be configured for selecting different sizes of virtual femoral components. A computer processor can be configured to allowing placing and moving of the virtual femoral component onto the physical distal femur 966 of the patient. The computer processor can be configured for selecting different sizes of implants, using, for example, voice commands, e.g. a size 6, and for aligning the virtual implant 960 with the physical distal femur of the live patient using gesture recognition configured to recognize an index finger 969 and thumb 972, in the example in FIG. 23B. The virtual implant can be registered and/or displayed in relationship to a common coordinate system. One or more optical markers 975, e.g. with QR codes, can be registered in the same coordinate system.

If a femoral condyle is significantly deformed from osteoarthritis or rheumatoid arthritis or of a femoral condyle is hypoplastic, the surgeon can select a femoral component with one or more radii different than those of the deformed or hypoplastic femoral condyle. The virtual femoral component can be selected so that the selected virtual femoral component creates a more normal shape, e.g. similar to a normal healthy condyle of the patient. For example, a virtual femoral component can be selected so that its articular surface is proud relative to a portion or all of a flattened, deformed or hypoplastic articular surface of a deformed or hypoplastic femoral condyle in osteoarthritis. For example, a virtual tibial component can be selected so that its articular surface is proud relative to a portion or all of a flattened, deformed articular surface of a deformed tibial plateau in osteoarthritis.

In embodiments, a virtual femoral, tibial and/or patellar component can be virtually sized and/or selected and/or placed and/or aligned so that one or more portions of its articular surfaces extends beyond the outer surface of at least a portion of one or more articular surfaces of the patient's physical femur, tibia or patella, e.g. one or more cartilage surfaces and/or shapes, e.g. normal, damaged or diseased, and/or one or more subchondral bone surfaces and/or shapes of one or both condyle(s), a medial tibial plateau, a lateral tibial plateau and/or the trochlea and/or the patella.

In embodiments, a virtual femoral, tibial and/or patellar component can be virtually sized and/or selected and/or placed and/or aligned so that one or more portions of its articular surfaces remains internal of the outer surface of at least a portion of one or more articular surfaces of the patient's physical femur, tibia or patella, e.g. one or more cartilage surfaces and/or shapes, e.g. normal, damaged or diseased, and/or one or more subchondral bone surfaces and/or shapes of one or both condyle(s), a medial tibial plateau, a lateral tibial plateau and/or the trochlea and/or the patella.

In embodiments, a virtual femoral, tibial and/or patellar component can be virtually sized and/or selected and/or placed and/or aligned so that one or more portions of its articular surfaces is aligned with and/or superimposed with the outer surface of at least a portion of one or more articular surfaces of the patient's physical femur, tibia or patella, e.g. one or more cartilage surfaces and/or shapes, e.g. normal, damaged or diseased, and/or one or more subchondral bone surfaces and/or shapes of one or both condyle(s), a medial tibial plateau, a lateral tibial plateau and/or the trochlea and/or the patella.

In embodiments, a virtual femoral, tibial and/or patellar component can be virtually sized and/or selected and/or placed and/or aligned so that one or more portions of its articular surfaces can be aligned with and/or superimposed with and/or can extend beyond and/or can remain inside, internal to the outer surface of at least a portion of one or more articular surfaces of the patient's physical femur, tibia or patella, e.g. one or more cartilage surfaces and/or shapes, e.g. normal, damaged or diseased, and/or one or more subchondral bone surfaces and/or shapes of one or both condyle(s), a medial tibial plateau, a lateral tibial plateau and/or the trochlea and/or the patella. The surgeon can virtually place the virtual component(s) according to one or more of the foregoing embodiments; the resultant position and/or orientation and/or alignment and/or coordinates of the virtual component(s) can be saved, stored and/or integrated into a virtual surgical plan. For example, they can be used to develop, adjust or modify a virtual surgical plan.

The foregoing virtual sizing, selecting, placing, and/or aligning of one or more virtual implant components relative to one or more portions of an articular surface or an entire articular surface of the patient, e.g. relative to one or more physical cartilage surfaces and/or shapes, e.g. normal, damaged or diseased, and/or one or more physical subchondral bone surfaces and/or shapes, with portions or all of the articular surface of the virtual implant component extending beyond, remaining inside and/or being aligned with and/or superimposed with at least portions of the patient's articular surface can be applied to all joints, e.g. for a femoral or acetabular component in hip replacement, a humeral or a glenoid component in shoulder replacement, using, for example, also articular surface features and or shapes and/or geometries as listed in Table 7 for hip and shoulder, for a tibial component or a talar component in ankle replacement, etc.

The surgeon can project, move, align, e.g. with the external surface of the medial and/or the lateral femoral condyle, multiple different virtual femoral component shapes, e.g. with multiple different offsets, until the surgeon has identified a virtual femoral component that yields the desired shape, for example, similar to that of the patient's distal femur and, in case of a tibial component, the patient's proximal tibia, e.g. a medial tibial plateau, a lateral tibial plateau and/or both, e.g. using one or more physical cartilage surfaces and/or shapes, e.g. normal, damaged or diseased, and/or one or more physical subchondral bone surfaces and/or shapes, and/or one or more physical articular surfaces and/or shapes. If a virtual femoral component is chosen with an offset between the medial and the lateral femoral component, a matching offset can optionally be selected for the tibial polyethylene, wherein the lateral portion of the tibial insert can be 1, 2, 3, 4, 5, 6, 7, 8 or more mm or a range of 0.1 to 10 mm thicker than the medial portion of the tibial insert, corresponding to the smaller radius of the lateral femoral condyle of the virtual femoral component. The coordinates of the final position of the virtual femoral component can be saved and can, optionally, be incorporated into a virtual surgical plan and/or can be used for determining the position and/or orientation and/or coordinates of a virtual surgical guide, e.g. a virtual cut block or placement indicator thereof, a virtual axis, and/or a virtual plane. If the virtual surgical plan indicates a variation in position, orientation, alignment, rotation, implant flexion of the virtual femoral component relative to the virtual surgical plan, the surgeon can adjust the position of the virtual femoral component to come closer to the intended position, orientation, alignment, rotation, implant flexion of the virtual surgical plan or to replicate it. Alternatively, the virtual surgical plan can be modified based on the position, orientation, alignment, rotation, implant flexion of the virtual femoral component.

In some embodiments, in a knee replacement, a virtual tibial component can be displayed near the surgical site including the exposed proximal tibia of a patient. A computer processor can be configured to move the virtual tibial component, using a virtual or other, e.g. voice, interface, e.g. a "touch zone" on the virtual representation of the virtual tibial component with image or video capture of the surgeon's hand and/or fingers and/or gesture tracking, and superimpose it onto the patient's exposed proximal tibia, optionally before and/or after any bone cuts. The computer processor can be configured to evaluate the size and fit of the virtual tibial component, e.g. relative to one or more physical articular surfaces and/or shapes, physical cartilage surfaces and/or shapes, e.g. normal, damaged or diseased, and/or one or more physical subchondral bone surfaces and/or shapes on the medial and/or lateral tibial plateau. The computer processor can be configured to evaluate the fit in three dimensions, anteriorly, posteriorly, at the medial aspect of the medial tibial plateau, at the lateral aspect of the lateral tibial plateau. The computer processor can be configured to evaluate the size and fit of the virtual tibial component for different levels of tibial resection and different tibial slopes and different degrees of tibial component rotation, e.g. external rotation. For example, the computer processor can be configured to evaluate the size and fit and the amount of tibial bone coverage for different resection levels and/or different tibial slopes. This can be important for implant selection since the perimeter and/or surface area of the tibia changes, e.g. decreases, with progressive tibial resection owing to the tapering shape of a normal tibia from proximal to distal. In addition, the perimeter and/or surface area of the tibia can change as the slope of the resection is being increased or decreased; for example, with increasing slope, the perimeter and shape of the resected tibial bone surface can elongate. Thus, the computer processor can be configured to virtually place and/or align a virtual tibial component, including, for example, a virtual metal backed component and/or a virtual polyethylene simulating, for example, a virtual resection level, e.g. for a desired and/or predetermined resection level and/or for a given medial and/or lateral and/or medial and lateral tibial component thickness, including, for example, a composite thickness of metal and polyethylene and/or other components, and/or for a desired articular surface pressure, e.g. medial and/or lateral, and/or a desired ligament tension. The computer processor can be configured to virtually place and/or align a virtual tibial component, including, for example, a virtual metal backed component and/or a virtual polyethylene for a desired, e.g. predetermined, tibial slope, e.g. zero, 1, 2, 3, 4, 5, or more degrees, or selected from a range from 0 to 10 degrees, e.g. using a fixed slope, or the patient's native medial and/or lateral slope. The computer processor can be configured to evaluate the fit and/or the anterior, posterior, medial and/or lateral bone coverage for the desired and/or predetermined tibial resection level and/or tibial slope and the computer processor can be configured to select a tibial implant component that optimizes the anterior, posterior, medial and/or lateral bone coverage; in addition, the computer processor can be configured to select a tibial component that minimizes implant overhang and potential soft-tissue impingement for a desired and/or predetermined tibial resection level and/or tibial slope. The computer processor can be configured to select a tibial implant component that optimizes the anterior, posterior, medial and/or lateral bone coverage and that minimizes implant overhang and potential soft-tissue impingement for a desired and/or predetermined tibial resection level and/or tibial slope, using, for example single or multi-parametric optimization and/or selection and/or fitting and/or alignment. Optionally, the ARDD can display numeric values and/or measurements, e.g. of a tibial slope for various tibial resection levels and/or tibial slopes, indicating, for example, the distance from the unresected articular surface and/or the tibial slope for a given virtual tibial implant component position and/or alignment.

Pedicle Screw, Spinal Rod Placement for Example for Correction of Spinal Deformities, Scoliosis and/or Fracture Treatment, Other Spinal Procedures Pedicle screw and rod placement is one of the most common spinal procedures. It can be performed for a number of different conditions, including, for example, spinal instability, correction of spinal deformities, e.g. scoliosis, kyphosis and combinations thereof, as well as congenital spinal defects. Pedicle screw and rod placement can be combined with bone graft, e.g. allograft or autograft. Sometimes, infusable or injectable bone morphogenic protein can be used during the procedure to facilitate healing and stabilization of bone graft.

Preoperatively, patients will commonly undergo x-ray imaging, for example in anteroposterior, lateral and oblique views. Special views of select regions, e.g. the sacrum or the occipito-atlantic junction can be obtained. X-rays can be obtained in standing and lying position. X-rays can also be obtained in prone or supine position. X-rays may be obtained with the patient erect, spinal flexion and spinal extension. X-rays may also be obtained with the patient bending to the left side or to the right side.

Patients may optionally undergo CT scanning or MRI scanning. CT scanning and MRI scanning have the added advantage of providing a 3D dataset of the patient's anatomy. Moreover, the thecal sac and the nerve roots can be visualized. With MRI, the spinal cord can also be visualized.

Virtual Surgical Plan

The surgeon can develop a virtual surgical plan for the pedicle screw and rod placement which can optionally incorporate any desired deformity correction. Typical criteria for placement of pedicle screws can include the following:

The entry point of the pedicle screw and any awl, probe, tap, k-wire, y-wire, other wires, and other surgical instruments can be chosen, for example, to be at the lateral border of the superior articular process with the intersect to a horizontal line bisecting the transverse processes on the left and right side.

In the lumbar spine, the trajectory of the pedicles will typically converge 5-10 degrees in the upper lumbar spine, 10-15 degrees in the lower lumbar spine. Typically no cephalad or caudad tilt of the trajectory is needed in the lumbar spine.

In the thoracic spine, the entry point can be just below the rim of the upper facet joint, and approximately 3 mm lateral to the center of the joint near the base of the transverse process.

In the thoracic spine, the pedicles and with that the screws can converge to the midline at approximately 7-10 degrees; in the sagittal plane, they can be oriented 10-20 degrees caudally. In accessing T12, the virtual surgical plan can include removal of transverse process to open the marrow space. The angulation can be medial and caudal angulation.

Surgeon can generally use between a lateral intersection method for pedicle screw placement, with the lateral border of the superior articular processes forming an intersect to a horizontal line bisecting the transverse processes on the left and right side. A more medial entry point can be chosen, in which case a rangeur may be required to remove the base of the articular process. This can be included in the virtual surgical plan.

For S1, the entry point can be chosen at the intersect of a vertical line tangential to the S1 articular process and a horizontal line tangential to its inferior border. Typically, at S1, pedicle screws converge, but an overhanging pelvis may limit this in vivo. The screws will typically aim at the superior border of sacral promontory. The instrument placement and the pedicle screw placement in the virtual surgical plan will be selected or defined in a manner where the pedicle screw and/or the instruments will avoid the S1 foramen and any nerve roots. If bicortical screws are used, the screw position will be selected or oriented in order to avoid any injury to the L5 nerve roots; any imaging test such as a CT scan or an MRI scan can be used to identify the L5 nerve root and to place the pedicle screw(s) in the virtual surgical plan, with optional display of the CT or MRI scan and the nerve root, so that its tip and body have a safety margin relative to the nerve root.

The virtual surgical plan can comprise a 2D or 3D display of the spinal structures. The 2D display can be a multiplanar display, for example showing the spine in axial, oblique axial, sagittal, oblique or curved sagittal, coronal, oblique or curved coronal projections. A 3D display can show the spine, for example, from a posterior projection, an anterior projection, a lateral projection, a projection from the top or the bottom, or a projection along a nerve root or the thecal sac or the cord. Representative bony structures that can be displayed in this manner include, for example, the spinous processes, the lamina, the facet joints, the pedicles and the vertebral bodies including the endplates, anterior, posterior, medial and lateral cortex. In some embodiments, the view perspective will be the perspective that the surgeon's head and the ARDD have relative to the surgical field and the patient. The perspective can be different for the left eye display and the right eye display, in particular when stereoscopic display technique is used, with substantially identical view angles of the virtual data of the patient seen by the surgeon's left eye through the display of the ARDD unit and the live data of the patient seen by the surgeon's left eye through the ARDD unit and substantially identical view angles of the virtual data of the patient seen by the surgeon's right eye through the display of the ARDD unit and the live data of the patient seen by the surgeon's right eye through the ARDD unit.

In some embodiments, the thecal sac, neural structures and nerve roots, e.g. L4, L5, and S1 are highlighted in the surgical plan in addition to the bony structures. The nerve roots can be highlighted using segmentation techniques known in the art, e.g. automatic or semi-automatic or manual segmentation. Alternatively, an operator or a surgeon can click on the nerve root in the vicinity of a pedicle or intended pedicle screw placement. The location of the click can be stored in the image data volume and can be highlighted with a different color. The area or volume that includes the click can be registered as a safety zone which the pedicle screw and any instruments used for the placement should not enter. A safety margin, e.g. of 2, 3, 4, 5, 7 or 10 mm can be added to the safety zone. The surgical plan and the placement or position or orientation of any pedicle screw and related instrumentation will be modified or adapted during the virtual planning to ensure that no nerve damage or impingement will be caused by the surgical procedure.

In some embodiments, vascular structures can be highlighted using automated, semi-automated, or manual segmentation techniques or simple clicks or image markings performed by a surgeon or operator. Such vascular structures can, for example, include the aorta, the inferior vena cava, any branches of the aorta or the inferior vena cava, intercostal arteries, the innominate artery. A safe zone and/or a safety margin of 2, 3, 4, 5, 7 or 10 mm or more mm can be defined around these vascular structures. The surgical plan and the placement or position or orientation of any pedicle screw and related instrumentation will be modified or adapted during the virtual planning to ensure that no vascular damage will be caused in the surgical procedure.

The virtual surgical plan can include

- Identifying the desired pedicle screw position and/or location and/or orientation
- Identifying the desired position and/or location and/or orientation and/or trajectory of any surgical instrument used for placing the pedicle screw, e.g. an awl, a probe, a wire, a tab, a screw driver and the like, including the pedicle screw itself.
- Identifying the desired rod position and/or location and/or orientation
- Identifying the desired spinal deformity correction if applicable, e.g. correction of kyphosis, lordosis, scoliosis, sagittal deformity, coronal deformity, rotational deformity, facture deformity
- Identifying sensitive structures, e.g. neural structures, nerve roots, vascular structures
- Defining safe zone, e.g. for cortical penetration, e.g. in a pedicle, neural structures, nerve roots and/or vascular structures The virtual surgical plan can include, optionally predefined, criteria to automated or semi-automated virtual placement of a pedicle screw in the patient's data. Such criteria can include the distance between the pedicle screw or related bone void to accept the pedicle screw to the medial, lateral, superior, and/or inferior endosteal surface or cortical surface in portions or all of the pedicle or the area or volume between pedicle screw or related bone void to accept the pedicle screw to the medial, lateral, superior, and/or inferior endosteal surface or cortical surface in portions or all of the pedicle. If the surgeon manually, visually places the virtual pedicle screw on the 2D or 3D display, the same or similar criteria can be applied by the software to highlight potential areas that may result in clinical problems, e.g. a cortical breach or a nerve root injury. For example, if a virtual pedicle screw comes within 1, 2, or 3 mm of the medial cortex of a pedicle, the software, using image processing and segmentation of the bone, endosteal bone or cortical bone, can highlight such proximity and potential risk. The highlighting can occur, for example, by color coding areas of proximity to a cortex or to a neural or vascular structure or by other visual cues and acoustic warning signals. Such highlighted areas can optionally also be displayed by the ARDD during the surgical procedure, stereoscopically or non-stereoscopically. Optionally, highlighted areas can be displayed in outline format.

The selection of a size, width, diameter or length of a pedicle screw can also be performed in a manual, semi-automatic or automatic matter using criteria such as the distance between the pedicle screw or related bone void to accept the pedicle screw to the medial, lateral, superior, and/or inferior endosteal surface or cortical surface in portions or all of the pedicle or the area or volume between pedicle screw or related bone void to accept the pedicle screw to the medial, lateral, superior, and/or inferior endosteal surface or cortical surface in portions or all of the pedicle.

The surgeon can place the digital hologram of the virtual pedicle screw manually, for example using a virtual interface, on the virtual display of the patient's hidden subsurface anatomy using criteria such as location of the pedicle screw including its tip in the vertebral body, location of the pedicle screw including its tip in relationship to a spinal/vertebral body fracture, location of the pedicle screw including its tip in relationship to a superior endplate, location of the pedicle screw including its tip in relationship to an inferior endplate, location of the pedicle screw including its tip in relationship to an anterior vertebral cortex and/or a posterior vertebral cortex, location of the pedicle screw including its tip in relationship to a vessel, location of the pedicle screw including its tip in relationship to the aorta, location of the pedicle screw including its tip in relationship to the inferior vena cava, location of the pedicle screw including its tip in relationship to neural structures, the thecal sac, nerve roots and/or the spinal cord, distance, area or volume between the pedicle screw including its tip to a spinal/vertebral body fracture, distance, area or volume between the pedicle screw including its tip to a superior endplate, distance, area or volume between of the pedicle screw including its tip to an inferior endplate, distance, area or volume between the pedicle screw including its tip to the an anterior and/or posterior vertebral cortex, distance, area or volume between the pedicle screw including its tip to a vessel, distance, area or volume between the pedicle screw including its tip to the aorta, distance, area or volume between the pedicle screw including its tip to the inferior vena cava, distance, area or volume between the pedicle screw including its tip to neural structures, the thecal sac, nerve roots and/or the spinal cord. The surgeon can use this information on location or distance or area or volume also to select the size, width, diameter or length of the pedicle screw in the virtual surgical plan or using the virtual representations of the pedicle screw(s) and the patient's anatomy. Safe zone criteria can be defined for the foregoing criteria, for example 1, 2 or 3 or 5 or more mm from a cortex or a neural structure. If the surgeon places the pedicle screw or any related surgical instruments for the placement of the pedicle screw too close to the safe zone or within the safe zone, the area can be highlighted or another visual or acoustic alert can be triggered by the software.

Alternatively, the software can place the pedicle screw automatically or semiautomatically on the virtual display of the patient using criteria such as location of the pedicle screw including its tip in the vertebral body, location of the pedicle screw including its tip in relationship to a spinal/vertebral body fracture, location of the pedicle screw including its tip in relationship to a superior endplate, location of the pedicle screw including its tip in relationship to an inferior endplate, location of the pedicle screw including its tip in relationship to the an anterior and/or posterior vertebral cortex, location of the pedicle screw including its tip in relationship to a vessel, location of the pedicle screw including its tip in relationship to the aorta, location of the pedicle screw including its tip in relationship to the inferior vena cava, location of the pedicle screw including its tip in relationship to neural structures, the thecal sac, nerve roots and/or the spinal cord, distance, area or volume between the pedicle screw including its tip to a spinal/vertebral body fracture, distance, area or volume between the pedicle screw including its tip to a superior endplate, distance, area or volume between of the pedicle screw including its tip to an inferior endplate, distance, area or volume between the pedicle screw including its tip to the an anterior and/or posterior vertebral cortex, distance, area or volume between the pedicle screw including its tip to a vessel, distance, area or volume between the pedicle screw including its tip to the aorta, distance, area or volume between the pedicle screw including its tip to the inferior vena cava, distance, area or volume between the pedicle screw including its tip to neural structures, the thecal sac, nerve roots and/or the spinal cord. The software can use the information on location or distance or area or volume can also to select the size, width, diameter or length of the pedicle screw in the virtual surgical plan. Safe zone criteria can be defined for the foregoing criteria, for example 1, 2 or 3 or more mm from a cortex or a neural structure. If the software cannot place the pedicle screw or any related surgical instruments for the placement of the pedicle screw without violating one of the safe zones or places it too close to the safe zone, the area can be highlighted or another visual or acoustic alert can be triggered by the software. The surgeon can then manually adjust the virtual position of the pedicle screw or any related surgical instruments for the placement of the pedicle screw such as an awl, a probe, a needle, a wire, a tap and the like.

The virtual surgical plan can only simulate the final desired placement of the pedicle screw(s) and any related rods. The desired trajectory of any surgical instruments used for placing the pedicle screw such as an awl, a probe, a needle, a wire, a tap and the like can then be projected during the surgery based on the virtual surgical plan and the final desired placement position of the pedicle screw(s) and any related rods.

In some embodiments, each instrument or, for example, the principal instruments used for the placement of the pedicle screw(s) and/or the rods can be displayed during the surgery in the virtual display. The physical instruments seen through the ARDD can be aligned with the corresponding virtual instruments displayed by the ARDD, optionally in 3D, stereoscopic or non-stereoscopic, thereby achieving the desired surgical alterations, for example according to the virtual surgical plan.

Figure 12A:
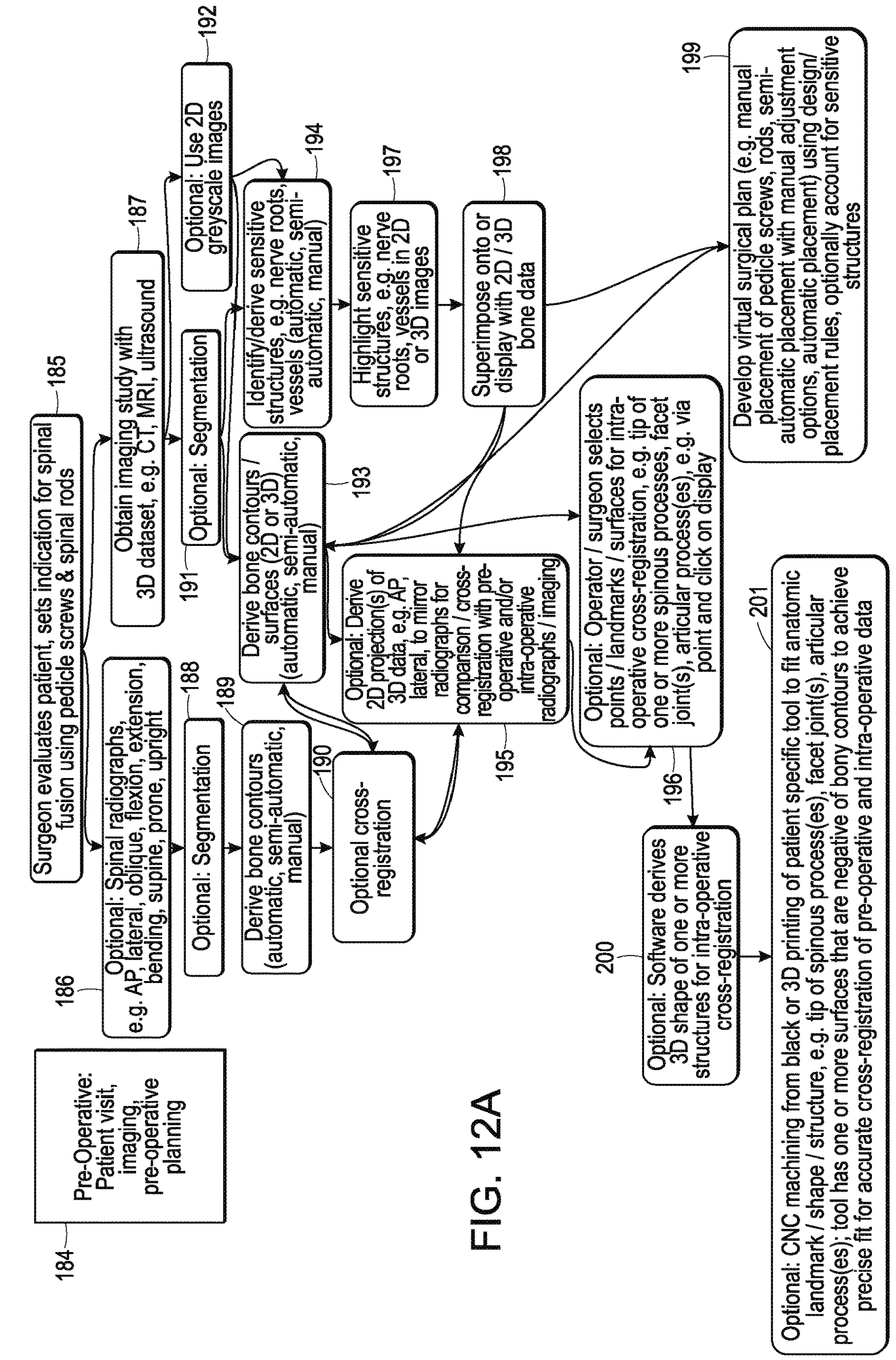
FIGS. 12A-12D are illustrative flow charts of select options and approaches for performing spine surgery in a mixed reality environment according to some embodiments of the present disclosure.
Figure 12B:
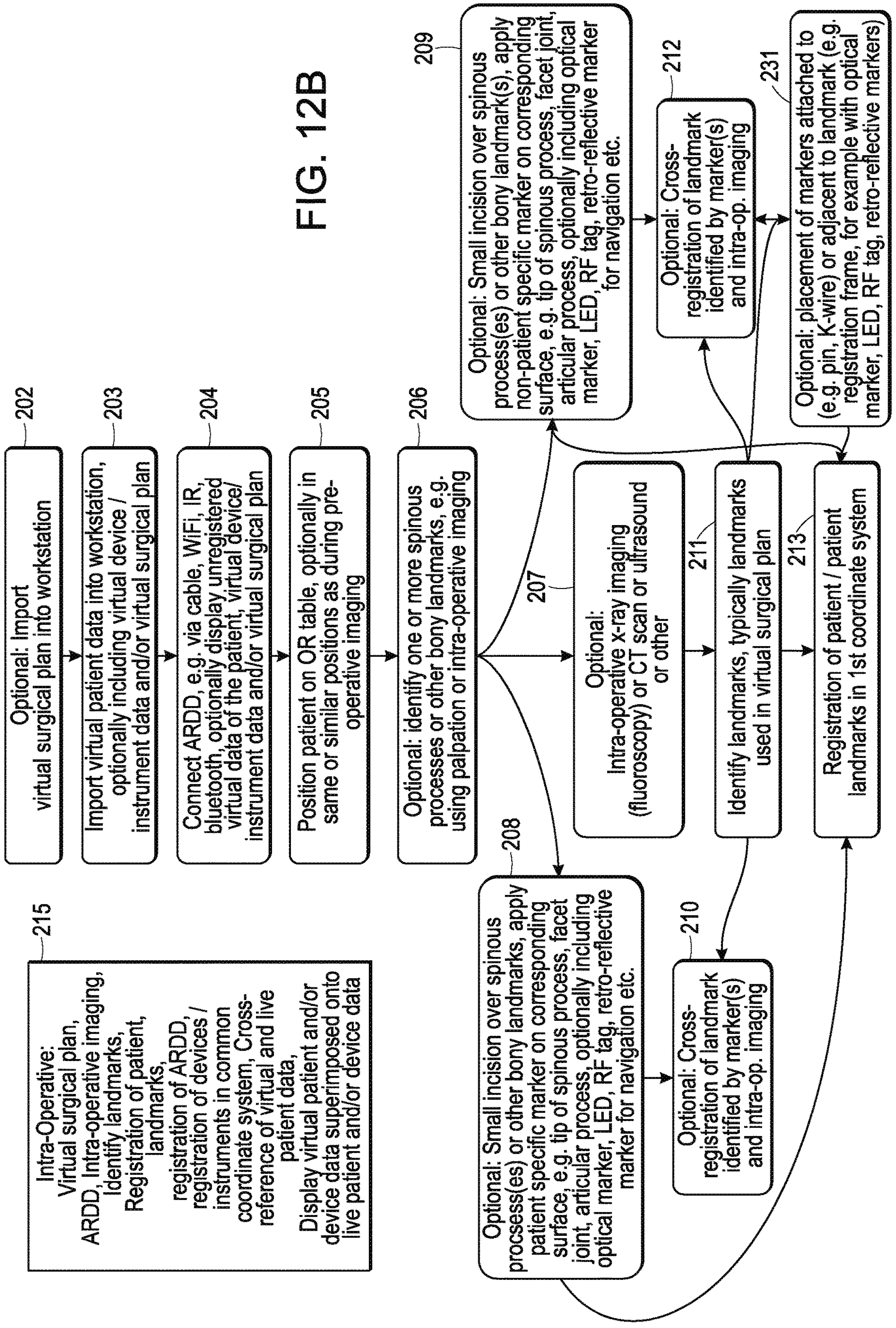

FIGS. 12A-12D are illustrative flow charts of select options and approaches for performing spine surgery in a mixed reality environment. In FIG. 12A, pre-operative patient visit, imaging, pre-operative planning 184, a surgeon evaluates a patient and sets the indication for spinal fusion using pedicle screws and spinal rods 185. Optionally spinal radiographs 186 and/or 3D imaging, e.g. CT or MRI 187, can be obtained. Optionally the data can be segmented 188 and 191. Optionally 2D data can be used 192. Bone contours can be derived automatically, semi-automatically or manually 189 from the radiographs 189 or CT or MRI 193. Optionally, sensitive structures such as nerve roots and vessels can be determined 194 and superimposed on the display of the 2D or 3D bone data 198. Bone contours from radiographs and other imaging studies such as CT or MRI can optionally be cross-registered, e.g. using coordinate transfer or using registration in a common coordinate system 190. Optionally, 2D projections of 3D data can be generated, for example to generate matching projections that can align with and/or be superimposed with intra-operative radiographs 195. Optionally, a surgeon or operator can select points or landmarks or surfaces for intra-operative registration 196. Bone contours 189 and/or 193 and other data, e.g. 198, 197, 196 can be used to develop a virtual surgical plan for placement of the pedicle screw(s) and rod(s) 199. Optionally, the shape of one or more structures used for intra-operative registration can be derived 200 using software as described for example in Data Segmentation. Optionally, a patient specific template can be generated for the spine 201, as described, for example in WO9325157A1. In FIG. 12B, intra-operative virtual surgical plan, imaging, landmarks, registration, cross-reference of virtual and live patient data 215, the data from FIG. 12A, e.g. 189, 193, 194, 195, 199, 200, can be imported into a workstation 202. The virtual data of the patient can also be imported, optionally including virtual instrument data, virtual device data and/or the virtual surgical plan 203. The ARDD can be connected to the workstation 204 and can, optionally, display unregistered virtual data 204. The patient can be positioned on the OR table, optionally in the same position as that used for pre-operative imaging 205. Step 205 can optionally be performed before 202, 203 and 204. Optionally, one or more spinous processes or other bone landmarks or skin references can be identified 206. Optionally, intra-operative imaging can be performed 207 using, for example, x-rays or CT/O-arm imaging 207. Optionally, an incision can be performed over a spinous process and a patient specific marker or template, an optical marker or other markers can be applied for registration 208 and 209. Landmarks, e.g. ones used in the virtual surgical plan 199, can be identified 211, and can optionally be cross-referenced or registered with landmarks identified by intra-operative imaging or patient specific markers or optical markers or other markers 210 and 212, for example in a common coordinate system, e.g. with the ARDD, or in different coordinate systems using coordinate transfers. The patient can then be registered in a common, e.g. first, coordinate system 213. Optionally, markers can be attached to rigid structures fixed to the spine and/or landmarks 231.

Figure 12C:
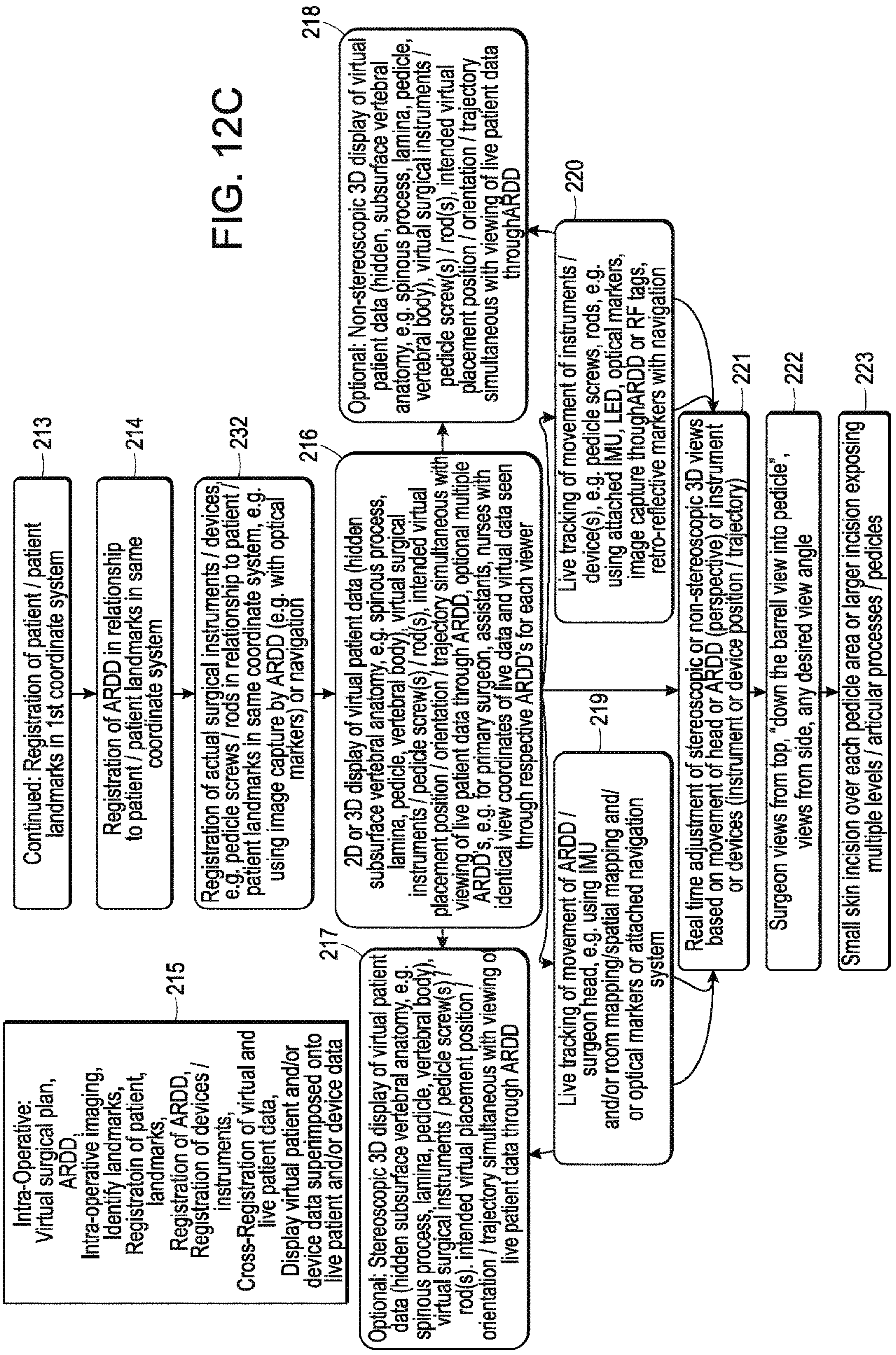

In FIG. 12C, continuation of intra-operative virtual surgical plan, imaging, landmarks, registration, cross-reference of virtual and live patient data 215, after the registration of patient landmarks 213 one or more ARDD/s can be registered in relationship to the patient or patient landmarks 214, e.g. using spatial mapping or optical markers or navigation markers or combinations thereof or any other registration technique described in the application. Actual surgical instruments such as awls and pins and implants such as pedicle screws and rods can also be registered 232. A 2D or 3D display can be generated, which can include hidden subsurface anatomy, e.g. of a vertebral body, pedicle, facet joints, virtual surgical instruments and virtual implants 216. These can be superimposed with and aligned with the corresponding live data of the patient, e.g. the center of a pedicle in which an awl or a screw can be placed in a predetermined position 216. Stereoscopic 217 and non-stereoscopic 218 displays can be generated. Multiple viewers can see the virtual data and the live data superimposed using multiple ARDD's each displaying the virtual data with the view perspective matching the view perspective of the live data for the individual viewer 216, 217, 218. The viewer(s) can move their head freely and the ARDD worn by each viewer can remain registered with the live data using, for example, one or more of IMU's attached to the ARDD, room mapping, spatial mapping, e.g. of the surgical site or the patient or both, optical markers or navigation markers 219. Instruments or implants, e.g. pedicle screws or rods, can also be tracked using, for example, IMU's, LED's, optical markers, or navigation markers 220. The display of the ARDD can be adjusted in real time, e.g. 30 frames per second or more, based on head movement or instrument or device movement or combinations thereof 221. The surgeon can obtain a down the barrel view of a pedicle for placing tools, such as pins, or screws, for example in real time 222. A skin incision can be performed over select pedicle or multiple spine levels 223.

Figure 12D:
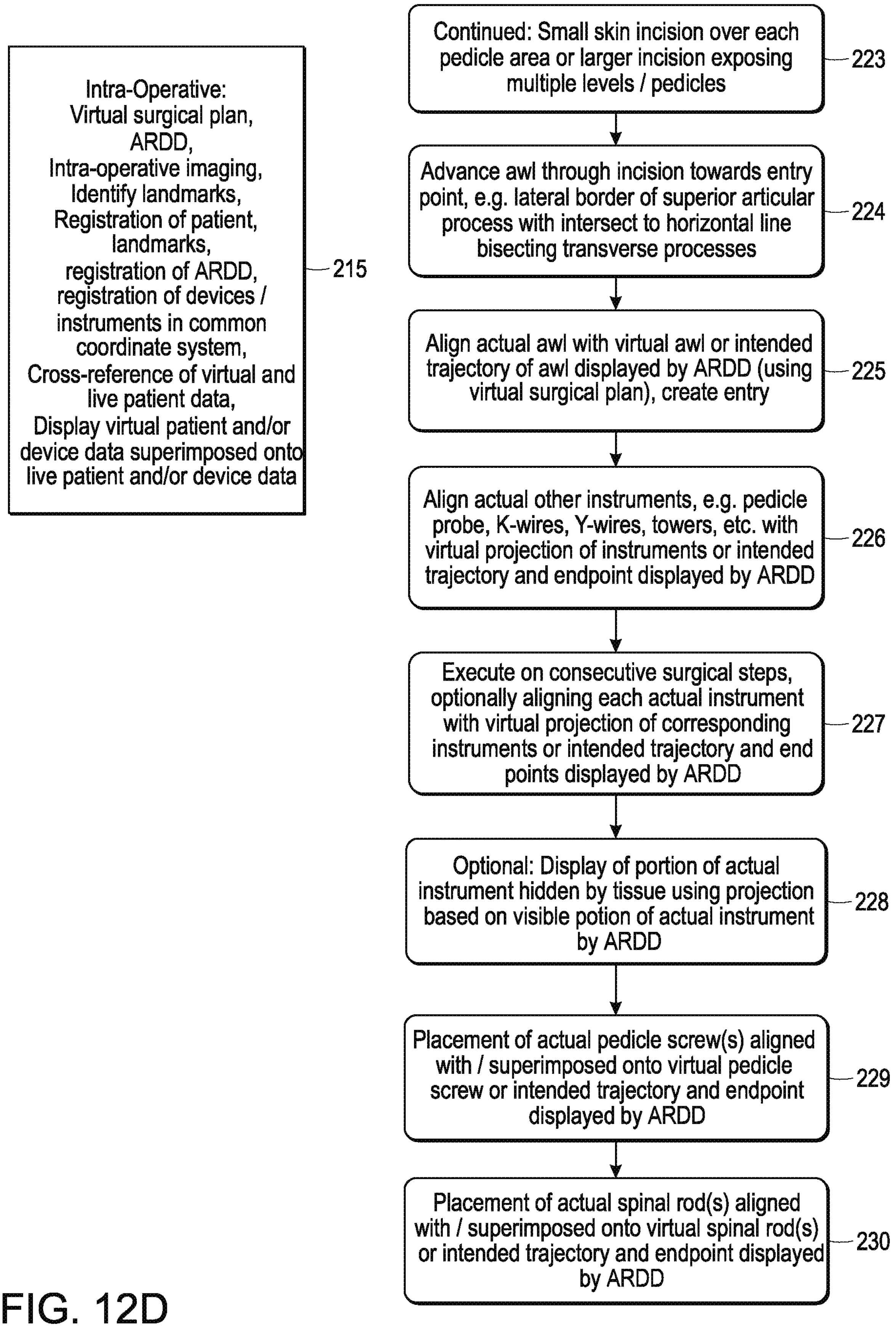

In FIG. 12D, continuation of intra-operative virtual surgical plan, imaging, landmarks, registration, cross-reference of virtual and live patient data 215, the surgeon can, for example, advance an awl towards the entry point for a pedicle screw 224. The actual or physical awl can be aligned with a virtual awl 225. Other physical instruments can be aligned with their corresponding virtual instrument or, for example, an intended path or endpoint 226. Consecutive surgical steps can be executed aligning physical with virtual tools, instruments or implants 227. Optionally, portions of the physical instrument that are hidden inside or by the tissue can be displayed in the virtual display in the augmented reality system using, for example, the alignment information from the visible portions of the instrument 228. For this purpose, optical markers or navigation markers can, for example, be attached to the instrument to register it and compute its hidden portions. The physical or actual pedicle screw can be placed aligned with or superimposed with the hidden subsurface anatomy, e.g. the pedicle, or a virtual pedicle screw, or an intended path or endpoint or combinations thereof 229. The physical spinal rod can be placed aligned with or superimposed onto a virtual spinal rod 230; optionally, the spinal rod can be placed aiming at virtual representations of the rod receptacle or receiving or holding or attachment mechanisms of the pedicle screw(s). The rod receptacle or receiving or holding or attachment mechanisms can be magnified by the ARDD for this purpose, for example around a central axis or central point, to facilitate aiming of the physical rod. The hidden portions of the physical rod can be virtually displayed by the ARDD, optionally also magnified, and aimed at the rod receptacle or receiving or holding or attachment mechanisms.

FIGS. 24A-24E provide illustrative, non-limiting examples of one or more augmented reality ARDD displays including a virtual user interface 990 for virtual placing, sizing, fitting, selecting and aligning of virtual pedicle screws and including ARDD displays for guidance of spinal instruments and implants. A virtual user interface 990 can be configured for selecting different sizes of virtual pedicle screws, e.g. in mm of diameter. A computer processor can be configured to allow placing and moving of the virtual pedicle screws onto the virtually displayed spine 993 of the patient, e.g. using a 3D model generated based on a pre-operative CT scan or an intra-operative O-arm scan. The computer processor can be configured for selecting different sizes of implants (e.g. in mm), using, for example, voice commands or gesture commands, e.g. a size 6.0 mm. A virtual path 996 can be displayed for guiding the placement of the one or more physical pedicle screws. A computer processor can be configured to move, place, size, and align virtual pedicle screws 1000 using, for example, gesture recognition or voice commands, and, optionally to display magnified views 1003, e.g. from a CT scan, demonstrating the pedicle 1006 including the medial wall of the pedicle 1009. A target placement location 1012 for the virtual pedicle screw 1000 can also be shown. The virtual screw can be adjusted to be placed in the center of the pedicle. The physical screw and/or awl or screwdriver can be tracked, e.g. using a navigation system or video system (for example with navigation markers or optical markers or direct optical tracking). When the screw path, awl path or screwdriver path extends beyond the medial wall of the pedicle, a computer processor can generate an alarm, e.g. via color coding or acoustic signals. Physical instruments, e.g. a physical awl 1015 (see FIG. 24C), can be aligned with and superimposed onto the virtual path 996 projected by an ARDD.

A computer processor can track the physical awl 1015, for example using direct video detection or one or more markers, e.g. navigation markers or optical markers (not shown), e.g. with a navigation system and/or image capture system and can track the percentage superimposition 1018 of the physical awl 1015 with the virtual path 996. The superimposition can be indicated as a percent volume superimposition between the physical awl and the virtual path, percent surface superimposition, percent area superimposition, percent superimposition in a first, second, and/or third direction, e.g. x-, y- and z-, e.g. in mm, percent superimposition with regard to angular alignment, e.g. in x-, y-, and z-direction, e.g. in degrees, percent coordinate superimposition, e.g. in mm (all optionally indicated in graphical, color coded and/or numerical form). The superimposition can be visualized using color coding, for example from red (e.g. "poor"), to orange (e.g. "medium") to green (e.g. "good"). When the physical awl 1015 is completely superimposed onto the virtual path 996 (e.g. 100% match or >95% match or >90% match, or any other amount), the physical awl can be advanced, for example to a predetermined endpoint (not shown).

Figure 24A:
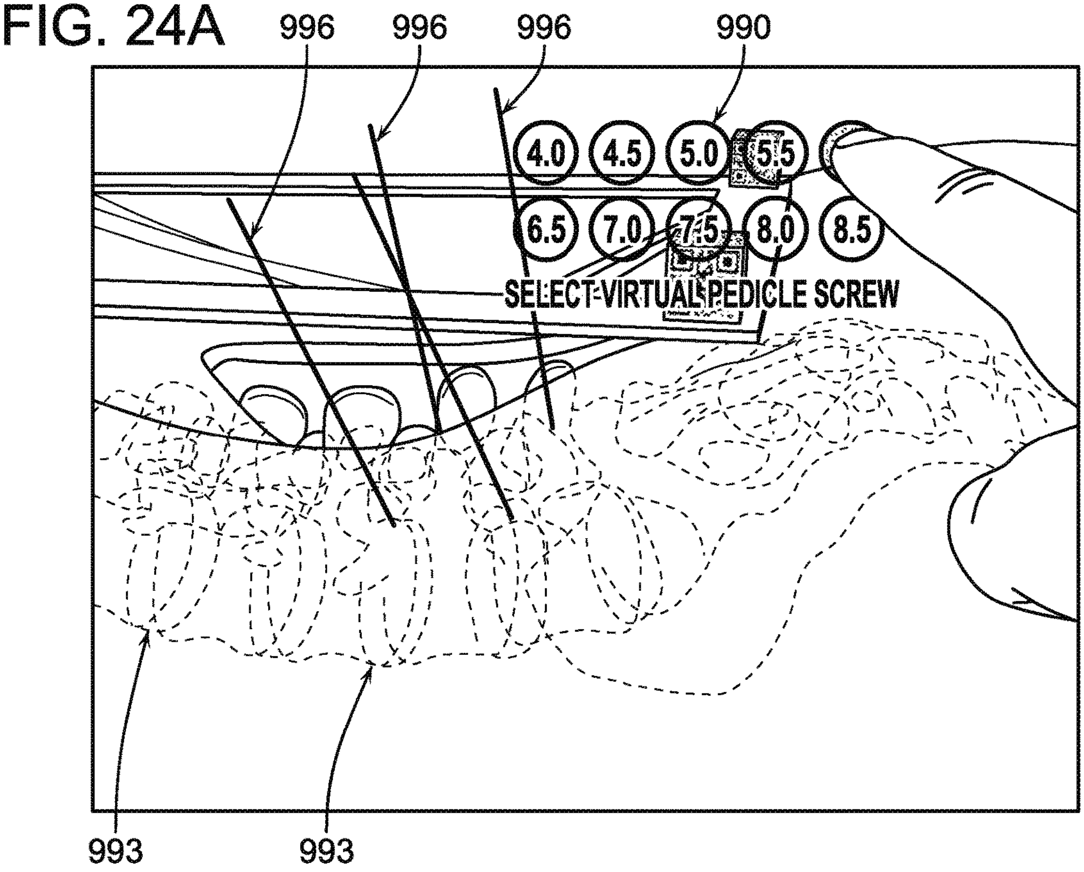
FIGS. 24A-24E provide illustrative, non-limiting examples of one or more ARDD (e.g. HMD) displays including a virtual user interface for virtual placing, sizing, fitting, selecting and aligning of virtual pedicle screws and including ARDD (e.g. HMD) displays for guidance of spinal instruments and implants according to some embodiments of the present disclosure.
Figure 24B:
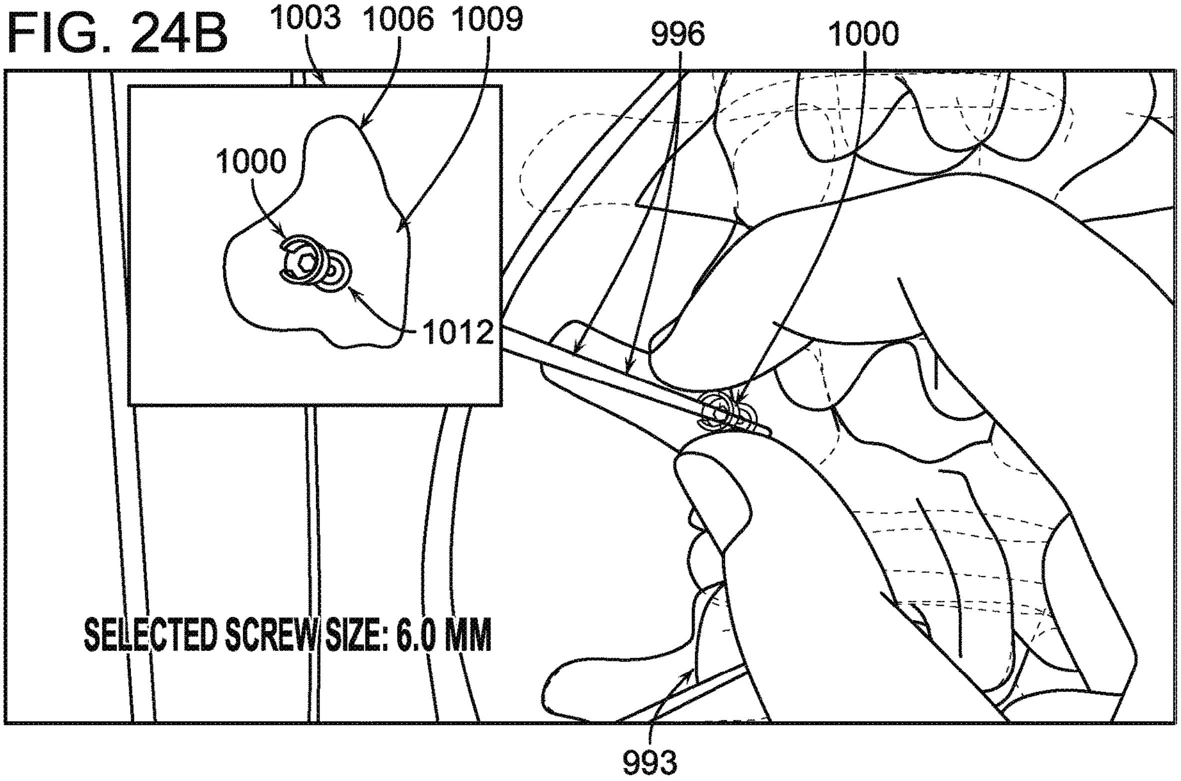
Figure 24C:
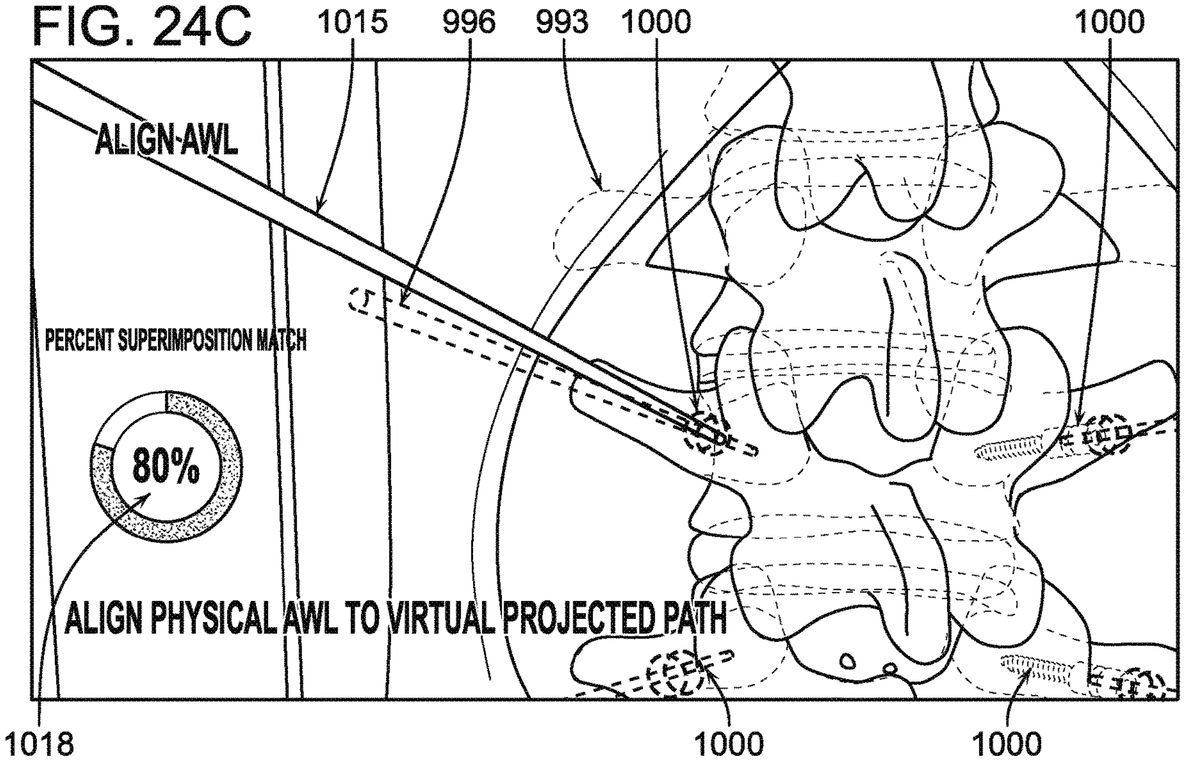
Figure 24D:
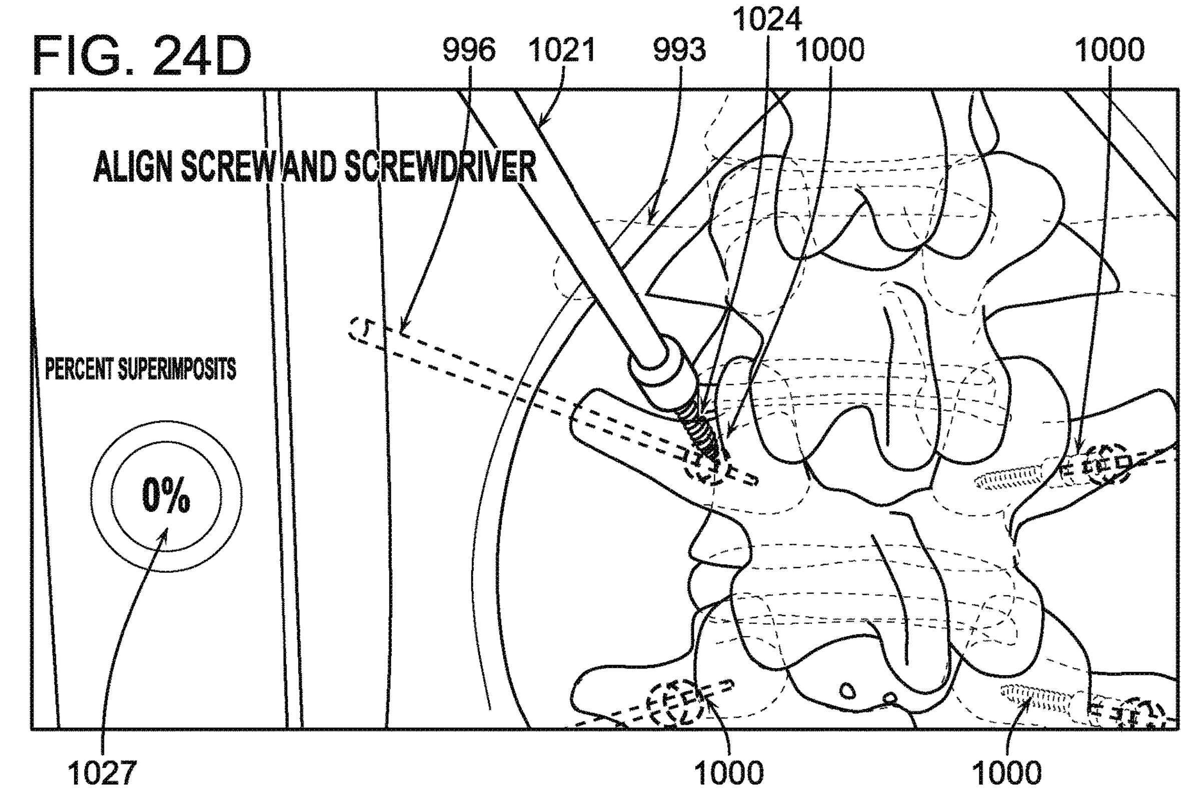
Figure 24E:
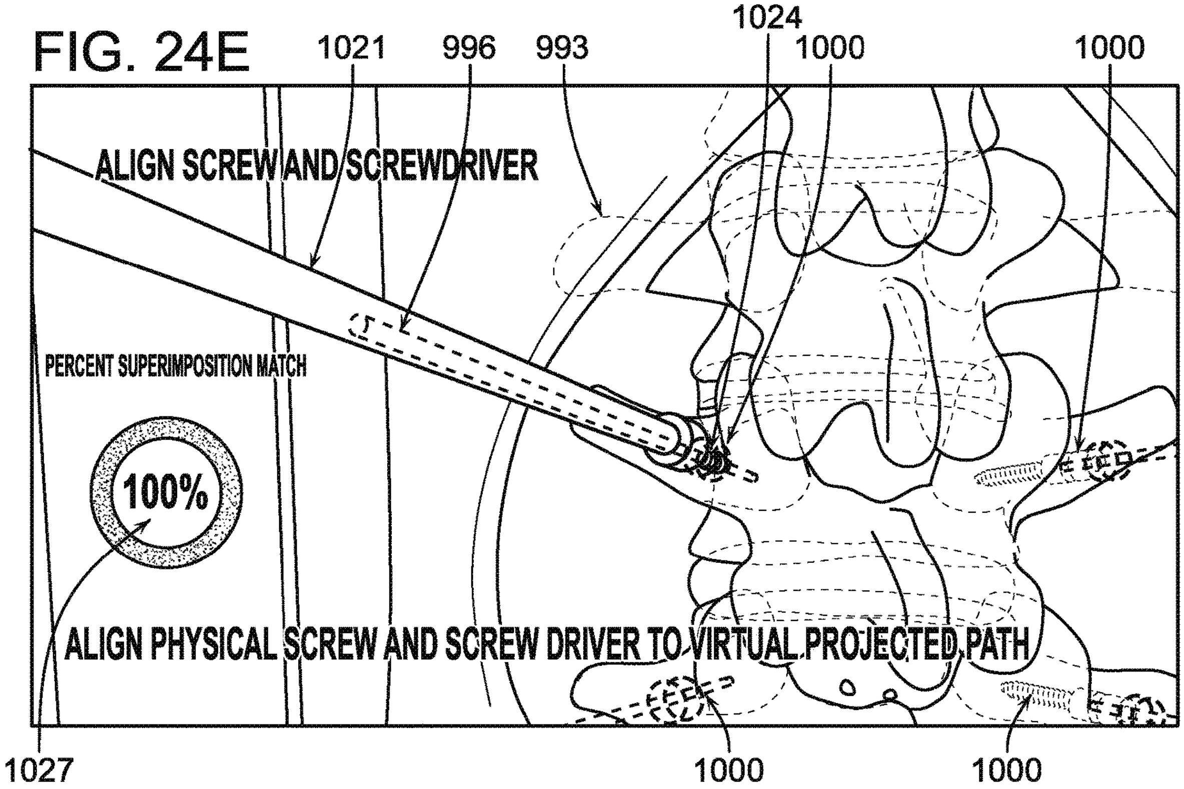

In the example of FIG. 24D, a computer processor can track the physical screw driver 1021 and, optionally, the physical screw 1024, for example using direct video detection or one or more markers, e.g. navigation markers or optical markers (not shown), e.g. with an image capture and/or a navigation system, and can track the percentage superimposition 1027 of the physical screw driver 1021 (and/or, optionally, the physical screw 1024) with the virtual path 996. The superimposition can be indicated as a percent volume superimposition between the physical screw driver (or screw) and the virtual path, percent surface superimposition, percent area superimposition, percent superimposition in a first, second, and/or third direction, e.g. x-, y- and z-, e.g. in mm, percent superimposition with regard to angular alignment, e.g. in x-, y-, and z-direction, e.g. in degrees, percent coordinate superimposition, e.g. in mm (all optionally indicated in graphical, color coded and/or numerical form). The superimposition can be visualized using color coding, for example from red (e.g. "poor"), to orange (e.g. "medium") to green (e.g. "good"). When the physical screwdriver 1021 (and/or, optionally, the physical screw 1024) is completely superimposed onto the virtual path 996 (e.g. 100% match or >90% match or >95% match, or any other amount), the physical screw driver and screw can be advanced, for example to a predetermined endpoint (not shown). Once the superimposition is completed (e.g. 100% match or >95% match or >90% match, or any other amount), the ARDD can provide an optical signal, e.g. a color change from red to green. Physical instruments and pedicle, in this example a screwdriver and a pedicle screw, can be aligned with and superimposed onto the virtual path projected by the ARDD. If the superimposition is incomplete (e.g. <100%, <97%, <94% or any other amount or value), the ARDD can provide an optical warning signal, e.g. a red color of the indicator. The foregoing embodiments on tracking and/or displaying and/or determining and/or measuring superimposition can be applied to many different embodiments throughout the application, e.g. for knee replacement, hip replacement, shoulder replacement, ankle replacement, ACL reconstruction or repair, dental surgery, root canals, dental implant placement, etc.

Any of the registration techniques and/or techniques described in the embodiments including implantable and attachable markers, calibration and registration phantoms including optical markers, navigation markers, infrared markers, RF markers, LED's with image capture and IMU's can be applied for spinal surgery and procedures. For example, in a spinal surgery or procedure, one or more patient specific markers or templates can be applied to one or more spinous processes or articular processes or transverse processes or other spinal structures, for example through a small incision. By applying the patient specific markers or templates to the corresponding structure(s) on the patient, reliable identification of spinal levels is possible, optionally without intraoperative imaging. Moreover, pedicle screws and related instruments or vertebroplasty or kyphoplasty needles and trocars and related instruments can be placed reliably following a trajectory or desired position of the pedicle screws and related instruments or vertebroplasty or kyphoplasty needles and trocars projected by the ARDD using an optional virtual surgical plan. Of note, reliable identification of spinal levels and reliable placement of pedicle screws, rods, and related instruments and or vertebroplasty or kyphoplasty needles and trocars is also possible using the ARDD with the other registration and cross-referencing techniques described in the disclosure or known in the art.

The same steps and ARDD guided spinal procedures are also possible using the ARDD with the other registration and cross-referencing techniques described in the disclosure or known in the art, such as, for example, registration using anatomic landmarks or registration or calibration phantoms including optical markers or image capture, optionally using optical markers, or surgical navigation.

In some embodiments, the registration of virtual patient data and live patient data using the techniques described herein can be repeated after one or more surgical steps have been performed in an ARDD guided spinal procedure. In this case, the surgically altered tissue or tissue surface or tissue contour or tissue perimeter or tissue volume or other tissue features in the live patient can be matched to, superimposed onto and/or registered with the surgically altered tissue or tissue surface or tissue contour or tissue perimeter or tissue volume or other tissue features in the virtual data of the patient, e.g. in a virtual surgical plan developed for the patient. The matching, superimposing and/or registering of the live data of the patient and the digital holograms of the patient's tissue and/or surgical site including hidden and/or obscured parts after the surgical tissue alteration can be performed using the same techniques described in the foregoing or any of the other registration techniques described in the disclosure or any other registration technique known in the art.

If there are any differences between an executed physical surgical plan or an alteration of a physical surgical site, e.g. a spine after a bone removal or placement of a spinal device, e.g. a pedicle screw, and a virtual surgical plan, corrective steps can be taken. These include, for example:

A). Modify the Last Surgical Step so that the physical appearance, physical properties and/or physical characteristics (including, for example, shape and dimensions, cut plane, perimeter of a cut plane/tissue plane, drill depth, angle, rotation, implant site etc.) of the surgically altered tissue in the live patient after the modification is more similar to and, optionally, more closely replicates the intended virtual appearance, virtual properties and/or virtual characteristics in the virtual data of the patient, e.g. a virtual surgical plan of the patient. This option can, for example, be chosen if the operator or surgeon is of the opinion that the last surgical step was subject to an inaccuracy, e.g. by a fluttering or deviating saw blade or a misaligned pin or a misaligned reamer or impactor or other problem, and should correct the inaccuracy. Once the modification has been completed, the surgeon or operator can again assess the physical change, physical appearance, physical properties and/or physical characteristics of the surgically altered tissue and compared it to the estimated or intended virtual change, virtual appearance, virtual properties and/or virtual characteristics of the tissue in the virtual data of the patient, for example the virtual surgical plan. Depending on the result of the assessment, the surgeon or operator can optionally repeat option A, or revert to options B or C.

B). Modify the Next Surgical Step(s) so that the physical appearance, physical properties and/or physical characteristics (including, for example, shape and dimensions, cut plane, perimeter of a cut plane/tissue plane, drill depth, angle, rotation, implant site etc.) of the surgically altered tissue in the live patient after the modification in the next surgical step(s) is more similar to and, optionally, more closely replicates the intended virtual appearance, virtual properties and/or virtual characteristics in the virtual data of the patient, e.g. a virtual surgical plan of the patient after the virtual modification in the next virtual surgical step(s). This option can, for example, be chosen if the operator or surgeon is of the opinion that the last surgical step was subject to an inaccuracy, e.g. by a fluttering or deviating saw blade or a misaligned pin or a misaligned reamer or impactor or other problem, and he or she should correct the inaccuracy in the next surgical step(s). Once the modification has been completed with the next surgical step(s), the surgeon or operator can again assess the physical change, physical appearance, physical properties and/or physical characteristics of the surgically altered tissue and compared it to the estimated or intended virtual change, virtual appearance, virtual properties and/or virtual characteristics of the tissue in the virtual data of the patient, for example the virtual surgical plan. Depending on the result of the assessment, the surgeon or operator can optionally repeat option A and/or B and/or revert to options C and/or D and/or E.

C). Modify the Virtual Surgical Plan of the patient so that the virtual appearance, virtual properties and/or virtual characteristics (including, for example, shape, volume and dimensions, cut plane, perimeter or surface/surface area of a cut plane/tissue plane, drill depth, angle, rotation, implant site etc.) of the surgically altered tissue in the virtual data of the patient after the modification is/are more similar to and, optionally, more closely replicates the physical appearance, physical properties and/or physical characteristics in the physical live data of the patient after the physical surgical alteration. This option can, for example, be chosen if the operator or surgeon is of the opinion that the last surgical step was accurate or accounted for unexpected variations in tissue conditions that were not accounted for in the virtual surgical plan. Such unexpected variations in tissue conditions can, for example, be ligament laxity or tightness as can be observed, for example, in knee replacement surgery or hip replacement or other joint replacement surgeries. If the modified surgical plan is modified in this manner, all subsequent virtual surgical steps can then be referenced off the last or preceding physical surgical step, thereby maintaining continuity of the procedure. The ARDD can then be used for projecting all or some of the subsequent virtual surgical steps, e.g. by projecting one or more of virtual surgical tool, virtual surgical instrument, virtual trial implant, virtual implant component, virtual implant or virtual device, all optionally selected from a virtual library, a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration. The subsequent virtual surgical steps are thus modified to allow completion of the procedure and, optionally, placement of an implant or implant component or device or graft or transplant taking into account the one or more modified preceding physical surgical steps. Optionally, the modified subsequent virtual surgical steps can be further modified based on local tissue conditions/characteristics after the virtual or physical modification, for example, if subsequent surgical steps were to fall into a tissue void or would result in impairment of implant component placement.

D). Modify the Registration of the Virtual Data of the Patient in Relationship to the Live Data of the Patient. The operator or surgeon can optionally repeat the registration procedure using any of the techniques described in the disclosure or known in the art for registering the virtual data of the patient, including, for example the virtual surgical plan, in relationship to the live data of the patient after the physical surgical alteration. Once the virtual data of the patient and the live data of the patient after the surgical alteration have been re-registered, all subsequent virtual surgical steps displayed by the ARDD and any related virtual surgical plan can be referenced off the re-registration of the virtual and live data of the patient. For example, the ARDD can then be used after the re-registration for projecting all subsequent virtual surgical steps, e.g. by projecting one or more of virtual surgical tool, virtual surgical instrument, virtual trial implant, virtual implant component, virtual implant or virtual device, all optionally selected from a virtual library, a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration.

E). Apply Registration Correction. If there are differences between the physical change in the physical surgically altered tissue and the virtually intended change in the virtually surgically altered tissue or if there are differences in the appearance, properties and/or characteristics of the physical surgically altered tissue and the virtually altered tissue, e.g. in the virtual data of the patient and/or the virtual surgical plan, the magnitude of the differences can be assessed and can be used to apply a coordinate correction, coordinate adjustment or coordinate transfer of registration of the virtual data of the patient, including, optionally, the virtual surgical plan, and the live data of the patient, e.g. for any subsequent surgical steps on surgical procedures. For example, the ARDD can then project/display all subsequent virtual surgical steps using the coordinate correction or adjustment or transfer, e.g. by projecting one or more of virtual surgical tool, virtual surgical instrument including virtual surgical guide or cut block, virtual trial implant, virtual implant component, virtual implant or virtual device, all optionally selected from a virtual library, a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration using the coordinate correction, adjustment and/or transfer.

Any combinations of the foregoing Options A, B, C, D and/or E are possible.

The position of the one or more pins or drills can be registered, for example using an image and/or video capture system integrated into, attached to or separate from the ARDD or using a 3D scanner that detects the one or more pins or drills. The position of the one or more pins or drills can be registered using attached or integrated optical markers or navigation markers including, but not limited to infrared markers, retroreflective markers, RF markers, e.g. with an optionally used navigation system, or IMU's. The position of the drill(s) or pin(s) can be detected using a touch probe or pointer, wherein the touch probe can be tracked directly using an image or video capture system and/or 3D scanner integrated into, attached to, or separate from the ARDD, and/or optionally including attached or integrated IMU's, optical markers, navigation markers including, but not limited to, infrared markers, retroreflective markers, RF markers and the like, for example for use with an image and/or video capture system and/or 3D scanner or a navigation system. If more than one marker is placed along the trajectory of the pin or drill or if image capture is used, the two or more markers or the trajectory of the visualized portions of the pin(s) or drill(s) using image capture can be used to estimate the trajectory of the pin(s) or drill(s) and to estimate a projected path as the pin(s) or drill(s) are advanced. If the length and the thickness of the pins are known, not only the endpoint outside the patient's tissue can be determined, but also the location of the tip can be estimated even though it can be seated deep inside the patient's tissue in spinal surgery, knee replacement, hip replacement, shoulder replacement, brain surgery and various types of other surgery.

The position of the pins or drills can be registered in relationship to the patient and/or the ARDD using any of the techniques described in the disclosure. The one or more optical markers can be retroreflective or can include LED's. Combinations of optical and RF markers can be used.

In some embodiments, a first drill or pin is registered, optionally followed by registration of a second or more pin and drills. The position and/or orientation of the one or more pins or drills can be used to maintain registration during the surgery, e.g. placement of pedicle screws and related devices, e.g. rods, or knee replacement with placement of one or more pins or drills in the femur and/or the tibia or hip replacement with placement of one or more pins or drills in the acetabulum or proximal femur. Since the one or more pins or drills are fixed to the bone, accurate registration can be maintained even if there is patient movement after the initial registration, if the pin or drill(s) are used for registration after the initial registration. Optionally, both the initial registration and the subsequent registration to the altered surgical surface/site after the placement of the pin or drill with registration to the pin or drill(s) can be used together. In this case, statistical techniques can be applied to reconcile small differences between the initial registration and the registration to the altered surgical surface or site including the one or more pins or drills. For example, the mean or the median of the different registrations can be used for any subsequent surgical steps.

In some embodiments, an initial registration can be performed between virtual data of the patient, e.g. pre-operative imaging, including optionally a virtual surgical plan for the patient, and live data of the patient during surgery. The initial registration can, for example, be performed using intra-operative imaging, which can be referenced to and registered with the live data of the patient. Any other technique of registration described in the disclosure or known in the art can be used for the initial registration. A first pin or drill or a first set of pins or drills can be placed using the initial registration of virtual data of the patient and live data of the patient.

Following the placement of a first pin or drill or a first set of pins or drills, intra-operative imaging can be repeated. In some embodiments, intra-operative imaging is used for the initial registration and the same intraoperative imaging modality and technique or similar intra-operative imaging modality or technique is used after placing the first pin or drill or the first set of pins or drills. Alternatively, a different intra-operative imaging modality is used after placing the first pin or drill or the first set of pins or drills. Intra-operative imaging modalities can include, for example, x-rays, e.g. AP, PA, lateral and oblique views, C-arm acquisition, optionally with CT capability, CT scan or ultrasound scan or MRI scan or any other imaging technique known in the art.

In some embodiments, after a first pin or drill or a first set of pins or drills is placed, the accuracy of the placement can be assessed. The accuracy of the placement can be assessed using, for example, any of the following:

- Intraoperative imaging, e.g. also if the initial registration was performed without use of intraoperative imaging
- Intraoperative imaging using the same or a different imaging modality used for an initial registration (if applicable)
- Image capture of the visible portions of the pin(s) or drill(s), with optional projection/estimation of the location and/or orientation of any non-visualized portions inside the patient's tissue
- Optical markers, navigation markers including, but not limited to, infrared markers, retroreflective markers, RF markers, IMU's, and any other electronic or optical or magnetic marker known in the art, with optional projection/estimation of the location and/or orientation of any non-visualized portions inside the patient's tissue Any deviations in the physical placement including the physical position and/or the physical orientation, and/or coordinates of a physical pin, drill, wire, k-wire, screw, pedicle screw, cage, implant, device, tool, instrument compared to the intended position and/or intended orientation of the virtual physical pin, drill, wire, k-wire, screw, pedicle screw, cage, implant, device, tool, instrument (optionally re-displayed after the placement of the physical physical pin, drill, wire, k-wire, screw, pedicle screw, cage, implant, device, tool, instrument) in the virtual surgical plan can be measured in this manner. If one or more of the physical pin, drill, wire, k-wire, screw, pedicle screw, cage, implant, device, tool, instrument show a deviation in physical vs. intended virtual position and/or orientation, the difference in coordinates can be determined and a coordinate transfer or coordinate correction can be applied for any subsequent registration that uses one or more of the pins or drills placed inside the patient's tissue. A coordinate transfer or coordinate correction can be applied globally, e.g. to all physical pins, drills, wires, k-wires, screws, pedicle screws, cages, implants, devices, tools, instruments placed using the same values. Alternatively, a coordinate transfer or coordinate correction can be applied individually to each physical pin, drill, wire, k-wire, screw, pedicle screw, cage, implant, device, tool, instrument accounting for their specific deviation from physical vs. intended virtual placement/position/and/or orientation. The former approach can be more time efficient. The latter approach can be more accurate for any subsequent registrations. A coordinate transfer or coordinate correction applied for each physical pin, drill, wire, k-wire, screw, pedicle screw, cage, implant, device, tool, instrument individually using data on the amount of deviation/difference in coordinates between physical placement/position/and/or orientation compared to intended virtual placement/position/and/or orientation based on the virtual surgical plan can be particularly helpful in spinal surgery, when one or more spinal segment can move in relationship to each other during the surgery, e.g. if the surgeon has to adjust the position of the patient on the table. In this case, one or more physical pin, drill, wire, k-wire, screw, pedicle screw, cage, implant, device, tool, instrument can optionally be placed at more than one spinal level, for example all spinal levels involved in the surgery, after the initial registration and the accuracy of the placement can be assessed using the foregoing techniques.

A coordinate transfer or coordinate correction can optionally be applied for more than one spinal level, e.g. all spinal levels involved in the surgery, wherein the difference in physical vs. intended virtual placement/position/and/or orientation of the physical pin, drill, wire, k-wire, screw, pedicle screw, cage, implant, device, tool, instrument can be used to improve the accuracy of any subsequent registration using the one or more placed physical pin, drill, wire, k-wire, screw, pedicle screw, cage, implant, device, tool, instrument for subsequent surgical steps for each spinal level for which the coordinate transfer or coordinate correction has been or will be applied.

A coordinate transfer or coordinate correction can optionally be applied for individual spinal levels. For example, after each screw or wire or device placed, or each level or each second level in which a screw, wire or device has been placed, the virtual surgical guide, e.g. a virtual axis, a virtual pin, drill, wire, k-wire, screw, pedicle screw, cage, implant, device, tool, instrument can be re-displayed and any difference in position, orientation and/or coordinates to the physical pin, drill, wire, k-wire, screw, pedicle screw, cage, implant, device, tool, instrument placed can be detected with subsequent coordinate correction, coordinate transfer, re-registration, e.g. for the next screw, wire or device, the next spinal level, the next two spinal levels, etc.

The coordinate correction can be performed using AR guidance and display, for example with use of an optical see through head mounted display. The surgeon can look at the physical pin, drill, wire, k-wire, screw, pedicle screw, cage, implant, device, tool, instrument placed during a preceding surgical step and visible directly through optical see through head mounted display. A computer processor can be configured to re-display a virtual surgical guide, e.g. a virtual axis, a virtual pin, drill, wire, k-wire, screw, pedicle screw, cage, implant, device, tool, instrument, e.g. used during the preceding surgical step. A user interface, for example using voice recognition, a foot pedal, a keyboard, a graphical interface, a virtual interface, gesture recognition or other user interfaces known in the art or described in the disclosure, powered by the same or a different computer processor, can be used to re-display the virtual surgical guide, e.g. a virtual axis, a virtual pin, drill, wire, k-wire, screw, pedicle screw, cage, implant, device, tool, instrument, e.g. from the preceding surgical step. If the physical pin, drill, wire, k-wire, screw, pedicle screw, cage, implant, device, tool, instrument and the corresponding virtual pin, drill, wire, k-wire, screw, pedicle screw, cage, implant, device, tool, instrument are not superimposed and aligned and the difference in position is more than 0.1 mm, 0.2 mm, 0.3 mm, 0.4 mm, 0.5 mm, 0.7 mm, 0.8 mm, 0.9 mm, 1.0 mm, 1.2 mm, 1.5 mm, 2.0 mm, 2.5 mm, 3.0 mm, 3.5 mm, 4.0 mm, 4.5 mm, 5.0 mm, 6.0 mm, 7.0 mm, 10.0 mm or any other value or the difference in orientation exceeds 0.1°, 0.2°, 0.3°, 0.4°, 0.5°, 0.7°, 0.8°, 0.9°, 1.0°, 1.2°, 1.5°, 2.0°, 2.5°, 3.0°, 3.5°, 4.0°, 4.5°, 5.0°, 6.0°, 7.0°, 10.0°, 15.0°, 20.0°, 35.0°, 30.0°, or any other value, a coordinate correction can be performed, for example using a user interface. The computer processor and/or the user interface can be configured to move, re-align, re-orient, change the coordinates of the virtual surgical guide, e.g. a virtual axis, the virtual pin, drill, wire, k-wire, screw, pedicle screw, cage, implant, device, tool, instrument to be superimposed and aligned with the corresponding physical pin, drill, wire, k-wire, screw, pedicle screw, cage, implant, device, tool, instrument implanted during the preceding surgical step. For example, a pointer, e.g. with at least one or more attached markers, e.g. optical markers, infrared markers, RF markers, or any other marker described in the disclosure or known in the art, for tracking with a navigation system or camera or video system, or any other device (including, for example, tracked directly with a video system or 3D scanner without attached markers) can be used for moving, re-aligning, re-orienting, changing the coordinates of the virtual surgical guide, e.g. a virtual axis, the virtual pin, drill, wire, k-wire, screw, pedicle screw, cage, implant, device, tool, instrument to superimpose and align them with the corresponding physical pin, drill, wire, k-wire, screw, pedicle screw, cage, implant, device, tool, instrument. A virtual user interface, e.g. with virtual sliders, for example activated or operated with a cursor moved via head movements or operated using gesture recognition, can be used for moving, re-aligning, re-orienting, changing the coordinates of the virtual surgical guide, e.g. a virtual axis, the virtual pin, drill, wire, k-wire, screw, pedicle screw, cage, implant, device, tool, instrument to superimpose and align them with the corresponding physical pin, drill, wire, k-wire, screw, pedicle screw, cage, implant, device, tool, instrument.

In another example, a finger tracked using a camera, e.g. a video camera, or image capture system can be used for moving, re-aligning, re-orienting, changing the coordinates of the virtual surgical guide, e.g. a virtual axis, the virtual pin, drill, wire, k-wire, screw, pedicle screw, cage, implant, device, tool, instrument to superimpose and align them with the corresponding physical pin, drill, wire, k-wire, screw, pedicle screw, cage, implant, device, tool, instrument. Optionally, a tracking function can be activated and deactivated for the pointer or other device (including also a finger) using a user interface, e.g. using a voice command or gesture command.

The change in coordinates of the tracked pointer, device and/or finger from the original position (e.g. when the physical and corresponding virtual pin, drill, wire, k-wire, screw, pedicle screw, cage, implant, device, tool, instrument are not superimposed and/or aligned) to the new position (e.g. when the physical and corresponding virtual pin, drill, wire, k-wire, screw, pedicle screw, cage, implant, device, tool, instrument are substantially superimposed and/or aligned within an acceptable range (e.g. in mm or degrees))

can be measured and can be used for a coordinate correction as described in the disclosure. If the virtual surgical guide is moved, e.g. using a virtual user interface, the change from the original position and/or orientation to the new position and/or orientation can be used to determine the difference in coordinates and to compute the coordinate correction. The coordinate correction can be used for any subsequent virtual display, including display of a virtual surgical guide, e.g. a virtual axis, the virtual pin, drill, wire, k-wire, screw, pedicle screw, cage, implant, device, tool, instrument for placing one or more additional physical pins, drills, wires, k-wires, screws, pedicle screws, cages, implants, devices, tools, instruments in subsequent steps. The coordinate correction can be a global correction, or a correction level by level, e.g. in a spine, as described in the disclosure.

In the example of spinal surgery, one or more pedicle screws can be placed, at the same spinal level or different spinal levels. Optionally, the accuracy of the physical placement/position and/or orientation of each pedicle screw can be assessed compared to the intended virtual placement/position/and/or orientation in the virtual surgical plan using any of the foregoing techniques. Optionally a coordinate transfer or coordinate correction can be determined based on any deviations between physical and intended virtual placement of the pedicle screw and the pedicle screw can be used for registration of the patient, the spine, and/or the ARDD during any subsequent surgical steps, e.g. placement of additional pedicle screws, e.g. at the same or other spinal levels, or placement of one or more connectors or rods and the like. During the placement of the pedicle screw, registration can be maintained by referencing one or more of the pins or drills or pedicle screws placed in the pedicles at the same or adjacent spinal levels.

Similarly, in other surgical procedures, e.g. knee replacement, hip replacement, shoulder replacement, ACL repair and reconstruction, cranial, maxillofacial and brain surgery, the physical position of any drill, pin, instrument, implant, device or device component can be determined using any of the techniques described in the disclosure and any deviations or differences between the physical and the intended virtual placement/position/and/or orientation can be determined. The differences measured can be used to determine a coordinate transfer or coordinate correction for any subsequent registrations for subsequent surgical steps using now the one or more drill, pin, instrument, implant, device or device component as the registration reference or marker.

By referencing a pin or drill that is fixed inside the bone or a hard tissue (following the first surgical alteration), it is possible to maintain accurate registration, e.g. during pedicle screw placement, knee replacement, hip replacement, ACL repair and/or reconstruction, maxillofacial surgery, cranial and/or brain surgery.

In this case, the pinned or drilled tissue of the live patient or portions thereof can be matched to or superimposed and/or registered with the corresponding pinned or drilled tissue in the virtual surgical plan. Once an adequate match of the live and virtual cut pinned or drilled area has been obtained, registration can optionally be repeated. In some embodiments, the bone void or hole created by any pinning or drilling can be used for any subsequent registrations. Optionally, a pin or drill can be temporarily placed back into the bone void or hole for any subsequent registration and subsequent surgical steps. If other surgical instruments are used, e.g. other than a drill or pin, such as a burr or a blade, other resultant bone voids can optionally also be used for any subsequent registrations.

Optionally, the position, location, and/or orientation and/or size and/or shape of any bone void or hole created by any surgical instrument can be assessed, e.g. using intraoperative imaging such as x-rays or ultrasound, and the difference between the physical and the intended virtual position, location, and/or orientation and/or size and/or shape of any bone void or hole can be assessed. The difference or deviation between the physical and the intended virtual position, location, and/or orientation and/or size and/or shape of the bone void or hole can be used to determine a coordinate difference or coordinate transfer or coordinate correction so that the bone void or hole can be used for any subsequent registration and subsequent surgical steps. Any subsequent registration can be performed by optionally introducing a partial or complete bone void filler (e.g. a pin or a drill) and registering the bone void filler. Any subsequent registration can also be performed by registering the bone void or hole directly, e.g. with intraoperative imaging. Any subsequent registration can also be performed by placing one or more IMU's, optical markers, and/or navigation markers including, but not limited to, infrared markers, retroreflective markers, RF markers inside or adjacent to the bone void and registered one or more of the IMU's, optical markers, LED's and/or navigation markers including, but not limited to, infrared markers, retroreflective markers, RF markers using any of the techniques described in the disclosure. Moreover, any subsequent registration can also be performed by marking portions or all of the bone void or hole with a color, e.g. toluidine blue, and by registering the marked and/or stained portions of the bone void or hole, e.g. using an image and/or video capture system and/or 3D scanner integrated into, attached to, or separate from the ARDD.

If a tissue cut is performed, for example with a scalpel or a saw, the registration procedure can be repeated after the tissue cut has been placed. In this case, the cut tissue surface of the live patient or portions thereof or the perimeter of the cut tissue surface of the live patient or portions thereof or the surface area of the cut tissue surface of the live patient or portions thereof or the volume of the removed tissue of the live patient or portions thereof can be matched to or superimposed and/or registered with the corresponding cut tissue surface of the virtual data or portions thereof or the perimeter of the cut tissue surface of the virtual data or portions thereof or the surface area of the cut tissue surface of the virtual data or portions thereof or the volume of the removed tissue of the virtual data or portions thereof in the virtual surgical plan. Once an adequate match of the live and virtual cut surfaces has been obtained, registration can optionally be repeated.

If a tissue cut is performed, the registration procedure can be repeated after the tissue cut has been completed. In this case, the cut tissue surface of the live patient or portions thereof or the perimeter of the cut tissue surface of the live patient or portions thereof can be matched to or superimposed onto and/or registered with the corresponding cut tissue surface or portions thereof in the virtual surgical plan or the perimeter of the cut tissue surface in the virtual surgical plan or portions thereof. Once an adequate match of the live and virtual cut surfaces has been obtained, registration can optionally be repeated.

If a bone cut is performed, for example with a saw, the registration procedure can be repeated after the bone cut has been placed. In this case, the cut bone surface of the live patient or portions thereof or the perimeter of the cut bone surface of the live patient or portions thereof or the surface area of the cut bone surface of the live patient or portions thereof or the volume of the removed bone of the live patient or portions thereof can be matched to or superimposed onto and/or registered with the corresponding cut bone surface of the virtual data or portions thereof or the perimeter of the cut bone surface of the virtual data or portions thereof or the surface area of the cut bone surface of the virtual data or portions thereof or the volume of the removed bone of the virtual data or portions thereof in the virtual surgical plan. Once an adequate match of the live and virtual cut surfaces has been obtained, registration can optionally be repeated.

If a milling, reaming or impacting procedure is performed, for example with a reamer, a mill or an impactor, the registration procedure can be repeated after the milling, reaming or impacting has been performed. In this case, the milled, reamed or impacted bone surface of the live patient or portions thereof or the perimeter of the milled, reamed or impacted bone surface of the live patient or portions thereof or the surface area of the milled, reamed or impacted bone surface of the live patient or portions thereof or the volume of the removed bone of the live patient or portions thereof can be matched to or superimposed onto and/or registered with the corresponding milled, reamed or impacted bone surface of the virtual data or portions thereof or the perimeter of the milled, reamed or impacted bone surface of the virtual data or portions thereof or the surface area of the milled, reamed or impacted bone surface of the virtual data or portions thereof or the volume of the removed bone of the virtual data or portions thereof in the virtual surgical plan. Once an adequate match of the live and virtual cut surfaces has been obtained, registration can optionally be repeated.

If a drilling procedure is performed, for example with a drill or a pin or a K-wire, the registration procedure can be repeated after the drill or pin or K-wire has been placed. In this case, the drilled surface of the live patient or portions thereof or the perimeter of the drilled surface of the live patient or portions thereof or the surface area of the drilled surface of the live patient or portions thereof or the volume of the removed bone of the live patient or portions thereof or the location of the drill hole or the orientation of the drill hole or the size of the drill hole or a marker such as a drill, a pin or a K-wire or an ink inserted into the drill hole can be matched to or superimposed onto and/or registered with the corresponding drilled surface in the virtual data or portions thereof or the perimeter of the drilled surface in the virtual data or portions thereof or the surface area of the drilled surface in the virtual data or portions thereof or the volume of the removed bone in the virtual data or portions thereof or the location of the drill hole in the virtual data or the orientation of the drill hole in the virtual data or the size of the drill hole in the virtual data or a marker such as a drill, a pin or a K-wire or an ink inserted into the drill hole in the virtual data, optionally in the virtual surgical plan. Once an adequate match of the live and virtual cut surfaces has been obtained, registration can optionally be repeated.

If a drilling procedure is performed, the drill holes can optionally be marked with india ink or another color in the live patient. The color marking can be recognized with use of an image and/or video capture system and/or 3D scanner integrated into, attached to or separate from the ARDD. The color markings in the live patient can then optionally be used to re-register the live data of the patient with the virtual data after one or more surgical alterations of the tissue has/have been performed. The color markings can be used with an image and/or video capture system and/or 3D scanner to detect them in the live patient data and to register them with the virtual patient data. Alternatively, the color markings can be used by the surgeon to identify the previously placed drill holes visually, for example after one or more surgical alterations or surgical steps have been performed. A drill, a pin, a K-wire, a screw, or another surgical instrument can then optionally be placed inside the drill hole and the registration of the live data and the virtual data can be performed by matching, superimposing and/or registering the live drill, pin, K-wire, screw, or other surgical instrument with a corresponding virtual drill, pin, K-wire, screw, or other surgical instrument or a corresponding drill hole in the virtual surgical plan.

For example, in a knee replacement procedure, a drill guide can be applied to the distal femur and/or the distal femoral condyles before the distal femoral cut and bone removal is performed. The drill guide can be integrated into the distal femoral cut block. Typically, two or more drill holes can be placed, for example with one or more drill holes located in the medial femoral condyle or in the medial femur and one or more drill holes located in the lateral femoral condyle or in the lateral femur. The location of the medial and lateral drill holes and the intersect between the two drill holes can be used to define the rotation axis of the femoral component.

The ARDD can display the desired location of the distal femoral cut block for achieving the desired mechanical axis correction and the desired location of the drill holes for setting the desired rotation axis of the femoral implant component. The drill holes can be drilled prior to performing the cut and can be optionally marked with ink prior to performing the distal femoral cut. The distal femoral cut can then be performed. The ink in the drill holes can then be identified on the cut surface. The ink seen in the live patient data can be registered using an image and/or video capture system and/or 3D scanner integrated into, attached to or separate from the ARDD and can be registered in relationship to the virtual drill holes as defined in the virtual surgical plan. Alternatively, the surgeon can elect to insert a drill, pin, K-wire, screw, or other surgical instrument into the drill holes in the live patient data and the location of the drill, pin, K-wire, screw, or other surgical instrument can be registered using an image and/or video capture system and/or 3D scanner integrated into, attached to or separate from the ARDD and can be registered in relationship to a virtual drill, pin, K-wire, screw or other surgical instrument optionally introduced into the virtual surgical plan.

In this manner, live patient data and virtual patient data can be re-registered after the distal femoral bone cut has been performed. The surgeon can also use the re-registration to check the accuracy of the initial registration and perform adjustments to the physical surgical plan or the virtual surgical plan depending on any discrepancies detected.

The foregoing embodiment can be applied to any type of joint replacement or joint sparing procedure including arthroscopy. Any of the embodiments described in the disclosure can be applied to any other spinal procedure, including, for example, cages, ALIF, PLIF, TLIF, diskectomies, laminotomies, laminectomies, facetectomies, plating, spinal fracture treatment, sacroiliac joint fusions etc.

Surgical Microscopes and Endoscopes

Aspects of the present disclosure describe systems and methods for augmented reality guidance in conjunction with surgical microscopes and/or surgical endoscopes. Surgical microscopes and/or endoscopes can be of 2D image type or 3D image type. Stereo microscopes can be used. Stereo endoscopes can be used.

Aspects of the present disclosure relate to systems, devices and methods for performing a surgical step or surgical procedure with visual guidance using a head mounted display. In some embodiments, the head mounted display can be a see-through head mounted display, e.g. an optical see-through head mounted display, for example for augmented reality applications. Non-limiting examples of optical see-through head mounted displays include Microsoft Hololens 2 (Microsoft, Redmond, WA, x-real Air 2 or nreal light (X-Real, Beijing, China). In some embodiments, the head mounted display can be a non-see-through head mounted display, e.g. video see through type, for virtual reality applications, optionally with video display including video streaming of live data from the patient, e.g. video feed from a camera integrated into, attached to, or separate from the head mounted display. The head mounted display can provide surgical guidance in a mixed reality environment. Various embodiments are described for adjusting the focal plane or focal point or selecting the focal plane or focal point and/or the field of view and/or the display size for displaying a virtual tissue, a virtual structure, virtual object, virtual instrument, virtual implant (e.g. a virtual implant component) or a virtual device using, for example, the distance between the head mounted display and the surgical site, e.g. an uncut or a cut bone in a joint replacement, a vertebral body or spinal element in a spinal procedure, a vessel or vascular structure in a cardiovascular, neurovascular, or general vascular procedure, an organ or any other tissue, or a tooth or gum in a dental procedure, or in any other surgical procedures, e.g. brain surgery, thoracic surgery, pelvic surgery, breast surgery etc., In any of the embodiments throughout the disclosure, a virtual structure, virtual object, virtual instrument, virtual implant (e.g. a virtual implant component), or a virtual device can be a 2D or 3D representation, e.g. a graphical 2D or 3D representation. In any of the embodiments throughout the disclosure, a virtual structure, virtual object, virtual instrument, virtual implant (e.g. a virtual implant component), or a virtual device can be a 2D or 3D representation of a tracked a physical structure, physical object, physical instrument, physical implant (e.g. a physical implant component) or a physical device.

AR Guidance for Microscopes or Endoscopes

A microscope, an endoscope, a surgical site, e.g. one or more unaltered and/or surgically altered anatomic structures and/or tissues (e.g. a brain before and after resection of a tumor or a vascular lesion, a spinal structure before and after a tissue resection, e.g. a decompression or discectomy) can be registered in a coordinate system using, for example, IMUs, optical markers, navigation markers including infrared markers, retroreflective markers, RF markers, active markers, e.g. an LED or RF marker, passive markers, image and/or video capture, e.g. using one or more cameras, 3D scanning, e.g. using a laser scanner, a light field imaging systems, and any other technique known in the art. Examples for registration using IMUs, optical markers, navigation markers including infrared markers, retroreflective markers, RF markers, active markers, e.g. an LED or RF marker, passive markers, image and/or video capture, cameras, 3D scanners, 3D scanning are provided, for example, in PCT application PCT/US19/15522, filed Jan. 29, 2019, which is hereby incorporated in its entirety. One or more IMUs, optical markers, navigation markers including infrared markers, retroreflective markers, RF markers, active markers, e.g. an LED or RF marker, passive markers, including combinations thereof can be attached to or integrated into the surgical microscope and/or the surgical endoscope. One or more IMUs, optical markers, navigation markers including infrared markers, retroreflective markers, RF markers, active markers, e.g. an LED or RF marker, passive markers, including combinations thereof can be attached to one or more anatomic structures, e.g. a spine, a spinal structure, a spinal tissue, partially exposed using a minimally invasive access portal, or an articular tissue. Registration can be performed, for example, through an access portal (e.g. for minimally invasive spinal surgery) using, for example, a navigation system, an image capture system, a video capture system, and/or a 3D scanner or laser scanner. Registration can include image based registration, for example using intra-operative x-rays, a CT scan, an O-arm scan, an MRI scan, an ultrasound scan. IMUs, optical markers, navigation markers including infrared markers, retroreflective markers, RF markers, active markers, e.g. an LED or RF marker, passive markers, including combinations thereof can include radiopaque elements for detection in the intra-operative imaging studies. Pre-operative imaging studies can optionally be registered with intra-operative imaging studies. Any technique known in the art for image based registration including registration of pre-operative and intra-operative imaging studies can be used, including 2D-3D registration and/or 3D-3D registration; non-limiting representative examples are provided in PCT application PCT/US19/15522, filed Jan. 29, 2019, which is hereby incorporated in its entirety. By attaching one or more IMUs, optical markers, navigation markers including infrared markers, retroreflective markers, RF markers, active markers, e.g. an LED or RF marker, passive markers, including combinations thereof to the surgical microscope and/or surgical endoscope, the surgical microscope and/or surgical endoscope can be registered in the coordinate system and can be tracked during movement in the coordinate system. Similarly, using an image or video capture system the surgical microscope and/or surgical endoscope can be registered in the coordinate system and can be tracked during movement in the coordinate system. By registering and tracking at least portions of the surgical microscope and/or surgical endoscope including, for example, the lenses through which the surgeon can observe the surgical site, e.g. anatomic structures, in the coordinate system the virtual display through the microscope and/or surgical endoscope can be maintained superimposed and/or aligned with one or more anatomic structures (e.g. gyri or spinal elements, spinal tissue, intra-articular tissues) even when the microscope and/or endoscope is moved and/or when the patient is moved.

By attaching one or more IMUs, optical markers, navigation markers including infrared markers, retroreflective markers, RF markers, active markers, e.g. an LED or RF marker, passive markers, including combinations thereof to the surgical site, e.g. the anatomic structures and/or tissues and/or landmarks accessed in the surgical site, for example through a minimally invasive access portal, or by scanning the surgical site, e.g. the anatomic structures and/or tissues and/or landmarks accessed in the surgical site, using an image capture and/or video system or 3D scanner, the surgical site including the anatomic structures and/or tissues and/or landmarks accessed in the surgical site, can be registered in the coordinate system and can be tracked during movement in the coordinate system. By registering and tracking the surgical site, e.g. one or more anatomic structures and/or surface and/or tissues and/or landmarks accessed in the surgical site, in the coordinate system, the virtual display through the microscope and/or endoscope can be maintained superimposed and/or aligned with one or more anatomic structures (e.g. gyri or spinal elements) even when the patient is moved, e.g. when the spine moves or rotates or changes its sagittal curvature during the surgery.

In some embodiments, the system can account for movement of the microscope and/or endoscope, the surgical site including the anatomic structures, and/or both by adjusting the virtual display, e.g. the virtual display of one or more virtual surgical plans, e.g. virtual surgical steps, virtual surgical techniques, virtual surgical guides, virtual surgical tools, virtual surgical instruments, virtual surgical devices, including virtual surgical implants, and by maintaining the virtual display superimposed and/or aligned with one or more anatomic structures with movement of the microscope and/or endoscope and/or the one or more anatomic structures. The virtual display can be in 2D and/or in 3D. The virtual display can be stereoscopic or non-stereoscopic, as described in more detail in PCT application PCT/US19/15522, filed Jan. 29, 2019, which is hereby incorporated in its entirety.

In any of the embodiments, the head mounted display can be of optical see-through type, with the anatomic structures directly visible to the user's eye through the transparent or partially transparent HMD. The head mounted display can be of video see-through type, optionally with the anatomic structure imaged using one or more video cameras, optionally stereoscopic, attached to the head mounted display, optionally with the anatomic structures imaged with the video cameras and then displayed by the head mounted display, but typically not directly visible to the user's eye. In some embodiments, hybrid applications of both can be used, for example with a partially transparent HMD that receives also feed from one or more video cameras for display by the HMD.

Augmented and/or virtual reality components, systems and/or devices can be the same or similar to those used in optical head mounted displays, e.g. video see through or optical see through optical head mounted displays, as described in exemplary fashion, for example, in PCT application PCT/US19/15522, filed Jan. 29, 2019, which is hereby incorporated in its entirety. Augmented reality and/or virtual components and/or display units can include, for example, cathode ray tubes, liquid crystal displays, liquid crystal on silicone, and/or organic light emitting diodes (OLED's); they can include mirrors, curved mirrors and/or waveguides; they can include combiners. Any type of waveguide known in the art can be used, e.g. planar waveguides, slab waveguides, dielectric waveguides, strip, rib, segmented waveguides, rectangular waveguides, photonic crystal waveguides, laser inscribed waveguides. They can include optical fibers and/or light pipes.

Augmented and/or virtual reality components and/or display units can be integrated in different parts of the microscopes and/or endoscopes and/or in different portions of the light beam. Augmented and/or virtual reality components and/or display units can be perpendicular to the light beam passing through the microscope optics and/or the display unit. Augmented and/or virtual reality components and/or display units can be at an angle to the light beam passing through the microscope optics and/or the display unit, e.g. a 45-degree angle or any other angle. Augmented and/or virtual reality components and/or display units can be parallel to the light beam passing through the microscope optics and/or the display unit. Augmented and/or virtual reality components and/or display units can be at an angle other than 90 degree or 180 degree to the light beam passing through the microscope optics and/or the display unit.

Augmented and/or virtual reality components and/or display units can be located between one or more optical elements, one or more any lens elements, one or more lens groups, one or more lenses of the microscope and/or endoscope. Microscopes and/or endoscopes can be of monocular type configuration or binocular type configuration; the latter can optionally be stereoscopic or non-stereoscopic.

When monocular microscopes and/or endoscopes are used augmented and/or virtual reality components and/or display units can be located between one or more optical elements, one or more any lens elements, one or more lens groups, one or more lenses of the light beam for the left eye and/or for the right eye. Augmented and/or virtual reality components and/or display units can be used for the left eye only, for the right eye only, or for both eyes.

When binocular microscopes and/or endoscopes (e.g. stereoscopic or non-stereoscopic) are used augmented and/or virtual reality components and/or display units can be located between one or more optical elements, one or more any lens elements, one or more lens groups, one or more lenses of the light beam for the left eye and/or of the light beam for the right eye. Augmented and/or virtual reality components and/or display units can be used for the left eye only, for the right eye only, or for both eyes.

Endoscopes

An endoscope can comprise of at least one optical lens, a light source, light transmission system, fiberoptics, image sensor, an optional eye piece, or a combination thereof. An endoscope can be used for examination and/or treatment of the gastrointestinal tract (e.g. esophagus, stomach, duodenum, small intestine, large intestine including colon, rectum); pancreas; biliary tract; lungs and bronchi; respiratory tract (e.g. nasal airways); urinary tract (e.g. bladder, urethra, urether, renal pelvis), joints (e.g. degenerative conditions, cartilage repair, cartilage damage, bone repair, bone damage, bone marrow lesions, bone marrow edema lesions, fractures, cartilage grafts, cartilage repair, instability, impingement, labral tears, ligament tears, any type of internal derangement).

It is expressly understood that the embodiments described throughout the disclosure can be applied to any endoscopic procedure, including all of the above listed anatomic areas. Endoscopes comprise "arthroscopes", i.e. endoscopes used for athroscopic procedures. The term "endoscope" can be used interchangeably with the term "arthroscope" throughout the disclosure, when the treatment is directed towards any type of joint disorder or "arthroscopic" treatments. It is expressly understood that all of the embodiments throughout the disclosure can be applied to any arthroscopic procedure, in any joint of the body, e.g. knee joint, hip joint, shoulder joint, ankle joint, elbow joint, wrist joint, temporomandibular joint etc. For example, in the knee, AR guided arthroscopy can be performed for degenerative conditions, cartilage repair, bone damage, bone marrow lesions, bone marrow edema lesions, fractures, cartilage grafts, cartilage damage, cartilage repair, ACL repair, ACL reconstruction, meniscal tears; in the hip joint, AR guided arthroscopy can be performed for degenerative conditions, cartilage repair, bone damage, bone marrow lesions, bone marrow edema lesions, fractures, cartilage grafts, cartilage damage, cartilage repair, impingement conditions, e.g. CAM and pincer type impingement, labral tears, cartilage wear; in the shoulder joint, AR guided arthroscopy can be performed for degenerative conditions, cartilage repair, bone damage, bone marrow lesions, bone marrow edema lesions, fractures, cartilage grafts, cartilage damage, cartilage repair, instability, impingement, labral tears, ligament tears, cartilage damage; in the wrist joint, AR guided arthroscopy can be performed for degenerative conditions, cartilage repair, bone damage, bone marrow lesions, bone marrow edema lesions, fractures, cartilage grafts, cartilage damage, cartilage repair, instability, impingement, labral tears, triangular fibrocartilage tears, ligament tears; in other joints, AR guided arthroscopy can be performed for degenerative conditions, cartilage repair, bone damage, bone marrow lesions, bone marrow edema lesions, fractures, cartilage grafts, cartilage damage, cartilage repair.

An endoscope can comprise a working channel, e.g. for introducing surgical instruments, for example for tissue biopsies or tissue ablation, tissue resection. An endoscope can be a rigid endoscope. An endoscope can be a flexible endoscope.

The embodiments described throughout the disclosure can be applied to any endoscopic procedure, including all of the above listed anatomic areas.

An endoscope can comprise a working channel, e.g. for introducing surgical instruments, for example for tissue biopsies or tissue ablation, tissue resection. An endoscope can be a rigid endoscope. An endoscope can be a flexible endoscope.

An endoscope can comprise one or more imaging sensors for generating high resolution video. The imaging sensors can have 1 k, 2 k, 4 k, 8 k, 16 k or higher resolution. An endoscope can have a round field of view. An endoscope can have a rectangular field of view. For example, a digital endoscope with an imaging sensor can have a rectangular field of view.

In addition to any of the other tracking techniques described throughout the disclosure, endoscope tracking can also be performed using a sensor-based electromagnetic system. The system can comprise miniaturized sub-millimeter coil sensors embedded in the endoscope and/or endoscope tip or other device (e.g. a guidewire, sheath). The coils can generate electrical currents once placed within an alternating electromagnetic field generated by a transmitter unit and can be tracked in real time.

The tracking system can be co-registered with fluoroscopy imaging, for example by installing the transmitter unit within the fluoroscopy detector of the x-ray imaging system. Using this or similar hardware setups, fluoroscopic imaging and electromagnetic sensor tracking can be pre-aligned and auto-registered. This can allow for 3-dimensional real-time tracking of a sensor-equipped endoscope and/or endoscope tip or other device (e.g. a guidewire, sheath) and projection of the endoscope and/or endoscope tip onto a 3D model of the anatomy derived from preoperative or intra-operative images by one or more ARDDs, optionally compensated for organ motion during respiration and patient movement. A reference sensor attached to the patient's body can also provide information about the spatial relationship between the patient and the tracking field.

Endoscope or device tracking methods that work independently from the x-ray fluoroscopy imaging, e.g. MRI-based tracking or electromagnetic tracking, do not require continuous updates of the x-ray image. Information about 3D position and orientation of the endoscope and/or endoscope tip can be available continuously and in real-time. It can be projected continuously and in real-time onto pre-operative and/or intra-operative images and/or 3D models created from pre-operative and/or intra-operative images, e.g. graphical representations including one or more virtual endoscope and/or endoscope. In some embodiments, radiation exposure to the patient and the physician can be greatly reduced.

An endoscope can be non-stereoscopic. An endoscope can be stereoscopic.

Figure 25A:
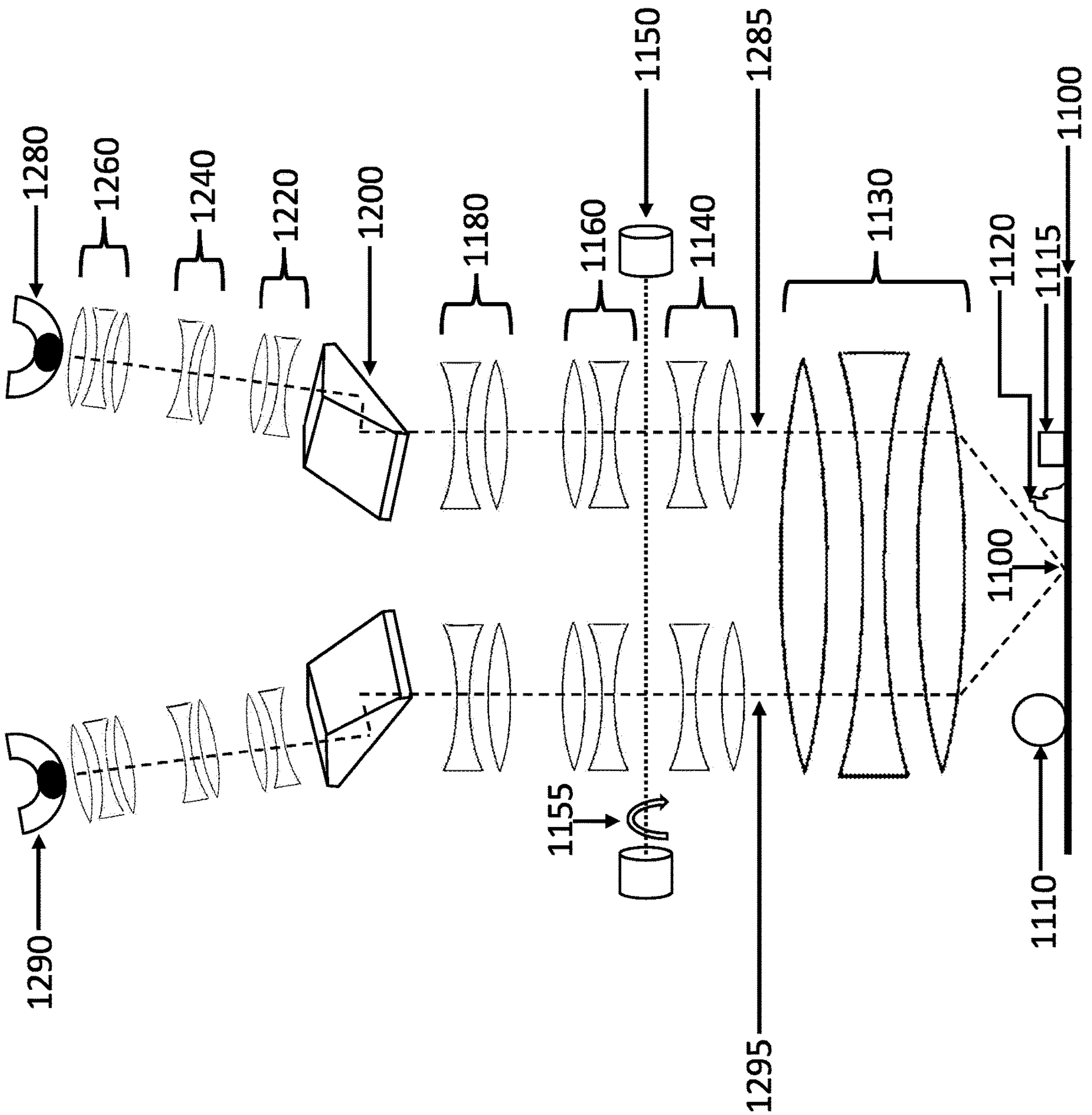
FIGS. 25A-25R provide illustrative, non-limiting examples of one or more microscope for use with ARDDs and augmented reality display units according to some embodiments of the present disclosure.
Figure 25B:
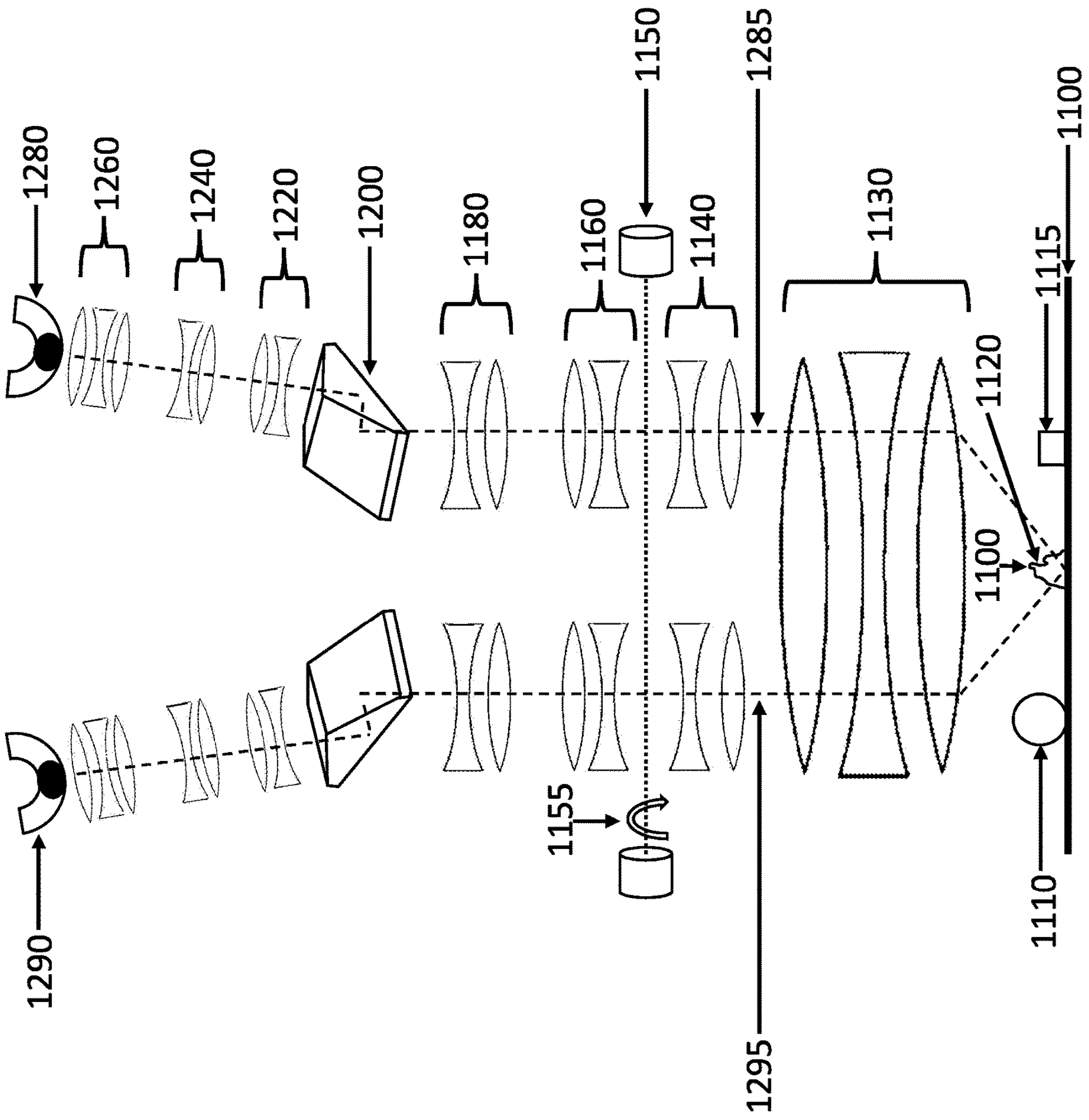
Figure 25C:
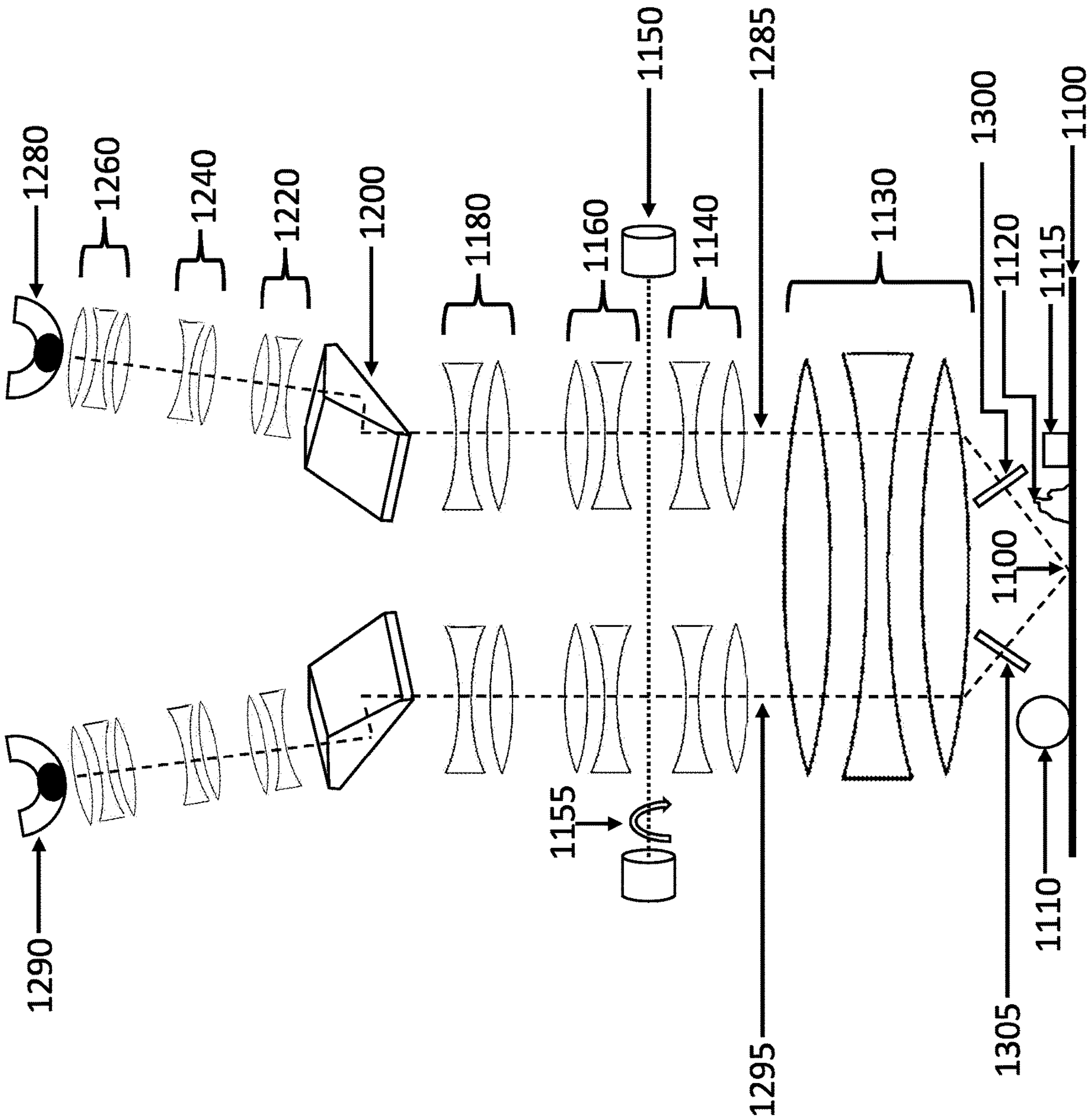
Figure 25D:
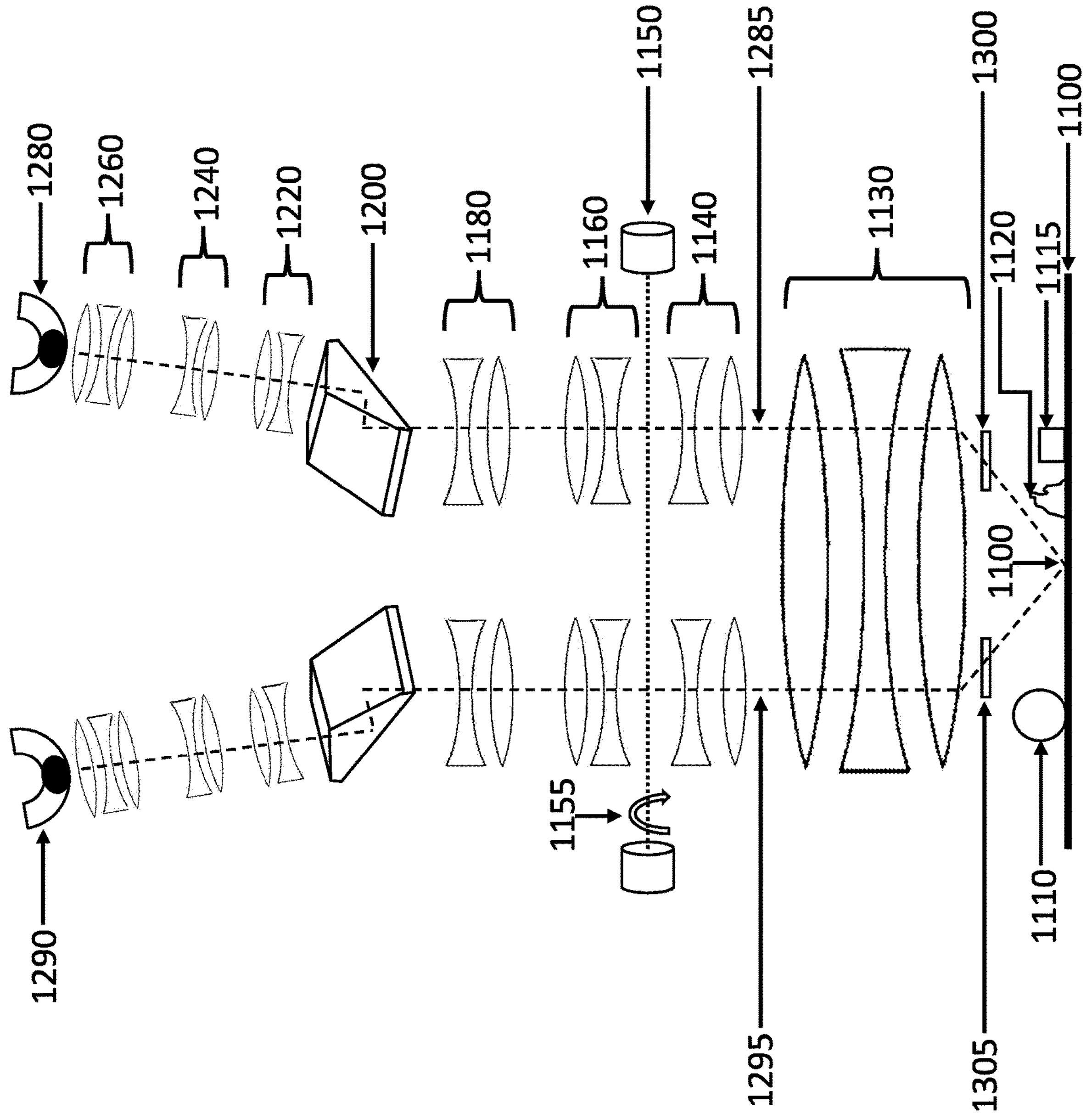
Figure 25E:
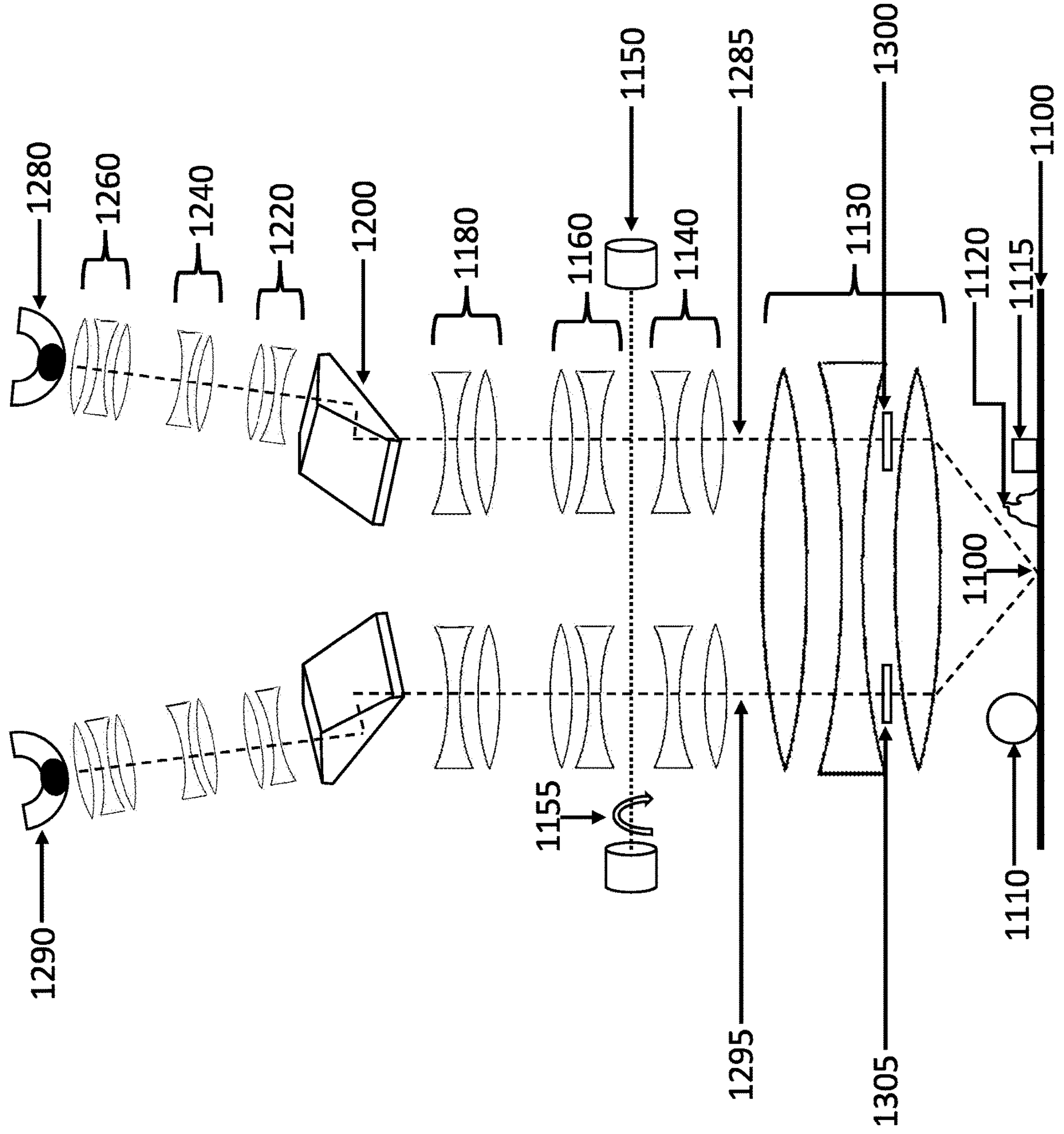
Figure 25F:
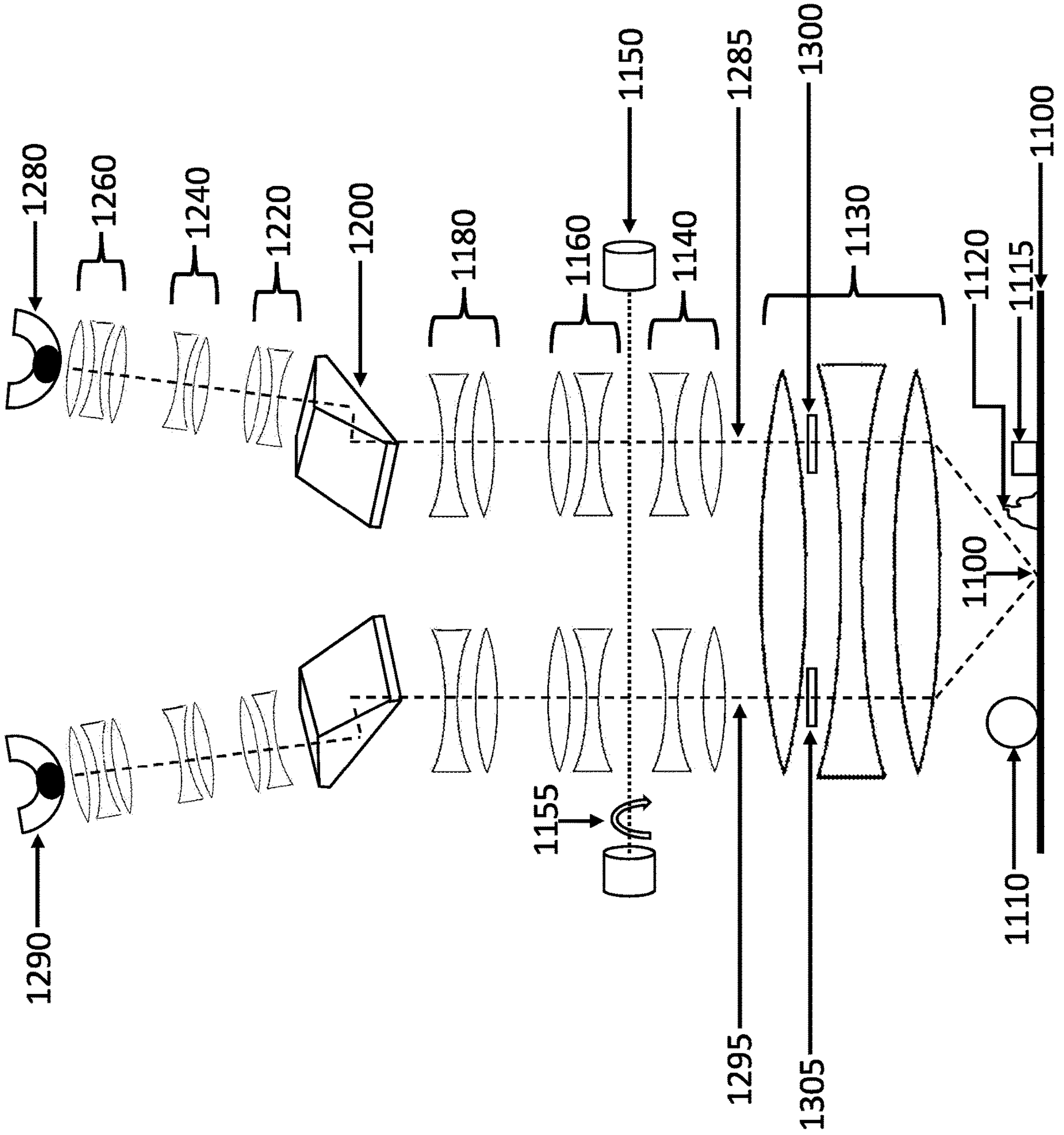
Figure 25G:
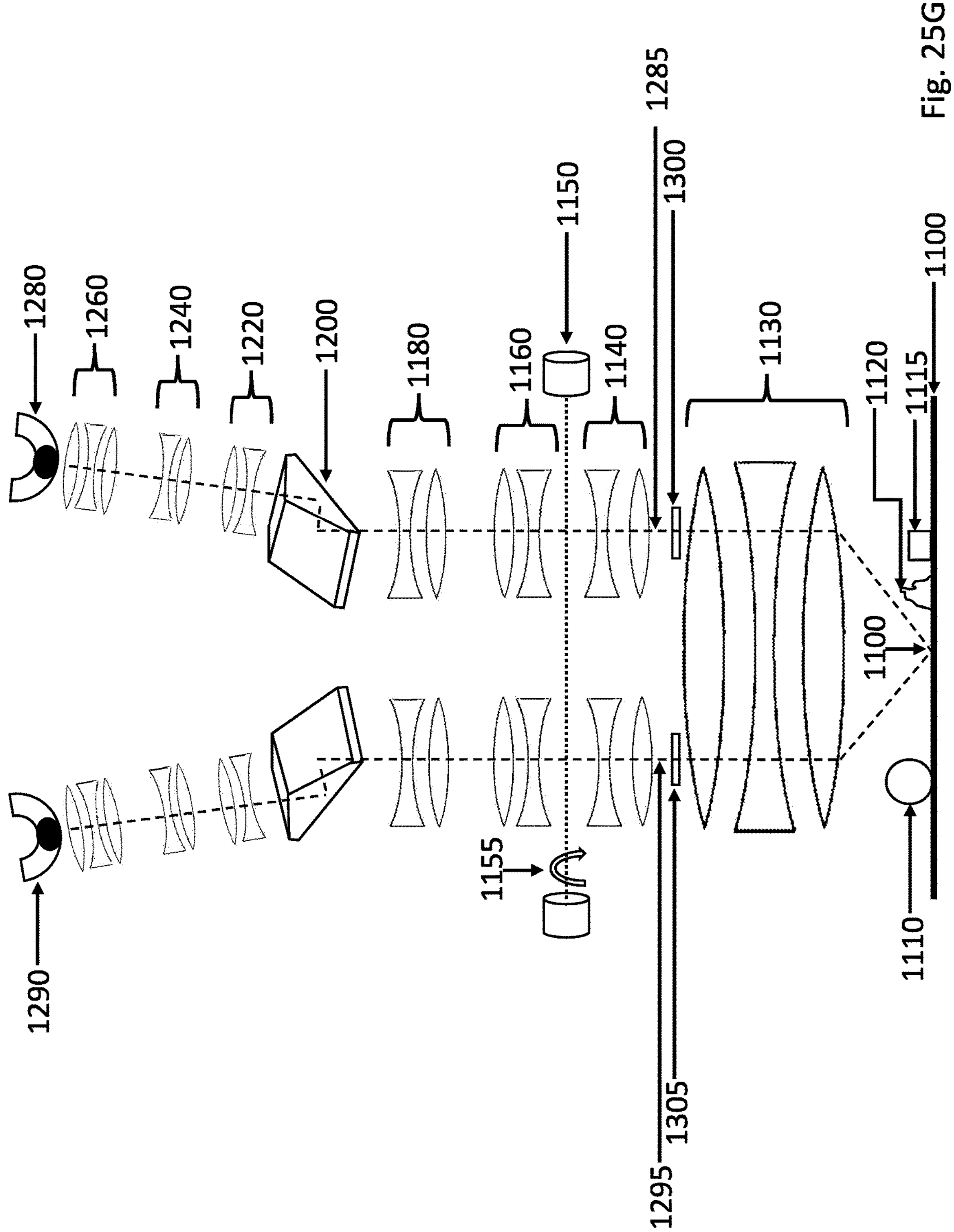
Figure 25H:
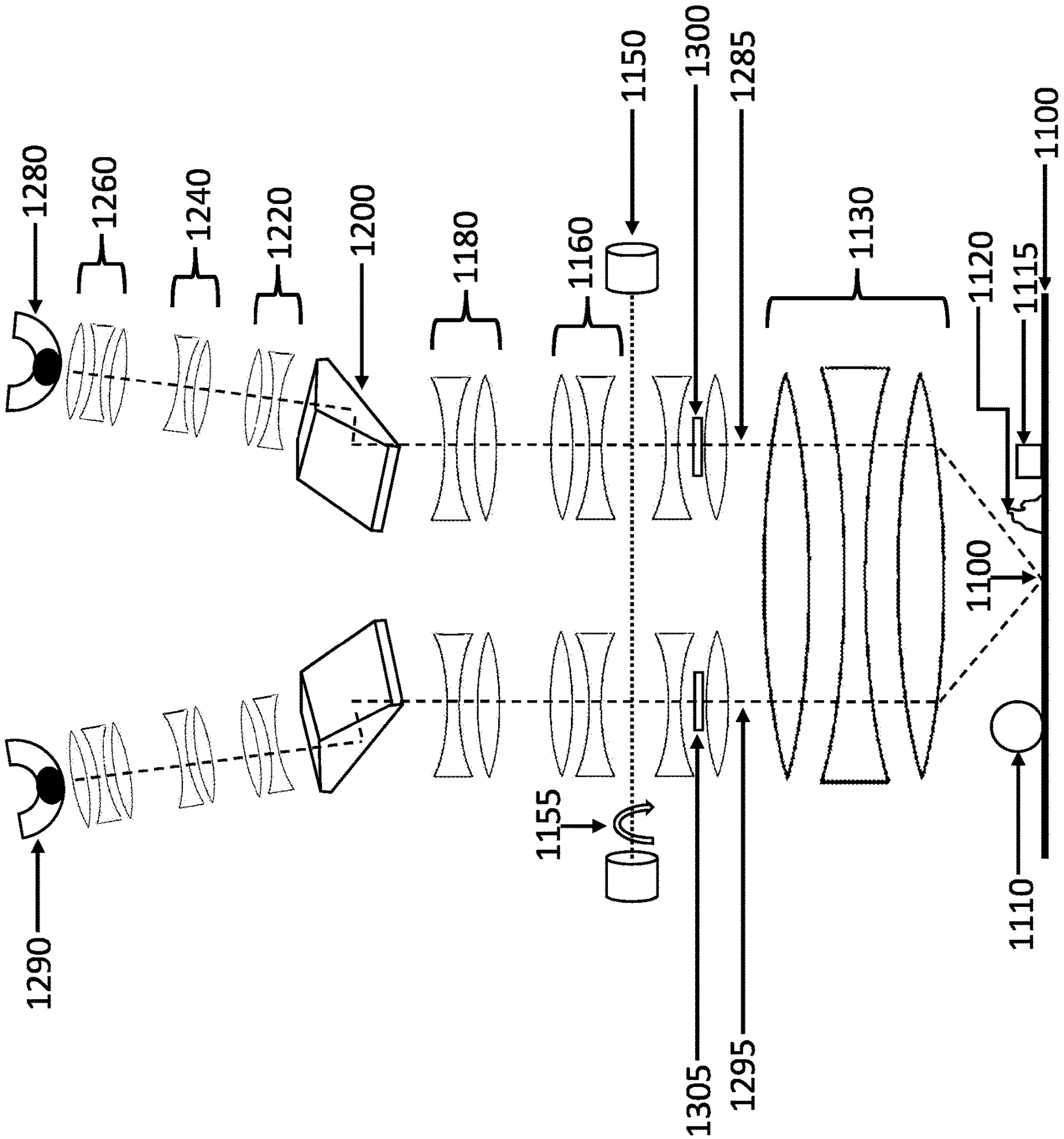
Figure 25I:
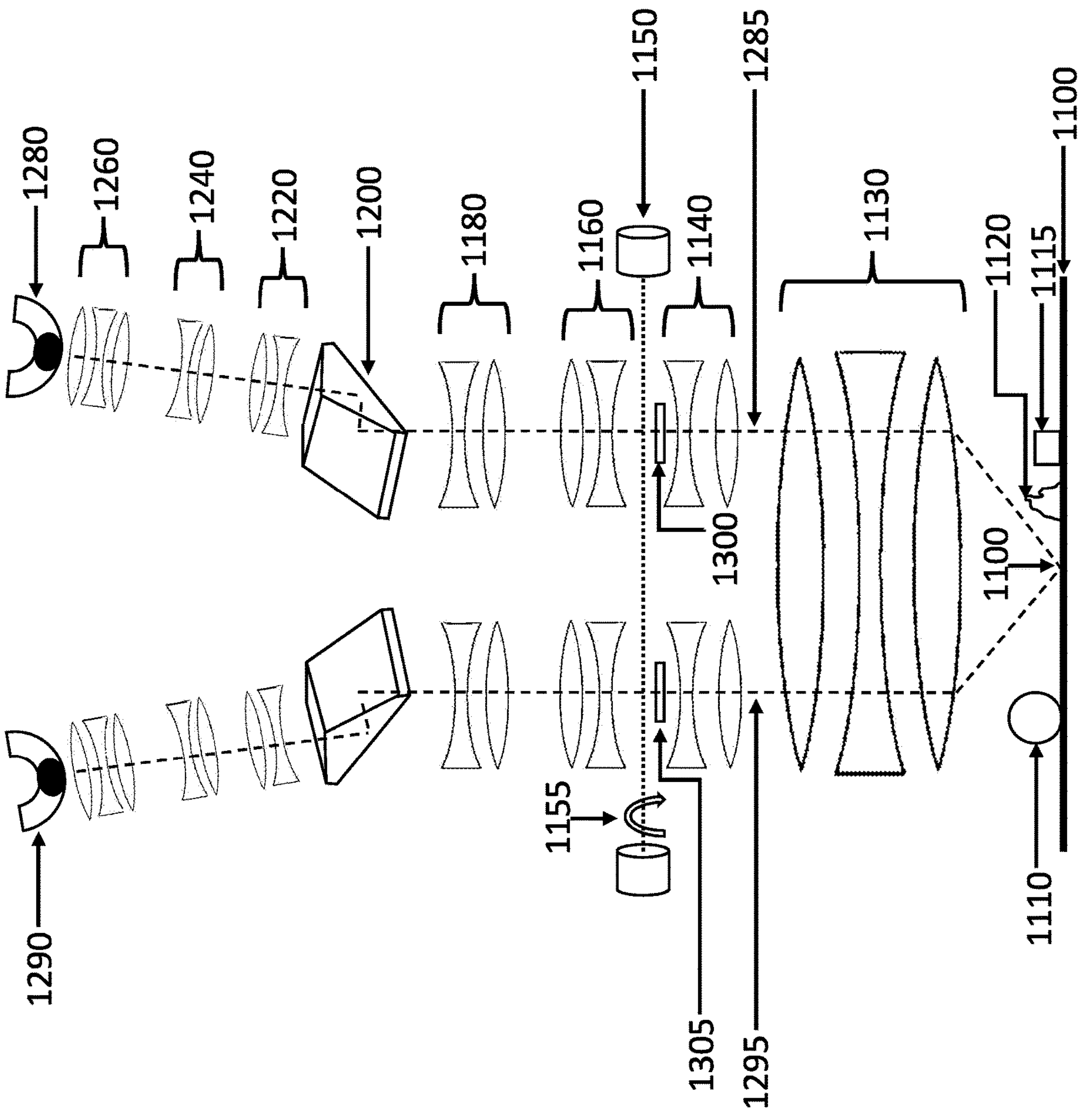
Figure 25J:
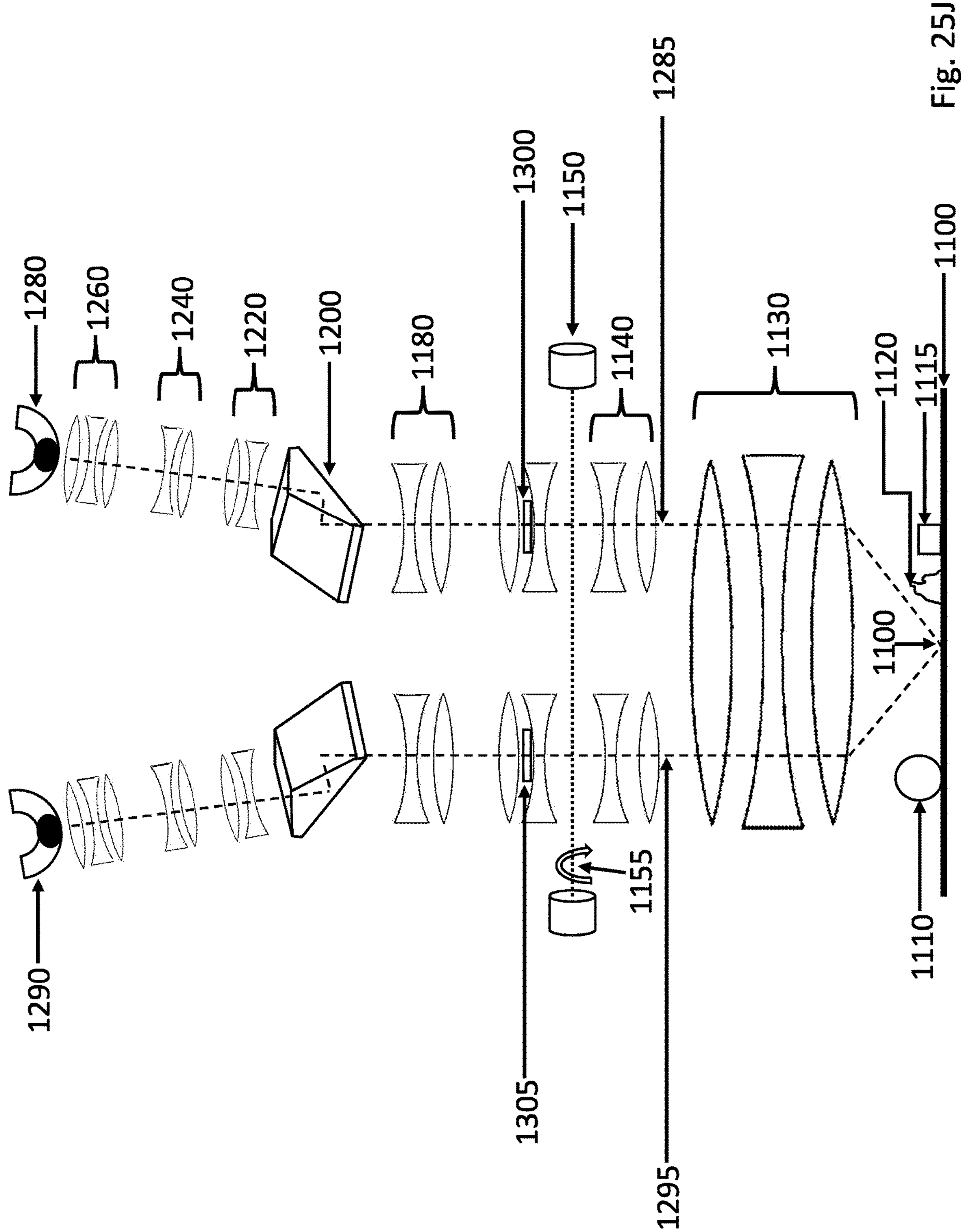
Figure 25K:
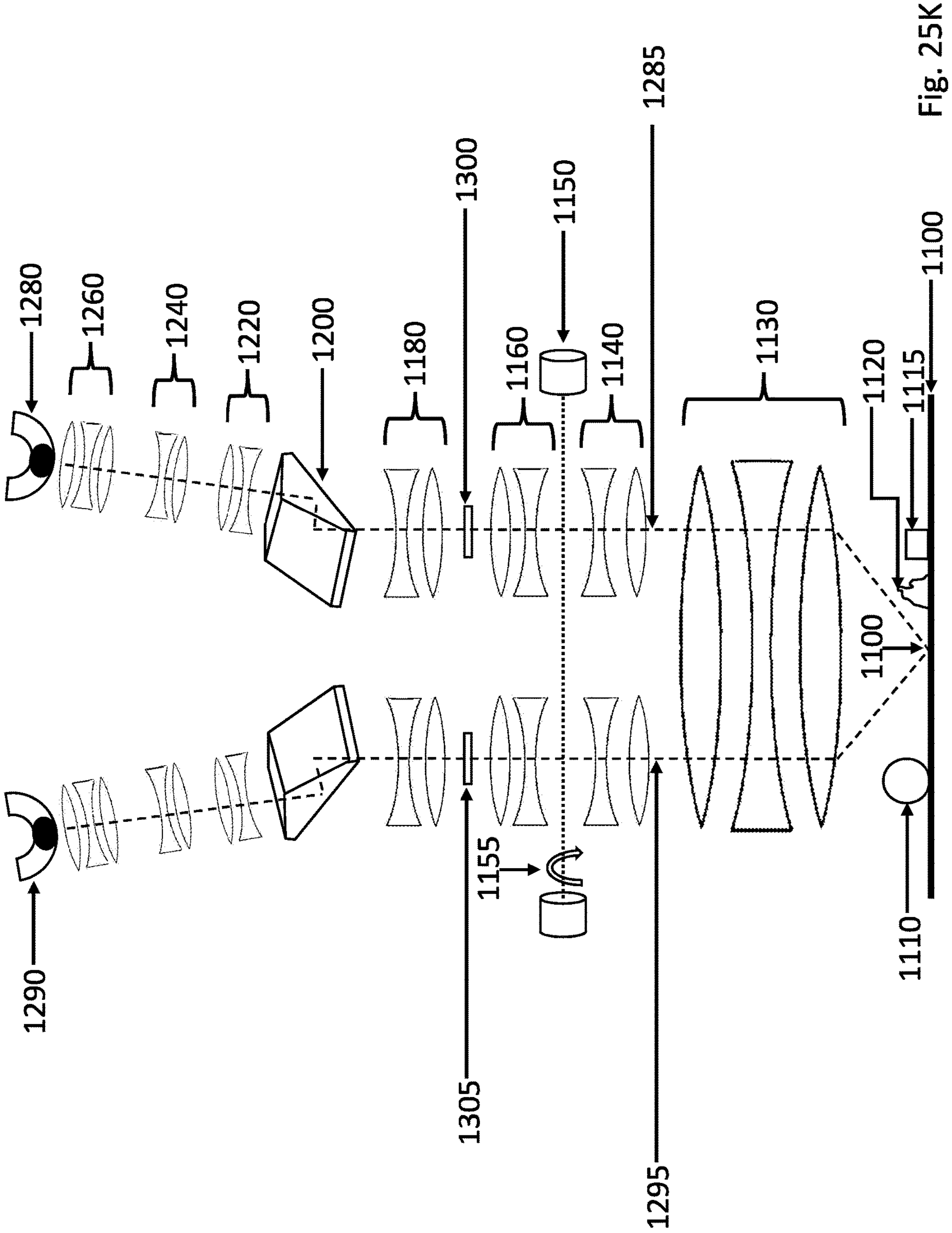
Figure 25L:
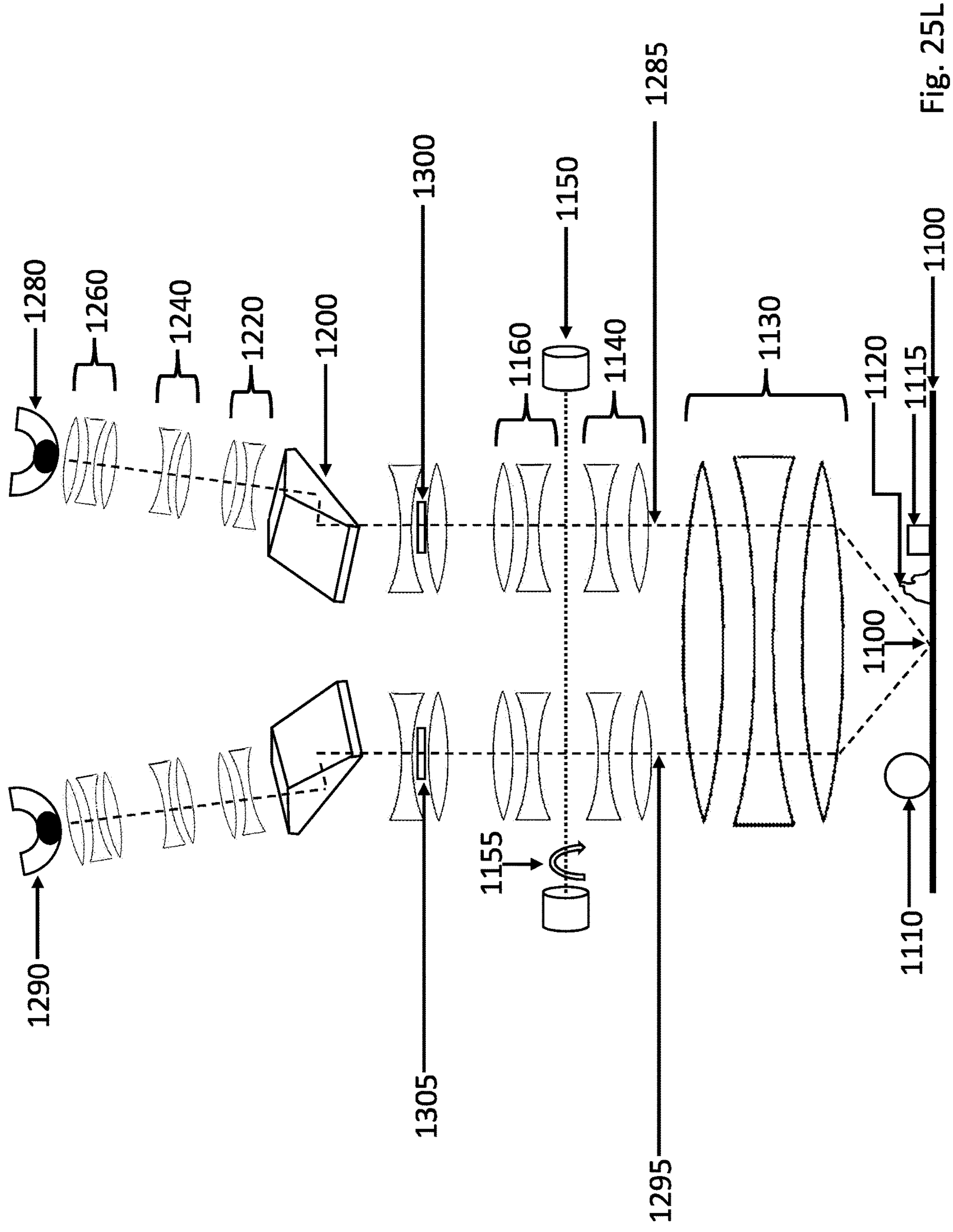
Figure 25M:
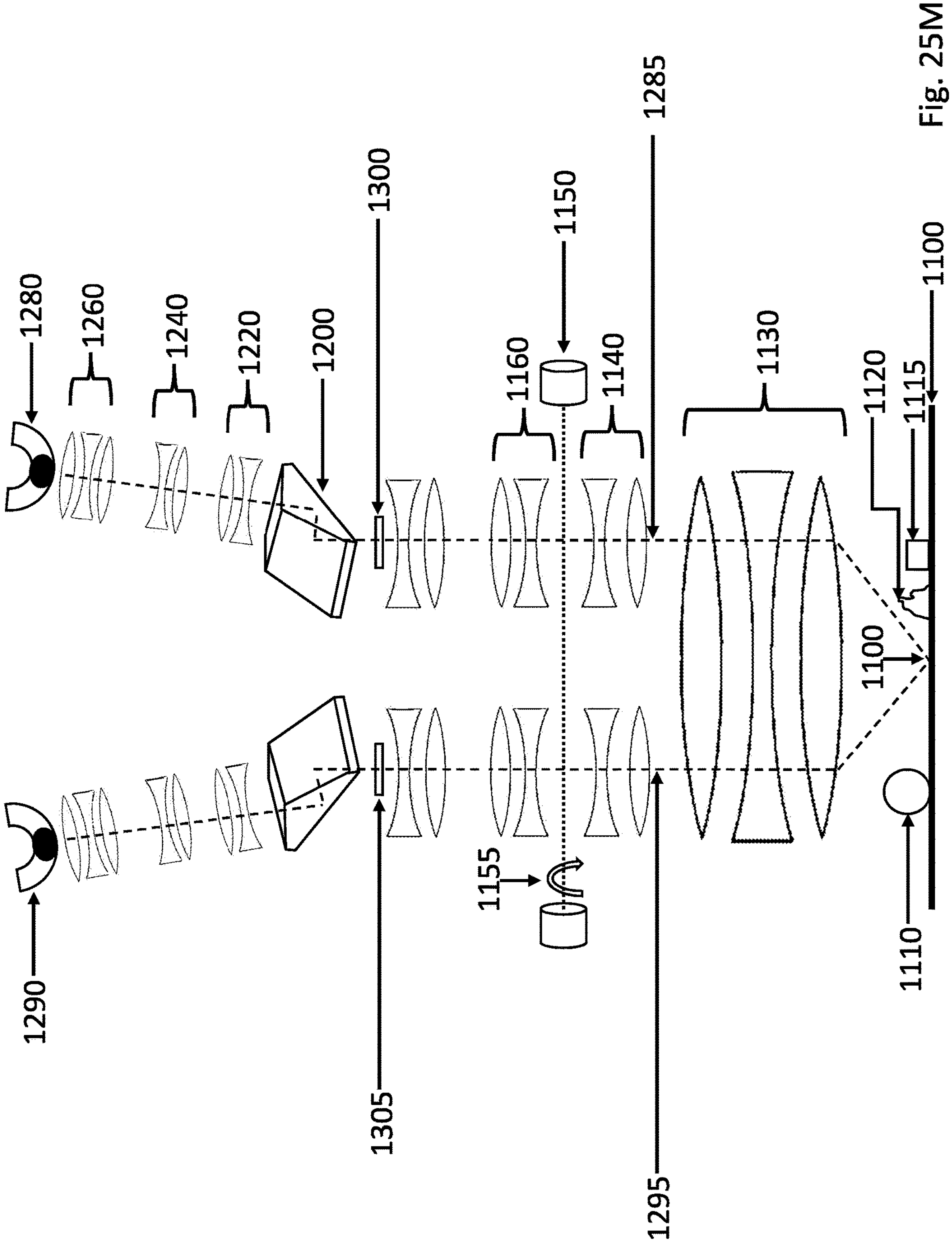
Figure 25N:
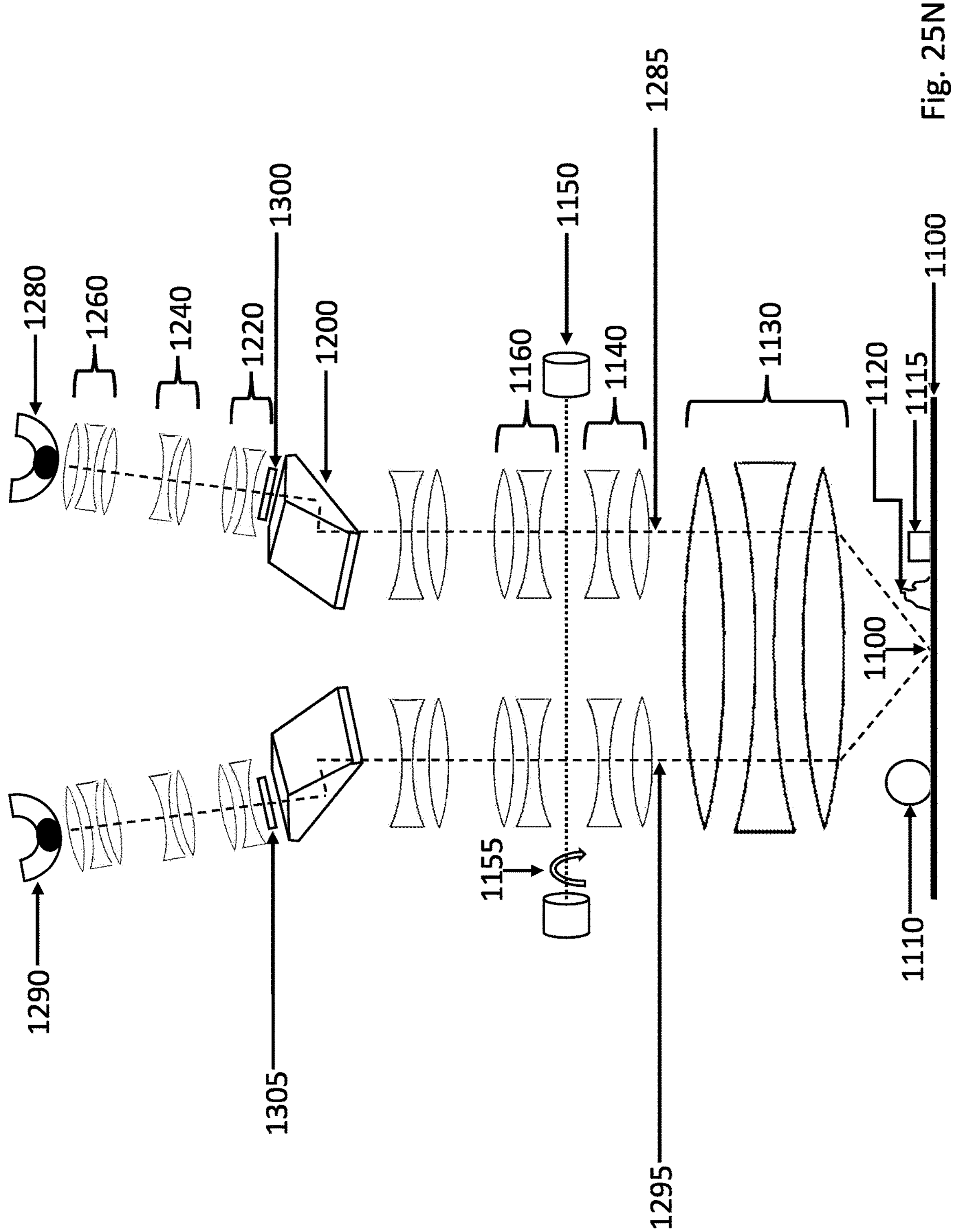
Figure 25O:
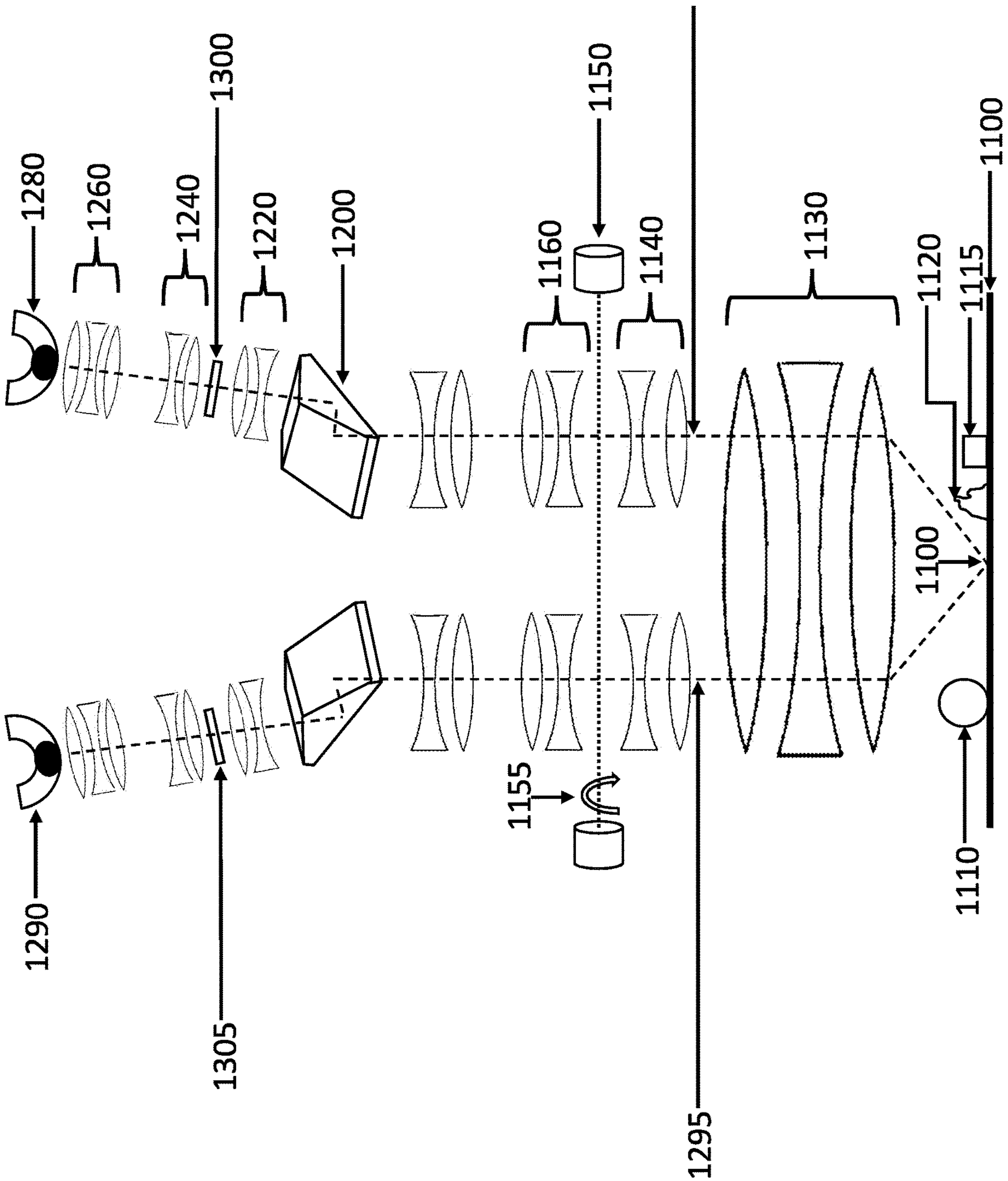
Figure 25P:
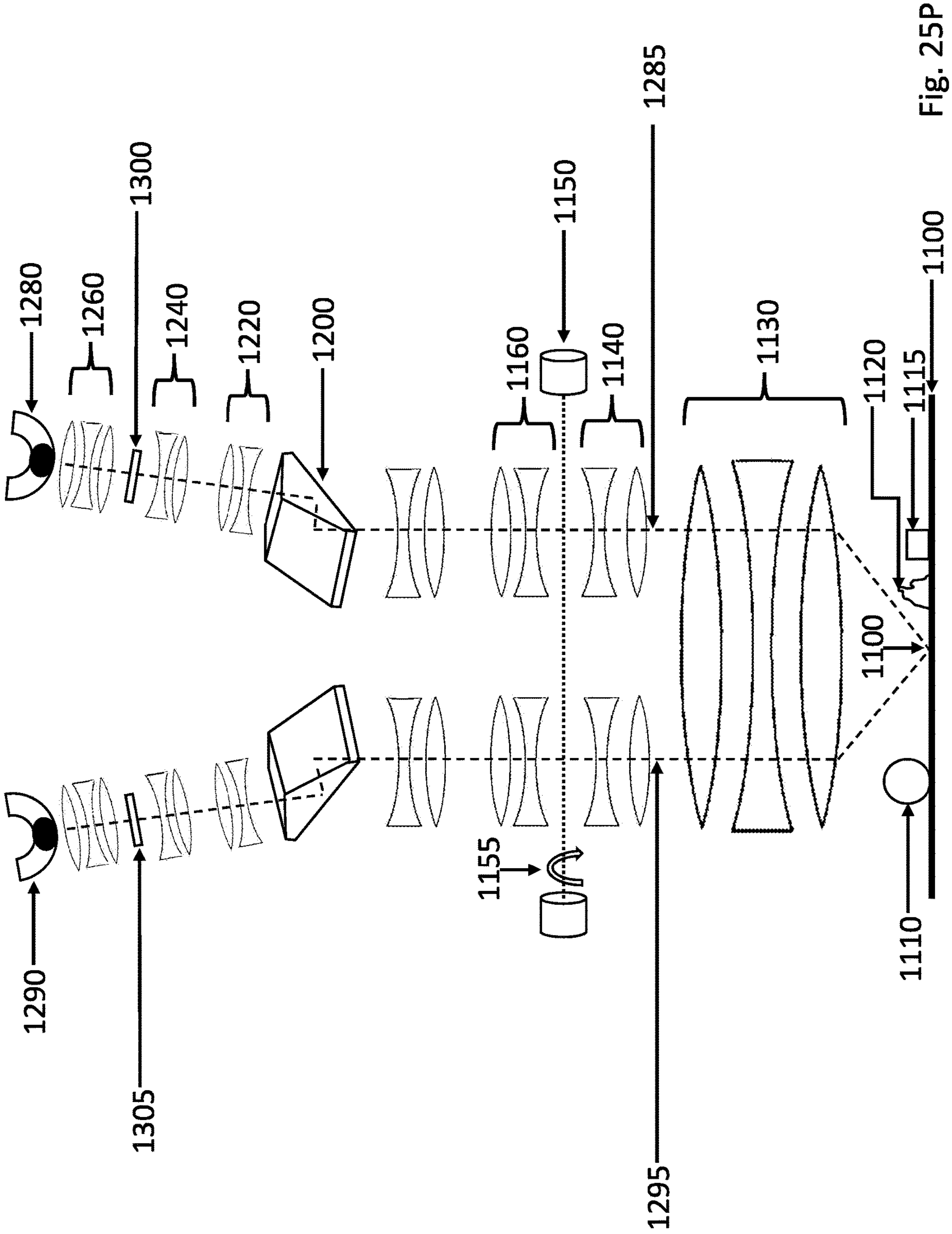

Microscope or Endoscope Focal Planes Vs. Focal Planes of Virtual Displays by ARRD FIGS. 25A-25R provide non-limiting representative examples how an augmented reality system for display of one or more virtual displays, for example of one or more virtual surgical plans, e.g. virtual surgical steps, virtual surgical techniques, virtual surgical guides, e.g. a virtual point, a virtual axis, a virtual plane (e.g. a virtual cut plane or resection plane), a virtual target tissue, virtual surgical tools, virtual surgical instruments, virtual surgical devices, including virtual surgical implants, can be integrated in a microscope, e.g. a stereo microscope, and/or an endoscope, e.g. a stereo endoscope.

A surgeon can access a surgical site with a microscope and/or an endoscope. In accessing the surgical site, the surgeon will expose a tissue or tissue plane. Optionally, a portal, an access portal, a tube, a retractor, or a combination thereof can be used for creating an access or exposing the tissue or tissue plane or for maintaining the access or exposure. A target tissue, e.g. a lesion, a tumor, a pathologic tissue, a herniated disc etc., can be located at a different location and/or coordinates than the accessed or exposed tissue or tissue plane visible by the microscope or endoscope; thus, the target tissue can be hidden from view by the tissue or tissue plane or additional interposed tissue. In order to direct the microscope and/or endoscope and any surgical instruments to the target tissue, it can be desirable to display the target tissue by an augmented reality display device (ARRD), which can be separate from the microscope or endoscope or, optionally, integrated with or attached to portions or components of the microscope or endoscope system. The microscope or endoscope will typically be focused on the accessed or exposed tissue or tissue plane, which means that the focal plane or focal points of the microscope or endoscope will be centered on the exposed or accessed tissue or tissue plane, with coordinates on the exposed or accessed tissue or tissue plane. If the ARRD display has a different focal plane or focal points, e.g. focused on the target tissue with focal plane or focal point coordinates on the target tissue, the virtual display of the augmented reality display unit will be blurred when the surgeon views the exposed or accessed tissue through the microscope or endoscope.

For example, in a spinal procedure, an exposure can comprise resection of a ligamentum flavum and/or a spinal lamina. The microscope or endoscope can be focused on the ligamentum flavum and the lamina during the resection; an underlying tumor or a disc herniation can be the target tissue of the operation and can be deeper seated, e.g. in this example further anterior and away from the microscope or endoscope focal plane (with coordinates different from the microscope or endoscope focal plane). If a virtual display by an ARDD has a focal plane centered through the target tissue, a tumor or disc herniation, the focal plane of the ARRD is different from, with different coordinates, the focal plane of the microscope or endoscope centered/focused on the ligamentum flavum and lamina. When a surgeon looks through the microscope or endoscope the ligamentum flavum and lamina can appear sharp, in focus, while the deeper seated target tissue (tumor or disc herniation) with a different focal plane of the virtual display will appear blurred. The blurred appearance of the virtual display in this example can limit the usefulness of the virtual display in directing the microscope or endoscope towards the target tissue.

In some non-limiting embodiments, the focal plane of a virtual display by an ARDD can be adjusted to be the same or similar of the focal plane of a microscope or an endoscope. For example, the focal plane, including the coordinates of the focal plane or coordinates of one or more points on the focal plane or coordinates of one or more tissue surface(s) on or within the focal plane of the microscope or endoscope (optionally including within the depth of field of the microscope or endoscope), can be digitally transferred from a computer processor of a microscope or endoscope to a computer processor of an augmented reality display device.

The computer processor of the microscope or endoscope and the computer processor of the augmented reality display device can be the same or different. The computer processor of the augmented reality display device can set or adjust the focal plane of the virtual display to be the same or similar as the focal plane of the microscope or endoscope. For example, the focal plane of the virtual display can comprise one or more coordinates, e.g. of one or more points of the virtual display, or coordinates of one or more surfaces of the virtual display, that are the same or similar to the coordinates of the focal plane or coordinates of points or surfaces on or within the focal plane (and optionally the depth of field) of the microscope or endoscope.

A surgeon or operator can change or adjust the focal plane of the microscope or endoscope, for example using a mechanical mechanism to move one or more lens groups of the microscope or endoscope, or using an electric motor or electromagnetic mechanism to move one or more lens groups of the microscope or endoscope, to view different exposed tissues or tissue planes at different depths. As the surgeon or user changes or the focal plane of the microscope or endoscope, the focal plane data, including coordinate data, can be electronically transferred, e.g. from a computer processor of the microscope or endoscope to a computer processor of the augmented reality display device, and the computer processor of the augmented reality display device can substantially match or match the focal plane of the virtual display to the focal plane of the microscope or endoscope. The changing or adjusting of the focal plane of the virtual display to the focal plane of the microscope or endoscope can be intermittent, e.g. at defined time intervals, or continuous. The change or adjusting of the focal plane of the focal plane of the virtual display can be in real-time to match changes in the focal plane of the microscope or endoscope.

In a spinal procedure, an exposure can comprise resection of a ligamentum flavum and/or a spinal lamina. The microscope or endoscope can be focused on the ligamentum flavum and the lamina during the resection; an underlying tumor or a disc herniation can be the target tissue of the operation and can be deeper seated, e.g. in this example further anterior and away from the microscope or endoscope focal plane (with coordinates different from the microscope or endoscope focal plane). In this example, a virtual display by an ARDD can have a focal plane centered not through the target tissue, a tumor or disc herniation, but the focal plane of the ARRD can be adjusted to have the same or similar coordinates as the focal plane of the microscope or endoscope centered/focused on the ligamentum flavum and lamina.

When a surgeon looks through the microscope or endoscope the ligamentum flavum and lamina can appear sharp, in focus, and the target tissue (tumor or disc herniation), while anatomically deeper seated, can also appear sharp since the focal plane of the virtual display by the ARDD has been set to match the focal plane of the microscope or endoscope, thereby facilitating targeting of the target tissue through the microscope or endoscope, including by advancing surgical tools or instruments towards the sharply displayed target tissue. While the focal plane or focal point(s) of the virtual display of the target tissue can be adjusted to be the same or similar to the focal plane of the microscope or endoscope, other aspects of the virtual display, e.g. shading, can remain specific to the coordinates of the target tissue and, with that, different from the spinal lamina or ligamentum flavum in this example, due to their different coordinates.

In some embodiments, an endoscope can have a fixed focal plane or focal point. In some embodiments, an endoscope can have a fixed depth of field.

In some embodiments, the zoom factor or magnification of a virtual display can be adjusted to be the same or similar to the zoom factor or magnification of a microscope or an endoscope. For example, the zoom factor or magnification of the microscope or endoscope can be digitally or electronically transferred from a computer processor of a microscope or endoscope to a computer processor of an augmented reality display device. The computer processor of the microscope or endoscope and the computer processor of the augmented reality display device can be the same or different. The computer processor of the augmented reality display device can set or adjust the zoom factor or magnification of the virtual display to be the same or similar to the zoom factor or magnification of the microscope or endoscope. For example, the distance between one or more points on a tissue surface seen through the microscope or endoscope can be the same or similar to the distance between one or more corresponding points of a virtual display generated by an augmented reality display device, by matching the zoom factor or magnification of the augmented reality display device to the zoom factor or magnification of the microscope or endoscope.

In any of the embodiments throughout the disclosure, a virtual structure, virtual object, virtual instrument, virtual implant (e.g. a virtual implant component), or a virtual device can be a 2D or 3D representation, e.g. a graphical 2D or 3D representation. In any of the embodiments throughout the disclosure, a virtual structure, virtual object, virtual instrument, virtual implant (e.g. a virtual implant component), or a virtual device can be a 2D or 3D representation of a tracked a physical structure, physical object, physical instrument, physical implant (e.g. a physical implant component) or a physical device.

A tissue plane 1100 can optionally be exposed and/or accessed using a surgical incision and/or exploration, e.g. through a surgical portal or access system, for example for minimally invasive spine or brain surgery, or any other surgery, e.g. endoscopic abdominal or retroperitoneal surgery, endoscopic/arthroscopic joint surgery. The tissue plane 1100 can be, for example, one or more gyri, a brain tissue, or a pedicle or a facet joint of a spine, a disk, a lamina, a tissue earmarked for resection/decompression, or a cartilage, a subchondral bone, an intercondylar notch, a ligament, an organ, a solid tissue, a tumor, or any other tissue. Optionally, one or more markers 1110 and/or 1115 can be attached to the tissue, for example using mechanical means such as a pin or screw or a tissue glue, e.g. fibrin glue, or other means known in the art. The one or more markers 1110 and/or 1115 can include or comprise one or more IMUs, optical markers (e.g. with geometric patterns, e.g. 2D or 3D), navigation markers including infrared markers, retroreflective markers, RF markers, active markers, e.g. an LED or RF marker, passive markers, including combinations thereof. The field of view can include one or more anatomic structures 1120. The one or more anatomic structures 1120 can be in the field of view but not located in the focal plane or focal point 1100 (see FIG. 25A). The one or more anatomic structures 1120 can be in the field of view and located in or near the focal plane or focal point 1100 (see FIG. 25A).

The microscope and/or endoscope can include an objective or first lens group 1130. The microscope and/or endoscope can optionally include a light beam 1295 for the left eye 1290 and a light beam 1285 for the right eye 1280. The microscope and/or endoscope can optionally include only a single light beam for the left eye 1290 or for the right eye 1280. The microscope and/or endoscope can include one or more moveable or rotating objectives or lens groups 1140 and/or 1160. The rotating 1155 or moving can be achieved using mechanical, e.g. knobs 1150 or buttons, or electrical means. At least one of the lens groups 1140 and/or 1160 can be stationary; at least one of the lens groups 1140 and/or 1160 can be rotatable or moveable; in some embodiments, both lens groups 1140 and 1160 can be rotatable or moveable. Multiple rotatable or moveable lens groups, e.g. 1140 and 1160, can be used, for example for focus control and/or zoom control. The microscope and/or endoscope can be of fixed magnification type. The microscope and/or endoscope can also optionally provide zoom function and/or magnification/minification function.

One or more internal objectives or lens groups 1180 and/or prisms 1200 can optionally be used. One or more relay lenses 1220, relay lens groups 1220, reticles or intermediate lenses or lens groups 1240, and/or one or more eye pieces and related lenses and/or lens groups 1260 can be used for guiding and/or centering the beam and/or light path into the left eye and pupil 1290 and/or the right eye and pupil 1280.

One or more augmented and/or virtual reality components and/or display units 1300 and 1305 can be used for the right eye light beam or path 1285 and/or the left eye light beam or path 1295. The one or more augmented and/or virtual reality components and/or display units 1300 and 1305 can be perpendicular to, parallel to or at an angle other than 90 or 180 degrees, e.g. 45 degrees or any other degree, relative to the right eye light beam or path 1285 and/or the left eye light beam or path 1295. Augmented and/or virtual reality components and/or display units can comprise, for example, cathode ray tubes, liquid crystal displays, liquid crystal on silicone, and/or organic light emitting diodes (OLED's); they can include mirrors, curved mirrors and/or waveguides; they can include combiners. FIG. 25C shows a non-limiting embodiment in which the one or more augmented and/or virtual reality components and/or display units 1300 and 1305 are perpendicular to the right eye light beam or path 1285 and/or the left eye light beam or path 1295. FIG. 25D is a non-limiting example of an embodiment in which the one or more augmented and/or virtual reality components and/or display units 1300 and 1305 are at an angle other than 90 degrees or 180 degrees to the right eye light beam or path 1285 and/or the left eye light beam or path 1295. The angle can be chosen and/or optimized based on the characteristics of the augmented reality system, the characteristics of the optical system(s) including of the microscope and/or endoscope, and/or the characteristics of the surgical site and/or the characteristics of the surgeon's eye sight.

In FIG. 25C and FIG. 25D, the one or more augmented and/or virtual reality components and/or display units 1300 and 1305 are positioned in front of the first lens group 1130. In some embodiments, the one or more augmented and/or virtual reality components and/or display units 1300 and 1305 can be positioned between lenses or lens elements of the first lens group 1130 (see FIG. 25E and FIG. 25F, for example). In FIG. 25G, the one or more augmented and/or virtual reality components and/or display units 1300 and 1305 are positioned in front of one or more moveable or rotatable lens units 1140.

Figure 25Q:
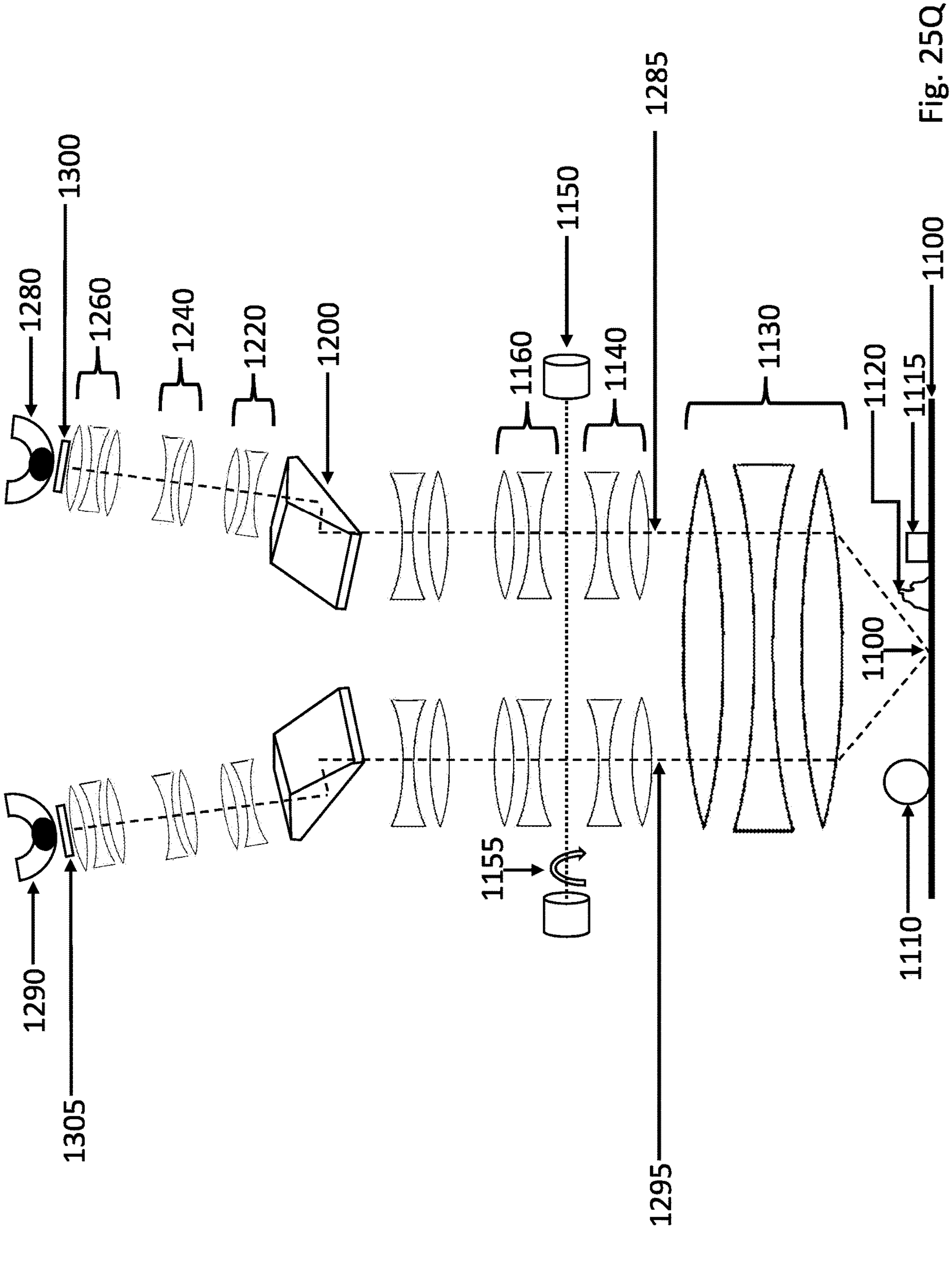
Figure 25R:
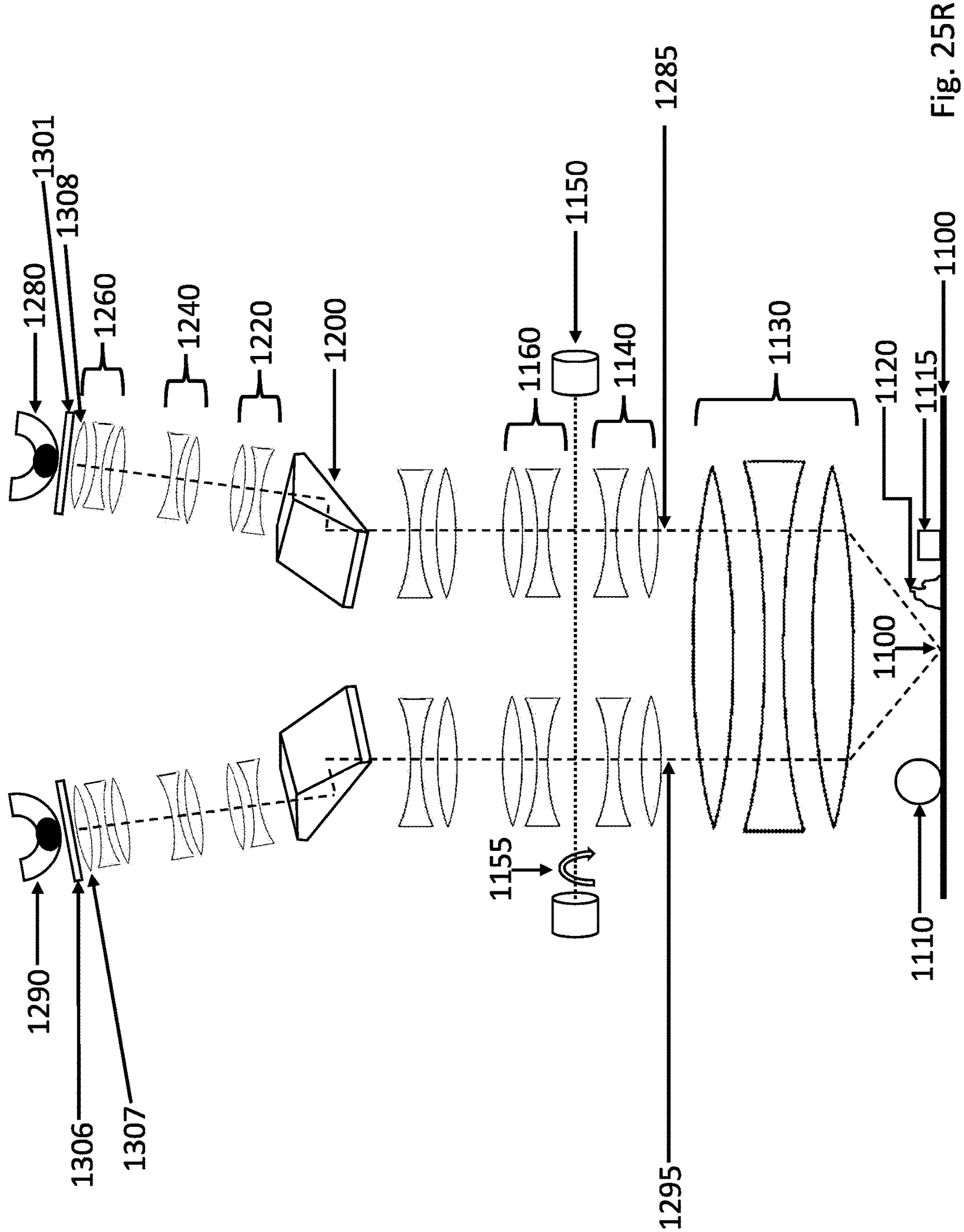

As shown in FIGS. 25C-25Q, the one or more augmented and/or virtual reality components and/or display units 1300 and/or 1305 can be positioned at multiple different locations within the right eye light beam or path 1285 and/or the left eye light beam or path 1295, e.g. in front of or between lenses and/or lens groups 1160, 1180, in front of prism 1200, in front of or between lenses and/or lens groups 1220, 1240, 1260, and also at the exit, after the lens group of the eye piece 1260 (see, for example, FIG. 25Q).

In some embodiments, the augmented and/or virtual reality display components and/or display units 1300, 1305 can have the same or a smaller field of view than the lens(es), optical component(s), and/or optical unit(s) 1130, 1140, 1160, 1180, 1200, 1220, 1240, 1260 of the microscope and/or endoscope (see, for example, FIGS. 25C-25Q).

In some embodiments, the augmented and/or virtual reality display components and/or display units 1301, 1306 can have a wider field of view than the lens(es) 1307, 1308, optical component(s), and/or optical unit(s) of the microscope and/or endoscope (FIG. 25R). In some embodiments, the augmented and/or virtual reality display components and/or display units 1301, 1306 can optionally be at the end of the optical path of the microscope and/or endoscope, facing, for example, the left eye 1290 and/or the right eye 1280. This can, for example, be helpful when a field of view is desired for the augmented and/or virtual reality display components and/or display units 1301, 1306 that is wider and/or less wide and/or the same than the field of view of the microscope and/or endoscope.

In some embodiments, the field of view of the augmented and/or virtual reality display components and/or display units 1301, 1306 and/or the microscope and/or endoscope can be round, ellipsoid, rectangular, square, and/or any other shape; any combinations thereof are possible, e.g. round with square, round with rectangular, small rectangular vs. large rectangular for augmented and/or virtual reality display components and/or display units 1301, 1306 and/or microscope and/or endoscope, or vice versa.

In some embodiments, the magnification of the display of the virtual data can be adjusted based on the magnification of the microscope and/or endoscope, e.g. as the microscope and/or endoscope magnification is increased or decreased the magnification of the display of the virtual data can be increased or decreased correspondingly, e.g. using the same magnification factor or using a different scale, e.g. 1:1.2, 1:1.5, 1:2, 1:3 of change in microscope/endoscope magnification to change in magnification of virtual data or vice versa.

In some embodiments, a stereoscopic display of the virtual data can be adjusted based on the interpupillary distance used in the microscope and/or for the microscope and/or the interpupillary distance of the surgeon user. For example, an interpupillary distance of a stereoscopic display can be adjusted so that the distance of the center of a left eye display unit and a right eye display unit or corresponding points of a left eye display unit and a right eye display unit is substantially the same as the interpupillary distance used for the eye pieces (or for lens groups of the eye pieces) of the microscope or the microscope and/or substantially the same as the interpupillary distance of the surgeon user. In this manner, a similar convergence can be achieved for viewing virtual data and/or tissue planes seen through the microscope.

In some embodiments, an interpupillary distance of a stereoscopic display can be adjusted so that the distance of the center of a left eye display unit and a right eye display unit or corresponding points of a left eye display unit and a right eye display unit are different from the interpupillary distance used for the eye pieces (or for lens groups of the eye pieces) of the microscope or the microscope and/or different from the interpupillary distance of the surgeon user. The difference can be, for example, 1 mm, 2 mm, 3 mm, 4 mm, 5 mm, 6 mm, 7 mm, 8 mm, 9 mm, 10 mm, 12 mm, 15 mm, or any other value. The difference can be adjusted to induce a different convergence for viewing virtual data and/or tissue planes seen through the microscope. Different stereoscopic display adjustments can be performed for a first and a second user, for example if they have different interpupillary distances.

In some embodiments, the focal plane of the display of the virtual data can be adjusted and/or can be matched to the tissue plane of interest, for example using the focus information and/or focus distance for a given tissue plane measured/obtained through the microscope and/or endoscope and/or the focus information and/or focus distance for a given tissue plane measured/obtained through the registration system and coordinate system.

Figure 26A:
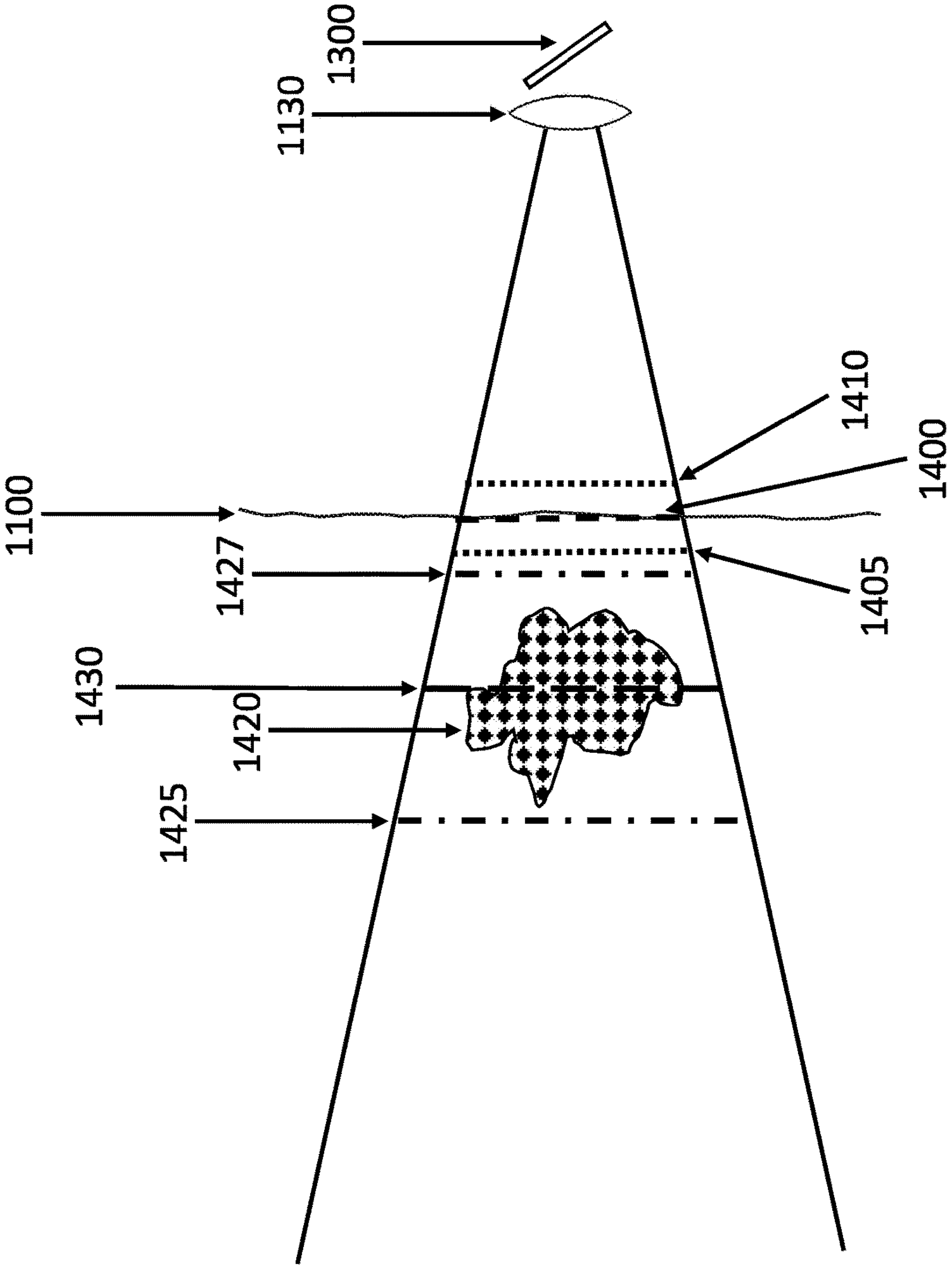
FIGS. 26A-26C provide illustrative, non-limiting examples of microscope focal planes and microscope depth of field and virtual display focal planes and virtual display depth of field for different ARDDs and adjustments in focal plane and depth of field of virtual displays according to some embodiments of the present disclosure.
Figure 26B:
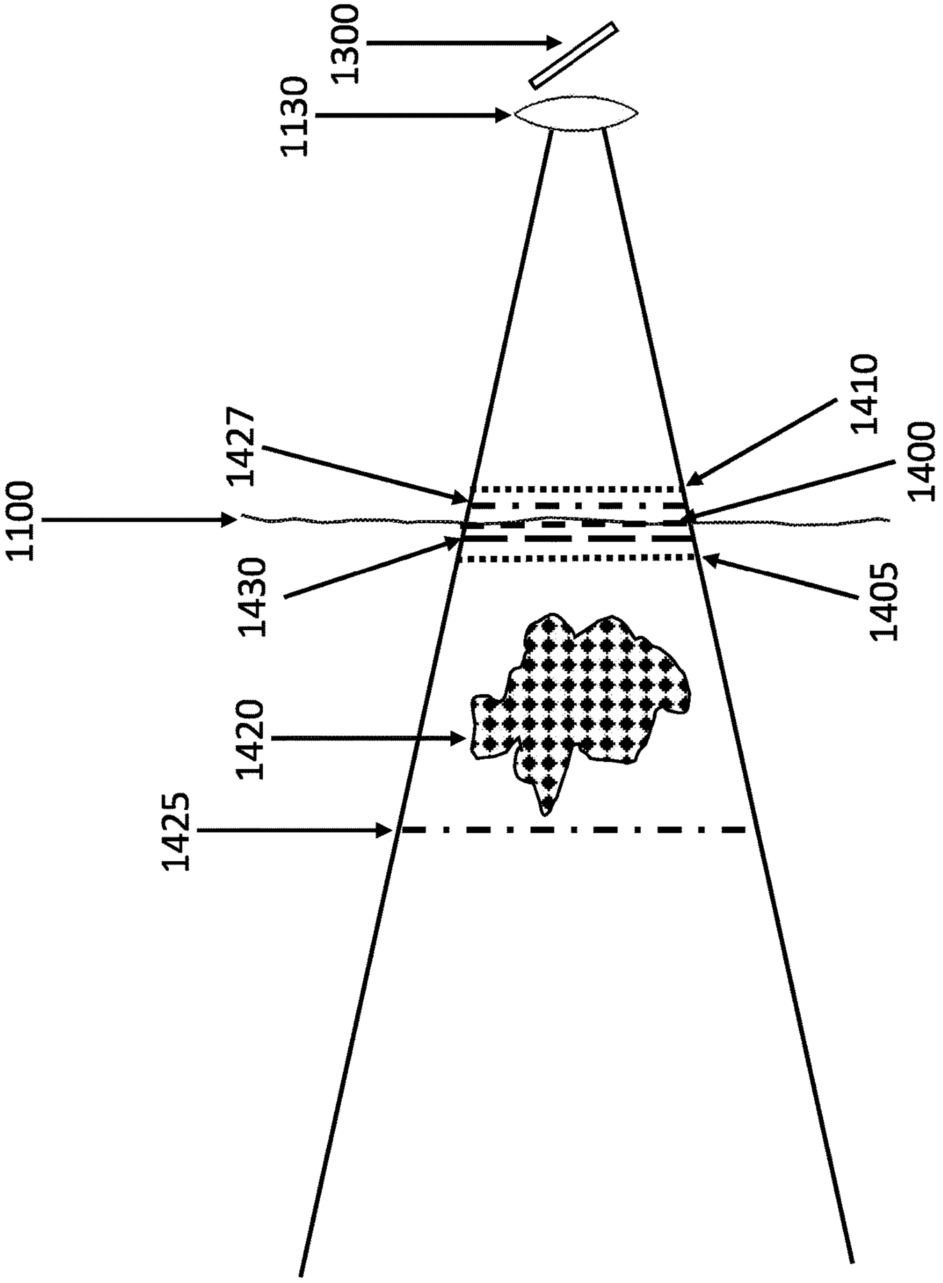
Figure 26C:
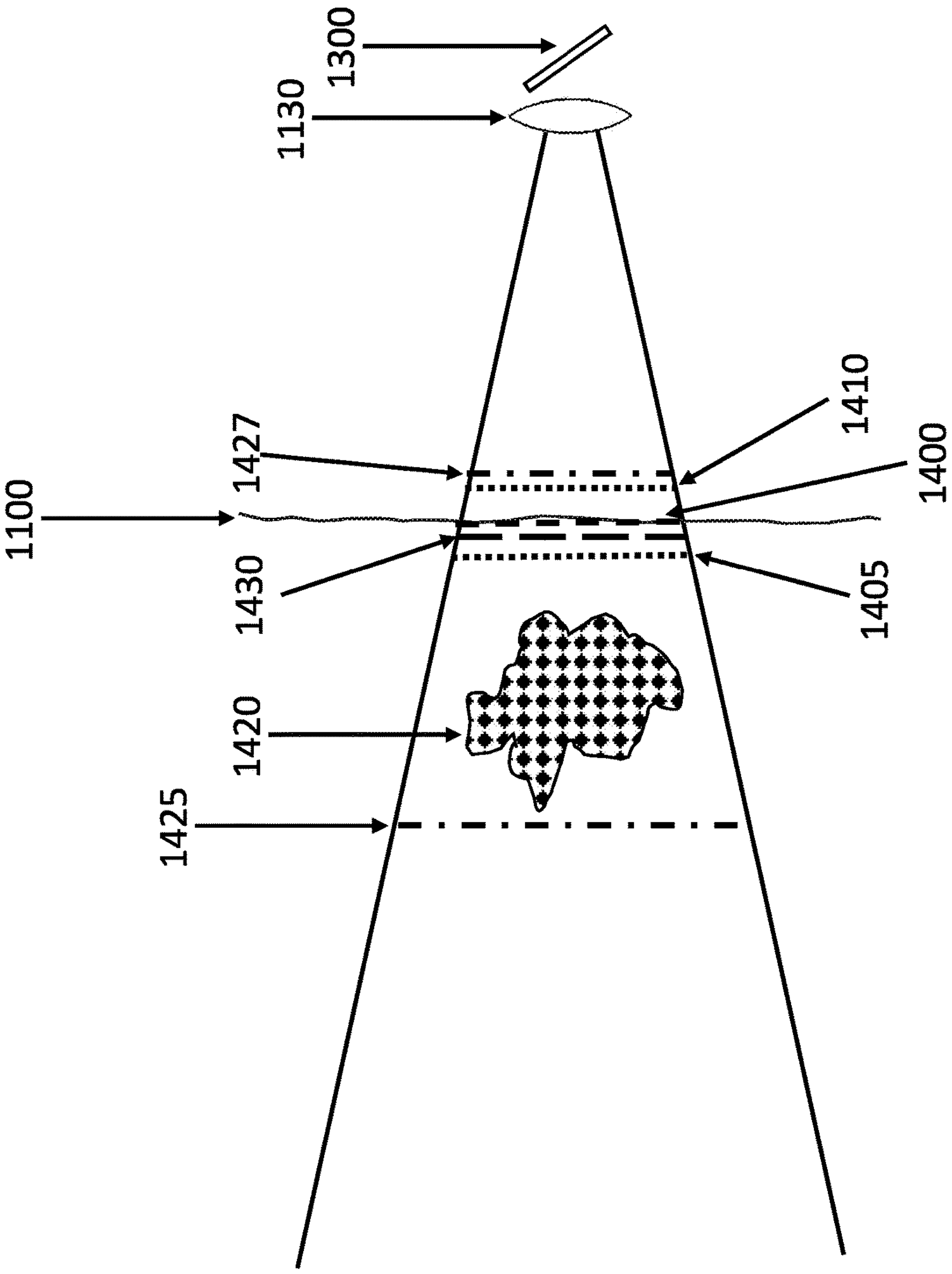

In some embodiments, the AR and/or VR display can be configured so that the virtual 3D display (optionally stereoscopic or non-stereoscopic) of virtual tissues and/or structures is superimposed and/or aligned with corresponding physical tissues and/or structures. The superimposition can, for example, be achieved by registering the virtual tissues and/or structures in the same coordinate system as the corresponding physical tissues and/or structures and/or by tracking the corresponding physical tissues and/or structures. The AR and/or VR display can be configured so that virtual tissues and/or structures located below, distant from, or subjacent to a physical tissue surface, e.g. exposed and/or accessed by a microscope and/or endoscope and/or a surgical tool or instrument are visible. For example, a brightness and/or color and/or transparency can be selected that allows for visualization of virtual tissues and/or structures located below or subjacent to an exposed physical tissue surface are visible. With VR displays, the exposed physical tissue surface can optionally be imaged using one or more cameras. While the exposed physical tissue can, for example, be white (e.g. dura, disk), yellow (e.g. fat), or red (e.g. blood, muscle), the virtual display can be configured to use distinctly different colors, e.g. green or blue in this non-limiting example. Virtual tissues and/or structures located below or subjacent to an exposed physical tissue surface can be at a different depth than the exposed physical tissue surface. The AR and/or VR display (for example shown as 1300) and/or the microscope or endoscope 1130 can optionally be configured so that:

1. The focal plane 1430 of the virtual display of the target tissue (TT) 1420 is different from the focal plane 1400 of the physical tissue surface 1100, e.g. a tissue surface exposed to or accessed by the microscope or endoscope with the microscope or endoscope focused on the tissue surface 1100 (TE) (see, for example, FIG. 26A).
2. The virtual depth of field of the virtual display with far boundary 1425 and near boundary 1427 does not overlap with the depth of field of the microscope or endoscope with far boundary 1405 and near boundary 1410 when the microscope or endoscope is focused on the physical tissue 1100 (TE) (see, for example, FIG. 26A).
3. The focal plane 1430 of the virtual display of the target tissue (TT) 1420 is similar to or the same as the focal plane 1400 of the physical tissue surface 1100, e.g. a tissue surface exposed to or accessed by the microscope or endoscope with the microscope or endoscope focused on the tissue surface 1100 (TE) (see, for example, FIG. 26B).
4. The virtual depth of field of the virtual display with far boundary 1425 and near boundary 1427 overlaps, at least partially, with the far boundary 1405 of the depth of field of the microscope or endoscope when the microscope or endoscope is focused on the physical tissue 1100 (see, for example, FIG. 26B).
5. The focal plane 1430 of the virtual display of the target tissue (TT) 1420 is similar to or the same as the focal plane 1400 of the physical tissue surface 1100, e.g. a tissue surface exposed to or accessed by the microscope or endoscope with the microscope or endoscope focused on the tissue surface 1100 (TE) (see, for example, FIG. 26B).
6. The virtual depth of field of the virtual display with far boundary 1425 and near boundary 1427 overlaps with the depth of field of the microscope or endoscope with far boundary 1405 and near boundary 1410 when the microscope or endoscope is focused on the physical tissue 1100 (TE) (see, for example, FIG. 26C).

With configuration 1 above, the virtual display of the target tissue 1420 will/may not be sharp when the surgeon is looking through the microscope or endoscope 1300, when the microscope or endoscope is focused on the focal plane 1400 at the tissue surface 1100 (e.g. a tissue surface exposed to or accessed by the microscope or endoscope), including a digital display of the microscope or endoscope images(s) (for example captured with one or more cameras), e.g. displayed by a computer monitor (for example for an exoscope).

With configuration 3 and/or 5 above, the virtual display of the target tissue 1420 will/can be sharp when the surgeon is looking through the microscope or endoscope 1300, when the microscope or endoscope is focused on the focal plane 1400 at the tissue surface 1100 (e.g. a tissue surface exposed to or accessed by the microscope or endoscope), including a digital display of the microscope or endoscope images(s) (for example captured with one or more cameras), e.g. displayed by a computer monitor (for example for an exoscope).

Notably, the AR and/or VR display (for example shown as 1300) can be behind the microscope or endoscope 1130 (e.g. FIGS. 25Q, 25R, 26A), interposed in the optical path of the microscope or endoscope (e.g. FIGS. 25C-25P), or in front of the optical path or elements of the microscope or endoscope (e.g. FIGS. 25C, 25D).

In some embodiments, the focal plane and/or the virtual depth of field of the virtual display can be adjusted by modifying one or more lenses, one or more any lens elements, one or more lens groups, one or more optical elements of the augmented or virtual reality display, of the microscope, of the endoscope or a combination thereof. The adjusting can comprise changing one or more spatial relationships, positions, orientations, geometries between different of the one or more lenses, one or more any lens elements, one or more lens groups, one or more optical elements. The adjusting can comprise deforming at least one of the one or more lenses, one or more any lens elements, one or more lens groups, one or more optical elements. The one or more lenses, one or more lens elements, one or more lens groups, one or more optical elements can comprise at least one or more mirrors, which can optionally be deformable.

In some embodiments, the focal plane and/or the virtual depth of field of the virtual display can be adjusted using software or computer programs configured to move, adjust, rotate, translate, bend the focal plane and/or the virtual depth of field of the virtual display. The software or computer programs can be configured to be adjustable, e.g. to match or approximate or be similar to or overlap with the focal plane and/or depth of field of a microscope or endoscope and/or to overlap with the depth of field of the microscope or endoscope, e.g. also as the focal plane of a microscope or endoscope changes for different depths of operation. The software or computer programs can be configured to provide a fixed focal plane and/or virtual depth of field of the virtual display, e.g. matching or approximating or be similar to or be overlapping with the focal plane and/or depth of field of an endoscope, e.g. an endoscope with a fixed focal plan and/or a fixed depth of field.

In some embodiments, a microscope or endoscope can be configured for automated adjustment (e.g. autofocus) of the focal plane and/or the depth of field of the microscope or endoscope. Software or computer programs can be configured to match the automated adjustment of the focal plane and/or the depth of field of the microscope or endoscope with the focal plane and/or the virtual depth of field of the virtual display. The software or computer programs can be configured to match or approximate or be similar to or to overlap the focal plane and/or virtual depth of field of the virtual display with the focal plane and/or depth of field of the microscope or endoscope and/or to overlap with the depth of field of the microscope or endoscope, e.g. also as the focal plane of a microscope or endoscope changes for different depths of operation.

In any of the foregoing embodiments, the virtual display generated by one or more computer processors can be configured so that the depth of field of the virtual display (virtual depth of field) is the same as the depth of field of the microscope or endoscope. In any of the foregoing embodiments, the virtual display generated by one or more computer processors can be configured so that the depth of field of the virtual display (virtual depth of field) is greater than the depth of field of the microscope or endoscope. In any of the foregoing embodiments, the virtual display generated by one or more computer processors can be configured so that the depth of field of the virtual display (virtual depth of field) is less than the depth of field of the microscope or endoscope.

In any of the foregoing embodiments, the depth of field of the virtual display (virtual depth of field) can be configured to be overlapping with the depth of field of the microscope or endoscope. In any of the foregoing embodiments, the depth of field of the virtual display (virtual depth of field) can be configured to be non-overlapping with the depth of field of the microscope or endoscope.

In any of the embodiments, the projection plane of the virtual display can be configured to be close to, similar to, to approximate, to coincide with, to be the same as the focal plane of the microscope or endoscope, e.g. for fixed focal distances and/or for adjustable focal distances.

For example, in a spinal procedure, an exposure can comprise resection of a ligamentum flavum and/or a spinal lamina. The microscope or endoscope can be focused on the ligamentum flavum and the lamina during the resection; an underlying tumor or a disc herniation can be the target tissue of the operation and can be deeper seated, e.g. in this example further anterior and away from the microscope or endoscope focal plane (with coordinates different from the microscope or endoscope focal plane). In this example, a virtual display by an ARDD can have a focal plane centered through the target tissue, tumor or disc herniation. The depth of field of the virtual display can also be different from that of the microscope or endoscope. The virtual display will appear blurred when the surgeon looks through the microscope or endoscope focused on the exposed ligamentum flavum and/or lamina.

In a different, non-limiting example, in a spinal procedure, an exposure can comprise resection of a ligamentum flavum and/or a spinal lamina. The microscope or endoscope can be focused on the ligamentum flavum and the lamina during the resection; an underlying tumor or a disc herniation can be the target tissue of the operation and can be deeper seated, e.g. in this example further anterior and away from the microscope or endoscope focal plane (with coordinates different from the microscope or endoscope focal plane). In this example, a virtual display by an ARDD can have a focal plane centered not through the target tissue, a tumor or disc herniation, but the focal plane of the ARRD can be adjusted to have the same or similar coordinates as the focal plane of the microscope or endoscope centered/focused on the ligamentum flavum and lamina. A depth of field of the virtual display can be adjusted to be at least partially overlapping with a depth of field of the microscope or endoscope. A depth of field of the virtual display can be adjusted to encompass or be the same as the depth of field of the microscope or endoscope. The virtual display will appear sharp when the surgeon looks through the microscope or endoscope focused on the exposed ligamentum flavum and/or lamina.

When a surgeon looks through the microscope or endoscope the ligamentum flavum and lamina can appear sharp, in focus, and the target tissue (tumor or disc herniation), while anatomically deeper seated, can also appear sharp since the focal plane and/or the depth of field of the virtual display by the ARDD has been set to match the focal plane and/or the depth of field of the microscope or endoscope, thereby facilitating targeting of the target tissue through the microscope or endoscope, including by advancing surgical tools or instruments towards the sharply displayed target tissue. While the focal plane or focal point(s) and/or the depth of field of the virtual display of the target tissue can be adjusted to be the same or similar to the focal plane and/or the depth of field of the microscope or endoscope, other aspects of the virtual display, e.g. shading, can remain specific to the coordinates of the target tissue and, with that, different from the spinal lamina or ligamentum flavum in this example, due to their different coordinates.

In any of the embodiments, a target tissue can be hidden from view through a microscope or endoscope, for example by an interposed tissue or tissues, including a tissue or tissue plane visible through the microscope or endoscope.

In any of the embodiments, the projection plane of the virtual display can be configured to be different from the focal plane of the microscope or endoscope, e.g. for fixed focal distances and/or for adjustable focal distances.

3D Perspective, Stereopsis, Size, Shading

In some embodiments, an object can be physically located at a different location, orientation, angle, depth, coordinates than the focal plane and/or depth of field of a microscope or endoscope, e.g. focused and/or set and/or placed on an exposed tissue or a tissue accessed by the microscope or endoscope. The object can be a physical tissue, e.g. a tissue (for example a target tissue and/or a portion thereof) identified or imaged using an imaging test, for example an x-ray, x-ray based imaging, cone beam CT, digital tomosynthesis, CT, MRI, SPECT, PET, ultrasound, any other imaging modality known in the art, or a combination thereof. The object can, for example, also be a medical device, e.g. an implant, a surgical tool, a surgical instrument, or a combination thereof. One or more computer processors can generate a virtual display of the object, e.g. for display by an augmented or virtual reality headset or display. The virtual display can be based on a 3D rendering of the object, a 3D surface of the object, a 3D volume of the object, a CAD file of the object, or any other 3D representation or 3D file of the object, or any combination thereof.

In some embodiments, the focal plane and/or the depth of field of the virtual display can be configured to be close to, similar to, to approximate, to coincide with, to be the same as the focal plane of the microscope or endoscope focused on a tissue exposed for or accessed by the microscope or endoscope and/or the depth of field of the microscope or endoscope relative to the focal plane of the microscope or endoscope. With the focal plane and/or the depth of field of the virtual display configured or adjusted to be close to, similar to, to approximate, to coincide with, to be the same as the focal plane and/or the depth of field of the microscope or endoscope, the virtual display of the object can be sharp for the user looking, for example, through the microscope or endoscope while looking at an exposed tissue or tissue plane or physical object. However, in this example the tissue, tissue plane or physical object can be physically at a different location, orientation, angle, depth, coordinates than the virtual display of the physical object. One or more computer processors can be configured to create a spatially correct or spatially adequate appearing display for the user for the physical location, orientation, angle, depth, coordinates of the physical object by adjusting one or more of the following parameters for the virtual display of the physical object rendered in the virtual display:

- Perspective of the virtual object, e.g. rendered for the physical location, orientation, angle, depth, coordinates of the physical object
- Size of the object, e.g. rendered for the physical location, orientation, angle, depth, coordinates of the physical object
- Occlusion of the object, e.g. for left and/or right eye, different view angles, e.g. rendered for the physical location, orientation, angle, depth, coordinates of the physical object
- Texture gradients, e.g. rendered for the physical location, orientation, angle, depth, coordinates of the physical object
- Shading, e.g. rendered for the physical location, orientation, angle, depth, coordinates of the physical object In any of the embodiments, convergence can be to the focal plane of the virtual display. With the focal plane and/or the depth of field of the virtual display configured to be close to, similar to, to approximate, to coincide with, to be the same as the focal plane and/or the depth of field of the microscope or endoscope focused on a tissue exposed for or accessed by the microscope or endoscope, a vergence conflict between the virtual display and the tissue exposed for or accessed by the microscope or endoscope will/may not exist when using an optical see through or video see through head mounted display or other augmented reality display device.

When the focal plane of the virtual display, e.g. of virtual tissues, virtual target tissues, virtual objects corresponding to physical tissues, physical target tissues, physical objects subjacent to the exposed physical tissue surface, is different than the focal plane of the microscope or endoscope for viewing the exposed physical tissue surface, the viewer may have to adjust the accommodation for viewing the virtual tissues vs. the exposed and/or accessed physical tissue surface, for example when the virtual depth of field is different from and not overlapping with the focal plane and/or the depth of field of the microscope or endoscope for a given focal plane.

In some embodiments, one or more computer processors can optionally be configured so that the AR display is configured so that 1. The depth of field of the virtual display is the same as the depth of field of the microscope or endoscope.
2. The depth of field of the virtual display is the same or greater than the depth of field of the microscope or endoscope.
3. The depth of field of the virtual display is greater than the depth of field of the microscope or endoscope.
4. The depth of field of the virtual display is overlapping with at least portions of the depth of field of the microscope or endoscope (which can be, for example, the case with examples 1-3 in this list).
5. The depth of field of the virtual display is different from and not overlapping with the depth of field of the microscope or endoscope (resulting in a blurred view of the virtual display when the user is looking at the focal plane (within the depth of field) of the microscope).

In some embodiments, one or more computer processors can optionally be configured so that the AR display is configured so that 1. The depth of field of the virtual display is the same as the depth of field of the microscope or endoscope and encompasses the focal plane of the microscope or endoscope focused on an exposed or accessed physical tissue surface.
2. The depth of field of the virtual display is the same or greater than the depth of field of the microscope or endoscope and encompasses the focal plane of the microscope or endoscope focused on an exposed or accessed physical tissue surface.
3. The depth of field of the virtual display is greater than the depth of field of the microscope or endoscope and encompasses the focal plane of the microscope or endoscope focused on an exposed or accessed physical tissue surface.
4. The depth of field of the virtual display is overlapping with at least portions of the depth of field of the microscope or endoscope (which can be, for example, the case with examples 1-3 in this list) and encompasses the focal plane of the microscope or endoscope focused on an exposed or accessed physical tissue surface.
5. The depth of field of the virtual display is overlapping with at least portions of the depth of field of the microscope or endoscope and does not encompass the focal plane of the microscope or endoscope focused on an exposed or accessed physical tissue surface, which can still result in a sharp perception of the virtual display by the ARDD when the user is looking at the tissue focused on by and seen through the microscope.

In any of the foregoing embodiments, focal plane and/or a depth of field data, including coordinates, of the microscope can be transmitted by a computer processor of the microscope to a computer processor of the ARDD; the computer processor of the ARDD can then set or adjust a focal plane and/or depth of field of a virtual display in accordance with the above embodiments.

In some embodiments, the focal plane of the virtual display can be the same as the focal plane of the focal plane of the microscope or endoscope focused on an exposed or accessed physical tissue surface.

In some embodiments, the focal plane and/or the depth of field of the microscope or endoscope can be fixed. In some embodiments, the focal plane and/or the depth of field of the microscope or endoscope can be variable. In some embodiments, one or more computer processors can be configured so that the focal plane and/or the depth of field of the virtual display can be variable. In some embodiments, one or more computer processors can be configured so that the focal plane and/or the depth of field of the virtual display can be adjusted, optionally in real time or near real time or not in real time, based on the focal plane and/or the depth of field of the microscope or endoscope.

The field of view of one or more of the display units of an AR or VR head mounted display, and/or the field of view of an AR or VR head mounted display, and/or the virtual display, displayed by an AR or VR head mounted display and/or a tablet computer and/or a computer monitor, can be round, ellipsoid, square, rectangular or any other shape. The field of view of the microscope or endoscope can be round, ellipsoid, square, rectangular or any other shape. Any combinations of the foregoing are possible.

In some embodiments, the system can be configured so that the field of view of one or more of the display units of the AR or VR head mounted display, and/or the field of view of the AR or VR head mounted display, and/or the virtual display, displayed by the AR or VR head mounted display and/or a tablet computer and/or a computer monitor, is smaller than the field of view of the microscope or endoscope.

In some embodiments, the system can be configured so that the field of view of one or more of the display units of the AR or VR head mounted display, and/or the field of view of the AR or VR head mounted display, and/or the virtual display, displayed by the AR or VR head mounted display and/or a tablet computer and/or a computer monitor, is the same as the field of view of the microscope or endoscope.

In some embodiments, the system can be configured so that the field of view of one or more of the display units of the AR or VR head mounted display, and/or the field of view of the AR or VR head mounted display, and/or the virtual display, displayed by the AR or VR head mounted display and/or a tablet computer and/or a computer monitor, is larger than the field of view of the microscope or endoscope.

In any of the embodiments throughout the application, the view(s) obtained or acquired by an endoscope or microscope, e.g. optionally captured by an image sensor, a video module or video camera, can be displayed by one or more ARDD, e.g. display units of an AR or VR head mounted display, and/or an AR or VR head mounted display, and/or a tablet computer, and/or a computer monitor, which can be the same or different than the one or more ARDD's, e.g. display units of an AR or VR head mounted display, and/or an AR or VR head mounted display, and/or a tablet computer, and/or a computer monitor displaying a virtual display, e.g. of one or more virtual objects as described throughout the disclosure in various embodiments.

Figure 27A:
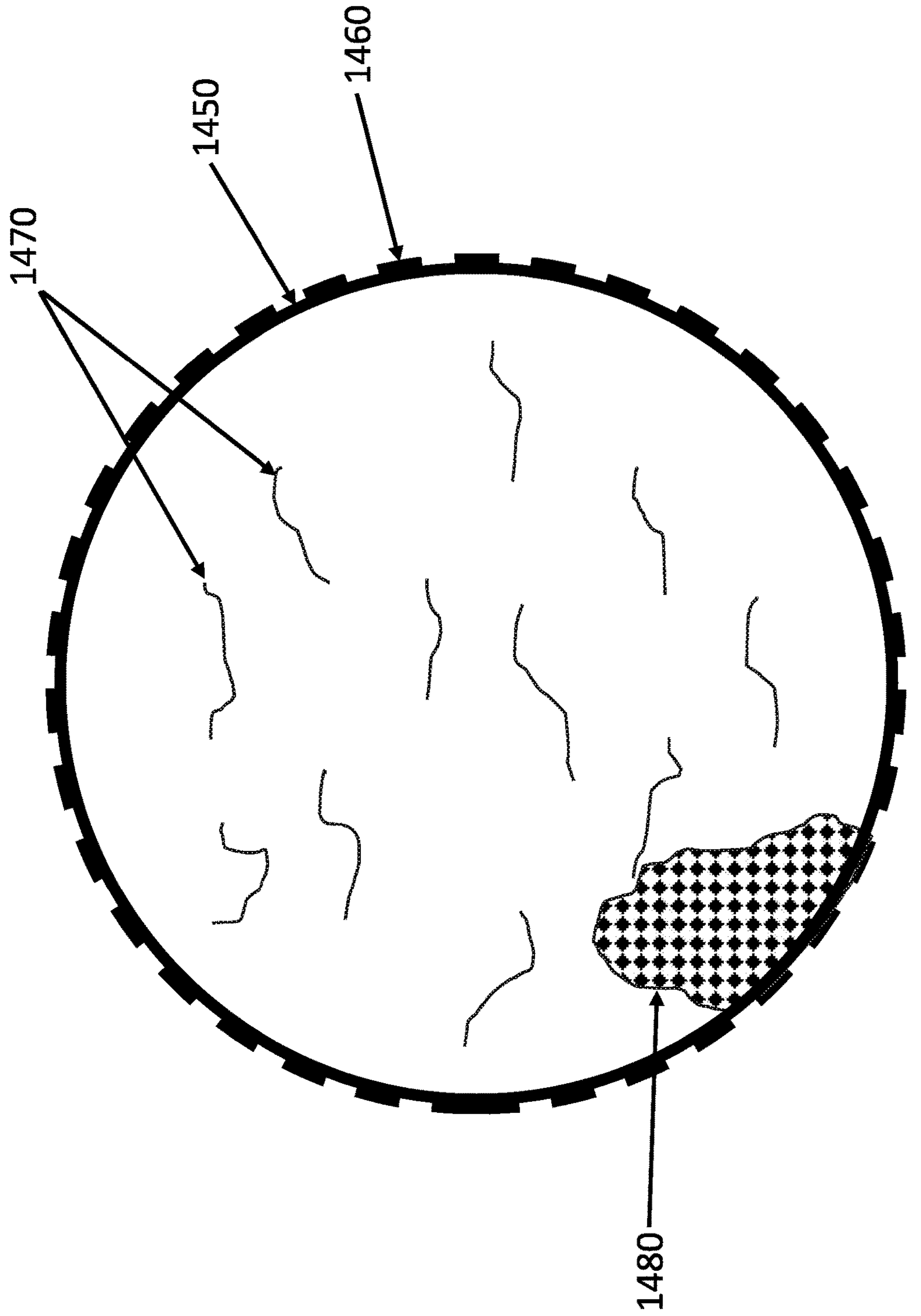
FIGS. 27A-27G provide illustrative, non-limiting examples of microscopes and endoscopes used in conjunction with ARDDs, where the ARDD optionally has a similar or a larger field of view than a microscope and endoscope and where the ARDD with a larger field of view can be configured to generate a virtual display of one or more target tissues that extend beyond the field of view of the microscope or endoscope in one or more dimensions according to some embodiments of the present disclosure.

FIG. 27A is a non-limiting example of a system configured so that the field of view of one or more of the display units of the AR or VR head mounted display, and/or the field of view of the AR or VR head mounted display, and/or the virtual display, displayed by the AR or VR head mounted display and/or a tablet computer and/or a computer monitor, 1450 (solid line) is the same or approximately the same as or similar to the field of view of the microscope or endoscope 1460 (broken line), optionally captured by a video module or camera and/or displayed by one or more of the display units of an AR or VR head mounted display, and/or an AR or VR head mounted display, and/or a tablet computer, and/or a computer monitor. A tissue 1470 exposed and/or accessed to/by the microscope or endoscope is seen through the microscope or endoscope. An object can be physically located at a different location, orientation, angle, depth, coordinates than the focal plane and/or depth of field of the microscope or endoscope, e.g. focused and/or set and/or placed on the exposed and/or accessed tissue 1470 by the microscope or endoscope. The object can be a physical tissue, e.g. a tissue (for example a target tissue and/or a portion thereof) identified or imaged using an imaging test, for example an x-ray, x-ray based imaging, cone beam CT, digital tomosynthesis, CT, MRI, SPECT, PET, ultrasound, any other imaging modality known in the art, (and optionally registered in a coordinate system, e.g. using a phantom, e.g. a radiopaque phantom, an MRI visible phantom, a PET visible phantom, a radiation emitting phantom etc.) or a combination thereof. The object can, for example, also be a medical device, e.g. an implant, a surgical tool, a surgical instrument, or a combination thereof. A virtual display 1480 of the object can be limited to the field of view of the one or more of the display units of the AR or VR head mounted display, and/or the field of view of the AR or VR head mounted display, the display of a tablet computer and/or a computer monitor, the field of view or the microscope or endoscope, optionally captured by a video module or camera and/or displayed by one or more of the display units of an AR or VR head mounted display, and/or an AR or VR head mounted display, and/or a tablet computer, and/or a computer monitor, or limited to a combination thereof. One or more computer processors can be configured so that the virtual display is limited and/or does not extend outside the field of view or the microscope or endoscope, optionally captured by a video module or camera and/or displayed by one or more of the display units of an AR or VR head mounted display, and/or an AR or VR head mounted display, and/or a tablet computer, and/or a computer monitor.

Figure 27B:
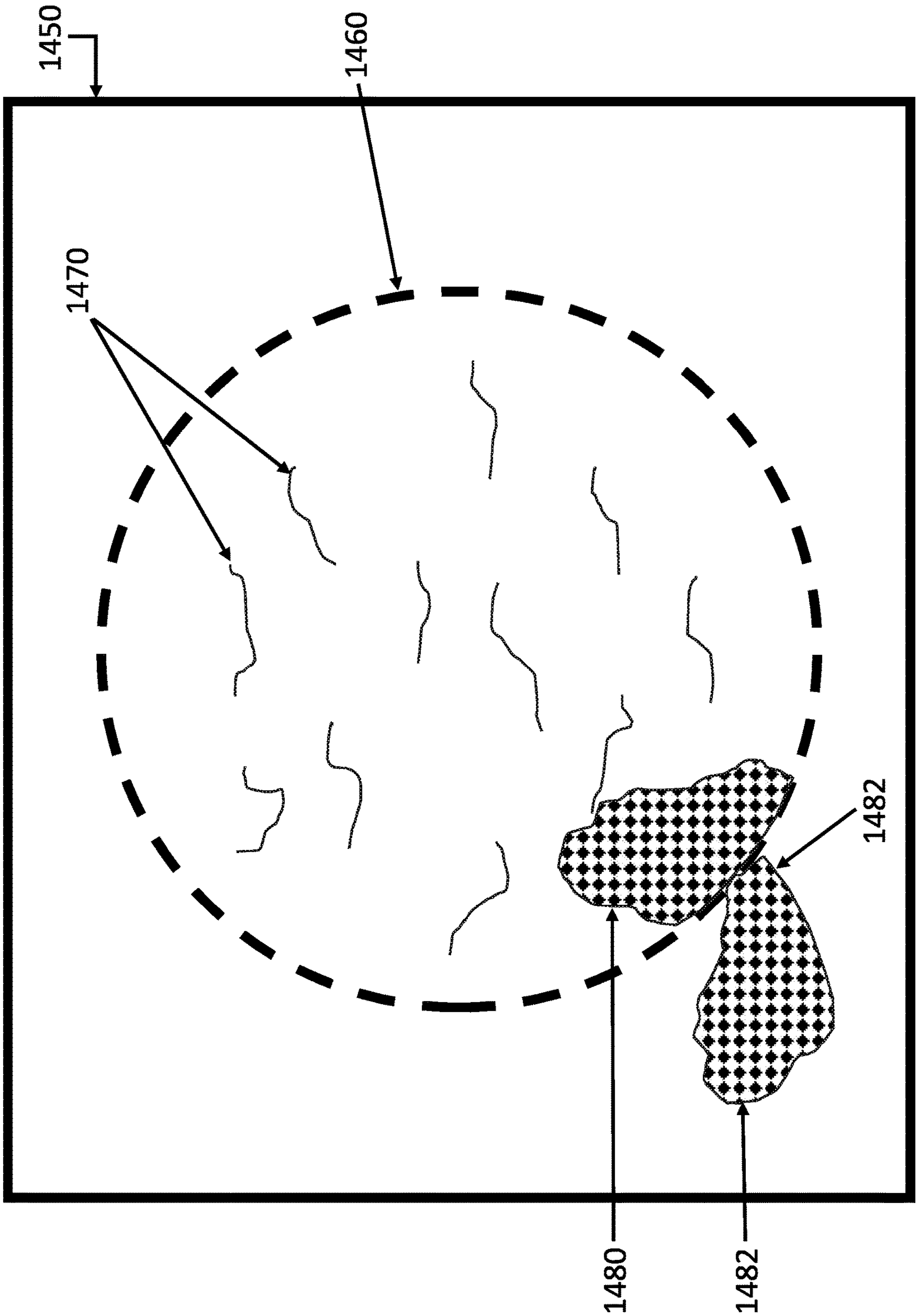

FIG. 27B is a non-limiting example of a system configured so that the field of view of one or more of the display units of the AR or VR head mounted display, and/or the field of view of the AR or VR head mounted display, and/or the virtual display, displayed by the AR or VR head mounted display and/or a tablet computer and/or a computer monitor, 1450 (solid line) is larger than the field of view of the microscope or endoscope 1460 (broken line), optionally captured by an image sensor, a video module or camera and/or displayed by one or more of the display units of an AR or VR head mounted display, and/or an AR or VR head mounted display, and/or a tablet computer, and/or a computer monitor. A tissue 1470 exposed and/or accessed to/by the microscope or endoscope is seen through the microscope or endoscope and displayed by the one or more of the display units of the AR or VR head mounted display, and/or the AR or VR head mounted display, and/or the tablet computer, and/or the computer monitor. An object can be physically located at a different location, orientation, angle, depth, coordinates than the focal plane and/or depth of field of the microscope or endoscope, e.g. focused and/or set and/or placed on the exposed and/or accessed tissue 1470 by the microscope or endoscope. The object can be a physical tissue, e.g. a tissue (for example a target tissue and/or a portion thereof) identified or imaged using an imaging test, for example an x-ray, x-ray based imaging, cone beam CT, digital tomosynthesis, CT, MRI, SPECT, PET, ultrasound, any other imaging modality known in the art, or a combination thereof. The object can, for example, also be a medical device, e.g. an implant, a surgical tool, a surgical instrument, or a combination thereof. A virtual display 1480 1482 of the object displayed by the one or more of the display units of the AR or VR head mounted display, and/or the AR or VR head mounted display, and/or the display of a tablet computer, and/or a computer monitor can be larger than and/or extend further than the field of view or the microscope or endoscope, optionally captured by a video module or camera and/or displayed by one or more of the display units of an AR or VR head mounted display, and/or an AR or VR head mounted display, and/or a tablet computer, and/or a computer monitor, or limited to a combination thereof. The virtual display 1480 1482 can extend outside 1482 and/or can be displayed outside 1482 the field of view of the microscope or endoscope 1460, optionally captured by a video module or camera and/or displayed by one or more of the display units of an AR or VR head mounted display, and/or an AR or VR head mounted display, and/or a tablet computer, and/or a computer monitor. One or more computer processors can be configured so that the virtual display is larger than and/or extends outside the field of view or the microscope or endoscope, optionally captured by an image sensor, a video module or camera and/or displayed by one or more of the display units of an AR or VR head mounted display, and/or an AR or VR head mounted display, and/or a tablet computer, and/or a computer monitor.

Figure 27C:
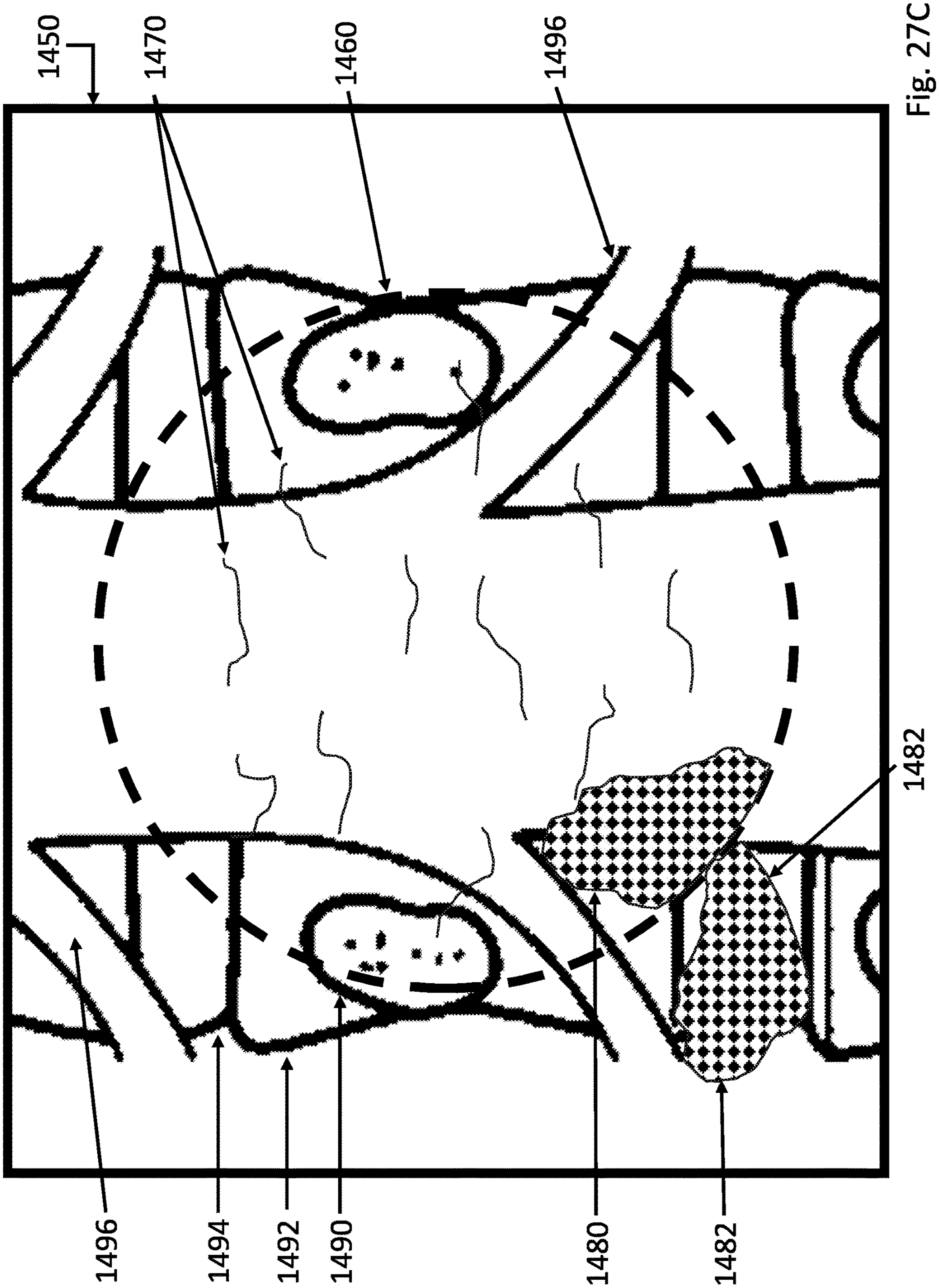

FIG. 27C is a non-limiting example of a system configured so that the field of view of one or more of the display units of the AR or VR head mounted display, and/or the field of view of the AR or VR head mounted display, and/or the virtual display, displayed by the AR or VR head mounted display and/or a tablet computer and/or a computer monitor, 1450 (solid line) is larger than the field of view of the microscope or endoscope 1460 (broken line), optionally captured by a video module or camera and/or displayed by one or more of the display units of an AR or VR head mounted display, and/or an AR or VR head mounted display, and/or a tablet computer, and/or a computer monitor. A tissue 1470 exposed and/or accessed to/by the microscope or endoscope is seen through the microscope or endoscope and optionally displayed by the one or more of the display units of the AR or VR head mounted display, and/or the AR or VR head mounted display, and/or the tablet computer, and/or the computer monitor. An object can be physically located at a different location, orientation, angle, depth, coordinates than the focal plane and/or depth of field of the microscope or endoscope, e.g. focused and/or set and/or placed on the exposed and/or accessed tissue 1470 by the microscope or endoscope. The object can be a physical tissue, e.g. a tissue (for example a target tissue and/or a portion thereof) identified or imaged using an imaging test, for example an x-ray, x-ray based imaging, cone beam CT, digital tomosynthesis, CT, MRI, SPECT, PET, ultrasound, any other imaging modality known in the art, or a combination thereof. The object can, for example, also be a medical device, e.g. an implant, a surgical tool, a surgical instrument, or a combination thereof. A virtual display 1480 1482 of the object displayed by the one or more of the display units of the AR or VR head mounted display, and/or the AR or VR head mounted display, and/or the display of a tablet computer, and/or a computer monitor can be larger than and/or extend further than the field of view or the microscope or endoscope, optionally captured by a video module or camera and/or displayed by one or more of the display units of an AR or VR head mounted display, and/or an AR or VR head mounted display, and/or a tablet computer, and/or a computer monitor, or limited to a combination thereof. The virtual display 1480 1482 can extend outside 1482 and/or can be displayed outside 1482 the field of view of the microscope or endoscope 1460, optionally captured by a video module or camera and/or displayed by one or more of the display units of the AR or VR head mounted display, and/or the AR or VR head mounted display, and/or the tablet computer, and/or the computer monitor. One or more computer processors can be configured so that the virtual display is larger than and/or extends outside the field of view or the microscope or endoscope, optionally captured by a video module or camera and/or displayed by one or more of the display units of an AR or VR head mounted display, and/or an AR or VR head mounted display, and/or a tablet computer, and/or a computer monitor. In this example, the system is configured so that the virtual display comprises the virtual object 1480 1482, e.g. a target tissue (e.g. a disk herniation, a tumor, a soft-tissue, an organ tissue etc., for example located at the same or a different location, position, orientation than the focal plane and/or depth of field of the microscope or endoscope), and various other tissues, for example brain tissue, heart tissue, or spinal tissue, e.g. bone (for example a pedicle) 1490, one or more vertebrae 1492, one or more intervertebral disks or disk tissue 1494, one or more neural structures, e.g. nerve roots 1496, or thecal sac.

Figure 27D:
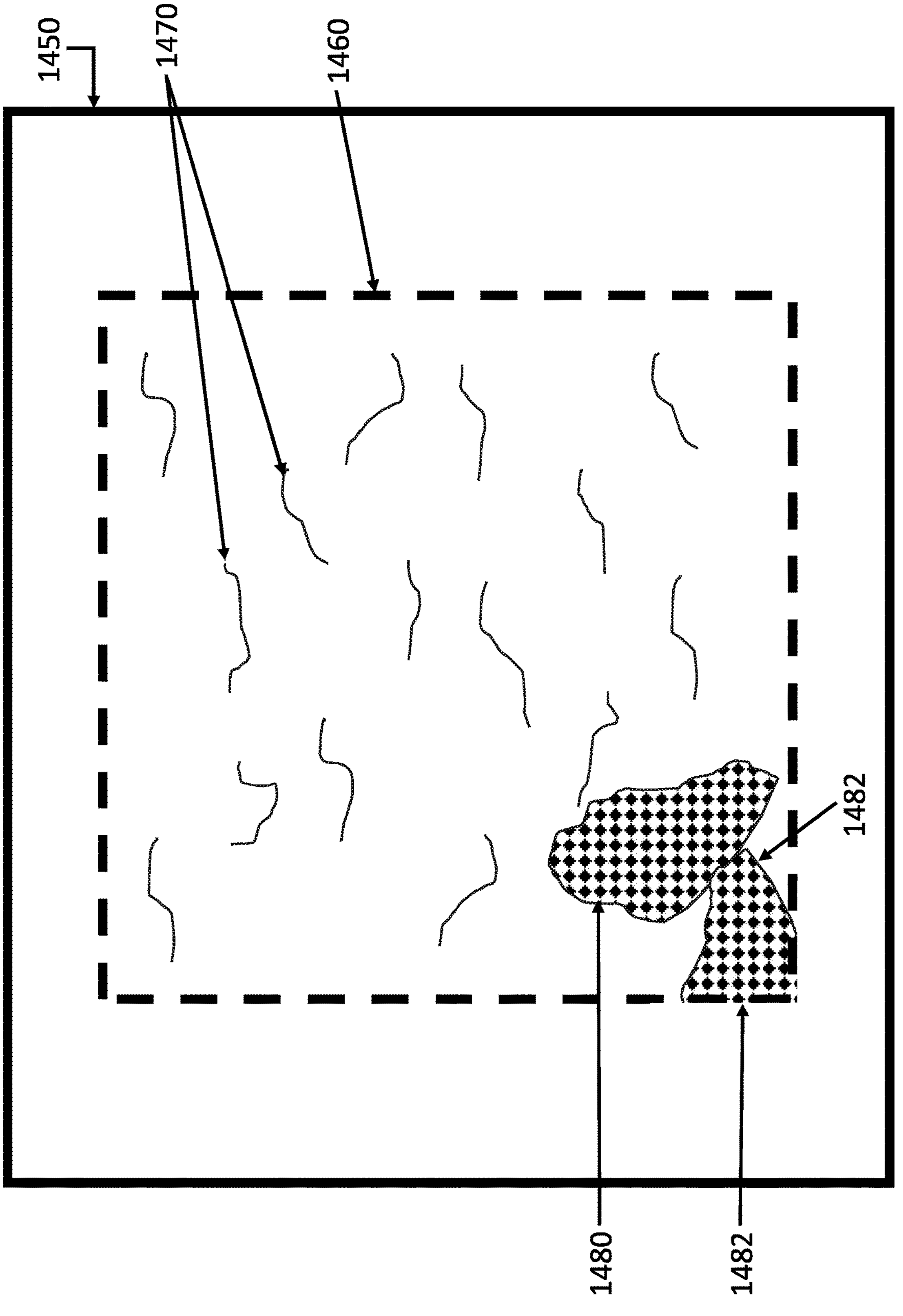

FIG. 27D is a non-limiting example of a system configured so that the field of view of one or more of the display units of the AR or VR head mounted display, and/or the field of view of the AR or VR head mounted display, and/or the virtual display, displayed by the AR or VR head mounted display and/or a tablet computer and/or a computer monitor, 1450 (solid line) is larger than the field of view of the microscope or endoscope 1460 (broken line), optionally captured by a video module or camera and/or displayed by one or more of display units of an AR or VR head mounted display, and/or an AR or VR head mounted display, and/or a tablet computer, and/or a computer monitor (optionally the same as the one used for displaying the virtual display). A tissue 1470 exposed and/or accessed to/by the microscope or endoscope is seen through the microscope or endoscope. An object can be physically located at a different location, orientation, angle, depth, coordinates than the focal plane and/or depth of field of the microscope or endoscope, e.g. focused and/or set and/or placed on the exposed and/or accessed tissue 1470 by the microscope or endoscope. The object can be a physical tissue, e.g. a tissue (for example a target tissue and/or a portion thereof) identified or imaged using an imaging test, for example an x-ray, x-ray based imaging, cone beam CT, digital tomosynthesis, CT, MRI, SPECT, PET, ultrasound, any other imaging modality known in the art, or a combination thereof. The object can, for example, also be a medical device, e.g. an implant, a surgical tool, a surgical instrument, or a combination thereof. A virtual display 1480 1482 of the object can be limited to the field of view of the one or more of the display units of the AR or VR head mounted display, and/or the field of view of the AR or VR head mounted display, and/or the display of a tablet computer and/or a computer monitor, and/or the field of view or the microscope or endoscope, optionally captured by a video module or camera and/or displayed by one or more of the display units of an AR or VR head mounted display, and/or an AR or VR head mounted display, and/or a tablet computer, and/or a computer monitor, or limited to a combination thereof. In this example, the system can be configured so that the virtual display 1480 1482 of the object can be limited to the field of view or the microscope or endoscope, optionally captured by a video module or camera and/or displayed by one or more of the display units of an AR or VR head mounted display, and/or an AR or VR head mounted display, and/or a tablet computer, and/or a computer monitor. One or more computer processors can be configured so that the virtual display is limited and/or does not extend outside the field of view or the microscope or endoscope, optionally captured by a video module or camera and/or displayed by one or more of the display units of an AR or VR head mounted display, and/or an AR or VR head mounted display, and/or a tablet computer, and/or a computer monitor.

Figure 27E:
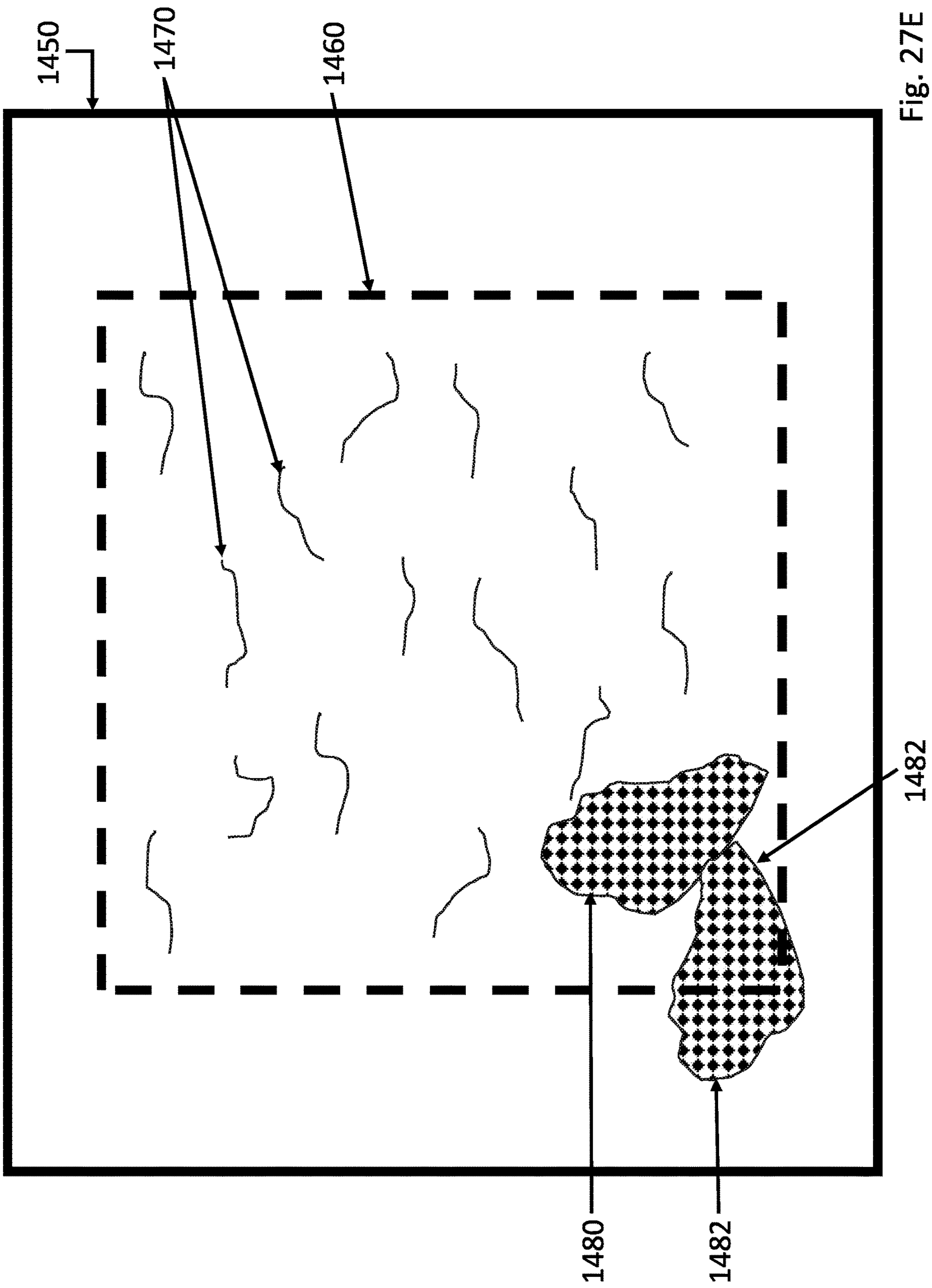

FIG. 27E is a non-limiting example of a system configured so that the field of view of one or more of the display units of the AR or VR head mounted display, and/or the field of view of the AR or VR head mounted display, and/or the virtual display, displayed by the AR or VR head mounted display and/or a tablet computer and/or a computer monitor, 1450 (solid line) is larger than the field of view of the microscope or endoscope 1460 (broken line), optionally captured by a video module or camera and/or displayed by one or more of the display units of the AR or VR head mounted display, and/or the AR or VR head mounted display, and/or the tablet computer, and/or the computer monitor. A tissue 1470 exposed and/or accessed to/by the microscope or endoscope is seen through the microscope or endoscope and displayed by the one or more of the display units of the AR or VR head mounted display, and/or the AR or VR head mounted display, and/or the tablet computer, and/or the computer monitor. An object can be physically located at a different location, orientation, angle, depth, coordinates than the focal plane and/or depth of field of the microscope or endoscope, e.g. focused and/or set and/or placed on the exposed and/or accessed tissue 1470 by the microscope or endoscope. The object can be a physical tissue, e.g. a tissue (for example a target tissue and/or a portion thereof) identified or imaged using an imaging test, for example an x-ray, x-ray based imaging, cone beam CT, digital tomosynthesis, CT, MRI, SPECT, PET, ultrasound, any other imaging modality known in the art, or a combination thereof. The object can, for example, also be a medical device, e.g. an implant, a surgical tool, a surgical instrument, or a combination thereof. The object can be hidden by interposed or superimposed tissue, including, for example, tissue 1470 exposed and/or accessed to/by and seen through the microscope or endoscope. A virtual display 1480 1482 of the object displayed by the one or more of the display units of the AR or VR head mounted display, and/or the AR or VR head mounted display, and/or the display of a tablet computer, and/or a computer monitor can be larger than and/or extend further than the field of view or the microscope or endoscope, optionally captured by a video module or camera and/or displayed by one or more of the display units of the AR or VR head mounted display, and/or the AR or VR head mounted display, and/or the tablet computer, and/or the computer monitor, or a combination thereof. The virtual display 1480 1482 can extend outside 1482 and/or can be displayed outside 1482 the field of view of the microscope or endoscope 1460, optionally captured by a video module or camera and/or displayed by one or more of the display units of the AR or VR head mounted display, and/or the AR or VR head mounted display, and/or the tablet computer, and/or the computer monitor. One or more computer processors can be configured so that the virtual display is larger than and/or extends outside the field of view or the microscope or endoscope, optionally captured by a video module or camera and/or displayed by one or more of the display units of the AR or VR head mounted display, and/or the AR or VR head mounted display, and/or the tablet computer, and/or the computer monitor.

Figure 27F:
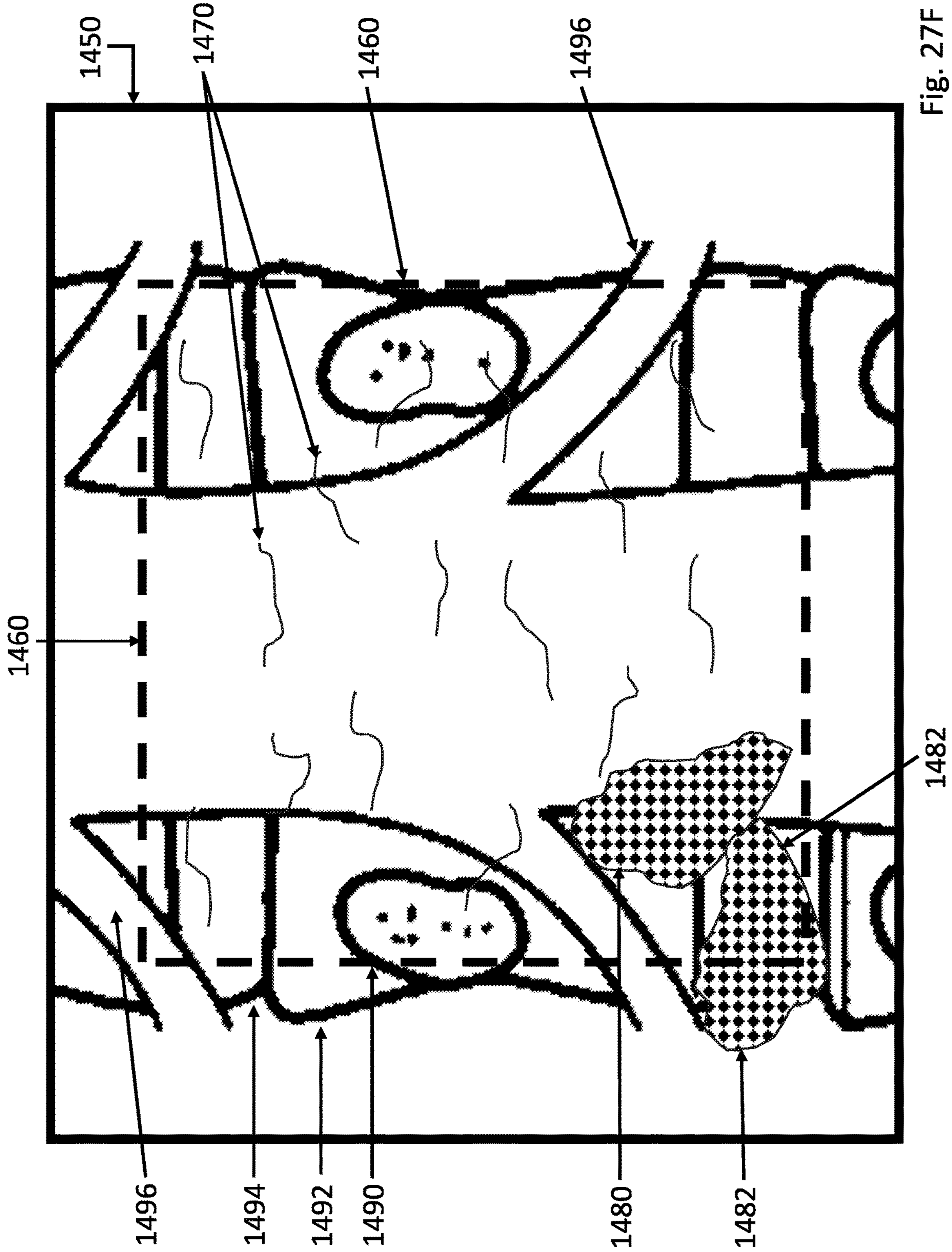

FIG. 27F is a non-limiting example of a system configured so that the field of view of one or more of the display units of the AR or VR head mounted display, and/or the field of view of the AR or VR head mounted display, and/or the virtual display, displayed by the AR or VR head mounted display and/or a tablet computer and/or a computer monitor, 1450 (solid line) is larger than the field of view of the microscope or endoscope 1460 (broken line), optionally captured by a video module or camera and/or displayed by one or more of the display units of an AR or VR head mounted display, and/or an AR or VR head mounted display, and/or a tablet computer, and/or a computer monitor. A tissue 1470 exposed and/or accessed to/by the microscope or endoscope is seen through the microscope or endoscope. An object can be physically located at a different location, orientation, angle, depth, coordinates than the focal plane and/or depth of field of the microscope or endoscope, e.g. focused and/or set and/or placed on the exposed and/or accessed tissue 1470 by the microscope or endoscope. The object can be a physical tissue, e.g. a tissue (for example a target tissue and/or a portion thereof) identified or imaged using an imaging test, for example an x-ray, x-ray based imaging, cone beam CT, digital tomosynthesis, CT, MRI, SPECT, PET, ultrasound, any other imaging modality known in the art, or a combination thereof. The object can, for example, also be a medical device, e.g. an implant, a surgical tool, a surgical instrument, or a combination thereof. A virtual display 1480 1482 of the object displayed by the one or more of the display units of the AR or VR head mounted display, and/or the AR or VR head mounted display, and/or the display of a tablet computer, and/or a computer monitor can be larger than and/or extend further than the field of view or the microscope or endoscope, optionally captured by a video module or camera and/or displayed by one or more of the display units of the AR or VR head mounted display, and/or the AR or VR head mounted display, and/or a tablet computer, and/or a computer monitor, or limited to a combination thereof. The virtual display 1480 1482 can extend outside 1482 and/or can be displayed outside 1482 the field of view of the microscope or endoscope 1460, optionally captured by a video module or camera and/or displayed by one or more of the display units of the AR or VR head mounted display, and/or the AR or VR head mounted display, and/or a tablet computer, and/or a computer monitor. One or more computer processors can be configured so that the virtual display is larger than and/or extends outside the field of view or the microscope or endoscope, optionally captured by a video module or camera and/or displayed by one or more of the display units of the AR or VR head mounted display, and/or the AR or VR head mounted display, and/or a tablet computer, and/or a computer monitor. In this example, the system is configured so that the virtual display comprises the virtual object 1480 1482, e.g. a target tissue (e.g. a disk herniation, a tumor, a soft-tissue, an organ tissue etc., for example located at the same or a different location, position, orientation than the focal plane and/or depth of field of the microscope or endoscope), and various other tissues, for example brain tissue, heart tissue, or spinal tissue, e.g. bone (for example a pedicle) 1490, one or more vertebrae 1492, one or more intervertebral disks or disk tissue 1494, one or more neural structures, e.g. nerve roots 1496, or thecal sac.

Figure 27G:
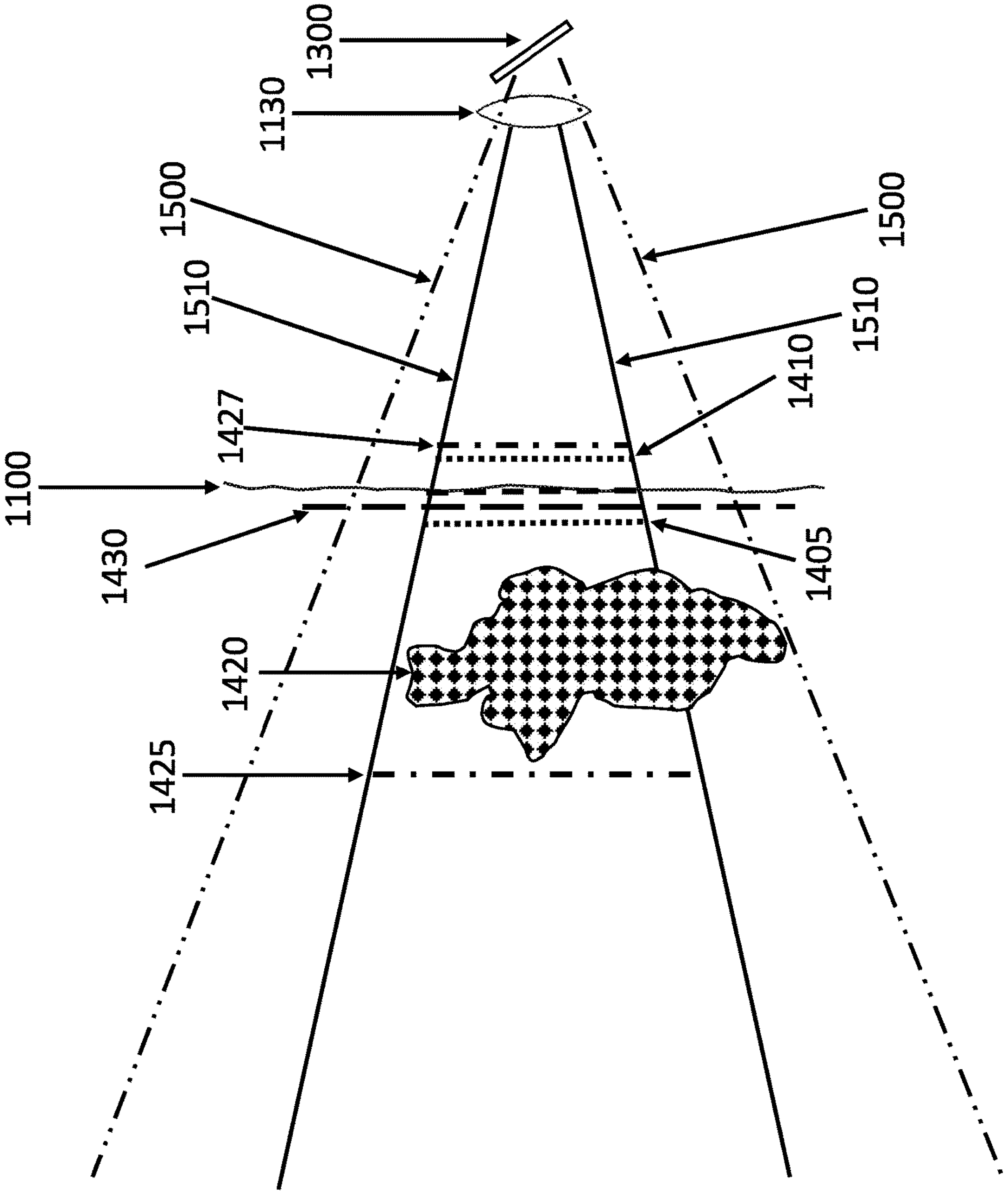

FIG. 27G is a non-limiting example of a system configured so that the field of view 1500 of one or more of the display units of the AR or VR head mounted display, and/or the field of view of the AR or VR head mounted display, and/or the virtual display, displayed by the AR or VR head mounted display (and its respective projection) is larger than the field of view 1510 of the microscope or endoscope (and its respective projection). In this non-limiting example, a first lens group 1130 of the microscope or endoscope and one or more augmented and/or virtual reality components and/or display units 1300 are also seen.

Figure 28A:
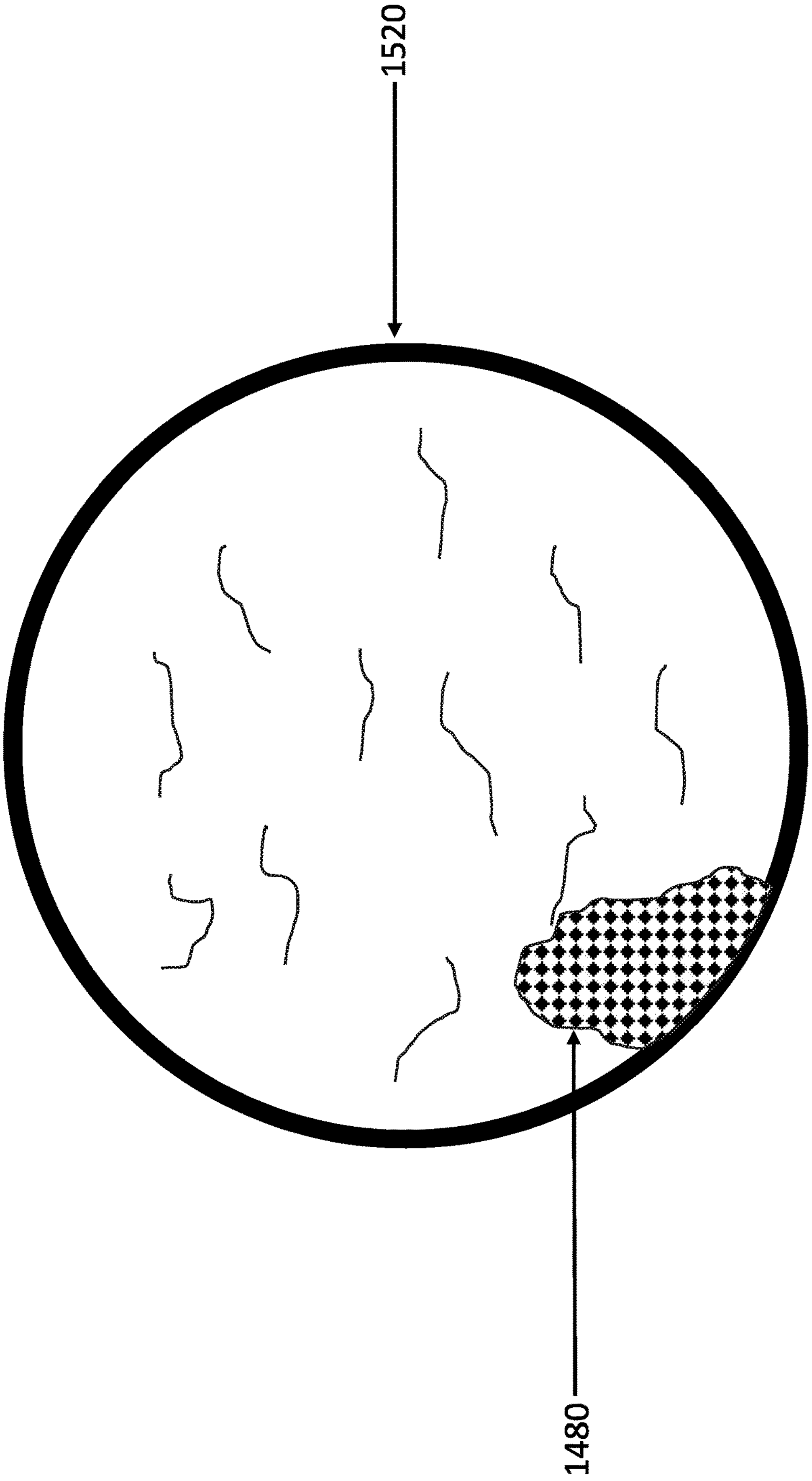
FIGS. 28A-28F provide illustrative, non-limiting examples of microscopes and endoscopes, optionally with a portal, access portal, tube, retractor or combination thereof, used in conjunction with ARDD, where the ARDD optionally has a similar or a larger field of view than a microscope and endoscope and/or larger than the opening of the portal, access portal, tube, retractor or combination thereof according to some embodiments of the present disclosure. The ARDD with a larger field of view can be configured to generate a virtual display of one or more target tissues that extend beyond the field of view of the microscope or endoscope and/or the opening of the portal, access portal, tube, retractor or combination thereof in one or more dimensions.

In some embodiments, an access, a portal, an access portal, a tube, a retractor, or a combination thereof 1520 can be used for creating, securing, and/or maintaining an access for a microscope, an endoscope, surgical tools, surgical instruments, devices, and/or implants. FIG. 28A is a non-limiting example of a system comprising an access, a portal, an access portal, a tube, a retractor, or a combination thereof 1520. FIG. 28A is a non-limiting example of a system with the field of view of one or more of the display units of the AR or VR head mounted display, and/or the field of view of the AR or VR head mounted display, and/or the virtual display (displayed by the AR or VR head mounted display and/or a tablet computer and/or a computer monitor) is the same or approximately the same as or similar to the diameter and/or the area, diameter, and/or surface of the tissue accessible and/or visible through the access, portal, access portal, tube, retractor, or a combination thereof 1520 for a microscope or endoscope.

Figure 28B:
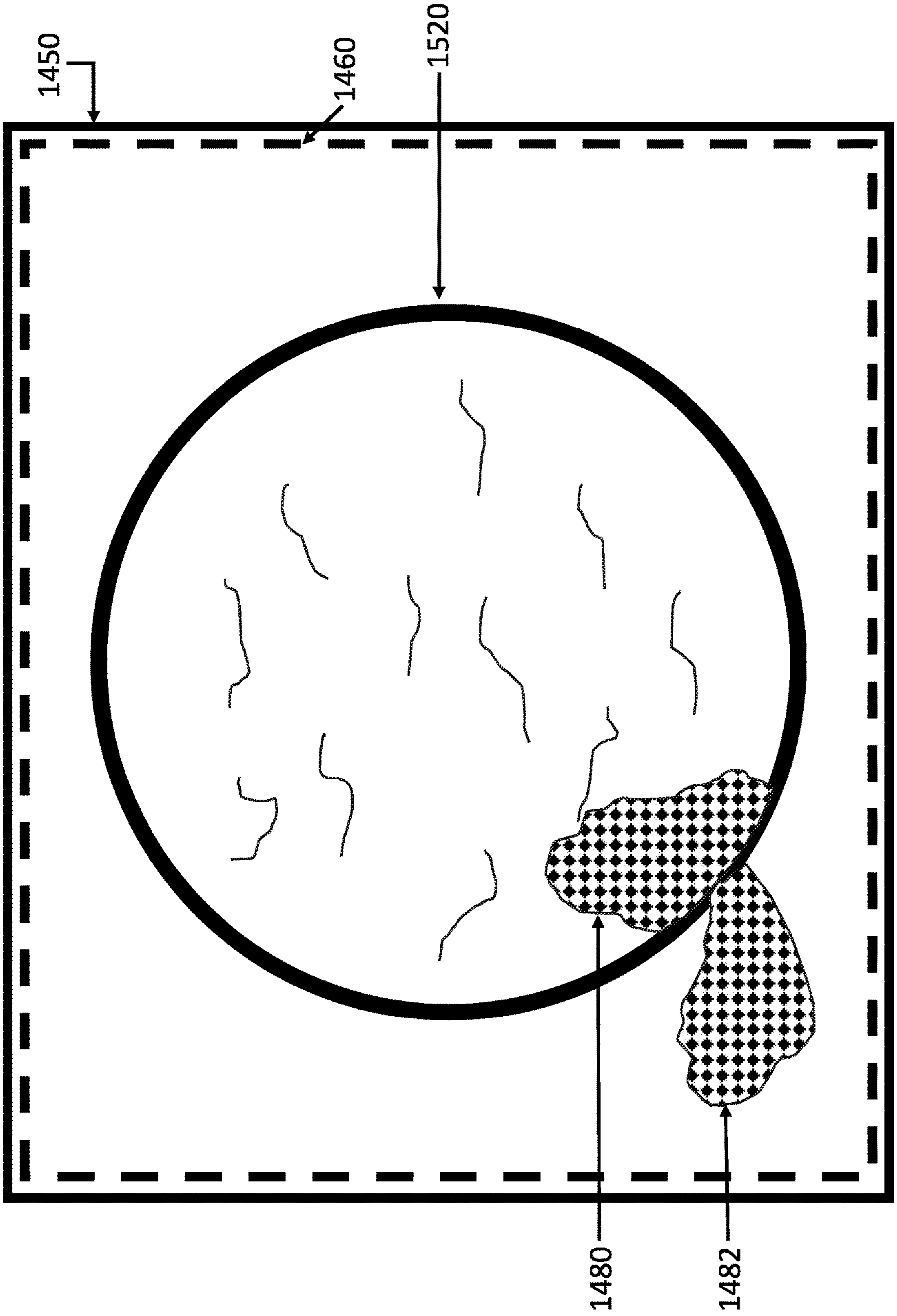

FIG. 28B is a non-limiting example of a system configured with the field of view of the microscope or endoscope 1460 (broken line), optionally captured by a video module or camera and/or displayed by one or more of display units of an AR or VR head mounted display, and/or an AR or VR head mounted display, and/or a tablet computer, and/or a computer monitor (optionally the same as the one used for displaying the virtual display) can be larger than or extend beyond the rim, edge, diameter, area, and/or surface of the access, portal, access portal, tube, retractor, or a combination thereof 1520 and/or the area, diameter, and/or surface of the tissue accessible and/or visible through the access, portal, access portal, tube, retractor, or a combination thereof 1520. In addition, the field of view of one or more of the display units of the AR or VR head mounted display, and/or the field of view of the AR or VR head mounted display, and/or the virtual display, displayed by the AR or VR head mounted display and/or a tablet computer and/or a computer monitor, 1450 (solid line) can be larger than or extend beyond the rim, edge, diameter, area, and/or surface of the access, portal, access portal, tube, retractor, or a combination thereof 1520 and/or the area, diameter, and/or surface of the tissue accessible and/or visible through the access, portal, access portal, tube, retractor, or a combination thereof 1520. A virtual display 1480 1482 of the object displayed by the one or more of the display units of the AR or VR head mounted display, and/or the AR or VR head mounted display, and/or the display of a tablet computer, and/or a computer monitor can be configured to be larger than and/or extend further than the rim, edge, diameter, area, and/or surface of the access, portal, access portal, tube, retractor, or a combination thereof 1520 and/or the area, diameter, and/or surface of the tissue accessible and/or visible through the access, portal, access portal, tube, retractor, or a combination thereof 1520. The virtual display 1480 1482 can be configured to extend outside 1482 and/or can be displayed outside 1482 the rim, edge, diameter, area, and/or surface of the access, portal, access portal, tube, retractor, or a combination thereof 1520 and/or the area, diameter, and/or surface of the tissue accessible and/or visible through the access, portal, access portal, tube, retractor, or a combination thereof 1520 through the microscope or endoscope. One or more computer processors can be configured so that the virtual display is larger than and/or extends outside the rim, edge, diameter, area, and/or surface of the access, portal, access portal, tube, retractor, or a combination thereof 1520 and/or the area, diameter, and/or surface of the tissue accessible and/or visible by the microscope or endoscope through the access, portal, access portal, tube, retractor, or a combination thereof 1520.

Figure 28C:
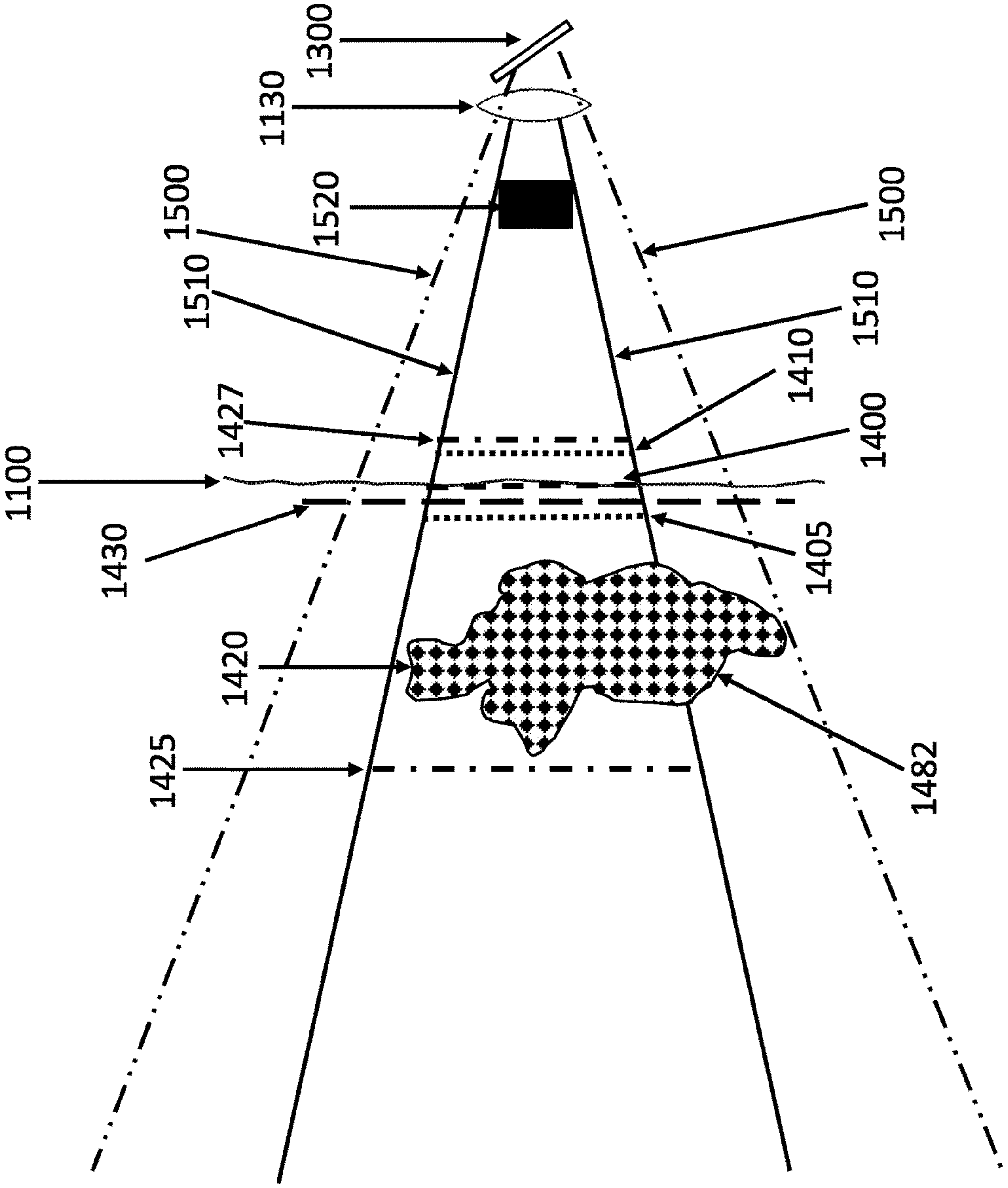

FIG. 28C is a non-limiting example of a side view of a system similar to or the same as configured in FIG. 28B. The access, portal, access portal, tube, retractor, or a combination thereof 1520 is shown, in this example in an implementation comprising a first lens group 1130 of the microscope or endoscope and one or more augmented and/or virtual reality components and/or display units 1300. A virtual display 1482 of a target tissue 1420 by the one or more of the display units of the AR or VR head mounted display, and/or the AR or VR head mounted display, and/or the display of a tablet computer, and/or a computer monitor can be configured to be larger than and/or extend further than the rim, edge, diameter, area, and/or surface of the access, portal, access portal, tube, retractor, or a combination thereof 1520 and/or the diameter, area, surface and/or volume of the tissue accessible and/or visible through the access, portal, access portal, tube, retractor, or a combination thereof 1520.

Figure 28D:
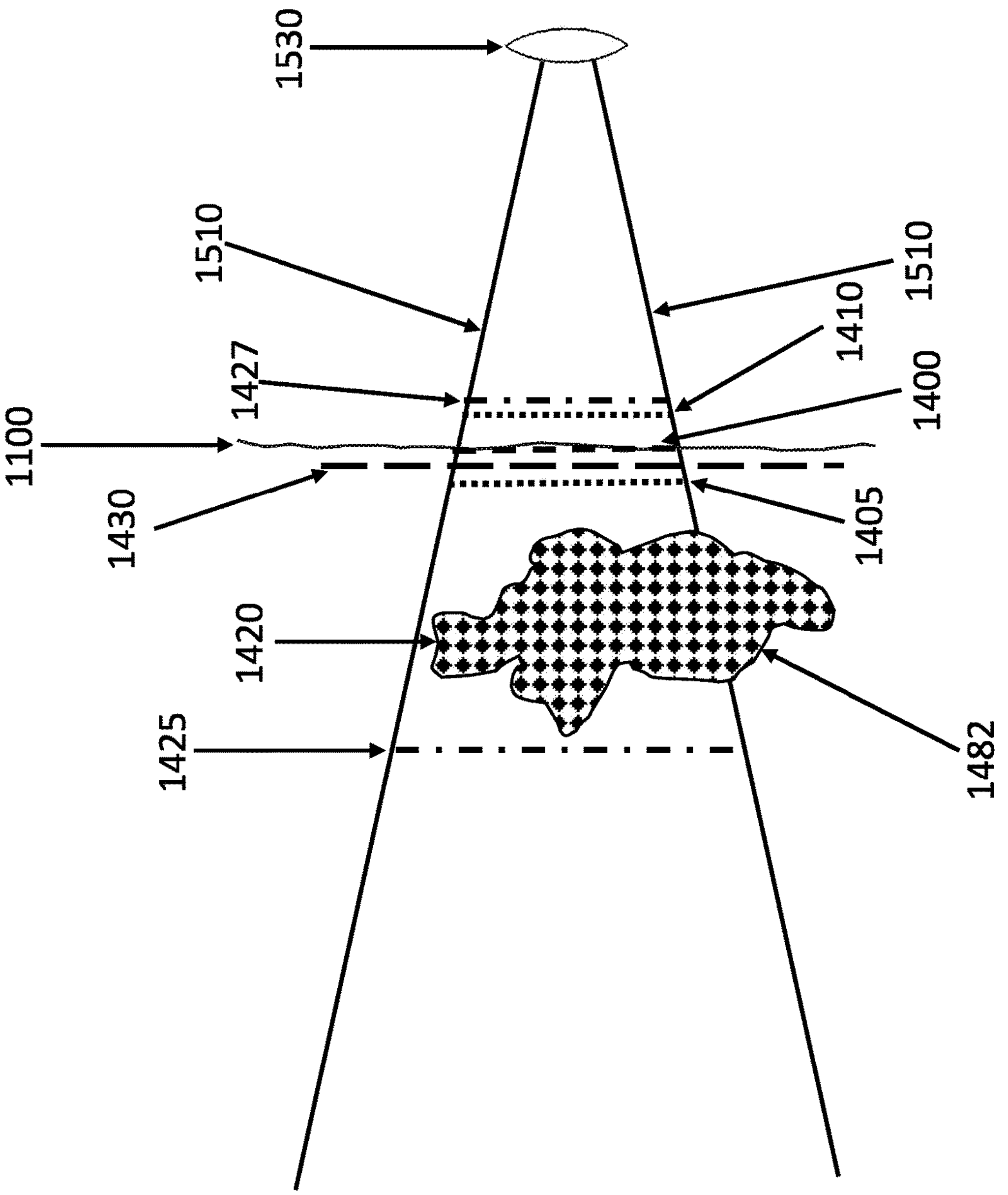

FIG. 28D is a non-limiting example of a side view of a system in an implementation with use of an endoscope. The endoscope view can be captured by an image sensor, a video module or camera and/or displayed by one or more of display units of an AR or VR head mounted display, and/or an AR or VR head mounted display, and/or a tablet computer, and/or a computer monitor (optionally the same as the one used for displaying the virtual display) (not shown here). A virtual display 1482 of a target tissue 1420 by the one or more of the display units of the AR or VR head mounted display, and/or the AR or VR head mounted display, and/or the display of a tablet computer, and/or a computer monitor can be configured to be larger than and/or extend further than the field of view of the endoscope 1510, optionally captured by an image sensor, a video module or camera and/or displayed by one or more of display units of the AR or VR head mounted display, and/or the AR or VR head mounted display, and/or the tablet computer, and/or the computer monitor displaying the virtual display 1482 of the target tissue 1420 or any other virtual object. This embodiment can be particularly useful for an endoscopist trying to direct the endoscope and any instruments advanced under endoscopic guidance towards a target tissue and/or an object, for example when the target tissue and/or object is hidden by interposed tissue, including, for example, tissue 1100 visible through the endoscope.

Figure 28E:
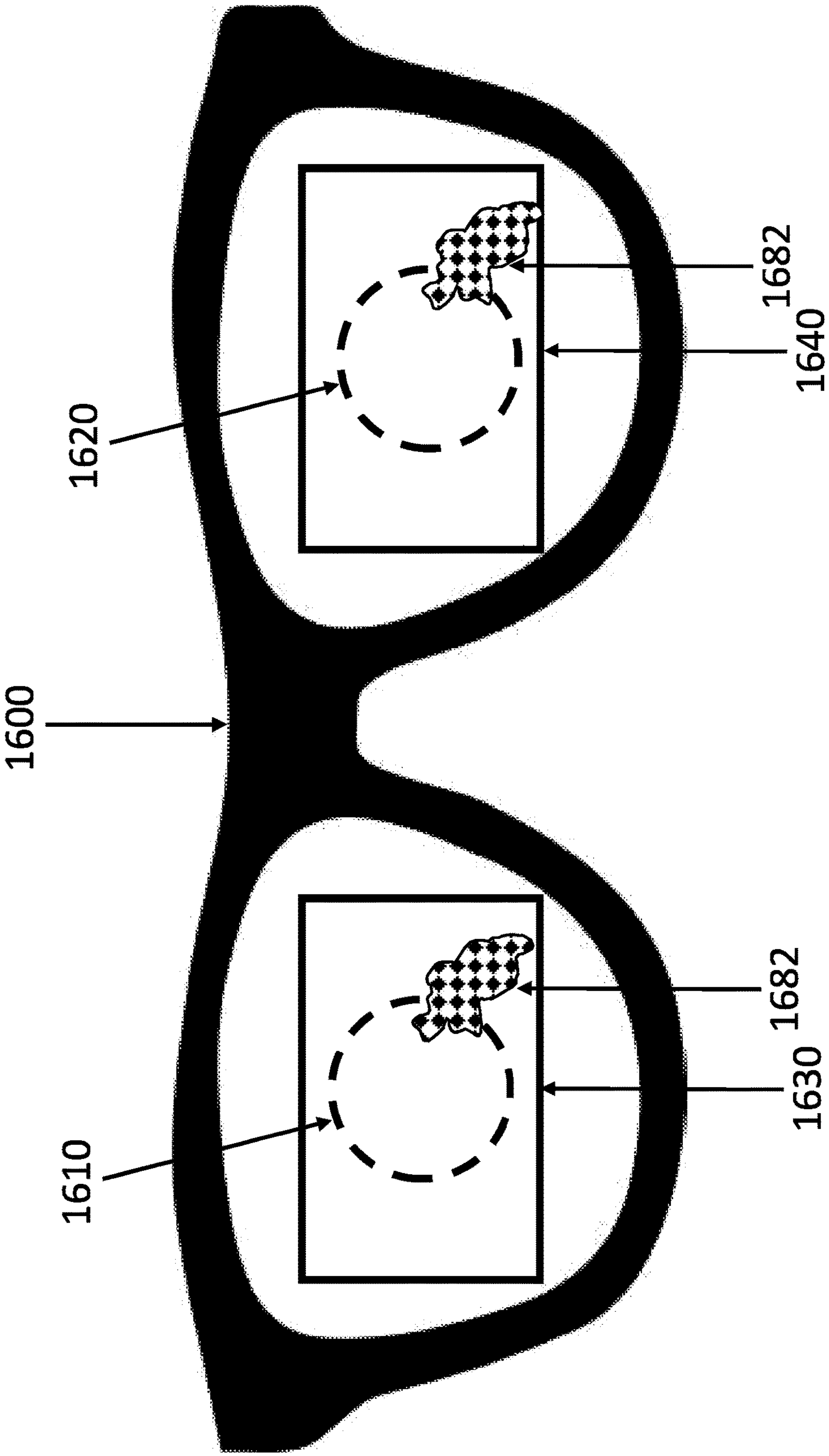

FIG. 28E is a non-limiting example of an AR or VR head mounted display with a display unit for a left eye and a display unit for a right eye. The field of view or view/display area 1610 1620 of the right eye and left eye display (2D or 3D, stereoscopic or non-stereoscopic) of the endoscopic view/images/video stream is shown. The field of view 1630 1640 of the right eye and left eye display unit of the AR or VR head mounted display is also shown. The field of view 1630 1640 of the right eye and left eye display unit of the AR or VR head mounted display is larger than the field of view or view/display area 1610 1620 of the right eye and left eye display (2D or 3D, stereoscopic or non-stereoscopic) of the endoscopic view/images/video stream displayed by the AR or VR head mounted display. The system is configured to generate a virtual display 1682 of a target tissue by the AR or VR head mounted display that is configured to be larger than and/or extend further than the field of view or view/display area 1610 1620 of the right eye and left eye display (2D or 3D, stereoscopic or non-stereoscopic) of the endoscopic view/images/video stream by the AR or VR head mounted display. The endoscopic view and the target tissue, including the virtual display 1682 of the target tissue, can be registered in a coordinate system as described throughout the disclosure, for example using intra-operative and/or pre-operative imaging, optionally with one or more reference phantoms and tracking techniques. The virtual display 1682 of the target tissue can be superimposed and/or overlaid on the endoscopic view/display, with both views in anatomically correct position relative to each other and/or scaled in relationship to each other. The virtual display 1682 of the target tissue can be superimposed and/or overlaid on the endoscopic view/display with both having approximately the same or the same magnification. The virtual display 1682 of the target tissue can be superimposed and/or overlaid on the endoscopic view/display with both having a different magnification, but, for example, the same center point or other point shared. Other virtual objects, e.g. virtual surgical guides, virtual tools, virtual instruments, virtual implants, and/or virtual devices, can optionally also be co-displayed, e.g. registered in the same coordinate system, optionally overlaid in a correct position (e.g. with the coordinate system) relative to the endoscopic display, within the virtual display and with the same and/or different magnification. This embodiment can be particularly useful for an endoscopist trying to direct the endoscope and any instruments advanced under endoscopic guidance towards a target tissue and/or an object. The virtual surgical guides, virtual tools, virtual instruments, virtual implants, and/or virtual devices can correspond to tracked physical surgical guides, physical tools, physical instruments, physical implants, and/or physical devices.

Figure 28F:
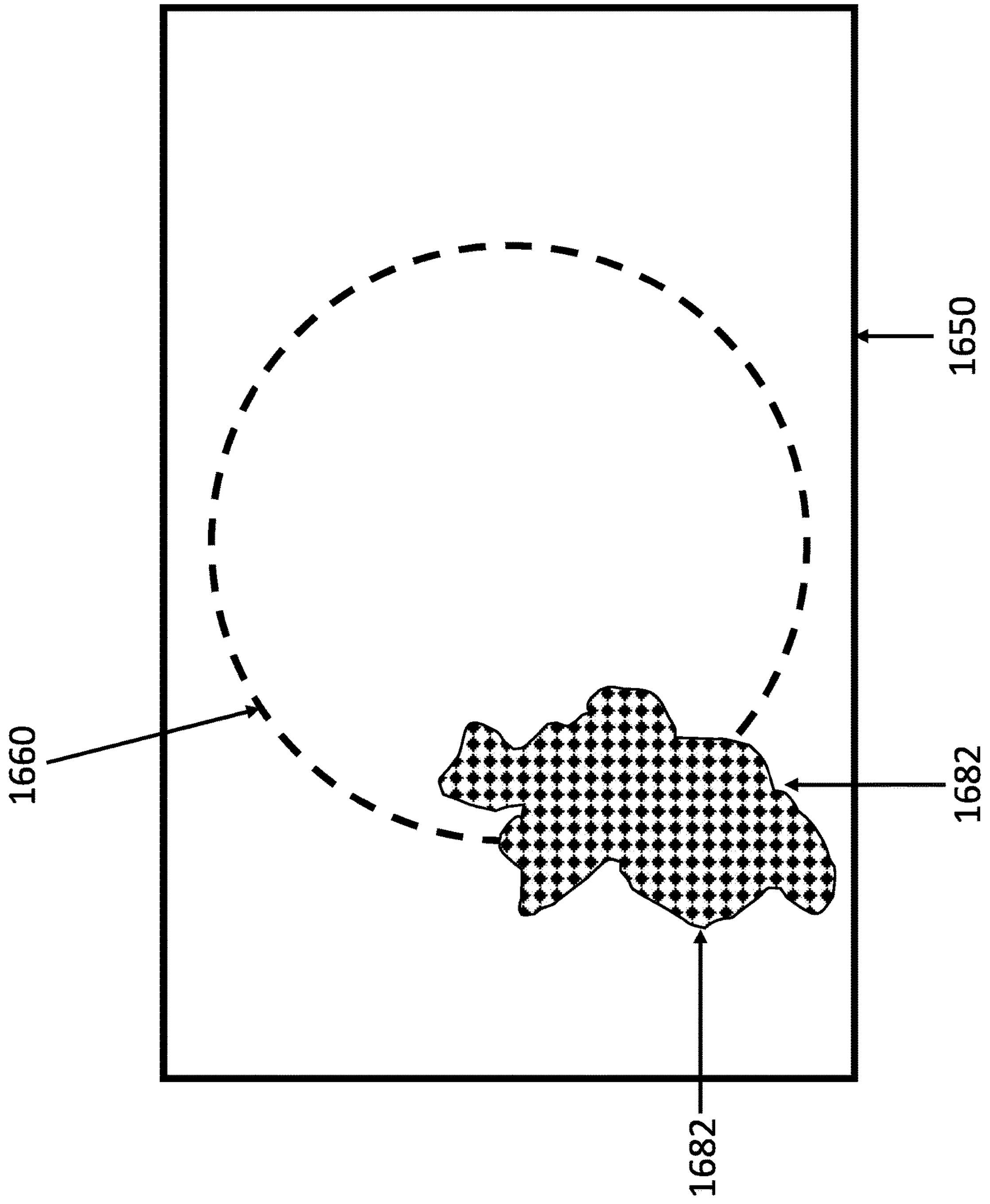

FIG. 28F is a non-limiting example of a tablet computer display or computer monitor 1650 used with a microscope or endoscope. The view/display area 1660 of the display of the endoscopic view/images/video stream is shown. The display dimension or size of the tablet computer display or computer monitor 1650 is larger than the view/display area 1660 of the endoscopic view/images/video stream displayed by the tablet computer display or computer monitor 1650. The system is configured to generate a virtual display 1682 of a target tissue by the tablet computer display or computer monitor 1650 that is configured to be larger than and/or extend further than the view/display area 1660 of the endoscopic view/images/video stream on the table computer display or computer monitor. The endoscopic view and the target tissue, including the virtual display 1682 of the target tissue, can be registered in a coordinate system. The virtual display 1682 of the target tissue can be superimposed and/or overlaid on the endoscopic view/display, with both views in anatomically correct position relative to each other and/or scaled in relationship to each other. The virtual display 1682 of the target tissue can have the same or a different magnification than the endoscopic view/display. Other virtual objects, e.g. virtual surgical guides, virtual tools, virtual instruments, virtual implants, and/or virtual devices, can optionally also be co-displayed, e.g. registered in the same coordinate system, optionally overlaid in a correct position (e.g. with the coordinate system) relative to the endoscopic display, within the virtual display, optionally with the same or different magnification. The virtual surgical guides, virtual tools, virtual instruments, virtual implants, and/or virtual devices can correspond to tracked physical surgical guides, physical tools, physical instruments, physical implants, and/or physical devices. This embodiment can be particularly useful for a surgeon trying to direct the microscope or endoscope and any instruments advanced under microscopic or endoscopic visualization with AR guidance towards a target tissue and/or an object.

In any of the foregoing embodiments, including the ones pertaining to different virtual focal planes, virtual depth of fields, microscope or endoscope focal planes, microscope or endoscope depth of fields, the virtual display can comprise a virtual display of 2D/3D anatomy (for example from a pre-operative and/or intra-operative imaging study), a virtual display of one or more virtual surgical plans, e.g. virtual surgical steps, virtual surgical techniques, virtual surgical guides (e.g. virtual axis, virtual plane, virtual resection plane), virtual surgical tools, virtual surgical instruments, virtual surgical devices, including virtual surgical implants. In any of the embodiments, a virtual display can be 2D and/or 3D, stereoscopic and/or non-stereoscopic, including any combinations thereof.

In some embodiments, the AR display can be configured so that an overlay of virtual data, e.g. a virtual display of 2D/3D anatomy (for example from a pre-operative and/or intra-operative imaging study), a virtual display of one or more virtual surgical plans, e.g. virtual surgical steps, virtual surgical techniques, virtual surgical guides (e.g. virtual axis, virtual plane, virtual resection plane), virtual surgical tools, virtual surgical instruments, virtual surgical devices, including virtual surgical implants are limited to the field of view of the microscope and/or endoscope, including any display of the field of view of the microscope and/or endoscope by an optical see through head mounted display, a video see through head mounted display, a tablet computer, and/or a computer monitor.

In some embodiments, the AR display can be configured so that an overlay of virtual data, e.g. a virtual display of 2D/3D anatomy (for example from a pre-operative and/or intra-operative imaging study), a virtual display of one or more virtual surgical plans, e.g. virtual surgical steps, virtual surgical techniques, virtual surgical guides (e.g. virtual axis, virtual plane, virtual resection plane), virtual surgical tools, virtual surgical instruments, virtual surgical devices, including virtual surgical implants can extend beyond the field of view of the microscope and/or endoscope and/or beyond the visible field, area or volume visible through a portal, an access, retractors or other tissue access means, including any display of the field of view of the microscope and/or endoscope by an optical see through head mounted display, a video see through head mounted display, a tablet computer, and/or a computer monitor.

ADDITIONAL EMBODIMENTS

1. A system comprising:

a microscope or an endoscope, an augmented reality display device, a computer processor, wherein the computer processor is configured for tracking the microscope or endoscope in a coordinate system, wherein the computer processor is configured for receiving at least one image of a physical target tissue, wherein the at least one image comprises an x-ray image, ultrasound image, computed tomography (CT) image, magnetic resonance imaging (MRI) image, single photon emission computed tomography (SPECT) image, positron emission tomography (PET) image, cone beam CT image, nuclear scintigraphy image or a combination thereof, wherein the at least one image is registered in the coordinate system, wherein the computer processor is configured for generating a virtual display of the physical target tissue, wherein the virtual display comprises a three-dimensional digital representation of the at least one image of the physical target tissue, wherein the computer processor is configured for tracking the patient, a physical tissue visible through the microscope or endoscope, the physical target tissue or a combination thereof in the coordinate system, wherein the computer processor is configured for generating an augmented view, the augmented view comprising the virtual display, wherein the augmented reality display device is configured to display the augmented view at the coordinates of the physical target tissue in the coordinate system, wherein the microscope or endoscope comprises a first field of view, wherein the augmented reality display device comprises a second field of view, wherein the second field of view is larger than the first field of view and comprises a portion that extends outside the first field of view, wherein the augmented reality display device is configured for displaying in at least one dimension a portion of the virtual display of the physical target tissue that extends outside the first field of view, outside a boundary of physical tissue visible through the microscope or endoscope, or a combination thereof.

2. The system of embodiment 1, wherein the system comprises an access, a portal, an access portal, a tube, a retractor, or a combination thereof configured to insert the microscope, the endoscope, a surgical tool, a surgical instrument, a device, an implant, or a combination thereof.

3. The system of embodiment 1, wherein the boundary comprises a wall, an edge, or a limit of one or more of an access, a portal, an access portal, a tube, a retractor, or a combination thereof, that limits area of the physical tissue visible through the microscope or endoscope.

4. The system of embodiment 2, wherein the access, portal, access portal, tube, retractor, or combination thereof is configured for viewing the physical tissue or the plane of the physical tissue through the microscope or endoscope, wherein the boundary is determined by the inner dimension of the access, portal, access portal, tube, retractor, or combination thereof.

5. The system of embodiment 1, wherein the field of view of the microscope or endoscope is an optical field of view.

6. The system of embodiment 1, wherein the field of view of the microscope or endoscope is a digital field of view.

7. The system of embodiment 1, wherein the augmented reality display device displays a digital image from the endoscope.

8. The system of embodiment 1, wherein the augmented reality display device is integrated into or attached to the microscope.

9. The system of embodiment 1, wherein the augmented view comprises a two dimensional (2D) stereoscopic view, a three-dimensional (3D) stereoscopic view or a combination thereof.

10. The system of embodiment 1, wherein the microscope is a digital microscope.

11. The system of embodiment 10, wherein the microscope is configured for capturing video images of the physical tissue.

12. The system of embodiment 1, wherein the microscope is a stereoscopic microscope.

13. The system of embodiment 1, wherein the endoscope is a digital endoscope.

14. The system of embodiment 13, wherein the endoscope is configured for capturing video images of the physical tissue.

15. The system of embodiment 1, wherein the endoscope is a stereoscopic endoscope.

16. The system of embodiment 1, wherein the at least one image of the physical target tissue is acquired by an imaging device intra-operatively, pre-operatively, or intra-operatively and pre-operatively.

17. The system of embodiment 16, wherein the imaging device is an x-ray device, ultrasound device, computed tomography (CT) device, magnetic resonance imaging (MRI) device, single photon emission computed tomography (SPECT) device, positron emission tomography (PET) device, cone beam CT device, or a nuclear scintigraphy device.

18. The system of embodiment 1, wherein the augmented reality display device is a computer monitor, a tablet computer, a head mounted display, a stereoscopic optical see through head mounted display, or a stereoscopic video see through head mounted display.

19. The system of embodiment 1, wherein the augmented reality display device is an augmented reality display unit integrated into or attached to a microscope or endoscope.

20. The system of embodiment 1, wherein the physical target tissue is, at least in part, hidden from the view through the microscope or endoscope by the physical tissue visible through the microscope or endoscope.

21. The system of embodiment 1, wherein the physical target tissue is not visible through the microscope or endoscope.

22. The system of embodiment 1, wherein the augmented reality display device comprises at least one augmented reality display unit.

23. The system of embodiment 22, wherein the augmented reality display unit comprises at least one of a cathode ray tube, liquid crystal display, organic light emitting diodes (OLED), mirror, waveguide, optical fiber, light pipe, combiner, or a combination thereof.

24. The system of embodiment 23, wherein the waveguide comprises at least one of a planar waveguide, slab waveguide, dielectric waveguide, strip waveguide, rib waveguide, segmented waveguide, rectangular waveguide, photonic crystal waveguide, laser inscribed waveguide, or a combination thereof.

25. The system of embodiment 22, wherein the field of view of the augmented reality display device is larger than the field of view of the microscope or endoscope.

26. The system of embodiment 1, wherein the at least one image of the physical target tissue comprises a volume of images.

27. The system of embodiment 26, wherein the volume of images of the physical target tissue extends in at least one dimension outside a boundary of the physical tissue or the plane of the physical tissue visible through the microscope or endoscope.

28. The system of embodiment 27, wherein the at least dimension comprises an x-dimension, y-dimension, z-dimension or a combination thereof.

29. The system of embodiment 1, wherein the virtual display comprises a 2D or a 3D representation of a virtual tool, virtual instrument, virtual implant, virtual device or a combination thereof, wherein the virtual tool, virtual instrument, virtual implant, virtual device or a combination thereof correspond to a physical tool, physical instrument, physical implant, physical device or a combination thereof.

30. The system of embodiment 29, comprising a tracking device configured for tracking the physical tool, physical instrument, physical implant, physical device or a combination thereof in the coordinate system.

31. The system of embodiment 30, wherein the physical tool, physical instrument, physical implant, physical device or a combination thereof comprises at least one infrared marker, retroreflective marker, radio frequency (RF) marker, active marker, passive marker, Inertial measurement unit (IMU), light emitting diode (LED), optical marker, geometric pattern, and the tracking device comprises a surgical navigation system, camera, video system, image capture system, depth sensor, laser scanner, 3D scanner, Lidar system, patient specific marker, patient specific template, x-ray system, imaging system, electromagnetic field, electromagnetic sensor, or combination thereof configured for tracking the physical tool, physical instrument, physical implant, physical device or combination thereof.

32. The system of embodiment 1, wherein the physical target tissue is a normal tissue, a diseased tissue, a neoplastic tissue, an inflamed tissue, an infected tissue, an edematous tissue, a tumor, a disc, a disc herniation, a free fragment, a bone, a bone spur, an organ tissue, a bowel, a bowel wall, a stomach, an esophagus, a stomach tissue, an esophageal wall, a bladder, a bladder all, a bladder tissue, a urethra, a urether, a renal pelvis, a renal tissue, a bronchus, a bronchial tissue, a trachea, a tracheal tissue, an intra-articular tissue, a ligament, a meniscus, a cartilage, a subchondral bone, a vessel, or a vascular tissue.

33. The system of embodiment 1, wherein the physical target tissue and the physical tissue are different.

34. The system of embodiment 1, wherein the computer processor is configured for real-time tracking of the microscope or endoscope, the patient, a physical tissue visible through the microscope or endoscope, the physical target tissue or a combination thereof in the coordinate system.

35. The system of embodiment 1, wherein the imaging system is different than the microscope or endoscope.

36. The system of embodiment 1, wherein the augmented reality display device is configured to display the augmented view at the coordinates of the physical target tissue in the coordinate system superimposed onto the physical tissue visible through the microscope or endoscope.

37. A computer-implemented method comprising:
tracking a microscope or an endoscope in a coordinate system,
receiving at least one image of a physical target tissue from an imaging system different than the microscope or endoscope,
wherein the physical target tissue is not visible through the microscope or endoscope,
registering the at least one image in the coordinate system,
generating a virtual display of the physical target tissue,
wherein the virtual display comprises a three-dimensional digital representation of the at least one image of the physical target tissue,
tracking a patient, a physical tissue visible through the microscope or endoscope, the physical target tissue or a combination thereof in the coordinate system,
wherein the physical target tissue and the physical tissue are different, generating an augmented view, the augmented view comprising the virtual display, displaying the augmented view at the coordinates of the physical target tissue in the coordinate system; and
displaying the physical target tissue outside a field of view of the microscope or endoscope,
wherein a portion of the augmented view extends outside the field of view of view of the microscope or endoscope.

38. The method of embodiment 37, comprising displaying the augmented view at the coordinates of the physical target tissue in the coordinate system superimposed onto the physical tissue visible through the microscope or endoscope.

39. The method of embodiment 37, comprising acquiring the at least one image of the physical target tissue intra-operatively, pre-operatively, or intra-operatively and pre-operatively.

40. The method of embodiment 38, wherein the at least one image comprises an x-ray, ultrasound scan, CT scan, MRI scan, SPECT scan, PET scan, cone beam CT scan, nuclear scintigraphy scan, or a combination thereof.

41. The method of embodiment 37, wherein the at least one image of the physical target tissue comprises a volume of images.

42. The method of embodiment 41, wherein the volume of images of the physical target tissue extends in at least one dimension outside a boundary of the physical tissue or the plane of the physical tissue visible through the microscope or endoscope.

43. The method of embodiment 42, wherein the at least dimension comprises an x-dimension, y-dimension, z-dimension or a combination thereof.

44. A surgical method comprising:
placing an access, a portal, an access portal, a tube, a retractor, or a combination thereof in a patient,
inserting a microscope, an endoscope, a surgical tool, a surgical instrument, a device, an implant, or a combination thereof through the access, a portal, an access portal, a tube, a retractor, or a combination thereof in a patient,
tracking the microscope or endoscope in a coordinate system,
receiving at least one image of a physical target tissue from an imaging system different than the microscope or endoscope,
wherein the physical target tissue is not visible through the microscope or endoscope,
registering the at least one image in the coordinate system,
generating a virtual display of the physical target tissue,
wherein the virtual display comprises a three-dimensional digital representation of the at least one image of the physical target tissue,
tracking a patient, a physical tissue visible through the microscope or endoscope, the physical target tissue or a combination thereof in the coordinate system, wherein the physical target tissue and the physical tissue are different,
generating an augmented view, the augmented view comprising the virtual display,
displaying the augmented view at the coordinates of the physical target tissue in the coordinate system,
displaying the physical target tissue outside a field of view of the microscope or endoscope, wherein a portion of the augmented view extends outside the field of view of view of the microscope or endoscope, generating a virtual display comprising a 2D or a 3D representation of a virtual tool, virtual instrument, virtual implant, virtual device or a combination thereof, wherein the virtual tool, virtual instrument, virtual implant, virtual device or a combination thereof correspond to a physical tool, physical instrument, physical implant, physical device or a combination thereof, tracking the surgical tool, surgical instrument, device, implant or combination thereof in the coordinate system outside the field of view of the microscope or endoscope.

45. A method of performing a surgery in a patient using a microscope or endoscope intra-operatively comprising:

tracking the microscope or endoscope in a coordinate system, adjusting a focal plane of the microscope or endoscope so that the focal plane extends, at least in part, through a physical tissue or a plane of a physical tissue exposed or accessed during the surgery, determining coordinates of the focal plane of the microscope or endoscope in the coordinate system, determining coordinates of a physical target tissue in the coordinate system or determining coordinates of an image of the physical target tissue in the coordinate system, wherein the physical target tissue has, at least in part, coordinates different from the physical tissue or the plane of the physical tissue, tracking the patient, the physical tissue or the plane or the physical tissue, the physical target tissue or a combination thereof in the coordinate system, displaying a computer-generated virtual display of the physical target tissue, a computer-generated virtual display of a three-dimensional (3D) representation of the image of the physical target tissue, or an image of the physical target tissue by an augmented reality display device at the coordinates of the physical target tissue in the coordinate system, and adjusting the focal plane of the virtual display or the focal plane of the image of the physical target tissue so that the focal plane of the virtual display or the image of the physical target tissue is the same as the focal plane of the microscope or endoscope, and/or so that a depth of field of the virtual display or of image of the physical target tissue overlaps, at least partially, with a depth of field of the microscope or endoscope.

46. The method of embodiment 45, wherein the focal plane of the microscope or endoscope is, at least in part, parallel to a portion of the physical tissue exposed or accessed during the surgery or to the plane of the physical tissue exposed or accessed during the surgery.

47. The method of embodiment 45, wherein the physical target tissue is, at least in part, hidden from the view through the microscope or endoscope by the physical tissue exposed or accessed during surgery or the plane of the physical tissue exposed or accessed during surgery.

48. The method of embodiment 45, comprising digitally transferring the coordinates of the focal plane of the microscope or endoscope from a computer processor of the microscope or endoscope to a computer processor of the augmented reality display device.

49. The method of embodiment 48, comprising adjusting the focal plane of the virtual display to be the same or similar as the focal plane of the microscope or endoscope using the computer processor of the augmented reality display device.

50. The method of embodiment 49, wherein the focal plane of the virtual display is parallel to the focal plane of the microscope or endoscope.

51. The method of embodiment 50, wherein the focal plane of the virtual display differs from the focal plane of the microscope or endoscope by from about 0.001 mm to about 10 mm.

52. The method of embodiment 45, wherein the focal plane of the virtual display comprises one or more coordinates that are the same as the coordinates of the focal plane of the microscope or endoscope.

53. The method of embodiment 45, wherein the field of view of the augmented reality device is the same or smaller than the field of view of the microscope or endoscope.

54. The method of embodiment 45, wherein the field of view of the augmented reality device is larger than the field of view of the microscope or endoscope.

55. The method of embodiment 45, wherein the image of the physical target tissue comprises a volume of images.

56. The method of embodiment 55, wherein the volume of images of the physical target tissue extends in at least one dimension outside a boundary of the physical tissue or the plane of the physical tissue visible through the microscope or endoscope.

57. The method of embodiment 56, comprising placing a tube for viewing the physical tissue or the plane of the physical tissue through the microscope or endoscope, wherein the boundary is determined by the inner dimension of the tube.

58. The method of embodiment 56, wherein the at least dimension comprises an x-dimension, y-dimension, z-dimension or a combination thereof.

59. The method of embodiment 57, comprising displaying by augmented reality display device a computer-generated virtual display comprising a portion of the physical target tissue, wherein the computer-generated virtual display extends outside the boundary, the field of view of the microscope or endoscope or a combination thereof, wherein the field of view of the augmented reality display device is wider than the boundary, the field of view of the microscope or endoscope or a combination thereof.

60. The method of embodiment 45, wherein the virtual display comprises the three-dimensional representation of the image of the physical target tissue.

61. The method of embodiment 60, comprising setting shading of the three-dimensional representation for the coordinates of the physical target tissue in the coordinate system or for the coordinates of the at least one image of the physical target tissue in the coordinate system.

62. The method of embodiment 45, comprising acquiring the image of the physical target tissue intra-operatively, pre-operatively, or intra-operatively and pre-operatively, wherein the image comprises an x-ray, ultrasound scan, CT scan, MRI scan, single photon emission computed tomography (SPECT) scan, positron emission tomography (PET) scan, cone beam CT scan, nuclear scintigraphy scan, or a combination thereof.

63. The method of embodiment 62, comprising displaying, by the augmented reality display device, at least one two-dimensional (2D) image of the patient, 2D image of the target tissue, or combination thereof in a window adjacent to a window displaying the tissue or tissue plane visible through the microscope or endoscope.

64. The method of embodiment 45, wherein the computer-generated virtual display comprises a 2D or a 3D representation of a virtual tool, virtual instrument, virtual implant, virtual device or a combination thereof, wherein the virtual tool, virtual instrument, virtual implant, virtual device or a combination thereof correspond to a physical tool, physical instrument, physical implant, physical device or a combination thereof.

65. The method of embodiment 64, comprising tracking the physical tool, physical instrument, physical implant, physical device or a combination thereof in the coordinate system.

66. The method of embodiment 65, comprising tracking the physical tool, physical instrument, physical implant, physical device or combination thereof with at least one infrared marker, retroreflective marker, RF marker, active marker, passive marker, IMU, LED, optical marker, geometric pattern, or a combination thereof using a surgical navigation system, camera, video system, image capture system, depth sensor, laser scanner, 3D scanner, Lidar system, patient specific marker, patient specific template, x-ray system, imaging system, electromagnetic field, electromagnetic sensor, or combination thereof.

67. The method of embodiment 45, wherein the depth of field of the virtual display by the augmented reality display device overlaps, at least in part, with the depth of field of the microscope or endoscope, wherein the overlap is from about 0.1 mm to about 40 mm.

68. The method of embodiment 45, comprising adjusting magnification of the computer-generated virtual display to match magnification of the microscope or endoscope, wherein the magnification of the microscope or endoscope is about 0.5× to about 30.0×.

69. The method of embodiment 68, wherein the magnified computer-generated virtual display comprises the image of the physical target tissue, a virtual 3D representation of the physical target tissue, a virtual surgical guide, a virtual axis, a virtual plane, a virtual tool, a virtual instrument, a virtual implant, a virtual device or a combination thereof.

70. The method of embodiment 45, wherein the target tissue is a normal tissue, a diseased tissue, a neoplastic tissue, an inflamed tissue, an infected tissue, an edematous tissue, a tumor, a disc, a disc herniation, a free fragment, a bone, a bone spur, an organ tissue, a bowel, a bowel wall, a stomach, an esophagus, a stomach tissue, an esophageal wall, a bladder, a bladder all, a bladder tissue, a urethra, a urether, a renal pelvis, a renal tissue, a bronchus, a bronchial tissue, a trachea, a tracheal tissue, an intra-articular tissue, a ligament, a meniscus, a cartilage, a subchondral bone, a vessel, or a vascular tissue.

71. The method of embodiment 45, comprising tracking in real-time the microscope or endoscope, the patient, a physical tissue visible through the microscope or endoscope, the physical target tissue or a combination thereof in the coordinate system.

72. The method of embodiment 45, comprising displaying the computer-generated virtual display by an augmented reality display device at the coordinates of the physical target tissue in the coordinate system overlaid onto the physical tissue or physical tissue plane visible through the microscope or endoscope.

73. The method of embodiment 45, wherein the physical target tissue is different than the physical tissue.

74. The method of embodiment 45, wherein the augmented reality display device comprises a computer monitor, a tablet computer, a head mounted display, a stereoscopic optical see through head mounted display, or a stereoscopic video see through head mounted display, or wherein the augmented reality display device comprises an augmented reality display united integrated or attached into the microscope or endoscope.

75. A method of performing a surgery in a patient using a microscope or endoscope intra-operatively comprising:

tracking the microscope or endoscope in a coordinate system, adjusting a focal plane of the microscope or endoscope so that the focal plane extends, at least in part, through a physical tissue or a plane of a physical tissue exposed or accessed during the surgery, determining coordinates of the focal plane of the microscope or endoscope in the coordinate system, determining coordinates of a physical target tissue in the coordinate system or determining coordinates of an image of the physical target tissue in the coordinate system, wherein the physical target tissue and the image of the physical target tissue have, at least in part, coordinates different from the physical tissue or the plane of the physical tissue, tracking the patient, the physical tissue or the plane of the physical tissue, the physical target tissue or a combination thereof in the coordinate system, generating, by a computer processor, a virtual display of the physical target tissue, wherein the virtual display is a three-dimensional representation of at least one image of the physical target tissue, displaying a computer-generated virtual display of the physical target tissue, a computer-generated virtual display of a three-dimensional (3D) representation of the image of the physical target tissue, or an image of the physical target tissue at the coordinates of the physical target tissue in the coordinate system, adjusting the focal plane of the virtual display or the image of the physical target tissue so that the focal plane of the virtual display or the image of the physical target tissue is the same as the focal plane of the microscope or endoscope, and/or so that a depth of field of the virtual display or of the image of the physical target tissue overlaps, at least partially, with a depth of field of the microscope or endoscope.

76. A method of performing a surgery in a patient using a microscope or endoscope intra-operatively comprising:

tracking the microscope or endoscope in a coordinate system, adjusting a focal plane of the microscope or endoscope so that the focal plane extends, at least in part, through a physical tissue or a plane of a physical tissue exposed or accessed during the surgery, determining coordinates of the focal plane of the microscope or endoscope in the coordinate system, determining coordinates of a physical target tissue in the coordinate system and/or determining coordinates of an image of the physical target tissue in the coordinate system, wherein the physical target tissue has, at least in part, coordinates different from the physical tissue or the plane of the physical tissue, tracking the patient, the physical tissue or the plane or the physical tissue, the physical target tissue or a combination thereof in the coordinate system, displaying a computer-generated virtual display of the physical target tissue, a computer-generated virtual display of a 3D representation of the image of the physical target tissue, or an image of the physical target tissue at the coordinates of the physical target tissue in the coordinate system, adjusting the depth of field of the virtual display or of the image of the physical target tissue so that the depth of field overlaps, at least partially, with a depth of field of the microscope or endoscope.

77. A system comprising:

a microscope or an endoscope, wherein the microscope or endoscope has an adjustable focal plane, an augmented reality device, a tracking device, and a computer processor, wherein the computer processor is configured to determine coordinates of the focal plane of the microscope or endoscope in the coordinate system, wherein the computer processor is configured to determine coordinates of a physical target tissue in the coordinate system and/or determining coordinates of an image of the physical target tissue in the coordinate system, wherein the physical target tissue has, at least in part, coordinates different from the physical tissue or the plane of the physical tissue, wherein the tracking device is configured to track the patient, the physical tissue or the plane or the physical tissue, the physical target tissue or a combination thereof in the coordinate system, wherein the augmented reality device is configured to display a virtual display of the physical target tissue, a virtual display of a 3D representation of the image of the physical target tissue, or an image of the physical target tissue at the coordinates of the physical target tissue in the coordinate system overlaid onto the physical tissue or physical tissue plane visible through the microscope or endoscope, wherein the computer processor is configured to adjust the depth of field of the virtual display or of the image of the physical target tissue so that the depth of field overlaps, at least partially, with a depth of field of the microscope or endoscope.

78. The system of embodiment 77, wherein the augmented reality display device is a computer monitor, a tablet computer, a head mounted display, a stereoscopic optical see through head mounted display, or a stereoscopic video see through head mounted display.

79. The system of embodiment 77, wherein the augmented reality display device is an augmented reality display unit integrated into or attached to a microscope or endoscope.

80. 33. The system of embodiment 77, wherein a computer processor of the microscope or endoscope and a computer processor of the augmented reality display device are the same.

81. 34. The system of embodiment 77, wherein a computer processor of the microscope or endoscope and a computer processor of the augmented reality display device are different.

82. The system of embodiment 77, wherein the augmented reality display device comprises at least one augmented reality display unit.

83. The system of embodiment 82, wherein the augmented reality display unit comprises at least one of a cathode ray tube, liquid crystal display, organic light emitting diodes (OLED), mirror, waveguide, optical fiber, light pipe, combiner, or a combination thereof.

84. The system of embodiment 83, wherein the waveguide comprises at least one of a planar waveguide, slab waveguide, dielectric waveguide, strip waveguide, rib waveguide, segmented waveguide, rectangular waveguide, photonic crystal waveguide, laser inscribed waveguide, or a combination thereof.

85. A method of performing a surgery in a patient using an endoscope intra-operatively comprising:

tracking the endoscope in a coordinate system, wherein a focal plane of the endoscope extends, at least in part, through a physical tissue or a plane of a physical tissue exposed or accessed during the surgery, determining coordinates of the focal plane of the endoscope in the coordinate system, determining coordinates of a physical target tissue in the coordinate system or determining coordinates of at least one image of the physical target tissue in the coordinate system, wherein the physical target tissue has, at least in part, coordinates different from the physical tissue or the plane of the physical tissue, tracking the patient, the physical tissue or the plane of the physical tissue, the physical target tissue or a combination thereof in the coordinate system, generating, by a computer processor, a virtual display of the physical target tissue, wherein the virtual display is a three-dimensional digital representation of at least one image of the physical target tissue, displaying a computer-generated virtual display of the physical target tissue by an augmented reality display device at the coordinates of the physical target tissue in the coordinate system, setting the focal plane of the virtual display so that the focal plane of the virtual display is the same as the focal plane of the endoscope, wherein a depth of field of the virtual display overlaps, at least partially, with a depth of field of the endoscope.

86. A method of performing a surgery in a patient using an endoscope intra-operatively comprising:

tracking the endoscope in a coordinate system, wherein a focal plane of the endoscope extends, at least in part, through a physical tissue or a plane of a physical tissue exposed or accessed during the surgery, determining coordinates of the focal plane of the endoscope in the coordinate system, determining coordinates of a physical target tissue in the coordinate system and/or determining coordinates of at least one image of the physical target tissue in the coordinate system, wherein the physical target tissue has, at least in part, coordinates different from the physical tissue or the plane of the physical tissue, tracking the patient, the physical tissue or the plane or the physical tissue, the physical target tissue or a combination thereof in the coordinate system, displaying a computer-generated virtual display of the physical target tissue by an augmented reality display device at the coordinates of the physical target tissue in the coordinate system, setting the focal plane of the virtual display so that the focal plane of the virtual display is the same as the focal plane of the endoscope, wherein a depth of field of the virtual display overlaps, at least partially, with a depth of field of the endoscope.

87. A method of performing a surgery in a patient using an endoscope intra-operatively comprising:

tracking the endoscope in a coordinate system, wherein a focal plane of the endoscope extends, at least in part, through a physical tissue or a plane of a physical tissue exposed or accessed during the surgery, determining coordinates of the focal plane and a depth of field of the endoscope in the coordinate system, determining coordinates of a physical target tissue in the coordinate system and/or determining coordinates of at least one image of the physical target tissue in the coordinate system, wherein the physical target tissue has, at least in part, coordinates different from the physical tissue or the plane of the physical tissue, tracking the patient, the physical tissue or the plane or the physical tissue, the physical target tissue or a combination thereof in the coordinate system, displaying a computer-generated virtual display of the physical target tissue by an augmented reality display device at the coordinates of the physical target tissue in the coordinate system, setting the depth of field of the virtual display so that the depth of field of the virtual display overlaps, at least partially, with a depth of field of the endoscope.

88. The method of embodiments 85-87 XX comprising displaying a computer-generated virtual display overlaid onto the physical tissue or physical tissue plane visible through the endoscope.

EXAMPLES

Example 1

In this example, a surgery is performed in a patient using a microscope or endoscope intra-operatively comprising: tracking the microscope or endoscope in a coordinate system, adjusting a focal plane of the microscope or endoscope so that the focal plane extends, at least in part, through a physical tissue or a plane of a physical tissue exposed or accessed during the surgery, determining coordinates of the focal plane of the microscope or endoscope in the coordinate system, determining coordinates of a physical target tissue in the coordinate system or determining coordinates of an image of the physical target tissue in the coordinate system, wherein the physical target tissue has, at least in part, coordinates different from the physical tissue or the plane of the physical tissue, tracking the patient, the physical tissue or the plane or the physical tissue, the physical target tissue or a combination thereof in the coordinate system, displaying a computer-generated virtual display of the physical target tissue, a computer-generated virtual display of a three-dimensional (3D) representation of the image of the physical target tissue, or an image of the physical target tissue by an augmented reality display device at the coordinates of the physical target tissue in the coordinate system, adjusting the focal plane of the virtual display or the focal plane of the image of the physical target tissue so that the focal plane of the virtual display or the image of the physical target tissue is the same as the focal plane of the microscope or endoscope, and/or so that a depth of field of the virtual display or image of the physical target tissue overlaps, at least partially, with a depth of field of the microscope or endoscope. In some embodiments, the focal plane of the microscope or endoscope is, at least in part, parallel to a portion of the physical tissue exposed or accessed during the surgery or to the plane of the physical tissue exposed or accessed during the surgery. In some embodiments, the physical target tissue is, at least in part, hidden from the view through the microscope or endoscope by the physical tissue exposed or accessed during surgery or the plane of the physical tissue exposed or accessed during surgery. The coordinates of the focal plane of the microscope or endoscope can be digitally transferred from a computer processor of the microscope or endoscope to a computer processor of the augmented reality display device. The focal plane of the virtual display can be adjusted to be the same or similar as the focal plane of the microscope or endoscope using the computer processor of the augmented reality display device. some embodiments, the focal plane of the virtual display is parallel to the focal plane of the microscope or endoscope. In some embodiments, the focal plane of the virtual display differs from the focal plane of the microscope or endoscope by from about 0.001 mm to about 10 mm. The focal plane of the virtual display can comprise one or more coordinates that are the same as the coordinates of the focal plane of the microscope or endoscope. The field of view of the augmented reality device can be the same or smaller than the field of view of the microscope or endoscope. The field of view of the augmented reality device can be larger than the field of view of the microscope or endoscope. The image of the physical target tissue can comprise a volume of images. The volume of images of the physical target tissue can extend in at least one dimension outside a boundary of the physical tissue or the plane of the physical tissue visible through the microscope or endoscope. A tube or access portal can be placed for viewing the physical tissue or the plane of the physical tissue through the microscope or endoscope, wherein the boundary is determined by the inner dimension of the tube or access portal. In some embodiments, the at least dimension comprises an x-dimension, y-dimension, z-dimension or a combination thereof. In a non-limiting extension, a computer-generated virtual display is displayed by an augmented reality display device comprising a portion of the physical target tissue, wherein the computer-generated virtual display extends outside the boundary, the field of view of the microscope or endoscope or a combination thereof, wherein the field of view of the augmented reality display device can be wider than the boundary, the field of view of the microscope or endoscope or a combination thereof. In some embodiments, the virtual display comprises a three-dimensional digital representation of the image of the physical target tissue. Some embodiments further comprise shading of the three-dimensional digital representation is set or defined for the coordinates of the physical target tissue in the coordinate system or for the coordinates of the at least one image of the physical target tissue in the coordinate system. Some embodiments further comprise acquiring the image of the physical target tissue intra-operatively, pre-operatively, or intra-operatively and pre-operatively, wherein the image comprises an x-ray, ultrasound scan, CT scan, MRI scan, single photon emission computed tomography (SPECT) scan, positron emission tomography (PET) scan, cone beam CT scan, nuclear scintigraphy scan, or a combination thereof. Some embodiments further comprise displaying, by the augmented reality display device, at least one two-dimensional (2D) image of the patient, 2D image of the target tissue, or combination thereof in a window adjacent to a window displaying the tissue or tissue plane visible through the microscope or endoscope. The computer-generated virtual display can also comprise a 2D or a 3D representation of a virtual tool, virtual instrument, virtual implant, virtual device or a combination thereof, wherein the virtual tool, virtual instrument, virtual implant, virtual device or a combination thereof correspond to a physical tool, physical instrument, physical implant, physical device or a combination thereof. Some embodiments further comprise tracking the physical tool, physical instrument, physical implant, physical device or a combination thereof in the coordinate system. Some embodiments further comprise tracking the physical tool, physical instrument, physical implant, physical device or combination thereof with at least one infrared marker, retroreflective marker, RF marker, active marker, passive marker, IMU, LED, optical marker, geometric pattern, or a combination thereof using a surgical navigation system, camera, video system, image capture system, depth sensor, laser scanner, 3D scanner, Lidar system, patient specific marker, patient specific template, x-ray system, imaging system, electromagnetic field, electromagnetic sensor, or combination thereof. The depth of field of the virtual display by the augmented reality display device can overlap, at least in part, with the depth of field of the microscope or endoscope, wherein the overlap is from about 0.1 mm to about 40 mm. Some embodiments further comprise adjusting magnification of the computer-generated virtual display to match magnification of the microscope or endoscope, wherein the magnification of the microscope or endoscope is about 0.5× to about 30.0×. The magnified computer-generated virtual display can comprise the image of the physical target tissue, a virtual 3D representation of the physical target tissue, a virtual surgical guide, a virtual axis, a virtual plane, a virtual tool, a virtual instrument, a virtual implant, a virtual device or a combination thereof. The target tissue can be a normal tissue, a diseased tissue, a neoplastic tissue, an inflamed tissue, an infected tissue, an edematous tissue, a tumor, a disc, a disc herniation, a free fragment, a bone, a bone spur, an organ tissue, a bowel, a bowel wall, a stomach, an esophagus, a stomach tissue, an esophageal wall, a bladder, a bladder all, a bladder tissue, a urethra, a urether, a renal pelvis, a renal tissue, a bronchus, a bronchial tissue, a trachea, a tracheal tissue, an intra-articular tissue, a ligament, a meniscus, a cartilage, a subchondral bone, a vessel, or a vascular tissue. Some embodiments further comprise tracking in real-time the microscope or endoscope, the patient, a physical tissue visible through the microscope or endoscope, the physical target tissue or a combination thereof in the coordinate system. Some embodiments further comprise displaying the computer-generated virtual display by an augmented reality display device at the coordinates of the physical target tissue in the coordinate system overlaid onto the physical tissue or physical tissue plane visible through the microscope or endoscope. The physical target tissue is different than the physical tissue. The augmented reality display device can comprise a computer monitor, a tablet computer, a head mounted display, a stereoscopic optical see through head mounted display, or a stereoscopic video see through head mounted display. The augmented reality display device can comprise at least one augmented reality display unite integrated or attached into the microscope or endoscope.

Example 2

In this example, a surgery is performed in a patient using a microscope or endoscope intra-operatively comprising: tracking the microscope or endoscope in a coordinate system, adjusting a focal plane of the microscope or endoscope so that the focal plane extends, at least in part, through a physical tissue or a plane of a physical tissue exposed or accessed during the surgery, determining coordinates of the focal plane of the microscope or endoscope in the coordinate system, determining coordinates of a physical target tissue in the coordinate system or determining coordinates of an image of the physical target tissue in the coordinate system, wherein the physical target tissue and the image of the physical target tissue have, at least in part, coordinates different from the physical tissue or the plane of the physical tissue, tracking the patient, the physical tissue or the plane of the physical tissue, the physical target tissue or a combination thereof in the coordinate system, generating, by a computer processor, a virtual display of the physical target tissue, wherein the virtual display is a three-dimensional digital representation of at least one image of the physical target tissue, displaying a computer-generated virtual display of the physical target tissue, a computer-generated virtual display of a three-dimensional (3D) representation of the image of the physical target tissue, or an image of the physical target tissue at the coordinates of the physical target tissue in the coordinate system, adjusting the focal plane of the virtual display or the image of the physical target tissue so that the focal plane of the virtual display or the image of the physical target tissue is the same as the focal plane of the microscope or endoscope, and/or so that a depth of field of the virtual display or the image of the physical target tissue overlaps, at least partially, with a depth of field of the microscope or endoscope.

Example 3

In this example, a surgery is performed in a patient using a microscope or endoscope intra-operatively comprising: tracking the microscope or endoscope in a coordinate system, adjusting a focal plane of the microscope or endoscope so that the focal plane extends, at least in part, through a physical tissue or a plane of a physical tissue exposed or accessed during the surgery, determining coordinates of the focal plane of the microscope or endoscope in the coordinate system, determining coordinates of a physical target tissue in the coordinate system and/or determining coordinates of an image of the physical target tissue in the coordinate system, wherein the physical target tissue has, at least in part, coordinates different from the physical tissue or the plane of the physical tissue, tracking the patient, the physical tissue or the plane or the physical tissue, the physical target tissue or a combination thereof in the coordinate system, displaying a computer-generated virtual display of the physical target tissue, a computer-generated virtual display of a 3D representation of the image of the physical target tissue, or an image of the physical target tissue at the coordinates of the physical target tissue in the coordinate system, adjusting the depth of field of the virtual display or the image of the physical target tissue so that the depth of field overlaps, at least partially, with a depth of field of the microscope or endoscope.

Example 4

In this example, a surgery is performed using a system comprising: a microscope or an endoscope, wherein the microscope or endoscope has an adjustable focal plane, an augmented reality device, a tracking device, and a computer processor, wherein the computer processor is configured to determine coordinates of the focal plane of the microscope or endoscope in the coordinate system, wherein the computer processor is configured to determine coordinates of a physical target tissue in the coordinate system and/or determining coordinates of an image of the physical target tissue in the coordinate system, wherein the physical target tissue has, at least in part, coordinates different from the physical tissue or the plane of the physical tissue, wherein the tracking device is configured to track the patient, the physical tissue or the plane or the physical tissue, the physical target tissue or a combination thereof in the coordinate system, wherein the augmented reality device is configured to display a virtual display of the physical target tissue, a virtual display of a 3D representation of the image of the physical target tissue, or an image of the physical target tissue at the coordinates of the physical target tissue in the coordinate system overlaid onto the physical tissue or physical tissue plane visible through the microscope or endoscope, wherein the computer processor is configured to adjust the depth of field of the virtual display or the image of the physical target tissue so that the depth of field overlaps, at least partially, with a depth of field of the microscope or endoscope. In some embodiments, the augmented reality display device is a computer monitor, a tablet computer, a head mounted display, a stereoscopic optical see through head mounted display, or a stereoscopic video see through head mounted display. In some embodiments, the augmented reality display device is an augmented reality display unit integrated into or attached to a microscope or endoscope. In some embodiments, a computer processor of the microscope or endoscope and a computer processor of the augmented reality display device are the same. In some embodiments, a computer processor of the microscope or endoscope and a computer processor of the augmented reality display device are different. In some embodiments, the augmented reality display device comprises at least one augmented reality display unit. In some embodiments, the augmented reality display unit comprises at least one of a cathode ray tube, liquid crystal display, organic light emitting diodes (OLED), mirror, waveguide, optical fiber, light pipe, combiner, or a combination thereof. some embodiments, the waveguide comprises at least one of a planar waveguide, slab waveguide, dielectric waveguide, strip waveguide, rib waveguide, segmented waveguide, rectangular waveguide, photonic crystal waveguide, laser inscribed waveguide, or a combination thereof.

Example 5

In this example, a surgery is performed in a patient using an endoscope intra-operatively comprising: tracking the endoscope in a coordinate system, wherein a focal plane of the endoscope extends, at least in part, through a physical tissue or a plane of a physical tissue exposed or accessed during the surgery, determining coordinates of the focal plane of the endoscope in the coordinate system, determining coordinates of a physical target tissue in the coordinate system or determining coordinates of at least one image of the physical target tissue in the coordinate system, wherein the physical target tissue has, at least in part, coordinates different from the physical tissue or the plane of the physical tissue, tracking the patient, the physical tissue or the plane of the physical tissue, the physical target tissue or a combination thereof in the coordinate system, generating, by a computer processor, a virtual display of the physical target tissue, wherein the virtual display is a three-dimensional digital representation of at least one image of the physical target tissue, displaying a computer-generated virtual display of the physical target tissue by an augmented reality display device at the coordinates of the physical target tissue in the coordinate system, setting the focal plane of the virtual display so that the focal plane of the virtual display is the same as the focal plane of the endoscope, wherein a depth of field of the virtual display overlaps, at least partially, with a depth of field of the endoscope.

Example 6

In this example, a surgery is performed in a patient using an endoscope intra-operatively comprising: tracking the endoscope in a coordinate system, wherein a focal plane of the endoscope extends, at least in part, through a physical tissue or a plane of a physical tissue exposed or accessed during the surgery, determining coordinates of the focal plane of the endoscope in the coordinate system, determining coordinates of a physical target tissue in the coordinate system and/or determining coordinates of at least one image of the physical target tissue in the coordinate system, wherein the physical target tissue has, at least in part, coordinates different from the physical tissue or the plane of the physical tissue, tracking the patient, the physical tissue or the plane or the physical tissue, the physical target tissue or a combination thereof in the coordinate system, displaying a computer-generated virtual display of the physical target tissue by an augmented reality display device at the coordinates of the physical target tissue in the coordinate system, setting the focal plane of the virtual display so that the focal plane of the virtual display is the same as the focal plane of the endoscope, wherein a depth of field of the virtual display overlaps, at least partially, with a depth of field of the endoscope.

Example 7

In this example, a surgery is performed in a patient using an endoscope intra-operatively comprising: tracking the endoscope in a coordinate system, wherein a focal plane of the endoscope extends, at least in part, through a physical tissue or a plane of a physical tissue exposed or accessed during the surgery, determining coordinates of the focal plane and a depth of field of the endoscope in the coordinate system, determining coordinates of a physical target tissue in the coordinate system and/or determining coordinates of at least one image of the physical target tissue in the coordinate system, wherein the physical target tissue has, at least in part, coordinates different from the physical tissue or the plane of the physical tissue, tracking the patient, the physical tissue or the plane or the physical tissue, the physical target tissue or a combination thereof in the coordinate system, displaying a computer-generated virtual display of the physical target tissue by an augmented reality display device at the coordinates of the physical target tissue in the coordinate system, setting the depth of field of the virtual display so that the depth of field of the virtual display overlaps, at least partially, with a depth of field of the endoscope. An extension of this example comprises displaying a computer-generated virtual display overlaid onto the physical tissue or physical tissue plane visible through the endoscope.

Example 8

In this example, a surgery is performed in a patient with a system comprising: a microscope or an endoscope, an augmented reality display device, a computer processor, wherein the computer processor is configured for tracking the microscope or endoscope in a coordinate system, wherein the computer processor is configured for receiving at least one image of a physical target tissue, wherein the at least one image comprises an x-ray image, ultrasound image, computed tomography (CT) image, magnetic resonance imaging (MRI) image, single photon emission computed tomography (SPECT) image, positron emission tomography (PET) image, cone beam CT image, nuclear scintigraphy image or a combination thereof, wherein the at least one image is registered in the coordinate system, wherein the computer processor is configured for generating a virtual display of the physical target tissue, wherein the virtual display comprises a three-dimensional digital representation of the at least one image of the physical target tissue, wherein the computer processor is configured for tracking the patient, a physical tissue visible through the microscope or endoscope, the physical target tissue or a combination thereof in the coordinate system, wherein the computer processor is configured for generating an augmented view, the augmented view comprising the virtual display, wherein the augmented reality display device is configured to display the augmented view at the coordinates of the physical target tissue in the coordinate system, wherein the microscope or endoscope comprises a first field of view, wherein the augmented reality display device comprises a second field of view, wherein the second field of view is larger than the first field of view and comprises a portion that extends outside the first field of view, wherein the augmented reality display device is configured for displaying in at least one dimension a portion of the virtual display of the physical target tissue that extends outside the first field of view, outside a boundary of physical tissue visible through the microscope or endoscope, or a combination thereof. In some embodiments, the system further comprises an access, a portal, an access portal, a tube, a retractor, or a combination thereof configured to insert the microscope, the endoscope, a surgical tool, a surgical instrument, a device, an implant, or a combination thereof. In some embodiments, the boundary comprises a wall, an edge, or a limit of one or more of an access, a portal, an access portal, a tube, a retractor, or a combination thereof, that limits area of the physical tissue visible through the microscope or endoscope. In some embodiments, the access, portal, access portal, tube, retractor, or combination thereof is configured for viewing the physical tissue or the plane of the physical tissue through the microscope or endoscope, wherein the boundary is determined by the inner dimension of the access, portal, access portal, tube, retractor, or combination thereof. In some embodiments, the field of view of the microscope or endoscope is an optical field of view. In some embodiments, the field of view of the microscope or endoscope is a digital field of view. In some embodiments, the microscope or endoscope comprises an image sensor or video module for capturing optical images from the optical elements of the microscope or endoscope. In some embodiments, one or more computer processors convert the microscope or endoscopic views to digital data, wherein the digital data can comprise a digital video feed. some embodiments, the augmented reality display device displays a digital image from the endoscope. some embodiments, the augmented reality display device is integrated into or attached to the microscope. In some embodiments, the augmented view comprises a two dimensional (2D) stereoscopic view, a three-dimensional (3D) stereoscopic view or a combination thereof. In some embodiments, the microscope is a digital microscope. In some embodiments, the microscope is configured for capturing video images of the physical tissue. In a non-limiting extension of this example, the microscope is a stereoscopic microscope. some embodiments, the endoscope is a digital endoscope. In some embodiments, the endoscope is configured for capturing video images of the physical tissue. In some embodiments, the endoscope is a stereoscopic endoscope. some embodiments, the at least one image of the physical target tissue is acquired by an imaging device intra-operatively, pre-operatively, or intra-operatively and pre-operatively. some embodiments, the imaging device is an x-ray device, ultrasound device, computed tomography (CT) device, magnetic resonance imaging (MRI) device, single photon emission computed tomography (SPECT) device, positron emission tomography (PET) device, cone beam CT device, or a nuclear scintigraphy device. In some embodiments, the augmented reality display device is a computer monitor, a tablet computer, a head mounted display, a stereoscopic optical see through head mounted display, or a stereoscopic video see through head mounted display. In some embodiments, the augmented reality display device is an augmented reality display unit integrated into or attached to a microscope or endoscope. In some embodiments, the physical target tissue is, at least in part, hidden from the view through the microscope or endoscope by the physical tissue visible through the microscope or endoscope. In some embodiments, the physical target tissue is not visible through the microscope or endoscope. some embodiments, the augmented reality display device comprises at least one augmented reality display unit. In some embodiments, the augmented reality display unit comprises at least one of a cathode ray tube, liquid crystal display, organic light emitting diodes (OLED), mirror, waveguide, optical fiber, light pipe, combiner, or a combination thereof. some embodiments, the waveguide comprises at least one of a planar waveguide, slab waveguide, dielectric waveguide, strip waveguide, rib waveguide, segmented waveguide, rectangular waveguide, photonic crystal waveguide, laser inscribed waveguide, or a combination thereof. In some embodiments, the field of view of the augmented reality display device is larger than the field of view of the microscope or endoscope. In some embodiments, the at least one image of the physical target tissue comprises a volume of images. The volume of images of the physical target tissue can extends in at least one dimension outside a boundary of the physical tissue or the plane of the physical tissue visible through the microscope or endoscope. The at least dimension can comprise an x-dimension, y-dimension, z-dimension or a combination thereof. some embodiments, the virtual display comprises a 2D or a 3D representation of a virtual tool, virtual instrument, virtual implant, virtual device or a combination thereof, wherein the virtual tool, virtual instrument, virtual implant, virtual device or a combination thereof correspond to a physical tool, physical instrument, physical implant, physical device or a combination thereof. Some embodiments further comprise tracking device configured for tracking the physical tool, physical instrument, physical implant, physical device or a combination thereof in the coordinate system. In some embodiments, the physical tool, physical instrument, physical implant, physical device or a combination thereof comprises at least one infrared marker, retroreflective marker, radio frequency (RF) marker, active marker, passive marker, Inertial measurement unit (IMU), light emitting diode (LED), optical marker, geometric pattern, and the tracking device comprises a surgical navigation system, camera, video system, image capture system, depth sensor, laser scanner, 3D scanner, Lidar system, patient specific marker, patient specific template, x-ray system, imaging system, electromagnetic field, electromagnetic sensor, or combination thereof configured for tracking the physical tool, physical instrument, physical implant, physical device or combination thereof. In some embodiments, the physical target tissue is a normal tissue, a diseased tissue, a neoplastic tissue, an inflamed tissue, an infected tissue, an edematous tissue, a tumor, a disc, a disc herniation, a free fragment, a bone, a bone spur, an organ tissue, a bowel, a bowel wall, a stomach, an esophagus, a stomach tissue, an esophageal wall, a bladder, a bladder all, a bladder tissue, a urethra, a urether, a renal pelvis, a renal tissue, a bronchus, a bronchial tissue, a trachea, a tracheal tissue, an intra-articular tissue, a ligament, a meniscus, a cartilage, a subchondral bone, a vessel, or a vascular tissue. In some embodiments, the physical target tissue and the physical tissue are different. In some embodiments, the computer processor is configured for real-time tracking of the microscope or endoscope, the patient, a physical tissue visible through the microscope or endoscope, the physical target tissue or a combination thereof in the coordinate system. In some embodiments, the imaging system is different than the microscope or endoscope; e.g. the imaging system can be an x-ray, ultrasound, CT, MRI, cone beam CT, SPECT, PET, nuclear scintigraphy system or a combination thereof. In some embodiments, the augmented reality display device is configured to display the augmented view at the coordinates of the physical target tissue in the coordinate system superimposed onto the physical tissue visible through the microscope or endoscope.

Example 9

In this example, a surgery is performed in a patient using a computer-implemented method comprising: tracking a microscope or an endoscope in a coordinate system, receiving at least one image of a physical target tissue from an imaging system different than the microscope or endoscope, wherein the physical target tissue is not visible through the microscope or endoscope, registering the at least one image in the coordinate system, generating a virtual display of the physical target tissue, wherein the virtual display comprises a three-dimensional digital representation of the at least one image of the physical target tissue, tracking a patient, a physical tissue visible through the microscope or endoscope, the physical target tissue or a combination thereof in the coordinate system, wherein the physical target tissue and the physical tissue are different, generating an augmented view, the augmented view comprising the virtual display, displaying the augmented view at the coordinates of the physical target tissue in the coordinate system, displaying the physical target tissue outside a field of view of the microscope or endoscope, wherein a portion of the augmented view extends outside the field of view of view of the microscope or endoscope. Some embodiments further comprise displaying the augmented view at the coordinates of the physical target tissue in the coordinate system superimposed onto the physical tissue visible through the microscope or endoscope. Some embodiments further comprise acquiring the at least one image of the physical target tissue intra-operatively, pre-operatively, or intra-operatively and pre-operatively. In a non-limiting extension of this example the at least one image comprises an x-ray, ultrasound scan, CT scan, MRI scan, SPECT scan, PET scan, cone beam CT scan, nuclear scintigraphy scan, or a combination thereof. In some embodiments, the at least one image of the physical target tissue comprises a volume of images. In some embodiments, the volume of images of the physical target tissue extends in at least one dimension outside a boundary of the physical tissue or the plane of the physical tissue visible through the microscope or endoscope. In some embodiments, the at least dimension comprises an x-dimension, y-dimension, z-dimension or a combination thereof.

Example 10

In this example, a surgery is performed in a patient comprising: placing an access, a portal, an access portal, a tube, a retractor, or a combination thereof in a patient, inserting a microscope, an endoscope, a surgical tool, a surgical instrument, a device, an implant, or a combination thereof through the access, a portal, an access portal, a tube, a retractor, or a combination thereof in a patient, tracking the microscope or endoscope in a coordinate system, receiving at least one image of a physical target tissue from an imaging system different than the microscope or endoscope, wherein the physical target tissue is not visible through the microscope or endoscope, registering the at least one image in the coordinate system, generating a virtual display of the physical target tissue, wherein the virtual display comprises a three-dimensional digital representation of the at least one image of the physical target tissue, tracking a patient, a physical tissue visible through the microscope or endoscope, the physical target tissue or a combination thereof in the coordinate system, wherein the physical target tissue and the physical tissue are different, generating an augmented view, the augmented view comprising the virtual display, displaying the augmented view at the coordinates of the physical target tissue in the coordinate system, displaying the physical target tissue outside a field of view of the microscope or endoscope, wherein a portion of the augmented view extends outside the field of view of view of the microscope or endoscope, generating a virtual display comprising a 2D or a 3D representation of a virtual tool, virtual instrument, virtual implant, virtual device or a combination thereof, wherein the virtual tool, virtual instrument, virtual implant, virtual device or a combination thereof correspond to a physical tool, physical instrument, physical implant, physical device or a combination thereof, tracking the surgical tool, surgical instrument, device, implant or combination thereof in the coordinate system outside the field of view of the microscope or endoscope.

Example 11

In this example, a surgery is performed using a head mounted display that is configured to switch from optical see through mode to video see through mode. The head mounted display can comprise at least one optical filter, polarizing filter, liquid crystal display (LCD) or combinations thereof. An optical filter can be designed to block light from passing through the HMD; an operator can move the optical filter from a non-light-blocking position for optical see through head mounted display application to a light-blocking position for video see-through head mounted display application. When polarizing light filters are used, an operator can move the polarizing filters from a non-light-blocking position for optical see through head mounted display application to a light-blocking position for video see through head mounted display application.

An LCD can be a flat panel style display or an electronically modulate optical device or display with light modulating properties of liquid crystals which can be combined with polarizers. Pixels of an LCD can consist of a layer of molecules aligned between transparent electrodes (typically two), which can, for example, be made of indium tin oxide and two polarizing filters. The polarizing filters can be parallel and perpendicular polarizing filters. Light passing through the first filter will be blocked by the second polarizing filter without the liquid crystal in between. Prior to activating an electric field, the orientation of the liquid-crystal molecules is determined by the alignment at the surfaces of electrodes. For example, in a so-called twisted nematic LCD device, the surface alignment direction at the first and second electrode are orthogonal to each other, with the molecules arranging themselves in a spiral or helical structure. This will cause the rotation of the polarization of the incident light; the device and the screen or surface where it is applied or integrated appears gray. If the voltage is sufficiently high, the liquid crystal molecules become almost entirely untwisted and the polarization of the incident light is not rotated as it passes through the liquid crystal layer. However, this light will be predominantly polarized perpendicular to the second filter, thereby being blocked with the pixel appearing black. In this manner, different voltages can be used for achieving different degrees of light passing through the LCD or being blocked from passing through the LCD. This and similar LCD designs and configurations can be used in head mounted displays. Thus, the transparency of a head mounted display can be modulated from optical see through head mounted display to video see-through head mounted display, whereby the "video" in this example implies that one or more images or video feed are displayed by the HMD such as video feed from a patient and surgical site, including video feed from a microscope (e.g. exoscope with video feed only) or endoscope.

A surgeon can change the transparency and switch an HMD from "optical see-through mode" to "video see-through mode" with use of a manual button, e.g. on the side of an HMD, voice control, or a virtual user interface, e.g. virtual buttons displayed by the HMD with activation via gaze tracking, as described in other parts of the disclosure.

The surgeon can operate, for example, initially in optical see through mode, which can be useful while the surgeon inserts, advances, directs, or re-directs an endoscope. Then, for example, when the surgeon has the endoscope in a desired position and orientation and the surgeon plans to perform a treatment or biopsy, requiring detailed visualization of a video feed from the endoscope, the surgeon can switch the endoscope to video see through mode, rendering the HMD non-transparent to external light (other than the video feed).

In select applications, the HMD can be configured so that an AR display of the HMD can have a wider field of view than the field of view of the endoscope (or microscope, if applicable). The AR display can display a target tissue, e.g. a tumor in the wall of an intestine, e.g. small intestine, colon or rectum, imaged, for example, pre-operatively with a contrast enhanced CT scan. Due to the wider field of view of the AR display compared to the field of view of the endoscope, the HMD can display the portions of the tumor (target tissue) extending outside the field of view of the endoscope, for example into the wall of the intestine and adjacent organs or structures, thereby facilitating accurate targeting with a biopsy needle, resection or ablation device.

In select embodiments, only sub-portions of an HMD can be switched from transparent to non-transparent. For example, inferior or lateral portions of the display can optionally remain transparent when the surgeon switches from optical see through to video see through mode. This can be advantageous when a surgeon desires to keep a perception of the operating room environment, while he or she performs portions of a procedure where otherwise video see through mode is preferred.

Example 12

In this example, a surgery of a knee joint is performed using an arthroscope with AR guidance. A surgeon is preparing the patient's knee for the arthroscopic procedure using standard preparation and technique. The surgeon is placing a first access portal, e.g. for the arthroscope. The surgeon is placing a second access portal, e.g. for surgical instruments. The surgeon is advancing the arthroscope through the first access portal. The arthroscope is tracked in a coordinate system, e.g. using tracking described throughout the disclosure, e.g. markers, cameras, 3D scanners. The surgical instruments are tracked in the coordinate system, e.g. using tracking described throughout the disclosure, e.g. markers, cameras, 3D scanners. The patient, specifically femur and, separately, tibia are tracked in the coordinate system, e.g. using tracking described throughout the disclosure, e.g. markers, cameras, 3D scanners. Optionally, a separate coordinate system is used for the femur (femoral coordinate system) and the tibia (tibial coordinate system). A pointer or stylus is tracked in the coordinate system, e.g. using tracking described throughout the disclosure, e.g. markers, cameras, 3D scanners. The pointer or stylus is introduced through one of the access portals to detect surface points on the distal femur and surface points on the tibial plateau. Pre-operative or intra-operative x-ray images of the knee are morphed from 2D to 3D models of the distal femur and/or the proximal tibial using any of the techniques described herein or known in the art. Artificial neural networks can also be used for bone segmentation and 2D to 3D morphing. The resultant 3D model of the distal femur is matched, by a computer processor, to the femoral surface points obtained with the pointer or stylus or a device with similar functionality for registration in the coordinate system. The resultant 3D model of the proximal tibia is matched, by a computer processor, to the tibial surface points obtained with the pointer or stylus (or a device with similar functionality for registration in the coordinate system.

The HMD is configured so that an AR display of the HMD has a wider field of view than the field of view of the arthroscope and the video feed from the arthroscope displayed by the HMD. The AR display can display a target tissue, e.g. femoral bone target or tibial bone target for resection/drilling/milling for placement of an ACL tunnel. The AR display can display a virtual femoral tunnel or a virtual tibial tunnel. The AR display can display a virtual axis for a reamer or mill in the femoral bone and the tibial bone for creating the femoral and/or tibial tunnel. Due to the wider field of view of the AR display compared to the field of view of the arthroscope and its video feed, the HMD can display the portions of the femoral bone targeted for the femoral tunnel placement, a virtual femoral tunnel, and/or a virtual femoral reaming axis extending outside the field of view of the arthroscope, thereby facilitating accurate targeting and placement of the femoral tunnel using AR guidance. Due to the wider field of view of the AR display compared to the field of view of the arthroscope, the HMD can display the portions of the tibial bone targeted for the tibial tunnel placement, a virtual tibial tunnel, and/or a virtual tibial reaming axis extending outside the field of view of the arthroscope and its video feed, thereby facilitating accurate targeting and placement of the tibial tunnel using AR guidance.

A surgeon may also elect to resect a posterior horn of a meniscus, e.g. a lateral meniscus. The surgeon may encounter difficulty visualizing at least a portion of the posterior horn of the lateral meniscus in the video feed from the arthroscope displayed by the HMD. The HMD can be configured so that the wider field of view of the AR display can be used to display the non-visualized portions of the posterior horn of the lateral meniscus, e.g. using data from a pre-operative MRI, with the virtual display of the non-visualized portions seen in the AR display outside the field of view of the arthroscope and its video feed, thereby allowing accurate targeting, for example for resection.

All patents, patent applications, and published references cited herein are hereby incorporated by reference in their entirety. It should be emphasized that the above-described embodiments of the present disclosure are merely possible examples of implementations, merely set forth for a clear understanding of the principles of the disclosure. Many variations and modifications may be made to the above-described embodiment(s) without departing substantially from the spirit and principles of the disclosure. It can be appreciated that several of the above-disclosed and other features and functions, or alternatives thereof, may be desirably combined into many other different systems or applications. All such modifications and variations are intended to be included herein within the scope of this disclosure, as fall within the scope of the appended claims.

The invention claimed is:

1. A system comprising:

a microscope or an endoscope, an augmented reality display device, and a computer processor, wherein the computer processor is configured for tracking the microscope or endoscope in a coordinate system, wherein the computer processor is configured for receiving at least one image of a physical target tissue, wherein the at least one image comprises an x-ray image, ultrasound image, computed tomography (CT) image, magnetic resonance imaging (MRI) image, single photon emission computed tomography (SPECT) image, positron emission tomography (PET) image, cone beam CT image, nuclear scintigraphy image or a combination thereof, wherein the at least one image is registered in the coordinate system, wherein the computer processor is configured for generating a virtual display of the physical target tissue, wherein the virtual display comprises a three-dimensional digital representation of the at least one image of the physical target tissue, wherein the computer processor is configured for tracking a patient, a physical tissue visible through the microscope or endoscope, the physical target tissue or a combination thereof in the coordinate system, wherein the computer processor is configured for generating an augmented view, the augmented view comprising the virtual display, wherein the augmented reality display device is configured to display the augmented view at the coordinates of the physical target tissue in the coordinate system, wherein the microscope or endoscope comprises a first field of view, wherein the augmented reality display device comprises a second field of view, wherein the second field of view is larger than the first field of view and comprises a portion that extends outside the first field of view, wherein the augmented reality display device is configured for displaying in at least one dimension a portion of the virtual display of the physical target tissue that extends outside the first field of view, outside a boundary of physical tissue visible through the microscope or endoscope, or a combination thereof.

2. The system of claim 1, wherein the boundary comprises a wall, an edge, or a limit of one or more of an access, a portal, an access portal, a tube, a retractor, or a combination thereof, that limits area of the physical tissue visible through the microscope or endoscope, wherein the access, portal, access portal, tube, retractor, or combination thereof is configured for viewing the physical tissue through the microscope or endoscope, and wherein the boundary is determined by an inner dimension of the access, portal, access portal, tube, retractor, or combination thereof.

3. The system of claim 1, wherein the first field of view of the microscope or endoscope is an optical field of view or is a digital field of view.

4. The system of claim 1, wherein the augmented reality display device is integrated into or attached to the microscope or to the endoscope.

5. The system of claim 1, wherein the microscope or endoscope is a digital microscope or a digital endoscope, and wherein the digital microscope or digital endoscope is configured for capturing video images of the physical tissue.

6. The system of claim 1, wherein the microscope or endoscope is a stereoscopic microscope or stereoscopic endoscope.

7. The system of claim 1, further comprising an imaging device configured to acquire the at least one image of the physical target tissue intra-operatively, pre-operatively, or intra-operatively and pre-operatively.

8. The system of claim 7, wherein the imaging device is an x-ray device, ultrasound device, computed tomography (CT) device, magnetic resonance imaging (MRI) device, single photon emission computed tomography (SPECT) device, positron emission tomography (PET) device, cone beam CT device, or a nuclear scintigraphy device.

9. The system of claim 1, wherein the augmented reality display device is a computer monitor, a tablet computer, a head mounted display, a stereoscopic optical see through head mounted display, or a stereoscopic video see through head mounted display.

10. The system of claim 1, wherein the augmented reality display device is an augmented reality display unit integrated into or attached to the microscope or endoscope.

11. The system of claim 1, wherein the physical target tissue is, at least in part, hidden from the view through the microscope or endoscope by the physical tissue visible through the microscope or endoscope, or wherein the physical target tissue is not visible through the microscope or endoscope.

12. The system of claim 1, wherein the augmented reality display device comprises at least one augmented reality display unit, or wherein the augmented reality display device comprises at least one augmented reality display unit comprising at least one of a cathode ray tube, liquid crystal display, organic light emitting diodes (OLED), mirror, waveguide, optical fiber, light pipe, combiner, or a combination thereof.

13. The system of claim 1, wherein the at least one image of the physical target tissue comprises a volume of images, or wherein the at least one image of the physical target tissue comprises a volume of images and wherein the volume of images of the physical target tissue extends in at least one dimension outside a boundary of the physical tissue visible through the microscope or endoscope.

14. The system of claim 1, wherein the virtual display comprises a 2D or a 3D representation of a virtual tool, virtual instrument, virtual implant, virtual device or a combination thereof, wherein the virtual tool, virtual instrument, virtual implant, virtual device or a combination thereof correspond to a physical tool, physical instrument, physical implant, physical device or a combination thereof.

15. The system of claim 14, further comprising a tracking device configured for tracking the physical tool, physical instrument, physical implant, physical device or a combination thereof in the coordinate system.

16. The system of claim 1, wherein the computer processor is configured for real-time tracking of the microscope or endoscope, the patient, a physical tissue visible through the microscope or endoscope, the physical target tissue, or a combination thereof, in the coordinate system.

17. The system of claim 1, wherein the imaging device is different than the microscope or endoscope.

18. The system of claim 1, wherein the augmented reality display device is configured to display the augmented view at the coordinates of the physical target tissue in the coordinate system superimposed onto the physical tissue visible through the microscope or endoscope.

19. A computer-implemented method comprising:

tracking a microscope or an endoscope in a coordinate system, receiving at least one image of a physical target tissue from an imaging system different than the microscope or endoscope, wherein the physical target tissue is not visible through the microscope or endoscope, registering the at least one image in the coordinate system, generating a virtual display of the physical target tissue, wherein the virtual display comprises three-dimensional digital representation of the at least one image of the physical target tissue, tracking a patient, a physical tissue visible through the microscope or endoscope, the physical target tissue or a combination thereof in the coordinate system, wherein the physical target tissue and the physical tissue are different, generating an augmented view, the augmented view comprising the virtual display, displaying the augmented view at the coordinates of the physical target tissue in the coordinate system; and displaying the physical target tissue outside a field of view of the microscope or endoscope, wherein a portion of the augmented view extends outside the field of view of view of the microscope or endoscope.

20. A surgical method comprising:

placing an access, a portal, an access portal, a tube, a retractor, or a combination thereof in a patient, positioning and/or advancing a microscope, an endoscope, a surgical tool, a surgical instrument, a device, an implant, or a combination thereof in relationship to the access, a portal, an access portal, a tube, a retractor, or a combination thereof in a patient, tracking the microscope or endoscope in a coordinate system, receiving at least one image of a physical target tissue from an imaging system different than the microscope or endoscope, wherein the physical target tissue is not visible through the microscope or endoscope, registering the at least one image in the coordinate system, generating a virtual display of the physical target tissue, wherein the virtual display comprises a three-dimensional digital representation of the at least one image of the physical target tissue, tracking a patient, a physical tissue visible through the microscope or endoscope, the physical target tissue or a combination thereof in the coordinate system, wherein the physical target tissue and the physical tissue are different, generating an augmented view, the augmented view comprising the virtual display, displaying the augmented view at the coordinates of the physical target tissue in the coordinate system, displaying the physical target tissue outside a field of view of the microscope or endoscope, wherein a portion of the augmented view extends outside the field of view of view of the microscope or endoscope, generating a virtual display comprising a 2D or a 3D representation of a virtual tool, virtual instrument, virtual implant, virtual device or a combination thereof, wherein the virtual tool, virtual instrument, virtual implant, virtual device or a combination thereof correspond to a physical tool, physical instrument, physical implant, physical device or a combination thereof, and tracking the surgical tool, surgical instrument, device, implant or combination thereof in the coordinate system.

* * * * *